United States Patent
Bayle et al.

(10) Patent No.: US 12,410,231 B2
(45) Date of Patent: Sep. 9, 2025

(54) NATURAL KILLER CELL PRODUCTS AND METHODS

(71) Applicant: Board of Regents of The University of Texas System, Austin, TX (US)

(72) Inventors: Joseph Henri Bayle, Houston, TX (US); Xiaomei Wang, Houston, TX (US); David Michael Spencer, Frisco, TX (US); Wei-Chun Chang, Glenside, PA (US)

(73) Assignee: Board of Regents of the University of Texas System, Austin, TX (US)

( * ) Notice: Subject to any disclaimer, the term of this patent is extended or adjusted under 35 U.S.C. 154(b) by 911 days.

(21) Appl. No.: 17/053,275

(22) PCT Filed: May 6, 2019

(86) PCT No.: PCT/US2019/030939
§ 371 (c)(1),
(2) Date: Nov. 5, 2020

(87) PCT Pub. No.: WO2019/217327
PCT Pub. Date: Nov. 14, 2019

(65) Prior Publication Data
US 2021/0107966 A1    Apr. 15, 2021

Related U.S. Application Data

(60) Provisional application No. 62/816,799, filed on Mar. 11, 2019, provisional application No. 62/756,442, filed on Nov. 6, 2018, provisional application No. 62/668,223, filed on May 7, 2018.

(51) Int. Cl.
| | |
|---|---|
| *C07K 14/00* | (2006.01) |
| *A61K 40/15* | (2025.01) |
| *A61K 40/31* | (2025.01) |
| *A61K 40/42* | (2025.01) |
| *C07K 14/54* | (2006.01) |
| *C07K 14/725* | (2006.01) |
| *C12N 5/0783* | (2010.01) |

(52) U.S. Cl.
CPC .......... *C07K 14/7051* (2013.01); *A61K 40/15* (2025.01); *A61K 40/31* (2025.01); *A61K 40/4205* (2025.01); *A61K 40/4215* (2025.01); *A61K 40/4217* (2025.01); *A61K 40/4224* (2025.01); *C07K 14/5443* (2013.01); *C12N 5/0646* (2013.01); *A61K 2239/31* (2023.05); *A61K 2239/38* (2023.05); *A61K 2239/48* (2023.05)

(58) Field of Classification Search
CPC . C07K 14/7051; C07K 14/5443; A61K 35/17
See application file for complete search history.

(56) References Cited

U.S. PATENT DOCUMENTS

| | | |
|---|---|---|
| 2016/0058857 A1 | 3/2016 | Spencer et al. |
| 2016/0175359 A1 | 6/2016 | Spencer et al. |
| 2017/0087185 A1 | 3/2017 | Crane et al. |

OTHER PUBLICATIONS

Collinson-Pautz et al., "Constitutively active MyD88/CD40 costimulation enhances expansion and efficacy of chimeric antigen receptor T cells targeting hematological malignancies," Leukemia, 33(9):2195-2207, 2019.
Diaconu et a.. "Inducible Caspase-9 Selectively Modulates the Toxicities of CD19-Specific Chimeric Antigen Receptor-Modified T Cells," Molecular Therapy, 25(3):580-592, 2017.
Duong et al., "Two-Dimensional Regulation of CAR-T Cell Therapy with Orthogonal Switches," Molecular Therapy: Oncolytics, 12:124-137, 2019.
Extended European Search Report issued in European Patent Application No. 19799828.9, dated Jun. 17, 2022.
Narayanan et al., "A composite MyD88/CD40 switch synergistically activates mouse and human dendritic cells for enhanced antitumor efficacy," Journal of Clinical Investigation, 121(4):1524-15344, 2011.
Office Communication issued in Australian Patent Application No. 2019267458, dated Jun. 24, 2024.
Office Communication issued in European Patent Application No. 19799828.9, dated Apr. 10, 2024.
PCT International Search Report issued in International Application No. PCT/US2019/030939, dated Sep. 10, 2019.
Wang et al., "Inducible MyD88/CD40 synergizes with IL-15 to enhance antitumor efficacy of CAR-NK cells," Blood Advances, 4(9): 1950-1964, 2020.
Wong et al., "IL-15 synergizes with CD40 agonist antibodies to induce durable immunity against bladder cancer," bioRxiv, Version 1, 35 pages, 2023. Available at doi: 10.1101/2023.01.30.526266.

*Primary Examiner* — Jeanette M Lieb
(74) *Attorney, Agent, or Firm* — Norton Rose Fulbright US LLP

(57) ABSTRACT

The technology relates generally to the field of immunology and relates in part to compositions and methods for growing and storing modified natural killer cells, including for example, conditional chemical regulation of natural killer cell function. The technology further relates to pharmaceutical compositions and treatment of subjects using modified natural killer cells.

18 Claims, 91 Drawing Sheets
Specification includes a Sequence Listing.

| Group # | NK cells | pBP | "Go" Drug | # of mice |
|---|---|---|---|---|
| 1 | NA | NA | 0 | 5 |
| 2 | iRC9.dCD19 | 1385 | 1 mg/kg rim. | 5 |
| 3 | iRC9.dCD19.iMC | 1664 | 0 | 5 |
| 4 | iRC9.dCD19.iMC | 1664 | 1 mg/kg rim. | 5 |
| 5 | iRC9.IL15.dCD19.iMC | 2811 | 0 | 5 |
| 6 | iRC9.IL15.dCD19.iMC | 2811 | 1 mg/kg rim. | 5 |
| | | | TOTAL # of mice | 30 |

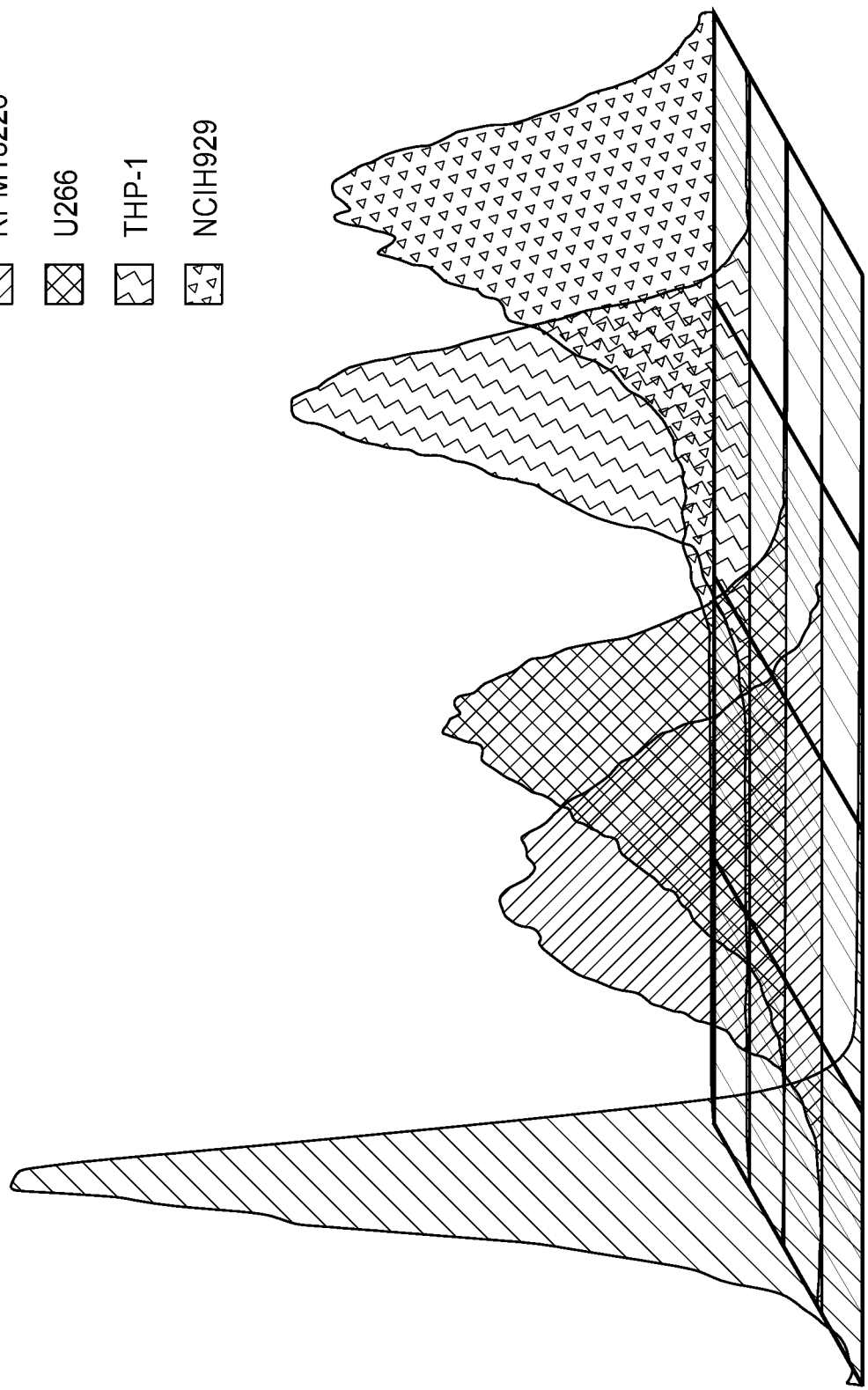

SEQUENCE LISTING

```
<160> NUMBER OF SEQ ID NOS: 156

<210> SEQ ID NO 1
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggctgcag gaggtcccgg cgcggggtct gcggccccgg tctcctccac atcctccctt      60 ccctggctg ctctcaacat gcgagtgcgg cgccgcctgt ctctgttctt gaacgtgcgg      120
acacaggtgg cggccgactg gaccgcgctg gcggaggaga tggactttga gtacttggag     180
atccggcaac tggagacaca agcggacccc actggcaggc tgctggacgc ctggcaggga     240
cgccctggcg cctctgtagg ccgactgctc gatctgctta ccaagctggg ccgcgacgac     300
gtgctgctgg agctgggacc cagcattgag gaggattgcc aaaagtatat cttgaagcag     360
cagcaggagg aggctgagaa gcctttacag gtggccgctg tagacagcag tgtcccacgg     420
acagcagagc tggcgggcat caccacactt gatgaccccc tggggcatat gcctgagcgt     480
ttcgatgcct tcatctgcta ttgccccagc gacatc                               516

<210> SEQ ID NO 2
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30
```

```
Leu Ser Leu Phe Leu Asn Val Arg Thr Gln Val Ala Ala Asp Trp Thr
             35                  40                  45
Ala Leu Ala Glu Glu Met Asp Phe Glu Tyr Leu Glu Ile Arg Gln Leu
 50                  55                  60
Glu Thr Gln Ala Asp Pro Thr Gly Arg Leu Leu Asp Ala Trp Gln Gly
 65                  70                  75                  80
Arg Pro Gly Ala Ser Val Gly Arg Leu Leu Asp Leu Leu Thr Lys Leu
                 85                  90                  95
Gly Arg Asp Asp Val Leu Leu Glu Leu Gly Pro Ser Ile Glu Glu Asp
                100                 105                 110
Cys Gln Lys Tyr Ile Leu Lys Gln Gln Gln Glu Glu Ala Glu Lys Pro
                115                 120                 125
Leu Gln Val Ala Ala Val Asp Ser Ser Val Pro Arg Thr Ala Glu Leu
                130                 135                 140
Ala Gly Ile Thr Thr Leu Asp Asp Pro Leu Gly His Met Pro Glu Arg
145                 150                 155                 160
Phe Asp Ala Phe Ile Cys Tyr Cys Pro Ser Asp Ile
                165                 170

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 ctcgag                                                                    6

<210> SEQ ID NO 4
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Leu Glu
1

<210> SEQ ID NO 5
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aggagtaaga ggagcaggct cctgcacagt gactacatga acatgactcc ccgccgcccc        60
gggcccaccc gcaagcatta ccagccctat gccccaccac gcgacttcgc agcctatcgc       120
tcc                                                                    123

<210> SEQ ID NO 6
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 6

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 7
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
agggaccaga ggctgccccc cgatgcccac aagcccctg ggggaggcag tttccggacc      60
cccatccaag aggagcaggc cgacgcccac tccaccctgg ccaagatc                 108

<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile Gly Ser Gly
        35

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ggatctggcc aattg                                                      15

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ser Gly Gln Leu
1               5

<210> SEQ ID NO 11
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
ggcgtccaag tcgaaaccat tagtcccggc gatggcagaa catttcctaa aaggggacaa     60
acatgtgtcg tccattatac aggcatgttg gaggacggca aaaaggtgga cagtagtaga    120
gatcgcaata aacctttcaa attcatgttg ggaaaacaag aagtcattag ggatgggag     180 gagggcgtgg ctcaaatgtc cgtcggccaa cgcgctaagc tcaccatcag ccccgactac    240
gcatacggcg ctaccggaca tcccggaatt attccccctc acgctacctt ggtgtttgac    300
gtcgaactgt tgaagctcga a                                              321

<210> SEQ ID NO 12
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 gtcgag                                                                 6

<210> SEQ ID NO 14
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Glu
1

<210> SEQ ID NO 15

<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
ggagtgcagg tggagactat ctccccagga gacgggcgca ccttccccaa gcgcggccag      60
acctgcgtgg tgcactacac cgggatgctt gaagatggaa agaaagttga ttcctcccgg     120
gacagaaaca agccctttaa gtttatgcta ggcaagcagg aggtgatccg aggctgggaa     180
gaaggggttg cccagatgag tgtgggtcag agagccaaac tgactatatc tccagattat     240
gcctatggtg ccactgggca cccaggcatc atcccaccac atgccactct cgtcttcgat     300
gtggagcttc taaaactgga a                                                321
```

<210> SEQ ID NO 16
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 17
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 17

```
ccgcgg                                                                  6
```

<210> SEQ ID NO 18
<211> LENGTH: 2
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

```
Pro Arg
1
```

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gagggcagag gcagcctcct gacatgtggg gacgtcgagg agaaccctgg ccca           54

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Gly Arg Gly Ser Leu Leu Thr Cys Gly Asp Val Glu Glu Asn Pro
1               5                   10                  15

Gly Pro

<210> SEQ ID NO 21
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21 ccttgg                                                                 6

<210> SEQ ID NO 22
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Pro Trp
1

<210> SEQ ID NO 23
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
atggagttcg gattgagctg gctgttcctg gtggcaatac tcaagggcgt tcaatgttca     60
cgg                                                                   63

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Met Glu Phe Gly Leu Ser Trp Leu Phe Leu Val Ala Ile Leu Lys Gly
1               5                   10                  15

Val Gln Cys Ser Arg
            20

<210> SEQ ID NO 25
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gacatccaac tgacgcaaag cccatctaca ctcagcgcta gcatggggga cagggtcaca      60
atcacgtgct ctgcctcaag ttccgttagg tttatccatt ggtatcagca gaaacctgga     120
aaggccccaa aaagactgat ctatgatacc agcaagctgg cttccggagt gccctcaagg     180
ttctcaggat ctggcagtgg gaccgatttc accctgacaa ttagcagcct tcagccagag     240
gatttcgcaa cctattactg tcagcaatgg gggtccagcc cattcacttt cggccaagga     300
acaaaggtgg agataaaa                                                   318

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Leu Thr Gln Ser Pro Ser Thr Leu Ser Ala Ser Met Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Gly Ser Ser Pro Phe Thr
                85                  90                  95

Phe Gly Gln Gly Thr Lys Val Glu Ile Lys
            100                 105

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggcggaggaa gcggaggtgg gggc                                             24

```
<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Ser Gly Gly Gly Gly
1               5

<210> SEQ ID NO 29
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 caggtg                                                                   6

<210> SEQ ID NO 30
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Val
1

<210> SEQ ID NO 31
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gaggtgcagc tcgtggagta tggcggggc ctggtgcagc ctggggggtag tctgaggctc          60 tcctgcgctg cctctggctt taacattaaa gactactaca tacattgggt gcggcaggcc         120
ccaggcaaag gctcgaatg ggtggcctgg attgaccctg agaatggtga cactgagttt          180
gtccccaagt ttcagggcag agccaccatg agcgctgaca caagcaaaaa cactgcttat         240
ctccaaatga atagcctgcg agctgaagat acagcagtct attactgcaa gacgggagga         300
ttctggggcc agggaactct ggtgacagtt agttcc                                   336

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Val Gln Leu Val Glu Tyr Gly Gly Gly Leu Val Gln Pro Gly Gly
1               5                   10                  15

Ser Leu Arg Leu Ser Cys Ala Ala Ser Gly Phe Asn Ile Lys Asp Tyr
            20                  25                  30
```

Tyr Ile His Trp Val Arg Gln Ala Pro Gly Lys Gly Leu Glu Trp Val
         35                  40                  45

Ala Trp Ile Asp Pro Glu Asn Gly Asp Thr Glu Phe Val Pro Lys Phe
 50                  55                  60

Gln Gly Arg Ala Thr Met Ser Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Lys Thr Gly Gly Phe Trp Gly Gln Gly Thr Leu Val Thr Val Ser Ser
                100                 105                 110

<210> SEQ ID NO 33
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33 ggatcc                                                                   6

<210> SEQ ID NO 34
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Ser
1

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gaacttccta ctcaggggac tttctcaaac gttagcacaa acgtaagt                    48

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Glu Leu Pro Thr Gln Gly Thr Phe Ser Asn Val Ser Thr Asn Val Ser
1               5                   10                  15

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gaacttccta ctcaggggac tttctcaaac gttagcacaa acgtaagt    48

<210> SEQ ID NO 38
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp
        35                  40
```

<210> SEQ ID NO 39
<211> LENGTH: 111
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
atctatatct gggcacctct cgctggcacc tgtggagtcc ttctgctcag cctggttatt    60
actctgtact gtaatcaccg gaatcgccgc cgcgtttgta agtgtcccag g            111

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn Arg Arg Arg Val
            20                  25                  30

Cys Lys Cys Pro Arg
        35
```

<210> SEQ ID NO 41
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41 gtcgac    6

<210> SEQ ID NO 42
<211> LENGTH: 2
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Val Asp
1

<210> SEQ ID NO 43
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
agagtgaagt tcagcaggag cgcagacgcc cccgcgtacc agcagggcca gaaccagctc    60
tataacgagc tcaatctagg acgaagagag gagtacgatg ttttggacaa gagacgtggc   120
cgggaccctg agatggggggg aaagccgaga aggaagaacc ctcaggaagg cctgtacaat   180
gaactgcaga aagataagat ggcggaggcc tacagtgaga ttgggatgaa aggcgagcgc   240 cggagggggca aggggcacga tggcctttac cagggtctca gtacagccac caaggacacc   300
tacgacgccc ttcacatgca agctcttcca cctcgt                              336
```

<210> SEQ ID NO 44
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 45
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
acaaaaaaga agtattcatc cagtgtgcac gaccctaacg gtgaatacat gttcatgaga    60
gcagtgaaca cagccaaaaa atctagactc acagatgtga cccta                    105
```

<210> SEQ ID NO 46

```
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35

<210> SEQ ID NO 47
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 atgctcgag                                                                 9

<210> SEQ ID NO 48
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Met Leu Glu
1

<210> SEQ ID NO 49
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
aaacggggca gaaagaaact cctgtatata ttcaaacaac catttatgag accagtacaa        60
actactcaag aggaagatgg ctgtagctgc cgatttccag aagaagaaga aggaggatgt       120
gaactg                                                                 126

<210> SEQ ID NO 50
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30
```

```
Pro Glu Glu Glu Glu Gly Gly Cys Glu Leu
        35                  40
```

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

```
atggggagta gcaagagcaa gcctaaggac cccagccagc gc                        42
```

<210> SEQ ID NO 52
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

```
Met Gly Ser Ser Lys Ser Lys Pro Lys Asp Pro Ser Gln Arg
1               5                   10
```

<210> SEQ ID NO 53
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53

```
agagcatgc                                                              9
```

<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

```
Arg Ala Cys
1
```

<210> SEQ ID NO 55
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
aaaaaggtgg ccaagaagcc aaccaataag gccccccacc ccaagcagga gccccaggag     60
atcaattttc ccgacgatct tcctggctcc aacactgctg ctccagtgca ggagacttta    120
catggatgcc agccggtcac ccaggaggat ggcaaagaga gtcgcatctc agtgcaggag    180
agacag                                                              186
```

<210> SEQ ID NO 56
<211> LENGTH: 62

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Lys Lys Val Ala Lys Lys Pro Thr Asn Lys Ala Pro His Pro Lys Gln
1               5                   10                  15

Glu Pro Gln Glu Ile Asn Phe Pro Asp Asp Leu Pro Gly Ser Asn Thr
            20                  25                  30

Ala Ala Pro Val Gln Glu Thr Leu His Gly Cys Gln Pro Val Thr Gln
        35                  40                  45

Glu Asp Gly Lys Glu Ser Arg Ile Ser Val Gln Glu Arg Gln
    50                  55                  60

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
atgctcgaga tgctggag                                                   18

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Met Leu Glu Met Leu Glu
1               5

<210> SEQ ID NO 59
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
ggagtgcagg tggagactat tagccccgga gatggcagaa cattccccaa aagaggacag      60
acttgcgtcg tgcattatac tggaatgctg gaagacggca agaaggtgga cagcagccgg     120
gaccgaaaca agcccttcaa gttcatgctg gggaagcagg aagtgatccg gggctgggag     180
gaaggagtcg cacagatgtc agtgggacag agggccaaac tgactattag cccagactac     240
gcttatggag caaccggcca ccccgggatc attccccctc atgctacact ggtcttcgat     300
gtggagctgc tgaagctgga a                                              321

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 60

```
Gly Val Gln Val Glu Thr Ile Ser Pro Gly Asp Gly Arg Thr Phe Pro
1               5                   10                  15
Lys Arg Gly Gln Thr Cys Val Val His Tyr Thr Gly Met Leu Glu Asp
            20                  25                  30
Gly Lys Lys Phe Asp Ser Ser Arg Asp Arg Asn Lys Pro Phe Lys Phe
        35                  40                  45
Met Leu Gly Lys Gln Glu Val Ile Arg Gly Trp Glu Glu Gly Val Ala
    50                  55                  60
Gln Met Ser Val Gly Gln Arg Ala Lys Leu Thr Ile Ser Pro Asp Tyr
65                  70                  75                  80
Ala Tyr Gly Ala Thr Gly His Pro Gly Ile Ile Pro Pro His Ala Thr
                85                  90                  95
Leu Val Phe Asp Val Glu Leu Leu Lys Leu Glu
            100                 105
```

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 61

```
agcggaggag gatccggagt ggac                                          24
```

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

```
Ser Gly Gly Gly Ser Gly Val Asp
1               5
```

<210> SEQ ID NO 63
<211> LENGTH: 858
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 63

```
gggtttggag atgtgggagc cctggaatcc ctgcggggca atgccgatct ggcttacatc    60
ctgtctatgg agccttgcgg ccactgtctg atcattaaca atgtgaactt ctgcagagag   120
agcgggctgc ggaccagaac aggatccaat attgactgtg aaaagctgcg agaaggttc    180
tctagtctgc actttatggt cgaggtgaaa ggcgatctga ccgctaagaa atggtgctg    240
gccctgctgg aactggctcg gcaggaccat ggggcactgg attgctgcgt ggtcgtgatc   300
ctgagtcacg gctgccaggc ttcacatctg cagttccctg ggcagtcta tggaactgac   360
ggctgtccag tcagcgtgga agatcgtga acatcttca acggcacctc ttgcccaagt   420
ctgggcggga agcccaaact gttctttatt caggcctgtg aggcgagca gaaagatcac   480
ggcttcgaag tggctagcac ctccccccgag gacgaatcac ctggaagcaa ccctgagcca   540
```

```
gatgcaaccc ccttccagga aggcctgagg acatttgacc agctggatgc catctcaagc    600
ctgcccacac cttctgacat tttcgtctct tacagtactt tccctggatt tgtgagctgg    660
cgcgatccaa agtcaggcag ctggtacgtg agacactgg acgatatctt tgagcagtgg     720
gcccattctg aagacctgca gagtctgctg ctgcgagtgg ccaatgctgt tctctgtgaag   780 gggatctaca aacagatgcc aggatgcttc aactttctga gaaagaaact gttctttaag    840
acctccgcat ctagggcc                                                  858
```

```
<210> SEQ ID NO 64
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64
```

Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Arg Gln Asp His Gly Ala Leu Asp Cys Cys
                85                  90                  95

Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
        115                 120                 125

Ile Val Asn Ile Phe Asn Gly Thr Ser Cys Pro Ser Leu Gly Gly Lys
    130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Glu Ser Pro Gly Ser
                165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
        195                 200                 205

Val Ser Tyr Ser Thr Phe Pro Gly Phe Val Ser Trp Arg Asp Pro Lys
    210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
                245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser Ala Ser Arg Ala
        275                 280                 285

```
<210> SEQ ID NO 65
```

```
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gaaggccgag ggagcctgct gacatgtggc gatgtggagg aaaacccagg acca          54

<210> SEQ ID NO 66
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66 ccatgg                                                                6

<210> SEQ ID NO 67
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atggagtttg gactttcttg gttgtttttg gtggcaattc tgaagggtgt ccagtgtagc    60
agg                                                                  63

<210> SEQ ID NO 68
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68
gacatccaga tgacacagac tacatcctcc ctgtctgcct ctctgggaga cagagtcacc    60
atcagttgca gggcaagtca ggacattagt aaatatttaa attggtatca gcagaaacca   120
gatggaactg ttaaactcct gatctaccat acatcaagat tacactcagg agtcccatca   180
aggttcagtg gcagtgggtc tggaacagat tattctctca ccattagcaa cctggagcaa   240
gaagatattg ccacttactt ttgccaacag ggtaatacgc ttccgtacac gttcggaggg   300
gggactaagt tggaaataac a                                             321

<210> SEQ ID NO 69
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30
```

-continued

Leu Asn Trp Tyr Gln Gln Lys Pro Asp Gly Thr Val Lys Leu Leu Ile
         35                  40                  45

Tyr His Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr
            100                 105

<210> SEQ ID NO 70
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
gaggtgaaac tgcaggagtc aggacctggc ctggtggcgc cctcacagag cctgtccgtc      60
acatgcactg tctcaggggt ctcattaccc gactatggtg taagctggat tcgccagcct     120
ccacgaaagg gtctggagtg gctgggagta atatggggta gtgaaaccac atactataat     180
tcagctctca atccagact gaccatcatc aaggacaact ccaagagcca agttttctta      240
aaaatgaaca gtctgcaaac tgatgacaca gccatttact actgtgccaa acattattac     300
tacggtggta gctatgctat ggactactgg ggtcaaggaa cctcagtcac cgtctcctca     360

<210> SEQ ID NO 71
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120

<210> SEQ ID NO 72
<211> LENGTH: 126
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 72
cccgccccaa gaccccccac acctgcgccg accattgctt ctcaacccct gagtttgaga      60
cccgaggcct gccggccagc tgccggcggg gccgtgcata caagaggact cgatttcgct     120
tgcgac                                                                126

<210> SEQ ID NO 73
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
gctactaact tcagcctgct gaagcaggct ggagacgtgg aggagaaccc cgggcct         57

<210> SEQ ID NO 74
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Thr Asn Phe Ser Leu Leu Lys Gln Ala Gly Asp Val Glu Glu Asn
1               5                   10                  15

Pro Gly Pro

<210> SEQ ID NO 75
<211> LENGTH: 186
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
aaaaaggtgg ccaagaagcc aaccaataag gccccccacc ccaagcagga gccccaggag      60
atcaattttc ccgacgatct tcctggctcc aacactgctg ctccagtgca ggagacttta    120
catggatgcc aaccggtcac ccaggaggat ggcaaagaga gtcgcatctc agtgcaggag    180
agacag                                                                186

<210> SEQ ID NO 76
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Met Gly Ser Ser Lys Ser Lys Pro Lys Asp Pro Ser Gln Arg Leu Asp
1               5                   10                  15

<210> SEQ ID NO 77
<211> LENGTH: 9
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 77 gcggccgct                                                                9

<210> SEQ ID NO 78
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Ala Ala
1

<210> SEQ ID NO 79
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 80
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 81
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
cagatccaac tggtgcagtc aggcccggaa ctgaagaagc caggggagac agtcaaaata    60
agttgtaaag ccagcggcta catatttact aattacggga tgaattgggt gaagcaagcg   120
ccgggcaaat cctttaaatg gatggggtgg ataaacacat acacaggaga gtcaacgtac   180
agcgcggact caaaggtcg attcgcgttc agtctcgaga ccagcgcgag tacagcttac   240
ctccacatca acgatcttaa aaacgaagac acggcaacct attttttgcgc ccggtcaggc   300

```
ggttacgacc ctatggacta ttggggccaa gggacctccg ttacggta              348
```

<210> SEQ ID NO 82
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val
        115

<210> SEQ ID NO 83
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83

```
cttcaggcgg tggcgggagt ggtggaggag gctcaggcgg cggggggatca           50
```

<210> SEQ ID NO 84
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ser Ser Gly Gly Gly Gly Ser Gly Gly Gly Gly Ser Gly Gly Gly Gly
1               5                   10                  15

Ser

<210> SEQ ID NO 85
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
gacatcgtac tgacccaatc tcccgctagc cttgcagtat ccttgggtca acgcgctaca    60
```

```
ataagttgcc gggctagtga gtccgtagac aactatggca acaccttcat gcattggtac    120
caacaaaaac caggtcagcc acccaaactt ctcatttaca gagcgtctaa tctcgaaagc    180
ggcatccctg ctcgattctc tggaagcgga agtagaaccg actttacact gactataaac    240
cccgtcgaag ccgatgatgt tgccacttat tactgtcaac agagcaatga ggacccaccg    300
acattcggtg ctggtaccaa gctggagttg aaggagtcaa atacgggcc tccctgtccc    360
```

<210> SEQ ID NO 86
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Thr Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

Glu Asp Pro Pro Thr Phe Gly Ala Gly Thr Lys Leu Glu Leu Lys Glu
            100                 105                 110

Ser Lys Tyr Gly Pro Pro Cys Pro
        115                 120
```

<210> SEQ ID NO 87
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

```
gatatcgtgc tgacccagtc ccccctagc ctggccatgt ccctgggcaa acgggccacc     60
atctcctgca gagcctccga gtccgtgacc atcctcggct ccacctgat ctactggtac    120 cagcagaagc ccggccagcc tcccacccctc cttatccagc tggccagcaa cgtgcagacc    180
ggcgtgcccg ctagattctc cggcagcggc tctagaaccg acttcaccct gaccatcgac    240
cccgtggaag aggacgatgt cgccgtgtac tattgcctgc agtccagaac catccctagg    300
acattcggcg gaggaaccaa gctggagatc aaa                                 333
```

<210> SEQ ID NO 88
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110
```

<210> SEQ ID NO 89
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gggggcggtg gcagcggtgg cggtgggtct gggggcggag gctct                45

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

```
Gly Gly Gly Gly Ser Gly Gly Gly Gly Ser Gly Gly Gly Gly Ser
1               5                   10                  15
```

<210> SEQ ID NO 91
<211> LENGTH: 352
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
cagatccagc tggtgcagtc cggccccgag ctgaagaaac ccggcgagac cgtgaagatc      60
tcctgcaagg ccagcggcta caccttcaga cactacagca tgaactgggt gaagcaggcc     120
cctggcaagg gcctgaagtg gatgggccgg atcaacaccg agtccggcgt gcccatctac     180
gccgacgatt tcaagggcag attcgccttc agcgtggaga cctccgcctc taccgcctac     240
ctggtgatca caaatctgaa ggacgaggac accgcctcct acttctgcag caacgactac     300
ctgtacagcc tggacttctg gggccagggc accgccctga ccgtgagctc cg             352

<210> SEQ ID NO 92
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg His Tyr
            20                  25                  30

Ser Met Asn Trp Val Lys Gln Ala Pro Gly Lys Gly Leu Lys Trp Met
        35                  40                  45

Gly Arg Ile Asn Thr Glu Ser Gly Val Pro Ile Tyr Ala Asp Asp Phe
    50                  55                  60

Lys Gly Arg Phe Ala Phe Ser Val Glu Thr Ser Ala Ser Thr Ala Tyr
65                  70                  75                  80

Leu Val Ile Asn Asn Leu Lys Asp Glu Asp Thr Ala Ser Tyr Phe Cys
                85                  90                  95

Ser Asn Asp Tyr Leu Tyr Ser Leu Asp Phe Trp Gly Gln Gly Thr Ala
            100                 105                 110

Leu Thr Val Ser Ser
        115

<210> SEQ ID NO 93
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ggatctggcg gccgc                                                  15

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Ser Gly Gly Arg
1               5

<210> SEQ ID NO 95
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
gagggaaggg gaagtcttct aacatgcggg gacgtggagg aaaatcccgg gccc       54

<210> SEQ ID NO 96
<211> LENGTH: 537
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gagggaaggg gaagtcttct aacatgcggg gacgtggagg aaaatcccgg gcccatgaga    60

-continued

```
atttcgaaac cacatttgag aagtatttcc atccagtgct acttgtgttt acttctaaac    120
agtcattttc taactgaagc tggcattcat gtcttcattt tgggctgttt cagtgcaggg    180
cttcctaaaa cagaagccaa ctgggtgaat gtaataagtg atttgaaaaa aattgaagac    240
cttattcaat ctatgcacat tgatgctact ttatatacgg aaagtgatgt tcaccccagt    300
tgcaaagtaa cagcaatgaa gtgctttctc ttggagttac aagttatttc acttgagtcc    360
ggagatgcaa gtattcatga tacagtagaa aatctgatca tcctagcaaa caacagtttg    420
tcttctaatg ggaatgtaac agaatctgga tgcaaagaat gtgaggaact ggaggagaag    480
aacatcaagg aattttttgca gagttttgta catattgtcc aaatgttcat caacact     537
```

<210> SEQ ID NO 97
<211> LENGTH: 161
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Met Arg Ile Ser Lys Pro His Leu Arg Ser Ile Ser Ile Gln Cys Tyr
1               5                  10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr
```

<210> SEQ ID NO 98
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 98

```
atgctcgagc aattg                                                     15
```

<210> SEQ ID NO 99
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 99

Met Leu Glu Gln Leu
1               5

<210> SEQ ID NO 100
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gaaatgtggc atgaagggtt ggaagaagct tcaaggctgt acttcggaga gaggaacgtg      60
aagggcatgt ttgaggttct tgaacctctg cacgccatga tggaacgggg accgcagaca     120
ctgaaagaaa cctcttttaa tcaggcctac ggcagagacc tgatggaggc ccaagaatgg     180
tgtagaaagt atatgaaatc cggtaacgtg aaagacctga ctcaggcctg ggacctttat     240
taccatgtgt tcaggcggat cagtaag                                         267

<210> SEQ ID NO 101
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Met Trp His Glu Gly Leu Glu Glu Ala Ser Arg Leu Tyr Phe Gly
1               5                   10                  15

Glu Arg Asn Val Lys Gly Met Phe Glu Val Leu Glu Pro Leu His Ala
                20                  25                  30

Met Met Glu Arg Gly Pro Gln Thr Leu Lys Glu Thr Ser Phe Asn Gln
            35                  40                  45

Ala Tyr Gly Arg Asp Leu Met Glu Ala Gln Glu Trp Cys Arg Lys Tyr
        50                  55                  60

Met Lys Ser Gly Asn Val Lys Asp Leu Thr Gln Ala Trp Asp Leu Tyr
65                  70                  75                  80

Tyr His Val Phe Arg Arg Ile Ser Lys
                85

<210> SEQ ID NO 102
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
ggcgggcaat tg                                                          12

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Gly Gln Leu
1

<210> SEQ ID NO 104
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
ggcgtccaag tcgaaaccat tagtcccggc gatggcagaa catttcctaa aaggggacaa      60
acatgtgtcg tccattatac aggcatgttg gaggacggca aaaagttcga cagtagtaga    120
gatcgcaata aacctttcaa attcatgttg ggaaaacaag aagtcattag gggatgggag    180
gagggcgtgg ctcaaatgtc cgtcggccaa cgcgctaagc tcaccatcag ccccgactac    240
gcatacggcg ctaccggaca tcccggaatt attccccctc acgctacctt ggtgtttgac    300
gtcgaactgt tgaagctc                                                   318
```

<210> SEQ ID NO 105
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu
            100                 105

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106

```
tcaggcggtg gctcaggtcc atgg                                             24
```

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ser Gly Gly Gly Ser Gly Pro Trp
1               5

<210> SEQ ID NO 108
<211> LENGTH: 858
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108

```
ggatttggtg atgtcggtgc tcttgagagt ttgaggggaa atgcagattt ggcttacatc      60
ctgagcatgg agccctgtgg ccactgcctc attatcaaca atgtgaactt ctgccgtgag     120
tccgggctcc gcacccgcac tggctccaac atcgactgtg agaagttgcg gcgtcgcttc     180
tcctcgctgc atttcatggt ggaggtgaag ggcgacctga ctgccaagaa aatggtgctg     240
gctttgctgg agctggcgcg gcaggaccac ggtgctctgg actgctgcgt ggtggtcatt     300
ctctctcacg gctgtcaggc cagccacctg cagttcccag gggctgtcta cggcacagat     360
ggatgccctg tgtcggtcga aagattgtg aacatcttca atgggaccag ctgccccagc     420
ctgggaggga agcccaagct cttttcatc caggcctgtg gtggggagca gaaagaccat     480
gggtttgagg tggcctccac ttcccctgaa gacgagtccc ctggcagtaa ccccgagcca     540
gatgccaccc cgttccagga aggtttgagg accttcgacc agctggacgc catatctagt     600
ttgcccacac ccagtgacat ctttgtgtcc tactctactt tcccaggttt tgtttcctgg     660
agggacccca agatggctc ctggtacgtt gagaccctgg acgacatctt tgagcagtgg     720
gctcactctg aagacctgca gtccctcctg cttagggtcg ctaatgctgt ttcggtgaaa     780
gggatttata aacagatgcc tggttgcttt aatttcctcc ggaaaaaact tttctttaaa     840
acatcagcta gcagagcc                                                  858
```

<210> SEQ ID NO 109
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
ggatctggac cgcgg                                                      15

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Ser Gly Pro Arg
1               5

<210> SEQ ID NO 111

-continued

```
<211> LENGTH: 999
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111
atgccaccac ctcgcctgct gttctttctg ctgttcctga cacctatgga ggtgcgacct      60
gaggaaccac tggtcgtgaa ggtcgaggaa ggcgacaatg ccgtgctgca gtgcctgaaa     120
ggcacttctg atgggccaac tcagcagctg acctggtcca gggagtctcc cctgaagcct     180
tttctgaaac tgagcctggg actgccagga ctgggaatcc acatgcgccc tctggctatc     240
tggctgttca tcttcaacgt gagccagcag atgggaggat ctacctgtgt ccagccagga     300
ccaccatccg agaaggcctg gcagcctgga tggaccgtca acgtggaggg gtctggagaa     360
ctgtttaggt ggaatgtgag tgacctggga ggactgggat gtgggctgaa gaaccgctcc     420
tctgaaggcc caagttcacc ctcagggaag ctgatgagcc aaaaactgta cgtgtgggcc     480
aaagatcggc ccgagatctg ggagggagaa cctccatgcc tgccacctag agacagcctg     540
aatcagagtc tgtcacagga tctgacaatg gccccgggt ccactctgtg gctgtcttgt      600
ggagtcccac ccgacagcgt gtccagaggc cctctgtcct ggacccacgt gcatcctaag     660
gggccaaaaa gtctgctgtc actggaactg aaggacgatc ggcctgccag agacatgtgg     720
gtcatggaga ctggactgct gctgccacga gcaaccgcac aggatgctgg aaaatactat     780
tgccaccggg gcaatctgac aatgtccttc catctggaga tcactgcaag gcccgtgctg     840
tggcactggc tgctgcgaac cggaggatgg aaggtcagtg ctgtgacact ggcatatctg     900
atcttttgcc tgtgctccct ggtgggcatt ctgcatctgc agagagccct ggtgctgcgg     960
agaaagagaa agagaatgac tgacccaaca agaaggttt                            999

<210> SEQ ID NO 112
<211> LENGTH: 333
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
```

```
            130                 135                 140
Ser Ser Pro Gly Lys Leu Met Ser Pro Lys Leu Tyr Val Trp Ala
145                 150                 155                 160

Lys Asp Arg Pro Glu Ile Trp Glu Gly Glu Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
                195                 200                 205

Arg Gly Pro Leu Ser Trp Thr His Val His Pro Lys Gly Pro Lys Ser
            210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
                260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
            290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe
                325                 330
```

<210> SEQ ID NO 113
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
ggagtgcagg tggagactat tagccccgga gatggcagaa cattccccaa aagaggacag    60
acttgcgtcg tgcattatac tggaatgctg gaagacggca agaaggtgga cagcagccgg   120
gaccgaaaca agcccttcaa gttcatgctg gggaagcagg aagtgatccg gggctgggag   180
gaaggagtcg cacagatgtc agtgggacag agggccaaac tgactattag cccagactac   240
gcttatggag caaccggcca ccccgggatc attccccctc atgctacact ggtcttcgat   300
gtggagctgc tgaagctgga a                                              321

<210> SEQ ID NO 114
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gcaacgaatt tttccctgct gaaacaggca ggggacgtag aggaaaatcc tggtcct      57

<210> SEQ ID NO 115
<211> LENGTH: 185
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 115
aaaaaggtgg ccaagaagcc aaccaataag gccccccacc ccaagcagga gccccaggag      60
atcaattttc ccgacgatct tcctggctcc aacactgctg ctccagtgca ggagacttta     120
catggatgcc aaccggtcac ccaggaggat ggcaaagaga gtcgcatctc agtgcaggag     180
agaca                                                                 185

<210> SEQ ID NO 116
<211> LENGTH: 483
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
atgagaattt cgaaaccaca tttgagaagt atttccatcc agtgctactt gtgtttactt      60
ctaaacagtc attttctaac tgaagctggc attcatgtct tcattttggg ctgtttcagt     120
gcagggcttc ctaaaacaga agccaactgg gtgaatgtaa taagtgattt gaaaaaaatt     180
gaagacctta ttcaatctat gcacattgat gctactttat atacggaaag tgatgttcac     240
cccagttgca aagtaacagc aatgaagtgc tttctcttgg agttacaagt tatttcactt     300
gagtccggag atgcaagtat tcatgataca gtagaaaatc tgatcatcct agcaaacaac     360
agtttgtctt ctaatgggaa tgtaacagaa tctggatgca aagaatgtga ggaactggag     420
gagaagaaca tcaaggaatt tttgcagagt tttgtacata ttgtccaaat gttcatcaac     480
act                                                                   483

<210> SEQ ID NO 117
<211> LENGTH: 888
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
atggctgcag gaggtcccgg cgcggggtct gcggccccgg tctcctccac atcctccctt      60
cccctggctg ctctcaacat gcgagtgcgg cgccgcctgt ctctgttctt gaacgtgcgg     120
acacaggtgg cggccgactg gaccgcgctg gcggaggaga tggactttga gtacttggag     180
atccggcaac tggagacaca gcggaccccc actggcaggc tgctggacgc ctggcaggga     240
cgccctggcg cctctgtagg ccgactgctc gagctgctta ccaagctggg ccgcgacgac     300
gtgctgctgg agctgggacc cagcattgag gaggattgcc aaaagtatat cttgaagcag     360
cagcaggagg aggctgagaa gccttttacag gtggccgctg tagacagcag tgtcccacgg     420
acagcagagc tggcgggcat caccacactt gatgaccccc tggggcatat gcctgagcgt     480
ttcgatgcct tcatctgcta ttgccccagc gacatccagt ttgtgcagga gatgatccgg     540
caactggaac agacaaacta tcgactgaag ttgtgtgtgt ctgaccgcga tgtcctgcct     600
ggcacctgtg tctggtctat tgctagtgag ctcatcgaaa agaggtgccg ccggatggtg     660
gtggttgtct ctgatgatta cctgcagagc aaggaatgtg acttccagac caaatttgca     720
ctcagcctct ctccaggtgc ccatcagaag cgactgatcc ccatcaagta caggcaatg     780
```

```
aagaaagagt tccccagcat cctgaggttc atcactgtct gcgactacac caaccctgc      840 accaaatctt ggttctggac tcgccttgcc aaggccttgt ccctgccc                  888
```

<210> SEQ ID NO 118
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Met Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg
            20                  25                  30

Leu Ser Leu Phe Leu Asn Val Arg Thr Gln Val Ala Ala Asp Trp Thr
            35                  40                  45

Ala Leu Ala Glu Glu Met Asp Phe Glu Tyr Leu Glu Ile Arg Gln Leu
        50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Glu Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Ala Glu Lys Pro
            115                 120                 125

Leu Gln Val Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln Phe Val Gln
                165                 170                 175

Glu Met Ile Arg Gln Leu Glu Gln Thr Asn Tyr Arg Leu Lys Leu Cys
            180                 185                 190

Val Ser Asp Arg Asp Val Leu Pro Gly Thr Cys Val Trp Ser Ile Ala
            195                 200                 205

Ser Glu Leu Ile Glu Lys Arg Cys Arg Arg Met Val Val Val Ser
    210                 215                 220

Asp Asp Tyr Leu Gln Ser Lys Glu Cys Asp Phe Gln Thr Lys Phe Ala
225                 230                 235                 240

Leu Ser Leu Ser Pro Gly Ala His Gln Lys Arg Leu Ile Pro Ile Lys
                245                 250                 255

Tyr Lys Ala Met Lys Lys Glu Phe Pro Ser Ile Leu Arg Phe Ile Thr
            260                 265                 270

Val Cys Asp Tyr Thr Asn Pro Cys Thr Lys Ser Trp Phe Trp Thr Arg
        275                 280                 285

Leu Ala Lys Ala Leu Ser Leu Pro
    290                 295
```

<210> SEQ ID NO 119
<211> LENGTH: 173
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 119

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Gln
                165                 170

<210> SEQ ID NO 120
<211> LENGTH: 16
<212> TYPE: PRT
<213> ORGANISM: Homo sapiens

<400> SEQUENCE: 120

Met Gly Ser Asn Lys Ser Lys Pro Lys Asp Ala Ser Gln Arg Arg Arg
1               5                   10                  15

<210> SEQ ID NO 121
<211> LENGTH: 91
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 121

Gln Leu Glu Met Trp His Glu Gly Leu Glu Glu Ala Ser Arg Leu Tyr
1               5                   10                  15

Phe Gly Glu Arg Asn Val Lys Gly Met Phe Glu Val Leu Glu Pro Leu
            20                  25                  30

His Ala Met Met Glu Arg Gly Pro Gln Thr Leu Lys Glu Thr Ser Phe
        35                  40                  45

Asn Gln Ala Tyr Gly Arg Asp Leu Met Glu Ala Gln Glu Trp Cys Arg
    50                  55                  60

Lys Tyr Met Lys Ser Gly Asn Val Lys Asp Leu Leu Gln Ala Trp Asp
65                  70                  75                  80

Leu Tyr Tyr His Val Phe Arg Arg Ile Ser Lys
                85                  90

```
<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Ser Gly Gly Gly Ser
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Gly Gly Gly Ser
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 124

Met Gly Cys Xaa Cys
1               5

<210> SEQ ID NO 125
<211> LENGTH: 2787
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
atggctgcag gaggtcccgg cgcggggtct gcggccccgg tctcctccac atcctccctt      60
cccctggctg ctctcaacat gcgagtgcgg cgccgcctgt ctctgttctt gaacgtgcgg     120
acacaggtgg cggccgactg gaccgcgctg gcggaggaga tggactttga gtacttggag     180
atccggcaac tggagacaca gcggacccc actggcaggc tgctggacgc ctggcaggga     240
cgccctggcg cctctgtagg ccgactgctc gatctgctta ccaagctggg ccgcgacgac     300
gtgctgctgg agctgggacc cagcattgag gaggattgcc aaaagtatat cttgaagcag     360
cagcaggagg aggctgagaa gcctttacag gtggccgctg tagacagcag tgtcccacgg     420
acagcagagc tggcgggcat caccacactt gatgaccccc tggggcatat gcctgagcgt     480
ttcgatgcct tcatctgcta ttgccccagc gacatcctcg agaggagtaa gaggagcagg     540
ctcctgcaca gtgactacat gaacatgact ccccgccgcc ccgggcccac ccgcaagcat     600
taccagcccc atgcccccac cacgcgacttc gcagcctatc gctccaggga ccagaggctg     660
ccccccgatg cccacaagcc ccctggggga ggcagtttcc ggacccccat ccaagaggag     720
```

```
caggccgacg cccactccac cctggccaag atcggatctg gccaattggg cgtccaagtc    780
gaaaccatta gtcccggcga tggcagaaca tttcctaaaa ggggacaaac atgtgtcgtc    840
cattatacag gcatgttgga ggacggcaaa aaggtggaca gtagtagaga tcgcaataaa    900
cctttcaaat tcatgttggg aaaacaagaa gtcattaggg gatgggagga gggcgtggct    960
caaatgtccg tcggccaacg cgctaagctc accatcagcc ccgactacgc atacggcgct   1020
accggacatc ccggaattat tccccctcac gctaccttgg tgtttgacgt cgaactgttg   1080
aagctcgaag tcgagggagt gcaggtggag actatctccc caggagacgg gcgcaccttc   1140
cccaagcgcg gccagacctg cgtggtgcac tacaccggga tgcttgaaga tggaaagaaa   1200
gttgattcct cccgggacag aaacaagccc tttaagttta tgctaggcaa gcaggaggtg   1260
atccgaggct gggaagaagg ggttgcccag atgagtgtgg gtcagagagc caaactgact   1320
atatctccag attatgccta tggtgccact gggcacccag gcatcatccc accacatgcc   1380
actctcgtct tcgatgtgga gcttctaaaa ctggaaccgc gggagggcag aggcagcctc   1440
ctgacatgtg gggacgtcga ggagaacccct ggcccacctt ggatggagtt cggattgagc   1500
tggctgttcc tggtggcaat actcaagggc gttcaatgtt cacggacat ccaactgacg    1560 caaagcccat ctacactcag cgctagcatg ggggacaggg tcacaatcac gtgctctgcc   1620
tcaagttccg ttaggtttat ccattggtat cagcagaaac tggaaaggc cccaaaaaga    1680 ctgatctatg ataccagcaa gctggcttcc ggagtgccct caaggttctc aggatctggc   1740
agtgggaccg atttcaccct gacaattagc agccttcagc cagaggattt cgcaacctat   1800
tactgtcagc aatgggggtc cagcccattc actttcggcc aaggaacaaa ggtggagata   1860
aaaggcggag gaagcggagg tgggggccag gtggaggtgc agctcgtgga gtatggcggg   1920
ggcctggtgc agcctggggg tagtctgagg ctctcctgcg ctgcctctgg ctttaacatt   1980
aaagactact acatacattg ggtgcggcag gccccaggca aagggctcga atgggtggcc   2040
tggattgacc ctgagaatgg tgacactgag tttgtcccca gtttcagggg cagagccacc   2100
atgagcgctg acacaagcaa aaacactgct tatctccaaa tgaatagcct gcgagctgaa   2160
gatacagcag tctattactg caagacggga ggattctggg gccagggaac tctggtgaca   2220
gttagttccg gatccgaact tcctactcag gggactttct caaacgttag cacaaacgta   2280
agtgaacttc ctactcaggg gactttctca aacgttagca caaacgtaag tatctatatc   2340
tgggcacctc tcgctggcac ctgtggagtc cttctgctca gcctggttat tactctgtac   2400
tgtaatcacc ggaatcgccg ccgcgtttgt aagtgtccca gggtcgacag agtgaagttc   2460
agcaggagcg cagacgcccc cgcgtaccag cagggccaga accagctcta taacgagctc   2520
aatctaggac gaagagagga gtacgatgtt ttggacaaga cgtggccg ggaccctgag     2580 atgggggaa agccgagaag gaagaaccct caggaaggcc tgtacaatga actgcagaaa    2640
gataagatgg cggaggccta cagtgagatt gggatgaaag cgagcgccg gaggggcaag    2700 gggcacgatg gcctttacca gggtctcagt acagccacca aggacaccta cgacgccctt   2760
cacatgcaag ctcttccacc tcgttga                                       2787
```

<210> SEQ ID NO 126
<211> LENGTH: 2661
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 126

```
atggctgcag gaggtcccgg cgcggggtct gcggccccgg tctcctccac atcctccctt      60
cccctggctg ctctcaacat gcgagtgcgg cgccgcctgt ctctgttctt gaacgtgcgg     120
acacaggtgg cggccgactg gaccgcgctg gcggaggaga tggactttga gtacttggag     180
atccggcaac tggagacaca agcggacccc actggcaggc tgctggacgc ctggcaggga     240
cgccctggcg cctctgtagg ccgactgctc gatctgctta ccaagctggg ccgcgacgac     300
gtgctgctgg agctgggacc cagcattgag gaggattgcc aaaagtatat cttgaagcag     360
cagcaggagg aggctgagaa gcctttacag gtggccgctg tagacagcag tgtcccacgg     420
acagcagagc tggcgggcat caccacactt gatgaccccc tggggcatat gcctgagcgt     480
ttcgatgcct tcatctgcta ttgccccagc gacatcctcg agacaaaaaa gaagtattca     540
tccagtgtgc acgaccctaa cggtgaatac atgttcatga gagcagtgaa cacagccaaa     600
aaatctagac tcacagatgt gaccctagga tctggccaat tgggcgtcca agtcgaaacc     660
attagtcccg gcgatggcag aacatttcct aaaagggac aaacatgtgt cgtccattat      720
acaggcatgt tggaggacgg caaaaaggtg gacagtagta gagatcgcaa taaacctttc     780
aaattcatgt tgggaaaaca agaagtcatt aggggatggg aggagggcgt ggctcaaatg     840
tccgtcggcc aacgcgctaa gctcaccatc agccccgact acgcatacgg cgctaccgga     900
catcccggaa ttattccccc tcacgctacc ttggtgtttg acgtcgaact gttgaagctc     960
gaagtcgagg gagtgcaggt ggagactatc tccccaggag acgggcgcac cttccccaag    1020
cgcggccaga cctgcgtggt gcactacacc gggatgcttg aagatggaaa gaaagttgat    1080
tcctcccggg acagaaacaa gcccctttaag tttatgctag caagcagga ggtgatccga     1140
ggctgggaag aaggggttgc ccagatgagt gtgggtcaga gagccaaact gactatatct    1200
ccagattatg cctatggtgc cactgggcac ccaggcatca tcccaccaca tgccactctc    1260
gtcttcgatg tggagcttct aaaactggaa ccgcgggagg gcagaggcag cctcctgaca    1320
tgtggggacg tcgaggagaa ccctggccca ccttggatgg agttcggatt gagctggctg    1380
ttcctggtgg caatactcaa gggcgttcaa tgttcacggg acatccaact gacgcaaagc    1440
ccatctacac tcagcgctag catgggggac agggtcacaa tcacgtgctc tgcctcaagt    1500
tccgttaggt ttatccattg gtatcagcag aaacctggaa aggccccaaa aagactgatc    1560
tatgatacca gcaagctggc ttccggagtg ccctcaaggt tctcaggatc tggcagtggg    1620
accgatttca ccctgacaat tagcagcctt cagccagagg atttcgcaac ctattactgt    1680
cagcaatggg ggtccagccc attcactttc ggccaaggaa caaaggtgga gataaaaggc    1740
ggaggaagcg gaggtggggg ccaggtggag gtgcagctcg tggagtatgg cggggcctg     1800
gtgcagcctg ggggtagtct gaggctctcc tgcgctgcct ctggctttaa cattaaagac    1860
tactacatac attgggtgcg gcaggcccca ggcaaagggc tcgaatgggt ggcctggatt    1920
gaccctgaga atggtgacac tgagtttgtc cccaagtttc agggcagagc caccatgagc    1980
gctgacacaa gcaaaaacac tgcttatctc caaatgaata gcctgcgagc tgaagataca    2040
gcagtctatt actgcaagac ggggaggattc tggggccagg gaactctggt gacagttagt    2100
tccggatccg aacttcctac tcaggggact ttctcaaacg ttagcacaaa cgtaagtgaa    2160
cttcctactc aggggacttt ctcaaacgtt agcacaaacg taagtatcta tatctgggca    2220
cctctcgctg gcacctgtgg agtccttctg ctcagcctgg ttattactct gtactgtaat    2280
```

| caccggaatc gccgccgcgt tgtaagtgt cccagggtcg acagagtgaa gttcagcagg | 2340 |
| agcgcagacg cccccgcgta ccagcagggc cagaaccagc tctataacga gctcaatcta | 2400 |
| ggacgaagag aggagtacga tgttttggac aagagacgtg gccgggaccc tgagatgggg | 2460 |
| ggaaagccga aaggaagaa ccctcaggaa ggcctgtaca atgaactgca gaaagataag | 2520 |
| atggcggagg cctacagtga gattgggatg aaaggcgagc gccggagggg caaggggcac | 2580 |
| gatggccttt accagggtct cagtacagcc accaaggaca cctacgacgc ccttcacatg | 2640 |
| caagctcttc cacctcgttg a | 2661 |

<210> SEQ ID NO 127
<211> LENGTH: 2169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 127

| atgctcgaga aacggggcag aaagaaactc ctgtatatat tcaaacaacc atttatgaga | 60 |
| ccagtacaaa ctactcaaga ggaagatggc tgtagctgcc gatttccaga agaagaagaa | 120 |
| ggaggatgtg aactgggatc tggccaattg gcgtccaag tcgaaaccat tagtcccggc | 180 |
| gatggcagaa catttcctaa aaggggacaa acatgtgtcg tccattatac aggcatgttg | 240 |
| gaggacggca aaaggtgga cagtagtaga gatcgcaata aacctttcaa attcatgttg | 300 |
| ggaaaacaag aagtcattag gggatggag gagggcgtgg ctcaaatgtc cgtcggccaa | 360 |
| cgcgctaagc tcaccatcag ccccgactac gcatacggcg ctaccggaca tcccggaatt | 420 |
| attcccctc acgctacctt ggtgtttgac gtcgaactgt tgaagctcga agtcgaggga | 480 |
| gtgcaggtgg agactatctc cccaggagac gggcgcacct tccccaagcg cggccagacc | 540 |
| tgcgtggtgc actacaccgg gatgcttgaa gatggaaaga agttgattc ctcccgggac | 600 |
| agaaacaagc cctttaagtt tatgctaggc aagcaggagg tgatccgagg ctgggaagaa | 660 |
| ggggttgccc agatgagtgt gggtcagaga gccaaactga ctatatctcc agattatgcc | 720 |
| tatggtgcca ctgggcaccc aggcatcatc ccaccacatg ccactctcgt cttcgatgtg | 780 |
| gagcttctaa aactggaacc gcgggagggc agaggcagcc tcctgacatg tggggacgtc | 840 |
| gaggagaacc ctgcccacc ttggatggag ttcggattga gctggctgtt cctggtggca | 900 |
| atactcaagg gcgttcaatg ttcacgggac atccaactga cgcaaagccc atctacactc | 960 |
| agcgctagca tggggacag ggtcacaatc acgtgctctg cctcaagttc cgttaggttt | 1020 |
| atccattggt atcagcagaa acctggaaag gccccaaaaa gactgatcta tgataccagc | 1080 |
| aagctggctt ccggagtgcc ctcaaggttc tcaggatctg gcagtgggac cgattcacc | 1140 |
| ctgacaatta gcagccttca gccagaggat ttcgcaacct attactgtca gcaatggggg | 1200 |
| tccagcccat tcacttttcgg ccaaggaaca aaggtggaga taaaggcgg aggaagcgga | 1260 |
| ggtggggcc aggtggaggt gcagctcgtg gagtatggcg ggggcctggt gcagcctggg | 1320 |
| ggtagtctga ggctctcctg cgctgcctct ggctttaaca ttaaagacta ctacatacat | 1380 |
| tgggtgcggc aggcccccagg caaagggctc gaatgggtgg cctggattga ccctgagaat | 1440 |
| ggtgacactg agtttgtccc caagtttcag ggcagagcca ccatgagcgc tgacacaagc | 1500 |
| aaaaacactg cttatctcca aatgaatagc ctgcgagctg aagatacagc agtctattac | 1560 |
| tgcaagacgg gaggattctg gggccaggga actctggtga cagttagttc cggatccgaa | 1620 |

| | |
|---|---|
| cttcctactc agggactttt ctcaaacgtt agcacaaacg taagtgaact tcctactcag | 1680 |
| gggactttct caaacgttag cacaaacgta agtatctata tctgggcacc tctcgctggc | 1740 |
| acctgtggag tccttctgct cagcctggtt attactctgt actgtaatca ccggaatcgc | 1800 |
| cgccgcgttt gtaagtgtcc cagggtcgac agagtgaagt tcagcaggag cgcagacgcc | 1860 |
| cccgcgtacc agcagggcca gaaccagctc tataacgagc tcaatctagg acgaagagag | 1920 |
| gagtacgatg ttttggacaa agacgtggc cgggaccctg agatggggg aaagccgaga | 1980 |
| aggaagaacc ctcaggaagg cctgtacaat gaactgcaga agataagat ggcggaggcc | 2040 |
| tacagtgaga ttgggatgaa aggcgagcgc cggaggggca aggggcacga tggcctttac | 2100 |
| cagggtctca gtacagccac caaggacacc tacgacgccc ttcacatgca agctcttcca | 2160 |
| cctcgttga | 2169 |

<210> SEQ ID NO 128
<211> LENGTH: 2601
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

| | |
|---|---|
| atggggagta gcaagagcaa gcctaaggac cccagccagc gcagagcatg catggctgca | 60 |
| ggaggtcccg gcgcggggtc tgcggccccg gtctcctcca catcctccct tcccctggct | 120 |
| gctctcaaca tgcgagtgcg cgccgcctg tctctgttct tgaacgtgcg acacaggtg | 180 |
| gcggccgact ggaccgcgct ggcggaggag atggactttg agtacttgga gatccggcaa | 240 |
| ctggagacac aagcggaccc cactggcagg ctgctggacg cctggcaggg acgccctggc | 300 |
| gcctctgtag gccgactgct cgatctgctt accaagctgg gccgcgacga cgtgctgctg | 360 |
| gagctgggac ccagcattga ggaggattgc caaaagtata tcttgaagca gcagcaggag | 420 |
| gaggctgaga agcctttaca ggtggccgct gtagacagca gtgtcccacg gacagcagag | 480 |
| ctggcgggca tcaccacact tgatgacccc ctggggcata tgcctgagcg tttcgatgcc | 540 |
| ttcatctgct attgccccag cgacatcgga tctggccaat tgggcgtcca agtcgaaacc | 600 |
| attagtcccg gcgatggcag aacatttcct aaaaggggac aaacatgtgt cgtccattat | 660 |
| acaggcatgt tggaggacgg caaaaaggtg gacagtagta gagatcgcaa taaacctttc | 720 |
| aaattcatgt tgggaaaaca agaagtcatt aggggatggg aggagggcgt ggctcaaatg | 780 |
| tccgtcggcc aacgcgctaa gctcaccatc agccccgact acgcatacgg cgctaccgga | 840 |
| catcccggaa ttattccccc tcacgctacc ttggtgtttg acgtcgaact gttgaagctc | 900 |
| gaagtcgagg gagtgcaggt ggagactatc tccccaggag acgggcgcac cttccccaag | 960 |
| cgcggccaga cctgcgtggt gcactacacc gggatgcttg aagatggaaa gaaagttgat | 1020 |
| tcctcccggg acagaaacaa gcccttaag tttatgctag gcaagcagga ggtgatccga | 1080 |
| ggctgggaag aagggggttgc ccagatgagt gtgggtcaga gagccaaact gactatatct | 1140 |
| ccagattatg cctatggtgc cactgggcac ccaggcatca tcccaccaca tgccactctc | 1200 |
| gtcttcgatg tggagcttct aaaactggaa ccgcgggagg gcagaggcag cctcctgaca | 1260 |
| tgtggggacg tcgaggagaa ccctggccca ccttggatgg agttcggatt gagctggctg | 1320 |
| ttcctggtgg caatactcaa gggcgttcaa tgttcacggg acatccaact gacgcaaagc | 1380 |
| ccatctacac tcagcgctag catggggac agggtcacaa tcacgtgctc tgcctcaagt | 1440 |

| tccgttaggt | ttatccattg | gtatcagcag | aaacctggaa | aggccccaaa | aagactgatc | 1500 |
| tatgatacca | gcaagctggc | ttccggagtg | ccctcaaggt | tctcaggatc | tggcagtggg | 1560 |
| accgatttca | ccctgacaat | tagcagcctt | cagccagagg | atttcgcaac | ctattactgt | 1620 |
| cagcaatggg | ggtccagccc | attcactttc | ggccaaggaa | caaaggtgga | gataaaaggc | 1680 |
| ggaggaagcg | gaggtggggg | ccaggtggag | gtgcagctcg | tggagtatgg | cggggggcctg | 1740 |
| gtgcagcctg | ggggtagtct | gaggctctcc | tgcgctgcct | ctggctttaa | cattaaagac | 1800 |
| tactacatac | attgggtgcg | gcaggcccca | ggcaaagggc | tcgaatgggt | ggcctggatt | 1860 |
| gaccctgaga | atggtgacac | tgagtttgtc | cccaagtttc | agggcagagc | caccatgagc | 1920 |
| gctgacacaa | gcaaaaacac | tgcttatctc | caaatgaata | gcctgcgagc | tgaagataca | 1980 |
| gcagtctatt | actgcaagac | gggaggattc | tggggccagg | gaactctggt | gacagttagt | 2040 |
| tccggatccg | aacttcctac | tcaggggact | ttctcaaacg | ttagcacaaa | cgtaagtgaa | 2100 |
| cttcctactc | aggggacttt | ctcaaacgtt | agcacaaacg | taagtatcta | tatctgggca | 2160 |
| cctctcgctg | gcacctgtgg | agtccttctg | ctcagcctgg | ttattactct | gtactgtaat | 2220 |
| caccggaatc | gccgccgcgt | ttgtaagtgt | cccagggtcg | acagagtgaa | gttcagcagg | 2280 |
| agcgcagacg | cccccgcgta | ccagcagggc | cagaaccagc | tctataacga | gctcaatcta | 2340 |
| ggacgaagag | aggagtacga | tgttttggac | aagagacgtg | gccgggaccc | tgagatgggg | 2400 |
| ggaaagccga | aaggaagaa | ccctcaggaa | ggcctgtaca | atgaactgca | gaaagataag | 2460 |
| atggcggagg | cctacagtga | gattgggatg | aaaggcgagc | gccggagggg | caaggggcac | 2520 |
| gatggccttt | accagggtct | cagtacagcc | accaaggaca | cctacgacgc | ccttcacatg | 2580 |
| caagctcttc | cacctcgttg | a | | | | 2601 |

<210> SEQ ID NO 129
<211> LENGTH: 2793
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129

| atggggagta | gcaagagcaa | gcctaaggac | cccagccagc | gcagagcatg | catggctgca | 60 |
| ggaggtcccg | gcgcggggtc | tgcggccccg | gtcctcca | catcctccct | tccctggct | 120 |
| gctctcaaca | tgcgagtgcg | cgccgcctg | tctctgttct | tgaacgtgcg | gacacaggtg | 180 |
| gcggccgact | ggaccgcgct | ggcggaggag | atggactttg | agtacttgga | gatccggcaa | 240 |
| ctggagacac | aagcggaccc | cactggcagg | ctgctggacg | cctggcaggg | acgccctggc | 300 |
| gcctctgtag | gccgactgct | cgatctgctt | accaagctgg | gccgcgacga | cgtgctgctg | 360 |
| gagctgggac | ccagcattga | ggaggattgc | caaaagtata | tcttgaagca | gcagcaggag | 420 |
| gaggctgaga | agcctttaca | ggtggccgct | gtagacagca | gtgtcccacg | gacagcagag | 480 |
| ctggcgggca | tcaccacact | tgatgacccc | ctggggcata | tgcctgagcg | tttcgatgcc | 540 |
| ttcatctgct | attgccccag | cgacatcctc | gagaaaaagg | tggccaagaa | gccaaccaat | 600 |
| aaggcccccc | accccaagca | ggagcccag | gagatcaatt | ttcccgacga | tcttcctggc | 660 |
| tccaacactg | ctgctccagt | gcaggagact | ttacatggat | gccagccggt | cacccaggag | 720 |
| gatggcaaag | agagtcgcat | ctcagtgcag | gagagacagg | gatctggcca | attgggcgtc | 780 |
| caagtcgaaa | ccattagtcc | cggcgatggc | agaacatttc | ctaaaagggg | acaaacatgt | 840 |

```
gtcgtccatt atacaggcat gttggaggac ggcaaaaagg tggacagtag tagagatcgc    900
aataaacctt tcaaattcat gttgggaaaa caagaagtca ttaggggatg ggaggagggc    960
gtggctcaaa tgtccgtcgg ccaacgcgct aagctcacca tcagcccga ctacgcatac    1020 ggcgctaccg gacatcccgg aattattccc cctcacgcta ccttggtgtt tgacgtcgaa    1080
ctgttgaagc tcgaagtcga gggagtgcag gtggagacta tctccccagg agacgggcgc    1140
accttcccca gcgcggcca gacctgcgtg gtgcactaca ccgggatgct tgaagatgga    1200
aagaaagttg attcctcccg ggacagaaac aagcccttta agtttatgct aggcaagcag    1260
gaggtgatcc gaggctggga agaagggtt gcccagatga gtgtgggtca gagagccaaa    1320
ctgactatat ctccagatta tgcctatggt gccactgggc acccaggcat catcccacca    1380
catgccactc tcgtcttcga tgtggagctt ctaaaactgg aaccgcggga gggcagaggc    1440
agcctcctga catgtgggga cgtcgaggag aaccctggcc caccttggat ggagttcgga    1500
ttgagctggc tgttcctggt ggcaatactc aagggcgttc aatgttcacg ggacatccaa    1560
ctgacgcaaa gcccatctac actcagcgct agcatggggg acagggtcac aatcacgtgc    1620
tctgcctcaa gttccgttag gtttatccat tggtatcagc agaaacctgg aaaggcccca    1680
aaaagactga tctatgatac cagcaagctg gcttccggag tgccctcaag gttctcagga    1740
tctggcagtg gaccgatttt caccctgaca attagcagcc ttcagccaga ggatttcgca    1800
acctattact gtcagcaatg ggggtccagc ccattcactt tcggccaagg aacaaaggtg    1860
gagataaaag gcggaggaag cggaggtggg ggccaggtgg aggtgcagct cgtggagtat    1920
ggcgggggcc tggtgcagcc tggggggtagt ctgaggctct cctgcgctgc ctctggcttt    1980
aacattaaag actactacat acattgggtg cggcaggccc caggcaaagg gctcgaatgg    2040
gtggcctgga ttgaccctga gaatggtgac actgagtttg tccccaagtt tcagggcaga    2100
gccaccatga gcgctgacac aagcaaaaac actgcttatc tccaaatgaa tagcctgcga    2160
gctgaagata cagcagtcta ttactgcaag acggaggat tctggggcca gggaactctg    2220
gtgacagtta gttccggatc cgaacttcct actcagggga ctttctcaaa cgttagcaca    2280
aacgtaagtg aacttcctac tcaggggact ttctcaaacg ttagcacaaa cgtaagtatc    2340
tatatctggg cacctctcgc tggcacctgt ggagtccttc tgctcagcct ggttattact    2400
ctgtactgta atcaccggaa tcgccgccgc gtttgtaagt gtcccagggt cgacagagtg    2460
aagttcagca ggagcgcaga cgcccccgcg taccagcagg ccagaaccaa gctctataac    2520
gagctcaatc taggacgaag agaggagtac gatgttttgg acaagagacg tggccgggac    2580
cctgagatgg ggggaaagcc gagaaggaag aaccctcagg aaggcctgta caatgaactg    2640
cagaaagata agatggcgga ggcctacagt gagattggga tgaaaggcga gcgccggagg    2700 ggcaagggc acgatggcct ttaccagggt ctcagtacag ccaccaagga cacctacgac    2760
gcccttcaca tgcaagctct tccacctcgt tga                                 2793
```

<210> SEQ ID NO 130
<211> LENGTH: 2229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 130

```
atgctcgaga aaaaggtggc caagaagcca accaataagg ccccccaccc caagcaggag     60
```

```
cccaggaga tcaattttcc cgacgatctt cctggctcca cactgctgc tccagtgcag    120 gagactttac atggatgcca gccggtcacc caggaggatg caaagagag tcgcatctca    180 gtgcaggaga gacagggatc tggccaattg ggcgtccaag tcgaaaccat tagtcccggc    240
gatggcagaa catttcctaa aaggggacaa acatgtgtcg tccattatac aggcatgttg    300
gaggacggca aaaggtgga cagtagtaga gatcgcaata aacctttcaa attcatgttg    360
ggaaaacaag aagtcattag gggatggag gagggcgtgg ctcaaatgtc cgtcggccaa    420
cgcgctaagc tcaccatcag ccccgactac gcatacggcg ctaccggaca tcccggaatt    480
attccccctc acgctacctt ggtgtttgac gtcgaactgt tgaagctcga agtcgaggga    540
gtgcaggtgg agactatctc cccaggagac gggcgcacct tccccaagcg cggccagacc    600
tgcgtggtgc actacaccgg gatgcttgaa gatggaaaga agttgattc ctcccgggac    660 agaaacaagc cctttaagtt tatgctaggc aagcaggagg tgatccgagg ctgggaagaa    720
ggggttgccc agatgagtgt gggtcagaga gccaaactga ctatatctcc agattatgcc    780
tatggtgcca ctgggcaccc aggcatcatc ccaccacatg ccactctcgt cttcgatgtg    840
gagcttctaa aactggaacc gcgggagggc agaggcagcc tcctgacatg tggggacgtc    900
gaggagaacc ctggcccacc ttggatggag ttcggattga ctggctgtt cctggtggca    960 atactcaagg gcgttcaatg ttcacgggac atccaactga cgcaaagccc atctacactc   1020
agcgctagca tggggacag gtcacaatc acgtgctctg cctcaagttc cgttaggttt   1080
atccattggt atcagcagaa acctggaaag gccccaaaaa gactgatcta tgataccagc   1140
aagctggctt ccggagtgcc ctcaaggttc tcaggatctg gcagtgggac cgatttcacc   1200
ctgacaatta gcagccttca gccagaggat ttcgcaacct attactgtca gcaatggggg   1260
tccagcccat tcactttcgg ccaaggaaca aaggtggaga taaaaggcgg aggaagcgga   1320
ggtgggggcc aggtggaggt gcagctcgtg gagtatggcg ggggcctggt gcagcctggg   1380
ggtagtctga ggctctcctg cgctgcctct ggctttaaca ttaaagacta ctacatacat   1440
tgggtgcggc aggccccagg caaagggctc gaatgggtgg cctggattga ccctgagaat   1500
ggtgacactg agtttgtccc caagtttcag ggcagagcca ccatgagcgc tgacacaagc   1560
aaaaacactg cttatctcca aatgaatagc ctgcgagctg aagatacagc agtctattac   1620
tgcaagacgg aggattctg gggccaggga actctggtga cagttagttc cggatccgaa   1680
cttcctactc aggggacttt ctcaaacgtt agcacaaacg taagtgaact tcctactcag   1740
gggactttct caaacgttag cacaaacgta agtatctata tctgggcacc tctcgctggc   1800
acctgtggag tccttctgct cagcctggtt attactctgt actgtaatca ccggaatcgc   1860
cgccgcgttt gtaagtgtcc cagggtcgac agagtgaagt tcagcaggag cgcagacgcc   1920
cccgcgtacc agcagggcca gaaccagctc tataacgagc tcaatctagg acgaagagag   1980
gagtacgatg ttttggacaa gagacgtggc cgggaccctg agatggggg aaagccgaga   2040 aggaagaacc tcaggaagg cctgtacaat gaactgcaga agataagat ggcggaggcc   2100 tacagtgaga ttgggatgaa aggcgagcgc cggaggggca aggggcacga tggcctttac   2160
cagggtctca gtacagccac caaggacacc tacgacgccc ttcacatgca agctcttcca   2220
cctcgttga                                                          2229
```

<210> SEQ ID NO 131
<211> LENGTH: 2271
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
atggggagta gcaagagcaa gcctaaggac cccagccagc gcagagcatg caaaaaggtg      60
gccaagaagc caaccaataa ggcccccac cccaagcagg agccccagga gatcaatttt     120
cccgacgatc ttcctggctc caacactgct gctccagtgc aggagacttt acatggatgc     180
cagccggtca cccaggagga tggcaaagag agtcgcatct cagtgcagga gagacaggga     240
tctggccaat gggcgtcca agtcgaaacc attagtcccg cgatggcag aacatttcct      300
aaaagggac aaacatgtgt cgtccattat acaggcatgt tggaggacgg caaaaaggtg     360
gacagtagta gagatcgcaa taaacctttc aaattcatgt tgggaaaaca agaagtcatt     420
aggggatggg aggagggcgt ggctcaaatg tccgtcggcc aacgcgctaa gctcaccatc     480
agccccgact acgcatacgg cgctaccgga catcccggaa ttattccccc tcacgctacc     540
ttggtgtttg acgtcgaact gttgaagctc gaagtcgagg gagtgcaggt ggagactatc     600
tccccaggag acgggcgcac cttccccaag cgcggccaga cctgcgtggt gcactacacc     660
gggatgcttg aagatggaaa gaaagttgat tcctcccggg acagaaacaa gcccttaag     720
tttatgctag gcaagcagga ggtgatccga ggctgggaag aggggttgc ccagatgagt     780
gtgggtcaga gagccaaact gactatatct ccagattatg cctatggtgc cactgggcac     840
ccaggcatca tcccaccaca tgccactctc gtcttcgatg tggagcttct aaaactggaa     900
ccgcggggag gcagaggcag cctcctgaca tgtggggacg tcgaggagaa ccctggccca     960
ccttggatgg agttcggatt gagctggctg ttcctggtgg caatactcaa gggcgttcaa    1020
tgttcacggg acatccaact gacgcaaagc ccatctacac tcagcgctag catggggac    1080
agggtcacaa tcacgtgctc tgcctcaagt tccgttaggt ttatccattg gtatcagcag    1140
aaacctggaa aggccccaaa aagactgatc tatgatacca gcaagctggc ttccggagtg    1200
ccctcaaggt tctcaggatc tggcagtggg accgatttca ccctgacaat tagcagcctt    1260
cagccagagg atttcgcaac ctattactgt cagcaatggg ggtccagccc attcactttc    1320
ggccaaggaa caaaggtgga gataaaaggc ggaggaagcg gaggtggggg ccaggtggag    1380
gtgcagctcg tggagtatgg cgggggcctg gtgcagcctg ggggtagtct gaggctctcc    1440
tgcgctgcct ctggctttaa cattaaagac tactacatac attgggtgcg gcaggcccca    1500
ggcaaagggc tcgaatgggt ggcctggatt gaccctgaga atggtgacac tgagtttgtc    1560
cccaagtttc agggcagagc caccatgagc gctgacacaa gcaaaaacac tgcttatctc    1620
caaatgaata gcctgcgagc tgaagataca gcagtctatt actgcaagac gggaggattc    1680
tggggccagg gaactctggt gacagttagt tccggatccg aacttcctac tcaggggact    1740
ttctcaaacg ttagcacaaa cgtaagtgaa cttcctactc aggggacttt ctcaaacgtt    1800
agcacaaacg taagtatcta tatctgggca cctctcgctg gcacctgtgg agtccttctg    1860
ctcagcctgg ttattactct gtactgtaat caccggaatc gccgccgcgt ttgtaagtgt    1920
cccagggtcg acagagtgaa gttcagcagg agcgcagacg cccccgcgta ccagcagggc    1980
cagaaccagc tctataacga gctcaatcta ggacgaagag aggagtacga tgttttggac    2040
aagagacgtg gccgggaccc tgagatgggg ggaaagccga aaggaagaa ccctcaggaa    2100
ggcctgtaca atgaactgca gaaagataag atggcggagg cctacagtga gattgggatg    2160
aaaggcgagc gccggagggg caaggggcac gatggccttt accagggtct cagtacagcc    2220
```

```
accaaggaca cctacgacgc ccttcacatg caagctcttc cacctcgttg a        2271
```

<210> SEQ ID NO 132
<211> LENGTH: 2742
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 132

```
atggctgcag gaggtcccgg cgcggggtct gcggccccgg tctcctccac atcctccctt    60
cccctggctg ctctcaacat gcgagtgcgg cgccgcctgt ctctgttctt gaacgtgcgg   120
acacaggtgg cggccgactg gaccgcgctg cggaggaga tggactttga gtacttggag    180
atccggcaac tggagacaca agcggacccc actggcaggc tgctggacgc ctggcaggga   240
cgccctggcg cctctgtagg ccgactgctc gatctgctta ccaagctggg ccgcgacgac   300
gtgctgctgg agctgggacc cagcattgag gaggattgcc aaaagtatat cttgaagcag   360
cagcaggagg aggctgagaa gcctttacag gtggccgctg tagacagcag tgtcccacgg   420
acagcagagc tggcgggcat caccacactt gatgaccccc tggggcatat gcctgagcgt   480
ttcgatgcct tcatctgcta ttgccccagc gacatcctcg agaaaaaggt ggccaagaag   540
ccaaccaata aggcccccca ccccaagcag gagccccagg agatcaattt ccccgacgat   600
cttcctggct ccaacactgc tgctccagtg caggagactt tacatggatg ccagccggtc   660
acccaggagg atggcaaaga gagtcgcatc tcagtgcagg agagacaggg atctggccaa   720
ttgggcgtcc aagtcgaaac cattagtccc ggcgatggca aacatttcc taaaagggga   780
caaacatgtg tcgtccatta tacaggcatg ttggaggacg caaaaaggt ggacagtagt   840
agagatcgca ataaaccttt caaattcatg ttgggaaaac aagaagtcat taggggatgg   900
gaggagggcg tggctcaaat gtccgtcggc aacgcgcta agctcaccat cagccccgac   960
tacgcatacg gcgctaccgg acatcccgga attattcccc ctcacgctac cttggtgttt  1020
gacgtcgaac tgttgaagct cgaagtcgag ggagtgcagg tggagactat ctccccagga  1080
gacgggcgca ccttccccaa gcgcggccag acctgcgtgg tgcactacac cgggatgctt  1140
gaagatggaa agaaagttga ttcctcccgg gacagaaaca agccctttaa gtttatgcta  1200
ggcaagcagg aggtgatccg aggctgggaa gaaggggttg cccagatgag tgtgggtcag  1260
agagccaaac tgactatatc tccagattat gcctatggtg ccactgggca cccaggcatc  1320
atcccaccac atgccactct cgtcttcgat gtggagcttc taaaactgga accgcgggag  1380
ggcagaggca gcctcctgac atgtgggac gtcgaggaga accctggccc accttggatg  1440
gagttcggat tgagctggct gttcctggtg caatactca agggcgttca atgttcacgg  1500
gacatccaac tgacgcaaag cccatctaca ctcagcgcta gcatggggga cagggtcaca  1560
atcacgtgct ctgcctcaag ttccgttagg tttatccatt ggtatcagca gaaacctgga  1620
aaggccccaa aaagactgat ctatgatacc agcaagctgg cttccggagt gccctcaagg  1680
ttctcaggat ctggcagtgg gaccgatttc accctgacaa ttagcagcct tcagccagag  1740
gatttcgcaa cctattactg tcagcaatgg gggtccagcc cattcacttt cggccaagga  1800
acaaaggtgg agataaaagg cggaggaagc ggaggtgggg gccaggtgga ggtgcagctc  1860
gtggagtatg gcggggcct ggtgcagcct ggggtagtc tgaggctctc ctgcgctgcc  1920
tctggctta acattaaga ctactacata cattgggtgc ggcaggcccc aggcaagggg  1980
```

```
ctcgaatggg tggcctggat tgaccctgag aatggtgaca ctgagtttgt ccccaagttt    2040
cagggcagag ccaccatgag cgctgacaca agcaaaaaca ctgcttatct ccaaatgaat    2100
agcctgcgag ctgaagatac agcagtctat tactgcaaga cgggaggatt ctggggccag    2160
ggaactctgg tgacagttag ttccggatcc gaacttccta ctcaggggac tttctcaaac    2220
gttagcacaa acgtaagtga acttcctact cagggggactt tctcaaacgt tagcacaaac    2280
gtaagtatct atatctgggc acctctcgct ggcacctgtg gagtccttct gctcagcctg    2340
gttattactc tgtactgtaa tcaccggaat cgccgccgcg tttgtaagtg tcccagggtc    2400
gacagagtga agttcagcag gagcgcagac gcccccgcgt accagcaggg ccagaaccag    2460
ctctataacg agctcaatct aggacgaaga gaggagtacg atgttttgga caagagacgt    2520
ggccgggacc ctgagatggg gggaaagccg agaaggaaga accctcagga aggcctgtac    2580
aatgaactgc agaaagataa gatggcggag gcctacagtg agattgggat gaaaggcgag    2640
cgccggaggg gcaaggggca cgatggcctt taccagggtc tcagtacagc caccaaggac    2700
acctacgacg cccttcacat gcaagctctt ccacctcgtt ga                      2742

<210> SEQ ID NO 133
<211> LENGTH: 2688
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
atgctcgaga tgctggaggg agtgcaggtg agagactatta gccccggaga tggcagaaca     60
ttccccaaaa gaggacagac ttgcgtcgtg cattatactg gaatgctgga agacggcaag    120
aaggtggaca gcagccggga ccgaaacaag cccttcaagt tcatgctggg gaagcaggaa    180
gtgatccggg gctggaggga aggagtcgca cagatgtcag tgggacagag ggccaaactg    240
actattagcc cagactacgc ttatggagca accggccacc ccgggatcat tccccctcat    300
gctacactgg tcttcgatgt ggagctgctg aagctggaaa gcgaggagg atccggagtg    360 gacgggtttg gagatgtggg agccctggaa tccctgcggg gcaatgccga tctggcttac    420
atcctgtcta tggagccttg cggcactgt ctgatcatta caatgtgaa cttctgcaga    480 gagagcgggc tgcggaccag aacaggatcc aatattgact gtgaaaagct gcggagaagg    540
ttctctagtc tgcactttat ggtcgaggtg aaaggcgatc tgaccgctaa gaaaatggtg    600
ctggccctgc tggaactggc tcggcaggac catggggcac tggattgctg cgtggtcgtg    660
atcctgagtc acggctgcca ggcttcacat ctgcagttcc ctggggcagt ctatggaact    720
gacggctgtc cagtcagcgt ggagaagatc gtgaacatct tcaacggcac ctcttgccca    780
agtctgggcg ggaagcccaa actgttcttt attcaggcct gtggaggcga gcagaaagat    840
cacggcttcg aagtggctag cacctccccc gaggacgaat cacctggaag caaccctgag    900
ccagatgcaa ccccccttcca ggaaggcctg aggacatttg accagctgga tgccatctca    960
agcctgccca caccttctga catttttcgtc tcttacagta cttttccctgg atttgtgagc    1020 tggcgcgatc caaagtcagg cagctggtac gtggagacac tggacgatat ctttgagcag    1080
tgggcccatt ctgaagacct gcagagtctg ctgctgcgag tggccaatgc tgtctctgtg    1140
aaggggatct acaaacagat gccaggatgc ttcaactttc tgagaaagaa actgttcttt    1200
aagacctccg catctagggc cccgcgggaa ggccgaggga gcctgctgac atgtggcgat    1260
```

```
gtggaggaaa acccaggacc accatggatg gagtttggac tttcttggtt gttttttggtg    1320 gcaattctga agggtgtcca gtgtagcagg gacatccaga tgacacagac tacatcctcc    1380
ctgtctgcct ctctgggaga cagagtcacc atcagttgca gggcaagtca ggacattagt    1440
aaatatttaa attggtatca gcagaaacca gatggaactg ttaaactcct gatctaccat    1500
acatcaagat tacactcagg agtcccatca aggttcagtg gcagtgggtc tggaacagat    1560
tattctctca ccattagcaa cctggagcaa gaagatattg ccacttactt ttgccaacag    1620
ggtaatacgc ttccgtacac gttcggaggg gggactaagt tggaaataac aggcggagga    1680
agcggaggtg ggggcgaggt gaaactgcag gagtcaggac ctggcctggt ggcgccctca    1740
cagagcctgt ccgtcacatg cactgtctca ggggtctcat acccgactat ggtgtaagc    1800 tggattcgcc agcctccacg aaagggtctg agtggctgg gagtaatatg gggtagtgaa     1860
accacatact ataattcagc tctcaaatcc agactgacca tcatcaagga caactccaag    1920
agccaagttt tcttaaaaat gaacagtctg caaactgatg acacagccat ttactactgt    1980
gccaaacatt attactacgg tggtagctat gctatggact actgggtca aggaacctca     2040 gtcaccgtct cctcaggatc cgaacttcct actcagggga cttcctcaaa cgttagcaca    2100
aacgtaagtc ccgccccaag accccccaca cctgcgccga ccattgcttc tcaaccctg     2160 agtttgagac ccgaggcctg ccggccagct gccggcgggg ccgtgcatac aagaggactc    2220
gatttcgctt gcgacatcta tatctgggca cctctcgctg gcacctgtgg agtccttctg    2280
ctcagcctgg ttattactct gtactgtaat caccggaatc gccgccgcgt ttgtaagtgt    2340
cccagggtcg acagagtgaa gttcagcagg agcgcagacg cccccgcgta ccagcagggc    2400
cagaaccagc tctataacga gctcaatcta ggacgaagag aggagtacga tgttttggac    2460
aagagacgtg gccgggaccc tgagatgggg ggaaagccga aaggaagaa ccctcaggaa     2520 ggcctgtaca atgaactgca gaaagataag atggcgagg cctacagtga gattgggatg     2580
aaaggcgagc gccggagggg caaggggcac gatggccttt accagggtct cagtacagcc    2640
accaaggaca cctacgacgc ccttcacatg caagctcttc caccctcgt                2688
```

<210> SEQ ID NO 134
<211> LENGTH: 3471
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
atgctcgaga tgctggaggg agtgcaggtg gagactatta gccccggaga tggcagaaca      60
ttccccaaaa gaggacagac ttgcgtcgtg cattatactg gaatgctgga agacggcaag     120
aaggtggaca gcagccggga ccgaaacaag cccttcaagt tcatgctggg gaagcaggaa     180
gtgatccggg gctggaggga aggagtcgca cagatgtcag tgggacagag ggccaaactg     240
actattagcc cagactacgc ttatggagca accggccacc ccgggatcat tccccctcat     300
gctacactgg tcttcgatgt ggagctgctg aagctggaaa gcggaggagg atccggagtg     360
gacgggtttg agatgtggg agccctggaa tccctgcggg gcaatgccga tctggcttac     420
atcctgtcta tggagccttg cggccactgt ctgatcatta caatgtgaa cttctgcaga     480 gagagcgggc tgcggaccag aacaggatcc aatattgact gtgaaaagct gcggagaagg    540
ttctctagtc tgcactttat ggtcgaggtg aaaggcgatc tgaccgctaa gaaaatggtg    600
```

```
ctggccctgc tggaactggc tcggcaggac catgggcac tggattgctg cgtggtcgtg      660
atcctgagtc acggctgcca ggcttcacat ctgcagttcc ctggggcagt ctatggaact     720
gacggctgtc cagtcagcgt ggagaagatc gtgaacatct tcaacggcac ctcttgccca    780
agtctgggcg ggaagcccaa actgttcttt attcaggcct gtggaggcga gcagaaagat    840
cacggcttcg aagtggctag cacctccccc gaggacgaat cacctggaag caaccctgag    900
ccagatgcaa ccccccttcca ggaaggcctg aggacatttg accagctgga tgccatctca    960
agcctgccca caccttctga cattttcgtc tcttacagta ctttccctgg atttgtgagc    1020
tggcgcgatc caaagtcagg cagctggtac gtggagacac tggacgatat ctttgagcag    1080
tgggcccatt ctgaagacct gcagagtctg ctgctgcgag tggccaatgc tgtctctgtg    1140
aagggatct acaaacagat gccaggatgc ttcaactttc tgagaaagaa actgttcttt     1200
aagacctccg catctagggc cccgcgggaa ggccgaggga gcctgctgac atgtggcgat    1260
gtggaggaaa acccaggacc accatggatg gagtttggac tttcttggtt gttttggtg     1320
gcaattctga agggtgtcca gtgtagcagg gacatccaga tgacacagac tacatcctcc    1380
ctgtctgcct ctctgggaga cagagtcacc atcagttgca gggcaagtca ggacattagt    1440
aaatatttaa attggtatca gcagaaacca gatggaactg ttaaactcct gatctaccat    1500
acatcaagat tacactcagg agtcccatca aggttcagtg gcagtgggtc tggaacagat    1560
tattctctca ccattagcaa cctggagcaa gaagatattg ccacttactt ttgccaacag    1620
ggtaatacgc ttccgtacac gttcggaggg gggactaagt tggaaataac aggcggagga    1680
agcggaggtg ggggcgaggt gaaactgcag gagtcaggac ctggcctggt ggcgccctca    1740
cagagcctgt ccgtcacatg cactgtctca ggggtctcat acccgactac tggtgtaagc    1800
tggattcgcc agcctccacg aaagggtctg gagtggctgg gagtaatatg gggtagtgaa    1860
accacatact ataattcagc tctcaaatcc agactgacca tcatcaagga caactccaag    1920
agccaagttt tcttaaaaat gaacagtctg caaactgatg acacagccat ttactactgt    1980
gccaaacatt attactacgg tggtagctat gctatggact actggggtca aggaaccctca   2040
gtcaccgtct cctcaggatc cgaacttcct actcagggga ctttctcaaa cgttagcaca    2100
aacgtaagtc cgccccaag acccccaca cctgcgccga ccattgcttc tcaaccctg       2160
agtttgagac ccgaggcctg ccggccagct gccggcgggg ccgtgcatac aagaggactc    2220
gatttcgctt gcgacatcta tatctgggca cctctcgctg gcacctgtgg agtccttctg    2280
ctcagcctgg ttattactct gtactgtaat caccggaatc gccgccgcgt ttgtaagtgt    2340
cccagggtcg acagagtgaa gttcagcagg agcgcagacg ccccgcgta ccagcagggc    2400
cagaaccagc tctataacga gctcaatcta ggacgaagag aggagtacga tgttttggac    2460
aagagacgtg gccgggaccc tgagatgggg ggaaagccga aaggaagaa ccctcaggaa    2520
ggcctgtaca tgaactgca gaaagataag atggcgagg cctacagtga gattgggatg     2580
aaaggcgagc gccggagggg caaggggcac gatggccttt accagggtct cagtacagcc    2640
accaaggaca cctacgacgc ccttcacatg caagctcttc cacctcgtat gctcgagatg    2700
ctggaggcta ctaacttcag cctgctgaag caggctggag acgtgagga aaccccggg     2760
cctatggctg caggaggtcc cggcgcgggg tctgcggccc cggtctcctc cacatcctcc    2820
cttcccctgg ctgctctcaa catgcgagtg cggcgccgcc tgtctctgtt cttgaacgtg    2880
cggacacagg tggcggccga ctggaccgcg ctggcggagg agatggactt tgagtacttg    2940
```

| | |
|---|---|
| gagatccggc aactggagac acaagcggac cccactggca ggctgctgga cgcctggcag | 3000 |
| ggacgccctg cgcctctgt aggccgactg ctcgatctgc ttaccaagct gggccgcgac | 3060 |
| gacgtgctgc tggagctggg acccagcatt gaggaggatt gccaaaagta tatcttgaag | 3120 |
| cagcagcagg aggaggctga gaagccttta caggtggccg ctgtagacag cagtgtccca | 3180 |
| cggacagcag agctggcggg catcaccaca cttgatgacc ccctgggca tatgcctgag | 3240 |
| cgtttcgatg ccttcatctg ctattgcccc agcgacatcg tcgagaaaaa ggtgccaag | 3300 |
| aagccaacca ataaggcccc ccaccccaag caggagcccc aggagatcaa ttttcccgac | 3360 |
| gatcttcctg ctccaacac tgctgctcca gtgcaggaga ctttacatgg atgccaaccg | 3420 |
| gtcacccagg aggatggcaa agagagtcgc atctcagtgc aggagagaca g | 3471 |

<210> SEQ ID NO 135
<211> LENGTH: 3456
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 135

| | |
|---|---|
| atgctcgaga tgctggaggg agtgcaggtg gagactatta gccccggaga tggcagaaca | 60 |
| ttccccaaaa gaggacagac ttgcgtcgtg cattatactg gaatgctgga agacggcaag | 120 |
| aaggtggaca gcagccggga ccgaaacaag cccttcaagt tcatgctggg gaagcaggaa | 180 |
| gtgatccggg gctgggagga aggagtcgca cagatgtcag tgggacagag ggccaaactg | 240 |
| actattagcc cagactacgc ttatggagca accggccacc ccgggatcat tccccctcat | 300 |
| gctacactgg tcttcgatgt ggagctgctg aagctggaaa gcgaggagg atccggagtg | 360 |
| gacgggtttg gagatgtggg agccctggaa tccctgcggg gcaatgccga tctggcttac | 420 |
| atcctgtcta tggagccttg cggccactgt ctgatcatta caatgtgaa cttctgcaga | 480 |
| gagagcgggc tgcggaccag aacaggatcc aatattgact gtgaaaagct gcggagaagg | 540 |
| ttctctagtc tgcacttat ggtcgaggtg aaaggcgatc tgaccgctaa gaaaatggtg | 600 |
| ctggccctgc tggaactggc tcggcaggac catggggcac tggattgctg cgtggtcgtg | 660 |
| atcctgagtc acggctgcca ggcttcacat ctgcagttcc ctggggcagt ctatggaact | 720 |
| gacggctgtc cagtcagcgt ggagaagatc gtgaacatct tcaacggcac ctcttgccca | 780 |
| agtctgggcg ggaagcccaa actgttcttt attcaggcct gtggaggcga gcagaaagat | 840 |
| cacggcttcg aagtggctag cacctcccc gaggacgaat cacctggaag caaccctgag | 900 |
| ccagatgcaa ccccttcca ggaaggcctg aggacatttg accagctgga tgccatctca | 960 |
| agcctgccca caccttctga catttcgtc tcttacagta cttcccctgg atttgtgagc | 1020 |
| tggcgcgatc caaagtcagg cagctggtac gtggagacac tggacgatat ctttgagcag | 1080 |
| tgggcccatt ctgaagacct gcagagtctg ctgctgcgag tggccaatgc tgtctctgtg | 1140 |
| aagggggatct acaaacagat gccaggatgc ttcaactttc tgagaaagaa actgttcttt | 1200 |
| aagacctccg catctagggc cccgcgggaa ggccgaggga gcctgctgac atgtggcgat | 1260 |
| gtggaggaaa acccaggacc accatggatg gagtttggac tttcttggtt gttttggtg | 1320 |
| gcaattctga agggtgtcca gtgtagcagg acatccagac tgacacagac tacatcctcc | 1380 |
| ctgtctgcct ctctgggaga cagagtcacc atcagttgca gggcaagtca ggacattagt | 1440 |
| aaatatttaa attggtatca gcagaaacca gatggaactg ttaaactcct gatctaccat | 1500 |

| | |
|---|---|
| acatcaagat tacactcagg agtcccatca aggttcagtg gcagtgggtc tggaacagat | 1560 |
| tattctctca ccattagcaa cctggagcaa gaagatattg ccacttactt ttgccaacag | 1620 |
| ggtaatacgc ttccgtacac gttcggaggg gggactaagt tggaaataac aggcggagga | 1680 |
| agcggaggtg ggggcgaggt gaaactgcag gagtcaggac ctggcctggt ggcgccctca | 1740 |
| cagagcctgt ccgtcacatg cactgtctca ggggtctcat tacccgacta tggtgtaagc | 1800 |
| tggattcgcc agcctccacg aaagggtctg gagtggctgg gagtaatatg gggtagtgaa | 1860 |
| accacatact ataattcagc tctcaaatcc agactgacca tcatcaagga caactccaag | 1920 |
| agccaagttt tcttaaaaat gaacagtctg caaactgatg acacagccat ttactactgt | 1980 |
| gccaaacatt attactacgg tggtagctat gctatggact actgggtca aggaacctca | 2040 |
| gtcaccgtct cctcaggatc cgaacttcct actcagggga cttcctcaaa cgttagcaca | 2100 |
| aacgtaagtc ccgccccaag accccccaca cctgcgccga ccattgcttc tcaacccctg | 2160 |
| agtttgagac ccgaggcctg ccggccagct gccggcgggg ccgtgcatac aagaggactc | 2220 |
| gatttcgctt gcgacatcta tatctgggca cctctcgctg gcacctgtgg agtccttctg | 2280 |
| ctcagcctgg ttattactct gtactgtaat caccggaatc gccgccgcgt ttgtaagtgt | 2340 |
| cccagggtcg acagagtgaa gttcagcagg agcgcagacg cccccgcgta ccagcagggc | 2400 |
| cagaaccagc tctataacga gctcaatcta ggacgaagag aggagtacga tgttttggac | 2460 |
| aagagacgtg gccgggaccc tgagatgggg ggaaagccga aaggaagaa ccctcaggaa | 2520 |
| ggcctgtaca atgaactgca gaaagataag atggcggagg cctacagtga gattgggatg | 2580 |
| aaaggcgagc gccggagggg caaggggcac gatggccttt accagggtct cagtacagcc | 2640 |
| accaaggaca cctacgacgc ccttcacatg caagctcttc cacctcgtat gctcgagatg | 2700 |
| ctggaggcta ctaacttcag cctgctgaag caggctggag acgtggagga aaccccgggg | 2760 |
| cctatgggga gtagcaagag caagcctaag gaccccagcc agcgcatggc tgcaggaggt | 2820 |
| cccggcgcgg gtctgcggc cccggtctcc tccacatcct cccttcccct ggctgctctc | 2880 |
| aacatgcgag tgcggcgccg cctgtctctg ttcttgaacg tgcggacaca ggtggcggcc | 2940 |
| gactggaccg cgctggcgga ggagatggac tttgagtact tggagatccg gcaactggag | 3000 |
| acacaagcgg accccactgg caggctgctg gacgcctggc agggacgccc tggcgcctct | 3060 |
| gtaggccgac tgctcgatct gcttaccaag ctgggccgcg acgacgtgct gctggagctg | 3120 |
| ggacccagca ttgaggagga ttgccaaaag tatatcttga gcagcagca ggaggaggct | 3180 |
| gagaagcctt tacaggtggc cgctgtagac agcagtgtcc cacggacagc agagctggcg | 3240 |
| ggcatcacca cacttgatga ccccctgggg catatgcctg agcgtttcga tgccttcatc | 3300 |
| tgctattgcc ccagcgacat cgcggccgct aaacggggca gaagaaact cctgtatata | 3360 |
| ttcaaacaac catttatgag accagtacaa actactcaag aggaagatgg ctgtagctgc | 3420 |
| cgatttccag aagaagaaga aggaggatgt gaactg | 3456 |

<210> SEQ ID NO 136
<211> LENGTH: 3414
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136

| | |
|---|---|
| atgctcgaga tgctggaggg agtgcaggtg gagactatta gccccggaga tggcagaaca | 60 |

| | |
|---|---|
| ttccccaaaa gaggacagac ttgcgtcgtg cattatactg gaatgctgga agacggcaag | 120 |
| aaggtggaca gcagccggga ccgaaacaag cccttcaagt tcatgctggg gaagcaggaa | 180 |
| gtgatccggg gctgggagga aggagtcgca cagatgtcag tgggacagag ggccaaactg | 240 |
| actattagcc cagactacgc ttatggagca accggccacc ccgggatcat tcccctcat | 300 |
| gctacactgg tcttcgatgt ggagctgctg aagctggaaa gcggaggagg atccggagtg | 360 |
| gacgggtttg gagatgtggg agccctggaa tccctgcggg gcaatgccga tctggcttac | 420 |
| atcctgtcta tggagccttg cggccactgt ctgatcatta caatgtgaa cttctgcaga | 480 |
| gagagcgggc tgcggaccag aacaggatcc aatattgact gtgaaaagct gcggagaagg | 540 |
| ttctctagtc tgcactttat ggtcgaggtg aaaggcgatc tgaccgctaa gaaaatggtg | 600 |
| ctggccctgc tggaactggc tcggcaggac catgggcac tggattgctg cgtggtcgtg | 660 |
| atcctgagtc acggctgcca ggcttcacat ctgcagttcc ctggggcagt ctatggaact | 720 |
| gacggctgtc cagtcagcgt ggagaagatc gtgaacatct tcaacggcac ctcttgccca | 780 |
| agtctgggcg ggaagcccaa actgttcttt attcaggcct gtggaggcga gcagaaagat | 840 |
| cacggcttcg aagtggctag cacctccccc gaggacgaat cacctggaag caaccctgag | 900 |
| ccagatgcaa ccccttcca ggaaggcctg aggacatttg accagctgga tgccatctca | 960 |
| agcctgccca caccttctga cattttcgtc tcttacagta ctttccctgg atttgtgagc | 1020 |
| tggcgcgatc caaagtcagg cagctggtac gtggagcac tggacgatat ctttgagcag | 1080 |
| tgggcccatt ctgaagacct gcagagtctg ctgctgcgag tggccaatgc tgtctctgtg | 1140 |
| aagggggatct acaaacagat gccaggatgc ttcaactttc tgagaaagaa actgttcttt | 1200 |
| aagacctccg catctagggc cccgcgggaa ggccgaggga gcctgctgac atgtggcgat | 1260 |
| gtggaggaaa acccaggacc accatggatg gagtttggac tttcttggtt gttttttggtg | 1320 |
| gcaattctga agggtgtcca gtgtagcagg gacatccaga tgacacagac tacatcctcc | 1380 |
| ctgtctgcct ctctgggaga cagagtcacc atcagttgca gggcaagtca ggacattagt | 1440 |
| aaatatttaa attggtatca gcagaaacca gatggaactg ttaaactcct gatctaccat | 1500 |
| acatcaagat tacactcagg agtcccatca aggttcagtg gcagtgggtc tggaacagat | 1560 |
| tattctctca ccattagcaa cctggagcaa gaagatattg ccacttactt ttgccaacag | 1620 |
| ggtaatacgc ttccgtacac gttcggaggg gggactaagt tggaaataac aggcggagga | 1680 |
| agcggaggtg ggggcgaggt gaaactgcag gagtcaggac ctggcctggt ggcgccctca | 1740 |
| cagagcctgt ccgtcacatg cactgtctca ggggtctcat tacccgacta tggtgtaagc | 1800 |
| tggattcgcc agcctccacg aaagggtctg gagtggctgg gagtaatatg gggtagtgaa | 1860 |
| accacatact ataattcagc tctcaaatcc agactgacca tcatcaagga caactccaag | 1920 |
| agccaagttt tcttaaaaat gaacagtctg caaactgatg acacagccat ttactactgt | 1980 |
| gccaaacatt attactacgg tggtagctat gctatggact actggggtca aggaacctca | 2040 |
| gtcaccgtct cctcaggatc cgaacttcct actcagggga cttttctcaaa cgttagcaca | 2100 |
| aacgtaagtc ccgccccaag acccccaca cctgcgccga ccattgcttc tcaacccctg | 2160 |
| agtttgagac ccgaggcctg ccggccagct gccggcgggg ccgtgcatac aagaggactc | 2220 |
| gatttcgctt gcgacatcta tatctgggca cctctcgctg gcacctgtgg agtccttctg | 2280 |
| ctcagcctgg ttattactct gtactgtaat caccggaatc gccgccgcgt ttgtaagtgt | 2340 |
| cccagggtcg acagagtgaa gttcagcagg agcgcagacg cccccgcgta ccagcagggc | 2400 |
| cagaaccagc tctataacga gctcaatcta ggacgaagag aggagtacga tgttttggac | 2460 |

```
aagagacgtg gccgggaccc tgagatgggg ggaaagccga gaaggaagaa ccctcaggaa    2520
ggcctgtaca atgaactgca gaaagataag atggcggagg cctacagtga gattgggatg    2580
aaaggcgagc gccggagggg caaggggcac gatggccttt accagggtct cagtacagcc    2640
accaaggaca cctacgacgc ccttcacatg caagctcttc cacctcgtat gctcgagatg    2700
ctggaggcta ctaacttcag cctgctgaag caggctggag acgtggagga aaccccggg    2760 cctatggcta caggaggtcc cggcgcgggg tctgcggccc cggtctcctc cacatcctcc    2820
cttcccctgg ctgctctcaa catgcgagtg cggcgccgcc tgtctctgtt cttgaacgtg    2880
cggacacagg tggcggccga ctggaccgcg ctggcggagg agatggactt tgagtacttg    2940
gagatccggc aactggagac acaagcggac cccactggca ggctgctgga cgcctggcag    3000
ggacgccctg cgcctctgt aggccgactg ctcgatctgc ttaccaagct gggccgcgac    3060
gacgtgctgc tggagctggg acccagcatt gaggaggatt gccaaaagta tatcttgaag    3120
cagcagcagg aggaggctga aagcctttta caggtggccg ctgtagacag cagtgtccca    3180
cggacagcag agctggcggg catcaccaca cttgatgacc ccctggggca tatgcctgag    3240
cgtttcgatg ccttcatctg ctattgcccc agcgacatcg cggccgctaa acggggcaga    3300
aagaaactcc tgtatatatt caaacaacca tttatgagac cagtacaaac tactcaagag    3360
gaagatggct gtagctgccg atttccagaa gaagaagaag aggatgtga actg          3414
```

<210> SEQ ID NO 137
<211> LENGTH: 1379
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 137

```
atggagttcg gattgagctg gctgttcctg gtggcaatac tcaagggcgt tcaatgttca     60
cggcagatcc aactggtgca gtcaggcccg gaactgaaga agccagggga gacagtcaaa    120
ataagttgta agccagcgg ctacatattt actaattacg ggatgaattg ggtgaagcaa    180
gcgccgggca atcctttaa atggatgggg tggataaaca catacacagg agagtcaacg    240
tacagcgcgg acttcaaagg tcgattcgcg ttcagtctcg agaccagcgc gagtacagct    300
tacctccaca tcaacgatct taaaaacgaa gacacggcaa cctatttttg cgcccggtca    360
ggcggttacg accctatgga ctattggggc caagggaccc ccgttacggt acttcaggcg    420
gtggcgggag tggtggagga ggctcaggcg gcggggatc agacatcgta ctgacccaat    480
ctcccgctag ccttgcagta tccttgggtc aacgcgctac aataagttgc cgggctagtg    540
agtccgtaga caactatggc aacaccttca tgcattggta ccaacaaaaa ccaggtcagc    600
cacccaaact tctcatttac agagcgtcta atctcgaaag cggcatccct gctcgattct    660
ctggaagcgg aagtagaacc gactttacac tgactataaa ccccgtcgaa gccgatgatg    720
ttgccactta ttactgtcaa cagagcaatg aggacccacc gacattcggt gctggtacca    780
agctggagtt gaaggagtca aaatacgggc tccctgtcc cggatccgaa cttcctactc    840 agggacttt ctcaaacgtt agcacaaacg taagtgaact tcctactcag gggactttct    900
caaacgttag cacaaacgta agtatctata tctgggcacc tctcgctggc acctgtggag    960
tccttctgct cagcctggtt attactctgt actgtaatca ccggaatcgc cgccgcgttt   1020
gtaagtgtcc cagggtcgac agagtgaagt tcagcaggag cgcagacgcc cccgcgtacc   1080
```

```
agcagggcca gaaccagctc tataacgagc tcaatctagg acgaagagag gagtacgatg    1140
ttttggacaa gagacgtggc cgggaccctg agatggggggg aaagccgaga aggaagaacc    1200
ctcaggaagg cctgtacaat gaactgcaga aagataagat ggcggaggcc tacagtgaga    1260
ttgggatgaa aggcgagcgc cggaggggca agggcacga tggcctttac cagggtctca    1320
gtacagccac caaggacacc tacgacgccc ttcacatgca agctcttcca cctcgttga    1379
```

<210> SEQ ID NO 138
<211> LENGTH: 3385
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 138

```
atggctgcag gaggtcccgg cgcggggtct gcggccccgg tctcctccac atcctccctt     60
cccctggctg ctctcaacat gcgagtgcgg cgccgcctgt ctctgttctt gaacgtgcgg    120
acacaggtgg cggccgactg gaccgcgctg gcggaggaga tggactttga gtacttggag    180
atccggcaac tggagacaca agcggacccc actggcaggc tgctgacgc ctggcaggga    240 cgccctggcg cctctgtagg ccgactgctc gatctgctta ccaagctggg ccgcgacgac    300
gtgctgctgg agctgggacc cagcattgag gaggattgcc aaaagtatat cttgaagcag    360
cagcaggagg aggctgagaa gcctttacag gtggccgctg tagacagcag tgtcccacgg    420
acagcagagc tggcgggcat caccacactt gatgaccccc tggggcatat gcctgagcgt    480
ttcgatgcct tcatctgcta ttgccccagc gacatcgtcg agaaaaaggt ggccaagaag    540
ccaaccaata aggccccca ccccaagcag gagccccagg agatcaattt tcccgacgat    600
cttcctggct ccaacactgc tgctccagtg caggagactt tacatggatg ccaaccggtc    660
acccaggagg atggcaaaga gagtcgcatc tcagtgcagg agagacaggt cgagggcgtc    720
caagtcgaaa ccattagtcc cggcgatggc agaacatttc ctaaaagggg acaaacatgt    780
gtcgtccatt atacaggcat gttggaggac ggcaaaaagg tggacagtag tagagatcgc    840
aataaacctt tcaaattcat gttgggaaaa caagaagtca ttaggggatg ggaggagggc    900
gtggctcaaa tgtccgtcgg ccaacgcgct aagctcacca tcagcccga ctacgcatac    960 ggcgctaccg acatcccgg aattattccc cctcacgcta ccttggtgtt tgacgtcgaa   1020
ctgttgaagc tcgaagtcga gggagtgcag gtggagacta tctccccagg agacgggcgc   1080
accttcccca agcgcggcca gacctgcgtg gtgcactaca ccgggatgct tgaagatgga   1140
aagaaagttg attcctcccg ggacagaaac aagccctta agtttatgct aggcaagcag   1200
gaggtgatcc gaggctggga agaaggggtt gcccagatga gtgtgggtca gagagccaaa   1260
ctgactatat ctccagatta tgcctatggt gccactgggc acccaggcat catcccacca   1320
catgccactc tcgtcttcga tgtggagctt ctaaaactgg aaccgcggga gggcagaggc   1380
agcctcctga catgtgggga cgtcgaggag aaccctggcc accttggat ggagttcgga   1440 ttgagctggc tgttcctggt ggcaatactc aaggggcgttc aatgttcacg ggatatcgtg   1500
ctgacccagt cccccctag cctggccatg tccctgggca acgggccac catctcctgc   1560 agagcctccg agtccgtgac catcctcggc tcccacctga tctactggta ccagcagaag   1620 cccgccagc ctcccacccct ccttatccag ctggccagca acgtgcagac cggcgtgccc   1680
gctagattct ccggcagcgg ctctagaacc gacttcaccc tgaccatcga ccccgtggaa   1740
```

-continued

```
gaggacgatg tcgccgtgta ctattgcctg cagtccagaa ccatccctag gacattcggc    1800
ggaggaacca agctggagat caaaggggc ggtggcagcg gtggcggtgg gtctgggggc    1860
ggaggctctc agatccagct ggtgcagtcc ggccccgagc tgaagaaacc cggcgagacc    1920
gtgaagatct cctgcaaggc cagcggctac accttcagac actacagcat gaactgggtg    1980
aagcaggccc ctggcaaggg cctgaagtgg atgggccgga tcaacaccga gtccggcgtg    2040
cccatctacg ccgacgattt caagggcaga ttcgccttca gcgtggagac ctccgcctct    2100
accgcctacc tggtgatcaa caatctgaag gacgaggaca ccgcctccta cttctgcagc    2160
aacgactacc tgtacagcct ggacttctgg gccagggca ccgccctgac cgtgagctcc    2220
gggatccgaa cttcctactc aggggacttt ctcaaacgtt agcacaaacg taagtgaact    2280
tcctactcag gggactttct caaacgttag cacaaacgta agtatctata tctgggcacc    2340
tctcgctggc acctgtggag tccttctgct cagcctggtt attactctgt actgtaatca    2400
ccggaatcgc cgccgcgttt gtaagtgtcc cagggtcgac agagtgaagt tcagcaggag    2460
cgcagacgcc cccgcgtacc agcagggcca gaaccagctc tataacgagc tcaatctagg    2520
acgaagagag gagtacgatg ttttggacaa gagacgtggc cgggaccctg agatgggggg    2580
aaagccgaga aggaagaacc ctcaggaagg cctgtacaat gaactgcaga aagataagat    2640
ggcggaggcc tacagtgaga ttgggatgaa aggcgagcgc cggaggggca aggggcacga    2700
tggcctttac cagggtctca gtacagccac caaggacacc tacgacgccc ttcacatgca    2760
agctcttcca cctcgtggat ctggcggccg cgagggaagg ggaagtcttc taacatgcgg    2820
ggacgtggag gaaaatcccg gccccgaggg aaggggaagt cttctaacat gcgggacgt    2880 ggaggaaaat cccgggccca tgagaatttc gaaaccacat tgagaagta tttccatcca    2940 gtgctacttg tgtttacttc taaacagtca ttttctaact gaagctggca ttcatgtctt    3000
cattttgggc tgtttcagtg cagggcttcc taaaacagaa gccaactggg tgaatgtaat    3060
aagtgatttg aaaaaaattg aagaccttat tcaatctatg cacattgatg ctactttata    3120
tacgaaaagt gatgttcacc ccagttgcaa agtaacagca atgaagtgct ttctcttgga    3180
gttacaagtt atttcacttg agtccggaga tgcaagtatt catgatacag tagaaaatct    3240
gatcatccta gcaaacaaca gtttgtcttc taatgggaat gtaacagaat ctggatgcaa    3300
agaatgtgag gaactggagg agaagaacat caaggaattt ttgcagagtt ttgtacatat    3360
tgtccaaatg ttcatcaaca cttga    3385
```

<210> SEQ ID NO 139
<211> LENGTH: 2565
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 139

```
atgctcgagc aattggaaat gtggcatgaa gggttggaag aagcttcaag gctgtacttc      60
ggagagagga acgtgaaggg catgtttgag gttcttgaac ctctgcacgc catgatggaa     120
cggggaccgc agacactgaa agaaacctct tttaatcagg cctacggcag agacctgatg     180
gaggcccaag aatggtgtag aaagtatatg aaatccggta acgtgaaaga cctgactcag     240
gcctgggacc tttattacca tgtgttcagg cggatcagta agggcgggca attgggcgtc     300
caagtcgaaa ccattagtcc cggcgatggc agaacatttc ctaaaagggg acaaacatgt     360
```

-continued

```
gtcgtccatt atacaggcat gttggaggac ggcaaaaagt tcgacagtag tagagatcgc    420
aataaacctt tcaaattcat gttgggaaaa caagaagtca ttaggggatg ggaggagggc    480
gtggctcaaa tgtccgtcgg ccaacgcgct aagctcacca tcagccccga ctacgcatac    540
ggcgctaccg gacatcccgg aattattccc cctcacgcta ccttggtgtt tgacgtcgaa    600
ctgttgaagc tctcaggcgg tggctcaggt ccatggggat tggtgatgt cggtgctctt     660 gagagtttga ggggaaatgc agatttggct tacatcctga gcatggagcc ctgtggccac    720
tgcctcatta tcaacaatgt gaacttctgc cgtgagtccg ggctccgcac ccgcactggc    780
tccaacatcg actgtgagaa gttgcggcgt cgcttctcct cgctgcattt catggtggag    840
gtgaagggcg acctgactgc caagaaaatg gtgctggctt tgctggagct ggcgcggcag    900
gaccacggtg ctctggactg ctgcgtggtg gtcattctct ctcacggctg tcaggccagc    960
cacctgcagt tcccaggggc tgtctacggc acagatggat gccctgtgtc ggtcgagaag   1020
attgtgaaca tcttcaatgg gaccagctgc cccagcctgg agggaagcc caagctcttt    1080 ttcatccagg cctgtggtgg ggagcagaaa gaccatgggt tgaggtggc ctccacttcc    1140 cctgaagacag agtcccctgg cagtaacccc gagccagatg ccaccccgtt ccaggaaggt   1200
ttgaggacct tcgaccagct ggacgccata tctagtttgc ccacacccag tgacatcttt   1260
gtgtcctact ctactttccc aggttttgtt tcctggaggg accccaagag tggctcctgg   1320
tacgttgaga ccctggacga catctttgag cagtgggctc actctgaaga cctgcagtcc   1380
ctcctgctta gggtcgctaa tgctgtttcg gtgaaaggga tttataaaca gatgcctggt   1440
tgctttaatt tcctccggaa aaaacttttc tttaaaacat cagctagcag agccggatct   1500
ggaccgcggg aaggccgagg gagcctgctg acatgtggcg atgtggagga aaacccagga   1560
ccaatgccac cacctcgcct gctgttcttt ctgctgttcc tgacacctat ggaggtgcga   1620
cctgaggaac cactggtcgt gaaggtcgag aaggcgaca atgccgtgct gcagtgcctg   1680
aaaggcactt ctgatgggcc aactcagcag ctgacctggt ccagggagtc tcccctgaag   1740 cctttctga aactgagcct gggactgcca ggactgggaa tccacatgcg ccctctggct    1800
atctggctgt tcatcttcaa cgtgagccag cagatggag gattctacct gtgccagcca   1860
ggaccaccat ccgagaaggc ctggcagcct ggatggaccg tcaacgtgga ggggtctgga   1920
gaactgttta ggtggaatgt gagtgacctg ggaggactgg gatgtgggct gaagaaccgc   1980
tcctctgaag gcccaagttc accctcaggg aagctgatga gcccaaaact gtacgtgtgg   2040
gccaaagatc ggccccgagat ctgggaggga gaacctccat gcctgccacc tagagacagc   2100
ctgaatcaga gtctgtcaca ggatctgaca atggcccccg gtccactctc gtggctgtct   2160 tgtgagtcc cacccgacag cgtgtccaga ggccctctgt cctggaccca cgtgcatcct   2220
aaggggccaa aaagtctgct gtcactggaa ctgaaggacg atcggcctgc cagagacatg   2280
tgggtcatgg agactggact gctgctgcca cgagcaaccg cacaggatgc tggaaaatac   2340
tattgccacc ggggcaatct gacaatgtcc ttccatctgg agatcactgc aaggcccgtg   2400
ctgtggcact ggctgctgcg aaccggagga tggaaggtca gtgctgtgac actggcatat   2460
ctgatctttt gcctgtgctc cctggtgggc attctgcatc tgcagagagc cctggtgctg   2520
cggagaaaga gaaagagaat gactgaccca acaagaaggt tttga                   2565
```

<210> SEQ ID NO 140
<211> LENGTH: 3957
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 140

```
atgctcgaga tgctggaggg agtgcaggtg gagactatta gccccggaga tggcagaaca    60
ttccccaaaa gaggacagac ttgcgtcgtg cattatactg gaatgctgga agacggcaag   120
aaggtggaca gcagccggga ccgaaacaag cccttcaagt tcatgctggg gaagcaggaa   180
gtgatccggg gctggaggaa aggagtcgca cagatgtcag tgggacagag ggccaaactg   240
actattagcc cagactacgc ttatggagca accggccacc ccgggatcat tcccccctcat  300
gctacactgg tcttcgatgt ggagctgctg aagctggaaa gcggaggagg atccggagtg   360
gacgggtttg gagatgtggg agccctggaa tccctgcggg gcaatgccga tctggcttac   420
atcctgtcta tggagccttg cggccactgt ctgatcatta caatgtgaa cttctgcaga    480
gagagcgggc tgcggaccag aacaggatcc aatattgact gtgaaaagct gcggagaagg   540
ttctctagtc tgcactttat ggtcgaggtg aaaggcgatc tgaccgctaa gaaaatggtg   600
ctggccctgc tggaactggc tcggcaggac catggggcac tggattgctg cgtggtcgtg   660
atcctgagtc acggctgcca ggcttcacat ctgcagttcc ctggggcagt ctatggaact   720
gacggctgtc cagtcagcgt ggagaagatc gtgaacatct tcaacggcac ctcttgccca   780
agtctgggcg ggaagcccaa actgttcttt attcaggcct gtggaggcga gcagaaagat   840
cacggcttcg aagtggctag cacctccccc gaggacgaat cacctggaag caaccctgag   900
ccagatgcaa ccccccttcca ggaaggcctg aggacatttg accagctgga tgccatctca   960
agcctgccca caccttctga catttttcgtc tcttacagta cttttccctgg atttgtgagc  1020
tggcgcgatc caaagtcagg cagctggtac gtggagacac tggacgatat ctttgagcag   1080
tgggcccatt ctgaagacct gcagagtctg ctgctgcgag tggccaatgc tgtctctgtg   1140
aagggggatct acaaacagat gccaggatgc ttcaactttc tgagaaagaa actgttcttt   1200
aagacctccg catctaggc cccgcgggag ggcagaggca gcctcctgac atgtggggac   1260
gtcgaggaga accctggccc accttggatg gagttcggat tgagctggct gttcctggtg   1320
gcaatactca agggcgttca atgttcacgg gatatcgtgc tgacccagtc ccccccctagc   1380
ctggccatgt ccctgggcaa acgggccacc atctcctgca gagcctccga gtccgtgacc   1440
atcctcggct cccacctgat ctactggtac cagcagaagc ccggccagcc tcccacccctc  1500
cttatccagc tggccagcaa cgtgcagacc ggcgtgcccg ctagattctc cggcagcggc   1560
tctagaaccg acttcacctc gaccatcgac ccgtggaag aggacgatgt cgccgtgtac   1620
tattgcctgc agtccagaac catccctagg acattcggcg gaggaaccaa gctggagatc   1680
aaaggggggcg gtggcagcgg tggcggtggg tctgggggcg gaggctctca gatccagctg   1740
gtgcagtccg gccccgagct gaagaaaccc ggcgagaccc tgaagatctc ctgcaaggcc   1800
agcggctaca ccttcagaca ctacagcatg aactgggtga agcaggcccc tggcaagggc   1860
ctgaagtgga tggccggat caacaccgag tccggcgtgc catctacgc cgacgatttc   1920
aagggcagat cgccttcag cgtggagacc tccgcctcta ccgcctacct ggtgatcaac   1980
aatctgaagg acgaggacac cgcctcctac ttctgcagca acgactacct gtacagcctg   2040
gacttctggg gccagggcac cgccctgacc gtgagctccg gatccgaac ttcctactca   2100
ggggactttc tcaaacgtta gcacaaacgt aagtgaactt cctactcagg ggactttctc   2160
```

```
aaacgttagc acaaacgtaa gtatctatat ctgggcacct ctcgctggca cctgtggagt   2220
ccttctgctc agcctggtta ttactctgta ctgtaatcac cggaatcgcc gccgcgtttg   2280
taagtgtccc agggtcgaca gagtgaagtt cagcaggagc gcagacgccc ccgcgtacca   2340
gcagggccag aaccagctct ataacgagct caatctagga cgaagagagg agtacgatgt   2400
tttggacaag agacgtggcc gggaccctga gatgggggga aagccgagaa ggaagaaccc   2460
tcaggaaggc ctgtacaatg aactgcagaa agataagatg gcggaggcct acagtgagat   2520
tgggatgaaa ggcgagcgcc ggaggggcaa ggggcacgat ggcctttacc agggtctcag   2580
tacagccacc aaggacacct acgacgccct tcacatgcaa gctcttccac ctcgtgcaac   2640
gaattttttcc ctgctgaaac aggcagggga cgtagaggaa atcctggtc ctatggctgc   2700
aggaggtccc ggcgcggggt ctgcggcccc ggtctcctcc acatcctccc ttcccctggc   2760
tgctctcaac atgcgagtgc ggcgccgcct gtctctgttc ttgaacgtgc ggacacaggt   2820
ggcggccgac tggaccgcgc tggcggagga gatggacttt gagtacttgg agatccggca   2880
actggagaca caagcggacc ccactggcag gctgctggac gcctggcagg gacgccctgg   2940
cgcctctgta ggccgactgc tcgatctgct taccaagctg ggccgcgacg acgtgctgct   3000
ggagctggga cccagcattg aggaggattg ccaaaagtat atcttgaagc agcagcagga   3060
ggaggctgag aagcctttac aggtggccgc tgtagacagc agtgtcccac ggacagcaga   3120
gctggcgggc atcaccacac ttgatgaccc cctggggcat atgcctgagc gtttcgatgc   3180
cttcatctgc tattgcccca gcgacatcgt cgagaaaaag gtggccaaga agccaaccaa   3240
taaggccccc caccccaagc aggagcccca ggagatcaat tttcccgacg atcttcctgg   3300
ctccaacact gctgctccag tgcaggagac tttacatgga tgccaaccgg tcacccagga   3360
ggatggcaaa gagagtcgca tctcagtgca ggagagacag gatctggcgg ccgcgaggga   3420
aggggaagtc ttctaacatg cggggacgtg gaggaaaatc ccgggccctg aatgagaatt   3480
tcgaaaccac atttgagaag tatttccatc cagtgctact tgtgtttact tctaaacagt   3540
cattttctaa ctgaagctgg cattcatgtc ttcattttgg gctgtttcag tgcagggctt   3600
cctaaaacag aagccaactg ggtgaatgta ataagtgatt tgaaaaaaat tgaagacctt   3660
attcaatcta tgcacattga tgctacttta tatacggaaa gtgatgttca ccccagttgc   3720
aaagtaacag caatgaagtg ctttctcttg gagttacaag ttatttcact tgagtccgga   3780
gatgcaagta ttcatgatac agtagaaaat ctgatcatcc tagcaaacaa cagtttgtct   3840
tctaatggga atgtaacaga atctggatgc aaagaatgtg aggaactgga ggagaagaac   3900
atcaaggaat ttttgcagag ttttgtacat attgtccaaa tgttcatcaa cacttga      3957
```

<210> SEQ ID NO 141
<211> LENGTH: 957
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 141

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

```
Ala Leu Ala Glu Glu Met Asp Phe Glu Tyr Leu Glu Ile Arg Gln Leu
 50                  55                  60

Glu Thr Gln Ala Asp Pro Thr Gly Arg Leu Leu Asp Ala Trp Gln Gly
 65                  70                  75                  80

Arg Pro Gly Ala Ser Val Gly Arg Leu Leu Asp Leu Leu Thr Lys Leu
                 85                  90                  95

Gly Arg Asp Asp Val Leu Leu Glu Leu Gly Pro Ser Ile Glu Glu Asp
             100                 105                 110

Cys Gln Lys Tyr Ile Leu Lys Gln Gln Gln Glu Gly Ala Glu Lys Pro
         115                 120                 125

Leu Gln Val Ala Ala Val Asp Ser Ser Val Pro Arg Thr Ala Glu Leu
 130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Leu Glu Arg Ser
                165                 170                 175

Lys Arg Ser Arg Leu Leu His Ser Asp Tyr Met Asn Met Thr Pro Arg
            180                 185                 190

Arg Pro Gly Pro Thr Arg Lys His Tyr Gln Pro Tyr Ala Pro Pro Arg
        195                 200                 205

Asp Phe Ala Ala Tyr Arg Ser Arg Asp Gln Arg Leu Pro Pro Asp Ala
210                 215                 220

His Lys Pro Pro Gly Gly Gly Ser Phe Arg Thr Pro Ile Gln Glu Glu
225                 230                 235                 240

Gln Ala Asp Ala His Ser Thr Leu Ala Lys Ile Gly Ser Gly Gly Ser
                245                 250                 255

Gly Gln Leu Gly Val Gln Val Glu Thr Ile Ser Pro Gly Asp Gly Arg
            260                 265                 270

Thr Phe Pro Lys Arg Gly Gln Thr Cys Val Val His Tyr Thr Gly Met
        275                 280                 285

Leu Glu Asp Gly Lys Lys Val Asp Ser Ser Arg Asp Arg Asn Lys Pro
290                 295                 300

Phe Lys Phe Met Leu Gly Lys Gln Glu Val Ile Arg Gly Trp Glu Glu
305                 310                 315                 320

Gly Val Ala Gln Met Ser Val Gly Gln Arg Ala Lys Leu Thr Ile Ser
                325                 330                 335

Pro Asp Tyr Ala Tyr Gly Ala Thr Gly His Pro Gly Ile Ile Pro Pro
            340                 345                 350

His Ala Thr Leu Val Phe Asp Val Glu Leu Leu Lys Leu Glu Val Glu
        355                 360                 365

Gly Val Gln Val Glu Thr Ile Ser Pro Gly Asp Gly Arg Thr Phe Pro
370                 375                 380

Lys Arg Gly Gln Thr Cys Val Val His Tyr Thr Gly Met Leu Glu Asp
385                 390                 395                 400

Gly Lys Lys Val Asp Ser Ser Arg Asp Arg Asn Lys Pro Phe Lys Phe
                405                 410                 415

Met Leu Gly Lys Gln Glu Val Ile Arg Gly Trp Glu Glu Gly Val Ala
            420                 425                 430

Gln Met Ser Val Gly Gln Arg Ala Lys Leu Thr Ile Ser Pro Asp Tyr
        435                 440                 445

Ala Tyr Gly Ala Thr Gly His Pro Gly Ile Ile Pro Pro His Ala Thr
450                 455                 460
```

```
Leu Val Phe Asp Val Glu Leu Leu Lys Leu Glu Pro Arg Glu Gly Arg
465                 470                 475                 480

Gly Ser Leu Leu Thr Cys Gly Asp Val Glu Glu Asn Pro Gly Pro Pro
            485                 490                 495

Trp Met Glu Phe Gly Leu Ser Trp Leu Phe Leu Val Ala Ile Leu Lys
            500                 505                 510

Gly Val Gln Cys Ser Arg Asp Ile Gln Leu Thr Gln Ser Pro Ser Thr
            515                 520                 525

Leu Ser Ala Ser Met Gly Asp Arg Val Thr Ile Thr Cys Ser Ala Ser
    530                 535                 540

Ser Ser Val Arg Phe Ile His Trp Tyr Gln Gln Lys Pro Gly Lys Ala
545                 550                 555                 560

Pro Lys Arg Leu Ile Tyr Asp Thr Ser Lys Leu Ala Ser Gly Val Pro
                565                 570                 575

Ser Arg Phe Ser Gly Ser Gly Ser Gly Thr Asp Phe Thr Leu Thr Ile
            580                 585                 590

Ser Ser Leu Gln Pro Glu Asp Phe Ala Thr Tyr Tyr Cys Gln Gln Trp
    595                 600                 605

Gly Ser Ser Pro Phe Thr Phe Gly Gln Gly Thr Lys Val Glu Ile Lys
            610                 615                 620

Gly Gly Gly Ser Gly Gly Gly Gly Gln Val Glu Val Gln Leu Val Glu
625                 630                 635                 640

Tyr Gly Gly Gly Leu Val Gln Pro Gly Gly Ser Leu Arg Leu Ser Cys
                645                 650                 655

Ala Ala Ser Gly Phe Asn Ile Lys Asp Tyr Tyr Ile His Trp Val Arg
            660                 665                 670

Gln Ala Pro Gly Lys Gly Leu Glu Trp Val Ala Trp Ile Asp Pro Glu
            675                 680                 685

Asn Gly Asp Thr Glu Phe Val Pro Lys Phe Gln Gly Arg Ala Thr Met
            690                 695                 700

Ser Ala Asp Thr Ser Lys Asn Thr Ala Tyr Leu Gln Met Asn Ser Leu
705                 710                 715                 720

Arg Ala Glu Asp Thr Ala Val Tyr Tyr Cys Lys Thr Gly Gly Phe Trp
                725                 730                 735

Gly Gln Gly Thr Leu Val Thr Val Ser Ser Gly Ser Glu Leu Pro Thr
            740                 745                 750

Gln Gly Thr Phe Ser Asn Val Ser Thr Asn Val Ser Pro Ala Pro Arg
            755                 760                 765

Pro Pro Thr Pro Ala Pro Thr Ile Ala Ser Gln Pro Leu Ser Leu Arg
            770                 775                 780

Pro Glu Ala Cys Arg Pro Ala Ala Gly Gly Ala Val His Thr Arg Gly
785                 790                 795                 800

Leu Asp Phe Ala Cys Asp Ile Tyr Ile Trp Ala Pro Leu Ala Gly Thr
                805                 810                 815

Cys Gly Val Leu Leu Leu Ser Leu Val Ile Thr Leu Tyr Cys Asn His
            820                 825                 830

Arg Asn Arg Arg Arg Val Cys Lys Cys Pro Arg Val Asp Arg Val Lys
            835                 840                 845

Phe Ser Arg Ser Ala Asp Ala Pro Ala Tyr Gln Gln Gly Gln Asn Gln
    850                 855                 860

Leu Tyr Asn Glu Leu Asn Leu Gly Arg Arg Glu Glu Tyr Asp Val Leu
865                 870                 875                 880

Asp Lys Arg Arg Gly Arg Asp Pro Glu Met Gly Gly Lys Pro Arg Arg
```

```
                        885                 890                 895
Lys Asn Pro Gln Glu Gly Leu Tyr Asn Glu Leu Gln Lys Asp Lys Met
            900                 905                 910

Ala Glu Ala Tyr Ser Glu Ile Gly Met Lys Gly Glu Arg Arg Arg Gly
            915                 920                 925

Lys Gly His Asp Gly Leu Tyr Gln Gly Leu Ser Thr Ala Thr Lys Asp
            930                 935                 940

Thr Tyr Asp Ala Leu His Met Gln Ala Leu Pro Pro Arg
945                 950                 955

<210> SEQ ID NO 142
<211> LENGTH: 912
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
        115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Leu Glu Thr Lys
                165                 170                 175

Lys Lys Tyr Ser Ser Val His Asp Pro Asn Gly Glu Tyr Met Phe
            180                 185                 190

Met Arg Ala Val Asn Thr Ala Lys Lys Ser Arg Leu Thr Asp Val Thr
        195                 200                 205

Leu Gly Ser Gly Gln Leu Gly Val Gln Val Glu Thr Ile Ser Pro Gly
    210                 215                 220

Asp Gly Arg Thr Phe Pro Lys Arg Gly Gln Thr Cys Val Val His Tyr
225                 230                 235                 240

Thr Gly Met Leu Glu Asp Gly Lys Lys Val Asp Ser Ser Arg Asp Arg
                245                 250                 255

Asn Lys Pro Phe Lys Phe Met Leu Gly Lys Gln Glu Val Ile Arg Gly
            260                 265                 270

Trp Glu Glu Gly Val Ala Gln Met Ser Val Gly Gln Arg Ala Lys Leu
        275                 280                 285
```

-continued

```
Thr Ile Ser Pro Asp Tyr Ala Tyr Gly Ala Thr Gly His Pro Gly Ile
    290                 295                 300

Ile Pro Pro His Ala Thr Leu Val Phe Asp Val Glu Leu Leu Lys Leu
305                 310                 315                 320

Glu Val Glu Gly Val Gln Val Glu Thr Ile Ser Pro Gly Asp Gly Arg
                325                 330                 335

Thr Phe Pro Lys Arg Gly Gln Thr Cys Val Val His Tyr Thr Gly Met
            340                 345                 350

Leu Glu Asp Gly Lys Lys Val Asp Ser Ser Arg Asp Arg Asn Lys Pro
        355                 360                 365

Phe Lys Phe Met Leu Gly Lys Gln Glu Val Ile Arg Gly Trp Glu Glu
370                 375                 380

Gly Val Ala Gln Met Ser Val Gly Gln Arg Ala Lys Leu Thr Ile Ser
385                 390                 395                 400

Pro Asp Tyr Ala Tyr Gly Ala Thr Gly His Pro Gly Ile Ile Pro Pro
                405                 410                 415

His Ala Thr Leu Val Phe Asp Val Glu Leu Leu Lys Leu Glu Pro Arg
            420                 425                 430

Glu Gly Arg Gly Ser Leu Leu Thr Cys Gly Asp Val Glu Glu Asn Pro
        435                 440                 445

Gly Pro Pro Trp Met Glu Phe Gly Leu Ser Trp Leu Phe Leu Val Ala
450                 455                 460

Ile Leu Lys Gly Val Gln Cys Ser Arg Asp Ile Gln Leu Thr Gln Ser
465                 470                 475                 480

Pro Ser Thr Leu Ser Ala Ser Met Gly Asp Arg Val Thr Ile Thr Cys
                485                 490                 495

Ser Ala Ser Ser Ser Val Arg Phe Ile His Trp Tyr Gln Gln Lys Pro
            500                 505                 510

Gly Lys Ala Pro Lys Arg Leu Ile Tyr Asp Thr Ser Lys Leu Ala Ser
        515                 520                 525

Gly Val Pro Ser Arg Phe Ser Gly Ser Gly Ser Gly Thr Asp Phe Thr
530                 535                 540

Leu Thr Ile Ser Ser Leu Gln Pro Glu Asp Phe Ala Thr Tyr Tyr Cys
545                 550                 555                 560

Gln Gln Trp Gly Ser Ser Pro Phe Thr Phe Gly Gln Gly Thr Lys Val
                565                 570                 575

Glu Ile Lys Gly Gly Ser Gly Gly Gly Gln Val Glu Val Gln
            580                 585                 590

Leu Val Glu Tyr Gly Gly Leu Val Gln Pro Gly Gly Ser Leu Arg
        595                 600                 605

Leu Ser Cys Ala Ala Ser Gly Phe Asn Ile Lys Asp Tyr Tyr Ile His
610                 615                 620

Trp Val Arg Gln Ala Pro Gly Lys Gly Leu Glu Trp Val Ala Trp Ile
625                 630                 635                 640

Asp Pro Glu Asn Gly Asp Thr Glu Phe Val Pro Lys Phe Gln Gly Arg
                645                 650                 655

Ala Thr Met Ser Ala Asp Thr Ser Lys Asn Thr Ala Tyr Leu Gln Met
            660                 665                 670

Asn Ser Leu Arg Ala Glu Asp Thr Ala Val Tyr Tyr Cys Lys Thr Gly
        675                 680                 685

Gly Phe Trp Gly Gln Gly Thr Leu Val Thr Val Ser Ser Gly Ser Glu
690                 695                 700

Leu Pro Thr Gln Gly Thr Phe Ser Asn Val Ser Thr Asn Val Ser Pro
```

```
                705                 710                 715                 720
Ala Pro Arg Pro Thr Pro Ala Pro Thr Ile Ala Ser Gln Pro Leu
                    725                 730                 735
Ser Leu Arg Pro Glu Ala Cys Arg Pro Ala Ala Gly Gly Ala Val His
                    740                 745                 750
Thr Arg Gly Leu Asp Phe Ala Cys Asp Ile Tyr Ile Trp Ala Pro Leu
                    755                 760                 765
Ala Gly Thr Cys Gly Val Leu Leu Leu Ser Leu Val Ile Thr Leu Tyr
            770                 775                 780
Cys Asn His Arg Asn Arg Arg Val Cys Lys Cys Pro Arg Val Asp
785                 790                 795                 800
Arg Val Lys Phe Ser Arg Ser Ala Asp Ala Pro Ala Tyr Gln Gln Gly
                    805                 810                 815
Gln Asn Gln Leu Tyr Asn Glu Leu Asn Leu Gly Arg Arg Glu Glu Tyr
                    820                 825                 830
Asp Val Leu Asp Lys Arg Arg Gly Arg Asp Pro Glu Met Gly Gly Lys
                    835                 840                 845
Pro Arg Arg Lys Asn Pro Gln Glu Gly Leu Tyr Asn Glu Leu Gln Lys
            850                 855                 860
Asp Lys Met Ala Glu Ala Tyr Ser Glu Ile Gly Met Lys Gly Glu Arg
865                 870                 875                 880
Arg Arg Gly Lys Gly His Asp Gly Leu Tyr Gln Gly Leu Ser Thr Ala
                    885                 890                 895
Thr Lys Asp Thr Tyr Asp Ala Leu His Met Gln Ala Leu Pro Pro Arg
                    900                 905                 910

<210> SEQ ID NO 143
<211> LENGTH: 748
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Met Leu Glu Lys Arg Gly Arg Lys Lys Leu Leu Tyr Ile Phe Lys Gln
1               5                   10                  15
Pro Phe Met Arg Pro Val Gln Thr Thr Gln Glu Glu Asp Gly Cys Ser
                20                  25                  30
Cys Arg Phe Pro Glu Glu Glu Gly Gly Cys Glu Leu Gly Ser Gly
            35                  40                  45
Gln Leu Gly Val Gln Val Glu Thr Ile Ser Pro Gly Asp Gly Arg Thr
    50                  55                  60
Phe Pro Lys Arg Gly Gln Thr Cys Val Val His Tyr Thr Gly Met Leu
65                  70                  75                  80
Glu Asp Gly Lys Lys Val Asp Ser Ser Arg Asp Arg Asn Lys Pro Phe
                85                  90                  95
Lys Phe Met Leu Gly Lys Gln Glu Val Ile Arg Gly Trp Glu Glu Gly
                100                 105                 110
Val Ala Gln Met Ser Val Gly Gln Arg Ala Lys Leu Thr Ile Ser Pro
            115                 120                 125
Asp Tyr Ala Tyr Gly Ala Thr Gly His Pro Gly Ile Ile Pro Pro His
        130                 135                 140
Ala Thr Leu Val Phe Asp Val Glu Leu Leu Lys Leu Glu Val Glu Gly
145                 150                 155                 160
```

-continued

```
Val Gln Val Glu Thr Ile Ser Pro Gly Asp Gly Arg Thr Phe Pro Lys
                165                 170                 175

Arg Gly Gln Thr Cys Val Val His Tyr Thr Gly Met Leu Glu Asp Gly
            180                 185                 190

Lys Lys Val Asp Ser Ser Arg Asp Arg Asn Lys Pro Phe Lys Phe Met
        195                 200                 205

Leu Gly Lys Gln Glu Val Ile Arg Gly Trp Glu Glu Gly Val Ala Gln
    210                 215                 220

Met Ser Val Gly Gln Arg Ala Lys Leu Thr Ile Ser Pro Asp Tyr Ala
225                 230                 235                 240

Tyr Gly Ala Thr Gly His Pro Gly Ile Ile Pro Pro His Ala Thr Leu
                245                 250                 255

Val Phe Asp Val Glu Leu Leu Lys Leu Glu Pro Arg Glu Gly Arg Gly
            260                 265                 270

Ser Leu Leu Thr Cys Gly Asp Val Glu Glu Asn Pro Gly Pro Pro Trp
        275                 280                 285

Met Glu Phe Gly Leu Ser Trp Leu Phe Leu Val Ala Ile Leu Lys Gly
    290                 295                 300

Val Gln Cys Ser Arg Asp Ile Gln Leu Thr Gln Ser Pro Ser Thr Leu
305                 310                 315                 320

Ser Ala Ser Met Gly Asp Arg Val Thr Ile Thr Cys Ser Ala Ser Ser
                325                 330                 335

Ser Val Arg Phe Ile His Trp Tyr Gln Gln Lys Pro Gly Lys Ala Pro
            340                 345                 350

Lys Arg Leu Ile Tyr Asp Thr Ser Lys Leu Ala Ser Gly Val Pro Ser
        355                 360                 365

Arg Phe Ser Gly Ser Gly Ser Gly Thr Asp Phe Thr Leu Thr Ile Ser
    370                 375                 380

Ser Leu Gln Pro Glu Asp Phe Ala Thr Tyr Tyr Cys Gln Gln Trp Gly
385                 390                 395                 400

Ser Ser Pro Phe Thr Phe Gly Gln Gly Thr Lys Val Glu Ile Lys Gly
                405                 410                 415

Gly Gly Ser Gly Gly Gly Gly Gln Val Glu Val Gln Leu Val Glu Tyr
            420                 425                 430

Gly Gly Gly Leu Val Gln Pro Gly Gly Ser Leu Arg Leu Ser Cys Ala
        435                 440                 445

Ala Ser Gly Phe Asn Ile Lys Asp Tyr Tyr Ile His Trp Val Arg Gln
    450                 455                 460

Ala Pro Gly Lys Gly Leu Glu Trp Val Ala Trp Ile Asp Pro Glu Asn
465                 470                 475                 480

Gly Asp Thr Glu Phe Val Pro Lys Phe Gln Gly Arg Ala Thr Met Ser
                485                 490                 495

Ala Asp Thr Ser Lys Asn Thr Ala Tyr Leu Gln Met Asn Ser Leu Arg
            500                 505                 510

Ala Glu Asp Thr Ala Val Tyr Tyr Cys Lys Thr Gly Gly Phe Trp Gly
        515                 520                 525

Gln Gly Thr Leu Val Thr Val Ser Ser Gly Ser Glu Leu Pro Thr Gln
    530                 535                 540

Gly Thr Phe Ser Asn Val Ser Thr Asn Val Ser Pro Ala Pro Arg Pro
545                 550                 555                 560

Pro Thr Pro Ala Pro Thr Ile Ala Ser Gln Pro Leu Ser Leu Arg Pro
                565                 570                 575

Glu Ala Cys Arg Pro Ala Ala Gly Gly Ala Val His Thr Arg Gly Leu
```

580                 585                 590
Asp Phe Ala Cys Asp Ile Tyr Ile Trp Ala Pro Leu Ala Gly Thr Cys
            595                 600                 605

Gly Val Leu Leu Leu Ser Leu Val Ile Thr Leu Tyr Cys Asn His Arg
    610                 615                 620

Asn Arg Arg Arg Val Cys Lys Cys Pro Arg Val Asp Arg Val Lys Phe
625                 630                 635                 640

Ser Arg Ser Ala Asp Ala Pro Ala Tyr Gln Gln Gly Gln Asn Gln Leu
                645                 650                 655

Tyr Asn Glu Leu Asn Leu Gly Arg Arg Glu Glu Tyr Asp Val Leu Asp
            660                 665                 670

Lys Arg Arg Gly Arg Asp Pro Glu Met Gly Gly Lys Pro Arg Arg Lys
        675                 680                 685

Asn Pro Gln Glu Gly Leu Tyr Asn Glu Leu Gln Lys Asp Lys Met Ala
    690                 695                 700

Glu Ala Tyr Ser Glu Ile Gly Met Lys Gly Glu Arg Arg Arg Gly Lys
705                 710                 715                 720

Gly His Asp Gly Leu Tyr Gln Gly Leu Ser Thr Ala Thr Lys Asp Thr
                725                 730                 735

Tyr Asp Ala Leu His Met Gln Ala Leu Pro Pro Arg
            740                 745

<210> SEQ ID NO 144
<211> LENGTH: 892
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Met Gly Ser Ser Lys Ser Lys Pro Lys Asp Pro Ser Gln Arg Arg Ala
1               5                   10                  15

Cys Met Ala Ala Gly Gly Pro Gly Ala Gly Ser Ala Ala Pro Val Ser
            20                  25                  30

Ser Thr Ser Ser Leu Pro Leu Ala Ala Leu Asn Met Arg Val Arg Arg
        35                  40                  45

Arg Leu Ser Leu Phe Leu Asn Val Arg Thr Gln Val Ala Ala Asp Trp
    50                  55                  60

Thr Ala Leu Ala Glu Glu Met Asp Phe Glu Tyr Leu Glu Ile Arg Gln
65                  70                  75                  80

Leu Glu Thr Gln Ala Asp Pro Thr Gly Arg Leu Leu Asp Ala Trp Gln
                85                  90                  95

Gly Arg Pro Gly Ala Ser Val Gly Arg Leu Leu Asp Leu Leu Thr Lys
            100                 105                 110

Leu Gly Arg Asp Asp Val Leu Leu Glu Leu Gly Pro Ser Ile Glu Glu
        115                 120                 125

Asp Cys Gln Lys Tyr Ile Leu Lys Gln Gln Gln Glu Glu Ala Glu Lys
    130                 135                 140

Pro Leu Gln Val Ala Ala Val Asp Ser Ser Val Pro Arg Thr Ala Glu
145                 150                 155                 160

Leu Ala Gly Ile Thr Thr Leu Asp Asp Pro Leu Gly His Met Pro Glu
                165                 170                 175

Arg Phe Asp Ala Phe Ile Cys Tyr Cys Pro Ser Asp Ile Gly Ser Gly
            180                 185                 190

```
Gln Leu Gly Val Gln Val Glu Thr Ile Ser Pro Gly Asp Gly Arg Thr
            195                 200                 205

Phe Pro Lys Arg Gly Gln Thr Cys Val Val His Tyr Thr Gly Met Leu
    210                 215                 220

Glu Asp Gly Lys Lys Val Asp Ser Ser Arg Asp Arg Asn Lys Pro Phe
225                 230                 235                 240

Lys Phe Met Leu Gly Lys Gln Glu Val Ile Arg Gly Trp Glu Glu Gly
                245                 250                 255

Val Ala Gln Met Ser Val Gly Gln Arg Ala Lys Leu Thr Ile Ser Pro
            260                 265                 270

Asp Tyr Ala Tyr Gly Ala Thr Gly His Pro Gly Ile Ile Pro Pro His
    275                 280                 285

Ala Thr Leu Val Phe Asp Val Glu Leu Leu Lys Leu Glu Val Glu Gly
    290                 295                 300

Val Gln Val Glu Thr Ile Ser Pro Gly Asp Gly Arg Thr Phe Pro Lys
305                 310                 315                 320

Arg Gly Gln Thr Cys Val Val His Tyr Thr Gly Met Leu Glu Asp Gly
                325                 330                 335

Lys Lys Val Asp Ser Ser Arg Asp Arg Asn Lys Pro Phe Lys Phe Met
            340                 345                 350

Leu Gly Lys Gln Glu Val Ile Arg Gly Trp Glu Glu Gly Val Ala Gln
    355                 360                 365

Met Ser Val Gly Gln Arg Ala Lys Leu Thr Ile Ser Pro Asp Tyr Ala
    370                 375                 380

Tyr Gly Ala Thr Gly His Pro Gly Ile Ile Pro Pro His Ala Thr Leu
385                 390                 395                 400

Val Phe Asp Val Glu Leu Leu Lys Leu Glu Pro Arg Glu Gly Arg Gly
                405                 410                 415

Ser Leu Leu Thr Cys Gly Asp Val Glu Glu Asn Pro Gly Pro Pro Trp
            420                 425                 430

Met Glu Phe Gly Leu Ser Trp Leu Phe Leu Val Ala Ile Leu Lys Gly
    435                 440                 445

Val Gln Cys Ser Arg Asp Ile Gln Leu Thr Gln Ser Pro Ser Thr Leu
    450                 455                 460

Ser Ala Ser Met Gly Asp Arg Val Thr Ile Thr Cys Ser Ala Ser Ser
465                 470                 475                 480

Ser Val Arg Phe Ile His Trp Tyr Gln Gln Lys Pro Gly Lys Ala Pro
                485                 490                 495

Lys Arg Leu Ile Tyr Asp Thr Ser Lys Leu Ala Ser Gly Val Pro Ser
            500                 505                 510

Arg Phe Ser Gly Ser Gly Ser Gly Thr Asp Phe Thr Leu Thr Ile Ser
    515                 520                 525

Ser Leu Gln Pro Glu Asp Phe Ala Thr Tyr Tyr Cys Gln Gln Trp Gly
    530                 535                 540

Ser Ser Pro Phe Thr Phe Gly Gln Gly Thr Lys Val Glu Ile Lys Gly
545                 550                 555                 560

Gly Gly Ser Gly Gly Gly Gly Gln Val Glu Val Gln Leu Val Glu Tyr
                565                 570                 575

Gly Gly Gly Leu Val Gln Pro Gly Gly Ser Leu Arg Leu Ser Cys Ala
            580                 585                 590

Ala Ser Gly Phe Asn Ile Lys Asp Tyr Tyr Ile His Trp Val Arg Gln
    595                 600                 605

Ala Pro Gly Lys Gly Leu Glu Trp Val Ala Trp Ile Asp Pro Glu Asn
```

```
                    610                 615                 620
Gly Asp Thr Glu Phe Val Pro Lys Phe Gln Gly Arg Ala Thr Met Ser
625                 630                 635                 640

Ala Asp Thr Ser Lys Asn Thr Ala Tyr Leu Gln Met Asn Ser Leu Arg
                    645                 650                 655

Ala Glu Asp Thr Ala Val Tyr Tyr Cys Lys Thr Gly Gly Phe Trp Gly
                    660                 665                 670

Gln Gly Thr Leu Val Thr Val Ser Ser Gly Ser Glu Leu Pro Thr Gln
                    675                 680                 685

Gly Thr Phe Ser Asn Val Ser Thr Asn Val Ser Pro Ala Pro Arg Pro
690                 695                 700

Pro Thr Pro Ala Pro Thr Ile Ala Ser Gln Pro Leu Ser Leu Arg Pro
705                 710                 715                 720

Glu Ala Cys Arg Pro Ala Ala Gly Gly Ala Val His Thr Arg Gly Leu
                    725                 730                 735

Asp Phe Ala Cys Asp Ile Tyr Ile Trp Ala Pro Leu Ala Gly Thr Cys
                    740                 745                 750

Gly Val Leu Leu Leu Ser Leu Val Ile Thr Leu Tyr Cys Asn His Arg
                    755                 760                 765

Asn Arg Arg Arg Val Cys Lys Cys Pro Arg Val Asp Arg Val Lys Phe
770                 775                 780

Ser Arg Ser Ala Asp Ala Pro Ala Tyr Gln Gln Gly Gln Asn Gln Leu
785                 790                 795                 800

Tyr Asn Glu Leu Asn Leu Gly Arg Arg Glu Glu Tyr Asp Val Leu Asp
                    805                 810                 815

Lys Arg Arg Gly Arg Asp Pro Glu Met Gly Gly Lys Pro Arg Arg Lys
                    820                 825                 830

Asn Pro Gln Glu Gly Leu Tyr Asn Glu Leu Gln Lys Asp Lys Met Ala
                    835                 840                 845

Glu Ala Tyr Ser Glu Ile Gly Met Lys Gly Glu Arg Arg Arg Gly Lys
                    850                 855                 860

Gly His Asp Gly Leu Tyr Gln Gly Leu Ser Thr Ala Thr Lys Asp Thr
865                 870                 875                 880

Tyr Asp Ala Leu His Met Gln Ala Leu Pro Pro Arg
                    885                 890

<210> SEQ ID NO 145
<211> LENGTH: 956
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Met Gly Ser Ser Lys Ser Lys Pro Lys Asp Pro Ser Gln Arg Arg Ala
1               5                   10                  15

Cys Met Ala Ala Gly Gly Pro Gly Ala Gly Ser Ala Ala Pro Val Ser
                    20                  25                  30

Ser Thr Ser Ser Leu Pro Leu Ala Ala Leu Asn Met Arg Val Arg Arg
                    35                  40                  45

Arg Leu Ser Leu Phe Leu Asn Val Arg Thr Gln Val Ala Ala Asp Trp
                    50                  55                  60

Thr Ala Leu Ala Glu Glu Met Asp Phe Glu Tyr Leu Glu Ile Arg Gln
65                  70                  75                  80
```

```
Leu Glu Thr Gln Ala Asp Pro Thr Gly Arg Leu Leu Asp Ala Trp Gln
                85                  90                  95
Gly Arg Pro Gly Ala Ser Val Gly Arg Leu Leu Asp Leu Leu Thr Lys
            100                 105                 110
Leu Gly Arg Asp Asp Val Leu Leu Glu Leu Gly Pro Ser Ile Glu Glu
        115                 120                 125
Asp Cys Gln Lys Tyr Ile Leu Lys Gln Gln Gln Glu Glu Ala Glu Lys
    130                 135                 140
Pro Leu Gln Val Ala Ala Val Asp Ser Ser Val Pro Arg Thr Ala Glu
145                 150                 155                 160
Leu Ala Gly Ile Thr Thr Leu Asp Asp Pro Leu Gly His Met Pro Glu
                165                 170                 175
Arg Phe Asp Ala Phe Ile Cys Tyr Cys Pro Ser Asp Ile Leu Glu Lys
            180                 185                 190
Lys Val Ala Lys Lys Pro Thr Asn Lys Ala Pro His Pro Lys Gln Glu
        195                 200                 205
Pro Gln Glu Ile Asn Phe Pro Asp Asp Leu Pro Gly Ser Asn Thr Ala
    210                 215                 220
Ala Pro Val Gln Glu Thr Leu His Gly Cys Gln Pro Val Thr Gln Glu
225                 230                 235                 240
Asp Gly Lys Glu Ser Arg Ile Ser Val Gln Glu Arg Gln Gly Ser Gly
                245                 250                 255
Gln Leu Gly Val Gln Val Glu Thr Ile Ser Pro Gly Asp Gly Arg Thr
            260                 265                 270
Phe Pro Lys Arg Gly Gln Thr Cys Val Val His Tyr Thr Gly Met Leu
        275                 280                 285
Glu Asp Gly Lys Lys Val Asp Ser Ser Arg Asp Arg Asn Lys Pro Phe
    290                 295                 300
Lys Phe Met Leu Gly Lys Gln Glu Val Ile Arg Gly Trp Glu Glu Gly
305                 310                 315                 320
Val Ala Gln Met Ser Val Gly Gln Arg Ala Lys Leu Thr Ile Ser Pro
                325                 330                 335
Asp Tyr Ala Tyr Gly Ala Thr Gly His Pro Gly Ile Ile Pro Pro His
            340                 345                 350
Ala Thr Leu Val Phe Asp Val Glu Leu Leu Lys Leu Glu Val Glu Gly
        355                 360                 365
Val Gln Val Glu Thr Ile Ser Pro Gly Asp Gly Arg Thr Phe Pro Lys
    370                 375                 380
Arg Gly Gln Thr Cys Val Val His Tyr Thr Gly Met Leu Glu Asp Gly
385                 390                 395                 400
Lys Lys Val Asp Ser Ser Arg Asp Arg Asn Lys Pro Phe Lys Phe Met
                405                 410                 415
Leu Gly Lys Gln Glu Val Ile Arg Gly Trp Glu Glu Gly Val Ala Gln
            420                 425                 430
Met Ser Val Gly Gln Arg Ala Lys Leu Thr Ile Ser Pro Asp Tyr Ala
        435                 440                 445
Tyr Gly Ala Thr Gly His Pro Gly Ile Ile Pro Pro His Ala Thr Leu
    450                 455                 460
Val Phe Asp Val Glu Leu Leu Lys Leu Glu Pro Arg Glu Gly Arg Gly
465                 470                 475                 480
Ser Leu Leu Thr Cys Gly Asp Val Glu Glu Asn Pro Gly Pro Pro Trp
                485                 490                 495
Met Glu Phe Gly Leu Ser Trp Leu Phe Leu Val Ala Ile Leu Lys Gly
```

-continued

```
                500                 505                 510
Val Gln Cys Ser Arg Asp Ile Gln Leu Thr Gln Ser Pro Ser Thr Leu
            515                 520                 525
Ser Ala Ser Met Gly Asp Arg Val Thr Ile Thr Cys Ser Ala Ser Ser
            530                 535                 540
Ser Val Arg Phe Ile His Trp Tyr Gln Gln Lys Pro Gly Lys Ala Pro
545                 550                 555                 560
Lys Arg Leu Ile Tyr Asp Thr Ser Lys Leu Ala Ser Gly Val Pro Ser
                565                 570                 575
Arg Phe Ser Gly Ser Gly Ser Gly Thr Asp Phe Thr Leu Thr Ile Ser
            580                 585                 590
Ser Leu Gln Pro Glu Asp Phe Ala Thr Tyr Tyr Cys Gln Gln Trp Gly
            595                 600                 605
Ser Ser Pro Phe Thr Phe Gly Gln Gly Thr Lys Val Glu Ile Lys Gly
            610                 615                 620
Gly Gly Ser Gly Gly Gly Gly Gln Val Glu Val Gln Leu Val Glu Tyr
625                 630                 635                 640
Gly Gly Gly Leu Val Gln Pro Gly Gly Ser Leu Arg Leu Ser Cys Ala
                645                 650                 655
Ala Ser Gly Phe Asn Ile Lys Asp Tyr Tyr Ile His Trp Val Arg Gln
            660                 665                 670
Ala Pro Gly Lys Gly Leu Glu Trp Val Ala Trp Ile Asp Pro Glu Asn
            675                 680                 685
Gly Asp Thr Glu Phe Val Pro Lys Phe Gln Gly Arg Ala Thr Met Ser
            690                 695                 700
Ala Asp Thr Ser Lys Asn Thr Ala Tyr Leu Gln Met Asn Ser Leu Arg
705                 710                 715                 720
Ala Glu Asp Thr Ala Val Tyr Tyr Cys Lys Thr Gly Gly Phe Trp Gly
                725                 730                 735
Gln Gly Thr Leu Val Thr Val Ser Ser Gly Ser Glu Leu Pro Thr Gln
            740                 745                 750
Gly Thr Phe Ser Asn Val Ser Thr Asn Val Ser Pro Ala Pro Arg Pro
            755                 760                 765
Pro Thr Pro Ala Pro Thr Ile Ala Ser Gln Pro Leu Ser Leu Arg Pro
            770                 775                 780
Glu Ala Cys Arg Pro Ala Ala Gly Gly Ala Val His Thr Arg Gly Leu
785                 790                 795                 800
Asp Phe Ala Cys Asp Ile Tyr Ile Trp Ala Pro Leu Ala Gly Thr Cys
                805                 810                 815
Gly Val Leu Leu Leu Ser Leu Val Ile Thr Leu Tyr Cys Asn His Arg
            820                 825                 830
Asn Arg Arg Arg Val Cys Lys Cys Pro Arg Val Asp Arg Val Lys Phe
            835                 840                 845
Ser Arg Ser Ala Asp Ala Pro Ala Tyr Gln Gln Gly Gln Asn Gln Leu
            850                 855                 860
Tyr Asn Glu Leu Asn Leu Gly Arg Arg Glu Glu Tyr Asp Val Leu Asp
865                 870                 875                 880
Lys Arg Arg Gly Arg Asp Pro Glu Met Gly Gly Lys Pro Arg Arg Lys
                885                 890                 895
Asn Pro Gln Glu Gly Leu Tyr Asn Glu Leu Gln Lys Asp Lys Met Ala
            900                 905                 910
Glu Ala Tyr Ser Glu Ile Gly Met Lys Gly Glu Arg Arg Arg Gly Lys
            915                 920                 925
```

Gly His Asp Gly Leu Tyr Gln Gly Leu Ser Thr Ala Thr Lys Asp Thr
            930                 935                 940

Tyr Asp Ala Leu His Met Gln Ala Leu Pro Pro Arg
945                 950                 955

<210> SEQ ID NO 146
<211> LENGTH: 768
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Met Leu Glu Lys Lys Val Ala Lys Pro Thr Asn Lys Ala Pro His
1               5                   10                  15

Pro Lys Gln Glu Pro Gln Glu Ile Asn Phe Pro Asp Asp Leu Pro Gly
                20                  25                  30

Ser Asn Thr Ala Ala Pro Val Gln Glu Thr Leu His Gly Cys Gln Pro
            35                  40                  45

Val Thr Gln Glu Asp Gly Lys Glu Ser Arg Ile Ser Val Gln Glu Arg
        50                  55                  60

Gln Gly Ser Gly Gln Leu Gly Val Gln Val Glu Thr Ile Ser Pro Gly
65                  70                  75                  80

Asp Gly Arg Thr Phe Pro Lys Arg Gly Gln Thr Cys Val Val His Tyr
                85                  90                  95

Thr Gly Met Leu Glu Asp Gly Lys Lys Val Asp Ser Ser Arg Asp Arg
            100                 105                 110

Asn Lys Pro Phe Lys Phe Met Leu Gly Lys Gln Glu Val Ile Arg Gly
        115                 120                 125

Trp Glu Glu Gly Val Ala Gln Met Ser Val Gly Gln Arg Ala Lys Leu
130                 135                 140

Thr Ile Ser Pro Asp Tyr Ala Tyr Gly Ala Thr Gly His Pro Gly Ile
145                 150                 155                 160

Ile Pro Pro His Ala Thr Leu Val Phe Asp Val Glu Leu Leu Lys Leu
                165                 170                 175

Glu Val Glu Gly Val Gln Val Glu Thr Ile Ser Pro Gly Asp Gly Arg
            180                 185                 190

Thr Phe Pro Lys Arg Gly Gln Thr Cys Val Val His Tyr Thr Gly Met
        195                 200                 205

Leu Glu Asp Gly Lys Lys Val Asp Ser Ser Arg Asp Arg Asn Lys Pro
210                 215                 220

Phe Lys Phe Met Leu Gly Lys Gln Glu Val Ile Arg Gly Trp Glu Glu
225                 230                 235                 240

Gly Val Ala Gln Met Ser Val Gly Gln Arg Ala Lys Leu Thr Ile Ser
                245                 250                 255

Pro Asp Tyr Ala Tyr Gly Ala Thr Gly His Pro Gly Ile Ile Pro Pro
            260                 265                 270

His Ala Thr Leu Val Phe Asp Val Glu Leu Leu Lys Leu Glu Pro Arg
        275                 280                 285

Glu Gly Arg Gly Ser Leu Leu Thr Cys Gly Asp Val Glu Glu Asn Pro
290                 295                 300

Gly Pro Pro Trp Met Glu Phe Gly Leu Ser Trp Leu Phe Leu Val Ala
305                 310                 315                 320

Ile Leu Lys Gly Val Gln Cys Ser Arg Asp Ile Gln Leu Thr Gln Ser

-continued

```
                325                 330                 335
Pro Ser Thr Leu Ser Ala Ser Met Gly Asp Arg Val Thr Ile Thr Cys
            340                 345                 350

Ser Ala Ser Ser Ser Val Arg Phe Ile His Trp Tyr Gln Gln Lys Pro
            355                 360                 365

Gly Lys Ala Pro Lys Arg Leu Ile Tyr Asp Thr Ser Lys Leu Ala Ser
            370                 375                 380

Gly Val Pro Ser Arg Phe Ser Gly Ser Gly Ser Gly Thr Asp Phe Thr
385                 390                 395                 400

Leu Thr Ile Ser Ser Leu Gln Pro Glu Asp Phe Ala Thr Tyr Tyr Cys
                405                 410                 415

Gln Gln Trp Gly Ser Ser Pro Phe Thr Phe Gly Gln Gly Thr Lys Val
                420                 425                 430

Glu Ile Lys Gly Gly Gly Ser Gly Gly Gly Gln Val Glu Val Gln
                435                 440                 445

Leu Val Glu Tyr Gly Gly Gly Leu Val Gln Pro Gly Gly Ser Leu Arg
                450                 455                 460

Leu Ser Cys Ala Ala Ser Gly Phe Asn Ile Lys Asp Tyr Tyr Ile His
465                 470                 475                 480

Trp Val Arg Gln Ala Pro Gly Lys Gly Leu Glu Trp Val Ala Trp Ile
                485                 490                 495

Asp Pro Glu Asn Gly Asp Thr Glu Phe Val Pro Lys Phe Gln Gly Arg
                500                 505                 510

Ala Thr Met Ser Ala Asp Thr Ser Lys Asn Thr Ala Tyr Leu Gln Met
                515                 520                 525

Asn Ser Leu Arg Ala Glu Asp Thr Ala Val Tyr Tyr Cys Lys Thr Gly
                530                 535                 540

Gly Phe Trp Gly Gln Gly Thr Leu Val Thr Val Ser Ser Gly Ser Glu
545                 550                 555                 560

Leu Pro Thr Gln Gly Thr Phe Ser Asn Val Ser Thr Asn Val Ser Pro
                565                 570                 575

Ala Pro Arg Pro Pro Thr Pro Ala Pro Thr Ile Ala Ser Gln Pro Leu
                580                 585                 590

Ser Leu Arg Pro Glu Ala Cys Arg Pro Ala Ala Gly Gly Ala Val His
                595                 600                 605

Thr Arg Gly Leu Asp Phe Ala Cys Asp Ile Tyr Ile Trp Ala Pro Leu
                610                 615                 620

Ala Gly Thr Cys Gly Val Leu Leu Leu Ser Leu Val Ile Thr Leu Tyr
625                 630                 635                 640

Cys Asn His Arg Asn Arg Arg Val Cys Lys Cys Pro Arg Val Asp
                645                 650                 655

Arg Val Lys Phe Ser Arg Ser Ala Asp Ala Pro Ala Tyr Gln Gln Gly
                660                 665                 670

Gln Asn Gln Leu Tyr Asn Glu Leu Asn Leu Gly Arg Arg Glu Glu Tyr
                675                 680                 685

Asp Val Leu Asp Lys Arg Arg Gly Arg Asp Pro Glu Met Gly Gly Lys
                690                 695                 700

Pro Arg Arg Lys Asn Pro Gln Glu Gly Leu Tyr Asn Glu Leu Gln Lys
705                 710                 715                 720

Asp Lys Met Ala Glu Ala Tyr Ser Glu Ile Gly Met Lys Gly Glu Arg
                725                 730                 735

Arg Arg Gly Lys Gly His Asp Gly Leu Tyr Gln Gly Leu Ser Thr Ala
                740                 745                 750
```

```
Thr Lys Asp Thr Tyr Asp Ala Leu His Met Gln Ala Leu Pro Pro Arg
        755                 760                 765
```

<210> SEQ ID NO 147
<211> LENGTH: 782
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

```
Met Gly Ser Ser Lys Ser Lys Pro Lys Asp Pro Ser Gln Arg Arg Ala
1               5                   10                  15

Cys Lys Lys Val Ala Lys Lys Pro Thr Asn Lys Ala Pro His Pro Lys
                20                  25                  30

Gln Glu Pro Gln Glu Ile Asn Phe Pro Asp Leu Pro Gly Ser Asn
            35                  40                  45

Thr Ala Ala Pro Val Gln Glu Thr Leu His Gly Cys Gln Pro Val Thr
    50                  55                  60

Gln Glu Asp Gly Lys Glu Ser Arg Ile Ser Val Gln Glu Arg Gln Gly
65                  70                  75                  80

Ser Gly Gln Leu Gly Val Gln Val Glu Thr Ile Ser Pro Gly Asp Gly
                85                  90                  95

Arg Thr Phe Pro Lys Arg Gly Gln Thr Cys Val Val His Tyr Thr Gly
                100                 105                 110

Met Leu Glu Asp Gly Lys Lys Val Asp Ser Ser Arg Asp Arg Asn Lys
            115                 120                 125

Pro Phe Lys Phe Met Leu Gly Lys Gln Glu Val Ile Arg Gly Trp Glu
        130                 135                 140

Glu Gly Val Ala Gln Met Ser Val Gly Gln Arg Ala Lys Leu Thr Ile
145                 150                 155                 160

Ser Pro Asp Tyr Ala Tyr Gly Ala Thr Gly His Pro Gly Ile Ile Pro
                165                 170                 175

Pro His Ala Thr Leu Val Phe Asp Val Glu Leu Leu Lys Leu Glu Val
            180                 185                 190

Glu Gly Val Gln Val Glu Thr Ile Ser Pro Gly Asp Gly Arg Thr Phe
        195                 200                 205

Pro Lys Arg Gly Gln Thr Cys Val Val His Tyr Thr Gly Met Leu Glu
    210                 215                 220

Asp Gly Lys Lys Val Asp Ser Ser Arg Asp Arg Asn Lys Pro Phe Lys
225                 230                 235                 240

Phe Met Leu Gly Lys Gln Glu Val Ile Arg Gly Trp Glu Glu Gly Val
                245                 250                 255

Ala Gln Met Ser Val Gly Gln Arg Ala Lys Leu Thr Ile Ser Pro Asp
            260                 265                 270

Tyr Ala Tyr Gly Ala Thr Gly His Pro Gly Ile Ile Pro Pro His Ala
        275                 280                 285

Thr Leu Val Phe Asp Val Glu Leu Leu Lys Leu Glu Pro Arg Glu Gly
    290                 295                 300

Arg Gly Ser Leu Leu Thr Cys Gly Asp Val Glu Glu Asn Pro Gly Pro
305                 310                 315                 320

Pro Trp Met Glu Phe Gly Leu Ser Trp Leu Phe Leu Val Ala Ile Leu
                325                 330                 335

Lys Gly Val Gln Cys Ser Arg Asp Ile Gln Leu Thr Gln Ser Pro Ser
```

-continued

```
                340                 345                 350
Thr Leu Ser Ala Ser Met Gly Asp Arg Val Thr Ile Thr Cys Ser Ala
            355                 360                 365

Ser Ser Ser Val Arg Phe Ile His Trp Tyr Gln Gln Lys Pro Gly Lys
        370                 375                 380

Ala Pro Lys Arg Leu Ile Tyr Asp Thr Ser Lys Leu Ala Ser Gly Val
385                 390                 395                 400

Pro Ser Arg Phe Ser Gly Ser Gly Ser Gly Thr Asp Phe Thr Leu Thr
                405                 410                 415

Ile Ser Ser Leu Gln Pro Glu Asp Phe Ala Thr Tyr Tyr Cys Gln Gln
            420                 425                 430

Trp Gly Ser Ser Pro Phe Thr Phe Gly Gln Gly Thr Lys Val Glu Ile
        435                 440                 445

Lys Gly Gly Gly Ser Gly Gly Gly Gly Gln Val Glu Val Gln Leu Val
            450                 455                 460

Glu Tyr Gly Gly Gly Leu Val Gln Pro Gly Gly Ser Leu Arg Leu Ser
465                 470                 475                 480

Cys Ala Ala Ser Gly Phe Asn Ile Lys Asp Tyr Tyr Ile His Trp Val
                485                 490                 495

Arg Gln Ala Pro Gly Lys Gly Leu Glu Trp Val Ala Trp Ile Asp Pro
            500                 505                 510

Glu Asn Gly Asp Thr Glu Phe Val Pro Lys Phe Gln Gly Arg Ala Thr
        515                 520                 525

Met Ser Ala Asp Thr Ser Lys Asn Thr Ala Tyr Leu Gln Met Asn Ser
        530                 535                 540

Leu Arg Ala Glu Asp Thr Ala Val Tyr Tyr Cys Lys Thr Gly Gly Phe
545                 550                 555                 560

Trp Gly Gln Gly Thr Leu Val Thr Val Ser Ser Gly Ser Glu Leu Pro
                565                 570                 575

Thr Gln Gly Thr Phe Ser Asn Val Ser Thr Asn Val Ser Pro Ala Pro
            580                 585                 590

Arg Pro Pro Thr Pro Ala Pro Thr Ile Ala Ser Gln Pro Leu Ser Leu
        595                 600                 605

Arg Pro Glu Ala Cys Arg Pro Ala Ala Gly Gly Ala Val His Thr Arg
        610                 615                 620

Gly Leu Asp Phe Ala Cys Asp Ile Tyr Ile Trp Ala Pro Leu Ala Gly
625                 630                 635                 640

Thr Cys Gly Val Leu Leu Leu Ser Leu Val Ile Thr Leu Tyr Cys Asn
                645                 650                 655

His Arg Asn Arg Arg Arg Val Cys Lys Cys Pro Arg Val Asp Arg Val
            660                 665                 670

Lys Phe Ser Arg Ser Ala Asp Ala Pro Ala Tyr Gln Gln Gly Gln Asn
        675                 680                 685

Gln Leu Tyr Asn Glu Leu Asn Leu Gly Arg Arg Glu Glu Tyr Asp Val
        690                 695                 700

Leu Asp Lys Arg Arg Gly Arg Asp Pro Glu Met Gly Gly Lys Pro Arg
705                 710                 715                 720

Arg Lys Asn Pro Gln Glu Gly Leu Tyr Asn Glu Leu Gln Lys Asp Lys
                725                 730                 735

Met Ala Glu Ala Tyr Ser Glu Ile Gly Met Lys Gly Glu Arg Arg Arg
            740                 745                 750

Gly Lys Gly His Asp Gly Leu Tyr Gln Gly Leu Ser Thr Ala Thr Lys
        755                 760                 765
```

```
Asp Thr Tyr Asp Ala Leu His Met Gln Ala Leu Pro Pro Arg
        770                 775                 780

<210> SEQ ID NO 148
<211> LENGTH: 939
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
                20                  25                  30

Leu Ser Leu Phe Leu Asn Val Arg Thr Gln Val Ala Ala Asp Trp Thr
            35                  40                  45

Ala Leu Ala Glu Glu Met Asp Phe Glu Tyr Leu Glu Ile Arg Gln Leu
    50                  55                  60

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Thr Lys Leu
                85                  90                  95

Gly Arg Asp Asp Val Leu Leu Glu Leu Gly Pro Ser Ile Glu Glu Asp
                100                 105                 110

Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
    130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Leu Glu Lys Lys
                165                 170                 175

Val Ala Lys Lys Pro Thr Asn Lys Ala Pro His Pro Lys Gln Glu Pro
            180                 185                 190

Gln Glu Ile Asn Phe Pro Asp Asp Leu Pro Gly Ser Asn Thr Ala Ala
    195                 200                 205

Pro Val Gln Glu Thr Leu His Gly Cys Gln Pro Val Thr Gln Glu Asp
    210                 215                 220

Gly Lys Glu Ser Arg Ile Ser Val Gln Glu Arg Gln Gly Ser Gly Gln
225                 230                 235                 240

Leu Gly Val Gln Val Glu Thr Ile Ser Pro Gly Asp Gly Arg Thr Phe
                245                 250                 255

Pro Lys Arg Gly Gln Thr Cys Val Val His Tyr Thr Gly Met Leu Glu
            260                 265                 270

Asp Gly Lys Lys Val Asp Ser Ser Arg Asp Arg Asn Lys Pro Phe Lys
    275                 280                 285

Phe Met Leu Gly Lys Gln Glu Val Ile Arg Gly Trp Glu Glu Gly Val
    290                 295                 300

Ala Gln Met Ser Val Gly Gln Arg Ala Lys Leu Thr Ile Ser Pro Asp
305                 310                 315                 320

Tyr Ala Tyr Gly Ala Thr Gly His Pro Gly Ile Ile Pro Pro His Ala
                325                 330                 335

Thr Leu Val Phe Asp Val Glu Leu Leu Lys Leu Glu Val Glu Gly Val
```

-continued

```
            340                 345                 350
Gln Val Glu Thr Ile Ser Pro Gly Asp Gly Arg Thr Phe Pro Lys Arg
        355                 360                 365
Gly Gln Thr Cys Val Val His Tyr Thr Gly Met Leu Glu Asp Gly Lys
        370                 375                 380
Lys Val Asp Ser Ser Arg Asp Arg Asn Lys Pro Phe Lys Phe Met Leu
385                 390                 395                 400
Gly Lys Gln Glu Val Ile Arg Gly Trp Glu Glu Gly Val Ala Gln Met
                405                 410                 415
Ser Val Gly Gln Arg Ala Lys Leu Thr Ile Ser Pro Asp Tyr Ala Tyr
            420                 425                 430
Gly Ala Thr Gly His Pro Gly Ile Ile Pro Pro His Ala Thr Leu Val
        435                 440                 445
Phe Asp Val Glu Leu Leu Lys Leu Glu Pro Arg Glu Gly Arg Gly Ser
        450                 455                 460
Leu Leu Thr Cys Gly Asp Val Glu Glu Asn Pro Gly Pro Pro Trp Met
465                 470                 475                 480
Glu Phe Gly Leu Ser Trp Leu Phe Leu Val Ala Ile Leu Lys Gly Val
                485                 490                 495
Gln Cys Ser Arg Asp Ile Gln Leu Thr Gln Ser Pro Ser Thr Leu Ser
            500                 505                 510
Ala Ser Met Gly Asp Arg Val Thr Ile Thr Cys Ser Ala Ser Ser Ser
        515                 520                 525
Val Arg Phe Ile His Trp Tyr Gln Gln Lys Pro Gly Lys Ala Pro Lys
        530                 535                 540
Arg Leu Ile Tyr Asp Thr Ser Lys Leu Ala Ser Gly Val Pro Ser Arg
545                 550                 555                 560
Phe Ser Gly Ser Gly Ser Gly Thr Asp Phe Thr Leu Thr Ile Ser Ser
                565                 570                 575
Leu Gln Pro Glu Asp Phe Ala Thr Tyr Tyr Cys Gln Gln Trp Gly Ser
            580                 585                 590
Ser Pro Phe Thr Phe Gly Gln Gly Thr Lys Val Glu Ile Lys Gly Gly
        595                 600                 605
Gly Ser Gly Gly Gly Gly Gln Val Glu Val Gln Leu Val Glu Tyr Gly
        610                 615                 620
Gly Gly Leu Val Gln Pro Gly Gly Ser Leu Arg Leu Ser Cys Ala Ala
625                 630                 635                 640
Ser Gly Phe Asn Ile Lys Asp Tyr Tyr Ile His Trp Val Arg Gln Ala
                645                 650                 655
Pro Gly Lys Gly Leu Glu Trp Val Ala Trp Ile Asp Pro Glu Asn Gly
            660                 665                 670
Asp Thr Glu Phe Val Pro Lys Phe Gln Gly Arg Ala Thr Met Ser Ala
        675                 680                 685
Asp Thr Ser Lys Asn Thr Ala Tyr Leu Gln Met Asn Ser Leu Arg Ala
        690                 695                 700
Glu Asp Thr Ala Val Tyr Tyr Cys Lys Thr Gly Gly Phe Trp Gly Gln
705                 710                 715                 720
Gly Thr Leu Val Thr Val Ser Ser Gly Ser Glu Leu Pro Thr Gln Gly
                725                 730                 735
Thr Phe Ser Asn Val Ser Thr Asn Val Ser Pro Ala Pro Arg Pro Pro
            740                 745                 750
Thr Pro Ala Pro Thr Ile Ala Ser Gln Pro Leu Ser Leu Arg Pro Glu
        755                 760                 765
```

```
Ala Cys Arg Pro Ala Ala Gly Gly Ala Val His Thr Arg Gly Leu Asp
        770                 775                 780

Phe Ala Cys Asp Ile Tyr Ile Trp Ala Pro Leu Ala Gly Thr Cys Gly
785                 790                 795                 800

Val Leu Leu Leu Ser Leu Val Ile Thr Leu Tyr Cys Asn His Arg Asn
            805                 810                 815

Arg Arg Arg Val Cys Lys Cys Pro Arg Val Asp Arg Val Lys Phe Ser
        820                 825                 830

Arg Ser Ala Asp Ala Pro Ala Tyr Gln Gln Gly Gln Asn Gln Leu Tyr
        835                 840                 845

Asn Glu Leu Asn Leu Gly Arg Arg Glu Glu Tyr Asp Val Leu Asp Lys
    850                 855                 860

Arg Arg Gly Arg Asp Pro Glu Met Gly Gly Lys Pro Arg Arg Lys Asn
865                 870                 875                 880

Pro Gln Glu Gly Leu Tyr Asn Glu Leu Gln Lys Asp Lys Met Ala Glu
                885                 890                 895

Ala Tyr Ser Glu Ile Gly Met Lys Gly Glu Arg Arg Arg Gly Lys Gly
                900                 905                 910

His Asp Gly Leu Tyr Gln Gly Leu Ser Thr Ala Thr Lys Asp Thr Tyr
            915                 920                 925

Asp Ala Leu His Met Gln Ala Leu Pro Pro Arg
    930                 935

<210> SEQ ID NO 149
<211> LENGTH: 896
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

Met Leu Glu Met Leu Glu Gly Val Gln Val Thr Ile Ser Pro Gly
1               5                   10                  15

Asp Gly Arg Thr Phe Pro Lys Arg Gly Gln Thr Cys Val Val His Tyr
            20                  25                  30

Thr Gly Met Leu Glu Asp Gly Lys Lys Phe Asp Ser Ser Arg Asp Arg
        35                  40                  45

Asn Lys Pro Phe Lys Phe Met Leu Gly Lys Gln Glu Val Ile Arg Gly
    50                  55                  60

Trp Glu Glu Gly Val Ala Gln Met Ser Val Gly Gln Arg Ala Lys Leu
65                  70                  75                  80

Thr Ile Ser Pro Asp Tyr Ala Tyr Gly Ala Thr Gly His Pro Gly Ile
                85                  90                  95

Ile Pro Pro His Ala Thr Leu Val Phe Asp Val Glu Leu Leu Lys Leu
            100                 105                 110

Glu Ser Gly Gly Gly Ser Gly Val Asp Gly Phe Gly Asp Val Gly Ala
        115                 120                 125

Leu Glu Ser Leu Arg Gly Asn Ala Asp Leu Ala Tyr Ile Leu Ser Met
    130                 135                 140

Glu Pro Cys Gly His Cys Leu Ile Ile Asn Asn Val Asn Phe Cys Arg
145                 150                 155                 160

Glu Ser Gly Leu Arg Thr Arg Thr Gly Ser Asn Ile Asp Cys Glu Lys
                165                 170                 175

Leu Arg Arg Arg Phe Ser Ser Leu His Phe Met Val Glu Val Lys Gly
```

```
                    180                 185                 190
Asp Leu Thr Ala Lys Lys Met Val Leu Ala Leu Leu Glu Leu Ala Arg
            195                 200                 205
Gln Asp His Gly Ala Leu Asp Cys Cys Val Val Ile Leu Ser His
            210                 215                 220
Gly Cys Gln Ala Ser His Leu Gln Phe Pro Gly Ala Val Tyr Gly Thr
225                 230                 235                 240
Asp Gly Cys Pro Val Ser Val Glu Lys Ile Val Asn Ile Phe Asn Gly
                    245                 250                 255
Thr Ser Cys Pro Ser Leu Gly Gly Lys Pro Lys Leu Phe Phe Ile Gln
                260                 265                 270
Ala Cys Gly Gly Glu Gln Lys Asp His Gly Phe Glu Val Ala Ser Thr
            275                 280                 285
Ser Pro Glu Asp Glu Ser Pro Gly Ser Asn Pro Glu Pro Asp Ala Thr
            290                 295                 300
Pro Phe Gln Glu Gly Leu Arg Thr Phe Asp Gln Leu Asp Ala Ile Ser
305                 310                 315                 320
Ser Leu Pro Thr Pro Ser Asp Ile Phe Val Ser Tyr Ser Thr Phe Pro
                325                 330                 335
Gly Phe Val Ser Trp Arg Asp Pro Lys Ser Gly Ser Trp Tyr Val Glu
                340                 345                 350
Thr Leu Asp Asp Ile Phe Glu Gln Trp Ala His Ser Glu Asp Leu Gln
            355                 360                 365
Ser Leu Leu Leu Arg Val Ala Asn Ala Val Ser Val Lys Gly Ile Tyr
            370                 375                 380
Lys Gln Met Pro Gly Cys Phe Asn Phe Leu Arg Lys Lys Leu Phe Phe
385                 390                 395                 400
Lys Thr Ser Ala Ser Arg Ala Pro Arg Glu Gly Arg Gly Ser Leu Leu
                405                 410                 415
Thr Cys Gly Asp Val Glu Glu Asn Pro Gly Pro Pro Trp Met Glu Phe
                420                 425                 430
Gly Leu Ser Trp Leu Phe Leu Val Ala Ile Leu Lys Gly Val Gln Cys
            435                 440                 445
Ser Arg Asp Ile Gln Met Thr Gln Thr Thr Ser Ser Leu Ser Ala Ser
            450                 455                 460
Leu Gly Asp Arg Val Thr Ile Ser Cys Arg Ala Ser Gln Asp Ile Ser
465                 470                 475                 480
Lys Tyr Leu Asn Trp Tyr Gln Gln Lys Pro Asp Gly Thr Val Lys Leu
                485                 490                 495
Leu Ile Tyr His Thr Ser Arg Leu His Ser Gly Val Pro Ser Arg Phe
                500                 505                 510
Ser Gly Ser Gly Ser Gly Thr Asp Tyr Ser Leu Thr Ile Ser Asn Leu
            515                 520                 525
Glu Gln Glu Asp Ile Ala Thr Tyr Phe Cys Gln Gln Gly Asn Thr Leu
            530                 535                 540
Pro Tyr Thr Phe Gly Gly Gly Thr Lys Leu Glu Ile Thr Gly Gly Gly
545                 550                 555                 560
Ser Gly Gly Gly Gly Glu Val Lys Leu Gln Glu Ser Gly Pro Gly Leu
                565                 570                 575
Val Ala Pro Ser Gln Ser Leu Ser Val Thr Cys Thr Val Ser Gly Val
            580                 585                 590
Ser Leu Pro Asp Tyr Gly Val Ser Trp Ile Arg Gln Pro Pro Arg Lys
            595                 600                 605
```

```
Gly Leu Glu Trp Leu Gly Val Ile Trp Gly Ser Glu Thr Thr Tyr Tyr
            610                 615                 620

Asn Ser Ala Leu Lys Ser Arg Leu Thr Ile Ile Lys Asp Asn Ser Lys
625                 630                 635                 640

Ser Gln Val Phe Leu Lys Met Asn Ser Leu Gln Thr Asp Asp Thr Ala
                645                 650                 655

Ile Tyr Tyr Cys Ala Lys His Tyr Tyr Gly Gly Ser Tyr Ala Met
                660                 665                 670

Asp Tyr Trp Gly Gln Gly Thr Ser Val Thr Val Ser Ser Gly Ser Glu
                675                 680                 685

Leu Pro Thr Gln Gly Thr Phe Ser Asn Val Ser Thr Asn Val Ser Pro
690                 695                 700

Ala Pro Arg Pro Pro Thr Pro Ala Pro Thr Ile Ala Ser Gln Pro Leu
705                 710                 715                 720

Ser Leu Arg Pro Glu Ala Cys Arg Pro Ala Ala Gly Gly Ala Val His
                725                 730                 735

Thr Arg Gly Leu Asp Phe Ala Cys Asp Ile Tyr Ile Trp Ala Pro Leu
                740                 745                 750

Ala Gly Thr Cys Gly Val Leu Leu Leu Ser Leu Val Ile Thr Leu Tyr
                755                 760                 765

Cys Asn His Arg Asn Arg Arg Arg Val Cys Lys Cys Pro Arg Val Asp
770                 775                 780

Arg Val Lys Phe Ser Arg Ser Ala Asp Ala Pro Ala Tyr Gln Gln Gly
785                 790                 795                 800

Gln Asn Gln Leu Tyr Asn Glu Leu Asn Leu Gly Arg Arg Glu Glu Tyr
                805                 810                 815

Asp Val Leu Asp Lys Arg Arg Gly Arg Asp Pro Glu Met Gly Gly Lys
                820                 825                 830

Pro Arg Arg Lys Asn Pro Gln Glu Gly Leu Tyr Asn Glu Leu Gln Lys
                835                 840                 845

Asp Lys Met Ala Glu Ala Tyr Ser Glu Ile Gly Met Lys Gly Glu Arg
850                 855                 860

Arg Arg Gly Lys Gly His Asp Gly Leu Tyr Gln Gly Leu Ser Thr Ala
865                 870                 875                 880

Thr Lys Asp Thr Tyr Asp Ala Leu His Met Gln Ala Leu Pro Pro Arg
                885                 890                 895

<210> SEQ ID NO 150
<211> LENGTH: 1157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

Met Leu Glu Met Leu Glu Gly Val Gln Val Thr Ile Ser Pro Gly
1               5                   10                  15

Asp Gly Arg Thr Phe Pro Lys Arg Gly Gln Thr Cys Val Val His Tyr
                20                  25                  30

Thr Gly Met Leu Glu Asp Gly Lys Lys Phe Asp Ser Ser Arg Asp Arg
                35                  40                  45

Asn Lys Pro Phe Lys Phe Met Leu Gly Lys Gln Glu Val Ile Arg Gly
50                  55                  60

Trp Glu Glu Gly Val Ala Gln Met Ser Val Gly Gln Arg Ala Lys Leu
```

```
              65                  70                  75                  80
         Thr Ile Ser Pro Asp Tyr Ala Tyr Gly Ala Thr Gly His Pro Gly Ile
                          85                  90                  95
         Ile Pro Pro His Ala Thr Leu Val Phe Asp Val Glu Leu Leu Lys Leu
                         100                 105                 110
         Glu Ser Gly Gly Ser Gly Val Asp Gly Phe Gly Asp Val Gly Ala
                 115                 120                 125
         Leu Glu Ser Leu Arg Gly Asn Ala Asp Leu Ala Tyr Ile Leu Ser Met
             130                 135                 140
         Glu Pro Cys Gly His Cys Leu Ile Ile Asn Asn Val Asn Phe Cys Arg
         145                 150                 155                 160
         Glu Ser Gly Leu Arg Thr Arg Thr Gly Ser Asn Ile Asp Cys Glu Lys
                         165                 170                 175
         Leu Arg Arg Arg Phe Ser Ser Leu His Phe Met Val Glu Val Lys Gly
                     180                 185                 190
         Asp Leu Thr Ala Lys Lys Met Val Leu Ala Leu Leu Glu Leu Ala Arg
                     195                 200                 205
         Gln Asp His Gly Ala Leu Asp Cys Cys Val Val Ile Leu Ser His
             210                 215                 220
         Gly Cys Gln Ala Ser His Leu Gln Phe Pro Gly Ala Val Tyr Gly Thr
         225                 230                 235                 240
         Asp Gly Cys Pro Val Ser Val Glu Lys Ile Val Asn Ile Phe Asn Gly
                         245                 250                 255
         Thr Ser Cys Pro Ser Leu Gly Gly Lys Pro Lys Leu Phe Phe Ile Gln
                         260                 265                 270
         Ala Cys Gly Gly Glu Gln Lys Asp His Gly Phe Glu Val Ala Ser Thr
                     275                 280                 285
         Ser Pro Glu Asp Glu Ser Pro Gly Ser Asn Pro Glu Pro Asp Ala Thr
                 290                 295                 300
         Pro Phe Gln Glu Gly Leu Arg Thr Phe Asp Gln Leu Asp Ala Ile Ser
         305                 310                 315                 320
         Ser Leu Pro Thr Pro Ser Asp Ile Phe Val Ser Tyr Ser Thr Phe Pro
                         325                 330                 335
         Gly Phe Val Ser Trp Arg Asp Pro Lys Ser Gly Ser Trp Tyr Val Glu
                     340                 345                 350
         Thr Leu Asp Asp Ile Phe Glu Gln Trp Ala His Ser Glu Asp Leu Gln
                     355                 360                 365
         Ser Leu Leu Leu Arg Val Ala Asn Ala Val Ser Val Lys Gly Ile Tyr
                 370                 375                 380
         Lys Gln Met Pro Gly Cys Phe Asn Phe Leu Arg Lys Lys Leu Phe Phe
         385                 390                 395                 400
         Lys Thr Ser Ala Ser Arg Ala Pro Arg Glu Gly Arg Gly Ser Leu Leu
                         405                 410                 415
         Thr Cys Gly Asp Val Glu Glu Asn Pro Gly Pro Pro Trp Met Glu Phe
                         420                 425                 430
         Gly Leu Ser Trp Leu Phe Leu Val Ala Ile Leu Lys Gly Val Gln Cys
                     435                 440                 445
         Ser Arg Asp Ile Gln Met Thr Gln Thr Thr Ser Ser Leu Ser Ala Ser
                 450                 455                 460
         Leu Gly Asp Arg Val Thr Ile Ser Cys Arg Ala Ser Gln Asp Ile Ser
         465                 470                 475                 480
         Lys Tyr Leu Asn Trp Tyr Gln Gln Lys Pro Asp Gly Thr Val Lys Leu
                         485                 490                 495
```

```
Leu Ile Tyr His Thr Ser Arg Leu His Ser Gly Val Pro Ser Arg Phe
            500                 505                 510

Ser Gly Ser Gly Ser Gly Thr Asp Tyr Ser Leu Thr Ile Ser Asn Leu
            515                 520                 525

Glu Gln Glu Asp Ile Ala Thr Tyr Phe Cys Gln Gln Gly Asn Thr Leu
            530                 535                 540

Pro Tyr Thr Phe Gly Gly Gly Thr Lys Leu Glu Ile Thr Gly Gly Gly
545                 550                 555                 560

Ser Gly Gly Gly Gly Glu Val Lys Leu Gln Glu Ser Gly Pro Gly Leu
            565                 570                 575

Val Ala Pro Ser Gln Ser Leu Ser Val Thr Cys Thr Val Ser Gly Val
            580                 585                 590

Ser Leu Pro Asp Tyr Gly Val Ser Trp Ile Arg Gln Pro Pro Arg Lys
            595                 600                 605

Gly Leu Glu Trp Leu Gly Val Ile Trp Gly Ser Glu Thr Thr Tyr Tyr
            610                 615                 620

Asn Ser Ala Leu Lys Ser Arg Leu Thr Ile Ile Lys Asp Asn Ser Lys
625                 630                 635                 640

Ser Gln Val Phe Leu Lys Met Asn Ser Leu Gln Thr Asp Asp Thr Ala
            645                 650                 655

Ile Tyr Tyr Cys Ala Lys His Tyr Tyr Tyr Gly Gly Ser Tyr Ala Met
            660                 665                 670

Asp Tyr Trp Gly Gln Gly Thr Ser Val Thr Val Ser Ser Gly Ser Glu
            675                 680                 685

Leu Pro Thr Gln Gly Thr Phe Ser Asn Val Ser Thr Asn Val Ser Pro
            690                 695                 700

Ala Pro Arg Pro Pro Thr Pro Ala Pro Thr Ile Ala Ser Gln Pro Leu
705                 710                 715                 720

Ser Leu Arg Pro Glu Ala Cys Arg Pro Ala Ala Gly Gly Ala Val His
            725                 730                 735

Thr Arg Gly Leu Asp Phe Ala Cys Asp Ile Tyr Ile Trp Ala Pro Leu
            740                 745                 750

Ala Gly Thr Cys Gly Val Leu Leu Leu Ser Leu Val Ile Thr Leu Tyr
            755                 760                 765

Cys Asn His Arg Asn Arg Arg Val Cys Lys Cys Pro Arg Val Asp
770                 775                 780

Arg Val Lys Phe Ser Arg Ser Ala Asp Ala Pro Ala Tyr Gln Gln Gly
785                 790                 795                 800

Gln Asn Gln Leu Tyr Asn Glu Leu Asn Leu Gly Arg Arg Glu Glu Tyr
            805                 810                 815

Asp Val Leu Asp Lys Arg Arg Gly Arg Asp Pro Glu Met Gly Gly Lys
            820                 825                 830

Pro Arg Arg Lys Asn Pro Gln Glu Gly Leu Tyr Asn Glu Leu Gln Lys
            835                 840                 845

Asp Lys Met Ala Glu Ala Tyr Ser Glu Ile Gly Met Lys Gly Glu Arg
            850                 855                 860

Arg Arg Gly Lys Gly His Asp Gly Leu Tyr Gln Gly Leu Ser Thr Ala
865                 870                 875                 880

Thr Lys Asp Thr Tyr Asp Ala Leu His Met Gln Ala Leu Pro Pro Arg
            885                 890                 895

Met Leu Glu Met Leu Glu Ala Thr Asn Phe Ser Leu Leu Lys Gln Ala
            900                 905                 910
```

```
Gly Asp Val Glu Glu Asn Pro Gly Pro Met Ala Ala Gly Gly Pro Gly
            915                 920                 925

Ala Gly Ser Ala Ala Pro Val Ser Ser Thr Ser Ser Leu Pro Leu Ala
    930                 935                 940

Ala Leu Asn Met Arg Val Arg Arg Arg Leu Ser Leu Phe Leu Asn Val
945                 950                 955                 960

Arg Thr Gln Val Ala Ala Asp Trp Thr Ala Leu Ala Glu Glu Met Asp
                965                 970                 975

Phe Glu Tyr Leu Glu Ile Arg Gln Leu Glu Thr Gln Ala Asp Pro Thr
            980                 985                 990

Gly Arg Leu Leu Asp Ala Trp Gln Gly Arg Pro Gly Ala Ser Val Gly
        995                 1000                1005

Arg Leu Leu Asp Leu Leu Thr Lys Leu Gly Arg Asp Asp Val Leu
    1010                1015                1020

Leu Glu Leu Gly Pro Ser Ile Glu Glu Asp Cys Gln Lys Tyr Ile
    1025                1030                1035

Leu Lys Gln Gln Gln Glu Glu Ala Glu Lys Pro Leu Gln Val Ala
    1040                1045                1050

Ala Val Asp Ser Ser Val Pro Arg Thr Ala Glu Leu Ala Gly Ile
    1055                1060                1065

Thr Thr Leu Asp Asp Pro Leu Gly His Met Pro Glu Arg Phe Asp
    1070                1075                1080

Ala Phe Ile Cys Tyr Cys Pro Ser Asp Ile Val Glu Lys Lys Val
    1085                1090                1095

Ala Lys Lys Pro Thr Asn Lys Ala Pro His Pro Lys Gln Glu Pro
    1100                1105                1110

Gln Glu Ile Asn Phe Pro Asp Leu Pro Gly Ser Asn Thr Ala
    1115                1120                1125

Ala Pro Val Gln Glu Thr Leu His Gly Cys Gln Pro Val Thr Gln
    1130                1135                1140

Glu Asp Gly Lys Glu Ser Arg Ile Ser Val Gln Glu Arg Gln
    1145                1150                1155

<210> SEQ ID NO 151
<211> LENGTH: 1154
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

Met Leu Glu Met Leu Glu Gly Val Gln Val Glu Thr Ile Ser Pro Gly
1               5                   10                  15

Asp Gly Arg Thr Phe Pro Lys Arg Gly Gln Thr Cys Val Val His Tyr
            20                  25                  30

Thr Gly Met Leu Glu Asp Gly Lys Lys Phe Asp Ser Ser Arg Asp Arg
        35                  40                  45

Asn Lys Pro Phe Lys Phe Met Leu Gly Lys Gln Glu Val Ile Arg Gly
    50                  55                  60

Trp Glu Glu Gly Val Ala Gln Met Ser Val Gly Gln Arg Ala Lys Leu
65                  70                  75                  80

Thr Ile Ser Pro Asp Tyr Ala Tyr Gly Ala Thr Gly His Pro Gly Ile
                85                  90                  95

Ile Pro Pro His Ala Thr Leu Val Phe Asp Val Glu Leu Leu Lys Leu
            100                 105                 110
```

```
Glu Ser Gly Gly Gly Ser Gly Val Asp Gly Phe Gly Asp Val Gly Ala
            115                 120                 125

Leu Glu Ser Leu Arg Gly Asn Ala Asp Leu Ala Tyr Ile Leu Ser Met
        130                 135                 140

Glu Pro Cys Gly His Cys Leu Ile Ile Asn Asn Val Asn Phe Cys Arg
145                 150                 155                 160

Glu Ser Gly Leu Arg Thr Arg Thr Gly Ser Asn Ile Asp Cys Glu Lys
                165                 170                 175

Leu Arg Arg Arg Phe Ser Ser Leu His Phe Met Val Glu Val Lys Gly
                180                 185                 190

Asp Leu Thr Ala Lys Lys Met Val Leu Ala Leu Leu Glu Leu Ala Arg
            195                 200                 205

Gln Asp His Gly Ala Leu Asp Cys Cys Val Val Val Ile Leu Ser His
        210                 215                 220

Gly Cys Gln Ala Ser His Leu Gln Phe Pro Gly Ala Val Tyr Gly Thr
225                 230                 235                 240

Asp Gly Cys Pro Val Ser Val Glu Lys Ile Val Asn Ile Phe Asn Gly
                245                 250                 255

Thr Ser Cys Pro Ser Leu Gly Gly Lys Pro Lys Leu Phe Phe Ile Gln
                260                 265                 270

Ala Cys Gly Gly Glu Gln Lys Asp His Gly Phe Glu Val Ala Ser Thr
            275                 280                 285

Ser Pro Glu Asp Glu Ser Pro Gly Ser Asn Pro Glu Pro Asp Ala Thr
        290                 295                 300

Pro Phe Gln Glu Gly Leu Arg Thr Phe Asp Gln Leu Asp Ala Ile Ser
305                 310                 315                 320

Ser Leu Pro Thr Pro Ser Asp Ile Phe Val Ser Tyr Ser Thr Phe Pro
                325                 330                 335

Gly Phe Val Ser Trp Arg Asp Pro Lys Ser Gly Ser Trp Tyr Val Glu
                340                 345                 350

Thr Leu Asp Asp Ile Phe Glu Gln Trp Ala His Ser Glu Asp Leu Gln
            355                 360                 365

Ser Leu Leu Leu Arg Val Ala Asn Ala Val Ser Val Lys Gly Ile Tyr
        370                 375                 380

Lys Gln Met Pro Gly Cys Phe Asn Phe Leu Arg Lys Lys Leu Phe Phe
385                 390                 395                 400

Lys Thr Ser Ala Ser Arg Ala Pro Arg Glu Gly Arg Gly Ser Leu Leu
                405                 410                 415

Thr Cys Gly Asp Val Glu Glu Asn Pro Gly Pro Trp Met Glu Phe
                420                 425                 430

Gly Leu Ser Trp Leu Phe Leu Val Ala Ile Leu Lys Gly Val Gln Cys
            435                 440                 445

Ser Arg Asp Ile Gln Met Thr Gln Thr Thr Ser Ser Leu Ser Ala Ser
        450                 455                 460

Leu Gly Asp Arg Val Thr Ile Ser Cys Arg Ala Ser Gln Asp Ile Ser
465                 470                 475                 480

Lys Tyr Leu Asn Trp Tyr Gln Gln Lys Pro Asp Gly Thr Val Lys Leu
                485                 490                 495

Leu Ile Tyr His Thr Ser Arg Leu His Ser Gly Val Pro Ser Arg Phe
                500                 505                 510

Ser Gly Ser Gly Ser Gly Thr Asp Tyr Ser Leu Thr Ile Ser Asn Leu
            515                 520                 525
```

```
Glu Gln Glu Asp Ile Ala Thr Tyr Phe Cys Gln Gln Gly Asn Thr Leu
530                 535                 540

Pro Tyr Thr Phe Gly Gly Gly Thr Lys Leu Glu Ile Thr Gly Gly Gly
545                 550                 555                 560

Ser Gly Gly Gly Gly Glu Val Lys Leu Gln Glu Ser Gly Pro Gly Leu
                565                 570                 575

Val Ala Pro Ser Gln Ser Leu Ser Val Thr Cys Thr Val Ser Gly Val
            580                 585                 590

Ser Leu Pro Asp Tyr Gly Val Ser Trp Ile Arg Gln Pro Pro Arg Lys
        595                 600                 605

Gly Leu Glu Trp Leu Gly Val Ile Trp Gly Ser Glu Thr Thr Tyr Tyr
610                 615                 620

Asn Ser Ala Leu Lys Ser Arg Leu Thr Ile Ile Lys Asp Asn Ser Lys
625                 630                 635                 640

Ser Gln Val Phe Leu Lys Met Asn Ser Leu Gln Thr Asp Asp Thr Ala
                645                 650                 655

Ile Tyr Tyr Cys Ala Lys His Tyr Tyr Tyr Gly Gly Ser Tyr Ala Met
            660                 665                 670

Asp Tyr Trp Gly Gln Gly Thr Ser Val Thr Val Ser Ser Gly Ser Glu
        675                 680                 685

Leu Pro Thr Gln Gly Thr Phe Ser Asn Val Ser Thr Asn Val Ser Pro
690                 695                 700

Ala Pro Arg Pro Pro Thr Pro Ala Pro Thr Ile Ala Ser Gln Pro Leu
705                 710                 715                 720

Ser Leu Arg Pro Glu Ala Cys Arg Pro Ala Ala Gly Gly Ala Val His
                725                 730                 735

Thr Arg Gly Leu Asp Phe Ala Cys Asp Ile Tyr Ile Trp Ala Pro Leu
            740                 745                 750

Ala Gly Thr Cys Gly Val Leu Leu Leu Ser Leu Val Ile Thr Leu Tyr
        755                 760                 765

Cys Asn His Arg Asn Arg Arg Val Cys Lys Cys Pro Arg Val Asp
770                 775                 780

Arg Val Lys Phe Ser Arg Ser Ala Asp Ala Pro Ala Tyr Gln Gln Gly
785                 790                 795                 800

Gln Asn Gln Leu Tyr Asn Glu Leu Asn Leu Gly Arg Arg Glu Glu Tyr
                805                 810                 815

Asp Val Leu Asp Lys Arg Arg Gly Arg Asp Pro Glu Met Gly Gly Lys
            820                 825                 830

Pro Arg Arg Lys Asn Pro Gln Glu Gly Leu Tyr Asn Glu Leu Gln Lys
        835                 840                 845

Asp Lys Met Ala Glu Ala Tyr Ser Glu Ile Gly Met Lys Gly Glu Arg
850                 855                 860

Arg Arg Gly Lys Gly His Asp Gly Leu Tyr Gln Gly Leu Ser Thr Ala
865                 870                 875                 880

Thr Lys Asp Thr Tyr Asp Ala Leu His Met Gln Ala Leu Pro Pro Arg
                885                 890                 895

Met Leu Glu Met Leu Glu Ala Thr Asn Phe Ser Leu Leu Lys Gln Ala
            900                 905                 910

Gly Asp Val Glu Glu Asn Pro Gly Pro Met Gly Ser Ser Lys Ser Lys
        915                 920                 925

Pro Lys Asp Pro Ser Gln Arg Leu Asp Met Ala Ala Gly Gly Pro Gly
930                 935                 940

Ala Gly Ser Ala Ala Pro Val Ser Ser Thr Ser Ser Leu Pro Leu Ala
```

```
            945                 950                 955                 960
Ala Leu Asn Met Arg Val Arg Arg Leu Ser Leu Phe Leu Asn Val
                    965                 970                 975

Arg Thr Gln Val Ala Ala Asp Trp Thr Ala Leu Ala Glu Glu Met Asp
                    980                 985                 990

Phe Glu Tyr Leu Glu Ile Arg Gln Leu Glu Thr Gln Ala Asp Pro Thr
                    995                 1000                1005

Gly Arg Leu Leu Asp Ala Trp Gln Gly Arg Pro Gly Ala Ser Val
    1010                1015                1020

Gly Arg Leu Leu Asp Leu Leu Thr Lys Leu Gly Arg Asp Asp Val
    1025                1030                1035

Leu Leu Glu Leu Gly Pro Ser Ile Glu Glu Asp Cys Gln Lys Tyr
    1040                1045                1050

Ile Leu Lys Gln Gln Gln Glu Ala Glu Lys Pro Leu Gln Val
    1055                1060                1065

Ala Ala Val Asp Ser Ser Val Pro Arg Thr Ala Glu Leu Ala Gly
    1070                1075                1080

Ile Thr Thr Leu Asp Asp Pro Leu Gly His Met Pro Glu Arg Phe
    1085                1090                1095

Asp Ala Phe Ile Cys Tyr Cys Pro Ser Asp Ile Ala Ala Ala Lys
    1100                1105                1110

Arg Gly Arg Lys Lys Leu Leu Tyr Ile Phe Lys Gln Pro Phe Met
    1115                1120                1125

Arg Pro Val Gln Thr Thr Gln Glu Glu Asp Gly Cys Ser Cys Arg
    1130                1135                1140

Phe Pro Glu Glu Glu Glu Gly Gly Cys Glu Leu
    1145                1150

<210> SEQ ID NO 152
<211> LENGTH: 1138
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Met Leu Glu Met Leu Glu Gly Val Gln Val Glu Thr Ile Ser Pro Gly
1               5                   10                  15

Asp Gly Arg Thr Phe Pro Lys Arg Gly Gln Thr Cys Val Val His Tyr
                20                  25                  30

Thr Gly Met Leu Glu Asp Gly Lys Lys Phe Asp Ser Ser Arg Asp Arg
            35                  40                  45

Asn Lys Pro Phe Lys Phe Met Leu Gly Lys Gln Glu Val Ile Arg Gly
        50                  55                  60

Trp Glu Glu Gly Val Ala Gln Met Ser Val Gly Gln Arg Ala Lys Leu
65                  70                  75                  80

Thr Ile Ser Pro Asp Tyr Ala Tyr Gly Ala Thr Gly His Pro Gly Ile
                85                  90                  95

Ile Pro Pro His Ala Thr Leu Val Phe Asp Val Glu Leu Leu Lys Leu
                100                 105                 110

Glu Ser Gly Gly Gly Ser Gly Val Asp Gly Phe Gly Asp Val Gly Ala
            115                 120                 125

Leu Glu Ser Leu Arg Gly Asn Ala Asp Leu Ala Tyr Ile Leu Ser Met
        130                 135                 140
```

-continued

Glu Pro Cys Gly His Cys Leu Ile Ile Asn Asn Val Asn Phe Cys Arg
145                 150                 155                 160

Glu Ser Gly Leu Arg Thr Arg Thr Gly Ser Asn Ile Asp Cys Glu Lys
            165                 170                 175

Leu Arg Arg Arg Phe Ser Ser Leu His Phe Met Val Glu Val Lys Gly
            180                 185                 190

Asp Leu Thr Ala Lys Lys Met Val Leu Ala Leu Leu Glu Leu Ala Arg
            195                 200                 205

Gln Asp His Gly Ala Leu Asp Cys Cys Val Val Ile Leu Ser His
    210                 215                 220

Gly Cys Gln Ala Ser His Leu Gln Phe Pro Gly Ala Val Tyr Gly Thr
225                 230                 235                 240

Asp Gly Cys Pro Val Ser Val Glu Lys Ile Val Asn Ile Phe Asn Gly
            245                 250                 255

Thr Ser Cys Pro Ser Leu Gly Gly Lys Pro Lys Leu Phe Phe Ile Gln
            260                 265                 270

Ala Cys Gly Gly Glu Gln Lys Asp His Gly Phe Glu Val Ala Ser Thr
            275                 280                 285

Ser Pro Glu Asp Glu Ser Pro Gly Ser Asn Pro Glu Pro Asp Ala Thr
290                 295                 300

Pro Phe Gln Glu Gly Leu Arg Thr Phe Asp Gln Leu Asp Ala Ile Ser
305                 310                 315                 320

Ser Leu Pro Thr Pro Ser Asp Ile Phe Val Ser Tyr Ser Thr Phe Pro
            325                 330                 335

Gly Phe Val Ser Trp Arg Asp Pro Lys Ser Gly Ser Trp Tyr Val Glu
            340                 345                 350

Thr Leu Asp Asp Ile Phe Glu Gln Trp Ala His Ser Glu Asp Leu Gln
            355                 360                 365

Ser Leu Leu Leu Arg Val Ala Asn Ala Val Ser Val Lys Gly Ile Tyr
            370                 375                 380

Lys Gln Met Pro Gly Cys Phe Asn Phe Leu Arg Lys Lys Leu Phe Phe
385                 390                 395                 400

Lys Thr Ser Ala Ser Arg Ala Pro Arg Glu Gly Arg Gly Ser Leu Leu
            405                 410                 415

Thr Cys Gly Asp Val Glu Glu Asn Pro Gly Pro Pro Trp Met Glu Phe
            420                 425                 430

Gly Leu Ser Trp Leu Phe Leu Val Ala Ile Leu Lys Gly Val Gln Cys
            435                 440                 445

Ser Arg Asp Ile Gln Met Thr Gln Thr Thr Ser Ser Leu Ser Ala Ser
450                 455                 460

Leu Gly Asp Arg Val Thr Ile Ser Cys Arg Ala Ser Gln Asp Ile Ser
465                 470                 475                 480

Lys Tyr Leu Asn Trp Tyr Gln Gln Lys Pro Asp Gly Thr Val Lys Leu
            485                 490                 495

Leu Ile Tyr His Thr Ser Arg Leu His Ser Gly Val Pro Ser Arg Phe
            500                 505                 510

Ser Gly Ser Gly Ser Gly Thr Asp Tyr Ser Leu Thr Ile Ser Asn Leu
            515                 520                 525

Glu Gln Glu Asp Ile Ala Thr Tyr Phe Cys Gln Gln Gly Asn Thr Leu
            530                 535                 540

Pro Tyr Thr Phe Gly Gly Gly Thr Lys Leu Glu Ile Thr Gly Gly Gly
545                 550                 555                 560

Ser Gly Gly Gly Gly Glu Val Lys Leu Gln Glu Ser Gly Pro Gly Leu

-continued

```
            565                 570                 575
Val Ala Pro Ser Gln Ser Leu Ser Val Thr Cys Thr Val Ser Gly Val
            580                 585                 590

Ser Leu Pro Asp Tyr Gly Val Ser Trp Ile Arg Gln Pro Pro Arg Lys
            595                 600                 605

Gly Leu Glu Trp Leu Gly Val Ile Trp Gly Ser Glu Thr Thr Tyr Tyr
            610                 615                 620

Asn Ser Ala Leu Lys Ser Arg Leu Thr Ile Ile Lys Asp Asn Ser Lys
625                 630                 635                 640

Ser Gln Val Phe Leu Lys Met Asn Ser Leu Gln Thr Asp Asp Thr Ala
                    645                 650                 655

Ile Tyr Tyr Cys Ala Lys His Tyr Tyr Tyr Gly Gly Ser Tyr Ala Met
                    660                 665                 670

Asp Tyr Trp Gly Gln Gly Thr Ser Val Thr Val Ser Ser Gly Ser Glu
            675                 680                 685

Leu Pro Thr Gln Gly Thr Phe Ser Asn Val Ser Thr Asn Val Ser Pro
            690                 695                 700

Ala Pro Arg Pro Pro Thr Pro Ala Pro Thr Ile Ala Ser Gln Pro Leu
705                 710                 715                 720

Ser Leu Arg Pro Glu Ala Cys Arg Pro Ala Ala Gly Gly Ala Val His
                    725                 730                 735

Thr Arg Gly Leu Asp Phe Ala Cys Asp Ile Tyr Ile Trp Ala Pro Leu
                    740                 745                 750

Ala Gly Thr Cys Gly Val Leu Leu Leu Ser Leu Val Ile Thr Leu Tyr
            755                 760                 765

Cys Asn His Arg Asn Arg Arg Val Cys Lys Cys Pro Arg Val Asp
770                 775                 780

Arg Val Lys Phe Ser Arg Ser Ala Asp Ala Pro Ala Tyr Gln Gln Gly
785                 790                 795                 800

Gln Asn Gln Leu Tyr Asn Glu Leu Asn Leu Gly Arg Arg Glu Glu Tyr
                    805                 810                 815

Asp Val Leu Asp Lys Arg Arg Gly Arg Asp Pro Glu Met Gly Gly Lys
            820                 825                 830

Pro Arg Arg Lys Asn Pro Gln Glu Gly Leu Tyr Asn Glu Leu Gln Lys
            835                 840                 845

Asp Lys Met Ala Glu Ala Tyr Ser Glu Ile Gly Met Lys Gly Glu Arg
850                 855                 860

Arg Arg Gly Lys Gly His Asp Gly Leu Tyr Gln Gly Leu Ser Thr Ala
865                 870                 875                 880

Thr Lys Asp Thr Tyr Asp Ala Leu His Met Gln Ala Leu Pro Pro Arg
                    885                 890                 895

Met Leu Glu Met Leu Glu Ala Thr Asn Phe Ser Leu Leu Lys Gln Ala
                    900                 905                 910

Gly Asp Val Glu Glu Asn Pro Gly Pro Met Ala Ala Gly Gly Pro Gly
            915                 920                 925

Ala Gly Ser Ala Ala Pro Val Ser Ser Thr Ser Ser Leu Pro Leu Ala
            930                 935                 940

Ala Leu Asn Met Arg Val Arg Arg Arg Leu Ser Leu Phe Leu Asn Val
945                 950                 955                 960

Arg Thr Gln Val Ala Ala Asp Trp Thr Ala Leu Ala Glu Glu Met Asp
                    965                 970                 975

Phe Glu Tyr Leu Glu Ile Arg Gln Leu Glu Thr Gln Ala Asp Pro Thr
            980                 985                 990
```

-continued

```
Gly Arg Leu Leu Asp Ala Trp Gln Gly Arg Pro Gly Ala Ser Val Gly
        995                1000                1005

Arg Leu Leu Asp Leu Leu Thr Lys Leu Gly Arg Asp Asp Val Leu
    1010                1015                1020

Leu Glu Leu Gly Pro Ser Ile Glu Glu Asp Cys Gln Lys Tyr Ile
    1025                1030                1035

Leu Lys Gln Gln Gln Glu Glu Ala Glu Lys Pro Leu Gln Val Ala
    1040                1045                1050

Ala Val Asp Ser Ser Val Pro Arg Thr Ala Glu Leu Ala Gly Ile
    1055                1060                1065

Thr Thr Leu Asp Asp Pro Leu Gly His Met Pro Glu Arg Phe Asp
    1070                1075                1080

Ala Phe Ile Cys Tyr Cys Pro Ser Asp Ile Ala Ala Ala Lys Arg
    1085                1090                1095

Gly Arg Lys Lys Leu Leu Tyr Ile Phe Lys Gln Pro Phe Met Arg
    1100                1105                1110

Pro Val Gln Thr Thr Gln Glu Glu Asp Gly Cys Ser Cys Arg Phe
    1115                1120                1125

Pro Glu Glu Glu Glu Gly Gly Cys Glu Leu
    1130                1135

<210> SEQ ID NO 153
<211> LENGTH: 485
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Glu Phe Gly Leu Ser Trp Leu Phe Leu Val Ala Ile Leu Lys Gly
1               5                   10                  15

Val Gln Cys Ser Arg Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Ile Phe Thr Asn Tyr Gly Met Asn Trp Val Lys Gln Ala Pro Gly Lys
    50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
                85                  90                  95

Ala Ser Thr Ala Tyr Leu His Ile Asn Asp Leu Lys Asn Glu Asp Thr
            100                 105                 110

Ala Thr Tyr Phe Cys Ala Arg Ser Gly Gly Tyr Asp Pro Met Asp Tyr
        115                 120                 125

Trp Gly Gln Gly Thr Ser Val Thr Val Ser Ser Gly Gly Gly Ser
    130                 135                 140

Gly Gly Gly Gly Ser Gly Gly Gly Ser Asp Ile Val Leu Thr Gln
145                 150                 155                 160

Ser Pro Ala Ser Leu Ala Val Ser Leu Gly Gln Arg Ala Thr Ile Ser
                165                 170                 175

Cys Arg Ala Ser Glu Ser Val Asp Asn Tyr Gly Asn Thr Phe Met His
            180                 185                 190

Trp Tyr Gln Gln Lys Pro Gly Gln Pro Pro Lys Leu Leu Ile Tyr Arg
```

195                 200                 205
Ala Ser Asn Leu Glu Ser Gly Ile Pro Ala Arg Phe Ser Gly Ser Gly
        210                 215                 220

Ser Arg Thr Asp Phe Thr Leu Thr Ile Asn Pro Val Glu Ala Asp Asp
225                 230                 235                 240

Val Ala Thr Tyr Tyr Cys Gln Gln Ser Asn Glu Asp Pro Pro Thr Phe
                245                 250                 255

Gly Ala Gly Thr Lys Leu Glu Leu Lys Glu Ser Lys Tyr Gly Pro Pro
            260                 265                 270

Cys Pro Gly Ser Glu Leu Pro Thr Gln Gly Thr Phe Ser Asn Val Ser
            275                 280                 285

Thr Asn Val Ser Pro Ala Pro Arg Pro Pro Thr Pro Ala Pro Thr Ile
        290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Phe Ala Cys Asp Ile Tyr
                325                 330                 335

Ile Trp Ala Pro Leu Ala Gly Thr Cys Gly Val Leu Leu Leu Ser Leu
            340                 345                 350

Val Ile Thr Leu Tyr Cys Asn His Arg Asn Arg Arg Arg Val Cys Lys
        355                 360                 365

Cys Pro Arg Val Asp Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
            450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 154
<211> LENGTH: 1135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Met Ala Ala Gly Gly Pro Gly Ala Gly Ser Ala Ala Pro Val Ser Ser
1               5                   10                  15

Thr Ser Ser Leu Pro Leu Ala Ala Leu Asn Met Arg Val Arg Arg Arg
            20                  25                  30

Leu Ser Leu Phe Leu Asn Val Arg Thr Gln Val Ala Ala Asp Trp Thr
        35                  40                  45

Ala Leu Ala Glu Glu Met Asp Phe Glu Tyr Leu Glu Ile Arg Gln Leu
50                  55                  60

-continued

Glu Thr Gln Ala Asp Pro Thr Gly Arg Leu Leu Asp Ala Trp Gln Gly
65                  70                  75                  80

Arg Pro Gly Ala Ser Val Gly Arg Leu Leu Asp Leu Leu Thr Lys Leu
                85                  90                  95

Gly Arg Asp Asp Val Leu Leu Glu Leu Gly Pro Ser Ile Glu Glu Asp
            100                 105                 110

Cys Gln Lys Tyr Ile Leu Lys Gln Gln Gln Glu Glu Ala Glu Lys Pro
            115                 120                 125

Leu Gln Val Ala Ala Val Asp Ser Ser Val Pro Arg Thr Ala Glu Leu
        130                 135                 140

Ala Gly Ile Thr Thr Leu Asp Asp Pro Leu Gly His Met Pro Glu Arg
145                 150                 155                 160

Phe Asp Ala Phe Ile Cys Tyr Cys Pro Ser Asp Ile Val Glu Lys Lys
                165                 170                 175

Val Ala Lys Lys Pro Thr Asn Lys Ala Pro His Pro Lys Gln Glu Pro
            180                 185                 190

Gln Glu Ile Asn Phe Pro Asp Asp Leu Pro Gly Ser Asn Thr Ala Ala
            195                 200                 205

Pro Val Gln Glu Thr Leu His Gly Cys Gln Pro Val Thr Gln Glu Asp
210                 215                 220

Gly Lys Glu Ser Arg Ile Ser Val Gln Glu Arg Gln Val Glu Gly Val
225                 230                 235                 240

Gln Val Glu Thr Ile Ser Pro Gly Asp Gly Arg Thr Phe Pro Lys Arg
                245                 250                 255

Gly Gln Thr Cys Val Val His Tyr Thr Gly Met Leu Glu Asp Gly Lys
            260                 265                 270

Lys Val Asp Ser Ser Arg Asp Arg Asn Lys Pro Phe Lys Phe Met Leu
        275                 280                 285

Gly Lys Gln Glu Val Ile Arg Gly Trp Glu Glu Gly Val Ala Gln Met
    290                 295                 300

Ser Val Gly Gln Arg Ala Lys Leu Thr Ile Ser Pro Asp Tyr Ala Tyr
305                 310                 315                 320

Gly Ala Thr Gly His Pro Gly Ile Ile Pro Pro His Ala Thr Leu Val
                325                 330                 335

Phe Asp Val Glu Leu Leu Lys Leu Glu Val Glu Gly Val Gln Val Glu
            340                 345                 350

Thr Ile Ser Pro Gly Asp Gly Arg Thr Phe Pro Lys Arg Gly Gln Thr
            355                 360                 365

Cys Val Val His Tyr Thr Gly Met Leu Glu Asp Gly Lys Lys Val Asp
        370                 375                 380

Ser Ser Arg Asp Arg Asn Lys Pro Phe Lys Phe Met Leu Gly Lys Gln
385                 390                 395                 400

Glu Val Ile Arg Gly Trp Glu Glu Gly Val Ala Gln Met Ser Val Gly
                405                 410                 415

Gln Arg Ala Lys Leu Thr Ile Ser Pro Asp Tyr Ala Tyr Gly Ala Thr
            420                 425                 430

Gly His Pro Gly Ile Ile Pro Pro His Ala Thr Leu Val Phe Asp Val
        435                 440                 445

Glu Leu Leu Lys Leu Glu Pro Arg Glu Gly Arg Gly Ser Leu Leu Thr
    450                 455                 460

Cys Gly Asp Val Glu Glu Asn Pro Gly Pro Pro Trp Met Glu Phe Gly
465                 470                 475                 480

Leu Ser Trp Leu Phe Leu Val Ala Ile Leu Lys Gly Val Gln Cys Ser

```
                485            490            495
Arg Asp Ile Val Leu Thr Gln Ser Pro Ser Leu Ala Met Ser Leu
            500            505            510

Gly Lys Arg Ala Thr Ile Ser Cys Arg Ala Ser Glu Ser Val Thr Ile
            515            520            525

Leu Gly Ser His Leu Ile Tyr Trp Tyr Gln Gln Lys Pro Gly Gln Pro
            530            535            540

Pro Thr Leu Leu Ile Gln Leu Ala Ser Asn Val Gln Thr Gly Val Pro
545            550            555            560

Ala Arg Phe Ser Gly Ser Gly Ser Arg Thr Asp Phe Thr Leu Thr Ile
            565            570            575

Asp Pro Val Glu Glu Asp Val Ala Val Tyr Tyr Cys Leu Gln Ser
            580            585            590

Arg Thr Ile Pro Arg Thr Phe Gly Gly Gly Thr Lys Leu Glu Ile Lys
            595            600            605

Gly Gly Gly Gly Ser Gly Gly Gly Ser Gly Gly Gly Gly Ser Gln
            610            615            620

Ile Gln Leu Val Gln Ser Gly Pro Glu Leu Lys Lys Pro Gly Glu Thr
625            630            635            640

Val Lys Ile Ser Cys Lys Ala Ser Gly Tyr Thr Phe Arg His Tyr Ser
            645            650            655

Met Asn Trp Val Lys Gln Ala Pro Gly Lys Gly Leu Lys Trp Met Gly
            660            665            670

Arg Ile Asn Thr Glu Ser Gly Val Pro Ile Tyr Ala Asp Asp Phe Lys
            675            680            685

Gly Arg Phe Ala Phe Ser Val Glu Thr Ser Ala Ser Thr Ala Tyr Leu
            690            695            700

Val Ile Asn Asn Leu Lys Asp Glu Asp Thr Ala Ser Tyr Phe Cys Ser
705            710            715            720

Asn Asp Tyr Leu Tyr Ser Leu Asp Phe Trp Gly Gln Gly Thr Ala Leu
            725            730            735

Thr Val Ser Ser Gly Ser Glu Leu Pro Thr Gln Gly Thr Phe Ser Asn
            740            745            750

Val Ser Thr Asn Val Ser Pro Ala Pro Arg Pro Pro Thr Pro Ala Pro
            755            760            765

Thr Ile Ala Ser Gln Pro Leu Ser Leu Arg Pro Glu Ala Cys Arg Pro
            770            775            780

Ala Ala Gly Gly Ala Val His Thr Arg Gly Leu Asp Phe Ala Cys Asp
785            790            795            800

Ile Tyr Ile Trp Ala Pro Leu Ala Gly Thr Cys Gly Val Leu Leu Leu
            805            810            815

Ser Leu Val Ile Thr Leu Tyr Cys Asn His Arg Asn Arg Arg Val
            820            825            830

Cys Lys Cys Pro Arg Val Asp Arg Val Lys Phe Ser Arg Ser Ala Asp
            835            840            845

Ala Pro Ala Tyr Gln Gln Gly Gln Asn Gln Leu Tyr Asn Glu Leu Asn
850            855            860

Leu Gly Arg Arg Glu Glu Tyr Asp Val Leu Asp Lys Arg Arg Gly Arg
865            870            875            880

Asp Pro Glu Met Gly Gly Lys Pro Arg Arg Lys Asn Pro Gln Glu Gly
            885            890            895

Leu Tyr Asn Glu Leu Gln Lys Asp Lys Met Ala Glu Ala Tyr Ser Glu
            900            905            910
```

```
Ile Gly Met Lys Gly Glu Arg Arg Gly Lys Gly His Asp Gly Leu
        915                 920                 925

Tyr Gln Gly Leu Ser Thr Ala Thr Lys Asp Thr Tyr Asp Ala Leu His
    930                 935                 940

Met Gln Ala Leu Pro Pro Arg Gly Ser Gly Gly Arg Glu Gly Arg Gly
945                 950                 955                 960

Ser Leu Leu Thr Cys Gly Asp Val Glu Glu Asn Pro Gly Pro Met Arg
                965                 970                 975

Ile Ser Lys Pro His Leu Arg Ser Ile Ser Ile Gln Cys Tyr Leu Cys
            980                 985                 990

Leu Leu Leu Asn Ser His Phe Leu Thr Glu Ala Gly Ile His Val Phe
        995                 1000                1005

Ile Leu Gly Cys Phe Ser Ala Gly Leu Pro Lys Thr Glu Ala Asn
        1010                1015                1020

Trp Val Asn Val Ile Ser Asp Leu Lys Lys Ile Glu Asp Leu Ile
        1025                1030                1035

Gln Ser Met His Ile Asp Ala Thr Leu Tyr Thr Glu Ser Asp Val
        1040                1045                1050

His Pro Ser Cys Lys Val Thr Ala Met Lys Cys Phe Leu Leu Glu
        1055                1060                1065

Leu Gln Val Ile Ser Leu Glu Ser Gly Asp Ala Ser Ile His Asp
        1070                1075                1080

Thr Val Glu Asn Leu Ile Ile Leu Ala Asn Asn Ser Leu Ser Ser
        1085                1090                1095

Asn Gly Asn Val Thr Glu Ser Gly Cys Lys Glu Cys Glu Glu Leu
        1100                1105                1110

Glu Glu Lys Asn Ile Lys Glu Phe Leu Gln Ser Phe Val His Ile
        1115                1120                1125

Val Gln Met Phe Ile Asn Thr
        1130                1135

<210> SEQ ID NO 155
<211> LENGTH: 854
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Leu Glu Gln Leu Glu Met Trp His Glu Gly Leu Glu Glu Ala Ser
1               5                   10                  15

Arg Leu Tyr Phe Gly Glu Arg Asn Val Lys Gly Met Phe Glu Val Leu
            20                  25                  30

Glu Pro Leu His Ala Met Met Glu Arg Gly Pro Gln Thr Leu Lys Glu
        35                  40                  45

Thr Ser Phe Asn Gln Ala Tyr Gly Arg Asp Leu Met Glu Ala Gln Glu
    50                  55                  60

Trp Cys Arg Lys Tyr Met Lys Ser Gly Asn Val Lys Asp Leu Thr Gln
65                  70                  75                  80

Ala Trp Asp Leu Tyr Tyr His Val Phe Arg Arg Ile Ser Lys Gly Gly
                85                  90                  95

Gln Leu Gly Val Gln Val Glu Thr Ile Ser Pro Gly Asp Gly Arg Thr
            100                 105                 110

Phe Pro Lys Arg Gly Gln Thr Cys Val Val His Tyr Thr Gly Met Leu
```

```
            115                 120                 125
Glu Asp Gly Lys Lys Phe Asp Ser Ser Arg Asp Arg Asn Lys Pro Phe
130                 135                 140
Lys Phe Met Leu Gly Lys Gln Glu Val Ile Arg Gly Trp Glu Glu Gly
145                 150                 155                 160
Val Ala Gln Met Ser Val Gly Gln Arg Ala Lys Leu Thr Ile Ser Pro
                165                 170                 175
Asp Tyr Ala Tyr Gly Ala Thr Gly His Pro Gly Ile Ile Pro Pro His
            180                 185                 190
Ala Thr Leu Val Phe Asp Val Glu Leu Leu Lys Leu Ser Gly Gly Gly
        195                 200                 205
Ser Gly Pro Trp Gly Phe Gly Asp Val Gly Ala Leu Glu Ser Leu Arg
210                 215                 220
Gly Asn Ala Asp Leu Ala Tyr Ile Leu Ser Met Glu Pro Cys Gly His
225                 230                 235                 240
Cys Leu Ile Ile Asn Asn Val Asn Phe Cys Arg Glu Ser Gly Leu Arg
                245                 250                 255
Thr Arg Thr Gly Ser Asn Ile Asp Cys Glu Lys Leu Arg Arg Arg Phe
            260                 265                 270
Ser Ser Leu His Phe Met Val Glu Val Lys Gly Asp Leu Thr Ala Lys
        275                 280                 285
Lys Met Val Leu Ala Leu Leu Glu Leu Ala Arg Gln Asp His Gly Ala
290                 295                 300
Leu Asp Cys Cys Val Val Val Ile Leu Ser His Gly Cys Gln Ala Ser
305                 310                 315                 320
His Leu Gln Phe Pro Gly Ala Val Tyr Gly Thr Asp Gly Cys Pro Val
                325                 330                 335
Ser Val Glu Lys Ile Val Asn Ile Phe Asn Gly Thr Ser Cys Pro Ser
            340                 345                 350
Leu Gly Gly Lys Pro Lys Leu Phe Phe Ile Gln Ala Cys Gly Gly Glu
        355                 360                 365
Gln Lys Asp His Gly Phe Glu Val Ala Ser Thr Ser Pro Glu Asp Glu
370                 375                 380
Ser Pro Gly Ser Asn Pro Glu Pro Asp Ala Thr Pro Phe Gln Glu Gly
385                 390                 395                 400
Leu Arg Thr Phe Asp Gln Leu Asp Ala Ile Ser Ser Leu Pro Thr Pro
                405                 410                 415
Ser Asp Ile Phe Val Ser Tyr Ser Thr Phe Pro Gly Phe Val Ser Trp
            420                 425                 430
Arg Asp Pro Lys Ser Gly Ser Trp Tyr Val Glu Thr Leu Asp Asp Ile
        435                 440                 445
Phe Glu Gln Trp Ala His Ser Glu Asp Leu Gln Ser Leu Leu Leu Arg
450                 455                 460
Val Ala Asn Ala Val Ser Val Lys Gly Ile Tyr Lys Gln Met Pro Gly
465                 470                 475                 480
Cys Phe Asn Phe Leu Arg Lys Lys Leu Phe Phe Lys Thr Ser Ala Ser
                485                 490                 495
Arg Ala Gly Ser Gly Pro Arg Glu Gly Arg Gly Ser Leu Leu Thr Cys
            500                 505                 510
Gly Asp Val Glu Glu Asn Pro Gly Pro Met Pro Pro Arg Leu Leu
        515                 520                 525
Phe Phe Leu Leu Phe Leu Thr Pro Met Glu Val Arg Pro Glu Glu Pro
530                 535                 540
```

Leu Val Lys Val Glu Glu Gly Asp Asn Ala Val Leu Gln Cys Leu
545                 550                 555                 560

Lys Gly Thr Ser Asp Gly Pro Thr Gln Gln Leu Thr Trp Ser Arg Glu
            565                 570                 575

Ser Pro Leu Lys Pro Phe Leu Lys Leu Ser Leu Gly Leu Pro Gly Leu
            580                 585                 590

Gly Ile His Met Arg Pro Leu Ala Ile Trp Leu Phe Ile Phe Asn Val
            595                 600                 605

Ser Gln Gln Met Gly Gly Phe Tyr Leu Cys Gln Pro Gly Pro Pro Ser
            610                 615                 620

Glu Lys Ala Trp Gln Pro Gly Trp Thr Val Asn Val Glu Gly Ser Gly
625                 630                 635                 640

Glu Leu Phe Arg Trp Asn Val Ser Asp Leu Gly Gly Leu Gly Cys Gly
            645                 650                 655

Leu Lys Asn Arg Ser Ser Glu Gly Pro Ser Ser Pro Ser Gly Lys Leu
            660                 665                 670

Met Ser Pro Lys Leu Tyr Val Trp Ala Lys Asp Arg Pro Glu Ile Trp
            675                 680                 685

Glu Gly Glu Pro Pro Cys Leu Pro Pro Arg Asp Ser Leu Asn Gln Ser
690                 695                 700

Leu Ser Gln Asp Leu Thr Met Ala Pro Gly Ser Thr Leu Trp Leu Ser
705                 710                 715                 720

Cys Gly Val Pro Pro Asp Ser Val Ser Arg Gly Pro Leu Ser Trp Thr
            725                 730                 735

His Val His Pro Lys Gly Pro Lys Ser Leu Leu Ser Leu Glu Leu Lys
            740                 745                 750

Asp Asp Arg Pro Ala Arg Asp Met Trp Val Met Glu Thr Gly Leu Leu
            755                 760                 765

Leu Pro Arg Ala Thr Ala Gln Asp Ala Gly Lys Tyr Tyr Cys His Arg
770                 775                 780

Gly Asn Leu Thr Met Ser Phe His Leu Glu Ile Thr Ala Arg Pro Val
785                 790                 795                 800

Leu Trp His Trp Leu Leu Arg Thr Gly Gly Trp Lys Val Ser Ala Val
            805                 810                 815

Thr Leu Ala Tyr Leu Ile Phe Cys Leu Cys Ser Leu Val Gly Ile Leu
            820                 825                 830

His Leu Gln Arg Ala Leu Val Leu Arg Arg Lys Arg Lys Arg Met Thr
            835                 840                 845

Asp Pro Thr Arg Arg Phe
    850

<210> SEQ ID NO 156
<211> LENGTH: 1182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Met Leu Glu Met Leu Glu Gly Val Gln Val Glu Thr Ile Ser Pro Gly
1               5                   10                  15

Asp Gly Arg Thr Phe Pro Lys Arg Gly Gln Thr Cys Val Val His Tyr
            20                  25                  30

Thr Gly Met Leu Glu Asp Gly Lys Lys Val Asp Ser Ser Arg Asp Arg

```
                35                  40                  45
Asn Lys Pro Phe Lys Phe Met Leu Gly Lys Gln Glu Val Ile Arg Gly
 50                  55                  60

Trp Glu Glu Gly Val Ala Gln Met Ser Val Gly Gln Arg Ala Lys Leu
 65                  70                  75                  80

Thr Ile Ser Pro Asp Tyr Ala Tyr Gly Ala Thr Gly His Pro Gly Ile
                     85                  90                  95

Ile Pro Pro His Ala Thr Leu Val Phe Asp Val Glu Leu Leu Lys Leu
                    100                 105                 110

Glu Ser Gly Gly Ser Gly Val Asp Gly Phe Gly Asp Val Gly Ala
            115                 120                 125

Leu Glu Ser Leu Arg Gly Asn Ala Asp Leu Ala Tyr Ile Leu Ser Met
130                 135                 140

Glu Pro Cys Gly His Cys Leu Ile Ile Asn Asn Val Asn Phe Cys Arg
145                 150                 155                 160

Glu Ser Gly Leu Arg Thr Arg Thr Gly Ser Asn Ile Asp Cys Glu Lys
                    165                 170                 175

Leu Arg Arg Arg Phe Ser Ser Leu His Phe Met Val Glu Val Lys Gly
                    180                 185                 190

Asp Leu Thr Ala Lys Lys Met Val Leu Ala Leu Leu Glu Leu Ala Arg
                    195                 200                 205

Gln Asp His Gly Ala Leu Asp Cys Cys Val Val Val Ile Leu Ser His
210                 215                 220

Gly Cys Gln Ala Ser His Leu Gln Phe Pro Gly Ala Val Tyr Gly Thr
225                 230                 235                 240

Asp Gly Cys Pro Val Ser Val Glu Lys Ile Val Asn Ile Phe Asn Gly
                    245                 250                 255

Thr Ser Cys Pro Ser Leu Gly Gly Lys Pro Lys Leu Phe Phe Ile Gln
                    260                 265                 270

Ala Cys Gly Gly Glu Gln Lys Asp His Gly Phe Glu Val Ala Ser Thr
                    275                 280                 285

Ser Pro Glu Asp Glu Ser Pro Gly Ser Asn Pro Glu Pro Asp Ala Thr
                    290                 295                 300

Pro Phe Gln Glu Gly Leu Arg Thr Phe Asp Gln Leu Asp Ala Ile Ser
305                 310                 315                 320

Ser Leu Pro Thr Pro Ser Asp Ile Phe Val Ser Tyr Ser Thr Phe Pro
                    325                 330                 335

Gly Phe Val Ser Trp Arg Asp Pro Lys Ser Gly Ser Trp Tyr Val Glu
                    340                 345                 350

Thr Leu Asp Asp Ile Phe Glu Gln Trp Ala His Ser Glu Asp Leu Gln
                    355                 360                 365

Ser Leu Leu Leu Arg Val Ala Asn Ala Val Ser Val Lys Gly Ile Tyr
                    370                 375                 380

Lys Gln Met Pro Gly Cys Phe Asn Phe Leu Arg Lys Lys Leu Phe Phe
385                 390                 395                 400

Lys Thr Ser Ala Ser Arg Ala Pro Arg Glu Gly Arg Gly Ser Leu Leu
                    405                 410                 415

Thr Cys Gly Asp Val Glu Glu Asn Pro Gly Pro Pro Trp Met Glu Phe
                    420                 425                 430

Gly Leu Ser Trp Leu Phe Leu Val Ala Ile Leu Lys Gly Val Gln Cys
                    435                 440                 445

Ser Arg Asp Ile Val Leu Thr Gln Ser Pro Pro Ser Leu Ala Met Ser
450                 455                 460
```

```
Leu Gly Lys Arg Ala Thr Ile Ser Cys Arg Ala Ser Glu Ser Val Thr
465                 470                 475                 480

Ile Leu Gly Ser His Leu Ile Tyr Trp Tyr Gln Gln Lys Pro Gly Gln
                485                 490                 495

Pro Pro Thr Leu Leu Ile Gln Leu Ala Ser Asn Val Gln Thr Gly Val
            500                 505                 510

Pro Ala Arg Phe Ser Gly Ser Gly Ser Arg Thr Asp Phe Thr Leu Thr
            515                 520                 525

Ile Asp Pro Val Glu Glu Asp Val Ala Val Tyr Tyr Cys Leu Gln
            530                 535                 540

Ser Arg Thr Ile Pro Arg Thr Phe Gly Gly Gly Thr Lys Leu Glu Ile
545                 550                 555                 560

Lys Gly Gly Gly Gly Ser Gly Gly Gly Gly Ser Gly Gly Gly Gly Ser
                565                 570                 575

Gln Ile Gln Leu Val Gln Ser Gly Pro Glu Leu Lys Lys Pro Gly Glu
            580                 585                 590

Thr Val Lys Ile Ser Cys Lys Ala Ser Gly Tyr Thr Phe Arg His Tyr
            595                 600                 605

Ser Met Asn Trp Val Lys Gln Ala Pro Gly Lys Gly Leu Lys Trp Met
610                 615                 620

Gly Arg Ile Asn Thr Glu Ser Gly Val Pro Ile Tyr Ala Asp Asp Phe
625                 630                 635                 640

Lys Gly Arg Phe Ala Phe Ser Val Glu Thr Ser Ala Ser Thr Ala Tyr
                645                 650                 655

Leu Val Ile Asn Asn Leu Lys Asp Glu Asp Thr Ala Ser Tyr Phe Cys
            660                 665                 670

Ser Asn Asp Tyr Leu Tyr Ser Leu Asp Phe Trp Gly Gln Gly Thr Ala
            675                 680                 685

Leu Thr Val Ser Ser Gly Ser Glu Leu Pro Thr Gln Gly Thr Phe Ser
690                 695                 700

Asn Val Ser Thr Asn Val Ser Pro Ala Pro Arg Pro Pro Thr Pro Ala
705                 710                 715                 720

Pro Thr Ile Ala Ser Gln Pro Leu Ser Leu Arg Pro Glu Ala Cys Arg
                725                 730                 735

Pro Ala Ala Gly Gly Ala Val His Thr Arg Gly Leu Asp Phe Ala Cys
            740                 745                 750

Asp Ile Tyr Ile Trp Ala Pro Leu Ala Gly Thr Cys Gly Val Leu Leu
            755                 760                 765

Leu Ser Leu Val Ile Thr Leu Tyr Cys Asn His Arg Asn Arg Arg
770                 775                 780

Val Cys Lys Cys Pro Arg Val Asp Arg Val Lys Phe Ser Arg Ser Ala
785                 790                 795                 800

Asp Ala Pro Ala Tyr Gln Gln Gly Gln Asn Gln Leu Tyr Asn Glu Leu
                805                 810                 815

Asn Leu Gly Arg Arg Glu Glu Tyr Asp Val Leu Asp Lys Arg Arg Gly
            820                 825                 830

Arg Asp Pro Glu Met Gly Gly Lys Pro Arg Arg Lys Asn Pro Gln Glu
            835                 840                 845

Gly Leu Tyr Asn Glu Leu Gln Lys Asp Lys Met Ala Glu Ala Tyr Ser
            850                 855                 860

Glu Ile Gly Met Lys Gly Glu Arg Arg Arg Gly Lys Gly His Asp Gly
865                 870                 875                 880
```

-continued

```
Leu Tyr Gln Gly Leu Ser Thr Ala Thr Lys Asp Thr Tyr Asp Ala Leu
                885                 890                 895

His Met Gln Ala Leu Pro Pro Arg Ala Thr Asn Phe Ser Leu Leu Lys
            900                 905                 910

Gln Ala Gly Asp Val Glu Glu Asn Pro Gly Pro Met Ala Ala Gly Gly
        915                 920                 925

Pro Gly Ala Gly Ser Ala Ala Pro Val Ser Ser Thr Ser Ser Leu Pro
    930                 935                 940

Leu Ala Ala Leu Asn Met Arg Val Arg Arg Arg Leu Ser Leu Phe Leu
945                 950                 955                 960

Asn Val Arg Thr Gln Val Ala Ala Asp Trp Thr Ala Leu Ala Glu Glu
                965                 970                 975

Met Asp Phe Glu Tyr Leu Glu Ile Arg Gln Leu Glu Thr Gln Ala Asp
                980                 985                 990

Pro Thr Gly Arg Leu Leu Asp Ala  Trp Gln Gly Arg Pro  Gly Ala Ser
            995                 1000                1005

Val Gly Arg Leu Leu Asp Leu  Leu Thr Lys Leu Gly  Arg Asp Asp
    1010                1015                1020

Val Leu Leu Glu Leu Gly Pro  Ser Ile Glu Glu Asp  Cys Gln Lys
    1025                1030                1035

Tyr Ile Leu Lys Gln Gln Gln  Glu Glu Ala Glu Lys  Pro Leu Gln
    1040                1045                1050

Val Ala Ala Val Asp Ser Ser  Val Pro Arg Thr Ala  Glu Leu Ala
    1055                1060                1065

Gly Ile Thr Thr Leu Asp Asp  Pro Leu Gly His Met  Pro Glu Arg
    1070                1075                1080

Phe Asp Ala Phe Ile Cys Tyr  Cys Pro Ser Asp Ile  Val Glu Lys
    1085                1090                1095

Lys Val Ala Lys Lys Pro Thr  Asn Lys Ala Pro His  Pro Lys Gln
    1100                1105                1110

Glu Pro Gln Glu Ile Asn Phe  Pro Asp Asp Leu Pro  Gly Ser Asn
    1115                1120                1125

Thr Ala Ala Pro Val Gln Glu  Thr Leu His Gly Cys  Gln Pro Val
    1130                1135                1140

Thr Gln Glu Asp Gly Lys Glu  Ser Arg Ile Ser Val  Gln Glu Arg
    1145                1150                1155

Gln Gly Ser Gly Gly Arg Glu  Gly Arg Gly Ser Leu  Leu Thr Cys
    1160                1165                1170

Gly Asp Val Glu Glu Asn Pro  Gly Pro
    1175                1180
```

NATURAL KILLER CELL PRODUCTS AND METHODS

This application is a national stage entry of International Application No. PCT/US2019/030939, filed May 6, 2019, which claims priority to U.S. Provisional Application No. 62/668,223, filed May 7, 20198, U.S. Provisional Application No. 62/756,442, filed Nov. 6, 2018, and U.S. Provisional Application No. 62/816,799, filed Mar. 11, 2019, each of which is incorporated by reference herein in its entirety.

SEQUENCE LISTING

This application incorporates by reference a Sequence Listing submitted with this application as text file entitled "14562-069-999_Sequence_Listing. TXT" created on Nov. 2, 2020, and having a size of 260,326 bytes.

BACKGROUND

Natural Killer ("NK") cells are lymphoid-derived cells that directly inject toxic proteins into target cells. NK cells are part of the innate immune system and identify target cells that are stressed, such as cancer cells, and infected cells that express stress markers on their cell surface. NKs produce potent, MHC-unrestricted cytotoxicity to eradicate virally infected and transformed cells by a number of mechanisms, including direct release of cytotoxic granules containing perforin and granzymes, induced targets killing via death receptors and NK cell-mediated antibody-dependent cellular cytotoxicity (ADCC). Furthermore, cancerous tumors contain cells that frequently reduce expression of MHC-I proteins that provide an inhibitory signal to NK cells. Additionally, NK cells secrete proinflammatory cytokines/chemokines to recruit and activate effector T cells to the tumor site, modulate activity of antigen-presenting myeloid cells, and modify the tumor microenvironment in favor of an antitumor response. NK cells are thereby attractive as a cell therapy for cancer [Rezvani K, et al., Mol Ther 2017, 25(8):1769-1781; Curti A, et al., Blood 2011, 118(12):3273-3279; Oberschmidt O, et al., Front Immunol 2017, 8:654].

NK cells offer an attractive alternative to T cell-based therapy. First, allogeneic NK cells are expected to have lower risks for graft-versus-host disease (GVHD) than allogeneic T cells, which even when HLA-matched still posed a risk of GVHD through their native αβ T cell receptor. Moreover, besides the specificity of chimeric antigen receptor ("CAR"), engineered NKs retain their intrinsic ability to recognize and target tumor cells due to their full array of native receptors.

Natural killer cells may be prepared from donor-derived sources for allogeneic transfer to cancer patients [Rubnitz J E, et al., J Clin Oncol 2010, 28(6):955-959]. They are educated to recognize a complement of activating and inhibitory cell surface markers primarily to attack 'self' tissues that are stressed. The ability to source NK cells from donor peripheral blood or banked umbilical cord blood allows a NK cell therapy to be expanded and standardized for multiple patient infusions [Liu E, et al., Leukemia 2017; Shah N, et al, PLoS One 2013, 8(10):e76781].

However, there are still major hurdles for clinical application of NK based therapy. Mature human NKs have a relatively limited life-span (estimated half-life 14 days, persistence in vivo around one month for adoptive transferred NKs), compared with years for CAR-T products. Hence, alternative approaches for NK prolonged survival is highly desirable in the field.

SUMMARY

In another aspect, provided herein is a nucleic acid, comprising a first polynucleotide and a second polynucleotide, wherein the first polynucleotide encodes a chimeric polypeptide (sometimes referred to herein as a chimeric signaling polypeptide or a chimeric stimulating molecule) comprising: (1) a ligand binding region; and (2) a signaling region, comprising (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide. In some embodiments, the nucleic acid further comprises a third polynucleotide, and wherein the third polynucleotide encodes either (i) a chimeric antigen receptor (CAR) or T-cell receptor, or (ii) a chimeric pro-apoptotic polypeptide comprising a second ligand binding region and a caspase-9 polypeptide lacking the caspase activation domain (CARD domain), and wherein the ligand binding region of the chimeric polypeptide is different than the second ligand binding domain of the chimeric pro-apoptotic polypeptide. The chimeric pro-apoptotic polypeptide is sometimes referred to herein as a safety switch. In some embodiments, the nucleic acid comprises a polynucleotide sequence encoding a marker (e.g., ΔCD19 polypeptide). In specific embodiments, a polynucleotide encoding a cleavage site, such as a 2A cleavage site or a 2A-like cleavage site, is used to link the polynucleotides. For examples of such cleavage sites, see, e.g., Donnelly et al., Analysis of the aphthovirus 2A/2B polyprotein 'cleavage' mechanism indicates not a proteolytic reaction, but a novel translational effect: a putative ribosomal 'skip.' J Gen Virol 2001; 82:1013-1025 and Quintarelli et al., Co-expression of cytokine and suicide genes to enhance the activity and safety of tumor-specific cytotoxic T lymphocytes. Blood 2007; 110:2793-2802.

In another aspect, provided herein is a nucleic acid, comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising: (1) a ligand binding region; and (2) a signaling region, comprising (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a chimeric antigen receptor (CAR) or a T cell receptor. In specific embodiments, the CAR targets PSMA, PSCA, Muc1 CD19, ROR1, Mesothelin, GD2, CD123, Muc16, CD33, CD38, CD44v6, Her2/Neu, CD20, CD30, BCMA, PRAME, NY-ESO-1, or EGFRvIII. In particular embodiments, the CAR targets HER-2, PSCA, CD123, or BCMA. In some embodiments, the nucleic acid further comprises a fourth polynucleotide, and wherein the fourth polynucleotide encodes a chimeric pro-apoptotic polypeptide comprising a second ligand binding region and a caspase-9 polypeptide lacking the caspase activation domain (CARD domain), and wherein the ligand binding region of the chimeric polypeptide is different than the second ligand binding domain of the chimeric pro-apoptotic polypeptide. In some embodiments, the nucleic acid comprises a polynucleotide sequence encoding a marker (e.g., ΔCD19 polypeptide). In specific embodiments, a polynucleotide encoding a cleavage site, such as a 2A cleavage site or a 2A-like cleavage site, is used to link the polynucleotides.

In another aspect, provided herein is a nucleic acid, comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising: (1) a ligand binding region; and (2) a signaling region, comprising (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a chimeric pro-apoptotic polypeptide comprising a second ligand binding region and a caspase-9 polypeptide lacking the caspase activation domain (CARD domain), and wherein the ligand binding region of the chimeric polypeptide is different than the second ligand binding domain of the chimeric pro-apoptotic polypeptide. In some embodiments, the nucleic acid further comprises a fourth polynucleotide, and wherein the fourth polynucleotide encodes a marker polypeptide (e.g., ΔCD19 polypeptide). In specific embodiments, a polynucleotide encoding a cleavage site, such as a 2A cleavage site or a 2A-like cleavage site, is used to link the polynucleotides.

In another aspect, provided herein is a nucleic acid, comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising: (1) a ligand binding region; and (2) a signaling region, comprising (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a marker polypeptide (e.g., ΔCD19 polypeptide).

In another aspect, provided herein is a nucleic acid, comprising a first polynucleotide and a second polynucleotide, wherein the first polynucleotide encodes a chimeric polypeptide (sometimes referred to herein as a chimeric signaling polypeptide or a chimeric stimulating molecule) comprising a signaling region, wherein the signaling region comprises: (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide. In some embodiments, the nucleic acid further comprises a third polynucleotide, and wherein the third polynucleotide encodes either (i) a chimeric antigen receptor (CAR) or T-cell receptor, or (ii) a chimeric pro-apoptotic polypeptide comprising a ligand binding region and a caspase-9 polypeptide lacking the caspase activation domain (CARD domain). In some embodiments, the nucleic acid comprises a polynucleotide sequence encoding a marker (e.g., ΔCD19 polypeptide). In some embodiments, the first polynucleotide further comprises a ligand binding region. In specific embodiments, a polynucleotide encoding a cleavage site, such as a 2A cleavage site or a 2A-like cleavage site, is used to link the polynucleotides.

In another aspect, provided herein is a nucleic acid, comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising a signaling region, wherein the signaling region comprises: (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a chimeric antigen receptor (CAR) or a T cell receptor. In specific embodiments, the CAR targets PSMA, PSCA, Muc1 CD19, ROR1, Mesothelin, GD2, CD123, Muc16, CD33, CD38, CD44v6, Her2/Neu, CD20, CD30, BCMA, PRAME, NY-ESO-1, or EGFRvIII. In particular embodiments, the CAR targets HER-2, PSCA, CD123, or BCMA. In some embodiments, the nucleic acid further comprises a fourth polynucleotide, and wherein the fourth polynucleotide encodes a chimeric pro-apoptotic polypeptide comprising a ligand binding region and a caspase-9 polypeptide lacking the caspase activation domain (CARD domain). In some embodiments, the nucleic acid comprises a polynucleotide sequence encoding a marker (e.g., ΔCD19 polypeptide). In some embodiments, the first polynucleotide further comprises a ligand binding region. In specific embodiments, a polynucleotide encoding a cleavage site, such as a 2A cleavage site or a 2A-like cleavage site, is used to link the polynucleotides.

In another aspect, provided herein is a nucleic acid, comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising a signaling region, wherein the signaling region comprises: (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a marker polypeptide (e.g., a ΔCD19 polypeptide). In some embodiments, the first polynucleotide further comprises a ligand binding region.

In some embodiments, a nucleic acid described herein is contained in a vector, such as a viral vector plasmid. In certain embodiments, a nucleic acid described herein is contained in an adenoviral vector, a retroviral vector, or a lentiviral vector. In some embodiments, a nucleic acid described herein is isolated. In certain embodiments, provided herein is a composition comprising a nucleic acid described herein.

In specific embodiments, a nucleic acid is one described in the Examples described herein below (e.g., Example 3 or 4). For example, in certain embodiments, a nucleic acid described herein is a construct described herein, such as, e.g., the BP2811 or BP2810 construct described herein (e.g., depicted in FIG. 1 and described in the Examples below). In some embodiments, a nucleic acid described herein contains the transgenes of a construct described herein, such as e.g., the BP2811 or BP2810 construct described herein (e.g., depicted in FIG. 1 and described in the Examples below).

In another aspect, provided herein is a modified natural killer (NK) cell comprising the nucleic acid described herein. In a specific embodiment, a modified NK cell is engineered to express a nucleic acid described herein. In another specific embodiment, a modified NK cell(s) is of the type described in the Examples below (e.g. Example 3 or 4, infra).

In another aspect, provided herein is a modified cell(s) comprising a first polynucleotide and a second polynucleotide, wherein the first polynucleotide encodes a chimeric polypeptide (sometimes referred to herein as a chimeric signaling polypeptide or a chimeric stimulating molecule) comprising: (1) a ligand binding region; and (2) a signaling region, comprising (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide. In some embodiments, the modified NK cell(s) further comprises a third polynucleotide, and wherein the third polynucleotide encodes either (i) a chimeric antigen receptor (CAR) or T-cell receptor, or (ii) a chimeric pro-apoptotic polypeptide comprising a second ligand binding region and a caspase-9 polypeptide lacking the caspase activation domain (CARD domain), and wherein the ligand binding region of the chimeric polypeptide is different than the second ligand binding domain of the chimeric pro-apoptotic polypeptide. In some embodiments, the nucleic acid comprises a polynucleotide sequence encoding a marker (e.g., ΔCD19 polypeptide).

In another aspect, provided herein is a modified NK cell(s) comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising: (1) a ligand binding region; and (2) a signaling region, comprising (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a chimeric antigen receptor (CAR) or a T cell receptor. In specific embodiments, the CAR targets PSMA, PSCA, Muc1 CD19, ROR1, Mesothelin, GD2, CD123, Muc16, CD33, CD38, CD44v6, Her2/Neu, CD20, CD30, BCMA, PRAME, NY-ESO-1, or EGFRvIII. In particular embodiments, the CAR targets HER-2, PSCA, CD123, or BCMA. In some embodiments, the modified NK cell(s) further comprises a fourth polynucleotide, and wherein the fourth polynucleotide encodes a chimeric pro-apoptotic polypeptide comprising a ligand binding region and a caspase-9 polypeptide lacking the caspase activation domain (CARD domain), and wherein the ligand binding region of the chimeric polypeptide is different than the second ligand binding domain of the chimeric pro-apoptotic polypeptide. In some embodiments, the nucleic acid comprises a polynucleotide sequence encoding a marker (e.g., ΔCD19 polypeptide).

In another aspect, provided herein is a modified NK cell(s) comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising: (1) a ligand binding region; and (2) a signaling region, comprising (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a chimeric pro-apoptotic polypeptide comprising a second ligand binding region and a caspase-9 polypeptide lacking the caspase activation domain (CARD domain), and wherein the ligand binding region of the chimeric polypeptide is different than the second ligand binding domain of the chimeric pro-apoptotic polypeptide. In some embodiments, the modified NK cell(s) further comprises a fourth polynucleotide, and wherein the fourth polynucleotide encodes a marker polypeptide (e.g., ΔCD19 polypeptide).

In another aspect, provided herein is a modified NK cell(s) comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising: (1) a ligand binding region; and (2) a signaling region, comprising (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a marker polypeptide (e.g., ΔCD19 polypeptide).

In another aspect, provided herein is a modified NK cell(s) comprising a first polynucleotide and a second polynucleotide, wherein the first polynucleotide encodes a chimeric polypeptide (sometimes referred to herein as a chimeric signaling polypeptide or a chimeric stimulating molecule) comprising a signaling region, wherein the signaling region comprises: (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide. In some embodiments, the modified NK cell(s) further comprises a third polynucleotide, and wherein the third polynucleotide encodes either (i) a chimeric antigen receptor (CAR) or T-cell receptor, or (ii) a chimeric pro-apoptotic polypeptide comprising a ligand binding region and a caspase-9 polypeptide lacking the caspase activation domain (CARD domain). In some embodiments, the first polynucleotide further comprises a ligand binding region. In some embodiments, the nucleic acid comprises a polynucleotide sequence encoding a marker (e.g., ΔCD19 polypeptide).

In another aspect, provided herein is a modified NK cell(s) comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising a signaling region, wherein the signaling region comprises: (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a chimeric antigen receptor (CAR) or a T cell receptor. In specific embodiments, the CAR targets PSMA, PSCA, Muc1 CD19, ROR1, Mesothelin, GD2, CD123, Muc16, CD33, CD38, CD44v6, Her2/Neu, CD20, CD30, BCMA, PRAME, NY-ESO-1, or EGFRvIII. In particular embodiments, the CAR targets HER-2, PSCA, CD123, or BCMA. In some embodiments, the modified NK cell(s) further comprises a fourth polynucleotide, and wherein the fourth polynucleotide encodes a chimeric pro-apoptotic polypeptide comprising a second ligand binding region and a caspase-9 polypeptide lacking the caspase activation domain (CARD domain). In some embodiments, the nucleic acid comprises a polynucleotide sequence encoding a marker (e.g., ΔCD19 polypeptide). In some embodiments, the first polynucleotide further comprises a ligand binding region.

In another aspect, provided herein is a modified NK cell(s) comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising a signaling region, wherein the signaling region comprises: (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a chimeric pro-apoptotic polypeptide comprising a second ligand binding region and a caspase-9 polypeptide lacking the caspase activation domain (CARD domain). In some embodiments, the modified NK cell(s) further comprises a fourth polynucleotide, and wherein the fourth polynucleotide encodes a marker polypeptide (e.g., ΔCD19 polypeptide). In some embodiments, the first polynucleotide further comprises a ligand binding region.

In another aspect, provided herein is a modified NK cell(s) comprising a first polynucleotide, a second polynucleotide and a third polynucleotide, wherein the first polynucleotide encodes a chimeric polypeptide (sometimes referred to herein as a chimeric signaling polypeptide or a chimeric stimulating molecule) comprising a signaling region, wherein the signaling region comprises: (a) a MyD88 polypeptide; (b) a truncated MyD88 polypeptide lacking the TIR domain; (c) a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; (d) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; (e) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or (f) a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40; and wherein the second polynucleotide encodes an IL-15 polypeptide; and wherein the third polynucleotide encodes a marker polypeptide (e.g., ΔCD19 polypeptide). In some embodiments, the first polynucleotide further comprises a ligand binding region.

In specific embodiments, a modified NK cell(s) described herein is(are) cryostored. In some embodiments, a modified NK cell(s) described herein has been cryostored. In some embodiments, a modified NK cell(s) has(have) been stored at a temperature of −150° C. or below.

In specific embodiments, a modified NK cell(s) has(have) not been grown on feeder cells. In specific embodiments, a modified NK cell(s) has(have) not been contacted with exogenous IL-15.

In a specific embodiment, a modified NK cell(s) described herein exhibits one, two, three or more, or all of the activities, functions or both of the modified NK cells described in the Examples described herein (e.g., Examples 3 and 4).

In a specific embodiment, a modified NK cell(s) described herein, which has been transduced with a nucleic acid comprising a polynucleotide encoding a chimeric polypeptide described herein and a polynucleotide encoding a chimeric pro-apoptotic polypeptide described herein, demonstrates enhanced proliferation in vitro relative to a modified NK cell(s), which has been transduced with a nucleic acid comprising a polynucleotide encoding the chimeric pro-apoptotic polypeptide. In another specific embodiment, proliferation of a modified NK cell(s) described herein, which has been transduced with a nucleic acid comprising a polynucleotide encoding a chimeric polypeptide described herein and a polynucleotide encoding a chimeric pro-apoptotic polypeptide described herein, in vitro is significantly enhanced following ligand (e.g., Rim) treatment compared the proliferation of a modified NK cell(s), which has been transduced with a nucleic acid comprising a polynucleotide encoding the chimeric pro-apoptotic polypeptide, treated with ligand (e.g., Rim). In a specific embodiment, the method used to assess the proliferation is the methodology described in Example 3 below.

In a specific embodiment, a modified NK cell(s) described herein, which has been transduced with a nucleic acid comprising a polynucleotide encoding a chimeric polypeptide described herein, a polynucleotide encoding IL-15, and a polynucleotide encoding a chimeric pro-apoptotic polypeptide described herein, demonstrates enhanced persistence in vivo in the presence of ligand (e.g., Rim) relative to the persistence in vivo of a modified NK cell(s), which has been transduced with a nucleic acid comprising a polynucleotide encoding the chimeric polypeptide and a polynucleotide encoding the chimeric pro-apoptotic polypeptide in the presence or absence of the ligand. In a specific embodiment, the method used to assess the NK cell persistence in vivo is the methodology described in Example 3 below.

In a specific embodiment, a modified NK cell(s) described herein, which has been transduced with a first nucleic acid comprising (i) a polynucleotide encoding a chimeric polypeptide described herein, (ii) a polynucleotide encoding IL-15, and (iii) a polynucleotide encoding a chimeric pro-apoptotic polypeptide described herein, and a second nucleic acid comprising a CAR, demonstrates superior killing of target cells at a high effector to target cell ratio (e.g., an effector to target cell ratio of 1:4, 1:5, 1:6, 1:7, 1:8, 1:9, or 1:10) in the presence of ligand (e.g., Rim) relative to a modified NK cell(s), which has been transduced with a nucleic acid comprising the first nucleic acid or the second nucleic acid. In a specific embodiment, the method used to assess the killing is the methodology described in Example 3 below.

In specific embodiments, a signaling region of a chimeric polypeptide described herein comprises a truncated MyD88 polypeptide lacking the TIR domain and a CD40 cytoplasmic polypeptide region lacking the CD40 extracellular domain. In a specific embodiment, the truncated MyD88 polypeptide lacking the TIR domain comprises the amino acid sequence of SEQ ID NO: 119 or an amino acid sequence that is 90% identical to SEQ ID NO: 119. In another specific embodiment, the truncated MyD88 polypeptide lacking the TIR domain comprises the amino acid sequence of SEQ ID NO:2 or an amino acid sequence that is 90% identical to SEQ ID NO:2. In another specific embodiment, the CD40 cytoplasmic polypeptide region lacking the CD40 extracellular region comprises the amino acid sequence of SEQ ID NO: 56 or an amino acid sequence that is 90% identical to SEQ ID NO:56.

In some embodiments, a signaling region of a chimeric polypeptide described herein comprises the MyD88 polypeptide. In a specific embodiment, the MyD88 polypeptide comprises the amino acid sequence of SEQ ID NO:118 or an amino acid sequence that is 90% identical to SEQ ID NO: 118.

In certain embodiments, a signal region of a chimeric polypeptide comprises a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions. In a specific embodiment, the MyD88 polypeptide comprises the amino acid sequence of SEQ ID NO: 119 or an amino acid sequence that is 90% identical to SEQ ID NO: 119. In another specific embodiment, the truncated MyD88 polypeptide lacking the TIR domain comprises the amino acid sequence of SEQ ID NO:2 or an amino acid sequence that is 90% identical to SEQ ID NO: 2.

In some embodiments, a signaling region of a chimeric polypeptide comprises a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions. In one embodiment, the co-stimulatory polypeptide cytoplasmic signaling region is selected from the group consisting of CD27, CD28, ICOS, 4-1BB, RANK/TRANCE-R, and OX40. In another embodiment, the co-stimulatory polypeptide cytoplasmic signaling region is selected from the group consisting of CD28, 4-1BB, OX40, and ICOS. In another embodiment, the co-stimulatory polypeptide cytoplasmic signaling region is selected from the group consisting of CD27, CD28, CD30, ICOS, 4-1BB, CD40, RANK/TRANCE-R, and OX40. In another embodiment, the co-stimulatory polypeptide cytoplasmic signaling region is selected from the group consisting of CD27, CD28, ICOS, 4-1BB, and OX40. In certain embodiments, the co-stimulatory polypeptide lacks an extracellular domain or lacks a functional extracellular domain. In a specific embodiment, the truncated MyD88 polypeptide lacking the TIR domain comprises the amino acid sequence of SEQ ID NO: 119 or an amino acid sequence that is 90% identical to SEQ ID NO: 119. In another embodiment, the truncated MyD88 polypeptide lacking the TIR domain comprises the amino acid sequence of SEQ ID NO: 2 or an amino acid sequence that is 90% identical to SEQ ID NO: 2. In another embodiment, the truncated MyD88 polypeptide lacking the TIR domain comprises the amino acid sequence of SEQ ID NO: 118 or an amino acid sequence that is 90% identical to SEQ ID NO: 118.

In certain embodiments, a signal region of a chimeric polypeptide comprises a first co-stimulatory polypeptide cytoplasmic signaling region selected from the group consisting of CD27, CD28, CD30, ICOS, 4-1BB, CD40, RANK/TRANCE-R, and OX40, and a second co-stimulatory polypeptide cytoplasmic signaling region selected from the group consisting of CD27, CD28, CD30, ICOS, 4-1BB, CD40, RANK/TRANCE-R, and OX40. In one embodiment, the signal region comprises a first co-stimulatory polypeptide cytoplasmic signaling region selected from the group consisting of CD27, CD28, ICOS, 4-1BB, CD40, RANK/TRANCE-R, and OX40, and a second co-stimulatory polypeptide cytoplasmic signaling region selected from the group consisting of CD27, CD28, ICOS, 4-1BB, CD40, RANK/TRANCE-R, and OX40. In another embodiment, the signaling region comprises a first co-stimulatory polypeptide cytoplasmic signaling region selected from the group consisting of CD27, CD28, ICOS, 4-1BB, RANK/TRANCE-R, and OX40, and a second co-stimulatory polypeptide cytoplasmic signaling region selected from the group consisting of CD27, CD28, ICOS, 4-1BB, RANK/TRANCE-R, and OX40. In another embodiment, the signaling region comprises a first co-stimulatory polypeptide cytoplasmic signaling region selected from the group consisting of CD28, 4-1BB, OX40, and ICOS, and a second co-stimulatory polypeptide cytoplasmic signaling region selected from the group consisting of CD28, 4-1BB, OX40, and ICOS. In another embodiment, the signaling region comprises a first co-stimulatory polypeptide cytoplasmic signaling region selected from the group consisting of CD27, CD28, CD3, ICOS, 4-1BB, CD40, RANK/TRANCE-R, and OX40, and a second co-stimulatory polypeptide cytoplasmic signaling region selected from the group consisting of CD27, CD28, CD3, ICOS, 4-1BB, CD40, RANK/TRANCE-R, and OX40. In another embodiment, the signaling region comprises a first co-stimulatory polypeptide cytoplasmic signaling region selected from the group consisting of CD27, CD28, ICOS, 4-1BB, RANK/TRANCE-R, and OX40, and a second co-stimulatory polypeptide cytoplasmic signaling region selected from the group consisting of CD27, CD28, ICOS, 4-1BB, RANK/TRANCE-R, and OX40.

In a specific embodiment, an OX40, CD28, ICOS, 4-1BB, MyD88 or CD40 sequence comprises (or consists of) a sequence disclosed herein (e.g., a sequence disclosed in the Examples below).

In some embodiments, a ligand binding domain described herein is a multimeric ligand binding region. In certain embodiments, the ligand binding region described herein comprises an FKBP variant polypeptide, such as a human protein FK506-binding protein (FKBP)12 (Fv) which contains a single acid substitution of phenylalanine to valine at amino acid position 36. In some embodiments, a ligand binding region described herein comprises multiple copies (e.g., two, three, or more copies) of an FKBP variant polypeptide, such as a human protein FKBP12 (Fv) which contains a single acid substitution of phenylalanine to valine at amino acid position 36. In a specific embodiment, a ligand binding domain described herein comprises two copies of FKBP12v36. In other embodiments, a ligand binding domain described herein comprises an FKBP12 polypeptide and an FKBP-rapamycin-binding region (FRB) polypeptide or an FRB variant polypeptide.

In a specific embodiment, a ligand binding region comprises FKBPV, FKBP", FKBPV', FKBV, FRBPwt, or FKB. In certain embodiments, FKBPV, FKBP", FKBPV', FKBV, FRBPwt, or FKB comprises a sequence disclosed herein (e.g., a sequence disclosed in the Examples below).

In a specific embodiment, a chimeric pro-apoptotic polypeptide comprises a Δcaspase-9 sequence disclosed herein (e.g. a sequence disclosed in the Examples below).

In a specific embodiment, ΔCD19 comprises (or consists of) a sequence disclosed herein (e.g., a sequence disclosed in the Examples below).

In specific embodiments, a ligand binding domain described herein binds to a chemical inducer of dimerization or multimerization. In some embodiments, a ligand binding domain of a nucleic acid described herein binds to rimiducid, AP20187, or AP1510. In certain embodiments, a ligand binding domain described herein binds to rapamycin or a rapalog.

In another aspect, provided herein is a method for stimulating an immune response comprising administering modified NK cells described herein to a subject (e.g., a human subject). In one embodiment, the subject has a disease or condition associated with an elevated level of expression of a target antigen expressed by a target cell. In a particular embodiment, a tumor has been detected in the subject administered the modified NK cells.

In another aspect, provided herein pharmaceutical compositions comprising modified NK cells or nucleic acids described herein. In some embodiments, pharmaceutical compositions are provided that are prepared by the methods of the present application. In specific embodiments, modified NK cells described or pharmaceutical compositions comprising modified NK cells described herein may be used in accordance with the methods of stimulating an immune response, methods of treatment, or both.

In another aspect, provided herein is a method for stimulating an immune response comprising administering (i) modified NK cells described herein to a subject (e.g., a human subject) and (ii) a ligand that binds to the ligand binding region of the chimeric polypeptide. In specific embodiments, the ligand is administered after the modified NK cells are administered to the subject. In certain embodiments, the subject has a disease or condition associated with an elevated level of expression of a target antigen expressed by a target cell. In specific embodiments, the ligand is administered to the subject in amount effective to reduce the number or concentration of the target antigen or target cells in the subject. In some embodiments, a tumor has been detected in the subject administered the modified NK cells. In specific embodiments, the ligand is administered to the subject in an amount effective to reduce the size of the tumor in the subject. In specific embodiments, the ligand administered to the subject is rimiducid, AP20187, or AP1510. In other specific embodiments, the ligand administered to the subject is rapamycin or a rapalog.

In another aspect, provided herein is a method for reducing the number of modified NK cells in the event of a negative symptom or condition, comprising administering to a subject (e.g., a human subject) who has been previously been administered a ligand that binds to the ligand binding region of a chimeric pro-apoptotic polypeptide in an amount effective to reduce the number or concentration of the modified NK cells in the subject. In a specific embodiment, the amount administered to the subject is effective to kill at least 30% of the cells that express the chimeric pro-apoptotic polypeptide. In another specific embodiment, the amount administered to the subject is effective to kill at least 60% of the cells that express the chimeric pro-apoptotic polypeptide. In a specific embodiment, the amount administered to the subject is effective to kill at least 90% of the cells that express the chimeric pro-apoptotic polypeptide. In another specific embodiment, the negative symptom or condition is graft-versus-host disease.

In some embodiments, a subject treated in accordance with the methods described herein has cancer. In certain embodiments, a subject treated in accordance with the methods described herein has been diagnosed as having a hyperproliferative disease. In some embodiments, a subject treated in accordance with the methods described herein has been diagnosed with sickle cell anemia or metachromatic leukodystrophy. In certain embodiments, a subject treated in accordance with the methods described herein has been diagnosed with a condition selected from the group consisting of a primary immune deficiency condition, hemophagocytosis lymphohistiocytosis (HAH) or another hemophagocytic condition, an inherited marrow failure condition, a hemoglobinopathy, a metabolic condition, and an osteoclast condition. In some embodiments, a subject treated in accordance with the methods described herein has been diagnosed with a disease or condition selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XAP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis. In certain embodiments, a subject treated in accordance with the methods described herein has been diagnosed with leukemia. In some embodiments, a subject treated in accordance with the methods described herein has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

In specific embodiments, the ligand administered to the subject is rimiducid, AP20187, or AP1510. In other specific embodiments, the ligand administered to the subject is rapamycin or a rapalog.

In certain embodiments, a pharmaceutical composition comprises a ligand that binds to a ligand binding region described herein. In a specific embodiment, a pharmaceutical composition comprises a ligand that binds to a ligand binding region described herein and a pharmaceutically acceptable carrier. In some embodiments, such a pharmaceutical composition may be used to bind to a ligand binding region of a chimeric polypeptide and induce dimerization or multimerization resulting in the activation or enhancement of activation of modified NK cells. In other embodiments, such a pharmaceutical composition may be used to bind to a ligand binding region of a chimeric pro-apoptotic polypeptide and induce dimerization or multimerization resulting in killing of modified NK cells.

In some embodiments, modified Natural Killer cells described herein have one or more of the functions of the Natural Killer cells described in the Examples below, e.g., Example 1, 3 or 4. In some embodiments, modified Natural Killer cells described herein are produced using a method described in the Examples below.

In some embodiments, the subject is a mammal. In some embodiments, the subject is a human

BRIEF DESCRIPTION OF THE DRAWINGS

The drawings illustrate certain embodiments of the technology and are not limiting. For clarity and ease of illustration, the drawings are not made to scale, and, in some instances, various aspects may be shown exaggerated or enlarged to facilitate an understanding of particular embodiments.

FIG. 8A: graph of GM-CSF concentration; FIG. 8B: graph of TNF-alpha concentration; FIG. 8C: MIP-1 alpha concentration; FIG. 8D: MIP-1-beta concentration.

FIGS. 9A-9D. FIG. 9A provides a timeline of an in vivo proliferation assay; FIG. 9B provides a table measuring proliferation of modified NK cells in mice. FIG. 9C provides luminescence images of mice used in the in vivo assays. FIG. 9D provides a graph of luminescence of NK cells in treated mice.

FIG. 10A provides a bar graph of percent THP-1 AML tumor cell killing by modified NK cells. FIG. 10B provides a line graph of percent THP-1 AML tumor cell killing by modified NK cells.

FIG. 11A provides a line graph of tumor growth in the presence of modified NK cells. FIG. 11B provides flow cytometry data of THP-GFP AML tumor cells incubated with modified NK cells.

FIG. 12A provides luminescence images of mice treated with modified NK cells. FIG. 12B provides a line graph of luminescence of tumor cells in the treated mice.

FIG. 13A provides a schematic of cryostorage (freezing) and thawing of modified NK cells used in the assays; FIG. 13B provides a graph of THP-luc killing at an E:T of 3:1 NK cells:THP-luciferase targets; FIG. 13C provides a graph of THP-luc killing at an E:T of 1:1 NK cells:THP-luciferase targets.

FIG. 15B: NK cells were labeled with CellTrace dye the day of transduction. Proliferation was assessed 9 days later. Representative histograms show CellTrace dilution in iRC9.iMC transduced NK cell population (gated on CD56+CD3-CD19+) in the presence of 1 nM rimiducid (dark gray) or not (light gray). FIG. 15C: MFI of CellTrace dye in iRC9 or iRC9.iMC transduced NK cells with or without 1 nM rimiducid. Paired t tests were used to compare indicated groups. *p<0.05; p<0.01; NS none significant. In vivo persistence of iRC9.iMC or iRC9.IL-15.iMC transduced NK cells in the absence (FIGS. 15D and 15E) or presence (FIG. 15F) of tumor targets (THP-1 cells) in NSG mice. 2-way ANOVA was used to access differences among groups of E; P<0.01. Multiple T tests were used to assess differences between iRC9 rimiducidand iRC9.IL15.iMC Rim, blue *P<0.001; and between iRC9.iMC Veh vs iRC9.iMC Rim, red **P<0.01.

FIG. 18A: iRC9, iRC9.iMC, iRC9.IL15.iMC NK cells phenotype based on the average expression of DNAM1, NKP30, NKP44, NKP46, NKG2D, CD16, Fas, FasL were characterized by multiparameter flow cytometry analysis. MFI or the percentages of positive cells were normalized according the average value of non-transduced NK cells. FIG. 18B: IFN-γ productions in supernatant by iRC9, iRC9.iMC, or iRC9.IL15.iMC transduced NK cells when co-culture with k562 cells at the E:T ratio 1:1 for 48 hrs. in the presences of variable rimiducid concentrations (0-100 nM). Two-way ANOVAs were used to compare groups. P<0.0001. FIG. 18C: 29-plex cytokine multiplex analysis of supernatant from iMC-iRC9, iMC.IL15, or iRC9 transduced NK cells co-cultured with/without THP-1 in the absence or presence of 1 nM rimiducid. FIGS. 18D and 18E: NT, iRC9, iRC9.iMC, or iRC9.IL15.iMC transduced NK cells, either untreated or treated with 1 nM rimiducid for 6 days. Transgene expression as indicated by CD19 positive percentage. Representative flow plots are shown in FIG. 18D and dot plots for N=4 in FIG. 18E. Paired t tests were used to compare groups. **p<0.01.

FIG. 19A: NK cells transduced with iMC.IL15.iRC9 were co-cultured with SKOV3RFP at a 2:1 E:T ratio at variable Herceptin concentrations (0-1200 ng/ml). SKOV3 (RFP, red) proliferation were measured by live-cell imaging using an IncuCyte imager. After 72 h, SKOV3 killing was calculated relative to tumor cells alone. FIG. 19B: iRC9 and iMC.IL15.iRC9 NK cell co-culture with SKOV3RFP at a 1:2 effector to target (E:T) ratio with or without 300 ng/ml Herceptin and 1 nM rimiducid. Two-way ANOVA was used to do comparison. P<0.0001. After 72 h of co-culture SKOV3RFP proliferation was measured by IncuCyte (FIG. 19C). After 71 h, co-culture with different transduced NK cells OE19GFP proliferation was measured by IncuCyte. Two-way ANOVA were used do comparison. P<0.01. (FIG. 19D)

FIG. 20A: Activated NK cells were transduced with γ-RV encoding CD123ζ CAR, dual switch DS.IL15 (iRC9.IL15.iMC), or DS.IL15+CD123ζ CAR. CD19 marker was used to check dual switch transduction efficiency, CD34 marker was used to check for CD123 CAR transduction efficiency. FIG. 20B:Transduced NK cells were co-cultured with THP-1-GFPFfluc at different E:T ratios in the presence or absence of 1 nM rimiducid. Luciferase activity was determined at 24 hrs. N=4 donors. Multiple t tests were used to compare DS.IL15 Rim and DS.IL15+CD123ζ CAR Rim. P<0.01. FIGS. 20C-20D: NSG mice were engrafted i.v. with 10⁷ NKs NT or transduced with CD123ζ CAR, DS.IL15, or DS.IL15+CD123ζ CAR; 3 days following i.v. implantation of 10⁶ THP-1-GFPFfluc tumor cells. 1 mg/kg rimiducid or vehicle was administrated i.p. weekly. BLI was monitored by IVIS. Multiple t tests were used to compare CD123ζ CAR Rim group with NT group. *P<0.001. FIG. 20E: At day 53 post NK therapy, DS.IL15+CD123ζ CAR Rim group was euthanized. Human NK cells were identified in spleen, bone marrow, and peripheral blood. Compared with DS.IL15+CD123ζ CAR vehicle group euthanized at day 35 post NK therapy (FIG. 20F). FIG. 20G: CD123 surface expression in THP-1-GFPFfluc tumor cells (GFP+ population) in spleen and bone marrow. All other groups were at timepoint day 35 except DS.IL15+CD123ζ CAR Rim group was obtained at day 53. 2-way ANOVA were used do comparison. P=0.47.

FIG. 22A: Transduction efficiency of DS.BCMA.ζ.IL15 NK, which was cotransduced with γ-RV encoding iMC.BCMA.ζ.IL15 and iRC9. FIGS. 22B and 22C: NSG mice were engrafted with 10⁷ NK cells either non-transduced or transduced with DS.BCMA.ζ.IL15 NK 3 days following intravenous ("i.v"). implantation of 10⁶ THP-1-GFPFfluc tumor cells. 1 mg/kg rimiducid or vehicle was administrated intraperitoneal ("i.p"). Five times a week for the first week, and three times a week for the rest time. Bioluminescence ("BLI") was monitored by IVIS. Multiple t tests were used to compare DS.BCMA.ζ.IL15 NK Rim group with tumor alone group. P<0.01, *P<0.001. FIGS. 22D and 22E: At day 40 to day 48, mice from NT, DS.BCMA.ζ.IL15 NK vehicle or rimiducid groups were euthanized. THP-1-GFPfluc cells were identified in bone marrow and spleen as GFP+ populations. FIGS. 22F-22G: Human NK cells were identified in spleen and bone marrow as mCD45-GFP-hCD45+hCD34+ populations. Student t tests were used to do comparisons. *P<0.05, ***P<0.001.

FIG. 23A shows relative expression of ILT2 and ILT4 in T cells and NK cells. FIG. 23B shows MFI HLA-ABC levels in K562, OE-19, THP-1, HPAC, SKOV3, and ISO cell lines and FIG. 23C shows MFI MICA/B levels in K562, OE-19, THP-1, HPAC, SKOV3, and ISO cell lines.

FIG. 24A: NSG mice were tail vein injected 5×10⁶ NK cells double transduced with RV encoding iRC9, iRC9.iMC, or iRC9.IL15.iMC, 5 and 12 days following i.v. implantation of 10⁶THP-1.GFPluc tumor cells. Rimiducid or vehicle was administrated i.p. weekly. Tumor cells growth (D-luciferin substrate) were monitored by IVIS. FIGS. 24B and 24C: Survival curves were plotted. Comparison of survival curves were done by Log-rank (Mantel-Cox) test. P<0.0001.

FIG. 25A: Annexin V staining was assessed by flow cytometry analysis. FIG. 25B: Temsirolimus at various concentration was administrated for 24 hrs. 7AAD staining was assessed by flow cytometry. Cells were first gated as CD56+CD19+ for transduced cells, CD56+ for NT non-transduced NK cells.

FIGS. 26A-H. Analysis of Dual Switch CAR-T and CAR-NK cells. Lymphocytes were separated from peripheral blood mononuclear cells (PBMCs) derived from three donor and separated into T cell and NK cell preparations by CD56 bead purification. T cells and NK cells were activated by αCD3/αCD28 antibodies and IL-15 followed by K562 cell stimulation respectively, as described previously. Cells were then transduced with BP2818 and BP1385 viruses encoding dual switch constructs iMC-αBCMACAR-IL15 and iC9-αCD19 (a marker for transduction). FIG. 26A: Flow cytometry panels documenting representative transduction efficiencies of CD34 (a CAR marker) and CD19 (a safety switch marker). FIG. 26B: Transduction efficiency for expression of both markers of transduction efficiencies in CAR-T cells and CAR-NK cells in each donor preparation. FIG. 26C: Expression of BCMA in four target tumor cell lines determined by flow cytometry. FIGS. 26D-26G: Co-cultures between non-transduced (NT) T cells and NK cells and Dual Switch transduced BCMA directed CAR-T and CAR-NK cells and target cell lines were prepared at decreasing Effector to Target (E:T) ratios to determine relative efficacy for cell killing. Failure of GFP-labeled tumor cells to grow over the course of 150 hours in the presence and absence of 1 nM rimiducid relative to tumor cells not containing effector cells was determined by Incucyte microscopy. Results were plotted for cocultures of NCIH929 (FIG. 26D), THP-1 (FIG. 26E), U266 (FIG. 26F) and RPMI8226 cells (FIG. 26G). Supernatants from cocultures of tumor cell targets and T and NK cells outlined in FIGS. 26D-26G at E:T of 1:4 were isolated and analysed for cytokine levels by Multiplex analysis (Biorad). Results indicated that dual switch CAR-NK cells activated with rimiducid and exposed to multiple tumor targets express similar levels of inflammatory cytokines IFN-γ, TNF-α and GM-CSF as dual switch CAR-T cells while secreting elevated amounts of IL-13 and IL-5 relative to dual switch CAR-T cells (FIG. 26H). Furthermore, the secretion of chemokines such as MIP1α, MIP1β and MCP1 was elevated in rim-treated dual switch CAR-NK cells relative to similar co-culture of dual switch CAR-T cells supporting the hypothesis that dual switch CAR-NK cells may produce a more pro-inflammatory tumor microenvironment than dual switch CAR-T cells by recruitment of dendritic cells, macrophage and lymphocytes to an anti-tumor response.

DETAILED DESCRIPTION

Figure 1:
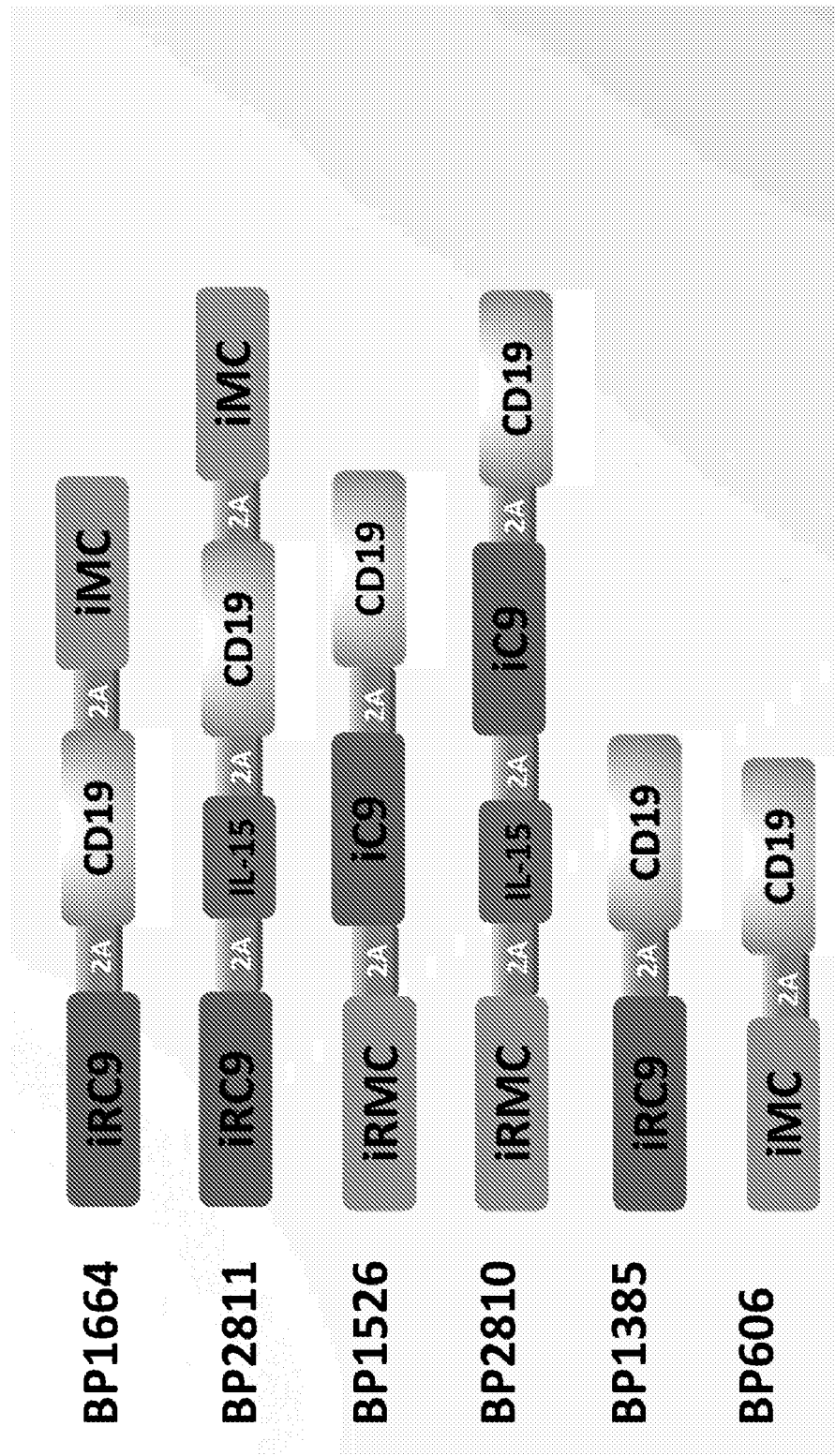
FIG. 1 provides schematics of expression constructs BP1664, BP2811, BP1526, BP2810, BP1385, and BP606.

The present invention relates generally to the field of immunology and relates in part to compositions, and methods for growing and storing modified natural killer cells, including for example, conditional chemical regulation of natural killer cell function. The technology further relates to pharmaceutical compositions and treatment of subjects using modified natural killer cells. Provided herein in some embodiments are allele systems in which the proliferation of human Natural Killer (NK) cells along with their persistence in vivo, production of immune activating cytokines and ability to kill tumor cells can be enhanced by the introduction of a protein-based molecular switch that could be constitutively activated or a protein-based molecular switch that could be responsive to a synthetic ligand. To mitigate cases of NK cell overactivity that may produce toxicity, a second protein-based molecular switch is included to ablate NK cell function by the induction of apoptosis. These dual switch NK cells may be used as a cell therapy for cancer or as an adjunct to other immunotherapies for cancer.

Introduction

Natural killer cells (NK cells) are cytotoxic lymphocytes that are part of the innate immune system. NK cells, in general, do not express markers indicative of T or B cells. NK cell markers include CD16 and/or CD56. NK cells act by killing target cells, such as tumor cells, infected cells, and antibody-targeted cells. NK cells may be obtained or isolated from, for example, peripheral blood, bone marrow, and umbilical cord blood, or they can be derived from stem cell populations including CD34 positive hematopoeitic stem cells themselves derived from Induced Pluripotent Stem (IPS) cells that can be genetically modified. The terms "inducible pluripotent stem cell" or "induced pluripotent stem cell" as used herein refers to adult, or differentiated cells, that are "reprogrammed" or induced by genetic (e.g., expression of genes that in turn activates pluripotency), biological (e.g., treatment viruses or retroviruses) and/or chemical (e.g., small molecules, peptides and the like) manipulation to generate cells that are capable of differentiating into many if not all cell types, like embryonic stem cells. Inducible pluripotent stem cells are distinguished from embryonic stem cells in that they achieve an intermediate or terminally differentiated state (e.g., skin cells, bone cells, fibroblasts, and the like) and then are induced to dedifferentiate, thereby regaining some or all of the ability to generate multipotent or pluripotent cells. CD34" as used herein refers to a cell surface glycoprotein (e.g., sialomucin protein) that often acts as a cell-cell adhesion factor and is involved in T cell entrance into lymph nodes, and is a member of the "cluster of differentiation" gene family.

As mentioned above, the use of allogeneic NK cells has potential in cell therapy. However, several deficiencies limit the widespread use of NK cells as a cell therapy for cancer: 1) NK cells have limited intrinsic potential for proliferation and persistence in vivo [Rezvani K, et al., Mol Ther 2017, 25(8):1769-1781; 3; Oberschmidt O, et al., Front Immunol 2017, 8:654; Fujisaki H, et al., Cancer Res 2009, 69(9): 4010-4017]; 2) NK cells are subject to non-viability and inefficacy when thawed from cryostorage and are therefore generally produced from fresh material and expanded for each use. This property limits there usage only to specialized centers. 3) While the risks of excessive cytokine release and GvHD are far less than those of T cell therapies, there is a potential for off-tumor systemic toxicity from the grafted cells [Bonifant C L, et al., Mol Ther Oncolytics 2016, 3:16011; Shah N N, et al., Blood 2015, 125(5):784-792].

Provided herein are compositions, and methods for growing and storing modified natural killer cells. The compositions and methods provide NK cells that proliferate and persist in vivo. Methods are provided for cryostoring and thawing NK cells, and optionally for growing NK cells in the absence of a feeder layer. NK cells provided in the present embodiments are viable and demonstrate efficacy in vitro and in vivo. In specific embodiments, NK cells provided herein are viable and demonstrate efficacy in vitro and in vivo even after cryopreservation. In some embodiments, the compositions and methods provide the ability to obtain, grow, store, expand, and administer NK cells, including allogeneic NK cells, while reducing certain cytotoxic effects.

In the examples and embodiments described herein, the inventors have established a novel approach to engineering NKs with superior effector functions, such as NK cell proliferation, in vivo persistence, cytokines production, and antitumor activity. In the examples described below NK cells derived from peripheral blood were transduced with retroviral vectors encoding costimulatory molecules, IL-15, a suicide gene, and in some experiments an additional tumor antigen specific CAR. In the experiment where an inducible costimulatory molecule was used, upon rimiducid administration the modified NK cells showed improved expansion in vitro and sustained persistence in NSG mice both in the presence and absence of tumor targets. The activated iMC gene modified NKs function better, in releasing more granules containing perforin, granzyme B, and effective cytokines IFN-γ TNF-α, resulted in effectively killing of either MHC class I high expressing NK resistant tumor cells and MHC class I low expressing NK sensitive tumor cells. Moreover, when combined with a CAR targeting tumor specific antigens, rimiducid-activated iMC modified NKs demonstrated potent antitumor responses against their target, associated with prolonged persistence in vivo and homing to bone marrow and spleen, sites of disease. Thus, surprisingly, the inventors observed that Rimiducid activated iMC modified NKs demonstrated enhanced proliferation, upregulated cytokines productions including IFN-γ and TNF-α, increased cytotoxicity as well as degranulation, perforin and granzyme B expression in response to tumor cell targets.

Furthermore, the inventors observed that CAR-NKs showed superior cytotoxicity against two BCMA antigen high expressing cell lines, when compared to CAR-T cells. Without intending to be limited to any theory, NKs have germline receptors on their surface including a variety of activating receptors and inhibitory receptors that can exert cytotoxicity via non-CAR as well as CAR-mediated modes, this is shown by the killing of tumor cells by non-transduced NKs. Thus, NK cells can provide an advantage in circumstances when heterogeneous tumor targets evade CAR-T therapy with tumor cells having lower antigen expressing on surface. Additionally, it was observed in the examples that CAR-NKs generally produced more cytokines (IFN-γ, TNF-α, GM-CSF, etc.) in response to target cells. This may play pivotal roles in shaping the adaptive immune responses against tumor via modulating the dual switch ("DS"), macrophages, and T cell responses.

Non-limiting examples of chimeric polypeptides useful for inducing cell activation, and related methods for inducing activation including, for example, expression constructs, methods for constructing vectors, and assays for activity or function, may also be found in the following patents and patent applications, each of which is incorporated by reference herein in its entirety for all purposes. U.S. patent application Ser. No. 14/842,710, filed Sep. 1, 2015, published as US2016-0058857-A1 on Mar. 3, 2016, entitled "COSTIMULATION OF CHIMERIC ANTIGEN RECEPTORS BY MYD88 AND CD40 POLYPEPTIDES," U.S. patent application Ser. No. 14/210,034, filed Mar. 13, 2014, entitled METHODS FOR CONTROLLING T CELL PROLIFERATION, published Sep. 25, 2014 as US2014-0286987-A1; International Patent Application No. PCT/US2014/026734, filed Mar. 13, 2014, published Sep. 25, 2014 as WO2014/151960, by Spencer et al.; U.S. patent application Ser. No. 14/622,018, filed Feb. 13, 2014, entitled METHODS FOR ACTIVATING T CELLS USING AN INDUCIBLE CHIMERIC POLYPEPTIDE, published Feb. 18, 2016 as US2016-0046700-A1; International Patent Application No. PCT/US2015/015829, filed Feb. 13, 2015, published Aug. 20, 2015 as WO2015/123527; U.S. patent application Ser. No. 10/781,384, filed Feb. 18, 2004, entitled INDUCED ACTIVATION OF DENDRITIC CELLS, published Oct. 21, 2004 as US2004-0209836-A1, issued Jun. 29, 2008 as U.S. Pat. No. 7,404,950, by Spencer et al.; International Patent Application No. PCT/US2004/004757, filed Feb. 18, 2004, published Mar. 24, 2005 as WO2004/073641A3; U.S. patent application Ser. No. 12/445,939, filed Oct. 26, 2010, entitled METHODS AND COMPOSITIONS FOR GENERATING AN IMMUNE RESPONSE BY INDUCING CD40 AND PATTERN RECOGNITION RECEPTORS AND ADAPTORS THEREOF, published Feb. 10, 2011 as US2011-0033388-A1, issued Apr. 8, 2014 as U.S. Pat. No. 8,691,210, by Spencer et al.; International Patent Application No. PCT/US2007/081963, filed Oct. 19, 2007, published Apr. 24, 2008 as WO2008/049113; U.S. patent application Ser. No. 13/763,591, filed Feb. 8, 2013, entitled METHODS AND COMPOSITIONS FOR GENERATING AN IMMUNE RESPONSE BY INDUCING CD40 AND PATTERN RECOGNITION RECEPTOR ADAPTERS, published Mar. 27, 2014 as US2014-0087468-A1, issued Apr. 19, 2016 as U.S. Pat. No. 9,315,559, by Spencer et al.; International Patent Application No. PCT/US2009/057738, filed Sep. 21, 2009, published Mar. 25, 2010 as WO201033949; U.S. patent application Ser. No. 13/087, 329, filed Apr. 14, 2011, entitled METHODS FOR TREATING SOLID TUMORS, published Nov. 24, 2011 as US2011-0287038-A1, by Slawin et al.; International Patent Application No. PCT/US2011/032572, filed Apr. 14, 2011, published Oct. 20, 2011 as WO2011/130566, by Slawin et al; U.S. patent application Ser. No. 14/968,853, filed Dec. 14, 2015, entitled METHODS FOR CONTROLLED ACTIVATION OR ELIMINATION OF THERAPEUTIC CELLS, published Jun. 23, 2016 as US2016-0175359-A1, by Spencer et al.; International Patent Application No. PCT/US2015/065646, filed Dec. 14, 2015, published Sep. 15, 2016 as WO2016/100241, by Spencer et al.; U.S. patent application Ser. No. 15/377,776, filed Dec. 13, 2016, entitled DUAL CONTROLS FOR THERAPEUTIC CELL ACTIVATION OR ELIMINATION, published Jun. 15, 2017 as US2017-0166877-A1, by Bayle et al.; International Patent Application No. PCT/US2016/066371, filed Dec. 13, 2016, published Jun. 22, 2017 as WO2017/106185, by Bayle et al.; and U.S. Provisional Patent Application No. 62/503,565, filed May 9, 2017, entitled METHODS TO AUGMENT OR ALTER SIGNAL TRANSDUCTION, by Bayle et al., each of which is incorporated by reference herein in its entirety for all purposes.

Non-limiting examples of chimeric polypeptides useful for inducing cell death or apoptosis, and related methods for inducing cell death or apoptosis, including expression constructs, methods for constructing vectors, assays for activity or function, and multimerization of the chimeric polypeptides by contacting cells that express inducible chimeric polypeptides with a multimeric compound, or a pharmaceutically acceptable salt thereof, that binds to the multimerizing region of the chimeric polypeptides both ex vivo and in vivo, administration of expression vectors, cells, or multimeric compounds described herein, or pharmaceutically acceptable salts thereof, to subjects, and administration of multimeric compounds described herein, or pharmaceutically acceptable salts thereof, to subjects who have been administered cells that express the inducible chimeric polypeptides, may also be found in the following patents and patent applications, each of which is incorporated by reference herein in its entirety for all purposes. U.S. patent application Ser. No. 13/112,739, filed May 20, 2011, entitled METHODS FOR INDUCING SELECTIVE APOPTOSIS, published Nov. 24, 2011, as US2011-0286980-A1, issued Jul. 28, 2015 as U.S. Pat. No. 9,089,520; U.S. patent application Ser. No. 13/792,135, filed Mar. 10, 2013, entitled MODIFIED CASPASE POLYPEPTIDES AND USES THEREOF, published Sep. 11, 2014 as US2014-0255360-A1, issued Sep. 6, 2016 as U.S. Pat. No. 9,434,935, by Spencer et al.; International Patent Application No. PCT/US2014/022004, filed Mar. 7, 2014, published Oct. 9, 2014 as WO2014/16438; U.S. patent application Ser. No. 14/296,404, filed Jun. 4, 2014, entitled METHODS FOR INDUCING PARTIAL APOPTOSIS USING CASPASE POLYPEPTIDES, published Jun. 2, 2016 as US2016-0151465-A1, by Slawin et al; International Application No. PCT/US2014/040964 filed Jun. 4, 2014, published as WO2014/197638 on Feb. 5, 2015, by Slawin et al.; U.S. patent application Ser. No. 14/640,553, filed Mar. 6, 2015, entitled CASPASE POLYPEPTIDES HAVING MODIFIED ACTIVITY AND USES THEREOF, published Nov. 19, 2015 as US2015-0328292-A1; International Patent Application No. PCT/US2015/019186, filed Mar. 6, 2015, published Sep. 11, 2015 as WO2015/134877, by Spencer et al.; U.S. patent application Ser. No. 14/968,737, filed Dec. 14, 2015, entitled METHODS FOR CONTROLLED ELIMINATION OF THERAPEUTIC CELLS, published Jun. 16, 2016 as US2016-0166613-A1, by Spencer et al.; International Patent Application No. PCT/US2015/065629 filed Dec. 14, 2015, published Jun. 23, 2016 as WO2016/100236, by Spencer et al.; U.S. patent application Ser. No. 14/968,853, filed Dec. 14, 2015, entitled METHODS FOR CONTROLLED ACTIVATION OR ELIMINATION OF THERAPEUTIC CELLS, published Jun. 23, 2016 as US2016-0175359-A1, by Spencer et al.; International Patent Application No. PCT/US2015/065646, filed Dec. 14, 2015, published Sep. 15, 2016 as WO2016/100241, by Spencer et al.; U.S. patent application Ser. No. 15/377,776, filed Dec. 13, 2016, entitled DUAL CONTROLS FOR THERAPEUTIC CELL ACTIVATION OR ELIMINATION, published Jun. 15, 2017 as US2017-0166877-A1, by Bayle et al.; and International Patent Application No. PCT/US2016/066371, filed Dec. 13, 2016, published Jun. 22, 2017 as WO2017/106185, by Bayle et al., each of which is incorporated by reference herein in its entirety for all purposes. Multimeric compounds described herein, or pharmaceutically acceptable salts thereof, may be used essentially as discussed in examples provided in these publications, and other examples provided herein.

Thus, provided in some embodiments is a modified NK cell, comprising a polynucleotide encoding a chimeric polypeptide, wherein the chimeric polypeptide comprises a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In some embodiments, the NK cell is cryostored. In some embodiments, the modified NK cell has been stored at a temperature of 0° C., −25 degrees C., −50 degrees C., −75 degrees C., −100 degrees C., −125 degrees C., −150 degrees C., −175 degrees C., or −200 degrees C. or below. In some embodiments, the modified cell comprises a polynucleotide that encodes an IL-15 polypeptide. In certain embodiments, the modified NK cell further comprises: one, two, or all of the following: (1) a polynucleotide encoding IL-15, (2) a polynucleotide encoding a chimeric pro-apoptotic polypeptide described herein, or (3) a CAR.

Provided in some embodiments is a method for cryopreserving NK cells, comprising storing modified NK cells at a temperature below −150° C., wherein the NK cells comprise a polynucleotide encoding a chimeric polypeptide, wherein the chimeric polypeptide comprises a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

In some embodiments, the modified NK cells may be cryopreserved or frozen at a temperature of 0, −25, −50, −75, −100, −125, −150, −175, or −200 degrees Celsius or below. In some embodiments, the modified NK cells may be thawed following storage at a temperature of 0, −25, −50, −75, −100, −125, −150, −175, or −200 degrees Celsius or below.

Provided in some embodiments is a method for growing NK cells ex vivo, comprising incubating modified NK cells in cell culture medium, wherein the modified NK cells comprise a polynucleotide encoding a chimeric polypeptide, wherein the chimeric polypeptide comprises a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In certain embodiments, the modified NK cells further comprise: one, two, or all of the following: (1) a polynucleotide encoding IL-15, (2) a polynucleotide encoding a chimeric pro-apoptotic polypeptide described herein, or (3) a CAR.

Provided in some embodiments is a method for thawing NK cells comprising thawing frozen modified NK cells, wherein the modified NK cells comprise a polynucleotide encoding a chimeric polypeptide, wherein the chimeric polypeptide comprises a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40, wherein the modified NK cells have been stored at a temperature of 0° C. or below. In some embodiments, the method comprises the step of transfecting or transducing NK cells with a nucleic acid comprising a polynucleotide encoding the chimeric polypeptide. In certain embodiments, the modified NK cells further comprise: one, two, or all of the following: (1) a polynucleotide encoding IL-15, (2) a polynucleotide encoding a chimeric pro-apoptotic polypeptide described herein, or (3) a CAR. In some embodiments, the method comprises cooling the modified NK cells to a temperature of 0° C. or below. In some embodiments, the method comprises cooling the modified NK cells to a temperature of −150° C. or below. In some embodiments, the method comprises thawing the modified NK cells.

In some embodiments, a method is provided for stimulating an immune response comprising transfecting or transducing a NK cell ex vivo with a nucleic acid comprising a polynucleotide encoding a chimeric polypeptide, wherein the chimeric polypeptide comprises a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In some embodiments, the method comprises the step of transfecting or transducing NK cells with a nucleic acid comprising a polynucleotide encoding the chimeric polypeptide. In some embodiments, the immune response is a cytotoxic response. In some embodiments, the immune response is a cytolytic response. In some embodiments, the immune response is an anti-tumor response. In certain embodiments, the modified NK cell further comprises: one, two, or all of the following: (1) a polynucleotide encoding IL-15, (2) a polynucleotide encoding a chimeric pro-apoptotic polypeptide described herein, or (3) a CAR.

In some embodiments, a method is provided for stimulating an immune response comprising administering modified NK cells to a subject, wherein the modified NK cells comprise a polynucleotide encoding a chimeric polypeptide, wherein the chimeric polypeptide comprises a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In certain embodiments, the modified NK cells further comprise: one, two, or all of the following: (1) a polynucleotide encoding IL-15, (2) a polynucleotide encoding a chimeric pro-apoptotic polypeptide described herein, or (3) a CAR.

In some embodiments, a method is provided for treating a subject having a disease or condition associated with an elevated expression of a target antigen expressed by a target cell, comprising transplanting an effective amount of modified NK cells into the subject; wherein the modified NK cells comprise a polynucleotide encoding a chimeric polypeptide, wherein the chimeric polypeptide comprises a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In certain embodiments, the modified NK cells further comprise: one, two, or all of the following: (1) a polynucleotide encoding IL-15, (2) a polynucleotide encoding a chimeric pro-apoptotic polypeptide described herein, or (3) a CAR. In some embodiments, the target antigen is a tumor antigen.

In some embodiments, a method is provided for reducing the size of a tumor in a subject, comprising transplanting an effective amount of modified NK cells into the subject; wherein the modified NK cells comprise a polynucleotide encoding a chimeric polypeptide, wherein the chimeric polypeptide comprises a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In certain embodiments, the modified NK cell further comprises: one, two, or all of the following: (1) a polynucleotide encoding IL-15, (2) a polynucleotide encoding a chimeric pro-apoptotic polypeptide described herein, or (3) a CAR.

In some embodiments, the method comprises administering an effective amount of a ligand that binds to a multimerizing region of the chimeric costimulating polypeptide to reduce the number or concentration of target antigen or to reduce the number of target cells in the subject. The method comprise transplanting an effective amount of modified NK cells into the subject; wherein the modified NK cells comprise a polynucleotide encoding a chimeric polypeptide, wherein the chimeric polypeptide comprises a ligand binding region; and a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In certain embodiments, the modified NK cell further comprises: one, two, or all of the following: (1) a polynucleotide encoding IL-15, (2) a polynucleotide encoding a chimeric pro-apoptotic polypeptide described herein, or (3) a CAR.

In some embodiments, a method is provided for administering a ligand to a human subject who has undergone cell therapy using modified NK cells, wherein the modified NK cells comprise a polynucleotide encoding a chimeric polypeptide, wherein the chimeric polypeptide comprises a ligand binding region; and a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In certain embodiments, the modified NK cells further comprise: one, two, or all of the following: (1) a polynucleotide encoding IL-15, (2) a polynucleotide encoding a chimeric pro-apoptotic polypeptide described herein, or (3) a CAR.

In some embodiments, a kit is provided, comprising modified natural killer (NK) cells described herein, wherein the modified NK cells have been stored at a temperature of 0° C. or below. In some embodiments, the kit comprises a ligand that binds to a ligand binding region. In some embodiments, the kit comprises an antibody. In some embodiments, the antibody binds to an antigen on a target cell. In some embodiments, the antibody is formulated for priming the NK cells stimulate an immune response against the target cell. In some embodiments, the target cell is a tumor cell.

In some embodiments, the chimeric polypeptide comprises a first ligand binding region and a second ligand binding region, wherein the first ligand binding region has a different amino acid sequence than the second ligand binding region, and the first and second ligand binding regions bind to a heterodimeric ligand. In some embodiments, the first ligand binding region binds to a first portion of the heterodimeric ligand, and the second ligand binding region binds to a second portion of the heterodimeric ligand. In some embodiments, the chimeric polypeptide of any one of embodiments described above is a first chimeric polypeptide, and the cell comprises a second chimeric polypeptide, the first ligand binding region of the first chimeric polypeptide and a second ligand binding region of the second chimeric polypeptide binds to the second portion of the heterodimeric ligand.

Provided in some embodiments is a modified natural killer (NK) cell, comprising a first and a second polynucleotide, wherein the first polynucleotide encodes a chimeric polypeptide comprising a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In some embodiments, the second polynucleotide encodes an IL-15 polypeptide. In some embodiments, the chimeric polypeptide comprises a ligand binding region.

In some embodiments, a nucleic acid is provided comprising a first and a second polynucleotide, wherein the first polynucleotide encodes a chimeric polypeptide comprising a signaling region, comprising a MyD88 polypeptide; a truncated MyD88 polypeptide lacking the TIR domain; a MyD88 polypeptide and a CD40 cytoplasmic polypeptide region lacking the CD40 extracellular domain; a truncated MyD88 polypeptide lacking the TIR domain and a CD40 cytoplasmic polypeptide region lacking the CD40 extracellular domain; a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40. In some embodiments, the chimeric polypeptide further comprises a ligand binding region. In some embodiments, the second polynucleotide encodes an IL-15 polypeptide. In some embodiments, the nucleic acid comprises a polynucleotide that encodes a chimeric antigen receptor (CAR) or a T-cell receptor. In some embodiments, a nucleic acid is provided comprising a first, a second, and a third polynucleotide, wherein the first polynucleotide encodes a chimeric polypeptide comprising a first ligand binding region, a second ligand binding region, a truncated MyD88 polypeptide lacking the TIR domain and a CD40 cytoplasmic polypeptide region lacking the CD40 extracellular domain, the second polynucleotide encodes an IL-15 polypeptide, and the third polynucleotide encodes a chimeric antigen receptor. In some embodiments the ligand binding region comprises an FKBP12v36 polypeptide. In some embodiments, the nucleic acid is incorporated in a modified NK cell.

In some embodiments, a nucleic acid is provided comprising a first, a second, and a third polynucleotide, wherein the first polynucleotide encodes a chimeric polypeptide comprising a truncated MyD88 polypeptide lacking the TIR domain and a CD40 cytoplasmic polypeptide region lacking the CD40 extracellular domain, the second polynucleotide encodes an IL-15 polypeptide, and the third polynucleotide encodes a chimeric polypeptide comprising a caspase-9 polypeptide lacking the CARD domain. The three polynucleotides may be positioned in various 5 to 3' order on the nucleic acid. In some embodiments, the chimeric polypeptide further comprises a ligand binding region. In some embodiments, the ligand binding region comprises an FKBP12v36 polypeptide. In some embodiments, the third polynucleotide encodes a chimeric polypeptide comprising a caspase-9 polypeptide lacking the CARD domain comprises a second and a third ligand binding region. In some embodiments, the second ligand binding region comprises an FKBP12 polypeptide and the third ligand binding region comprises an FRB polypeptide or an FRB variant polypeptide. In some embodiments, the nucleic acid comprises a polynucleotide encoding a marker polypeptide, in some embodiments the marker polypeptide comprises a truncated CD19 polypeptide. In some embodiments, the nucleic acid is incorporated in a modified NK cell. In some embodiments, the modified NK cell comprises a second nucleic acid comprising a polynucleotide that encodes a chimeric antigen receptor. In some embodiments, the second nucleic acid comprises a polynucleotide encoding a marker polypeptide, in some embodiments the marker polypeptide comprises a truncated CD19 polypeptide. In some embodiments, a modified NK cell is provided that comprises a first nucleic acid and a second nucleic acid, where the first nucleic acid comprises a first polynucleotide encoding two FKBP12v36 polypeptides, a truncated MyD88 polypeptide, and a CD40 cytoplasmic polypeptide region lacking the CD40 extracellular domain; a second polynucleotide encoding an IL-15 polypeptide, and a third polynucleotide encoding chimeric polypeptide comprising a caspase-9 polypeptide lacking the CARD domain, an FKBP12 polypeptide, and an FRB polypeptide or FRB variant polypeptide, and a fourth nucleic acid comprising a polynucleotide encoding a chimeric antigen receptor, and wherein the first nucleic acid or the second nucleic acid optionally comprise a polynucleotide encoding a marker polypeptide.

In some embodiments, a nucleic acid is provided comprising a first, a second, and a third polynucleotide, wherein the first polynucleotide encodes a chimeric polypeptide comprising a first ligand binding region, a second ligand binding region, a truncated MyD88 polypeptide lacking the TIR domain and a CD40 cytoplasmic polypeptide region lacking the CD40 extracellular domain, the second polynucleotide encodes an IL-15 polypeptide, and the third polynucleotide encodes a chimeric antigen receptor. The three polynucleotides may be positioned in various 5 to 3' order on the nucleic acid. In some embodiments, the first, second, and third polynucleotides are positioned on the nucleic acid in 5' to 3' order of first polynucleotide, third polynucleotide, and second polynucleotide. In some embodiments the first ligand binding region comprises an FKBP12v36 polypeptide and the second ligand binding region comprises an FKBP12v36 polypeptide. In some embodiments, the nucleic acid is incorporated in a modified NK cell. In some embodiments, the modified NK cell comprises a second nucleic acid comprising a polynucleotide that encodes a chimeric polypeptide comprising a caspase-9 polypeptide lacking the CARD domain, and a third and a fourth ligand binding region. In some embodiments, the third ligand binding region comprises an FKBP12 polypeptide and the fourth ligand binding region comprises an FRB polypeptide or an FRB variant polypeptide. In some embodiments, the second nucleic acid comprises a polynucleotide encoding a marker polypeptide, in some embodiments the marker polypeptide comprises a truncated CD19 polypeptide. In some embodiments, a first nucleic acid is provided that comprises a first polynucleotide encoding two FKBP12v36 polypeptides, a truncated MyD88 polypeptide, and a CD40 cytoplasmic polypeptide region lacking the CD40 extracellular domain; a second polynucleotide encoding an IL-15 polypeptide, and a third polynucleotide encoding a chimeric antigen receptor. In some embodiments, a modified cell is provided comprising the first nucleic acid. In some embodiments, the modified cell is a NK cell. In some embodiments, a modified cell is provided comprising the first nucleic acid and a second nucleic acid, where the second nucleic acid comprises a polynucleotide encoding a chimeric polypeptide comprising a caspase-9 polypeptide lacking the CARD domain, an FKBP12 polypeptide, and an FRB polypeptide or FRB variant polypeptide, and wherein the first nucleic acid or the second nucleic acid optionally comprise a polynucleotide encoding a marker polypeptide.

In some embodiments, pharmaceutical compositions are provided that comprise the modified cells or nucleic acids of the present application. In some embodiments, pharmaceutical compositions are provided that are prepared by the methods of the present application.

In some embodiments, the modified NK cell, method, kit, nucleic acid, or pharmaceutical composition of the present embodiments comprise a polynucleotide encoding an IL-15 polypeptide. In some embodiments, the modified NK cell, kit, or pharmaceutical composition is transfected or transduced with a nucleic acid that comprises a polynucleotide encoding an IL-15 polypeptide.

Expression of recombinant vectors encoding gene fusions between a truncation allele of MyD88 (myeloid differentiation primary response 88) and the intracellular signaling domains of certain transmembrane receptors generates signaling nodes that enhance the signaling capacity of MyD88 itself. These chimeric signaling polypeptides may have constitutive activity, or may include multimeric ligand binding regions that, upon binding to a multimeric ligand induce multimerization and activation of the chimeric signaling polypeptide. Immune cells may express the chimeric signaling polypeptide as part of a chimeric antigen receptor polypeptide, or the chimeric signaling polypeptide may be expressed as a separate polypeptide from the antigen recognition polypeptide, for example, the CAR (chimeric antigen receptor) or rTCR (recombinant T cell receptor).

In some embodiments, the natural killer cells are transduced or transfected with a nucleic acid comprising a promoter operably linked to a polynucleotide encoding a chimeric signaling polypeptide, wherein the polypeptide comprises a MyD88 polypeptide or a truncated MyD88 polypeptide lacking a TIR domain; and a CD40 polypeptide cytoplasmic region that is lacking the extracellular domain. In some embodiments, the promoter is operably linked to a polynucleotide encoding a chimeric signaling polypeptide, wherein the polypeptide comprises a multimeric ligand binding region that binds to a multimeric ligand; a MyD88 polypeptide or a truncated MyD88 polypeptide lacking a TIR domain; and a CD40 polypeptide cytoplasmic region that is lacking the extracellular domain. In some embodiments, the natural killer cells are transduced or transfected with a nucleic acid comprising a promoter operably linked to a polynucleotide encoding a chimeric signaling polypeptide, a MyD88 polypeptide or a truncated MyD88 polypeptide lacking a TIR domain; and a co-stimulatory polypeptide cytoplasmic signaling region with the proviso that the co-stimulatory polypeptide cytoplasmic signaling region is not CD40. In some embodiments, the co-stimulatory polypeptide cytoplasmic signaling region is selected from the group consisting of CD27, CD28, ICOS, 4-1BB, RANK/TRANCE-R, OX40, CD30, TweakR, TAC1, BCMA and HVEM cytoplasmic signaling regions and is not a CD40 polypeptide. In some embodiments, the chimeric signaling polypeptide is an inducible chimeric signaling polypeptide comprising a multimeric ligand binding region that binds to a multimeric ligand. In other embodiments, the co-stimulatory polypeptide cytoplasmic signaling region is selected from the group consisting of CD27, CD28, ICOS, 4-1BB, RANK/TRANCE-R, and OX40, and the inducible chimeric signaling polypeptide further comprises a CD40 polypeptide lacking the extracellular region.

Co-stimulatory polypeptide cytoplasmic signaling regions of the inducible chimeric signaling polypeptides and chimeric signaling polypeptides herein may, for example, activate the NF-κB pathway, and are selected from non-CD40 NF-κB inducers such as, for example, CD28 or TNFR family members.

Also provided in some embodiments the NK cells are transduced or transfected with nucleic acids comprising a polynucleotide encoding an inducible chimeric signaling polypeptide, wherein the chimeric signaling polypeptide comprises functional domains, or functional regions. Functional domains or functional regions may be selected from the group consisting of MyD88 polypeptides or truncated MyD88 polypeptides, co-stimulatory polypeptide cytoplasmic signaling regions, multimeric ligand binding regions, and membrane targeting regions. In some embodiments, the functional domains consist of a) one or more multimeric ligand binding regions that bind to a multimeric ligand; b) a MyD88 polypeptide or a truncated MyD88 polypeptide lacking the TIR domain; and c) a costimulatory polypeptide cytoplasmic signaling region. Thus, in some embodiments, the MyD88 polypeptide domain comprises a full length MyD88 polypeptide, in some embodiments, the MyD88 polypeptide domain comprises a truncated MyD88 polypeptide lacking the TIR domain, in some embodiments, the truncated MyD88 polypeptide comprises a polypeptide that comprises the amino acid sequence of SEQ ID NO: 2 or SEQ ID NO: 119, in some embodiments, the truncated MyD88 polypeptide consists of the amino acid sequence of SEQ ID NO: 2 or SEQ ID NO: 119. Also, in some embodiments, the MyD88 polypeptide domain consists of a full length MyD88 polypeptide, in some embodiments, the MyD88 polypeptide domain consists of a truncated MyD88 polypeptide lacking the TIR domain, in some embodiments, the truncated MyD88 polypeptide consists of a polypeptide that comprises the amino acid sequence of SEQ ID NO: 2 or SEQ ID NO: 119. The chimeric signaling polypeptides may also comprise additional polypeptides, which may also be referred to as non-functional polypeptides, such as, for example, 2A polypeptides, marker polypeptides, and linker polypeptides. In some embodiments, the multimeric ligand binding regions comprise FKBP12 variant polypeptides of the present application, such as, for example, FKBP12 variant polypeptides having amino acid substitutions at position 36, and, for example, FKBP12v36. In some embodiments, functional domain (a) comprises two FKBP12 variant polypeptides, such as, for example, FKBP12 variant polypeptides having amino acid substitutions at position 36, and, for example, FKBP12v36. In some examples domain (b) comprises a truncated MyD88 polypeptide lacking the TIR domain, such as, for example, the truncated MyD88 polypeptides of the present application. In some embodiments, the costimulatory polypeptide is a CD40 polypeptide cytoplasmic region lacking the extracellular domain. In some embodiments, the costimulatory polypeptide of domain (c) is selected from the group consisting of CD27, CD28, ICOS, 4-1BB, RANK/TRANCE-R, OX40, CD30, TweakR, TAC1, BCMA and HVEM cytoplasmic signaling regions, or a functional fragment thereof. In other embodiments, the co-stimulatory polypeptide cytoplasmic signaling region is selected from the group consisting of CD27, CD28, ICOS, 4-1BB, RANK/TRANCE-R, and OX40 cytoplasmic signaling regions, and is not a CD40 polypeptide. In other embodiments, the co-stimulatory polypeptide cytoplasmic signaling region is selected from the group consisting of CD27, CD28, ICOS, 4-1BB, RANK/TRANCE-R, and OX40, or a functional fragment thereof. In some embodiments, the co-stimulatory polypeptide cytoplasmic signaling region consists of a cytoplasmic signaling region of a co-stimulatory polypeptide selected from the group consisting of CD27, CD28, ICOS, 4-1BB, RANK/TRANCE-R and OX40, or a functional fragment thereof. In some embodiments, the co-stimulatory polypeptide cytoplasmic signaling region comprises a cytoplasmic signaling region of a co-stimulatory polypeptide selected from the group consisting of CD28, ICOS, 4-1BB, and OX40. In some embodiments, the co-stimulatory polypeptide cytoplasmic signaling region consists of a cytoplasmic signaling region of a co-stimulatory polypeptide selected from the group consisting of CD28, ICOS, 4-1BB, and OX40.

In some embodiments, the NK cell is transduced or transfected with a nucleic acid that comprises a polynucleotide coding for a chimeric signaling polypeptide or an inducible chimeric signaling polypeptide that further comprises a membrane targeting region. In some embodiments, the membrane targeting region is selected from the group consisting of a myristoylation region, a palmitoylation region, a prenylation region, and transmembrane sequences of receptors. In some embodiments, the membrane-targeting region is a myristoylation region.

In some embodiments, the nucleic acid further comprises a polynucleotide encoding a chimeric Caspase-9 polypeptide comprising a multimeric ligand binding region and a Caspase-9 polypeptide.

Provided in some embodiments are modified cells, wherein the cell is transduced or transfected with a nucleic acid of any one of the present embodiments. In some embodiments, the cell is also transduced or transfected with a nucleic acid comprising a polynucleotide coding for a heterologous protein, a marker polypeptide, a chimeric antigen receptor, a recombinant T cell receptor. Also provided in certain embodiments are methods for expressing an inducible chimeric signaling polypeptide, or a chimeric signaling polypeptide in a cell, comprising contacting a nucleic acid of any one of the present embodiments with a cell under conditions in which the nucleic acid is incorporated into the cell, whereby the cell expresses the inducible chimeric signaling polypeptide or the chimeric signaling polypeptide from the incorporated nucleic acid.

Provided in certain embodiments are methods for stimulating a cell-mediated immune response in a subject, comprising administering a modified cell transfected or transduced with a nucleic acid as described herein.

Costimulation

In some embodiments, the invention provides compositions and methods comprising a NK cell population comprising a costimulatory polypeptide.

The costimulatory polypeptide of the present invention can be inducible or constitutively activated. The costimulatory polypeptide can comprise one or more costimulatory signaling regions such as CD27, ICOS, RANK, TRANCE, CD28, 4-1BB, OX40, DAP10, MyD88, or CD40 or, for example, the cytoplasmic regions thereof. The costimulatory polypeptide can comprise one or more suitable costimulatory signaling regions that activate the signaling pathways activated by CD27, ICOS, RANK, TRANCE, CD28, 4-1BB, OX40, DAP10, MyD88, or CD40. Costimulating polypeptides include any molecule or polypeptide that activates the NF-κB pathway, Akt pathway, and/or p38 pathway of tumor necrosis factor receptor (TNFR) family (i.e., CD40, RANK/TRANCE-R, OX40, 4-1BB) and CD28 family members (CD28, ICOS). More than one costimulating polypeptide or costimulating polypeptide cytoplasmic region may be expressed in the modified T cells discussed herein.

Costimulation Provided by MyD88 and CD40

In some embodiments, the NK cell population describe herein comprise a costimulatory polypeptide. The costimulatory polypeptide can comprise one or more costimulatory signaling regions that activate the signaling pathways activated by CD27, ICOS, RANK, TRANCE, CD28, 4-1BB, OX40, DAP10, MyD88, or CD40.

Provided herein are NK cells that comprise chimeric signaling polypeptides, including, for example, chimeric signaling polypeptides where the truncated MyD88 polypeptide has also been fused with signaling domains of receptor mediators of costimulation, such as, for example, CD40, CD27, CD28, 4-1BB, OX40, or ICOS.

In some embodiments, the NK cell population described herein comprises a costimulatory polypeptide comprising one or more costimulatory signaling regions that activate the signaling pathways activated by MyD88, CD40 and/or MyD88-CD40 fusion chimeric polypeptide.

MyD88 is an universal adaptor molecule for TLRs and a critical signaling component of the innate immune system, triggering an alert for foreign invaders, priming immune cell recruitment and activation. MyD88 is a cytosolic adapter protein that plays a central role in the innate and adaptive immune response. This protein functions as an essential signal transducer in the interleukin-1 and Toll-like receptor signaling pathways. These pathways regulate that activation of numerous proinflammatory genes. The encoded protein consists of an N-terminal death domain and a C-terminal Toll-interleukin1 receptor domain. MyD88 TIR domain is able to heterodimerize with TLRs and homodimerize with other MyD88 proteins. This in turn results in recruitment and activation of IRAK family kinases through interaction of the death domains (DD) at the amino terminus of MyD88 and IRAK kinases which thereby initiates a signaling pathway that leads to activation of JNK, p38 MAPK (mitogen-activated protein kinase) and NF-κB, a transcription factor that induces expression of cytokine- and chemokine-encoding genes (as well as other genes). MyD88 acts via IRAK1, IRAK2, IRF7 and TRAF6, leading to NF-kappa-B activation, cytokine secretion and the inflammatory response. It also activates IRF1 resulting in its rapid migration into the nucleus to mediate an efficient induction of IFN-beta, NOS2/INOS, and IL12A genes. MyD88-mediated signaling in intestinal epithelial cells is crucial for maintenance of gut homeostasis and controls the expression of the antimicrobial lectin REG3G in the small intestine.

CD40 is an important part of the adaptive immune response, aiding to activate APCs through engagement with its cognate CD40L, in turn polarizing a stronger CTL response. The CD40/CD154 signaling system is an important component in T cell function and B cell-T cell interactions. CD40 signaling proceeds through formation of CD40 homodimers and interactions with TNFR-associated factors (TRAFs), carried out by recruitment of TRAFs to the cytoplasmic domain of CD40, which leads to T cell activation involving several secondary signals such as the NF-κB, JNK and AKT pathways Inducible MyD88/CD40 (iMC): This activation switch includes a fusion of the signaling domains for MyD88 and the intracellular signaling domain of CD40 together with ligand binding domains derived from FKBP12 that are sensitive to the presence of dimerizing analogs of FK506 and rapamycin, typically rimiducid (also known as AP1903). Ligand binding induces the oligomerization of iMC which nucleates downstream signaling events, leading to gene expression, cytokine production, cell proliferation and cell survival. When coexpressed in T cells with a first-generation Chimeric Antigen Receptor (CAR), iMC provides costimulation that is enhanced by ligand binding.

Fusions of a truncated MyD88 polypeptide, lacking the TIR domain with the intracellular domain of CD40 ("MC") to produce a chimeric polypeptide amplifies certain signals directed by MyD88. When T cells are transfected or transduced with nucleic acids that encode MC, in combination with a Chimeric Antigen Receptor (CAR), MC delivers potent costimulatory signals that enhance T cell growth, persistence, and cytotoxic activity against cells specifically targeted by the CAR. (see, for example, U.S. patent application Ser. No. 14/842,710, titled Costimulation of Chimeric Antigen Receptors by MyD88 and CD40 polypeptide, by Spencer, D., et al, filed Sep. 1, 2015, published as US-2016-0058857A1 on Mar. 3, 2016; and International Patent Application PCT/US2015/047957, filed Dec. 14, 2015, published as WO/2016/036746 on Mar. 10, 2016, all incorporated herein by reference in their entireties).

In some embodiments, inducible chimeric signaling polypeptides may comprise a truncated MyD88 polypeptide lacking the TIR domain, a cytoplasmic signaling domain selected from the group consisting of CD40, CD28, 4-1BB, OX-40, and ICOS, and a multimeric ligand binding region such as an FKBP12 multimeric ligand binding region, for example, a wild type FKBP12 multimeric ligand binding region (Fwt) or a FKBP12 variant polypeptide that is inducible with the dimerizing small molecule AP1903 (rimiducid) or AP20187, such as, for example, a FKBP12 variant polypeptide that has an amino acid substitution at amino acid 36, substituting a different amino acid for the phenylalanine residue at position 36, for example, valine (FKBP12v36, Fv). The inducible forms of these fusions generate differential activity to transduce activating signals to the NF-κB family of transcription factors when activated with rimiducid. NF-κB is a key mediator of costimulation, cell survival and cytokine production.

In some embodiments, the cell populations provided herein comprise NK cells designed to provide constitutively active therapy. In some embodiments, the NK cells comprise a nucleic acid comprising a first polynucleotide encoding the CAR, and a second polynucleotide encoding a chimeric signaling polypeptide. In some embodiments, the second polynucleotide is positioned 5' of the first polynucleotide. In some embodiments, the second polynucleotide is positioned 3' of the first polynucleotide. In some embodiments, a third polynucleotide encoding a linker polypeptide is positioned between the first and second polynucleotides. Where the third polynucleotide is positioned 3' of the first polynucleotide and 5' of the second polynucleotide, the linker polypeptide, may remain intact following translation, or may separate the polypeptides encoded by the first and second polynucleotides during, or after translation. In some embodiments, the linker polypeptide is a 2A polypeptide, which may separate the polypeptides encoded by the first and second polynucleotides during, or after translation. High level costimulation is provided constitutively through an alternate mechanism in which a leaky 2A cotranslational sequence, for example one derived from porcine teschovirus-1 (P2A), is used to separate the CAR from the chimeric signaling polypeptide. Where the 2A separation is incomplete, for example from a leaky 2A sequence, most of the expressed chimeric signaling polypeptide molecules are separated from the chimeric antigen receptor polypeptide and may remain cytosolic, and some portion or the chimeric signaling polypeptide molecules remain attached, or linked, to the CAR.

By "constitutively active" is meant that the chimeric stimulating molecule's (e.g., chimeric signaling polypeptide's) NK cell activation activity, as demonstrated herein, is active in the absence of an inducer. Constitutively active chimeric stimulating molecules in the present application (e.g., chimeric signaling polypeptides) do not comprise a multimeric ligand binding region, or a functional multimeric ligand binding region, and are not inducible by AP1903, AP20187, or other CID.

In some embodiments, the chimeric signaling polypeptide comprises a truncated MyD88 polypeptide and a CD40 polypeptide lacking the extracellular domain, or two costimulatory polypeptides cytoplasmic signaling regions. In some embodiments, the chimeric signaling polypeptide comprises two costimulatory polypeptides cytoplasmic signaling regions, such as, for example, 4-1BB and CD28, or one, or two or more costimulatory polypeptide cytoplasmic signaling regions selected from the group consisting of CD27, ICOS, RANK, TRANCE, CD28, 4-1BB, OX40, DAP10. In some embodiments, the chimeric signaling polypeptide comprises a MyD88 polypeptide or a truncated MyD88 polypeptide and a costimulatory polypeptide cytoplasmic signaling region selected from the group consisting of CD27, ICOS, RANK, TRANCE, CD28, 4-1BB, OX40, DAP10.

Also provided in some embodiments, are cell populations provided herein that comprise an inducible safety switch, to stop, or reduce the level of, the therapy when needed. In some embodiments, immune cells, such as NK cells, express a chimeric antigen receptor, and a chimeric signaling polypeptide comprising, for example, a truncated MyD88 polypeptide and a CD40 polypeptide lacking the extracellular domain, or two costimulatory polypeptides cytoplasmic signaling regions Costimulation in T cells that express chimeric antigen receptors by MyD88 and CD40 polypeptides, and by chimeric signaling polypeptides comprising costimulatory polypeptide cytoplasmic signaling regions is discussed in U.S. patent application Ser. No. 14/842,710, filed Sep. 1, 2015, published as US2016-0058857-A1 on Mar. 3, 2016, entitled "Costimulation of Chimeric Antigen Receptors by MyD88 and CD40 Polypeptides," and to in U.S. Provisional Patent Application Ser. No. 62/503,565, filed May 9, 2017, entitled "Methods to Augment or Alter Signal Transduction."

Non-limiting examples of chimeric polypeptides useful for inducing cell activation, and related methods for inducing CAR-T cell activation including, for example, expression constructs, methods for constructing vectors, and assays for activity or function, may also be found in the following patents and patent applications, each of which is incorporated by reference herein in its entirety for all purposes. U.S. patent application Ser. No. 14/210,034, filed Mar. 13, 2014, entitled METHODS FOR CONTROLLING T CELL PROLIFERATION, published Sep. 25, 2014 as US2014-0286987-A1; International Patent Application No. PCT/US2014/026734, filed Mar. 13, 2014, published Sep. 25, 2014 as WO2014/151960, by Spencer et al.; U.S. patent application Ser. No. 14/622,018, filed Feb. 13, 2014, entitled METHODS FOR ACTIVATING T CELLS USING AN INDUCIBLE CHIMERIC POLYPEPTIDE, published Feb. 18, 2016 as US2016-0046700-A1; International Patent Application No. PCT/US2015/015829, filed Feb. 13, 2015, published Aug. 20, 2015 as WO2015/123527; U.S. patent application Ser. No. 10/781,384, filed Feb. 18, 2004, entitled INDUCED ACTIVATION OF DENDRITIC CELLS, published Oct. 21, 2004 as US2004-0209836-A1, issued Jun. 29, 2008 as U.S. Pat. No. 7,404,950, by Spencer et al.; International Patent Application No. PCT/US2004/004757, filed Feb. 18, 2004, published Mar. 24, 2005 as WO2004/073641A3; U.S. patent application Ser. No. 12/445,939, filed Oct. 26, 2010, entitled METHODS AND COMPOSITIONS FOR GENERATING AN IMMUNE RESPONSE BY INDUCING CD40 AND PATTERN RECOGNITION RECEPTORS AND ADAPTORS THEREOF, published Feb. 10, 2011 as US2011-0033388-A1, issued Apr. 8, 2014 as U.S. Pat. No. 8,691,210, by Spencer et al.; International Patent Application No. PCT/US2007/081963, filed Oct. 19, 2007, published Apr. 24, 2008 as WO2008/049113; U.S. patent application Ser. No. 13/763,591, filed Feb. 8, 2013, entitled METHODS AND COMPOSITIONS FOR GENERATING AN IMMUNE RESPONSE BY INDUCING CD40 AND PATTERN RECOGNITION RECEPTOR ADAPTERS, published Mar. 27, 2014 as US2014-0087468-A1, issued Apr. 19, 2016 as U.S. Pat. No. 9,315,559, by Spencer et al.; International Patent Application No. PCT/US2009/057738, filed Sep. 21, 2009, published Mar. 25, 2010 as WO201033949; U.S. patent application Ser. No. 13/087,329, filed Apr. 14, 2011, entitled METHODS FOR TREATING SOLID TUMORS, published Nov. 24, 2011 as US2011-0287038-A1, by Slawin et al.; International Patent Application No. PCT/US2011/032572, filed Apr. 14, 2011, published Oct. 20, 2011 as WO2011/130566, by Slawin et al; U.S. patent application Ser. No. 14/968,853, filed Dec. 14, 2015, entitled METHODS FOR CONTROLLED ACTIVATION OR ELIMINATION OF THERAPEUTIC CELLS, published Jun. 23, 2016 as US2016-0175359-A1, by Spencer et al.; International Patent Application No. PCT/US2015/047957, published as WO2016/036746 on Mar. 10, 2016, entitled COSTIMULATION OF CHIMERIC ANTIGEN RECEPTORS BY MYD88 AND CD40 POLYPEPTIDES; International Patent Application No. PCT/US2015/065646, filed Dec. 14, 2015, published Sep. 15, 2016 as WO2016/100241, by Spencer et al.; U.S. patent application Ser. No. 15/377,776, filed Dec. 13, 2016, entitled DUAL CONTROLS FOR THERAPEUTIC CELL ACTIVATION OR ELIMINATION, published Jun. 15, 2017 as US2017-0166877-A1, by Bayle et al.; International Patent Application No. PCT/US2016/066371, filed Dec. 13, 2016, published Jun. 22, 2017 as WO2017/106185, by Bayle et al.; International Patent Application No. PCT/US2018/031689, filed May 8, 2018, entitled METHODS TO AUGMENT OR ALTER SIGNAL TRANSDUCTION, published Nov. 15, 2018 as WO2018/208849, by Bayle et al., each of which is incorporated by reference herein in its entirety, including all text, tables and drawings, for all purposes.

IL-15

In a specific embodiment, IL-15 encoded by a polynucleotide described herein may by any naturally occurring interleukin-15 (e.g., mammalian IL-15), including the immature or precursor and mature forms. Non-limiting examples of GeneBank Accession Nos. for the amino acid sequence of various species of native mammalian interleukin-15 include NP_000576 (human, immature form), CAA62616 (human, immature form), NP_001009207 (*Felis catus*, immature form), AAB94536 (*rattus*, immature form), AAB41697 (*rattus*, immature form), NP_032383 (*Mus musculus*, immature form), AAR19080 (canine), AAB60398 (*Macaca mulatta*, immature form), AA100964 (human, immature form), AAH23698 (*Mus musculus*, immature form), and AAH18149 (human). In a specific embodiment, IL-15 encoded by a polynucleotide described herein is an immature/precursor form of a naturally occurring human IL-15, which comprises an IL-15 signal peptide. In another embodiment, IL-15 encoded by a polynucleotide described herein is a mature form of a naturally occurring human IL-15.

In some embodiments, IL-15 encoded by a polynucleotide described herein is a derivative of a mammalian IL-15. The IL-15 derivative may include: (a) a polypeptide that is at least 40%, 45%, 50%, 55%, 60%, 65%, 70%, 75%, 80%, 85%, 90%, 95%, 98% or 99% identical to a naturally occurring mammalian IL-15 polypeptide; (b) a polypeptide encoded by a nucleic acid sequence that is at least 40%, 45%, 50%, 55%, 60%, 65%, 70%, 75%, 80%, 85%, 90%, 95%, 98% or 99% identical a nucleic acid sequence encoding a naturally occurring mammalian IL-15 polypeptide; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to a naturally occurring mammalian IL-15 polypeptide; (d) a polypeptide encoded by nucleic acids can hybridize under high, moderate or typical stringency hybridization conditions to nucleic acids encoding a naturally occurring mammalian IL-15 polypeptide; (e) a polypeptide encoded by a nucleic acid sequence that can hybridize under high, moderate or typical stringency hybridization conditions to a nucleic acid sequence encoding a fragment of a naturally occurring mammalian IL-15 polypeptide of at least 20 contiguous amino acids, at least 30 contiguous amino acids, at least 40 contiguous amino acids, at least 50 contiguous amino acids, at least 100 contiguous amino acids, or at least 150 contiguous amino acids; or (f) a fragment of a naturally occurring mammalian IL-15 polypeptide. IL-15 derivatives also include a polypeptide that comprises the amino acid sequence of a naturally occurring mature form of a mammalian IL-15 polypeptide and a heterologous signal peptide amino acid sequence. In a specific embodiment, an IL-15 derivative is a derivative of a naturally occurring human IL-15 polypeptide. In another embodiment, an IL-15 derivative is a derivative of an immature or precursor form of naturally occurring human IL-15 polypeptide. In another embodiment, an IL-15 derivative is a derivative of a mature form of naturally occurring human IL-15 polypeptide.

In a specific embodiment, a polynucleotide encoding IL-15 comprises the nucleotide sequence of any naturally occurring nucleic acid sequences encoding IL-15 (e.g., mammalian interleukin-15), including the immature or precursor and mature forms. Non-limiting examples of GeneBank Accession Nos. for the nucleotide sequence of various species of native mammalian IL-15 include NM_000585 (human), NM_008357 (*Mus musculus*), and RNU69272 (*Rattus norvegicus*). In a specific embodiment, a polynucleotide encoding IL-15 comprises a nucleotide sequence encoding a naturally occurring human IL-15 (e.g., a mature or immature/precursor form of human IL-15).

In another embodiment, a polynucleotide encoding IL-15 comprises the nucleotide sequence of a derivative of a naturally occurring nucleic acid sequences encoding mammalian interleukin-15, including the immature or precursor and mature forms.

In a specific embodiment, a polynucleotide sequence encoding IL-15 comprises (or consists of) the nucleotide sequence of SEQ ID NO: 96. In another specific embodiment, IL-15 comprises (or consists of) the amino acid sequence of SEQ ID NO: 97.

Safety Switches

Genetically-modified NK cells of the invention may express a safety switch, also known as an inducible suicide gene or suicide switch, which can be used to eradicate the NK cells in vivo if desired e.g. if GVHD develops. In some examples, NK cells that express a chimeric antigen receptor are provided to the patient that trigger an adverse event, such as off-target toxicity. In some therapeutic instances, a patient might experience a negative symptom during therapy using chimeric antigen receptor-modified cells. In some cases, these therapies have led to side effects due, in part, to non-specific attacks on healthy tissue. In some examples, the therapeutic NK cells may no longer be needed, or the therapy is intended for a specified amount of time, for example, the therapeutic NK cells may work to decrease the tumor cell, or tumor size, and may no longer be needed. Therefore, in some embodiments are provided nucleic acids, cells, and methods wherein the modified NK cell also expresses an inducible Caspase-9 polypeptide. If there is a need, for example, to reduce the number of chimeric antigen receptor modified NK cells, an inducible ligand may be administered to the patient, thereby inducing apoptosis of the modified T cells.

These switches respond to a trigger, such as a pharmacological agent, which is supplied when it is desired to eradicate the NK cells, and which leads to cell death (e.g. by triggering necrosis or apoptosis). These agents can lead to expression of a toxic gene product, but a more rapid response can be obtained if the genetically-modified NK cells already express a protein which is switched into a toxic form in response to the agent.

In some embodiments, a safety switch is based on a pro-apoptotic protein that can be triggered by administering a chemical inducer of dimerization to a subject. If the pro-apoptotic protein is fused to a polypeptide sequence which binds to the chemical inducer of dimerization, delivery of this chemical inducer can bring two pro-apoptotic proteins into proximity such that they trigger apoptosis. For instance, Caspase-9 can be fused to a modified human FK-binding protein which can be induced to dimerize in response to the pharmacological agent rimiducid (AP1903). The use of a safety switch based on a human pro-apoptotic protein, such as, for example, Caspase-9 minimizes the risk that cells expressing the switch will be recognized as foreign by a human subject's immune system. Delivery of rimiducid to a subject can therefore trigger apoptosis of T cells which express the caspase-9 switch.

Inducible Caspase 9 (iC9): This proapoptotic switch includes a fusion of caspase-9 with FKBP12 or derivatives. It is latent in the absence of ligand but drives dimerization of the Initiator caspase, caspase-9, from the intrinsic pathway for cell apoptosis. Dimerization leads to caspase-9 activation, cleavage and activation of the effector caspase, caspase-3, and rapid cell death by apoptosis. Inducible Caspase-9 has utility as a safety switch in cell therapies to block toxic responses.

Rapamycin and rapalog sensitive switches—Rapamycin is a macrolide that binds with subnanomolar affinity with FKBP12 and simultaneously with the target of rapamycin mTOR. An 89-amino acid domain derived from mTOR, FRB, is sufficient to dimerize with an FKBP12-rapamycin complex. Fusion of FKBP in tandem with FRB together with a signaling domain facilitates homodimerization and activates signaling in the presence of the heterodimerizer rapamycin or analogs of rapamycin, generically termed rapalogs. Rapamycin and certain rapalogs are cell-permeable, stable in vivo and bind their targets with high affinity and specificity.

Rapamycin/rapalog-sensitive switches iRC9 and iRMC—Fusion of FKBP12-FRB to the amino terminus of Caspase-9 generates a rapamycin-sensitive safety switch that operates with high efficiency and dose sensitivity. Fusion of FKBP12-FRB with MyD88/CD40 generates a rapamycin or rapalog sensitive costimulatory switch. The FKBP and FRB components can be put in tandem in either an FRB-FKBP or FKBP—FRB orientation and can be fused with the MC signaling components at the amino or carboxy terminus.

FKBP12-allele specific binding by rimiducid. Rimiducid binds with high affinity (~0.1 nM) to the valine 36 allele of FKBP12 but with low affinity (~500 nM) to the wild-type phenylalanine 36 FKBP12 allele. Rapamycin and rapalogs can bind to either FKBP allele.

Non-immunosuppressive C7-rapamycin analogs. The natural target of rapamycin, mTOR is essential for cell growth and rapamycin is immunosuppressive at low dose (~1 nM). Rapalogs replacing the methoxy group at C7 with groups that have more bulk, typified by BPC015, bind with mTOR with low affinity. Mutation of the FRB in iRC9 or iRMC (or similar) to substitute threonine 2098 with leucine accommodates the derivatized rapalog and permits high affinity dimerization and signaling.

Orthogonal use of rimiducid and rapamycin sensitive switches to generate dual switch NK cells. iRC9 contains the rimiducid-insensitive F36 allele of FKBP12 and can be coexpressed with iMC in T cells. Doses of rimiducid capable of activating iMC and driving costimulation are incapable of activating the proapoptotic iRC9 switch. Rapamycin or rapalogs can activate the safety switch. Similarly, coexpression of iRMC with iC9 can generate dual switch CAR-T cells with the opposite specificity. Rapalogs are obligate heterodimerizers and can bind to but not activate the iC9 switch containing only FKBP12. Rimiducid can dimerize and activate the safety switch.

Caspase-9 switches are described in Di Stasi et al. (2011) supra; see also Yagyu et al. (2015) Mol Ther 23(9):1475-85; Rossigloni et al. (2018) Cancer Gene Ther doi.org/10.1038/s41417-018-0034-1; Jones et al. (2014) Front Pharmacol doi.org/10.3389/fphar.2014.00254; U.S. Pat. No. 9,434,935, issued Sep. 16, 2016, entitled Modified Caspase Polypeptides and Uses Thereof; U.S. Pat. No. 9,913,882, issued Mar. 13, 2018, entitled Methods for Inducing Partial Apoptosis Using Caspase Polypeptides; U.S. Pat. No. 9,393,292, issued Jul. 19, 2016, entitled Methods for Inducing Selective Apoptosis; and patent application US2015/0328292, published Nov. 19, 2015, entitled Caspase Polypeptides Having Modified Activity and Uses Thereof. Suicide switches may also be based on Fas or on HSV thymidine kinase.

Examples of ligand inducers for the switches include, for example, those discussed in Kopytek, S. J., et al., Chemistry & Biology 7:313-321 (2000) and in Gestwicki, J. E., et al., Combinatorial Chem. & High Throughput Screening 10:667-675 (2007); Clackson T (2006) Chem Biol Drug Des 67:440-2; Clackson, T., in Chemical Biology: From Small Molecules to Systems Biology and Drug Design (Schreiber, s., et al., eds., Wiley, 2007)

The ligand binding regions incorporated in the safety switches may comprise the FKBP12v36 modified FKBP12 polypeptide, or other suitable FKBP12 variant polypeptides, including variant polypeptides that bind to AP1903, or other synthetic homodimerizers such as, for example, AP20187 or AP2015. Variants may include, for example, an FKBP region that has an amino acid substitution at position 36 selected from the group consisting of valine, leucine, isoleucine and alanine (Clackson T, et al., Proc Natl Acad Sci USA. 1998, 95:10437-10442). AP1903, also known as rimiducid, (CAS Index Name: 2-Piperidinecarboxylic acid, 1-[(2S)-1-oxo-2-(3, 4,5-trimethoxyphenyl)butyl]-, 1,2-ethanediylbis[imino(2-oxo-2,1-ethanediyl)oxy-3,1-phenylene [(1R)-3-(3,4-dimethoxyphenyl)propylidene]] ester, [2S-[1 (R*),2R*[S*[S*[1(R*),2R*]]]]]-(9Cl) CAS Registry Number: 195514-63-7; Molecular Formula: $C_{78}H_{98}N_4O_{20}$ Molecular Weight: 1411.65), is a synthetic molecule that has proven safe in healthy volunteers (Iuliucci J D, et al., J Clin Pharmacol. 2001, 41:870-879).

Provided in some embodiments are safety switches such as, for example, the safety switches discussed in Di Stasi et al. (2011) supra, which consists of the sequence of the human FK506-binding protein (FKBP12) (GenBank AH002 818) with an F36V mutation, connected through a SGGGS linker to a modified human caspase 9 (CASP9) which lacks its endogenous caspase activation and recruitment domain. The F36V mutation increases the binding affinity of FKBP12 to synthetic homodimerizers AP20187 and AP1903 (rimiducid).

The safety switch may comprise a modified Caspase-9 polypeptide having modified activity, such as, for example, reduced basal activity in the absence of the homodimerizer ligand. Modified Caspase-9 polypeptides are discussed in, for example, U.S. Pat. No. 9,913,882 and US-2015-0328292, supra, and may include, for example, amino acid substitutions at position 330 (e.g., D330E or D330A) or, for example, amino acid substitutions at position 450 (e.g., N405Q), or combinations thereof, including, for example, D330E-N405Q and D330A-N405Q. Caspase-9 polypeptide with lower basal activity have been described previously, e.g. in U.S. Pat. Nos. 9,434,935, 9,932,572 and 9,913,882, and U.S. Patent Application Nos. 62/668,223, 62/756,442, 62/816,799, Ser. Nos. 15/901,556, 15/888,948.

In a specific embodiment, provided herein is a pharmaceutical composition comprising a dimerizing or multimerizing ligand. In another specific embodiment, provided herein is a pharmaceutical composition comprising an effective amount of a dimerizing or multimerizing ligand.

In a specific embodiment, provided herein is a pharmaceutical composition comprising a dimerizing or multimerizing ligand and a pharmaceutically acceptable carrier. In another specific embodiment, provided herein is a pharmaceutical composition comprising a pharmaceutically acceptable carrier and an effective amount of a dimerizing or multimerizing ligand.

An effective amount of a pharmaceutical composition, such as the dimerizing or multimerizing ligand presented herein, would be the amount that achieves this selected result of inducing apoptosis in the Caspase-9-expressing cells NK cells, such that over 60%, 70%, 80%, 85%, 90%, 95%, or 97%, or that under 80%, 70%, 60%, 50%, 40%, 30%, 20%, or 10% of the therapeutic cells are killed. The term is also synonymous with "sufficient amount." Any appropriate assay may be used to determine the percent of therapeutic cells that are killed. An assay may include the steps of obtaining a first sample from a subject before administration of the dimerizing or multimerizing ligand and obtaining a second sample from the subject after administration of the dimerizing or multimerizing ligand and comparing the number or concentration of therapeutic cells in the first and second samples to determine the percent of therapeutic cells that are killed. One can empirically determine the effective amount of a particular composition presented herein without necessitating undue experimentation.

Non-limiting examples of chimeric polypeptides useful for inducing cell death or apoptosis, and related methods for inducing cell death or apoptosis, including expression constructs, methods for constructing vectors, assays for activity or function, and multimerization of the chimeric polypeptides by contacting cells that express inducible chimeric polypeptides with a multimeric compound, or a pharmaceutically acceptable salt thereof, that binds to the multimerizing region of the chimeric polypeptides both ex vivo and in vivo, administration of expression vectors, cells, or multimeric compounds described herein, or pharmaceutically acceptable salts thereof, to subjects, and administration of multimeric compounds described herein, or pharmaceutically acceptable salts thereof, to subjects who have been administered cells that express the inducible chimeric polypeptides, may also be found in the following patents and patent applications, each of which is incorporated by reference herein in its entirety for all purposes. U.S. patent application Ser. No. 13/112,739, filed May 20, 2011, entitled METHODS FOR INDUCING SELECTIVE APOPTOSIS, published Nov. 24, 2011, as US2011-0286980-A1, issued Jul. 28, 2015 as U.S. Pat. No. 9,089,520; U.S. patent application Ser. No. 13/792,135, filed Mar. 10, 2013, entitled MODIFIED CASPASE POLYPEPTIDES AND USES THEREOF, published Sep. 11, 2014 as US2014-0255360-A1, issued Sep. 6, 2016 as U.S. Pat. No. 9,434,935, by Spencer et al.; International Patent Application No. PCT/US2014/022004, filed Mar. 7, 2014, published Oct. 9, 2014 as WO2014/16438; U.S. patent application Ser. No. 14/296,404, filed Jun. 4, 2014, entitled METHODS FOR INDUCING PARTIAL APOPTOSIS USING CASPASE POLYPEPTIDES, published Jun. 2, 2016 as US2016-0151465-A1, by Slawin et al; International Application No. PCT/US2014/040964 filed Jun. 4, 2014, published as WO2014/197638 on Feb. 5, 2015, by Slawin et al.; U.S. patent application Ser. No. 14/640,553, filed Mar. 6, 2015, entitled CASPASE POLYPEPTIDES HAVING MODIFIED ACTIVITY AND USES THEREOF, published Nov. 19, 2015 as US2015-0328292-A1; International Patent Application No. PCT/US2015/019186, filed Mar. 6, 2015, published Sep. 11, 2015 as WO2015/134877, by Spencer et al.; U.S. patent application Ser. No. 14/968,737, filed Dec. 14, 2015, entitled METHODS FOR CONTROLLED ELIMINATION OF THERAPEUTIC CELLS, published Jun. 16, 2016 as US2016-0166613-A1, by Spencer et al.; International Patent Application No. PCT/US2015/065629 filed Dec. 14, 2015, published Jun. 23, 2016 as WO2016/100236, by Spencer et al.; U.S. patent application Ser. No. 14/968,853, filed Dec. 14, 2015, entitled METHODS FOR CONTROLLED ACTIVATION OR ELIMINATION OF THERAPEUTIC CELLS, published Jun. 23, 2016 as US2016-0175359-A1, by Spencer et al.; International Patent Application No. PCT/US2015/065646, filed Dec. 14, 2015, published Sep. 15, 2016 as WO2016/100241, by Spencer et al.; U.S. patent application Ser. No. 15/377,776, filed Dec. 13, 2016, entitled DUAL CONTROLS FOR THERAPEUTIC CELL ACTIVATION OR ELIMINATION, published Jun. 15, 2017 as US2017-0166877-A1., by Bayle et al.; and International Patent Application No. PCT/US2016/066371, filed Dec. 13, 2016, published Jun. 22, 2017 as WO2017/106185, by Bayle et al., each of which is incorporated by reference herein in its entirety, including all text, tables and drawings, for all purposes. Multimeric compounds described herein, or pharmaceutically acceptable salts thereof, may be used essentially as discussed in examples provided in these publications, and other examples provided herein.

As used herein, the term "pharmaceutically or pharmacologically acceptable" refers to molecular entities and compositions that do not produce adverse, allergic, or other untoward reactions when administered to an animal or a human.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells presented herein, its use in therapeutic compositions is contemplated. Supplementary active ingredients also can be incorporated into the compositions. In some embodiments, the subject is a mammal.

By "kill" or "killing" as in a percent of cells killed, is meant the death of a cell through apoptosis, as measured using any method known for measuring apoptosis. The term may also refer to cell ablation.

Chemical Induction of Dimerization—Dual Switch

Chemical Induction of Dimerization (CID) with small molecules is an effective technology used to generate switches of protein function to alter cell physiology. A high specificity, efficient dimerizer is rimiducid (AP1903), which has two identical, protein-binding surfaces arranged tail-to-tail, each with high affinity and specificity for a mutant of FKBP12: FKBP12(F36V) (FKBP12v36, $F_{v36}$ or $F_v$), Attachment of one or more Fv domains onto one or more cell signaling molecules that normally rely on homodimerization can convert that protein to rimiducid control. Homodimerization with rimiducid is used in the context of an inducible caspase safety switch, and an inducible activation switch for cellular therapy, where MyD88 and a costimulatory polypeptide cytoplasmic region are used to stimulate immune activity.

Another CID that may be used to activate the inducible chimeric signaling polypeptides is based on a heterodimerizer, such as Rapamycin, or a rapamycin analog ("rapalog"). In these embodiments, the multimeric ligand binding region provided in the inducible chimeric signaling polypeptides, or the multimeric ligand binding region provided in the inducible chimeric caspase polypeptides binds to Rapamycin or a rapalog and does not bind to rimiducid. Rapamycin binds to FKBP12, and its variants, and can induce heterodimerization of signaling domains that are fused to FKBP12 by binding to both FKBP12 and to polypeptides that contain the FKBP-rapamycin-binding (FRB) domain of mTOR.

In some embodiments, a dual switch is provided where the nucleic acid that encodes the inducible chimeric signaling polypeptide also encodes an inducible chimeric caspase polypeptide, for example, an inducible chimeric caspase 9 polypeptide. In some embodiments, modified cells are provided that express an inducible chimeric signaling polypeptide and an inducible chimeric caspase polypeptide, for example, an inducible chimeric caspase 9 polypeptide. The multimeric ligand binding regions provided in these two distinct polypeptides are different. In one example, the inducible chimeric signaling polypeptide comprises an FRB multimeric ligand binding domain, and the inducible chimeric caspase 9 polypeptide comprises an FKBP12 variant that binds to rimiducid. In this example, a dual control system is provided. Contacting the cells with rapamycin or a rapalog induces the immune cell activity by multimerizing the inducible chimeric signaling polypeptide. Contacting the cells with rimiducid induces apoptosis by multimerizing the inducible chimeric caspase polypeptide. In other embodiments, a rapamycin or rapalog-inducible pro-apoptotic polypeptide, such as, for example, Caspase-9 or a rapamycin or rapalog-inducible chimeric signaling polypeptide, such as, for example, MyD88/4-1BB, OX40, ICOS, or CD28, (iM-X) is used in combination with a rimiducid-inducible pro-apoptotic polypeptide, such as, for example, Caspase-9, or a rimiducid-inducible iM-X, to produce dual switches. These dual switches can be used to control both cell proliferation and activity, and apoptosis selectively by administration of either of two distinct ligand inducers.

The multimerizing regions, such as FKBP12/FRB, FRB/FKBP12, and FKBP12v36, may be located amino terminal to the pro-apoptotic polypeptide or signaling polypeptide, or, in other examples, may be located carboxyl terminal to the pro-apoptotic polypeptide or signaling polypeptide. Additional polypeptides, such as, for example, linker polypeptides, stem polypeptides, spacer polypeptides, or in some examples, marker polypeptides, may be located between the multimerizing region and the pro-apoptotic polypeptide or costimulatory polypeptide, in the chimeric polypeptides.

As used here, the term "rapalog" is meant as an analog of the natural antibiotic rapamycin. Certain rapalogs in the present embodiments have properties such as stability in serum, a poor affinity to wildtype FRB (and hence the parent protein, mTOR, leading to reduction or elimination of immunosuppressive properties), and a relatively high affinity to a mutant FRB domain. For commercial purposes, in certain embodiments, the rapalogs have useful scaling and production properties. Examples of rapalogs include, but are not limited to, S-o,p-dimethoxyphenyl (DMOP)-rapamycin; R-Isopropoxyrapamycin; C7-1 sobutyloxyrapamycin; S-Butanesulfonamidorap (AP23050); 40-(S)-Fluoro-Rapamycin; 40-(S)-Chloro-Rapamycin; 40-(S)-Bromo-Rapamycin; 40-(S)-Iodo-Rapamycin; 40-(S)-Amino-Rapamycin; 40-(S)-Fluoro-7-(S)-DMOP-Rapamycin; 40-(S)-Chloro-7-(S)-DMOP-Rapamycin; 40-(S)-Iodo-7-(S)-DMOP-Rapamycin; 40-(S)-Azide-7-(S)-DMOP-Rapamycin; 40-(R)-p-Bromomethylbenzoyl-Rapamycin; 40-(R)-p-Chloromethylbenzoyl-Rapamycin; 40-(R)-((4-methylpiperazin-1-yl)p-methylbenzoyl)-Rapamycin; di-p-Bromomethylbenzoyl-Rapamycin; and 40-(S)—N-(3-(4-methylpiperazin-1-yl)propyl)-Rapamycinamine (see, e.g., U.S. Patent Application Publication No. US2017/0166877, which is incorporated by reference herein).

The term "FRB" refers to the FKBP12-Rapamycin-Binding (FRB) domain (residues 2015-2114 encoded within mTOR), and analogs thereof. In certain embodiments, FRB variants are provided. The properties of an FRB variant are stability (some variants are more labile than others) and ability to bind to various rapalogs. Based on the crystal structure conjugated to rapamycin, there are 3 key rapamycin-interacting residues that have been most analyzed, K2095, T2098, and W2101. Mutation of all three leads to an unstable protein that can be stabilized in the presence of rapamycin or some rapalogs. This feature can be used to further increase the signal:noise ratio in some applications. Examples of mutants are discussed in Bayle et al (06) Chem & Bio 13: 99-107; Stankunas et al (07) Chembiochem 8:1162-1169; and Liberles S (97) PNAS 94:7825-30). Examples of FRB regions of the present embodiments include, but are not limited to, KLW (with L2098); KTF (with F2101); and KLF (L2098, F2101). Heterodimerization is discussed in, for example, Belshaw, P., et al., PNAS 93:4604-4607 (1996). Additional compositions and methods are discussed, for example, in U.S. patent application Ser. No. 14/968,737, titled Methods for Controlled Elimination of Therapeutic Cells by Spencer, D., et al., filed Dec. 14, 2015, published as US-2016-0166613A1 on Jun. 16, 2016; International Patent Application PCT/US2015/065629, published as WO2016/100236 on Jun. 23, 2016; U.S. patent application Ser. No. 14/968,853 titled Methods for Controlled Activation or Elimination of Therapeutic Cells, by Spencer, D., et al., filed Dec. 14, 2015, published as US-2016-0175359A1 on Jun. 23, 2016; International Patent Application PCT/US2015/065646 filed Dec. 14, 2015, published as WO2016/100241 on Sep. 15, 2016; International Patent Application PCT/US2015/065629, filed Dec. 14, 2015, published as WO2016/100236 on Jun. 23, 2016; International Patent Application PCT/US2016/066371, filed Dec. 13, 2016, titled Dual Controls for Therapeutic Cell Activation or Elimination, by Bayle, J. H., et al.; and U.S. patent application Ser. No. 15/377,776, filed Dec. 13, 2016, titled Dual Controls for Therapeutic Cell Activation or Elimination, by Bayle, J. H., et al., each of which is hereby incorporated by reference herein in its entirety.

The ligands used are capable of binding to two or more of the ligand binding domains. The chimeric proteins may be able to bind to more than one ligand when they contain more than one ligand binding domain. The ligand is typically a non-protein or a chemical. Exemplary ligands include, but are not limited to FK506 (e.g., FK1012).

Other ligand binding regions may be, for example, dimeric regions, or modified ligand binding regions with a wobble substitution, such as, for example, FKBP12(V36): The human 12 kDa FK506-binding protein with an F36 to V substitution, the complete mature coding sequence (amino acids 1-107), provides a binding site for synthetic dimerizer drug rimiducid (Jemal, A. et al., CA Cancer J. Clinic. 58, 71-96 (2008); Scher, H. I. and Kelly, W. K., Journal of Clinical Oncology 11, 1566-72 (1993)). Two tandem copies of the protein may also be used in the construct so that higher-order oligomers are induced upon cross-linking by rimiducid.

FKBP12 variants may also be used in the FKBP12/FRB multimerizing regions. Variants used in these fusions, in some embodiments, will bind to rapamycin, or rapalogs, but will bind to less affinity to rimiducid than, for example, FKBP12v36. Examples of FKBP12 variants include those from many species, including, for example, yeast. In one embodiment, the FKBP12 variant is FKBP12.6 (calstablin).

Other heterodimers are contemplated in the present application. In one embodiment, a calcineurin-A polypeptide, or region may be used in place of the FRB multimerizing region. In some embodiments, the first unit of the first multimerizing region is a calcineurin-A polypeptide. In some embodiments, the first unit of the first multimerizing region is a calcineurin-A polypeptide region and the second unit of the first multimerizing region is a FKBP12 or FKBP12 variant multimerizing region. In some embodiments, the first unit of the first multimerizing region is a FKBP12 or FKBP12 variant multimerizing region and the second unit of the first multimerizing region is a calcineurin-A polypeptide region. In these embodiments, the first ligand comprises, for example, cyclosporine.

Chimeric Antigen Receptors and Cell Therapy

In some examples of cell therapy, NK cells, such as, for example, NK cells that comprise the chimeric polypeptides of the present application may comprise a chimeric antigen receptor. These modified NK cells may be used for cell therapy.

Chimeric antigen receptors (CARs) are artificial receptors designed to convey antigen specificity to T cells. They generally include an antigen-specific component, a transmembrane component, and an intracellular component selected to activate the cell and provide specific immunity. Chimeric antigen receptor-expressing NK cells may be used in various therapies, including cancer therapies. While effective against tumors, in some cases these therapies have led to side effects due, in part to non-specific attacks on healthy tissue. Thus, a method for controllable NK cell therapy is needed that provides a strong immunotherapeutic response and avoids toxic side effects.

By "chimeric antigen receptor" or "CAR" is meant, for example, a chimeric polypeptide which comprises a polypeptide sequence that recognizes a target antigen (an antigen-recognition domain) linked to a transmembrane polypeptide and intracellular domain polypeptide selected to activate the cell and provide specific immunity. The antigen-recognition domain may be a single-chain variable fragment (scFv), or may, for example, be derived from other molecules such as, for example, a T cell receptor Pattern Recognition Receptor. The intracellular domain comprises at least one polypeptide which causes activation of the cell, such as, for example, but not limited to, CD3 zeta, and, for example, co-stimulatory molecules, for example, but not limited to, CD28, OX40 and 4-1BB. In a specific embodiment, CD28, OX40, ICOS, 4-1BB, or CD3 zeta comprises (or consists) of a sequence disclosed herein (e.g., a sequence disclosed in the Examples below). The term "chimeric antigen receptor" may also refer to chimeric receptors that are not derived from antibodies but are chimeric T cell receptors. These chimeric T cell receptors may comprise a polypeptide sequence that recognizes a target antigen, where the recognition sequence may be, for example, but not limited to, the recognition sequence derived from a T cell receptor a scFv. The intracellular domain polypeptides are those that act to activate the T cell. Chimeric T cell receptors are discussed in, for example, Gross, G., and Eshar, Z., FASEB Journal 6:3370-3378 (1992), and Zhang, Y., et al., PLOS Pathogens 6:1-13 (2010).

Transmembrane Regions

A chimeric protein herein may include a single-pass or multiple pass transmembrane sequence (e.g., at the N-terminus or C-terminus of the chimeric protein). Single pass transmembrane regions are found in certain CD molecules, tyrosine kinase receptors, serine/threonine kinase receptors, TGFβ, BMP, activin and phosphatases. Single pass transmembrane regions often include a signal peptide region and a transmembrane region of about 20 to about 25 amino acids, many of which are hydrophobic amino acids and can form an alpha helix. A short track of positively charged amino acids often follows the transmembrane span to anchor the protein in the membrane. Multiple pass proteins include ion pumps, ion channels, and transporters, and include two or more helices that span the membrane multiple times. All or substantially all of a multiple pass protein sometimes is incorporated in a chimeric protein. Sequences for single pass and multiple pass transmembrane regions are known and can be selected for incorporation into a chimeric protein molecule.

In some embodiments, the transmembrane domain is fused to the extracellular domain of the CAR. In one embodiment, the transmembrane domain that naturally is associated with one of the domains in the CAR is used. In other embodiments, a transmembrane domain that is not naturally associated with one of the domains in the CAR is used. In some instances, the transmembrane domain can be selected or modified by amino acid substitution (e.g., typically charged to a hydrophobic residue) to avoid binding of such domains to the transmembrane domains of the same or different surface membrane proteins to minimize interactions with other members of the receptor complex.

Transmembrane domains may, for example, be derived from the alpha, beta, or zeta chain of the T cell receptor, CD3-ε, CD3 ζ, CD4, CD5, CD8, CD8a, CD9, CD16, CD22, CD28, CD33, CD38, CD64, CD80, CD86, CD134, CD137, or CD154. Or, in some examples, the transmembrane domain may be synthesized de novo, comprising mostly hydrophobic residues, such as, for example, leucine and valine. In certain embodiments a short polypeptide linker may form the linkage between the transmembrane domain and the intracellular domain of the chimeric antigen receptor. The chimeric antigen receptors may further comprise a stalk, that is, an extracellular region of amino acids between the extracellular domain and the transmembrane domain. For example, the stalk may be a sequence of amino acids naturally associated with the selected transmembrane domain. In some embodiments, the chimeric antigen receptor comprises a CD8 transmembrane domain, in certain embodiments, the chimeric antigen receptor comprises a CD8 transmembrane domain, and additional amino acids on the extracellular portion of the transmembrane domain, in certain embodiments, the chimeric antigen receptor comprises a CD8 transmembrane domain and a CD8 stalk. In a specific embodiment, a CD8 transmembrane comprises (or consists of) a sequence disclosed herein (e.g., a sequence disclosed in the Examples below). In another specific embodiment, a CD8 stalk comprises (or consists of) a sequence disclosed herein (e.g., a sequence disclosed in the Examples below). The chimeric antigen receptor may further comprise a region of amino acids between the transmembrane domain and the cytoplasmic domain, which are naturally associated with the polypeptide from which the transmembrane domain is derived.

Target Antigens

Chimeric antigen receptors bind to target antigens. When assaying NK cell activation in vitro or ex vivo, target antigens may be obtained or isolated from various sources. The target antigen, as used herein, is an antigen or immunological epitope on the antigen, which is crucial in immune recognition and ultimate elimination or control of the disease-causing agent or disease state in a mammal. The immune recognition may be cellular and/or humoral. In the case of intracellular pathogens and cancer, immune recognition may, for example, be a T lymphocyte response.

The target antigen may be derived or isolated from, for example, a pathogenic microorganism such as viruses including HIV, (Korber et al, eds HIV Molecular Immunology Database, Los Alamos National Laboratory, Los Alamos, N. Mex. 1977) influenza, Herpes simplex, human papilloma virus (U.S. Pat. No. 5,719,054), Hepatitis B (U.S. Pat. No. 5,780,036), Hepatitis C (U.S. Pat. No. 5,709,995), EBV, Cytomegalovirus (CMV) and the like. Target antigen may be derived or isolated from pathogenic bacteria such as, for example, from *Chlamydia* (U.S. Pat. No. 5,869,608), *Mycobacteria, Legionella, Meningiococcus,* Group A *Streptococcus, Salmonella, Listeria, Hemophilus influenzae* (U.S. Pat. No. 5,955,596) and the like). Target antigen may be derived or isolated from, for example, pathogenic yeast including *Aspergillus*, invasive *Candida* (U.S. Pat. No. 5,645,992), *Nocardia, Histoplasmosis, Cryptosporidia* and the like. Target antigen may be derived or isolated from, for example, a pathogenic protozoan and pathogenic parasites including but not limited to *Pneumocystis carinii, Trypanosoma, Leishmania* (U.S. Pat. No. 5,965,242), *Plasmodium* (U.S. Pat. No. 5,589,343) and *Toxoplasma gondii.*

The term "antigen" as used herein is defined as a molecule that provokes an immune response. This immune response may involve either antibody production, or the activation of specific immunologically competent cells, or both. An antigen can be derived from organisms, subunits of proteins/antigens, killed or inactivated whole cells or lysates. Therefore, any macromolecules, including virtually all proteins or peptides, can serve as antigens. Furthermore, antigens can be derived from recombinant or genomic DNA, including, for example, any DNA that contains nucleotide sequences or partial nucleotide sequences of a pathogenic genome or a gene or a fragment of a gene for a protein that elicits an immune response results in synthesis of an antigen.

Target antigen includes an antigen associated with a preneoplastic or hyperplastic state. Target antigen may also be associated with, or causative of cancer. Such target antigen may be, for example, tumor specific antigen, tumor associated antigen (TAA) or tissue specific antigen, epitope thereof, and epitope agonist thereof. Such target antigens include but are not limited to carcinoembryonic antigen (CEA) and epitopes thereof such as CAP-1, CAP-1-6D and the like (GenBank Accession No. M29540), MART-1 (Kawakarni et al, J. Exp. Med. 180:347-352, 1994), MAGE-1 (U.S. Pat. No. 5,750,395), MAGE-3, GAGE (U.S. Pat. No. 5,648,226), GP-100 (Kawakami et al Proc. Nat'l Acad. Sci. USA 91:6458-6462, 1992), MUC-1, MUC-2, point mutated ras oncogene, normal and point mutated p53 oncogenes (Hollstein et al Nucleic Acids Res. 22:3551-3555, 1994), PSMA (Israeli et al Cancer Res. 53:227-230, 1993), tyrosinase (Kwon et al PNAS 84:7473-7477, 1987) TRP-1 (gp75) (Cohen et al Nucleic Acid Res. 18:2807-2808, 1990; U.S. Pat. No. 5,840,839), NY-ESO-1 (Chen et al PNAS 94: 1914-1918, 1997), TRP-2 (Jackson et al EMBOJ, 11:527-535, 1992), TAG72, KSA, CA-125, CD-123, PSA, HER-2/neu/c-erb/B2, (U.S. Pat. No. 5,550,214), BRC—I, BRC-II, bcr-abl, pax3-fkhr, ews-fli-1, modifications of TAAs and tissue specific antigen, splice variants of TAAs, epitope agonists, and the like. Other TAAs may be identified, isolated and cloned by methods known in the art such as those disclosed in U.S. Pat. No. 4,514,506. Target antigen may also include one or more growth factors and splice variants of each. A tumor antigen is any antigen such as, for example, a peptide or polypeptide, that triggers an immune response in a host against a tumor. The tumor antigen may be a tumor-associated antigen, which is associated with a neoplastic tumor cell.

In one type of chimeric antigen receptor (CAR), the variable heavy (VH) and light (VL) chains for a tumor-specific monoclonal antibody are fused in-frame with the CD3 zeta chain (ζ) from the T cell receptor complex. The VH and VL are generally connected together using a flexible glycine-serine linker, and then attached to the transmembrane domain by a spacer (CH2CH3) to extend the scFv away from the cell surface so that it can interact with tumor antigens. Following transduction, NK cells now express the CAR on their surface, and upon contact and ligation with a tumor antigen, signal through the CD3 zeta chain inducing cytotoxicity and cellular activation.

Immune Cell Therapy and Inducible Chimeric Signaling Polypeptides

In some embodiments, NK cells are modified to express a chimeric antigen receptor that comprises a single chain antibody variable fragment (scFv) fused with a transmembrane domain containing linker region and an intracellular domain derived from the CD3 zeta component. In natural T cells signals from CD3zeta drive the initial activation of the T cell through signaling to the NF-ATc transcription factor. These signals are necessary to drive target cell killing in cytotoxic T lymphocytes and synergize with costimulatory signaling pathways to drive the robust cell proliferation of T cell immune response. The T cells may be modified by transduction or transfection with a nucleic acid that expresses the CAR in the absence of any coding region for a chimeric signaling polypeptide. Or, in other examples, the polynucleotide that encodes the CAR may be provided as part of a nucleic acid that also comprises a polynucleotide that encodes a chimeric signaling polypeptide.

For inducible co-stimulation, the CAR-NK cells are also modified, for example, by transfection or transduction of the cells with a nucleic acid that expresses an inducible chimeric signaling polypeptide. For example, in some embodiments, the polypeptide is inducible based on a drug inducible mediator of costimulatory signaling in which FKBP12 in two copies is fused with MyD88. FKBP12 is a small (107 amino acid) prolylyl isomerase that is also the ligand for the natural antibiotic and immunosuppressant macrolides rapamycin, FK-506 and ascomycin. In certain embodiments, a single mutant of FKBP12 substituting valine at amino acid 36 for phenylalanine (Fv) confers inducibility to Fv fusions with the synthetic ligand rimiducid (AP1903) by homodimerization of FKBP12 moieties. MyD88 is critical mediator of signals in the innate immune response downstream of Toll-Like Receptors (TLR) typically in myeloid cells but also in lymphocytes. These signals activate transcription regulators including the family of NF-κB factors.

Rimiducid is a tail-to-tail linkage of a high affinity synthetic ligand specific for Fv and not wild-type FKBP12. It is a dimerizing ligand because it can simultaneously bind with two Fv moieties. The drug-directed dimerizing event thereby juxtaposes the fused MyD88 moieties which initiates robust signal transduction. This is demonstrated in retroviral construct 1810 and is denoted iM.

The Fv-MyD88 fusion is linked with a second costimulatory signaling domain derived from the intracellular domain of CD40 to generate iMC. iMC has been utilized to activate proliferation and cytokine production in myeloid cells and in CAR-T cells and retroviral vector BP2212 is an example of an iMC-CAR expression construct.

Alternative signaling domains, when fused with iMyD88, generate distinct signaling outcomes. In some embodiments, a construct expresses an inducible fusion of MyD88 with the intracellular domain of CD28, the canonical costimulatory receptor for the CD80/CD86 ligands of antigen presenting cells. In some embodiments, construct BP1815 fuses iMyD88 with the intracellular signaling domain of 4-1BB (also called CD137, a costimulatory receptor present in activated T cells). In some embodiments, construct BP1801 expresses iMyD88 fused with the signaling domain of OX40. OX40 is a member of the Tumor Necrosis Factor Receptor (TNFR) superfamily that signal to NF-κB through TRAF proteins. In some embodiments, construct BP1802 expresses iMyD88 fused with the signaling domain of ICOS (Inducible COSstimulator, also called CD278) a member of the CD28 family which signals to NF-κB through a mechanism distinct from TNF-R family members. In some embodiments, Construct BP1800 expresses iMyD88 fused with the signaling domains of OX40 and CD28.

Immune Cell Therapy and Constitutive Chimeric Signaling Polypeptides

Immune cell therapies may also be designed to provide constitutively active therapy, such as constitutively active CAR-T cells or constitutively active NK-cells, but provide an inducible safety switch, to stop, or reduce the level of, the therapy when needed. In some embodiments, immune cells, such as CAR-T cells or CAR-NK cells, express a chimeric antigen receptor, and a chimeric signaling polypeptide comprising a truncated MyD88 polypeptide and a stimulating polypeptide. In this format, the multimeric ligand binding region is not fused with the truncated MyD88 polypeptide. High level costimulation is provided constitutively through an alternate mechanism in which a leaky 2A cotranslational sequence, for example one derived from porcine teschovirus-1 (P2A), is used to separate the CAR from the chimeric MyD88 polypeptide. When the chimeric MyD88 polypeptide is a MyD88-CD40 polypeptide, most MC remains cytosolic but the leakiness in the P2A sequence retains a portion (estimated to be about 10%) of MC fused with the CAR and thereby expressed at the plasma membrane. This membrane proximal expression produces a high level of signaling activity.

In some embodiments, the modified cells comprise a non-inducible chimeric polypeptide that is not induced by contact with a ligand inducer, or dimerizer, or CID, such as, for example, rimiducid AP20187, or AP1510. In some embodiments, the modified cells comprise a chimeric polypeptide that does not bind rapamycin, a rapalog, rimiducid, AP20187, or AP1510. In some embodiments, the modified cells comprise a chimeric polypeptide that does not comprise a multimeric ligand binding region, and does not comprise, for example, an FKBP12 polypeptide region or an FRB region, or variants thereof. In some embodiments, the chimeric polypeptide does not have a multimeric ligand binding region, and does not have an FKBP12 polypeptide region, or FRB region, or variants thereof. In some embodiments, the chimeric polypeptide does not have a functional multimeric ligand binding region.

The inducible component in these modified cells is an inducible Caspase-9 polypeptide, for example, an Fv fusion with caspase 9 (iC9) that rapidly induces apoptosis, or programmed cell death, in a rimiducid dependent fashion. This iC9 safety switch can thereby be deployed to block adverse events that may result from CAR-NK therapy such as graft versus host disease or cytokine release syndrome. In animal studies inducible caspase-9 polypeptide-expressing NK cells containing MyD88-CD40 (MC) produce robust anti-tumor effects that may have toxic effects on the animals that necessitate rimiducid treatment to remove the most active CAR-NK cells. The toxic effects are consistent with a cytokine release syndrome that is likely due to excessive production of inflammatory cytokines such as TNF-α and IL-6.

Also provided herein are chimeric signaling polypeptides that do not include a multimeric ligand binding region. These polypeptides provide constitutive NK cell activation activity; the polypeptides may be provided in immune cells, such as NK cells, in which an inducible apoptotic polypeptide, such as Caspase 9 may be expressed.

Expansion and Storage of Natural Killer Cells and Natural Killer Cells in Cell Therapy In some embodiments of the present application, the expression of MC in NK cells increases the rate of NK cell proliferation in culture. In some embodiments, the activation of iMC or iRMC with their respective dimerizing ligand, or the constitutively activated MC, increases the tumor cell killing activity of NK cells in culture. In some embodiments, the dimerization of iMC with rimiducid, or the constitutively activated MC, activates the production of cytokines that stimulate NK cell function, but are not normally produced by NK cells, including IL-12 p70, IL-2, and IL-15. In some embodiments, activation of MC in NK cells stimulates NK cell proliferation and antitumor efficacy in a whole animal model. In some embodiments, expression and activation of MC prior to cryostorage generates resistance to the inactivating effect of cryostorage on NK cell function. In some embodiments, activation of the iRC9 safety switch with rapamycin causes rapid NK cell apoptosis.

In some embodiments, natural killer cells of the present application are used in cell therapy targeting cancer. NK cells are currently in clinical trials as anti-tumor cell therapies. Because NK cells grow poorly in vivo, multiple cell infusions are typically necessary to generate therapeutic effect [Ciurea S O, et al., Phase 1 clinical trial using mbIL21 ex vivo-expanded donor-derived NK cells after haploidentical transplantation. Blood 2017, 130(16):1857-1868]. Generation of dual-switch NK (DS NK) cells augmented with the iMC switch or MC may facilitate NK cell proliferation and anti-tumor efficacy with dimerizing-drug dosage. Incidences of off-tumor targeting, cytokine release syndrome or GvHD can be quickly and efficiently reversed with activation of the safety switch. The resistance of DS NK cells to cryostorage will make possible the large-scale production of standardized lots for cell therapy.

In some embodiments, NK cells of the present application may express chimeric antigen receptors, and in certain embodiments, the chimeric antigen receptors may be under the control of a dual-switch system. Addition of a Chimeric Antigen Receptor containing a fusion of a single chain variable fragment (for target specificity) a transmembrane domain and an intracellular signaling domain to promote NK cell activation may produce target-specific NK cells in which proliferation and cytokine production is ligand inducible while safety is promoted by the caspase-9 safety switch.

In some embodiments, NK cells of the present application may be modified for use in therapeutic antibody therapy. NK cells express the CD16 Fcγ-receptor that binds to the constant region of IgG-immunoglobulins. CD16 links with NK cell signaling proteins that activate cells for target killing [Shevtsov M, et al. Front Immunol 2016, 7:492.15]. Preincubation or co-infusion of DS NK cells with tumor-target specific therapeutic antibodies may generate tumor specific responses augmented by inducible MC and made safer by the proapoptotic switch.

In some embodiments, NK cells of the present application may be used as an adjunct to checkpoint inhibition, and in certain embodiments, under the control of a dual-switch system. Tumor infiltrating lymphocytes (TILs) are frequently inhibited by activation of checkpoint inhibitory receptors, including CTLA4, PD1 and LAG3. Blockade of these receptors with their tumor-resident ligands can reactivate these TILs and produce robust clinical responses. A subset of tumor cells can reduce the CTL response by downregulating MHC-I surface expression. These cells are subject to attack by NK cells. Inclusion of DS NK cells with checkpoint inhibition may enhance the rate of tumor elimination.

In some embodiments, NK cells of the present application may be used as an adjunct to CAR-T or TCR-T therapy, and in certain embodiments, under the control of a dual-switch system. CD19-specific CAR-T cells and T cell products expressing tumor specific TCRs produce robust clinical responses, yet tumor relapses are common [Jackson H J, et al., Driving CAR T-cells forward. Nat Rev Clin Oncol 2016, 13(6):370-383; Brudno J N, et al., Chimeric antigen receptor T-cell therapies for lymphoma. Nat Rev Clin Oncol 2018, 15(1):31-46; Wang J, et al., Acute lymphoblastic leukemia relapse after CD19-targeted chimeric antigen receptor T cell therapy. J Leukoc Biol 2017, 102(6):1347-1356]. Frequently, these relapses are the result of loss of the epitope for the CAR in a small population of tumor that later proliferates [Grupp S A, et al., Chimeric antigen receptor-modified T cells for acute lymphoid leukemia. N Engl J Med 2013, 368(16):1509-1518; Wang J, et al., Acute lymphoblastic leukemia relapse after CD19-targeted chimeric antigen receptor T cell therapy. J Leukoc Biol 2017, 102(6):1347-1356]. Inclusion of long-lasting NK cells coincident or following CAR-T cell infusion may target this minor population with unspecific but highly tumor-responsive DS NK cells.

Provided in certain embodiments are methods for stimulating a cell-mediated immune response in a subject, comprising administering a modified cell transfected or transduced with a nucleic acid that expresses an inducible chimeric signaling polypeptide of the present embodiments to the subject; and administering an effective amount of a multimeric ligand that binds to the multimeric ligand binding region to stimulate a cell-mediated immune response in the subject. In some embodiments, the modified cell expresses a chimeric antigen receptor, an inducible chimeric antigen receptor polypeptide, or a recombinant T cell receptor, that binds to a target cell. In some embodiments, the target cell is a tumor cell. In some embodiments, the number or concentration of target cells in the subject is reduced following administration of the modified cell and the multimeric ligand. In some embodiments, the methods further comprise measuring the number or concentration of target cells in a first sample obtained from the subject before administering the modified cell or ligand, measuring the number or concentration of target cells in a second sample obtained from the subject after administration of the modified cell and ligand, and determining an increase or decrease of the number or concentration of target cells in the second sample compared to the number or concentration of target cells in the first sample. In some embodiments, the number of target cells is reduced 10, 20, 30, 40, 50, 60, 70, 80, 90, or 95% or more in the second sample, compared to the number or concentration of target cells in the first sample.

In some embodiments, the reduction in the number or concentration of target cells is determined in vitro, or ex vivo, using a cytotoxicity assay, and cytotoxicity of the modified NK cells is compared to either a control group of target cells that are not contacted with NK cells, a control group of non-modified NK cells, or a control group of modified NK cells that do not comprise the inducible co-stimulatory polypeptide discussed herein. In some embodiments, the amount of cytotoxicity induced by contacting the target cells with the modified NK cells is 10, 20, 30, 40, 50, 60, 70, 80, 90, or 95% or more greater than the amount of cytotoxicity induced by contacting the target cells with a control, or in target cells alone. In some embodiments, the amount of cytotoxicity induced by contacting the target cells with the modified NK cells is 2, 3, 4, 5, 6, 7, 8, 9, 10, 20, 30, 40, 50, 60, 70, 80, 90, 100, 200, 300, 400, 500, 600, 700, 800, 900, or 100 fold or more than the amount of cytotoxicity induced by contacting the target cells with a control, or in target cells alone. In some embodiments, the amount of cytotoxicity induced by contacting the target cells with the modified NK cells in the presence of the ligand inducer, such as, for example, rimiducid, is 10, 20, 30, 40, 50, 60, 70, 80, 90, or 95% or more greater than the amount of cytotoxicity induced by contacting the target cells with a control, or in target cells alone. In some embodiments, the amount of cytotoxicity induced by contacting the target cells with the modified NK cells in the presence of the ligand inducer, such as, for example, rimiducid, is 2, 3, 4, 5, 6, 7, 8, 9, 10, 20, 30, 40, 50, 60, 70, 80, 90, 100, 200, 300, 400, 500, 600, 700, 800, 900, or 100 fold or more than the amount of cytotoxicity induced by contacting the target cells with a control, or in target cells alone.

In some embodiments, an additional dose of ligand is administered to the subject. In some embodiments, an effective amount of multimeric ligand is an amount effective to reduce the number or concentration of target cells or to reduce the symptoms of cytotoxicity. In some embodiments, the cell-mediated response is a T cell-mediated response, a NK-cell mediated response, or a NK-T cell mediated response.

Also provided in some embodiments are methods for treating a subject having a disease or condition associated with expression of a target antigen, comprising administering a multimeric ligand that binds to a multimeric ligand binding region, wherein modified NK cells circulating in the subject express (i) an inducible chimeric signaling polypeptide of the present embodiments and chimeric antigen receptor that binds to the target antigen; or (ii) an inducible chimeric antigen receptor polypeptide of the present embodiments that binds to the target antigen, wherein the target antigen is present on target cells circulating in the subject; and wherein the number or concentration of target cells in the subject is reduced following administration of the multimeric ligand. In some embodiments, the target antigen is expressed by a tumor cell, and the chimeric antigen receptor the inducible chimeric antigen receptor polypeptide binds to the tumor cell. In some embodiments, following administration of the multimeric ligand, the number or concentration of target cells in the subject is determined, and (i) the administration of the multimeric ligand is discontinued or (ii) an additional dose of multimeric ligand is administered that is lower than the previous dose of multimeric ligand administered. In some embodiments, following administration of the multimeric ligand, the number or concentration of target cells in the subject is determined, and an additional dose of multimeric ligand is administered that is higher than the previous dose of multimeric ligand administered. In some embodiments, the additional dose of multimeric ligand is greater than the previous dose, in some embodiments, the additional dose of multimeric ligand is 10%, 20%, 30%, 40%, 50%, 60%, 70%, 80%, 90%, 100%, 125%, 150%, 175%, 200%, 225%, 250%, 275%, 300%, 400%, 500%, 600%, 700%, 800%, or 1000% greater than the previous dose.

In some embodiments, the multimeric ligand that binds to the multimeric ligand binding region is rimiducid or AP21087

Also provided in some embodiments are methods for stimulating a cell-mediated immune response in a subject, comprising administering an effective amount of modified cells that have been transduced or transfected with a nucleic acid of the present embodiments that express a chimeric signaling polypeptide of the present embodiments to the subject. In some embodiments, the cell-mediated immune response is directed against a target cell. In some embodiments, the modified cell comprises a chimeric antigen receptor, a chimeric antigen receptor polypeptide of the present embodiments, or a recombinant T cell receptor, that binds to an antigen on a target cell. In some embodiments, the target cell is a tumor cell. In some embodiments, the number or concentration of target cells in the subject is reduced following administration of the modified cells. In some embodiments, an additional dose of modified cells is administered to the subject. In some embodiments, the-mediated response is a T cell-mediated response, a NK cell-mediated response, or a NK-T cell-mediated response. Also provided in certain embodiments are methods for providing anti-tumor immunity to a subject, comprising administering to the subject an effective amount of a modified cell that expresses a chimeric signaling polypeptide of any one of the present embodiments. Also provided in certain embodiments are methods for treating a subject having a disease or condition associated with an elevated expression of a target antigen, comprising administering to the subject an effective amount of a modified cell of any one of the present embodiments. In some embodiments, the target antigen is a tumor antigen. Also provided in certain embodiments are methods for reducing the size of a tumor in a subject, comprising administering a modified cell of any one of the present embodiments to the subject, wherein the modified cell comprises a chimeric antigen receptor, a chimeric antigen receptor polypeptide of the present embodiments, or a recombinant T cell receptor, comprising an antigen recognition moiety that binds to an antigen on the tumor.

An "antigen recognition moiety" may be any polypeptide or fragment thereof, such as, for example, an antibody fragment variable domain, either naturally-derived, or synthetic, which binds to an antigen. Examples of antigen recognition moieties include, but are not limited to, polypeptides derived from antibodies, such as, for example, single chain variable fragments (scFv), Fab, Fab', F(ab')2, and Fv fragments; polypeptides derived from T Cell receptors, such as, for example, TCR variable domains; and any ligand or receptor fragment that binds to the extracellular cognate protein.

In some embodiments, the modified cell comprises a chimeric Caspase-9 polypeptide comprising a multimeric ligand binding region and a Caspase-9 polypeptide. In some embodiments, the method further comprises administering a multimeric ligand that binds to the multimeric ligand binding region to the subject following administration of the modified cells to the subject. In some embodiments, after administration of the multimeric ligand, the number of modified cells comprising the chimeric Caspase-9 polypeptide is reduced.

In some embodiments of the present methods, the subject has been diagnosed as having a tumor. In some embodiments, the subject has cancer. In some embodiments, the subject has a solid tumor. In some embodiments, the cancer is present in the blood or bone marrow of the subject. In some embodiments, the subject has a blood or bone marrow disease. In some embodiments, the subject has been diagnosed with any condition or condition that can be alleviated by stem cell transplantation. In some embodiments, the subject has been diagnosed with sickle cell anemia or metachromatic leukodystrophy. In some embodiments, the subject has been diagnosed with a condition selected from the group consisting of a primary immune deficiency condition, hemophagocytosis lymphohistiocytosis (HAH) or other hemophagocytic condition, an inherited marrow failure condition, a hemoglobinopathy, a metabolic condition, and an osteoclast condition. In some embodiments, the subject has been diagnosed with a disease or condition selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XAP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis. In some embodiments, the subject has been diagnosed with leukemia. In some embodiments, the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

The term "cancer" as used herein is defined as a hyperproliferation of cells whose unique trait-loss of normal controls—results in unregulated growth, lack of differentiation, local tissue invasion, and metastasis. Examples include but are not limited to, melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The term "hyperproliferative disease" is defined as a disease that results from a hyperproliferation of cells. Exemplary hyperproliferative diseases include, but are not limited to cancer or autoimmune diseases. Other hyperproliferative diseases may include vascular occlusion, restenosis, atherosclerosis, or inflammatory bowel disease.

The terms "blood disease", "blood disease" and/or "diseases of the blood" as used herein, refers to conditions that affect the production of blood and its components, including but not limited to, blood cells, hemoglobin, blood proteins, the mechanism of coagulation, production of blood, production of blood proteins, the like and combinations thereof. Non-limiting examples of blood diseases include anemias, leukemias, lymphomas, hematological neoplasms, albuminemias, haemophilias and the like.

The term "bone marrow disease" as used herein, refers to conditions leading to a decrease in the production of blood cells and blood platelets. In some bone marrow diseases, normal bone marrow architecture can be displaced by infections (e.g., tuberculosis) or malignancies, which in turn can lead to the decrease in production of blood cells and blood platelets. Non-limiting examples of bone marrow diseases include leukemias, bacterial infections (e.g., tuberculosis), radiation sickness or poisoning, apnoctyopenia, anemia, multiple myeloma and the like.

The term "patient" or "subject" are interchangeable, and as used herein include, but are not limited to, an organism or animal; a mammal, including, e.g., a human, non-human primate (e.g., monkey), mouse, pig, cow, goat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate.

Engineering Expression Constructs

Expression constructs that express the present chimeric antigen receptors, chimeric signaling polypeptides, and inducible safety switches are provided herein. In some examples, one or more polypeptide is said to be "operatively linked." In general, the term "operably linked" is meant to indicate that the promoter sequence is functionally linked to a second sequence, wherein the promoter sequence initiates and mediates transcription of the DNA corresponding to the second sequence.

As used herein, the term "cDNA" is intended to refer to DNA prepared using messenger RNA (mRNA) as template. The advantage of using a cDNA, as opposed to genomic DNA or DNA polymerized from a genomic, non- or partially processed RNA template, is that the cDNA primarily contains coding sequences of the corresponding protein. There are times when the full or partial genomic sequence is used, such as where the non-coding regions are required for optimal expression or where non-coding regions such as introns are to be targeted in an antisense strategy.

As used herein, the term "polypeptide" is defined as a chain of amino acid residues, usually having a defined sequence. As used herein the term polypeptide may be interchangeable with the term "proteins".

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. The term "therapeutic construct" may also be used to refer to the expression construct or transgene. The expression construct or transgene may be used, for example, as a therapy to treat hyperproliferative diseases or disorders, such as cancer, thus the expression construct or transgene is a therapeutic construct or a prophylactic construct. As used herein with reference to a disease, disorder or condition, the terms "treatment", "treat", "treated", or "treating" refer to prophylaxis and/or therapy.

Expression constructs may comprise one or more isolated nucleic acids. The term "isolation" as applied to a nucleic acid refers to the separation of one region of a nucleotide sequence from other regions of the nucleotide sequence. Thus, isolated nucleic acids are isolated from chromosomes. Isolation may, for example, be performed using an amplification reaction, such as, for example, PCR; in other examples, nucleic acids may be isolated from the cells from which they naturally are found. A pool of isolated nucleic acids may be enriched in nucleic acid segments containing only sequences for a particular region of interest. In some embodiments, isolated nucleic acids are shorter than full length sequences encoding an entire protein.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are discussed infra.

In certain examples, a polynucleotide coding for the chimeric antigen receptor, is included in the same vector, such as, for example, a viral or plasmid vector, as a polynucleotide coding for a second polypeptide. This second polypeptide may be, for example, a chimeric signaling polypeptide, an inducible caspase polypeptide, as discussed herein, or a marker polypeptide. In these examples, the construct may be designed with one promoter operably linked to a nucleic acid comprising a polynucleotide coding for the two polypeptides, linked by a 2A polypeptide. In this example, the first and second polypeptides are separated during translation, resulting in two polypeptides, or, in examples including a leaky 2A, either one, or two polypeptides. In other examples, the two polypeptides may be expressed separately from the same vector, where each nucleic acid comprising a polynucleotide coding for one of the polypeptides is operably linked to a separate promoter. In yet other examples, one promoter may be operably linked to the two polynucleotides, directing the production of two separate RNA transcripts, and thus two polypeptides; in one example, the promoter may be bi-directional, and the coding regions may be in opposite directions 5'-3'. Therefore, the expression constructs discussed herein may comprise at least one, or at least two promoters.

In some embodiments, a nucleic acid construct is contained within a viral vector. In certain embodiments, the viral vector is a retroviral vector. In certain embodiments, the viral vector is an adenoviral vector a lentiviral vector. It is understood that in some embodiments, a cell is contacted with the viral vector ex vivo, and in some embodiments, the cell is contacted with the viral vector in vivo. Thus, an expression construct may be inserted into a vector, for example a viral vector plasmid. The steps of the methods provided may be performed using any suitable method; these methods include, without limitation, methods of transducing, transforming, or otherwise providing nucleic acid to the cell, described herein.

As used herein, the term "gene" is defined as a functional protein-, polypeptide-, or peptide-encoding unit. As will be understood, this functional term includes genomic sequences, cDNA sequences, and smaller engineered gene segments that express, or are adapted to express, proteins, polypeptides, domains, peptides, fusion proteins and/or mutants.

A "nucleic acid" as used herein generally refers to a molecule (one, two or more strands) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompasses the terms "oligonucleotide" and "polynucleotide," each as a subgenus of the term "nucleic acid."

As used herein, the term "polynucleotide" is defined as a chain of nucleotides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PORT", and the like, and by synthetic means. Furthermore, polynucleotides include mutations of the polynucleotides, include but are not limited to, mutation of the nucleotides, or nucleosides by methods well known in the art. A nucleic acid may comprise one or more polynucleotides.

Nucleic acids may be, be at least, be at most, or be about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleotides, or any range derivable therein, in length.

Nucleic acids herein provided may have regions of identity or complementarity to another nucleic acid. It is contemplated that the region of complementarity or identity can be at least 5 contiguous residues, though it is specifically contemplated that the region is, is at least, is at most, or is about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous nucleotides.

"Function-conservative variants" are proteins or enzymes in which a given amino acid residue has been changed without altering overall conformation and function of the protein or enzyme, including, but not limited to, replacement of an amino acid with one having similar properties, including polar or non-polar character, size, shape and charge. Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

Amino acids other than those indicated as conserved may differ in a protein or enzyme so that the percent protein or amino acid sequence similarity between any two proteins of similar function may vary and can be, for example, at least 70%, at least 80%, at least 90%, and at least 95%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA. When using any of these programs, the settings may be selected that result in the highest sequence similarity.

As used herein, the term "promoter" is defined as a DNA sequence recognized by the synthetic machinery of the cell, or introduced synthetic machinery, required to initiate the specific transcription of a gene. In some embodiments, the promoter is a developmentally regulated promoter. The term "developmentally regulated promoter" as used herein refers to a promoter that acts as the initial binding site for RNA polymerase to transcribe a gene which is expressed under certain conditions that are controlled, initiated by or influenced by a developmental program or pathway. As used herein, the term "under transcriptional control," "operably linked," or "operatively linked" is defined as the promoter is in the correct location and orientation in relation to the nucleic acid to control RNA polymerase initiation and expression of the gene. In general, the term "operably linked" is meant to indicate that the promoter sequence is functionally linked to a second sequence, wherein, for example, the promoter sequence initiates and mediates transcription of the DNA corresponding to the second sequence.

The particular promoter employed to control the expression of a polynucleotide sequence of interest is not believed to be important, so long as it is capable of directing the expression of the polynucleotide in the targeted cell. Thus, where a human cell is targeted the polynucleotide sequence-coding region may, for example, be placed adjacent to and under the control of a promoter that is capable of being expressed in a human cell. Generally speaking, such a promoter might include either a human or viral promoter. Promoters may be selected that are appropriate for the vector used to express the CARs and other polypeptides provided herein.

In various embodiments, where, for example, the expression vector is a retrovirus, an example of an appropriate promoter is the Murine Moloney leukemia virus promoter. In other embodiments, the promoter may be, for example, the (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Promoters, and other regulatory elements, are selected such that they are functional in the desired cells or tissue. In addition, this list of promoters should not be construed to be exhaustive or limiting; other promoters that are used in conjunction with the promoters and methods disclosed herein.

The nucleic acids discussed herein may comprise one or more polynucleotides. In some embodiments, one or more polynucleotides may be described as being positioned, or "is" "5'" or "3'" of another polynucleotide, or positioned in "5' to 3' order". The reference 5' to 3' in these contexts is understood to refer to the direction of the coding regions of the polynucleotides in the nucleic acid, for example, where a first polynucleotide is positioned 5' of a second polynucleotide and connected with a third polynucleotide encoding a non-cleave able linker polypeptide, the translation product would result in the polypeptide encoded by the first polynucleotide positioned at the amino terminal end of a larger polypeptide comprising the translation products of the first, third, and second polynucleotides.

In yet other examples, two polypeptides, such as, for example, the chimeric stimulating molecule or a MyD88/CD40 chimeric antigen receptor polypeptide, and a second polypeptide, may be expressed in a cell using two separate vectors. The cells may be co-transfected or co-transformed with the vectors, or the vectors may be introduced to the cells at different times.

The polypeptides may vary in their order, from the amino terminus to the carboxy terminus. For example, in the chimeric stimulating molecule, the order of the MyD88 polypeptide, CD40 polypeptide, and any additional polypeptide, may vary. In the chimeric antigen receptor, the order of the MyD88 polypeptide, CD40 polypeptide, and any additional polypeptide, such as, for example, the CD3 ζ polypeptide may vary. The order of the various domains may be assayed using methods such as, for example, those discussed herein, to obtain the optimal expression and activity.

In some embodiments, where an expression construct encodes a MyD88 polypeptide, the polypeptide may be a portion of the full-length MyD88 polypeptide. By MyD88, or MyD88 polypeptide, is meant the polypeptide product of the myeloid differentiation primary response gene 88, for example, but not limited to the human version, cited as NCBI Gene ID 4615. In some embodiments, an expression construct encodes a portion of the MyD88 polypeptide lacking the TIR domain. In some embodiments, the expression construct encodes a portion of the MyD88 polypeptide containing the DD (death domain) or the DD and intermediary domains. By "truncated," is meant that the protein is not full length and may lack, for example, a domain. For example, a truncated MyD88 is not full length and may, for example, be missing the TIR domain. In some embodiments, the truncated MyD88 polypeptide has an amino acid sequence of SEQ ID NO: 2 or SEQ ID NO: 119, or a functionally equivalent fragment thereof. In some embodiments, the truncated MyD88 polypeptide is encoded by the nucleotide sequences of SEQ ID NO: 1, or a functionally equivalent fragment thereof. A functionally equivalent portion of the MyD88 polypeptide has substantially the same ability to stimulate intracellular signaling as the polypeptide of SEQ ID NO 118, with at least 50%, 60%, 70%, 80%, 90%, or 95% of the activity of the polypeptide of SEQ ID NO: 118. By a nucleic acid sequence coding for "truncated MyD88" is meant the nucleic acid sequence coding for a truncated MyD88 polypeptide, the term may also refer to the nucleic acid sequence including the portion coding for any amino acids added as an artifact of cloning, including any amino acids coded for by the linkers.

It is understood that where a method or construct refers to a truncated MyD88 polypeptide, the method may also be used, or the construct designed to refer to another MyD88 polypeptide, such as a full length MyD88 polypeptide. Where a method or construct refers to a full length MyD88 polypeptide, the method may also be used, or the construct designed to refer to a truncated MyD88 polypeptide. In the methods herein, in which a chimeric polypeptide comprises a MyD88 polypeptide (or portion thereof) and a CD40 polypeptide (or portion thereof), the MyD88 polypeptide of the chimeric polypeptide may be located either upstream or downstream from the CD40 polypeptide. In certain embodiments, the MyD88 polypeptide (or portion thereof) is located upstream of the CD40 polypeptide (or portion thereof). As used herein, the term "functionally equivalent," as it relates to MyD88, or a portion thereof, for example, refers to a MyD88 polypeptide that stimulates a cell-signaling response or a nucleic acid encoding such a MyD88 polypeptide. "Functionally equivalent" refers, for example, to a MyD88 polypeptide that is lacking a TIR domain but is capable of stimulating a cell-signaling response.

In certain embodiments, a modified cell populations comprise a nucleic acid molecule that comprises a promoter operably linked to a first polynucleotide encoding a chimeric stimulating molecule, wherein the chimeric stimulating molecule comprises (i) a MyD88 polypeptide or a truncated MyD88 polypeptide lacking the TIR domain; and (ii) a CD40 cytoplasmic polypeptide region lacking the CD40 extracellular domain, and wherein the chimeric stimulating molecule does not include a membrane targeting region; and b) a second polynucleotide encoding a T cell receptor, a T cell receptor-based chimeric antigen receptor, or a chimeric antigen receptor; and c) a third polynucleotide encoding a chimeric Caspase-9 polypeptide comprising a multimeric ligand binding region and a Caspase-9 polypeptide. It is understood that the order of the polynucleotides may vary and may be tested to determine the suitability of the construct for any particular method, thus, the nucleic acid may include the polynucleotides in the varying orders, which also take into account a variation in the order of the MyD88 polypeptide or truncated MyD88 polypeptide-encoding sequence and the CD40 cytoplasmic polypeptide region-encoding sequence in the first polynucleotide. Thus, the first polynucleotide may encode a polypeptide having and order of MyD88/CD40, truncated-MyD88/CD40, CD40/MyD88, or CD40/truncated MyD88. And, the nucleic acid may include the first through third polynucleotides in any of the following orders, where 1, 2, 3, indicate a first, second, or third order of the polynucleotides in the nucleic acid from the 5' to 3' direction. It is understood that other polynucleotides, such as those that code for a 2A polypeptide, for example, may be present between the three listed polynucleotides; this Table is meant to designate the order of the first through third polynucleotides:

TABLE 1

| First polynucleotide encoding a Chimeric stimulating molecule comprising MyD88 or truncated MyD88 and CD40 cytoplasmic polypeptide region. | Second polynucleotide encoding a T cell receptor, a T cell receptor-based chimeric antigen receptor, or a chimeric antigen receptor. | Third polynucleotide encoding a chimeric caspse-9 polypeptide. |
|---|---|---|
| 1 | 2 | 3 |
| 1 | 3 | 2 |
| 2 | 1 | 3 |
| 3 | 1 | 2 |
| 2 | 3 | 1 |
| 3 | 2 | 1 |

Similarly, the nucleic acids may include only two of the polynucleotides, coding for two of the polypeptides provided in the table above. In some examples, a cell is transfected or transduced with a nucleic acid comprising the three polynucleotides included in Table A above. In other examples, a cell is transfected or transduced with a nucleic acid that encodes two of the polynucleotides, coding for two of the polypeptides, as provided, for example, in Table B.

TABLE 2

| First polynucleotide encoding a Chimeric stimulating molecule comprising MyD88 or truncated MyD88 and CD40 cytoplasmic polypeptide region. | Second polynucleotide encoding a T cell receptor, a T cell receptor-based chimeric antigen receptor, or a chimeric antigen receptor. | Third polynucleotide encoding a chimeric caspse-9 polypeptide. |
|---|---|---|
| 1 | 2 | |
| 1 | | 2 |
| 2 | 1 | |
| | 1 | 2 |
| 2 | | 1 |
| | 2 | 1 |

In some embodiments, the cell is transfected or transduced with the nucleic acid that encodes two of the polynucleotides, and the cell also comprises a nucleic acid comprising a polynucleotide coding for the third polypeptide. For example, a cell may comprise a nucleic acid comprising the first and second polynucleotides, and the cell may also comprise a nucleic acid comprising a polynucleotide coding for a chimeric Caspase-9 polypeptide. Also, a cell may comprise a nucleic acid comprising the first and third polynucleotides, and the cell may also comprise a nucleic acid comprising a polynucleotide coding for a T cell receptor, a T cell receptor-based chimeric antigen receptor, or a chimeric antigen receptor.

The steps of the methods provided may be performed using any suitable method; these methods include, without limitation, methods of transducing, transforming, or otherwise providing nucleic acid to the cell, presented herein. In some embodiments, the truncated MyD88 peptide is encoded by the nucleotide sequence of SEQ ID NO: 1 (with or without DNA linkers or has the amino acid sequence of SEQ ID NO:2 or SEQ ID NO: 119). In some embodiments, the CD40 cytoplasmic polypeptide region is encoded by a polynucleotide sequence in SEQ ID NO: 56.

Vectors

It is understood that the vectors provided herein may be modified using methods known in the art to vary the position or order of the regions, to substitute one region for another. For example, a vector comprising a polynucleotide encoding a chimeric signaling polypeptide comprising truncated MC may be substituted with a polynucleotide encoding chimeric signaling polypeptide comprising one, or two or more co-stimulatory polypeptide cytoplasmic signaling regions such as, for example, those selected from the group consisting of CD27, CD28, 4-1BB, OX40, ICOS, RANK, TRANCE, and DAP10. The polynucleotide encoding the CAR may also be modified so that the scFv region may be substituted with one having the same, or different target specificity; the transmembrane region may be substituted with a different transmembrane region; a stalk polypeptide may be added. Polynucleotides encoding marker polypeptides may be included within or separate from one of the polypeptides; polynucleotides encoding additional polypeptides coding for safety switches may be added, polynucleotides coding for linker polypeptides, or non-coding polynucleotides or spacers may be added, or the order of the polynucleotides 5' to 3' may be changed.

The vectors provided in the present application may be modified as discussed herein, for example, to substitute polynucleotides coding for regions of the chimeric antigen receptor, for example, the CD19-specific scFV, or other scFvs provided, with a scFv directed against other target antigens, such as, for example, BCMA, CD33, NKG2D, PSMA, PSCA, MUC1, CD19, ROR1, Mesothelin, GD2, CD123, MUC16, Her2/Neu, CD20, CD30, PRAME, NY-ESO-1, and EGFRvIII. scFvs that target these antigens are known in the art, see, e.g., Berahovich et al., 2018 Cancers 10, 323; Wang et al., 2015, Molecular Therapy 23(1): 184-191; Han et al. 2018, Am J Cancer Res 8(1):106-119; Qin et al., 2017; Hematol & Oncol. 10:68; Jachimowicz et al. 2011, Molecular Cancer Therapeutics 10(6): 1036-1045; Schau et al. 2019, Scientific reports 9:3299; Han et al. 2017, Clin Cancer Res 23(13):3385-3395; Nejatollahi et al., 2013, Journal of Oncology Vol. 2013, Article ID 839831; Kugler et al, 2010 BJH Vol 150, 574-586. In a specific embodiment, a PSCA scFv comprises (or consists of) a sequence(s) disclosed herein (e.g., VH and VL sequences disclosed in the Examples below). In another specific embodiment, a CD123 scFv comprises (or consists of) a sequence(s) disclosed herein (e.g., VH and VL sequences disclosed in the Examples below). In another specific embodiment, a BCMA scFv comprises (or consists of) a sequence(s) disclosed herein (e.g., VH and VL sequences disclosed in the Examples below). The vector may also be modified with appropriate substitutions of each polypeptide region, as discussed herein. The vector may be modified to remove the inducible caspase-9 safety switch (1), to position the inducible caspase-9 safety switch to a position 3' of the MyD88-CD40 polypeptide (**), to substitute the inducible caspase-9 safety switch with a different inducible caspase polypeptide-based switch, or to substitute the inducible caspase-9 safety switch with a different polypeptide safety switch.

The vectors provided herein may be modified to substitute the MyD88-CD40 (MC) portions with one, or two or more co-stimulatory polypeptide cytoplasmic signaling regions such as, for example, those selected from the group consisting of CD27, CD28, 4-1BB, OX40, ICOS, RANK, TRANCE, and DAP10. Co-stimulating polypeptides may comprise, but are not limited to, the amino acid sequences provided herein, and may include functional conservative mutations, including deletions or truncations, and may comprise amino acid sequences that are 70%, 75%, 80%, 85%, 90%, 95% or 100% identical to the amino acid sequences provided herein.

The vectors provided herein may be modified to substitute a polynucleotide coding for a linker sequence, where the linker polypeptide is not a 2A polypeptide, between the CAR polypeptide and the MC polypeptide or other co-stimulatory polypeptide. For example, nucleic acids provided herein may comprise, a polynucleotide coding for a MC polypeptide, or a co-stimulatory polypeptide signaling region 3' of a polynucleotide coding for the CD3ζ portion of the CAR, where the two polynucleotides are separated by a polynucleotide coding for a 2A linker, or, where the two polynucleotides are not separated by a polynucleotide coding for a 2A linker. In some embodiments, the two polynucleotides may be separated by a polynucleotide coding for a linker polypeptide having, for example, about 5 to 20 amino acids, or, for example, about 6 to 10 amino acids, where the linker polypeptide does not comprise a 2A polypeptide sequence.

Selectable Markers

In certain embodiments, the expression constructs contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as Herpes Simplex Virus thymidine kinase (tk) are employed. Immunologic surface markers containing the extracellular, non-signaling domains or various proteins (e.g. CD34, CD19, LNGFR) also can be employed, permitting a straightforward method for magnetic or fluorescence antibody-mediated sorting. The selectable marker employed is not believed to be important, so long as it is capable of being expressed simultaneously with the nucleic acid encoding a gene product. Further examples of selectable markers include, for example, reporters such as GFP, EGFP, β-gal or chloramphenicol acetyltransferase (CAT). In certain embodiments, the marker protein, such as, for example, CD19 is used for selection of the cells for transfusion, such as, for example, in immunomagnetic selection. As discussed herein, a CD19 marker is distinguished from an anti-CD19 antibody, or, for example, an scFv, TCR, or other antigen recognition moiety that binds to CD19.

In certain embodiments, the marker polypeptide is linked to the inducible chimeric stimulating molecule. For example, the marker polypeptide may be linked to the inducible chimeric stimulating molecule via a polypeptide sequence, such as, for example, a cleavable 2A-like sequence.

The NK cells provided herein may express a cell surface transgene marker, present on an expression vector that expresses the CAR, or, in some embodiments, present on an expression vector that encodes a protein other than the CAR, such as, for example a pro-apoptotic polypeptide safety switch, such as i-Casp9, or the costimulatory polypeptide that is co-expressed with the CAR.

In one embodiment, the cell surface transgene marker is a truncated CD19 (ΔCD19) polypeptide (Di Stasi et al. (2011) supra, that comprises a human CD19 truncated at amino acid 333 to remove most of the intracytoplasmic domain. The extracellular CD19 domain can still be recognised (e.g. in flow cytometry, FACS or MACS) but the potential to trigger intracellular signalling is minimised. CD19 is normally expressed by B cells, rather than by T cells or NK, so selection of CD19+ T cells permits the genetically-modified NK cells to be separated from unmodified donor NK cells.

In some embodiments, a polypeptide may be included in the polypeptide, for example, the CAR encoded by the expression vector to aid in sorting cells. In some embodiments, the expression vectors used to express the chimeric antigen receptors or chimeric stimulating molecules provided herein further comprise a polynucleotide that encodes the 16 amino acid CD34 minimal epitope. In some embodiments, such as certain embodiments provided in the examples herein, the CD34 minimal epitope is incorporated at the amino terminal position of the CD8 stalk.

Linker Polypeptides

Linker polypeptides include, for example, cleavable and non-cleavable linker polypeptides. Non-cleavable polypeptides may include, for example, any polypeptide that may be operably linked between the MyD88-CD40 chimeric polypeptide, the MyD88 polypeptide, the CD40 polypeptide, or the costimulatory polypeptide cytoplasmic signaling region and the CD3ζ portion of the chimeric antigen receptor. Linker polypeptides include those for example, consisting of about 2 to about 30 amino acids, (e.g., furin cleavage site, $(GGGGS)_n$). In some embodiments, the linker polypeptide consists of about 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids. In some embodiments, the linker polypeptide consists of about 18 to 22 amino acids. In some embodiments, the linker polypeptide consists of 20 amino acids. In a specific embodiment, the linker comprises (consists of) a sequence disclosed herein (e.g., a sequence disclosed in the Examples below). In some embodiments, cleavable linkers include linkers that are cleaved by an enzyme exogenous to the modified cells in the population, for example, an enzyme encoded by a polynucleotide that is introduced into the cells by transfection or transduction, either at the same time or a different time as the polynucleotide that encodes the linker. In some embodiments, cleavable linkers include linkers that are cleaved by an enzyme endogenous to the modified cells in the population, including, for example, enzymes that are naturally expressed in the cell, and enzymes encoded by polynucleotides native to the cell, such as, for example, lysozyme.

2A Peptide Bond-Skipping Sequences 2A-like sequences, or "peptide bond-skipping" 2A sequences, are derived from, for example, many different viruses, including, for example, from *Thosea asigna*. These sequences are sometimes also known as "peptide skipping sequences." When this type of sequence is placed within a cistron, between two polypeptides that are intended to be separated, the ribosome appears to skip a peptide bond, in the case of *Thosea asigna* sequence; the bond between the Gly and Pro amino acids at the carboxy terminal "P-G-P" is omitted. This may, leave two to three polypeptides, for example, an inducible chimeric pro-apoptotic polypeptide and a chimeric antigen receptor, or, for example, a marker polypeptide and an inducible chimeric pro-apoptotic polypeptide. When this sequence is used, the polypeptide that is encoded 5' of the 2A sequence may end up with additional amino acids at the carboxy terminus, including the Gly residue and any upstream residues in the 2A sequence. The peptide that is encoded 3' of the 2A sequence may end up with additional amino acids at the amino terminus, including the Pro residue and any downstream residues following the 2A sequence. In some embodiments, the cleavable linker is a 2A polypeptide derived from porcine teschovirus-1 (P2A). In some embodiments, the 2A cotranslational sequence is a 2A-like sequence. In some embodiments, the 2A cotranslational sequence is T2A (*thosea asigna* virus 2A), F2A (foot and mouth disease virus 2A), P2A (porcine teschovirus-1 2A), BmCPV 2A (cytoplasmic polyhedrosis virus 2A) BmIFV 2A (flacherie virus of *B. mori* 2A), or E2A (equine rhinitis A virus 2A). In some embodiments, the 2A cotranslational sequence is T2A-GSG, F2A-GSG, P2A-GSG, or E2A-GSG. In some embodiments, the 2A cotranslational sequence is selected from the group consisting of T2A, P2A and F2A. By "cleavable linker" is meant that the linker is cleaved by any means, including, for example, non-enzymatic means, such as peptide skipping, or enzymatic means. (Donnelly, M L 2001, J. Gen. Virol. 82:1013-25). In a specific embodiment, a 2TA comprises (or consists of) a sequence disclosed herein. comprises (consists of) a sequence disclosed herein (e.g., a sequence disclosed in the Examples below).

The 2A-like sequences are sometimes "leaky" in that some of the polypeptides are not separated during translation, and instead, remain as one long polypeptide following translation. One theory as to the cause of the leaky linker, is that the short 2A sequence occasionally may not fold into the required structure that promotes ribosome skipping (a "2A fold"). In these instances, ribosomes may not miss the proline peptide bond, which then results in a fusion protein. To reduce the level of leakiness, and thus reduce the number of fusion proteins that form, a GSG (or similar) linker may be added to the amino terminal side of the 2A polypeptide; the GSG linker blocks secondary structures of newly-translated polypeptides from spontaneously folding and disrupting the '2A fold'. In certain embodiments, a 2A linker includes the amino acid sequence of SEQ ID NO: 20. In certain embodiments, the 2A linker further includes a GSG amino acid sequence at the amino terminus of the polypeptide, in other embodiments, the 2A linker includes a GSGPR amino acid sequence at the amino terminus of the polypeptide. Thus, by a "2A" sequence, the term may refer to a 2A sequence in an example described herein or may also refer to a 2A sequence as listed herein further comprising a GSG or GSGPR sequence at the amino terminus of the linker.

In some embodiments, the linker, for example, the 2A linker, is cleaved in about 10, 20, 30, 40, 50, 60, 70, 75, 80, 85, 90, 95, 98, or 99% of the chimeric antigen receptors, that is, the chimeric antigen receptor portion is separated from the chimeric MyD88 and CD40, the MyD88 polypeptide, the CD40 polypeptide, or the costimulatory polypeptide cytoplasmic signaling region, such as, CD28, OX40, 4-1BB or the like. In other embodiments the 2A linker is cleaved in about 75, 80, 85, 90, 95, 98, or 99% of the chimeric antigen receptors. In some embodiments, the 2A linker is cleaved in about 80-99% of the chimeric antigen receptors. In some embodiments, the 2A linker is cleaved in about 90% of the chimeric antigen receptors. In some embodiments, a constitutive active chimeric antigen receptor polypeptide is present in the modified cells, where the 2A linker is not cleaved, that is, the chimeric antigen receptor portion is linked to the chimeric MyD88 and CD40, the MyD88 polypeptide, the CD40 polypeptide, or the costimulatory polypeptide cytoplasmic signaling region, such as, CD28, OX40, 4-1BB or the like, representing about 1, 2, 5, 10, 15, 20, 25, 30, 40, 50, 60, 70, 80, or 90% of the chimeric antigen receptor polypeptide. In other embodiments the 2A linker is not cleaved in about 5, 10, 15, 20, or 25% of the chimeric antigen receptors. In some embodiments, the 2A linker is not cleaved in about 5-20% of the chimeric antigen receptors. In some embodiments, the 2A linker is not cleaved in about 10% of the chimeric antigen receptors.

Membrane-Targeting

A membrane-targeting sequence provides for transport of the chimeric protein to the cell surface membrane, where the same or other sequences can encode binding of the chimeric protein to the cell surface membrane. Molecules in association with cell membranes contain certain regions that facilitate the membrane association, and such regions can be incorporated into a chimeric protein molecule to generate membrane-targeted molecules. For example, some proteins contain sequences at the N-terminus or C-terminus that are acylated, and these acyl moieties facilitate membrane association. Such sequences are recognized by acyltransferases and often conform to a particular sequence motif. Certain acylation motifs are capable of being modified with a single acyl moiety (often followed by several positively charged residues (e.g. human c-Src: M-G-S—N—K—S—K—P—K-D-A-S-Q-R—R—R, SEQ ID NO:120) to improve association with anionic lipid head groups) and others are capable of being modified with multiple acyl moieties. For example, the N-terminal sequence of the protein tyrosine kinase Src can comprise a single myristoyl moiety. Dual acylation regions are located within the N-terminal regions of certain protein kinases, such as a subset of Src family members (e.g., Yes, Fyn, Lck) and G-protein alpha subunits. Such dual acylation regions often are located within the first eighteen amino acids of such proteins, and conform to the sequence motif Met-Gly-Cys-Xaa-Cys, where the Met is cleaved, the Gly is N-acylated and one of the Cys residues is S-acylated. The Gly often is myristoylated and a Cys can be palmitoylated. Acylation regions conforming to the sequence motif Cys-Ala-Ala-Xaa (so called "CAAX boxes"), which can be modified with C15 or 010 isoprenyl moieties, from the C-terminus of G-protein gamma subunits and other proteins (e.g., World Wide Web address ebi.ac.uk/interpro/DisplaylproEntry?ac=IPR001230) also can be utilized. These and other acylation motifs include, for example, those discussed in Gauthier-Campbell et al., Molecular Biology of the Cell 15: 2205-2217 (2004); Glabati et al., Biochem. J. 303: 697-700 (1994) and Zlakine et al., J. Cell Science 110: 673-679 (1997), and can be incorporated in chimeric molecules to induce membrane localization. In some embodiments, a chimeric polypeptide comprising a costimulatory polypeptide cytoplasmic signaling region provided herein comprises a membrane-targeting region, and optionally, a multimeric ligand binding region, in some embodiments, chimeric MyD88, chimeric truncated MyD88, chimeric MyD88-CD40, or chimeric truncated MyD88-CD40, polypeptides provided herein, comprise a membrane-targeting region, and optionally, a multimeric ligand binding region. In some embodiments, the membrane-targeting region comprises a myristoylation region. In some embodiments, the membrane-targeting region is selected from the group consisting of myristoylation-targeting sequence, palmitoylation-targeting sequence, prenylation sequences (i.e., farnesylation, geranyl-geranylation, CAAX Box), protein-protein interaction motifs or transmembrane sequences (utilizing signal peptides) from receptors. Examples include those discussed in, for example, ten Klooster J P et al, Biology of the Cell (2007) 99, 1-12, Vincent, S., et al., Nature Biotechnology 21:936-40, 1098 (2003). In a specific embodiment, a myristolyation peptide comprises (or consists of) a sequence disclosed herein (e.g., a sequence disclosed in the Examples disclosed herein).

Where a polypeptide does not include a membrane-targeting region, or lacks a membrane-targeting region, such as certain chimeric polypeptides provided herein, the polypeptide does not include a region that provides for transport of the chimeric protein to a cell membrane. The polypeptide may, for example, not include a sequence that transports the polypeptide to the cell surface membrane, or the polypeptide may, for example, include a dysfunctional membrane-targeting region, that does not transport the polypeptide to the cell surface membrane, for example, a myristoylation region that includes a proline that disrupts the function of the myristoylation-targeting region. (see, for example, Resh, M. D., Biochim. Biophys. Acta. 1451:1-16 (1999)). Polypeptides that are not transported to the membrane are considered to be cytoplasmic polypeptides.

Methods of Gene Transfer/Genetic Modification of NK Cells

In order to mediate the effect of the transgene expression in a cell, it will be necessary to transfer the expression constructs into a cell. Such transfer may employ viral or non-viral methods of gene transfer. This section provides a discussion of methods and compositions of gene transfer.

A transformed cell comprising an expression vector is generated by introducing into the cell the expression vector. Suitable methods for polynucleotide delivery for transformation of an organelle, a cell, a tissue or an organism for use with the current methods include virtually any method by which a polynucleotide (e.g., DNA) can be introduced into an organelle, a cell, a tissue or an organism.

The terms "cell," "cell line," and "cell culture" as used herein may be used interchangeably. All of these terms also include their progeny, which are any and all subsequent generations. It is understood that all progeny may not be identical due to deliberate or inadvertent mutations. As used herein, the term "ex vivo" refers to "outside" the body. The terms "ex vivo" and "in vitro" can be used interchangeably herein.

The term "transfection" and "transduction" are interchangeable and refer to the process by which an exogenous nucleic acid sequence is introduced into a eukaryotic host cell. Transfection (or transduction) can be achieved by any one of a number of means including electroporation, microinjection, gene gun delivery, retroviral infection, lipofection, superfection and the like.

Any appropriate method may be used to transfect or transform the cells, for example, the NK cells, or to administer the nucleotide sequences or compositions of the present methods. Certain non-limiting examples are presented herein. In some embodiments, the virsl vector is an SFG-based viral vector, as discussed in Tey et al. (2007) *Biol Blood Marrow Transpl* 13:913-24 and by Di Stasi et al., (2011) *N Engl J Med* 365:1673-83 (2011).

NK cells that are genetically modified as disclosed herein are useful for administering to subjects who can benefit from donor lymphocyte administration. These subjects will typically be humans, so the invention will typically be performed using human NK cells.

The modified cells may be obtained from a donor, or may be cells obtained from the patient, for example, the cells may be autologous, syngeneic, or allogeneic. The cells may, for example, be used in regeneration, for example, to replace the function of diseased cells. The cells may also be modified to express a heterologous gene so that biological agents may be delivered to specific microenvironments such as, for example, diseased bone marrow or metastatic deposits. By "therapeutic cell" is meant a cell used for cell therapy, that is, a cell administered to a subject to treat or prevent a condition or disease.

By "obtained or prepared" as, for example, in the case of cells, is meant that the cells or cell culture are isolated, purified, or partially purified from the source, where the source may be, for example, umbilical cord blood, bone marrow, or peripheral blood. The terms may also apply to the case where the original source, or a cell culture, has been cultured and the cells have replicated, and where the progeny cells are now derived from the original source.

Peripheral blood: The term "peripheral blood" as used herein, refers to cellular components of blood (e.g., red blood cells, white blood cells and platelets), which are obtained or prepared from the circulating pool of blood and not sequestered within the lymphatic system, spleen, liver or bone marrow.

Umbilical cord blood: Umbilical cord blood is distinct from peripheral blood and blood sequestered within the lymphatic system, spleen, liver or bone marrow. The terms "umbilical cord blood", "umbilical blood" or "cord blood", which can be used interchangeably, refers to blood that remains in the placenta and in the attached umbilical cord after child birth. Cord blood often contains stem cells including hematopoietic cells.

The term "allogeneic" as used herein, refers to HLA or MHC loci that are antigenically distinct between the host and donor cells. Thus, cells or tissue transferred from the same species can be antigenically distinct. Syngeneic mice can differ at one or more loci (congenics) and allogeneic mice can have the same background. The term "autologous" means a cell, nucleic acid, protein, polypeptide, or the like derived from the same individual to which it is later administered. The modified cells of the present methods may, for example, be autologous cells, such as, for example, autologous NK cells.

As used herein, the term "syngeneic" refers to cells, tissues or animals that have genotypes that are identical or closely related enough to allow tissue transplant, or are immunologically compatible. For example, identical twins or animals of the same inbred strain. Syngeneic and isogeneic can be used interchangeably.

Donor NK cells can be cultured prior to being genetically modified by any suitable method known in the art including the one described herein.

The NK cells can be transduced using a viral vector encoding polynucleotides of the present application. Suitable transduction techniques may involve fibronectin fragment CH-296. As an alternative to transduction using a viral vector, cells can be transfected with any suitable method known in the art such as with DNA encoding the suicide switch of interest and a cell surface transgene marker of interest e.g. using calcium phosphate, cationic polymers (such as PEI), magnetic beads, electroporation and commercial lipid-based reagents such as Lipofectamine™ and Fugene™. One result of the transduction/transfection step is that various donor NK cells will now be genetically-modified NK cells which can express the suicide switch of interest.

In some embodiments, the viral vector used for transduction is the retroviral vector disclosed by Tey et al. (2007) *Biol Blood Marrow Transpl* 13:913-24 and by Di Stasi et al. (2011) supra. This vector is based on Gibbon ape leukemia virus (Gal-V) pseudotyped retrovirus encoding an iCasp9 suicide switch and a ΔCD19 cell surface transgene marker (see further below). It can be produced in the PG13 packaging cell line, as discussed by Tey et al. (2007) supra. Other viral vectors encoding the desired proteins can also be used. In some embodiments, retroviral vectors that can provide a high copy number of proviral integrants per cell are used for transduction.

After transduction/transfection, cells can be separated from transduction/transfection materials and cultured again, to permit the genetically-modified NK cells to expand. TNK cells can be expanded so that a desired minimum number of genetically-modified NK cells is achieved.

Genetically-modified NK cells can then be selected from the population of cells which has been obtained. The suicide switch will usually not be suitable for positive selection of desired NK cells, so in some embodiments, the genetically-modified NK cells should express a cell surface transgene marker of interest. Cells which express this surface marker can be selected e.g. using immunomagnetic techniques. For instance, paramagnetic beads conjugated to monoclonal antibodies which recognise the cell surface transgene marker of interest can be used, for example, using a CliniMACS system (available from Miltenyi Biotec).

In an alternative procedure, genetically-modified NK cells are selected after a step of transduction, are cultured, and are then fed. Thus, the order of transduction, feeding, and selection can be varied.

The result of these procedures is a composition containing donor NK cells which have been genetically modified, and which can thus express, e.g. the costimulatory polypeptide and/or the suicide switch of interest (and, typically, the cell surface transgene marker of interest). These genetically-modified NK cells can be administered to a recipient, but they will usually be cryopreserved (optionally after further expansion) before being administered.

Methods for Treating a Disease

The present methods also encompass methods of treatment or prevention of a disease where administration of cells by, for example, infusion, may be beneficial.

The cells described herein may be used for cell therapy. The cells may be from a donor may be cells obtained from the patient. The cells may, for example, be used in regeneration, for example, to replace the function of diseased cells. The cells may also be modified to express a heterologous gene so that biological agents may be delivered to specific microenvironments such as, for example, diseased bone marrow or metastatic deposits. The cells provided in the present application contain a safety switch that may be valuable in a situation where following cell therapy, the activity of the therapeutic cells needs to be removed, increased, or decreased. For example, where progenitor NK cells that express a chimeric antigen receptor are provided to the patient, in some situations there may be an adverse event, such as inappropriate differentiation of the cell into a more mature cell type, or an undesired invitation into another tissue off-target toxicity.

Ceasing the administration of the ligand would return the therapeutic NK cells to a non-activated state, remaining at a low, non-toxic, level of expression. Or, for example, where it is necessary to remove the therapeutic cells. The therapeutic cell may work to decrease the tumor cell, or tumor size, and may no longer be needed. In this situation, administration of the ligand may cease, and the therapeutic cells would no longer be activated. If the tumor cells return, or the tumor size increases following the initial therapy, the ligand may be administered again, in order to activate the chimeric antigen receptor-expressing NK cells, and re-treat the patient. In some embodiments, cells are transfected or transduced with nucleic acids that encode the chimeric signaling polypeptides and inducible chimeric signaling polypeptides of the present application.

By "therapeutic cell" is meant a cell used for cell therapy, that is, a cell administered to a subject to treat or prevent a condition or disease. Therapeutic cells may, for example, be NK cells. The therapeutic cells may be, for example, any cell administered to a patient for a desired therapeutic result. The therapeutic cells may be, for example, immune cells such as, for example, T cells, natural killer cells, B cells, tumor infiltrating lymphocytes, or macrophages, or a combination thereof; the therapeutic cells may be, for example, peripheral blood cells, hematopoietic progenitor cells, bone marrow cells, or tumor cells. To further improve the tumor microenvironment to be more immunogenic, the treatment may be combined with one or more adjuvants (e.g., IL-12, TLRs, IDO inhibitors, etc.). In some embodiments, the cells may be delivered to treat a solid tumor, such as, for example, delivery of the cells to a tumor bed.

Also provided in some embodiments are nucleic acid vaccines, such as DNA vaccines, wherein the vaccine comprises a nucleic acid comprising a polynucleotide that encodes an inducible, or constitutive chimeric signaling polypeptide of the present application. The vaccine may be administered to a subject, thereby transforming or transducing target cells in vivo.

As used herein, the term "vaccine" refers to a formulation that contains a composition presented herein which is in a form that is capable of being administered to an animal. Typically, the vaccine comprises a conventional saline or buffered aqueous solution medium in which the composition is suspended or dissolved. In this form, the composition can be used conveniently to prevent, ameliorate, or otherwise treat a condition. Upon introduction into a subject, the vaccine is able to provoke an immune response including, but not limited to, the production of antibodies, cytokines and/or other cellular responses.

An effective amount of the pharmaceutical composition, such as the multimeric ligand presented herein, would be the amount that achieves this selected result of activating the inducible chimeric signaling polypeptide-expressing NK cells, such that over 60%, 70%, 80%, 85%, 90%, 95%, or 97%, or that under 80%, 70%, 60%, 50%, 40%, 30%, 20%, or 10% of the therapeutic cells are activated. The term is also synonymous with "sufficient amount." The effective amount may also be the amount that achieves the desired therapeutic response, such as, the reduction of tumor size, the decrease in the level of tumor cells, or the decrease in the level of CD19-expressing leukemic cells, compared to the time before the ligand inducer is administered.

By administering a modified cell, it is understood that an effective amount of modified cells is administered.

To determine if an effective amount of ligand or modified cells is administered, any means of assaying or measuring the number of target cells, or amount of target antigen, or size of a tumor may be used to determine whether the number of target cells, amount of target antigen or size of a tumor has increased, decreased, or remained the same. Samples, images, or other means of measurement taken before administration of the modified cells or ligand may be used to compare with samples, images, or other means of measurement taken after administration of the modified cells or ligand. Thus, for example, to determine whether the amount or concentration of cells expressing a target antigen has increased, decreased, or remained the same, a first sample may be obtained from a subject before administration of the ligand or modified cells, and a second sample may be obtained from a subject after administration of the ligand or modified cells. The amount or concentration of cells expressing the target antigen in the first sample may be compared with the amount or concentration of cells expressing the target antigen in the second sample, in order to determine whether the amount or concentration of cells expressing the target antigen has increased, decreased, or remained the same following administration of the ligand or modified cell.

The effective amount for any particular application can vary depending on such factors as the disease or condition being treated, the particular composition being administered, the size of the subject, and/or the severity of the disease or condition. One can empirically determine the effective amount of a particular composition presented herein.

The terms "contacted" and "exposed," when applied to a cell, tissue or organism, are used herein to describe the process by which the pharmaceutical composition and/or another agent, such as for example a chemotherapeutic or radiotherapeutic agent, are delivered to a target cell, tissue or organism or are placed in direct juxtaposition with the target cell, tissue or organism. To achieve cell killing or stasis, the pharmaceutical composition and/or additional agent(s) are delivered to one or more cells in a combined amount effective to kill the cell(s) or prevent them from dividing.

The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein, and one or more agents may be employed.

Diseases that may be treated or prevented include diseases caused by viruses, bacteria, yeast, parasites, protozoa, cancer cells and the like. The pharmaceutical composition (transduced NK cells, expression vector, expression construct, etc.) may be used as a generalized immune enhancer (NK cell activating composition or system) and as such has utility in treating diseases. Exemplary diseases that can be treated and/or prevented include, but are not limited, to infections of viral etiology such as HIV, influenza, Herpes, viral hepatitis, Epstein Bar, polio, viral encephalitis, measles, chicken pox, Papilloma virus etc.; or infections of bacterial etiology such as pneumonia, tuberculosis, syphilis, etc.; or infections of parasitic etiology such as malaria, trypanosomiasis, leishmaniasis, trichomoniasis, amoebiasis, etc.

Preneoplastic or hyperplastic states which may be treated or prevented using the pharmaceutical composition (transduced NK cells, expression vector, expression construct, etc.) include but are not limited to preneoplastic or hyperplastic states such as colon polyps, Crohn's disease, ulcerative colitis, breast lesions and the like.

Cancers, including solid tumors, which may be treated using the pharmaceutical composition include, but are not limited to primary or metastatic melanoma, adenocarcinoma, squamous cell carcinoma, adenosquamous cell carcinoma, thymoma, lymphoma, sarcoma, lung cancer, liver cancer, non-Hodgkin's lymphoma, Hodgkin's lymphoma, leukemias, uterine cancer, breast cancer, prostate cancer, ovarian cancer, pancreatic cancer, colon cancer, multiple myeloma, neuroblastoma, NPC, bladder cancer, cervical cancer and the like.

Other hyperproliferative diseases, including solid tumors, that may be treated using the NK cell and other therapeutic cell activation system presented herein include, but are not limited to rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

Methods of treatment may include methods for prophylactic or therapeutic purposes. When provided prophylactically, the pharmaceutical composition, for example, the expression construct, expression vector, fused protein, transduced cells, activated immune cells, transduced or loaded immune cells, is provided in advance of any detected or reported symptom. The prophylactic administration of pharmaceutical composition serves to prevent or ameliorate any subsequent infection or disease. When provided therapeutically, the pharmaceutical composition is provided at or after the onset of a symptom of infection or disease. Thus, the compositions presented herein may be provided either prior to the anticipated exposure to a disease-causing agent or disease state or after the initiation of the infection or disease. Thus, provided herein are methods for prophylactic treatment of solid tumors such as those found in cancer, or for example, but not limited to, prostate cancer, using the nucleic acids and ligands discussed herein.

For example, methods are provided of prophylactically preventing or reducing the size of a tumor, or reducing the concentration or number of target cells, in a subject comprising administering a nucleic acid comprising a promoter operably linked to a polynucleotide that encodes a chimeric signaling polypeptide, and a nucleic acid that encodes a CAR or a recombinant TCR. The chimeric signaling polypeptide may, or may not comprise a membrane targeting region, and may optionally be inducible or constitutive. The chimeric signaling polypeptide may also be provided as part of the CAR polypeptide. The nucleic acid, and optionally the multimeric ligand are administered in an amount effect to prevent or reduce the size of a tumor, or the concentration or number of target cells in a subject. The term multimerization region or multimeric ligand binding region may be used in place of the term ligand binding region for purposes of this application.

Solid tumors from any tissue or organ may be treated using the present methods, including, for example, any tumor expressing PSA, for example, PSMA, in the vasculature, for example, solid tumors present in, for example, lungs, bone, liver, prostate, or brain, and also, for example, in breast, ovary, bowel, testes, colon, pancreas, kidney, bladder, neuroendocrine system, soft tissue, boney mass, and lymphatic system. Other solid tumors that may be treated include, for example, glioblastoma, and malignant myeloma.

Combination Therapies

In order to increase the effectiveness of the modified cells presented herein, it may be desirable to combine these compositions and methods with an agent effective in the treatment of the disease.

In certain embodiments, anti-cancer agents may be used in combination with the present methods. An "anti-cancer" agent is capable of negatively affecting cancer in a subject, for example, by killing one or more cancer cells, inducing apoptosis in one or more cancer cells, reducing the growth rate of one or more cancer cells, reducing the incidence or number of metastases, reducing a tumor's size, inhibiting a tumor's growth, reducing the blood supply to a tumor one or more cancer cells, promoting an immune response against one or more cancer cells or a tumor, preventing or inhibiting the progression of a cancer, or increasing the lifespan of a subject with a cancer. Anti-cancer agents include, for example, chemotherapy agents (chemotherapy), radiotherapy agents (radiotherapy), a surgical procedure (surgery), immune therapy agents (immunotherapy), genetic therapy agents (gene therapy), hormonal therapy, other biological agents (biotherapy) and/or alternative therapies.

In some embodiments, the modified NK cells described herein are used in combination with other cell therapies, such as, for example, T cells, tumor infiltrating lymphocytes, natural killer cells, TCR-expressing cells, natural killer T cells, or progenitor cells, such as, for example, hematopoietic stem cells, mesenchymal stromal cells, stem cells, pluripotent stem cells, and embryonic stem cells The terms "mesenchymal stromal cell" or "bone marrow derived mesenchymal stromal cell" as used herein, refer to multipotent stem cells that can differentiate ex vivo, in vitro and in vivo into adipocytes, osteoblasts and chondroblasts, and may be further defined as a fraction of mononuclear bone marrow cells that adhere to plastic culture dishes in standard culture conditions, are negative for hematopoietic lineage markers and are positive for CD73, CD90 and CD105.

The term "embryonic stem cell" as used herein, refers to pluripotent stem cells derived from the inner cell mass of the blastocyst, an early-stage embryo of between 50 to 150 cells. Embryonic stem cells are characterized by their ability to renew themselves indefinitely and by their ability to differentiate into derivatives of all three primary germ layers, ectoderm, endoderm and mesoderm. Pluripotent is distinguished from multipotent in that pluripotent cells can generate all cell types, while multipotent cells (e.g., adult stem cells) can only produce a limited number of cell types.

Tumor infiltrating lymphocytes (TILs) refer to T cells having various receptors which infiltrate tumors and kill tumor cells in a targeted manor.

In further embodiments antibiotics can be used in combination with the pharmaceutical composition to treat and/or prevent an infectious disease. Such antibiotics include, but are not limited to, amikacin, aminoglycosides (e.g., gentamycin), amoxicillin, amphotericin B, ampicillin, antimonials, atovaquone sodium stibogluconate, azithromycin, capreomycin, cefotaxime, cefoxitin, ceftriaxone, chloramphenicol, clarithromycin, clindamycin, clofazimine, cycloserine, dapsone, doxycycline, ethambutol, ethionamide, fluconazole, fluoroquinolones, isoniazid, itraconazole, kanamycin, ketoconazole, minocycline, ofloxacin), para-aminosalicylic acid, pentamidine, polymixin definsins, prothionamide, pyrazinamide, pyrimethamine sulfadiazine, quinolones (e.g., ciprofloxacin), rifabutin, rifampin, sparfloxacin, streptomycin, sulfonamides, tetracyclines, thiacetazone, trimethaprim-sulfamethoxazole, viomycin or combinations thereof.

More generally, such an agent would be provided in a combined amount with modified cells effective to kill or inhibit proliferation of a cancer cell and/or microorganism. This process may involve contacting the cell(s) with an agent(s) and the pharmaceutical composition at the same time or within a period of time wherein separate administration of the pharmaceutical composition and an agent to a cell, tissue or organism produces a desired therapeutic benefit. This may be achieved by contacting the cell, tissue or organism with a single composition or pharmacological formulation that includes both the pharmaceutical composition and one or more agents, or by contacting the cell with two or more distinct compositions or formulations, wherein one composition includes the pharmaceutical composition and the other includes one or more agents.

The administration of the pharmaceutical composition may precede, be concurrent with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered from substantially simultaneously, about 1 minute, to about 24 hours to about 7 days to about 1 to about 8 weeks or more, and any range derivable therein, prior to and/or after administering the expression vector. Yet further, various combination regimens of the pharmaceutical composition presented herein, and one or more agents may be employed.

In some embodiments, the methods further comprise administering a chemotherapeutic agent. In some embodiments, the composition, ligand, and the chemotherapeutic agent are administered in an amount effective to treat cancer, such as, for example, prostate cancer, in the subject. In some embodiments, the composition or the nucleotide sequences, the ligand, and the chemotherapeutic agent are administered in an amount effective to treat cancer in the subject. In some embodiments, the chemotherapeutic agent is selected from the group consisting of carboplatin, estramustine phosphate (Emcyt), and thalidomide. In some embodiments, the chemotherapeutic agent is a taxane. The taxane may be, for example, selected from the group consisting of docetaxel (Taxotere), paclitaxel, and cabazitaxel. In some embodiments, the taxane is docetaxel. In some embodiments, the chemotherapeutic agent is administered at the same time or within one week after the administration of the cell, nucleic acid or the ligand. In other embodiments, the chemotherapeutic agent is administered after the administration of the ligand. In other embodiments, the chemotherapeutic agent is administered from 1 to 4 weeks or from 1 week to 1 month, 1 week to 2 months, or 1 week to 3 months after the administration of the ligand. In other embodiments, the methods further comprise administering the chemotherapeutic agent from 1 to 4 weeks, or from 1 week to 1 month, 1 week to 2 months, or 1 week to 3 months before the administration of the cell or nucleic acid. In some embodiments, the chemotherapeutic agent is administered at least 2 weeks before administering the cell or nucleic acid. In some embodiments, the chemotherapeutic agent is administered at least 1 month before administering the cell or nucleic acid. In some embodiments, the chemotherapeutic agent is administered after administering the multimeric ligand. In some embodiments, the chemotherapeutic agent is administered at least 2 weeks after administering the multimeric ligand. In some embodiments, wherein the chemotherapeutic agent is administered at least 1 month after administering the multimeric ligand.

In some embodiments, the chemotherapeutic agent may be Taxotere (docetaxel), or another taxane, such as, for example, cabazitaxel. The chemotherapeutic may be administered either before, during, or after treatment with the cells and inducer. For example, the chemotherapeutic may be administered about 1 year, 11, 10, 9, 8, 7, 6, 5, or 4 months, or 18, 17, 16, 15, 14, 13, 12, 11, 10, 9, 8, 7, 6, 5, 4, 3, 2, weeks or 1 week prior to administering the first dose of activated nucleic acid. Or, for example, the chemotherapeutic may be administered about 1 week or 2, 3, 4, 5, 6, 7, 8, 9, 10, 11, 12, 13, 14, 15, 16, 17, or 18 weeks or 4, 5, 6, 7, 8, 9, 10, or 11 months or 1 year after administering the first dose of cells or inducer.

Administration of a chemotherapeutic agent may comprise the administration of more than one chemotherapeutic agent. For example, cisplatin may be administered in addition to Taxotere or other taxane, such as, for example, cabazitaxel.

In some embodiments, the methods further comprise administering two or more chemotherapeutic agents. In some embodiments, the chemotherapeutic agents are selected from the group consisting of carboplatin, Estramustine phosphate, and thalidomide. In some embodiments, at least one chemotherapeutic agent is a taxane. The taxane may be, for example, selected from the group consisting of docetaxel, paclitaxel, and cabazitaxel. In some embodiments, the taxane is docetaxel. In some embodiments, the chemotherapeutic agents are administered at the same time or within one week after the administration of the cell, nucleic acid or the ligand. In other embodiments, the chemotherapeutic agents are administered after the administration of the ligand. In other embodiments, the chemotherapeutic agents are administered from 1 to 4 weeks or from 1 week to 1 month, 1 week to 2 months, or 1 week to 3 months after the administration of the ligand. In other embodiments, the methods further comprise administering the chemotherapeutic agents from 1 to 4 weeks or from 1 week to 1 month, 1 week to 2 months, or 1 week to 3 months before the administration of the cell or nucleic acid.

Optimized and Personalized Therapeutic Treatment

The dosage and administration schedule of the ligand inducer may be optimized by determining the level of the disease or condition to be treated. For example, the size of any remaining solid tumor, or the level of targeted cells such as, for example, tumor cells that may remain in the patient, may be determined.

For example, determining that a patient has clinically relevant levels of tumor cells, or a solid tumor, after initial therapy, provides an indication to a clinician that it may be necessary to activate the chimeric-antigen receptor-expressing NK cells by activating the cells by administering the multimeric ligand. In another example, determining that a patient has a reduced level of tumor cells or reduced tumor size after treatment with the multimeric ligand may indicate to the clinician that no additional dose of the multimeric ligand is needed. Similarly, after treatment with the multimeric ligand, determining that the patient continues to exhibit disease or condition symptoms, or suffers a relapse of symptoms may indicate to the clinician that it may be necessary to administer at least one additional dose of multimeric ligand. The term "dosage" is meant to include both the amount of the dose and the frequency of administration, such as, for example, the timing of the next dose. The term "dosage level" refers to the amount of the multimeric ligand administered in relation to the body weight of the subject. Thus, increasing the dosage level would mean increasing the amount of the ligand administered relative to the subject's weight. In addition, increasing the concentration of the dose administered, such as, for example, when the multimeric ligand is administered using a continuous infusion pump would mean that the concentration administered (and thus the amount administered) per minute, or second, is increased.

Thus, for example, in certain embodiments where cells that express an inducible chimeric signaling polypeptide or an inducible chimeric antigen receptor polypeptide are administered to a patient, the methods comprise determining the presence or absence of a tumor size increase and/or increase in the number of tumor cells in a subject relative to the tumor size and/or the number of tumor cells following administration of the multimeric ligand, and administering an additional dose of the multimeric ligand to the subject in the event the presence of a tumor size increase and/or increase in the number of tumor cells is determined. In these embodiments, for example, the patient is initially treated with the therapeutic cells and ligand according to the methods provided herein. Following the initial treatment, the size of the tumor, or the number of tumor cells, may decrease relative to the time prior to the initial treatment. At a certain time after this initial treatment, the patient is again tested, or the patient may be continually monitored for disease symptoms. If it is determined that the size of the tumor, or the number of tumor cells, for example, is increased relative to the time just after the initial treatment, then the ligand may be administered for an additional dose. This monitoring and treatment schedule may continue, because the therapeutic cells that express inducible chimeric signaling polypeptides remain in the patient, although in a relatively inactive state in the absence of additional ligand.

In other examples where cells that express an inducible chimeric signaling polypeptide or an inducible chimeric antigen receptor polypeptide are administered to a patient, and where the target cell is not a tumor cell, the methods comprise determining the presence or absence of the concentration or number of target cells in a subject relative to the concentration or number of target cells following administration of the multimeric ligand, and administering an additional dose of the multimeric ligand to the subject in the event the presence of an increase in the concentration or number of target cells is determined. For this analysis, the concentration or number of target cells refers to the concentration or number of target cells in a sample obtained from the patient. these embodiments, for example, the patient is initially treated with the therapeutic cells and ligand according to the methods provided herein. Following the initial treatment, the concentration or the number of target cells may decrease relative to the time prior to the initial treatment. At a certain time after this initial treatment, the patient is again tested, or the patient may be continually monitored for disease symptoms. If it is determined that the concentration or number of target cells, for example, is increased relative to the time just after the initial treatment, then the ligand may be administered for an additional dose. This monitoring and treatment schedule may continue, because the therapeutic cells that express inducible chimeric signaling polypeptides remain in the patient, although in a relatively inactive state in the absence of additional ligand.

An indication of adjusting or maintaining a subsequent drug dose, such as, for example, a subsequent dose of the multimeric ligand, and/or the subsequent drug dosage, can be provided in any convenient manner. An indication may be provided in tabular form (e.g., in a physical or electronic medium) in some embodiments. For example, the size of the tumor cell, or the number or level of tumor cells in a sample may be provided in a table, and a clinician may compare the symptoms with a list or table of stages of the disease. The clinician then can identify from the table an indication for subsequent drug dose. In certain embodiments, an indication can be presented (e.g., displayed) by a computer, after the symptoms are provided to the computer (e.g., entered into memory on the computer). For example, this information can be provided to a computer (e.g., entered into computer memory by a user or transmitted to a computer via a remote device in a computer network), and software in the computer can generate an indication for adjusting or maintaining a subsequent drug dose, and/or provide the subsequent drug dose amount.

Once a subsequent dose is determined based on the indication, a clinician may administer the subsequent dose or provide instructions to adjust the dose to another person or entity. The term "clinician" as used herein refers to a decision maker, and a clinician is a medical professional in certain embodiments. A decision maker can be a computer or a displayed computer program output in some embodiments, and a health service provider may act on the indication or subsequent drug dose displayed by the computer. A decision maker may administer the subsequent dose directly (e.g., infuse the subsequent dose into the subject) or remotely (e.g., pump parameters may be changed remotely by a decision maker).

Methods as presented herein include without limitation the delivery of an effective amount of a modified cell, a nucleic acid, an expression construct encoding the same, or the multimeric ligand. An "effective amount" of the pharmaceutical composition, cell, nucleic acid, expression construct, or multimeric ligand, generally, is defined as that amount sufficient to detectably and repeatedly to achieve the stated desired result, for example, to ameliorate, reduce, minimize or limit the extent of the disease or its symptoms. Other more rigorous definitions may apply, including elimination, eradication or cure of disease. In some embodiments there may be a step of monitoring the biomarkers to evaluate the effectiveness of treatment and to control toxicity.

Enhancement of an Immune Response

In certain embodiments, an immune cell activation strategy is contemplated, that incorporates the manipulation of signaling co-stimulatory polypeptides that activate biological pathways, for example, immunological pathways, such as, for example, NF-κB pathways, Akt pathways, and/or p38 pathways. This immune cell activation system can be used in conjunction with or without standard vaccines to enhance the immune response. For example, release of IFNγ by IL-12-stimulated NK cells can lead to upregulation of MHC on target cells along with improvements in antigen presentation. Furthermore, the release of chemokines such as MCP1, XCL1, XCL2, CCL5 and CXCL10 by activated NK cells in an anti-tumor response can recruit and induce the differentiation of dendritic cells and induce the expansion of an adaptive immune response by native T lymphocytes as well as recruiting macrophages and other immune cells as part of an overall inflammatory response (Bottcher et al. (2018) Cell 172: p1022-1037.

In certain embodiments the cells are in an animal, such as human, non-human primate, cow, horse, pig, sheep, goat, dog, cat, or rodent. The subject may be, for example, an animal, such as a mammal, for example, a human, non-human primate, cow, horse, pig, sheep, goat, dog, cat, or rodent. The subject may be, for example, human, for example, a patient suffering from an infectious disease, and/or a subject that is immunocompromised, or is suffering from a hyperproliferative disease.

In further embodiments, the expression construct and/or expression vector can be utilized as a composition or substance that activates cells. Such a composition that "activates cells" or "enhances the activity cells" refers to the ability to stimulate one or more activities associated with cells. For example, a composition, such as the expression construct or vector of the present methods, can stimulate upregulation of co-stimulatory molecules on cells, induce nuclear translocation of NF-kappaB in cells, activate toll-like receptors in cells, or other activities involving cytokines or chemokines.

The expression construct, expression vector and/or transduced cells can enhance or contribute to the effectiveness of a vaccine by, for example, enhancing the immunogenicity of weaker antigens such as highly purified or recombinant antigens, reducing the amount of antigen required for an immune response, reducing the frequency of immunization required to provide protective immunity, improving the efficacy of vaccines in subjects with reduced or weakened immune responses, such as newborns, the aged, and immunocompromised individuals, and enhancing the immunity at a target tissue, such as mucosal immunity, or promote cell-mediated or humoral immunity by eliciting a particular cytokine profile.

In certain embodiments, the cell is also contacted with an antigen. Often, the cell is contacted with the antigen ex vivo. Sometimes, the cell is contacted with the antigen in vivo. In some embodiments, the cell is in a subject and an immune response is generated against the antigen. Sometimes, the immune response is a cytotoxic T-lymphocyte (CTL) immune response. Sometimes, the immune response is generated against a tumor antigen. In certain embodiments, the cell is activated without the addition of an adjuvant.

In some embodiments, the cell is transduced with the nucleic acid ex vivo and administered to the subject by intradermal administration. In some embodiments, the cell is transduced with the nucleic acid ex vivo and administered to the subject by subcutaneous administration. Sometimes, the cell is transduced with the nucleic acid ex vivo. Sometimes, the cell is transduced with the nucleic acid in vivo.

In certain embodiments, the cell can be transduced ex vivo or in vivo with a nucleic acid that encodes the chimeric protein. The cell may be sensitized to the antigen at the same time the cell is contacted with the multimeric ligand, or the cell can be pre-sensitized to the antigen before the cell is contacted with the multimerization ligand. In some embodiments, the cell is contacted with the antigen ex vivo. In certain embodiments the cell is transduced with the nucleic acid ex vivo and administered to the subject by intradermal administration, and sometimes the cell is transduced with the nucleic acid ex vivo and administered to the subject by subcutaneous administration. The antigen may be a tumor antigen, and the CTL immune response can be induced by migration of the cell to a draining lymph node. A tumor antigen is any antigen such as, for example, a peptide or polypeptide, that triggers an immune response in a host. The tumor antigen may be a tumor-associated antigen that is associated with a neoplastic tumor cell.

The term "immunocompromised" as used herein is defined as a subject that has reduced or weakened immune system. In some embodiments, an immunocompromised individual or subject is a subject that has a reduced or weakened immune response. Such individuals may also include a subject that has undergone chemotherapy or any other therapy resulting in a weakened immune system, a transplant recipient, a subject currently taking immunosuppressants, an aging individual, or any individual that has a reduced and/or impaired CD4 T helper cells. It is contemplated that the present methods can be utilized to enhance the amount and/or activity of CD4 T helper cells in an immunocompromised subject.

Challenge with Target Antigens

In specific embodiments, prior to administering the transduced cell, the cells may be challenged with antigens (also referred herein as "target antigens"). After challenge, the transduced, loaded cells are administered to the subject parenterally, intradermally, intranodally, or intralymphatically. Additional parenteral routes include, but are not limited to subcutaneous, intramuscular, intraperitoneal, intravenous, intraarterial, intramyocardial, transendocardial, transepicardial, intrathecal, intraprotatic, intratumor, and infusion techniques.

The target antigen, as used herein, is an antigen or immunological epitope on the antigen, which is crucial in immune recognition and ultimate elimination or control of the disease-causing agent or disease state in a mammal. The immune recognition may be cellular and/or humoral. In the case of intracellular pathogens and cancer, immune recognition may, for example, be a T lymphocyte response.

The target antigen may be derived or isolated from, for example, a pathogenic microorganism such as viruses including HIV, (Korber et al, eds HIV Molecular Immunology Database, Los Alamos National Laboratory, Los Alamos, N. Mex. 1977) influenza, Herpes simplex, human papilloma virus (U.S. Pat. No. 5,719,054), Hepatitis B (U.S. Pat. No. 5,780,036), Hepatitis C (U.S. Pat. No. 5,709,995), EBV, Cytomegalovirus (CMV) and the like. Target antigen may be derived or isolated from pathogenic bacteria such as, for example, from *Chlamydia* (U.S. Pat. No. 5,869,608), *Mycobacteria, Legionella, Meningiococcus*, Group A *Streptococcus, Salmonella, Listeria, Hemophilus influenzae* (U.S. Pat. No. 5,955,596) and the like.

Target antigen may be derived or isolated from, for example, pathogenic yeast including *Aspergillus*, invasive *Candida* (U.S. Pat. No. 5,645,992), *Nocardia, Histoplasmosis, Cryptosporidia* and the like.

Target antigen may be derived or isolated from, for example, a pathogenic protozoan and pathogenic parasites including but not limited to *Pneumocystis carinii, Trypanosoma, Leishmania* (U.S. Pat. No. 5,965,242), *Plasmodium* (U.S. Pat. No. 5,589,343) and *Toxoplasma gondii*.

Target antigen includes an antigen associated with a preneoplastic or hyperplastic state. Target antigen may also be associated with, or causative of cancer. Such target antigen may be, for example, tumor specific antigen, tumor associated antigen (TAA) or tissue specific antigen, epitope thereof, and epitope agonist thereof. Such target antigens include but are not limited to carcinoembryonic antigen (CEA) and epitopes thereof such as CAP-1, CAP-1-6D and the like (GenBank Accession No. M29540), MART-1 (Kawakarni et al, J. Exp. Med. 180:347-352, 1994), MAGE-1 (U.S. Pat. No. 5,750,395), MAGE-3, GAGE (U.S. Pat. No. 5,648,226), GP-100 (Kawakami et al Proc. Nat'l Acad. Sci. USA 91:6458-6462, 1992), MUC-1, MUC-2, point mutated ras oncogene, normal and point mutated p53 oncogenes (Hollstein et al Nucleic Acids Res. 22:3551-3555, 1994), PSMA (Israeli et al Cancer Res. 53:227-230, 1993), tyrosinase (Kwon et al PNAS 84:7473-7477, 1987) TRP-1 (gp75) (Cohen et al Nucleic Acid Res. 18:2807-2808, 1990; U.S. Pat. No. 5,840,839), NY-ESO-1 (Chen et al PNAS 94: 1914-1918, 1997), TRP-2 (Jackson et al EMBOJ, 11:527-535, 1992), TAG72, KSA, CA-125, PSA, HER-2/neu/c-erb/B2, (U.S. Pat. No. 5,550,214), BRC—I, BRC-II, bcr-abl, pax3-fkhr, ews-fli-1, modifications of TAAs and tissue specific antigen, splice variants of TAAs, epitope agonists, and the like. Other TAAs may be identified, isolated and cloned by methods known in the art such as those disclosed in U.S. Pat. No. 4,514,506. Target antigen may also include one or more growth factors and splice variants of each.

An antigen may be expressed more frequently in cancer cells than in non-cancer cells. The antigen may result from contacting the modified dendritic cell with a prostate specific membrane antigen, for example, a prostate specific membrane antigen (PSMA) or fragment thereof.

Cytokine Measurement for Optimized and Personalized Treatment

Cytokines are a large and diverse family of polypeptide regulators produced widely throughout the body by cells of diverse origin. Cytokines are small secreted proteins, including peptides and glycoproteins, which mediate and regulate immunity, inflammation, and hematopoiesis. They are produced de novo in response to an immune stimulus. Cytokines generally (although not always) act over short distances and short time spans and at low concentration. They generally act by binding to specific membrane receptors, which then signal the cell via signaling proteins, often tyrosine kinases of the Janus family or coupled G proteins to alter cell behavior (e.g., gene expression). Responses to cytokines include, for example, increasing or decreasing expression of membrane proteins (including cytokine receptors), proliferation, blockage or promotion of apoptosis, differentiation and secretion of effector molecules.

The term "cytokine" is a general description of a large family of proteins and glycoproteins. Other names include lymphokine (cytokines made by lymphocytes), monokine (cytokines made by monocytes), chemokine (cytokines with chemotactic activities), and interleukin (cytokines made by one leukocyte and acting on other leukocytes). Cytokines may act on cells that secrete them (autocrine action), on nearby cells (paracrine action), or in some instances on distant cells (endocrine action).

Examples of cytokines include, without limitation, interleukins (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18 and the like), interferons (e.g., IFN-beta, IFN-gamma and the like), tumor necrosis factors (e.g., TNF-alpha, TNF-beta and the like), lymphokines, monokines and chemokines; growth factors (e.g., transforming growth factors (e.g., TGF-alpha, TGF-beta and the like)); colony-stimulating factors (e.g. GM-CSF, granulocyte colony-stimulating factor (G-CSF) etc.); IP-10, MCP-1, and the like.

A cytokine often acts via a cell-surface receptor counterpart. Subsequent cascades of intracellular signaling then alter cell functions. This signaling may include upregulation and/or downregulation of several genes and their transcription factors, resulting in the production of other cytokines, an increase in the number of surface receptors for other molecules, or the suppression of their own effect by feedback inhibition.

Treatment using immune system activating cells discussed herein may be optimized by determining the concentration of certain cytokine biomarkers, such as, for example, cytokines discussed herein, including, for example, IL-2, IP-10, IL-5, and MCP-1, and, for example, IL-6, IL6-sR, or VCAM-1 during the course of treatment. In a specific embodiment, a cytokine, such as one, two, three or more of those described in the Examples below (e.g., Example 3, infra) is measured during one, two or all of these timepoints: prior to, during, or subsequent to treatment described herein (e.g., administration of modified NK cells). IL-6 refers to interleukin 6. IL-6sR refers to the IL-6 soluble receptor, the levels of which often correlate closely with levels of IL-6. VCAM-1 refers to vascular cell adhesion molecule. Different patients having different stages or types of cancer, may react differently to various therapies. The response to treatment may be monitored by following the cytokine concentrations or levels in various body fluids or tissues. The determination of the concentration, level, or amount of a cytokine polypeptide may include detection of the full-length polypeptide, or a fragment or variant thereof. The fragment or variant may be sufficient to be detected by, for example, immunological methods, mass spectrometry, nucleic acid hybridization, and the like. Optimizing treatment for individual patients may help to avoid side effects as a result of overdosing, may help to determine when the treatment is ineffective and to change the course of treatment, or may help to determine when doses may be increased. Technology discussed herein optimizes therapeutic methods for treating solid tumor cancers by allowing a clinician to track a biomarker, such as, for example, IL-6, IL-6sR, or VCAM-1, and determine whether a subsequent dose of a drug or vaccine for administration to a subject may be maintained, reduced or increased, and to determine the timing for the subsequent dose. Technology discussed herein optimizes therapeutic methods for treating solid tumor cancers by allowing a clinician to assay the level of or track a biomarker, such as, for example, IL-2, IP-10, IL-5, or MCP-1, and determine whether a subsequent dose of a drug or vaccine for administration to a subject may be maintained, reduced or increased, to determine the timing for the subsequent dose, or to determine which inducible or constitutive chimeric signaling polypeptide should be selected for the therapeutic cells.

Treatment for solid tumor cancers, including, for example, prostate cancer, may also be optimized by determining the concentration of urokinase-type plasminogen activator receptor (uPAR), hepatocyte growth factor (HGF), epidermal growth factor (EGF), or vascular endothelial growth factor (VEGF) during the course of treatment. Different patients having different stages or types of cancer, may react differently to various therapies. The levels of uPAR, HGF, EGF, and VEGF may show systemic perturbation of hypoxic factors in serum, which may indicate a positive response to treatment. Thus, the response to treatment may be monitored, for example, by following the one or more cytokine concentrations or levels in various body fluids or tissues.

Optimizing treatment for individual patients may help to avoid side effects as a result of over activity of the modified cells, may help to determine when the treatment is ineffective and to change the course of treatment, or may help to determine when doses may be increased. Technology discussed herein optimizes therapeutic methods for treating diseases, e.g. cancers, by allowing a clinician to track a biomarker, such as, for example, a cytokine, and determine whether a subsequent dose of a modified cell and/or ligand for administration to a subject may be maintained, reduced or increased, and to determine the timing for the subsequent dose.

Cytokines may be detected as full-length (e.g., whole) proteins, polypeptides, metabolites, messenger RNA (mRNA), complementary DNA (cDNA), and various intermediate products and fragments of the foregoing (e.g., cleavage products (e.g., peptides, mRNA fragments)). For example, IL-6 protein may be detected as the complete, full-length molecule or as any fragment large enough to provide varying levels of positive identification. Such a fragment may comprise amino acids numbering less than 10, from 10 to 20, from 20 to 50, from 50 to 100, from 100 to 150, from 150 to 200 and above. Likewise, VCAM-1 protein can be detected as the complete, full-length amino acid molecule or as any fragment large enough to provide varying levels of positive identification. Such a fragment may comprise amino acids numbering less than 10, from 10 to 20, from 20 to 50, from 50 to 100, from 100 to 150 and above.

In certain embodiments, cytokine mRNA may be detected by targeting a complete sequence or any sufficient fragment for specific detection. An mRNA fragment may include fewer than 10 nucleotides or any larger number. A fragment may comprise the 3' end of the mRNA strand with any portion of the strand, the 5' end with any portion of the strand, and any center portion of the strand.

Detection may be performed using any suitable method, including, without limitation, mass spectrometry (e.g., matrix-assisted laser desorption ionization mass spectrometry (MALDI-MS), electrospray mass spectrometry (ES-MS)), electrophoresis (e.g., capillary electrophoresis), high performance liquid chromatography (HPLC), nucleic acid affinity (e.g., hybridization), amplification and detection (e.g., real-time or reverse-transcriptase polymerase chain reaction (RT-PCR)), and antibody assays (e.g., antibody array, enzyme-linked immunosorbant assay (ELISA)). Examples of IL-6 and other cytokine assays include, for example, those provided by Millipore, Inc., (Milliplex Human Cytokine/Chemokine Panel). Examples of IL6-sR assays include, for example, those provided by Invitrogen, Inc. (Soluble IL-6R: (Invitrogen Luminex® Bead-based assay)). Examples of VCAM-1 assays include, for example, those provided by R & D Systems ((CD106) ELISA development Kit, DuoSet from R&D Systems (#DY809)).

As used herein, "hybridization", "hybridizes" or "capable of hybridizing" is understood to mean forming a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but preclude hybridization of random sequences. Stringent conditions tolerate little, if any, mismatch between a nucleic acid and a target strand. Such conditions are known, and are often used for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.5 M NaCl at temperatures of about 42 degrees C. to about 70 degrees C. It is understood that the temperature and ionic strength of a desired stringency are determined in part by the length of the particular nucleic acid(s), the length and nucleobase content of the target sequence(s), the charge composition of the nucleic acid(s), and the presence or concentration of formamide, tetramethylammonium chloride or other solvent(s) in a hybridization mixture.

It is understood that these ranges, compositions and conditions for hybridization are mentioned by way of non-limiting examples only, and that the desired stringency for a particular hybridization reaction is often determined empirically by comparison to one or more positive or negative controls. Depending on the application envisioned varying conditions of hybridization may be employed to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20 degrees C. to about 50 degrees C. The low or high stringency conditions may be further modified to suit a particular application.

Sources of Biomarkers

In some embodiments, treatment using immune system activating cells discussed herein may be optimized by determining the concentration of certain biomarkers. Biomarkers levels can be used to optimize therapeutic methods for treating diseases, e.g. cancers, by for example, determining whether a subsequent dose of a modified cell and/or ligand administration to a subject may be maintained, reduced or increased, and to determine the timing for the subsequent dose.

The presence, absence or amount of a biomarker can be determined within a subject (e.g., in situ) or outside a subject (e.g., ex vivo). In some embodiments, presence, absence or amount of a biomarker can be determined in cells (e.g., differentiated cells, stem cells), and in certain embodiments, presence, absence or amount of a biomarker can be determined in a substantially cell-free medium (e.g., in vitro). The term "identifying the presence, absence or amount of a biomarker in a subject" as used herein refers to any method known in the art for assessing the biomarker and inferring the presence, absence or amount in the subject (e.g., in situ, ex vivo or in vitro methods).

A fluid or tissue sample often is obtained from a subject for determining presence, absence or amount of biomarker ex vivo. Non-limiting parts of the body from which a tissue sample may be obtained include leg, arm, abdomen, upper back, lower back, chest, hand, finger, fingernail, foot, toe, toenail, neck, rectum, nose, throat, mouth, scalp, face, spine, throat, heart, lung, breast, kidney, liver, intestine, colon, pancreas, bladder, cervix, testes, muscle, skin, hair, tumor area surrounding a tumor, and the like, in some embodiments. A tissue sample can be obtained by any suitable method known in the art, including, without limitation, biopsy (e.g., shave, punch, incisional, excisional, curettage, fine needle aspirate, scoop, scallop, core needle, vacuum assisted, open surgical biopsies) and the like, in certain embodiments. Examples of a fluid that can be obtained from a subject includes, without limitation, blood, cerebrospinal fluid, spinal fluid, lavage fluid (e.g., bronchoalveolar, gastric, peritoneal, ductal, ear, arthroscopic), urine, interstitial fluid, feces, sputum, saliva, nasal mucous, prostate fluid, lavage, semen, lymphatic fluid, bile, tears, sweat, breast milk, breast fluid, fluid from region of inflammation, fluid from region of muscle wasting and the like, in some embodiments.

A sample from a subject may be processed prior to determining presence, absence or amount of a biomarker. For example, a blood sample from a subject may be processed to yield a certain fraction, including without limitation, plasma, serum, buffy coat, red blood cell layer and the like, and biomarker presence, absence or amount can be determined in the fraction. In certain embodiments, a tissue sample (e.g., tumor biopsy sample) can be processed by slicing the tissue sample and observing the sample under a microscope before and/or after the sliced sample is contacted with an agent that visualizes a biomarker (e.g., antibody). In some embodiments, a tissue sample can be exposed to one or more of the following non-limiting conditions: washing, exposure to high salt or low salt solution (e.g., hypertonic, hypotonic, isotonic solution), exposure to shearing conditions (e.g., sonication, press (e.g., French press)), mincing, centrifugation, separation of cells, separation of tissue and the like. In certain embodiments, a biomarker can be separated from tissue and the presence, absence or amount determined in vitro. A sample also may be stored for a period of time prior to determining the presence, absence or amount of a biomarker (e.g., a sample may be frozen, cryopreserved, maintained in a preservation medium (e.g., formaldehyde)).

A sample can be obtained from a subject at any suitable time of collection before or after the modified cell is delivered to the subject. For example, a sample may be collected within about one hour after a modified cell is delivered to a subject (e.g., within about 5, 10, 15, 20, 25, 30, 35, 40, 45, 55 or 60 minutes of delivering a drug), within about one day after a modified cell is delivered to a subject (e.g., within about 2, 3, 4, 5, 6, 7, 8, 9, 10, 11, 12, 13, 14, 15, 16, 17, 18, 19, 20, 21, 22, 23 or 24 hours of delivering a drug) or within about two weeks after a modified cell is delivered to a subject (e.g., within about 2, 3, 4, 5, 6, 7, 8, 9, 10, 11, 12, 13 or 14 days of delivering the drug). A collection may be made on a specified schedule including hourly, daily, semi-weekly, weekly, bi-weekly, monthly, bi-monthly, quarterly, and yearly, and the like, for example. If a modified cell is administered continuously over a time period (e.g., infusion), the delay may be determined from the first moment of drug is introduced to the subject, from the time the drug administration ceases, or a point in-between (e.g., administration time frame midpoint or other point).

Biomarker Detection

The presence, absence or amount of one or more biomarkers may be determined by any suitable method known in the art, and non-limiting determination methods are discussed herein. Determining the presence, absence or amount of a biomarker sometimes comprises use of a biological assay. In a biological assay, one or more signals detected in the assay can be converted to the presence, absence or amount of a biomarker. Converting a signal detected in the assay can comprise, for example, use of a standard curve, one or more standards (e.g., internal, external), a chart, a computer program that converts a signal to a presence, absence or amount of biomarker, and the like, and combinations of the foregoing.

Biomarker detected in an assay can be full-length biomarker, a biomarker fragment, an altered or modified biomarker (e.g., biomarker derivative, biomarker metabolite), or sum of two or more of the foregoing, for example. Modified biomarkers often have substantial sequence identity to a biomarker discussed herein. For example, percent identity between a modified biomarker and a biomarker discussed herein may be in the range of 15-20%, 20-30%, 31-40%, 41-50%, 51-60%, 61-70%, 71-80%, 81-90% and 91-100%, (e.g. 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, and 100 percent identity). A modified biomarker often has a sequence (e.g., amino acid sequence or nucleotide sequence) that is 90% or more identical to a sequence of a biomarker discussed herein. Percent sequence identity can be determined using alignment methods known in the art.

Detection of biomarkers may be performed using any suitable method known in the art, including, without limitation, mass spectrometry, antibody assay (e.g., ELISA), nucleic acid affinity, microarray hybridization, Northern blot, reverse PCR and RT-PCR. For example, RNA purity and concentration may be determined spectrophotometrically (260/280>1.9) on a Nanodrop 1000. RNA quality may be assessed using methods known in the art (e.g., Agilent 2100 Bioanalyzer; RNA 6000 Nano LabChip® and the like).

EXAMPLES

Examples herein that discuss the methods for transforming or transfecting cells in vitro, or ex vivo, provide examples of, but do not limit, the use of nucleic acids that express chimeric polypeptides. Examples of the delivery of the transduced or transfected cells, and ligand inducer, to laboratory animals or human subjects provide examples of, but do not limit, the direct administration of nucleic acids expressing chimeric polypeptides, tumor antigens, and ligand inducer to subjects in need thereof.

The present examples provide non-limiting examples of the expression of chimeric polypeptides comprising signaling regions in Natural Killer cells. The modified NK cells may be used to improve growth, storage, and efficacy of NK cells, and may be used, for example, for conditional chemical regulation of NK cell function.

The examples set forth below illustrate certain embodiments and do not limit the technology.

Example 1: Expression of Chimeric Polypeptides in Natural Killer Cells

FIG. 1—Schematic representations of expression constructs used to transduce NK cells. Genes encoding the MC go signal are indicated in green, the proapoptotic C9 signal in red. These genes are encoded in the pSFG γ-retrovirus vector. The letter i indicates that the gene is inducible by fusion of the signaling domain with FKBP12v36 (i alone) or FKBP12f36-FRB (iR). IL-15 indicates the gene encoding interleukin-15, a cytokine that normally not produced by NK cells, but which acts in a normal inflammatory immune response to promote NK cell growth and survival. Ectopic expression of this transgene acts in an autocrine manner to further augment DS NK cell activity. CD19 encodes the extracellular and transmembrane domains, but deleting intracellular signaling domains of the CD19 protein. This is used as a molecular marker to identify transduced NK cell populations.

Figure 2:
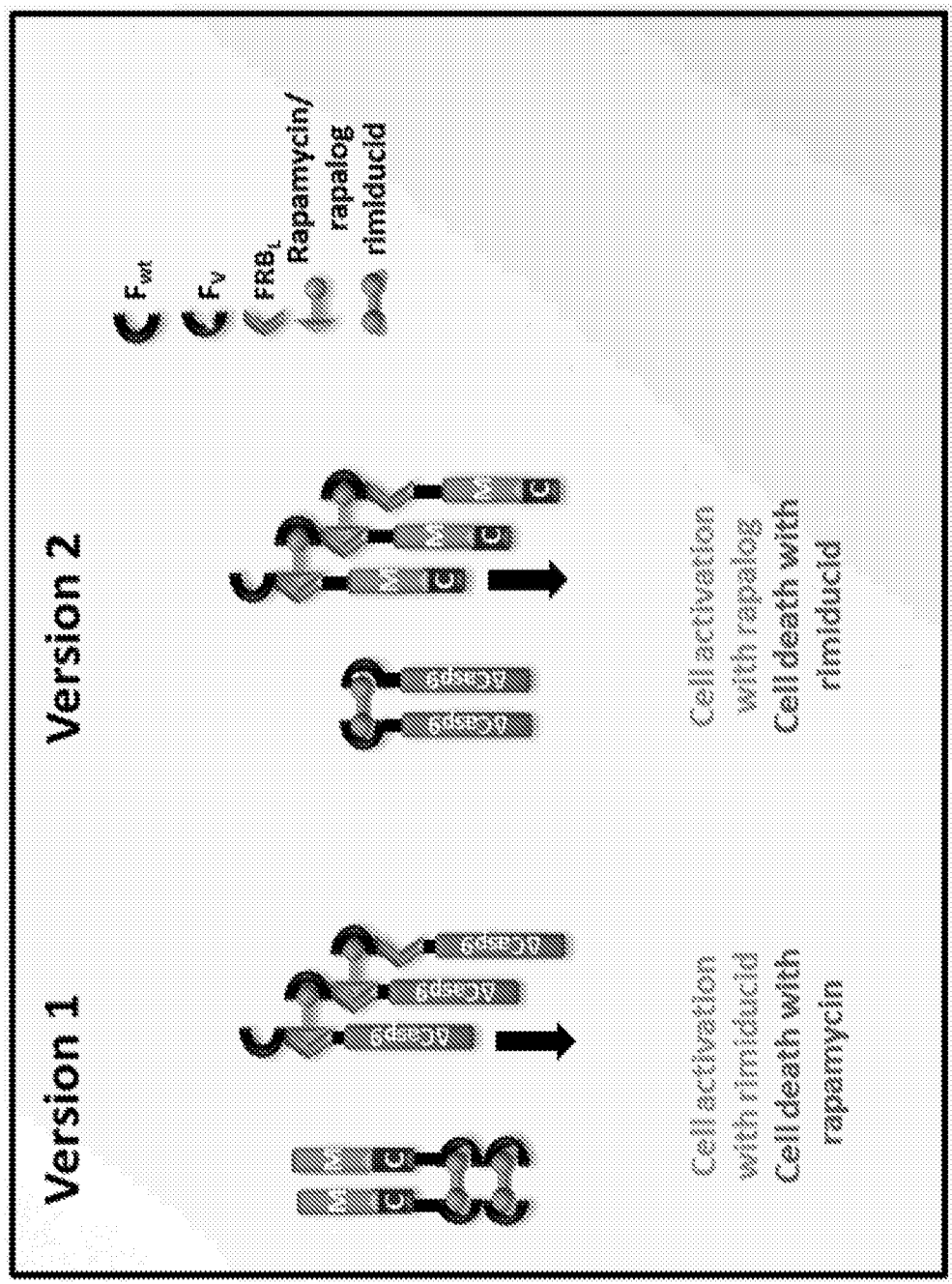
FIG. 2 provides a schematic representation of dual switch components. Version 1: MyD88/CD40 is fused at its carboxyl terminus with two copies of Fv (FKBP12v36), and coexpressed with a chimeric caspase 9 polypeptide lacking the CARD domain fused at its amino terminus with Fwt (FKBP12f36, wild type) and FRB (T2098L). Version 2: MyD88/CD40 is fused at its amino terminus with tandem Fwt and FRB, coexpressed with chimeric caspase-9 polypeptide lacking the CARD domain fused at its amino terminus with Fv.

FIG. 2—Schematic representation of dual switch components. Version 1. MyD88/CD40 is fused at its carboxy terminus with two copies of FKBP12v36 (Fv). This is co-expressed with caspase-9 lacking the CARD domain fused at its amino terminus with tandem FKBP12f36 (Fwt) and FRB. Version 2. MyD88/CD40 is fused at its amino terminus with tandem FKBP12f36 (Fwt) and FRB(T2098L). This is co-expressed with caspase-9 lacking the CARD domain fused at its amino terminus with FKBP12v36.

Figure 3:
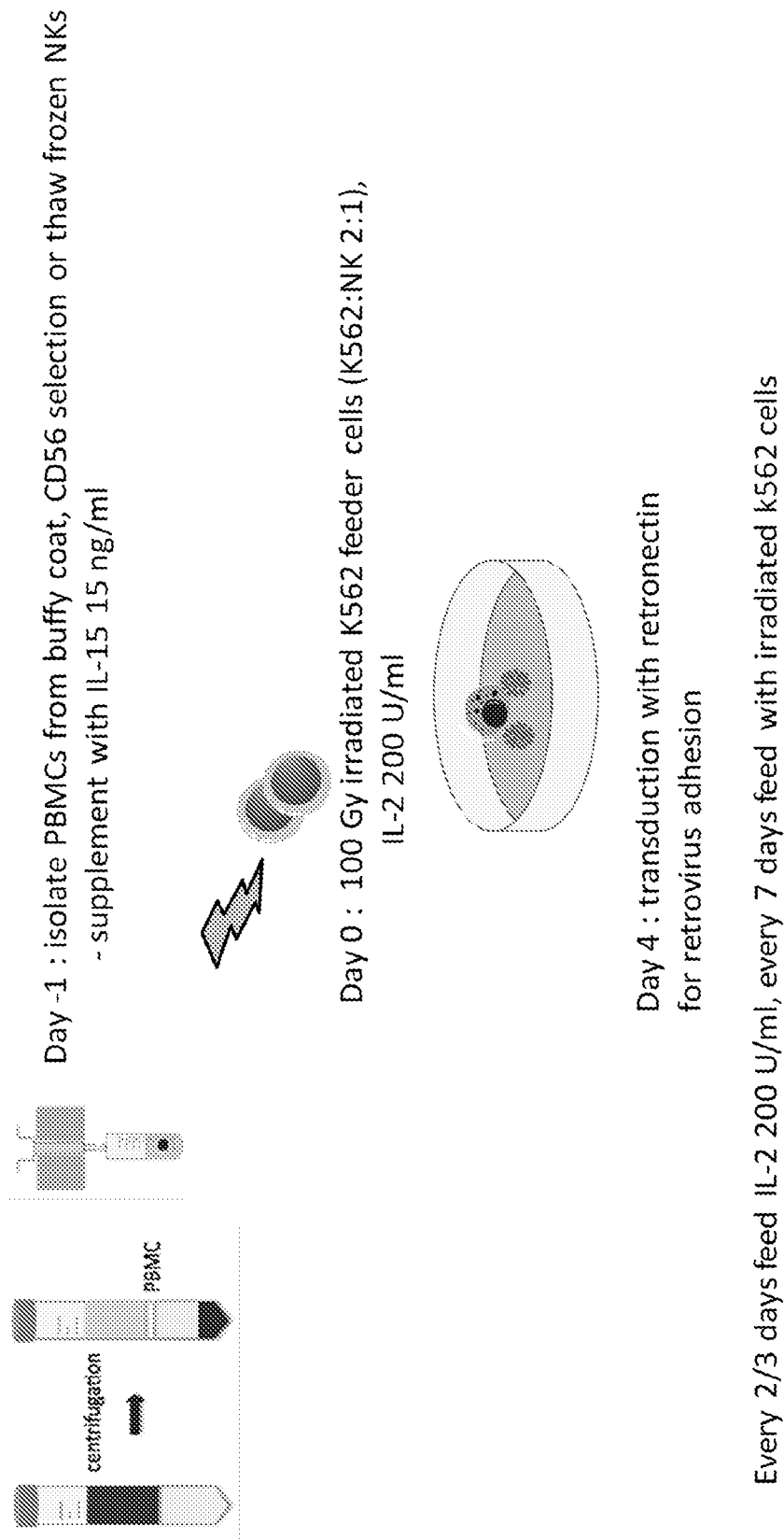
FIG. 3 provides a schematic of a transduction protocol that may be used to transduce natural killer cells. Methods outlined are essentially as discussed in Gene Modification of Human Natural Killer Cells Using a Retroviral Vector. Kellner J N, Cruz C R, Bollard C M, Yvon E S. Methods Mol Biol. 2016; 1441:203-13.

FIG. 3—Methods to isolate, culture and transduce Natural Killer cells. Cell components from human blood sourced from healthy adult donors was separated by centrifugation in Ficoll with the 'buffy coat' further fractionated to provide peripheral blood mononuclear cells (T and B lymphocytes, NK cells and monocytes). NK cells were isolated by selection with a column of magnetic beads fused with antibody to CD56 expressed on NK cells. IL-15 (15 ng/mL) was added to activate the NK cells and they were plated on a feeder layer of K562 myelogenous leukemia cells previously irradiated to block their growth and further supplemented with interleukin-2 (200 units/mL). Cells were transduced with retrovirus (FIG. 1) seated by centrifugation on retronectin coated plates. On the next day NK cells were fed every 48-72 hours with fresh feeder cells and IL-2 and without supplementary IL-15. Modification of NK cells was performed essentially as discussed in Kellner, J. N., et al., Methods Mol. Biol. 2016, 1441:203-13.

Figure 4:
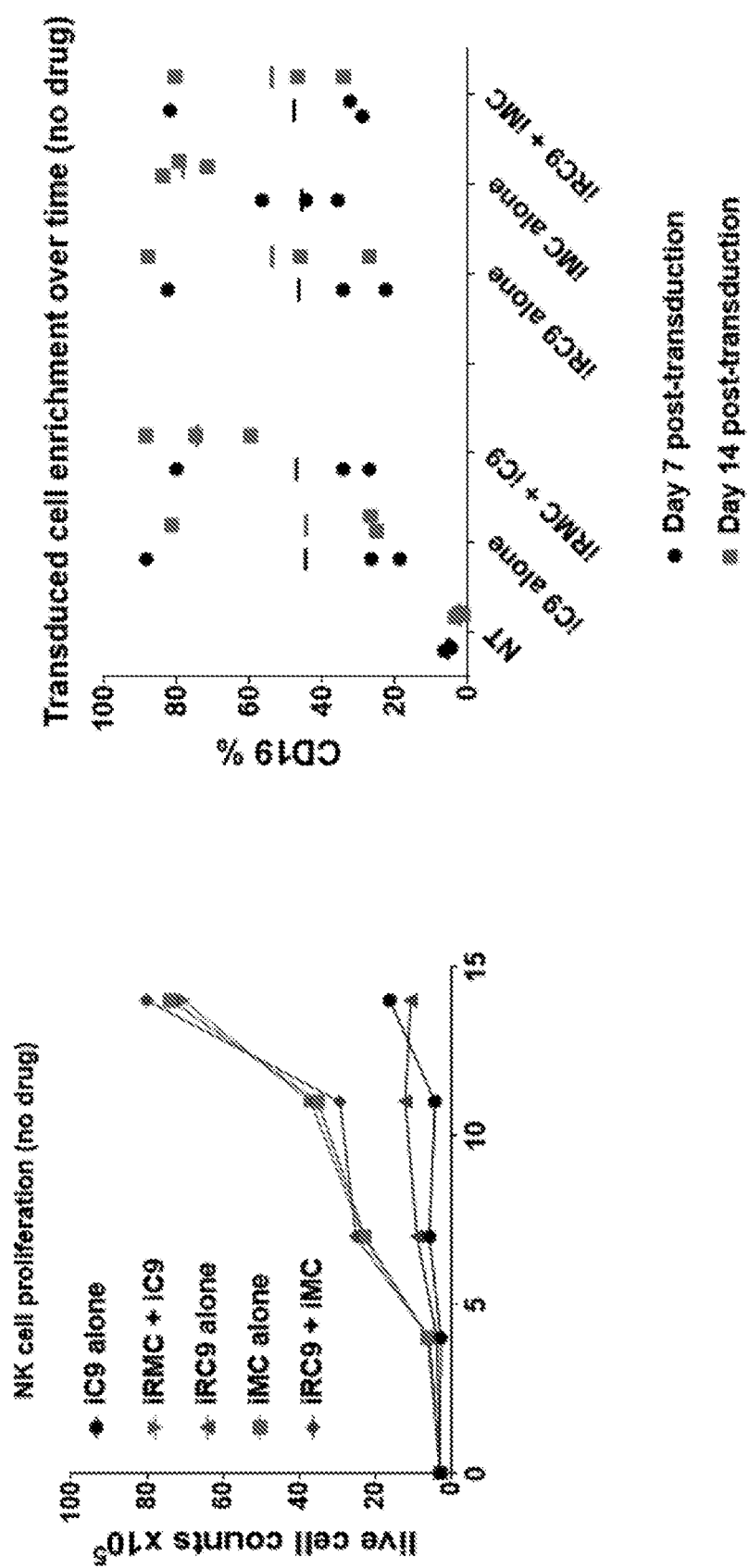
FIG. 4 provides the results of growth assays in modified NK cells. Right: Graph showing percent CD19-expressing cells. Left: line graph of live cell counts.

FIG. 4—MC expression leads to enhanced NK cell growth. (left) NK cells derived from three separate blood donors were transduced to express the indicated genes. NT indicates not transduced NK cells. The proportion of cells marked with CD19 was determined after 7 and 14 days of culture. An increase in the proportion of transduced cells at 14 days indicated selective outgrowth of the MC containing populations. (right) In a separate experiment, total live cell counts were taken at 2-4 day intervals for two weeks. Cells expressing MC even without added rimiducid selectively outgrew NK cells expressing only the safety switch. The presence of the iRMC chimeric polypeptide provided a growth advantage to the modified NK cells. In the presence of Interleukin-2 in culture, tonic iMC signaling promoted proliferation and survival.

Figure 5:
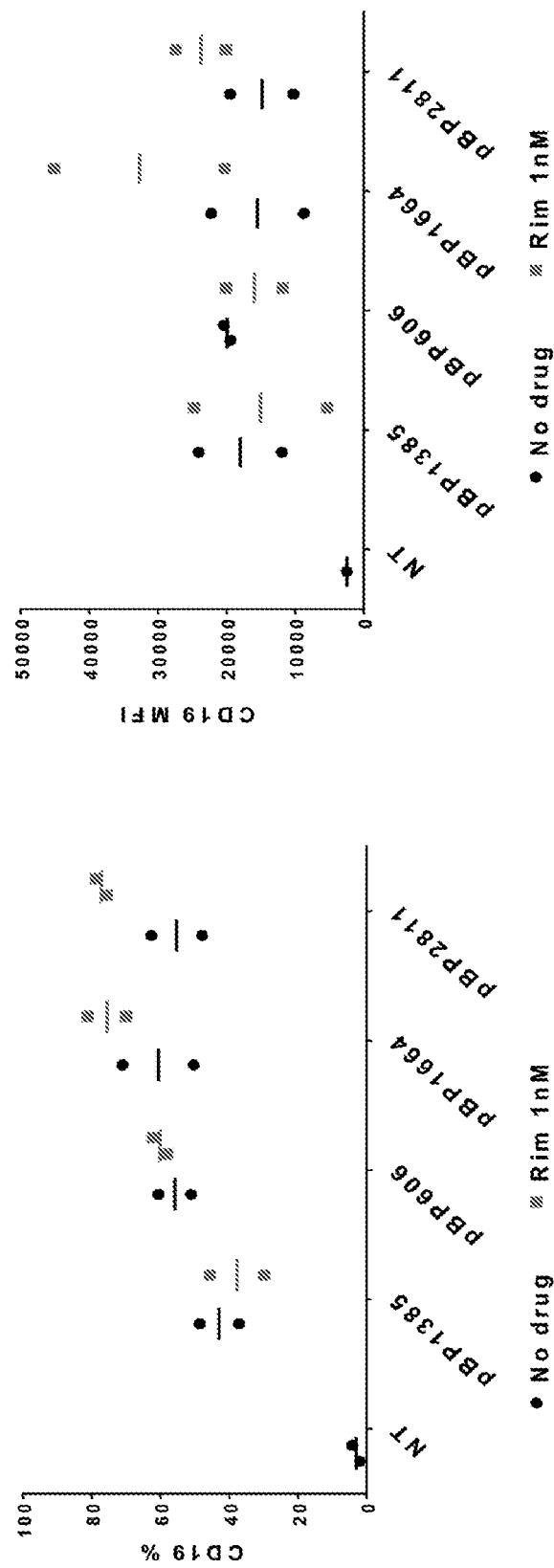
FIG. 5 provides the results of proliferation assays in modified NK cells with and without activation of iMyD88/CD40 with rimiducid (AP1903). Left: Graph of percent CD19-expressing cells. Right: graph of CD19 Mean Fluorescence Intensity (MFI).

FIG. 5—NK cell proliferation with iMC activation. NK cells from two separate donors were transduced with 1385 (iRC9 alone), 606 (iMC alone), 1664 (iMC+iRC9) or 2811 (iMC+iRC9+IL-15). Cultures were split and left untreated (black) or 1 nM rimiducid added. Transduced NK cells (marked with CD19) were incubated with rimiducid for six days and the number of transduced NK cells relative to untransduced NK cells was assessed. An increase in the proportion of transduced cells after 6 days with drug treatment indicated selective outgrowth of activated iMC containing populations. MFI=Mean fluorescence intensity of CD19 in flow cytometry analysis, indicating a proportional growth advantage of highly expressing cells. Modified NK cells comprising the iMC or iRMC chimeric polypeptides had a growth advantage over NK cells that do not comprise iMC or iRMC chimeric polypeptides.

Figure 6:
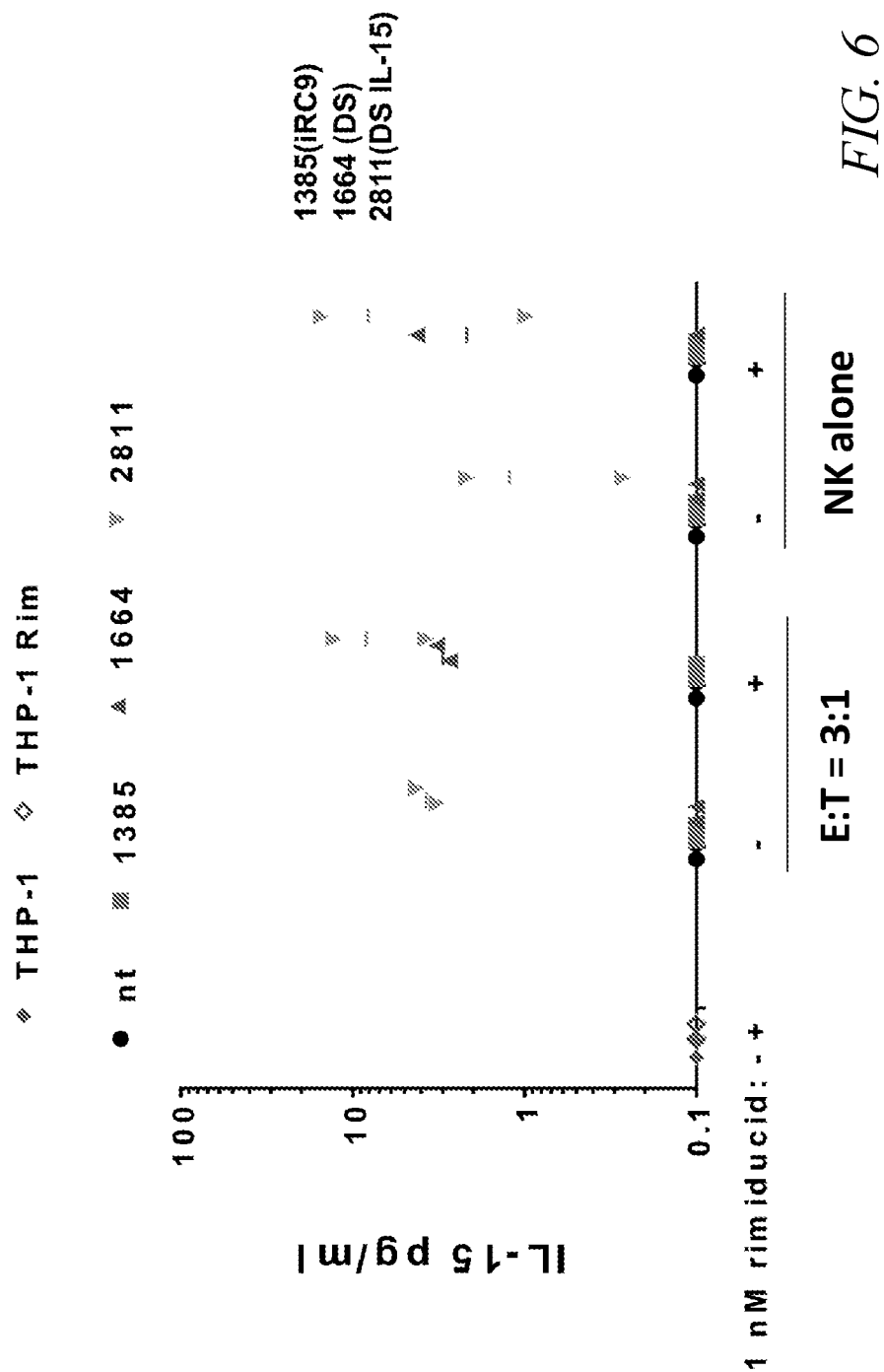
FIG. 6 provides a graph of IL-15 production in dual switch-modified NK cells.

FIG. 6—IL-15 production in dual switch NK cells. NK cells derived from two donors were cultured in the presence of tumor target THP1 at an effector to target of 3:1 which activates NK cells naturally or NK cells were incubated alone in the presence or absence of 1 nM rimiducid. IL-15 levels in culture supernatant after 48 hours was assessed by multiplex bead analysis. Cytokine levels beneath the range of detection in the ELISA assay were assigned as 0.1 pg/ml. Without rimiducid, only transduced cells with IL-15 as a transgene produced IL-15. Stimulation of iMC activated endogenous IL-15 production. In the presence of rimiducid, modified NK cells that expressed iMC, nonmodified by an IL-15 transgene, also produced IL-15.

Figure 7:
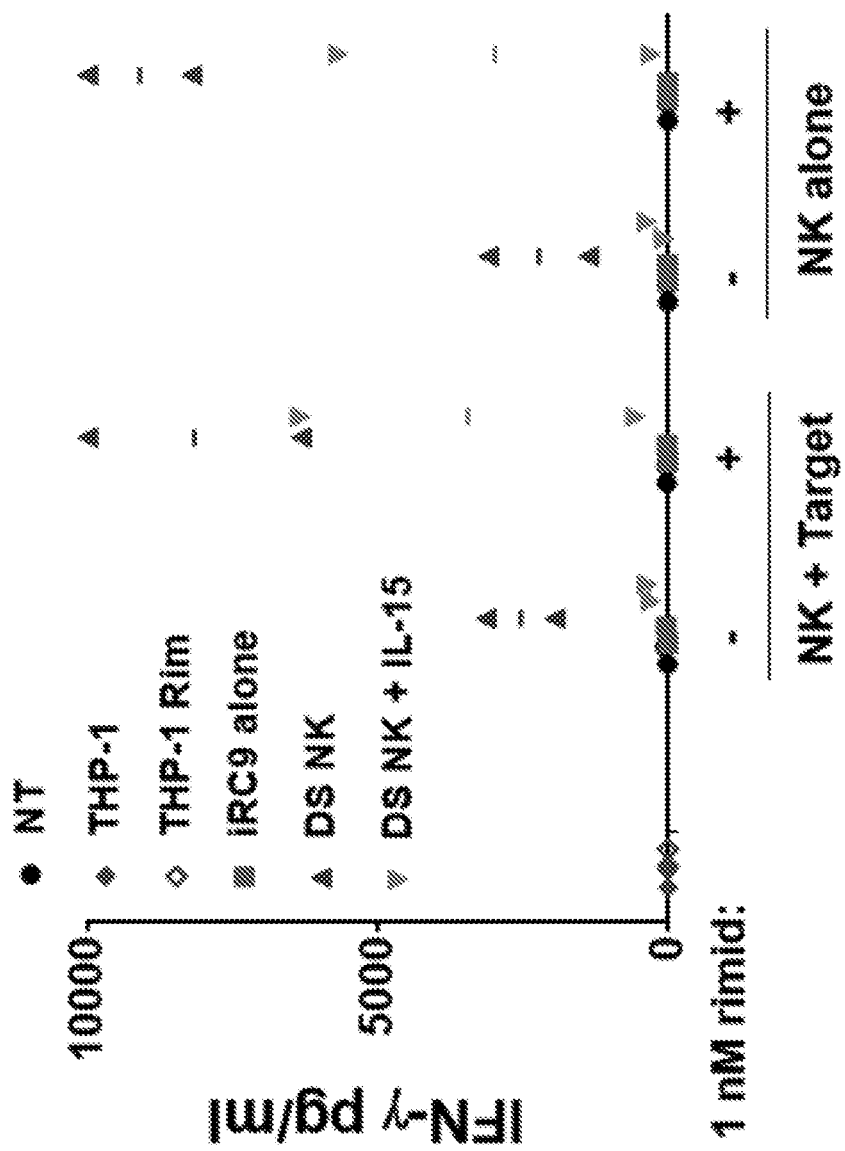
FIG. 7 provides a graph of Interferon production in dual switch-modified NK cells.
Figures 8A, 8B:
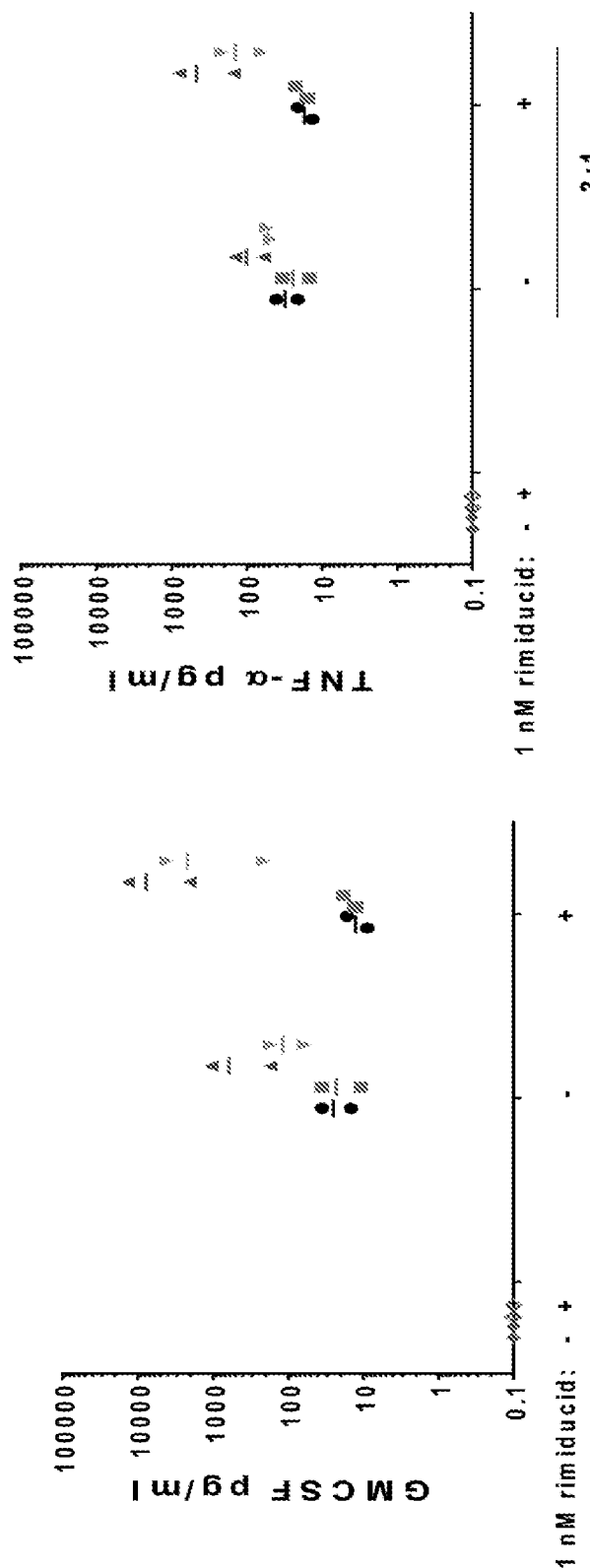
FIGS. 8A-8D provides four graphs of cytokine and chemokine production bu NK cells comprising the dual switch.
Figures 8C, 8D:
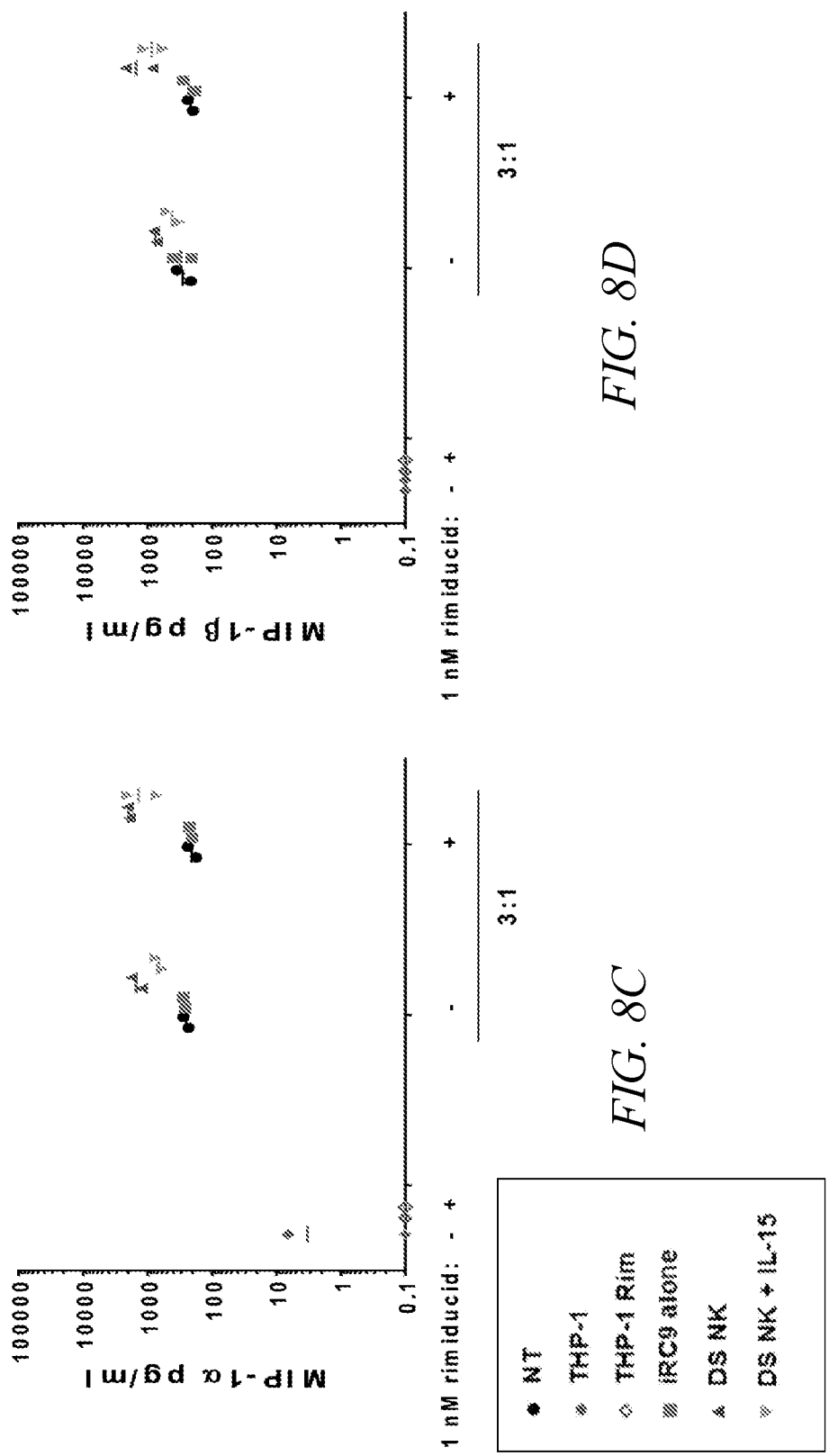

FIG. 7—InterferonY production in dual switch NK cells. NK cells derived from two donors were cultured in the presence of tumor target THP1 at an effector to target of 3:1 which activates NK cells naturally in the presence or absence of 1 nM rimiducid. IFNγ levels in culture supernatant after 48 hours was assessed by multiplex bead analysis. Stimulation of iMC activated IFNγ production. Rimiducid-dependent iMC activation led to high-level cytokine secretion. The modified cells demonstrated a relatively muted production of pro-inflammatory cytokines, such as TNF-α and IL-6.

FIGS. 8A-8D—Cytokine and chemokine production in dual switch NK cells. NK cells derived from two donors were cultured in the presence of tumor target THP1 at an effector to target of 3:1 which activates NK cells naturally in the presence or absence of 1 nM rimiducid. GM-CSF (FIG. 8A), TNF-α (FIG. 8B) and the chemokines MIP1a (FIG. 8C) and MIP1β (FIG. 8D) in culture supernatant after 48 hours was assessed by multiplex bead analysis. Activation of iMC stimulated production of these factors already produced by activated NK cells.

Figure 9A:
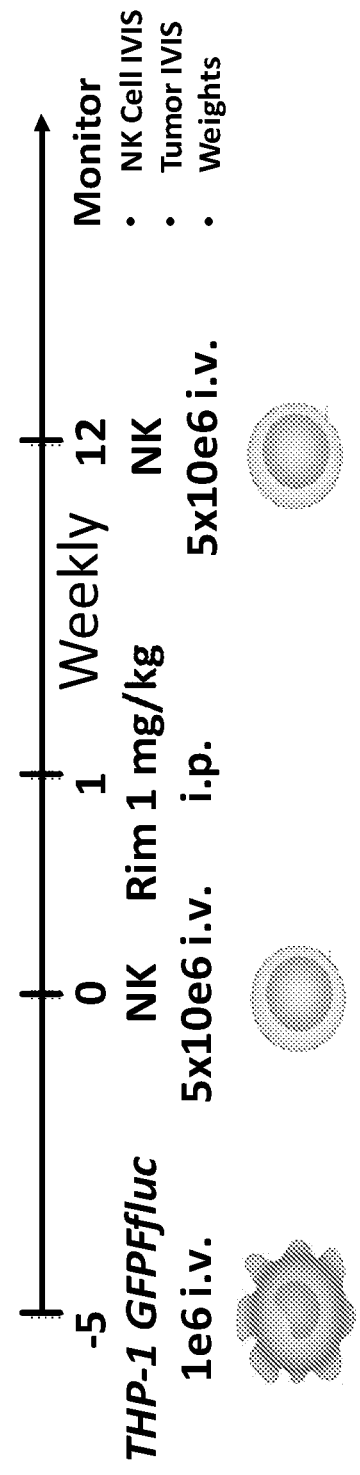
Figure 9C:
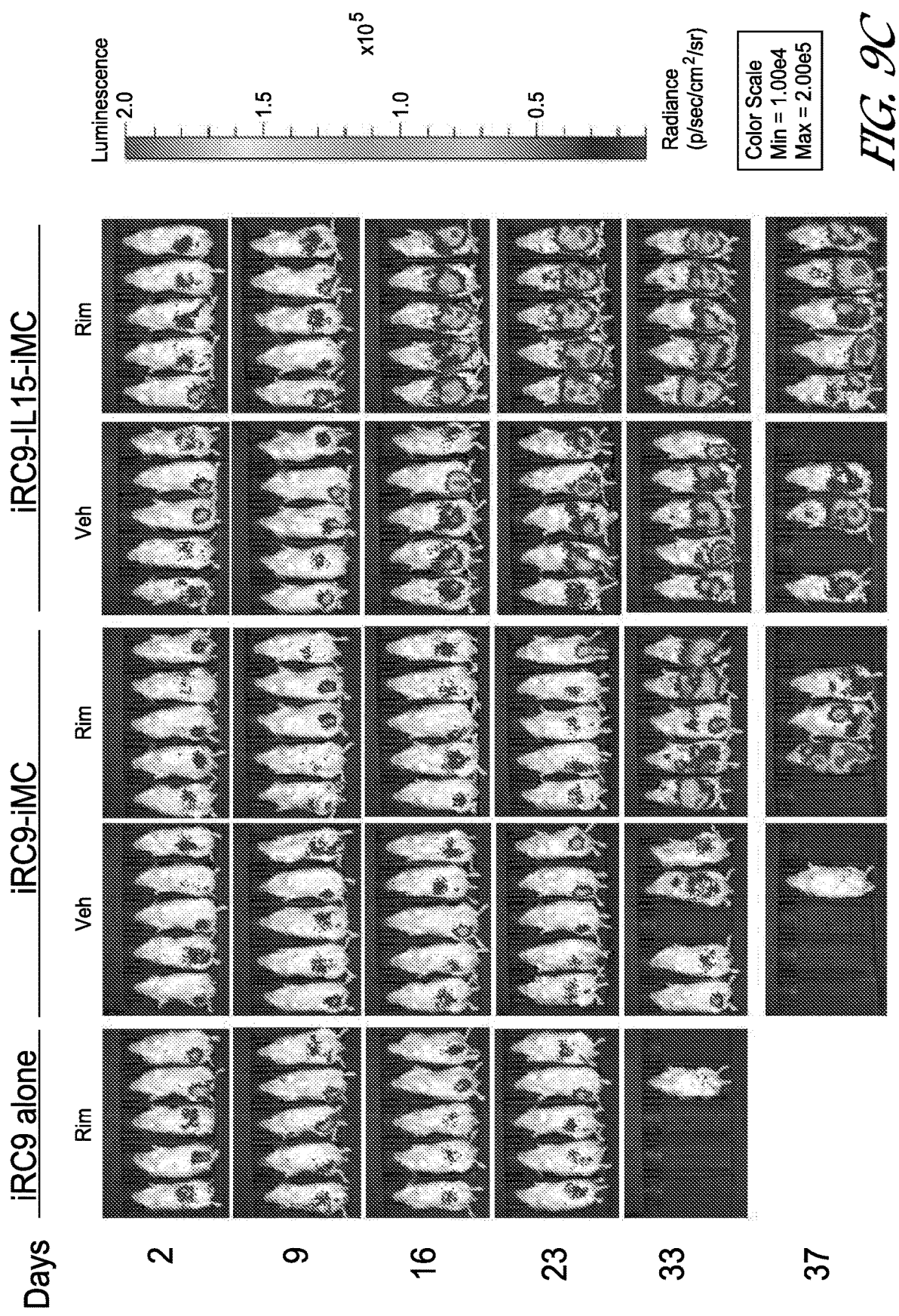
Figure 9D:
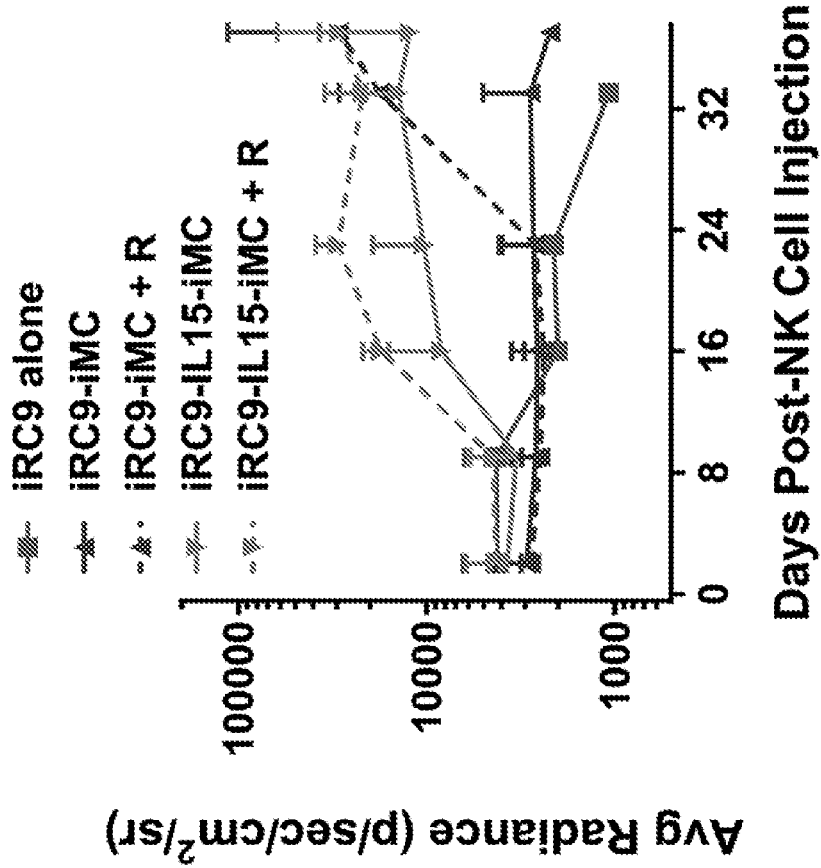

FIGS. 9A-9D—Proliferation of DS NK cells in vivo. FIG. 9A: Schematic describing engraftment of NSG immunodeficient mice with human THP1 tumor cells labeled with a GFP-Firefly luciferase reporter followed 5 days later by infusion with human DS NK cells labeled with Renilla luciferase. Rimiducid was added one day afterward and weekly thereafter at 1 mg/kg bodyweight. FIG. 9B: Table depicting groups of mice engrafted with NK cells transduced with expression viruses for iRC9 alone, with iMC or with iMC and autocrine IL-15. FIG. 9C: IVIS images of NK cells levels by biologic light imaging (BLI) of ren-luciferase activity with coelentrazine. FIG. 9D: Quantitation of BLI radiance for each mouse group at each timepoint in FIG. 9C. NK proliferation was evident with iMC and IL-15 presence and was further stimulated by activation of iMC with rimiducid. IL-15 augmented iMC-driven expansion in vivo.

Figure 10A:
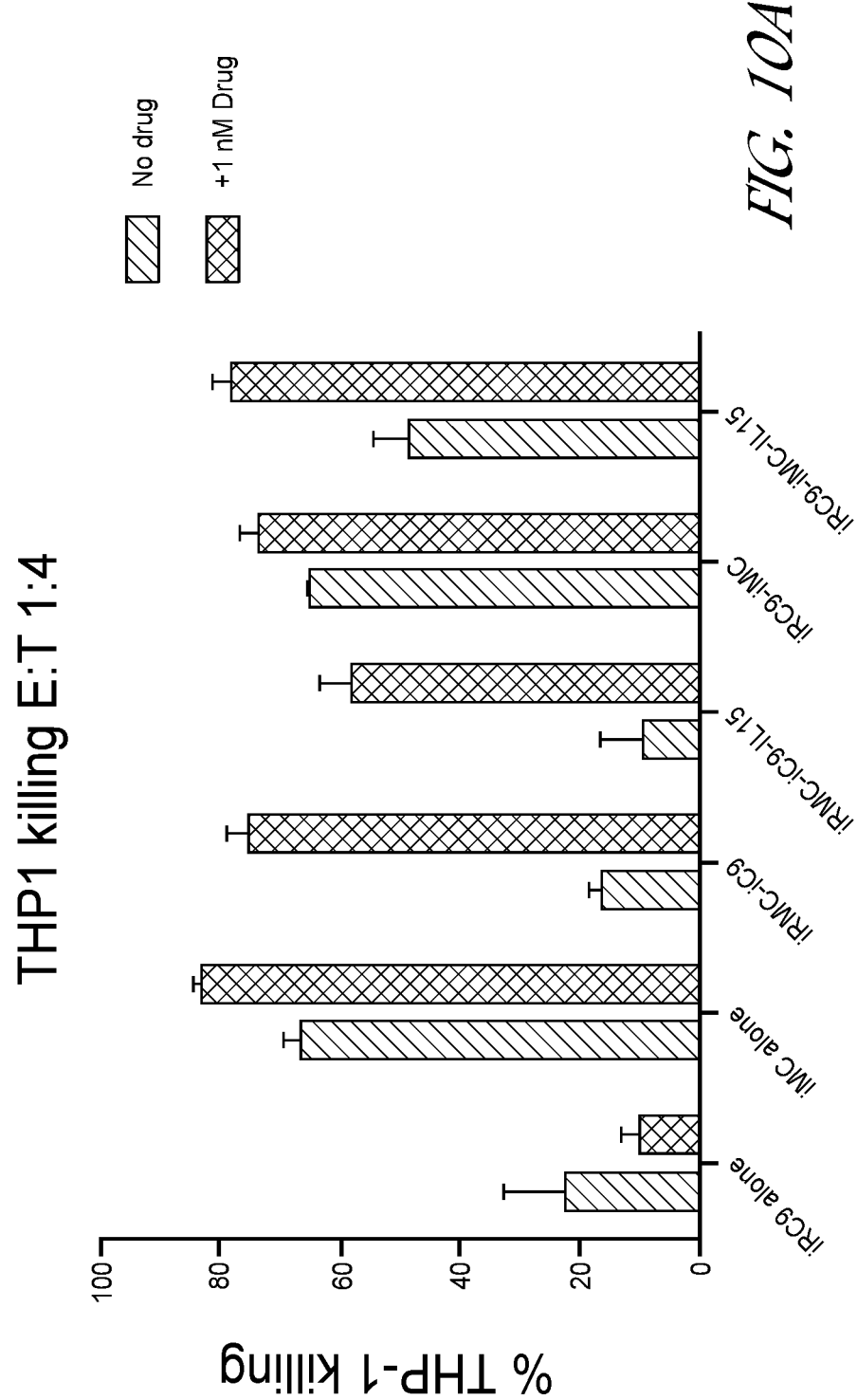
FIGS. 10A-10B.
Figure 10B:
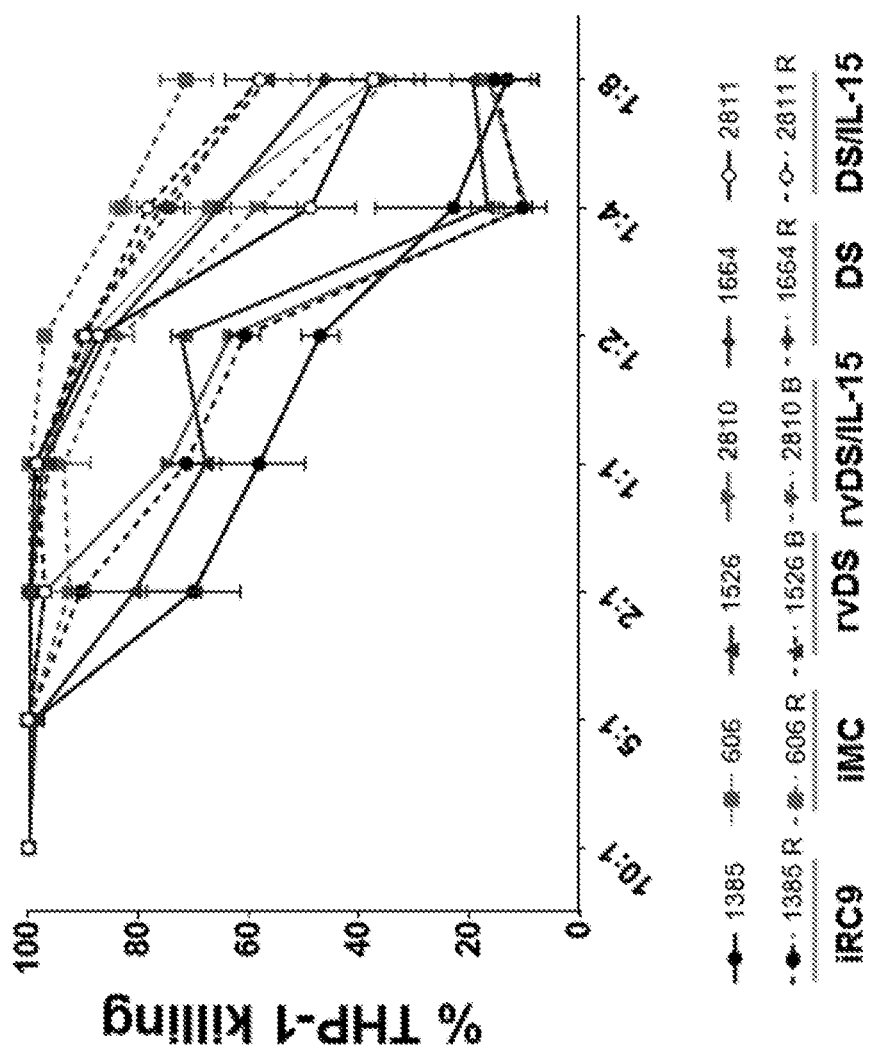

FIGS. 10A-10B—NK cell killing is enhanced by MC induction in vitro. THP1 AML tumor cells labeled with GFP luciferase were incubated for 24 hours alone (for reference) or in the presence of NK cells transduced with the indicated retroviral expression constructs. FIG. 10A: Specific lysis calculated by THP1 luciferase when targeted by NK cells at an effector to target ratio (E:T) of 1:4. Cells containing iMC alone have robust killing activity that is enhanced by rimiducid activity. iRMC containing NK cells have low basal killing activity without BPC-015 but are greatly enhanced for killing by addition of this drug. FIG. 10B: Plot of killing for each construct with and without activating ligand at decreasing E:T ratio. In this set of assays, the iRMC-expressing NK cells appeared to show a greater dependence on ligand than the iMC-expressing NK cells.

Figure 11A:
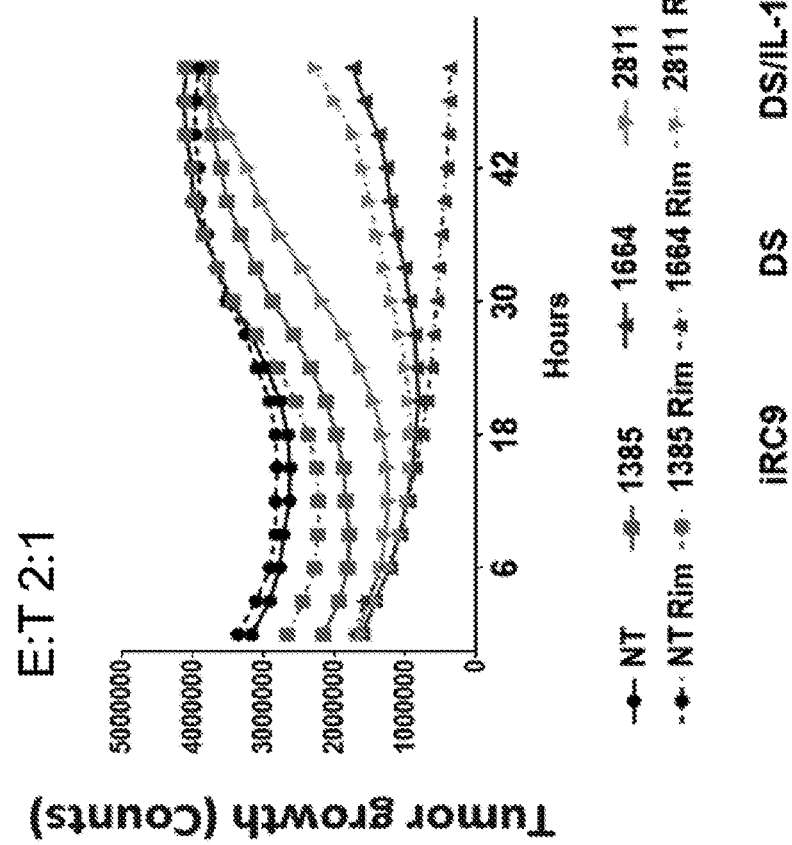
FIGS. 11A-11B.
Figure 11B:
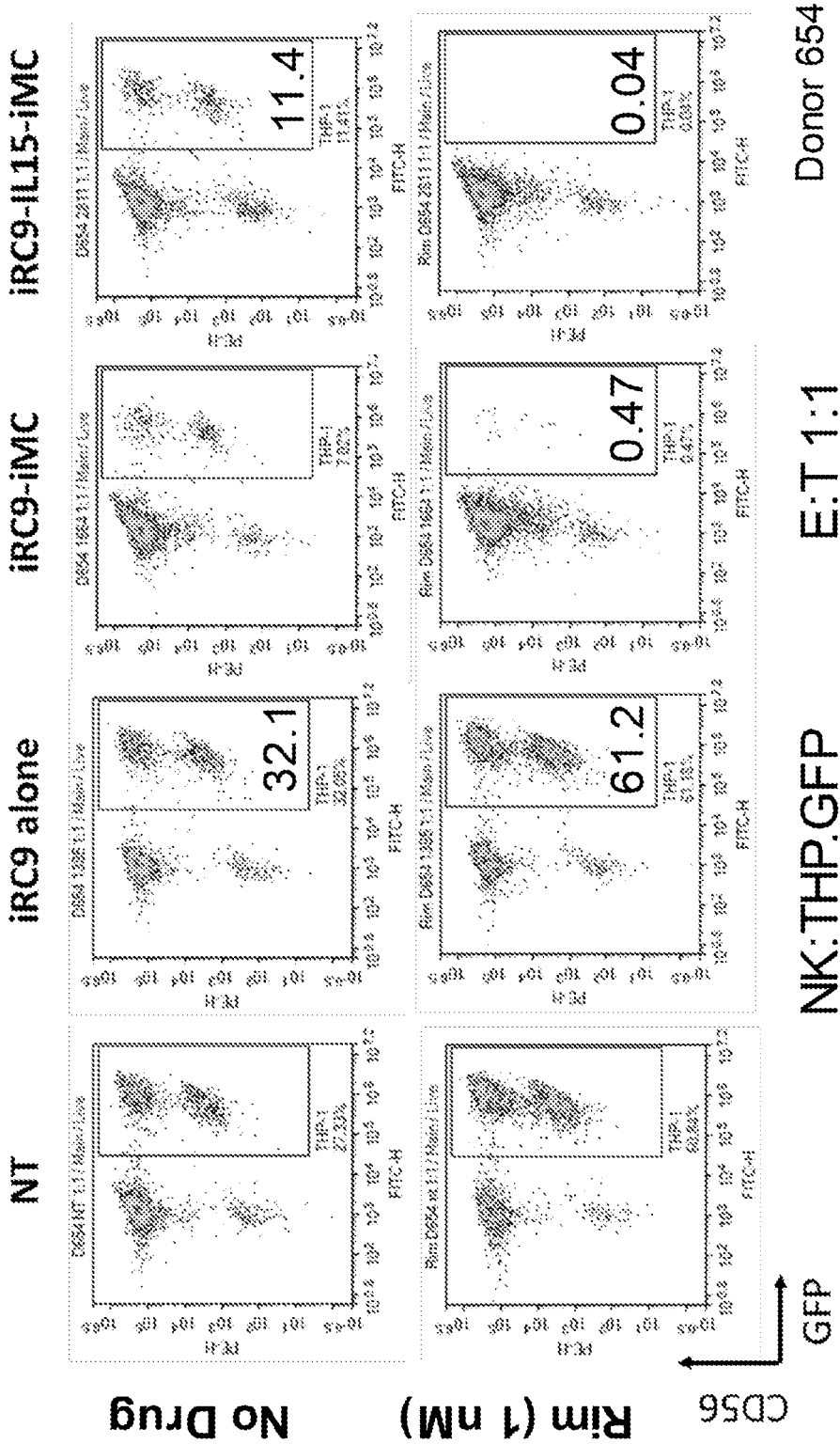

FIGS. 11A-11B—NK cell killing is enhanced by iMC in vitro. FIG. 11A: HPAC-GFP pancreatic cancer cells were incubated with NK cells transduced with the indicated retroviral expression constructs at an E:T of 2:1. Cells were placed in an incucyte real time live imaging chamber and GFP fluorescence measured every 3 hours for 2 days to indicate HPAC cell growth or control by the NK cells. iMC enabled DS NK cells controlled HPAC growth and this was enhanced by stimulation with 1 nM rimiducid. FIG. 11B: THP1-GFP AML cells were incubated with transduced NK cells at an E:T of 1:1 for 48 hours and the presence of GFP positive populations detected by flow cytometry. iMC enabled DS NK cells rapidly killed the target and this was enhanced by stimulation with 1 nM rimiducid. iMC-dependent activation improved NK-mediated HPAC (E:T 2:1) and THP-1 (1:1) tumor control.

Figure 12A:
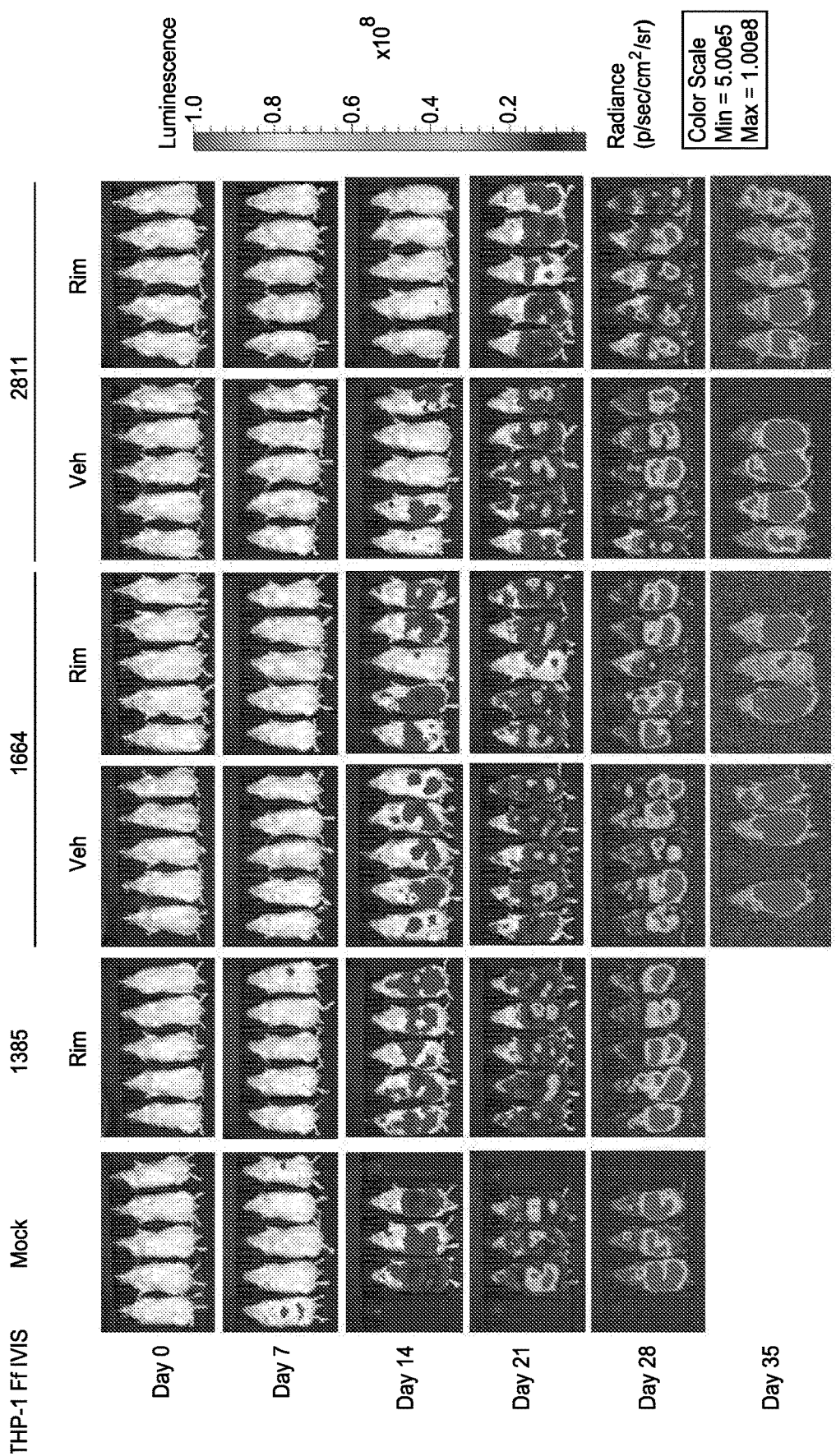
FIGS. 12A-12B.
Figure 12B:
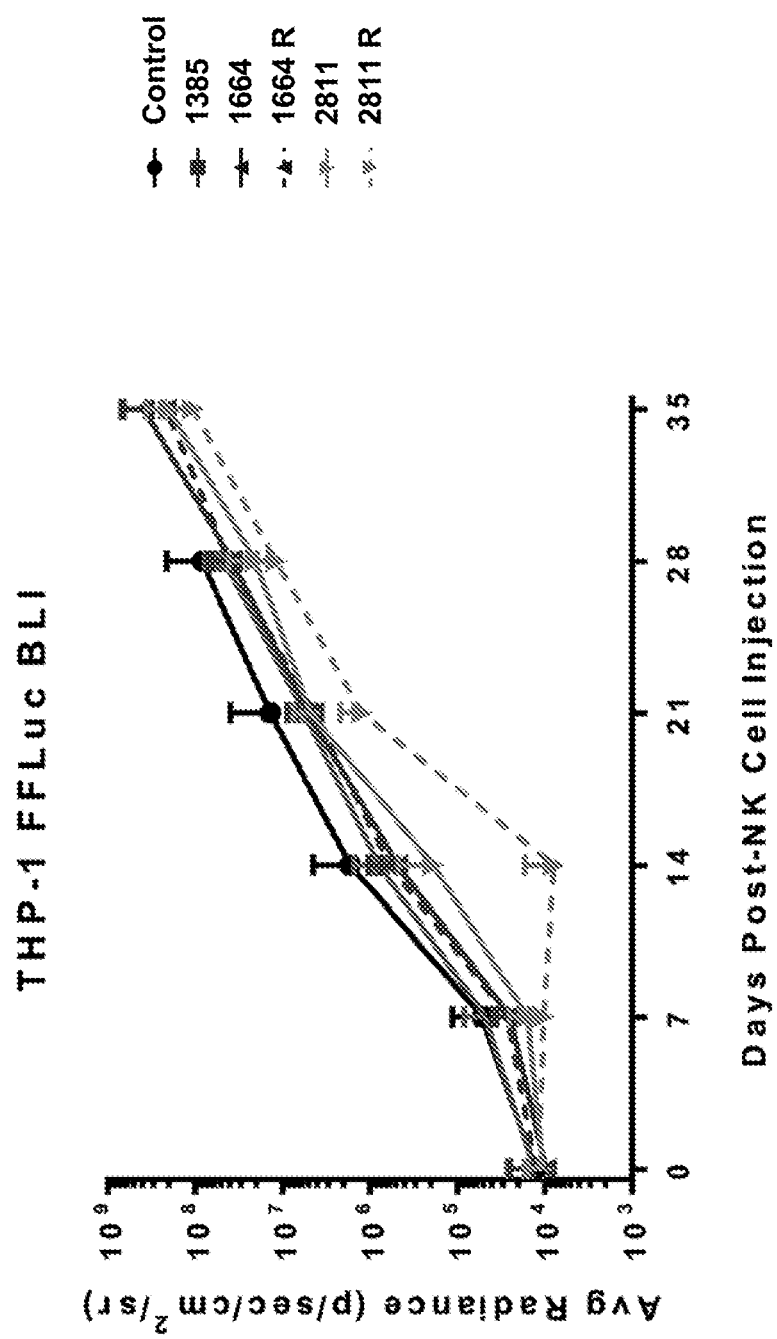

FIGS. 12A-12B—Anti-tumor efficacy of DS NK cells. The protocol for combining DS NK cells with THP1-ffLUC labeled tumor cells is as described in FIGS. 9A and 9B. FIG. 12A: IVIS images of THP1 levels by biologic light imaging (BLI) of firefly-luciferase activity with luciferin. FIG. 12B: Quantitation of BLI radiance for each mouse group at each timepoint in FIG. 12A. Tumor expansion is delayed with iMC and IL-15 presence and is further stimulated by activation of iMC with rimiducid. IL-15 and activation of iMC combined to increase the control of tumor expansion.

Figure 13A:
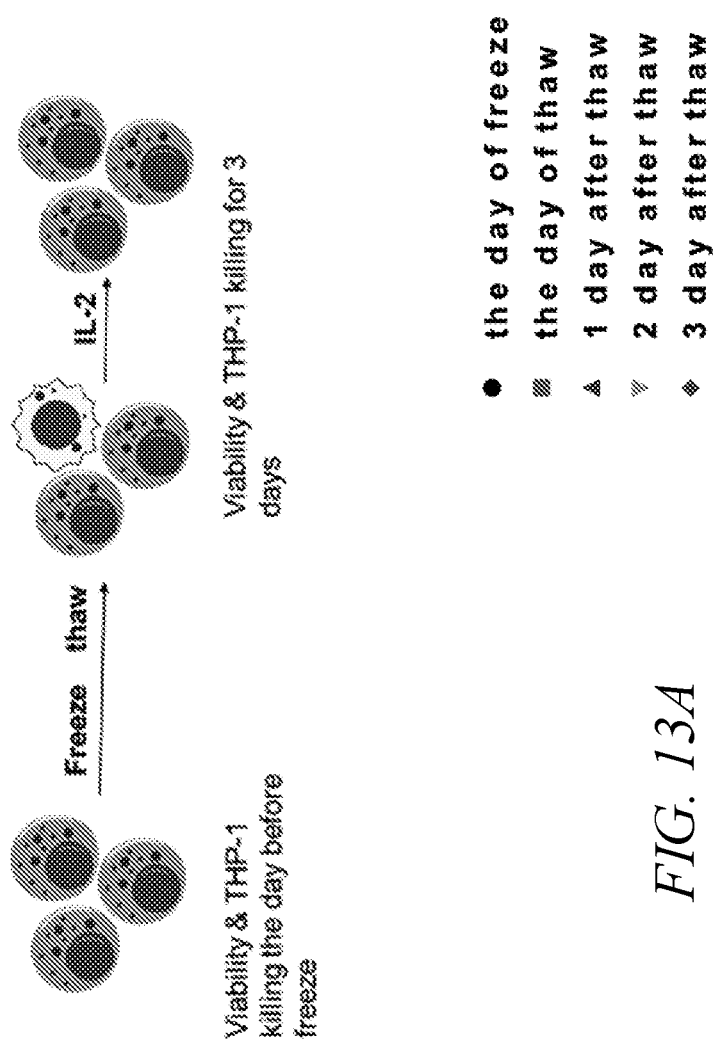
FIGS. 13A-13C.
Figure 13B:
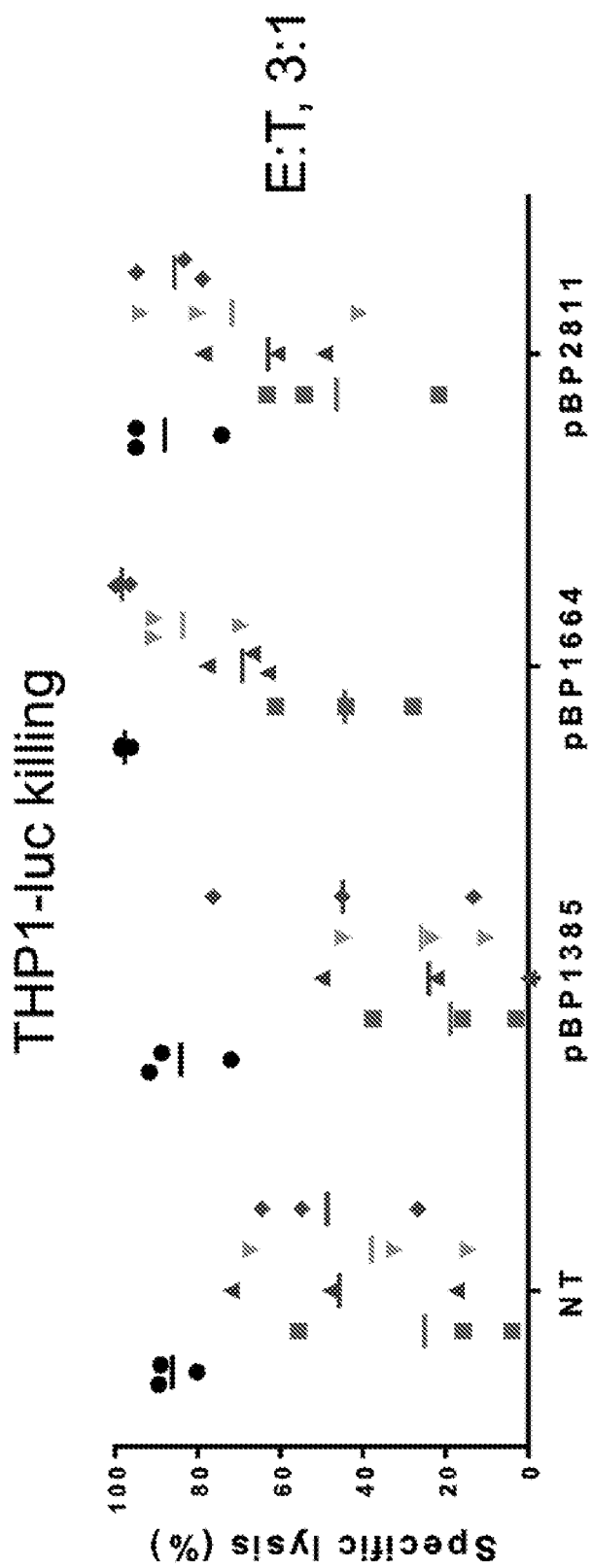
Figure 13C:
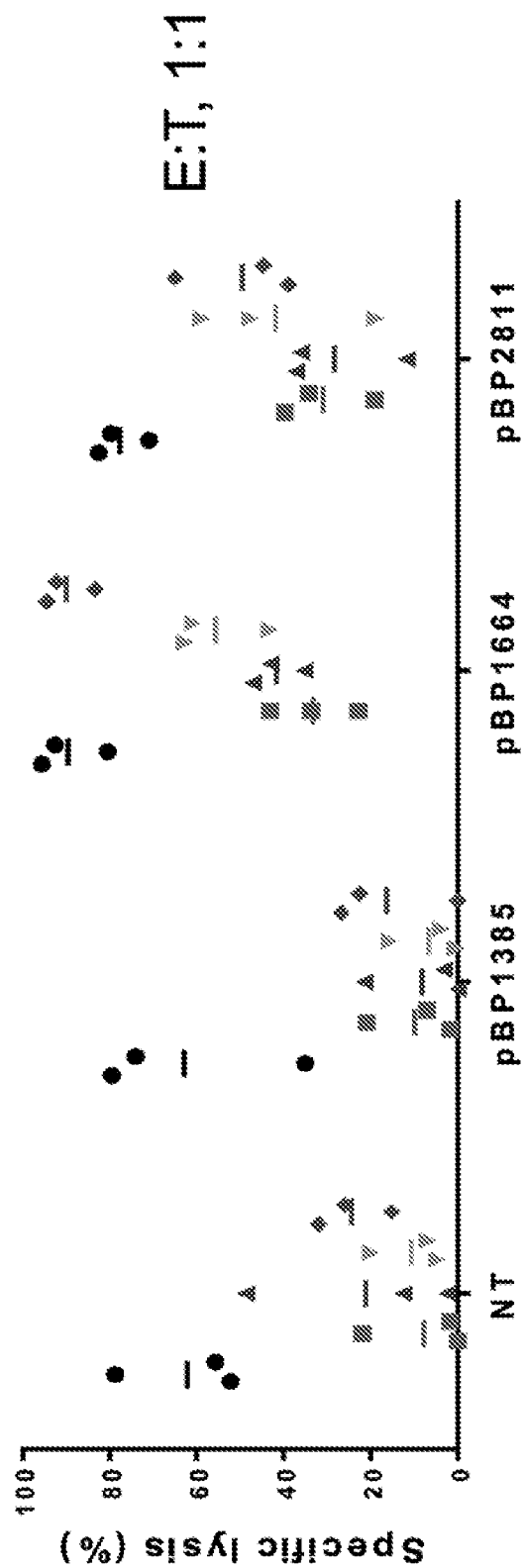

FIGS. 13A-13C—iMC blocks NK cell inefficacy following cryostorage. FIG. 13A: Transduced NK cells were maintained in standard culture conditions. Cells were slowly frozen in 90% fetal calf serum/10% dimethylsulfoxide and stored below −150° C. for up to four weeks. Overall NK viability after freeze-thaw was similar for each group. The graphs provided in this figure (FIGS. 13B and 13C) relate to efficacy. Cell viability was poor in for each transductant immediately following thaw and replating but recovered over three days of standard culture. NK cells prior to and after the indicated period of recovery from freeze/thaw were cultured with THP1-luciferase targets for 24 hours at an E:T of 3:1 (FIG. 13B) or 1:1 (FIG. 13C) to assess killing efficacy. DS NK cells with iMC were capable of regaining their potency over 48 to 72 hours after cryostorage while cells lacking iMC lacked efficacy.

Figure 14:
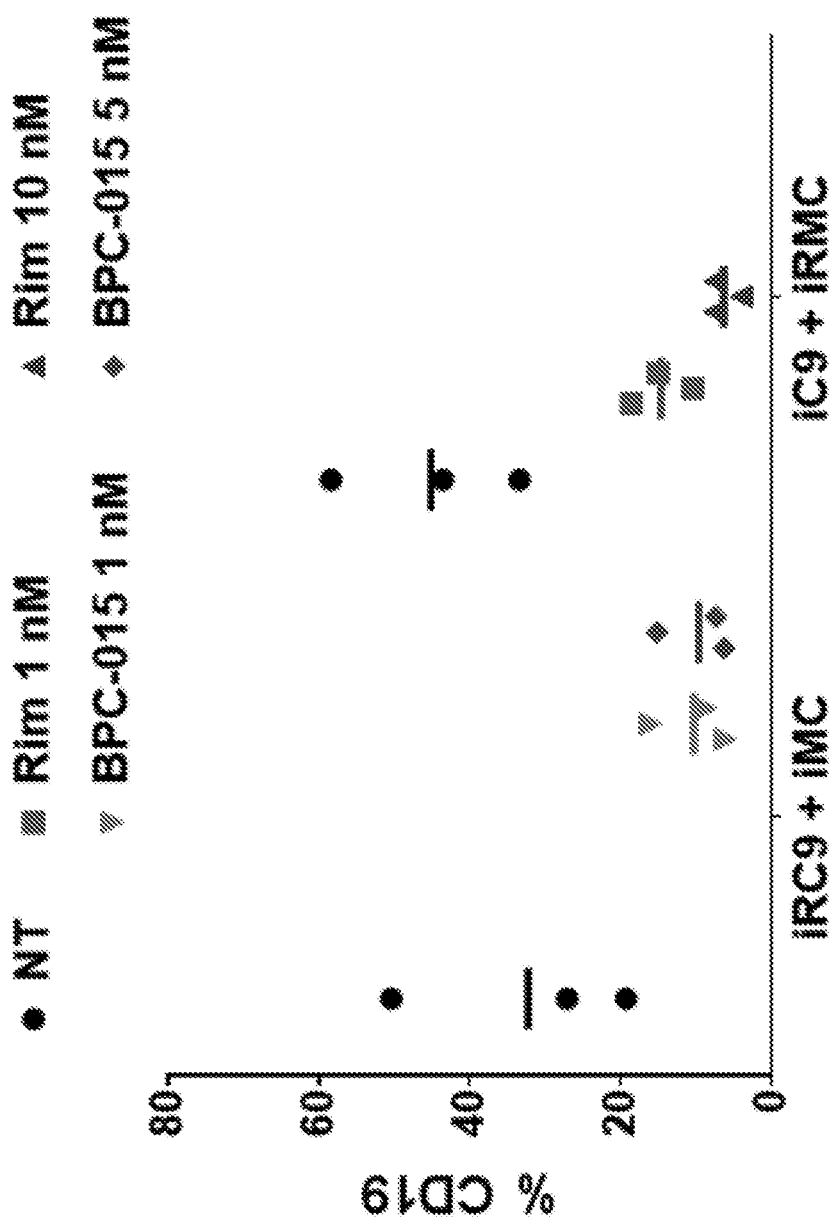
FIG. 14 provides a graph of caspase-9 activation in modified NK cells, assayed by percent CD19-expressing cells.

FIG. 14—Caspase-9 activation ablates DS NK cells. NK cells from three separate donors were transduced with recombinant retroviruses 1664 (iMC+iRC9) or 1531 (iC9+ iRMC) and expanded. Cultures were split and left untreated (black) or dimerizing drugs BPC015 or rimiducid added. After 24 hours NK cells were assayed for presence of the CD19 marker cotransduced with the switches. Drug-specific loss of the transduced cell population indicated targeted apoptosis by activation of the safety switch. Activation with cognate drug reduced viability of transduced NK cell in either dual switch configuration (iRMC+iC9, or iRC9+ iMC). MFI=Mean fluorescence intensity of CD19 in flow cytometry, indicating a proportional growth advantage of highly expressing cells.

Example 2. Examples of Particular Nucleic Acid and Amino Acid Sequences

The following tables include examples of polypeptide and nucleotide sequences coding for the polypeptides of the chimeric signaling polypeptides. It is understood that sequences of individual polypeptides provided in these examples, such as, for example, the truncated MyD88 polypeptides, co-stimulatory polypeptide cytoplasmic signaling regions, FKBP12 variant regions, and caspase polypeptides, may be used to construct other expression vectors that encode chimeric signaling polypeptides of the present embodiments.

TABLE

| | | Plasmid C: pBP1800-SFG-MyD88.CD28.OX40.Fv.Fv.T2A. aPSCAscFv.CD34e.CD8stm.zeta | | |
|---|---|---|---|---|
| Fragment | SEQ ID # | Nucleotide | SEQ ID # | Peptide |
| MyD88 | 1 | ATGGCTGCAGGAGGTCCCGGCGCGGGGTCTGC GGCCCCGGTCTCCTCCACATCCTCCCTTCCCCT GGCTGCTCTCAACATGCGAGTGCGGCGCCGCCT GTCTCTGTTCTTGAACGTGCGGACACAGGTGGC GGCCGACTGGACCGCGCTGGCGGAGGAGATGGA CTTTGAGTACTTGGAGATCCGGCAACTGGAGAC ACAAGCGGACCCCACTGGCAGGCTGCTGGACGC CTGGCAGGGACGCCCTGGCGCCTCTGTAGGCCG ACTGCTCGATCTGCTTACCAAGCTGGGCCGCGA CGACGTGCTGCTGGAGCTGGGACCCAGCATTGA GGAGGATTGCCAAAAGTATATCTTGAAGCAGCA GCAGGAGGAGGCTGAGAAGCCTTTACAGGTGGC CGCTGTAGACAGCAGTGTCCCACGGACAGCAGA GCTGGCGGGCATCACCACACTTGATGACCCCCT GGGGCATATGCCTGAGCGTTTCGATGCCTTCATC TGCTATTGCCCCAGCGACATC | 2 | MAAGGPGAGSAAPVSSTSSL PLAALNMRVRRRLSLFLNVR TQVAADWTALAEEMDFEYLE IRQLETQADPTGRLLDAWQG RPGASVGRLLDLLTKLGRDD VLLELGPSIEEDCQKYILKQ QQEEAEKPLQVAAVDSSVPR TAELAGITTLDDPLGHMPER FDAFICYCPSDI |

TABLE-continued

Plasmid C: pBP1800-SFG-MyD88.CD28.OX40.Fv.Fv.T2A.
aPSCAscFv.CD34e.CD8stm.zeta

| Fragment | SEQ ID # Nucleotide | | SEQ ID # Peptide | |
|---|---|---|---|---|
| Linker | 3 | CTCGAG | 4 | LE |
| CD28 signaling domain | 5 | AGGAGTAAGAGGAGCAGGCTCCTGCACAGTGAC TACATGAACATGACTCCCCGCCGCCCCGGGCCC ACCCGCAAGCATTACCAGCCCTATGCCCCACCA CGCGACTTCGCAGCCTATCGCTCC | 6 | RSKRSRLLHSDYMNMTPRR PGPTRKHYQPYAPPRDFAA YRS |
| OX40 signaling domain | 7 | AGGGACCAGAGGCTGCCCCCCGATGCCCACAAG CCCCCTGGGGGAGGCAGTTTCCGGACCCCCATC CAAGAGGAGCAGGCCGACGCCCACTCCACCCTG GCCAAGATC | 8 | RDQRLPPDAHKPPGGGSFR TPIQEEQADAHSTLAKIGS G |
| Linker | 9 | GGATCTGGCCAATTG | 10 | GSGQL |
| FKBP$_v$, | 11 | GGCGTCCAAGTCGAAACCATTAGTCCCGGCGAT GGCAGAACATTTCCTAAAAGGGGACAAACATGTG TCGTCCATTATACAGGCATGTTGGAGGACGGCAA AAAGGTGGACAGTAGTAGAGATCGCAATAAACCT TTCAAATTCATGTTGGGAAAACAAGAAGTCATTA GGGGATGGGAGGAGGGCGTGGCTCAAATGTCCGT CGGCCAACGCGCTAAGCTCACCATCAGCCCCGA CTACGCATACGCGCTACCGGACATCCCGGAAT TATTCCCCCTCACGCTACCTTGGTGTTTGACGTC GAACTGTTGAAGCTCGAA | 12 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 13 | GTCGAG | 14 | VE |
| FKBP$_v$ | 15 | GGAGTGCAGGTGGAGACTATCTCCCCAGGAGAC GGGCGCACCTTCCCCAAGCGCGGCCAGACCTGC GTGGTGCACTACACCGGGATGCTTGAAGATGGA AAGAAAGTTGATTCCTCCCGGGACAGAAACAAGC CCTTTAAGTTTATGCTAGGCAAGCAGGAGGTGAT CCGAGGCTGGGAAGAAGGGGTTGCCCAGATGAG TGTGGGTCAGAGAGCCAAACTGACTATATCTCCA GATTATGCCTATGGTGCCACTGGGCACCCAGGC ATCATCCCACCACATGCCACTCTCGTCTTCGATG TGGAGCTTCTAAAACTGGAA | 16 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 17 | CCGCGG | 18 | PR |
| T2A | 19 | GAGGGCAGAGGCAGCCTCCTGACATGTGGGGAC GTCGAGGAGAACCCTGGCCCA | 20 | EGRGSLLTCGDVEENPGP |
| Linker | 21 | CCTTGG | 22 | PW |
| Signal Peptide | 23 | ATGGAGTTCGGATTGAGCTGGCTGTTCCTGGTG GCAATACTCAAGGGCGTTCAATGTTCACGG | 24 | MEFGLSWLFLVAILKGVQC SR |
| PSCA(A11) V$_L$ | 25 | GACATCCAACTGACGCAAAGCCCATCTACACTCA GCGCTAGCATGGGGGACAGGGTCACAATCACGT GCTCTGCCTCAAGTTCCGTTAGGTTTATCCATTG GTATCAGCAGAAACCTGGAAAGGCCCCAAAAAG ACTGATCTATGATACCAGCAAGCTGGCTTCCGGA GTGCCCTCAAGGTTCTCAGGATCTGGCAGTGGG ACCGATTTCACCCTGACAATTAGCAGCCTTCAGC CAGAGGATTTCGCAACCTATTACTGTCAGCAATG GGGGTCCAGCCCATTCACTTTCGGCCAAGGAAC AAAGGTGGAGATAAAA | 26 | DIQLTQSPSTLSASMGDRVTI TCSASSSVRFIHWYQQKPGKA PKRLIYDTSKLASGVPSRFSG SGSGTDFTLTISSLQPEDFAT YYCQQWGSSPFTFGQGTKVEI K |
| Flex | 27 | GGCGGAGGAAGCGGAGGTGGGGGC | 28 | GGGSGGGG |
| Linker | 29 | CAGGT | 30 | QV |
| PSCA(A11) V$_H$ | 31 | GAGGTGCAGCTCGTGGAGTATGGCGGGGGCCT GGTGCAGCCTGGGGGTAGTCTGAGGCTCTCCTG CGCTGCCTCTGGCTTTAACATTAAAGACTACTAC ATACATTGGGTGCGGCAGGCCCCAGGCAAGGG CTCGAATGGGTGGCCTGGATTGACCCTGAGAAT GGTGACACTGAGTTTGTCCCCAAGTTTCAGGGCA GAGCCACCATGAGCGCTGACACAAGCAAAAACA CTGCTTATCTCCAAATGAATAGCCTGCGAGCTGA AGATACAGCAGTCTATTACTGCAAGACGGGAGGA TTCTGGGGCCAGGGAACTCTGGTGACAGTTAGTT CC | 32 | EVQLVEYGGGLVQPGGSLRL SCAASGFNIKDYYIHWVRQA PGKGLEWVAWIDPENGDTEF VPKFQGRATMSADTSKNTAY LQMNSLRAEDTAVYYCKTGG FWGQGTLVTVSS |

TABLE-continued

Plasmid C: pBP1800-SFG-MyD88.CD28.OX40.Fv.Fv.T2A.aPSCAscFv.CD34e.CD8stm.zeta

| Fragment | SEQ ID # | Nucleotide | SEQ ID # | Peptide |
|---|---|---|---|---|
| Linker | 33 | GGATCC | 34 | GS |
| CD34 epitope | 35 | GAACTTCCTACTCAGGGGACTTTCTCAAACGTTAGCACAAACGTAAGT | 36 | ELPTQGTFSNVSTNVS |
| CD8 stalk | 37 | GAACTTCCTACTCAGGGGACTTTCTCAAACGTTAGCACAAACGTAAGT | 38 | PAPRPPTPAPTIASQPLSLRPEACRPAAGGAVHTRGLDFACD |
| CD8 transmembrane | 39 | ATCTATATCTGGGCACCTCTCGCTGGCACCTGTGGAGTCCTTCTGCTCAGCCTGGTTATTACTCTGTACTGTAATCACCGGAATCGCCGCCGCGTTTGTAAGTGTCCCAGG | 40 | IYIWAPLAGTCGVLLLSLVITLYCNHRNRRRVCKCPR |
| Linker | 41 | GTCGAC | 42 | VD |
| CD3ζ | 43 | AGAGTGAAGTTCAGCAGGAGCGCAGACGCCCCCGCGTACCAGCAGGGCCAGAACCAGCTCTATAACGAGCTCAATCTAGGACGAAGAGAGGAGTACGATGTTTTGGACAAGAGACGTGGCCGGGACCCTGAGATGGGGGGAAAGCCGAGAAGGAAGAACCCTCAGGAAGGCCTGTACAATGAACTGCAGAAAGATAAGATGGCGGAGGCCTACAGTGAGATTGGGATGAAAGGCGAGCGCCGGAGGGGCAAGGGGCACGATGGCCTTTACCAGGGTCTCAGTACAGCCACCAAGGACACCTACGACGCCCTTCACATGCAAGCTCTTCCACCTCGT | 44 | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR |
| STOP | | TGA | | STOP |

TABLE

Plasmid E: pBP1802-SFG-MyD88.ICOS.Fv.Fv.T2A.aPSCAscFv.CD34e.CD8stm.zeta

| Fragment | SEQ ID # | Nucleotide | SEQ ID # | Peptide |
|---|---|---|---|---|
| MyD88 | 1 | ATGGCTGCAGGAGGTCCCGGCGCGGGGTCTGCGGCCCCGGTCTCCTCCACATCCTCCCTTCCCCTGGCTGCTCTCAACATGCGAGTGCGGCGCCGCCTGTCTCTGTTCTTGAACGTGCGGACACAGGTGGCGGCCGACTGGACCGCGCTGGCGGAGGAGATGGACTTTGAGTACTTGGAGATCCGGCAACTGGAGACACAAGCGGACCCCACTGGCAGGCTGCTGGACGCCTGGCAGGGACGCCCTGGCGCCTCTGTAGGCCGACTGCTCGATCTGCTTACCAAGCTGGGCCGCGACGACGTGCTGCTGGAGCTGGGACCCAGCATTGAGGAGGATTGCCAAAAGTATATCTTGAAGCAGCAGCAGGAGGAGGCTGAGAAGCCTTTACAGGTGGCCGCTGTAGACAGCAGTGTCCCACGGACAGCAGAGCTGGCGGGCATCACCACACTTGATGACCCCCTGGGGCATATGCCTGAGCGTTTCGATGCCTTCATCTGCTATTGCCCCAGCGACATC | 2 | MAAGGPGAGSAAPVSSTSSLPLAALNMRVRRRLSLFLNVRTQVAADWTALAEEMDFEYLEIRQLETQADPTGRLLDAWQGRPGASVGRLLDLLTKLGRDDVLLELGPSIEEDCQKYILKQQQEEAEKPLQVAAVDSSVPRTAELAGITTLDDPLGHMPERFDAFICYPSDI |
| Linker | 3 | CTCGAG | 4 | LE |
| ICOS signaling domain | 45 | ACAAAAAAGAAGTATTCATCCAGTGTGCACGACCCTAACGGTGAATACATGTTCATGAGAGCAGTGAACACAGCCAAAAAATCTAGACTCACAGATGTGACCCTA | 46 | TKKKYSSSVHDPNGEYMFMRAVNTAKKSRLTDVTL |
| Linker | 9 | GGATCTGGCCAATTG | 10 | GSGQL |
| FKBP$_v$ | 11 | GGCGTCCAAGTCGAAACCATTAGTCCCGGCGATGGCAGAACATTTCCTAAAAGGGGACAAACATGTGTCGTCCATTATACAGGCATGTTGGAGGACGGCAAAAAGGTGGACAGTAGTAGAGATCGCAATAAACCTTTCAAATTCATGTTGGGAAAACAAGAAGTCATTAGGGGATGGGAGGAGGGCGTGGCTCAAATGTCCGT | 12 | GVQVETISPGDGRTFPKRGQTCVVHYTGMLEDGKKVDSSRDRNKPFKFMLGKQEVIRGWEEGVAQMSVGQRAKLTISPDYAYGATGHPGIIPPHATLVFDVELLKLE |

TABLE-continued

Plasmid E: pBP1802-SFG-MyD88.ICOS.Fv.Fv.T2A.aPSCAscFv.CD34e.CD8stm.zeta

| Fragment | SEQ ID # | Nucleotide | SEQ ID # | Peptide |
|---|---|---|---|---|
| | | CGGCCAACGCGCTAAGCTCACCATCAGCCCCGA CTACGCATACGGCGCTACCGGACATCCCGGAAT TATTCCCCCTCACGCTACCTTGGTGTTTGACGTC GAACTGTTGAAGCTCGAA | | |
| Linker | 13 | GTCGAG | 14 | VE |
| FKBP$_v$ | 15 | GGAGTGCAGGTGGAGACTATCTCCCCAGGAGAC GGGCGCACCTTCCCCAAGCGCGGCCAGACCTGC GTGGTGCACTACACCGGGATGCTTGAAGATGGA AAGAAAGTTGATTCCTCCCGGGACAGAAACAAGC CCTTTAAGTTTATGCTAGGCAAGCAGGAGGTGAT CCGAGGCTGGGAAGAAGGGGTTGCCCAGATGAG TGTGGGTCAGAGAGCCAAACTGACTATATCCCA GATTATGCCTATGGTGCCACTGGGCACCCAGGC ATCATCCCACCACATGCCACTCTCGTCTTCGATG TGGAGCTTCTAAAACTGGAA | 16 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 17 | CCGCGG | 18 | PR |
| T2A | 19 | GAGGGCAGAGGCAGCCTCCTGACATGTGGGGAC GTCGAGGAGAACCCTGGCCCA | 20 | EGRGSLLTCGDVEENPGP |
| Linker | 21 | CCTTGG | 22 | PW |
| Signal Peptide | 23 | ATGGAGTTCGGATTGAGCTGGCTGTTCCTGGTG GCAATACTCAAGGGCGTTCAATGTTCACGG | 24 | MEFGLSWLFLVAILKGVQC SR |
| PSCA(A11) V$_L$ | 25 | GACATCCAACTGACGCAAAGCCCATCTACACTCA GCGCTAGCATGGGGGACAGGGTCACAATCACGT GCTCTGCCTCAAGTTCCGTTAGGTTTATCCATTG GTATCAGCAGAAACCTGGAAAGGCCCCAAAAAG ACTGATCTATGATACCAGCAAGCTGGCTTCCGGA GTGCCCTCAAGGTTCTCAGGATCTGGCAGTGGG ACCGATTTCACCCTGACAATTAGCAGCCTTCAGC CAGAGGATTTCGCAACCTATTACTGTCAGCAATG GGGGTCCAGCCCATTCACTTTCGGCCAAGGAAC AAAGGTGGAGATAAAA | 26 | DIQLTQSPSTLSASMGDRVTI TCSASSSVRFIHWYQQKPGK APKRLIYDTSKLASGVPSRFS GSGSGTDFTLTISSLQPEDFA TYYCQQWGSSPFTFGQGTK VEIK |
| Flex | 27 | GGCGGAGGAAGCGGAGGTGGGGGC | 28 | GGGSGGGG |
| Linker | 29 | CAGGTG | 30 | QV |
| PSCA(A11) V$_H$ | 31 | GAGGTGCAGCTCGTGGAGTATGGCGGGGGCCT GGTGCAGCCTGGGGGTAGTCTGAGGCTCTCCTG CGCTGCCTCTGGCTTTAACATTAAAGACTACTAC ATACATTGGGTGCGGCAGGCCCCAGGCAAAGGG CTCGAATGGGTGGCCTGGATTGACCCTGAGAAT GGTGACACTGAGTTTGTCCCCAAGTTTCAGGGCA GAGCCACCATGAGCGCTGACACAAGCAAAAACA CTGCTTATCTCCAAATGAATAGCCTGCGAGCTGA AGATACAGCAGTCTATTACTGCAAGACGGGAGGA TTCTGGGGCCAGGGAACTCTGGTGACAGTTAGTT CC | 32 | EVQLVEYGGGLVQPGGSLRL SCAASGFNIKDYYIHWVRQA PGKGLEWVAWIDPENGDTEF VPKFQGRATMSADTSKNTAY LQMNSLRAEDTAVYYCKTGG FWGQGTLVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 37 | GAACTTCCTACTCAGGGGACTTTCTCAAACGTTA GCACAAACGTAAGT | 38 | PAPRPPTPAPTIASQPLSLR PEACRPAAGGAVHTRGLDFA CD |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYIWAPLAGTCGVLLLSLVIT LYCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG | 44 | RVKFSRSADAPAYQQGQNQ LYNELNLGRREEYDVLDKRR GRDPEMGGKPRRKNPQEGL YNELQKDKMAEAYSEIGMKG |

TABLE-continued

Plasmid E: pBP1802-SFG-MyD88.ICOS.Fv.Fv.T2A.aPSCAscFv.CD34e.CD8stm.zeta

| Fragment | SEQ ID # | Nucleotide | SEQ ID # | Peptide |
|---|---|---|---|---|
| | | ATGGGGGGAAAGCCGAGAAGGAAGAACCCTCAG GAAGGCCTGTACAATGAACTGCAGAAAGATAAGA TGGCGGAGGCCTACAGTGAGATTGGGATGAAAG GCGAGCGCCGAGGGGCAAGGGGCACGATGGC CTTTACCAGGGTCTCAGTACAGCCACCAAGGACA CCTACGACGCCCTTCACATGCAAGCTCTTCCACC TCGT | | ERRRGKGHDGLYQGLSTAT KDTYDALHMQALPPR |
| STOP | | TGA | | STOP |

TABLE

Plasmid H: pBP1815-SFG-4-1BB.Fv.Fv.T2A.aPSCAscFv.CD34e.CD8stm.zeta

| Fragment | SEQ ID # | Nucleotide | SEQ ID # | Peptide |
|---|---|---|---|---|
| Leader | 47 | ATGCTCGAG | 48 | MLE |
| 4-1BB/CD137 signaling domain | 49 | AAACGGGGCAGAAGAAACTCCTGTATATATTCA AACAACCATTTATGAGACCAGTACAAACTACTCAA GAGGAAGATGGCTGTAGCTGCCGATTTCCAGAA GAAGAAGAAGGAGGATGTGAACTG | 50 | KRGRKKLLYIFKQPFMRPV QTTQEEDGCSCRFPEEEEG CEL |
| Linker | 9 | GGATCTGGCCAATTG | 10 | GSGQL |
| FKBP$_v$. | 11 | GGCGTCCAAGTCGAAACCATTAGTCCCGGCGAT GGCAGAACATTTCCTAAAAGGGGACAAACATGTG TCGTCCATTATACAGGCATGTTGGAGGACGGCAA AAAGGTGGACAGTAGTAGAGATCGCAATAAACCT TTCAAATTCATGTTGGGAAAACAAGAAGTCATTAG GGGATGGGAGGAGGGCGTGGCTCAAATGTCCGT CGGCCAACGCGCTAAGCTCACCATCAGCCCCGA CTACGCATACGGCGCTACCGGACATCCCGGAAT TATTCCCCCTCACGCTACCTTGGTGTTTGACGTC GAACTGTTGAAGCTCGAA | 12 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 13 | GTCGAG | 14 | VE |
| FKBP$_v$ | 15 | GGAGTGCAGGTGGAGACTATCTCCCCAGGAGAC GGGCGCACCTTCCCCAAGCGCGGCCAGACCTGC GTGGTGCACTACACCGGGATGCTTGAAGATGGA AAGAAAGTTGATTCCTCCCGGGACAGAAACAAGC CCTTTAAGTTTATGCTAGGCAAGCAGGAGGTGAT CCGAGGCTGGGAAGAAGGGGTTGCCCAGATGAG TGTGGGTCAGAGAGCCAAACTGACTATATCTCCA GATTATGCCTATGGTGCCACTGGGCACCCAGGC ATCATCCCACCACATGCCACTCTCGTCTTCGATG TGGAGCTTCTAAAACTGGAA | 16 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 17 | CCGCGG | 18 | PR |
| T2A | 19 | GAGGGCAGAGGCAGCCTCCTGACATGTGGGGAC GTCGAGGAGAACCCTGGCCCA | 20 | EGRGSLLTCGDVEENPGP |
| Linker | 21 | CCTTGG | 22 | PW |
| Signal Peptide | 23 | ATGGAGTTCGGATTGAGCTGGCTGTTCCTGGTG GCAATACTCAAGGGCGTTCAATGTTCACGG | 24 | MEFGLSWLFLVAILKGVQC SR |
| PSCA(A11) V$_L$ | 25 | GACATCCAACTGACGCAAAGCCCATCTACACTCA GCGCTAGCATGGGGGACAGGGTCACAATCACGT GCTCTGCCTCAAGTTCCGTTAGGTTTATCCATTG GTATCAGCAGAAACCTGGAAAGGCCCCAAAAAG ACTGATCTATGATACCAGCAAGCTGGCTTCCGGA GTGCCCTCAAGGTTCTCAGGATCTGGCAGTGGG ACCGATTTCACCCTGACAATTAGCAGCCTTCAGC CAGAGGATTTCGCAACCTATTACTGTCAGCAATG GGGGTCCAGCCCATTCACTTTCGGCCAAGGAAC AAAGGTGGAGATAAAA | 26 | DIQLTQSPSTLSASMGDRVT ITCSASSSVRFIHWYQQKPG KAPKRLIYDTSKLASGVPSR FSGSGSGTDFTLTISSLQPE DFATYYCQQWGSSPFTFGQG TKVEIK |
| Flex | 27 | GGCGGAGGAAGCGGAGGTGGGGGC | 28 | GGGSGGGG |

TABLE-continued

Plasmid H: pBP1815-SFG-4-1BB.Fv.Fv.T2A.aPSCAscFv.CD34e.CD8stm.zeta

| Fragment | SEQ ID # | Nucleotide | SEQ ID # | Peptide |
|---|---|---|---|---|
| Linker | 29 | CAGGTG | 30 | QV |
| PSCA(A11) V$_H$ | 31 | GAGGTGCAGCTCGTGGAGTATGGCGGGGGCCT GGTGCAGCCTGGGGGTAGTCTGAGGCTCTCCTG CGCTGCCTCTGGCTTTAACATTAAAGACTACTAC ATACATTGGGTGCGGCAGGCCCCAGGCAAAGGG CTCGAATGGGTGGCCTGGATTGACCCTGAGAAT GGTGACACTGAGTTTGTCCCCAAGTTTCAGGGCA GAGCCACCATGAGCGCTGACACAAGCAAAAACA CTGCTTATCTCCAAATGAATAGCCTGCGAGCTGA AGATACAGCAGTCTATTACTGCAAGACGGGAGGA TTCTGGGGCCAGGGAACTCTGGTGACAGTTAGTT CC | 32 | EVQLVEYGGGLVQPGGSLRL SCAASGFNIKDYYIHWVRQA PGKGLEWVAWIDPENGDTEF VPKFQGRATMSADTSKNTAY LQMNSLRAEDTAVYYCKTGG FWGQGTLVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 37 | GAACTTCCTACTCAGGGGACTTTCTCAAACGTTA GCACAAACGTAAGT | 38 | PAPRPPTPAPTIASQPLSLRP EACRPAAGGAVHTRGLDFAC D |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYIWAPLAGTCGVLLLSLVI TLYCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAGA TGGCGGAGGCCTACAGTGAGATTGGGATGAAAG GCGAGCGCCGGAGGGGCAAGGGGCACGATGGC CTTTACCAGGGTCTCAGTACAGCCACCAAGGACA CCTACGACGCCCTTCACATGCAAGCTCTTCCACC TCGT | 44 | RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST DATKTYDALHMQALPPR |
| STOP | | TGA | | STOP |

TABLE

Plasmid L: pBP2205-SFG-Myr-MyD88.Fv.Fv.T2A.aPSCAscFv.CD34e.CD8stm.zeta

| Fragment | SEQ ID # | Nucleotide | SEQ ID # | Peptide |
|---|---|---|---|---|
| Myristoylation peptide | 51 | ATGGGGAGTAGCAAGAGCAAGCCTAAGGACCCC AGCCAGCGC | 52 | MGSSKSKPKDPSQR |
| Linker | 53 | AGAGCATGC | 54 | RAC |
| MyD88 | 1 | ATGGCTGCAGGAGGTCCCGGCGCGGGGTCTGC GGCCCCGGTCTCCTCCACATCCTCCCTTCCCCT GGCTGCTCTCAACATGCGAGTGCGGCGCCTGC GTCTCTGTTCTTGAACGTGCGGACACAGGTGGC GGCCGACTGGACCGCTGGCGGAGGAGATGG ACTTTGAGTACTGGAGATCCGGCAACTGGAGAC ACAAGCGGACCCCACTGGCAGGCTGCTGGACGC CTGGCAGGGACGCCCTGGCGCCTCTGTAGGCC GACTGCTCGATCTGCTTACCAAGCTGGGCCGCG ACGACGTGCTGCTGGAGCTGGGACCCAGCATTG AGGAGGATTGCCAAAAGTATATCTTGAAGCAGCA GCAGGAGGAGGCTGAGAAGCCTTTACAGGTGGC CGCTGTAGACAGCAGTGTCCCACGGACAGCAGA GCTGGCGGGCATCACCACACTTGATGACCCCCT GGGGCATATGCCTGAGCGTTTCGATGCCTTCATC TGCTATTGCCCCAGCGACATC | 2 | MAAGGPGAGSAAPVSSTSSL PLAALNMRVRRRLSLFLNVR TQVAADWTALAEEMDFEYLE IRQLETQADPTGRLLDAWQG RPGASVGRLLDLLTKLGRDD VLLELGPSIEEDCQKYILKQ QQEEAEKPLQVAAVDSSVPR TAELAGITTLDDPLGHMPER FDAFICYCPSDI |

TABLE-continued

Plasmid L: pBP2205-SFG-Myr-MyD88.Fv.Fv.T2A.aPSCAscFv.CD34e.CD8stm.zeta

| Fragment | SEQ ID # | Nucleotide | SEQ ID # | Peptide |
|---|---|---|---|---|
| Linker | 9 | GGATCTGGCCAATTG | 10 | GSGQL |
| $FKBP_{v'}$ | 11 | GGCGTCCAAGTCGAAACCATTAGTCCCGGCGAT GGCAGAACATTTCCTAAAAGGGGACAAACATGTG TCGTCCATTATACAGGCATGTTGGAGGACGGCAA AAAGGTGGACAGTAGTAGAGATCGCAATAAACCT TTCAAATTCATGTTGGGAAAACAAGAAGTCATTAG GGGATGGGAGGAGGGCGTGGCTCAAATGTCCGT CGGCCAACGCGCTAAGCTCACCATCAGCCCCGA CTACGCATACGCGCTACCGGACATCCCGGAAT TATTCCCCCTCACGCTACCTTGGTGTTTGACGTC GAACTGTTGAAGCTCGAA | 12 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 13 | GTCGAG | 14 | VE |
| $FKBP_v$ | 15 | GGAGTGCAGGTGGAGACTATCTCCCCAGGAGAC GGGCGCACCTTCCCCAAGCGCGGCCAGACCTGC GTGGTGCACTACACCGGGATGCTTGAAGATGGA AAGAAAGTTGATTCCTCCCGGGACAGAAACAAGC CCTTTAAGTTTATGCTAGGCAAGCAGGAGGTGAT CCGAGGCTGGGAAGAAGGGGTTGCCCAGATGAG TGTGGGTCAGAGAGCCAAACTGACTATATCTCCA GATTATGCCTATGGTGCCACTGGGCACCCAGGC ATCATCCCACCACATGCCACTCTCGTCTTCGATG TGGAGCTTCTAAAACTGGAA | 16 | GVQVETISPGDGRTFPKRGQ TCVVHYTGMLEDGKKVDSSRD RNKPFKFMLGKQEVIRGWEE GVAQMSVGQRAKLTISPDYA YGATGHPGIIPPHATLVFDV ELLKLE |
| Linker | 17 | CCGCGG | 18 | PR |
| T2A | 19 | GAGGGCAGAGGCAGCCTCCTGACATGTGGGGAC GTCGAGGAGAACCCTGGCCCA | 20 | EGRGSLLTCGDVEENPGP |
| Linker | 21 | CCTTGG | 22 | PW |
| Signal Peptide | 23 | ATGGAGTTCGGATTGAGCTGGCTGTTCCTGGTG GCAATACTCAAGGGCGTTCAATGTCACGG | 24 | MEFGLSWLFLVAILKGVQCS R |
| PSCA(A11) $V_L$ | 25 | GACATCCAACTGACGCAAAGCCCATCTACACTCA GCGCTAGCATGGGGGACAGGGTCACAATCACGT GCTCTGCCTCAAGTTCCGTTAGGTTTATCCATTG GTATCAGCAGAAACCTGGAAAGGCCCCAAAAAG ACTGATCTATGATACCAGCAAGCTGGCTTCCGGA GTGCCCTCAAGGTTCTCAGGATCTGGCAGTGGG ACCGATTTCACCCTGACAATTAGCAGCCTTCAGC CAGAGGATTTCGCAACCTATTACTGTCAGCAATG GGGGTCCAGCCCATTCACTTTCGGCCAAGGAAC AAAGGTGGAGATAAAA | 26 | DIQLTQSPSTLSASMGDRVT ITCSASSSVRFIHWYQQKPG KAPKRLIYDTSKLASGVPSR FSGSGSGTDFTLTISSLQPE DFATYYCQQWGSSPFTFGQG TKVEIK |
| Flex | 27 | GGCGGAGGAAGCGGAGGTGGGGC | 28 | GGGSGGGG |
| Linker | 29 | CAGGTG | 30 | QV |
| PSCA(A11) $V_H$ | 31 | GAGGTGCAGCTCGTGGAGTATGGCGGGGGCCT GGTGCAGCCTGGGGGTAGTCTGAGGCTCTCCTG CGCTGCCTCTGGCTTTAACATTAAAGACTACTAC ATACATTGGGTGCGGCAGGCCCCAGGCAAAGGG CTCGAATGGGTGGCCTGGATTGACCCTGAGAAT GGTGACACTGAGTTTGTCCCCAAGTTTCAGGGCA GAGCCACCATGAGCGCTGACACAAGCAAAAACA CTGCTTATCTCCAAATGAATAGCCTGCGAGCTGA AGATACAGCAGTCTATTACTGCAAGACGGGAGGA TTCTGGGGCCAGGGAACTCTGGTGACAGTTAGTT CC | 32 | EVQLVEYGGGLVQPGGSLRL SCAASGFNIKDYYIHWVRQA PGKGLEWVAWIDPENGDTEF VPKFQGRATMSADTSKNTAY LQMNSLRAEDTAVYYCKTGG FWGQGTLVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 37 | GAACTTCCTACTCAGGGGACTTTCTCAAACGTTA GCACAAACGTAAGT | 38 | PAPRPPTPAPTIASQPLSLRP EACRPAAGGAVHTRGLDFAC D |

TABLE-continued

Plasmid L: pBP2205-SFG-Myr-MyD88.Fv.Fv.T2A.aPSCAscFv.CD34e.CD8stm.zeta

| Fragment | SEQ ID # | Nucleotide | SEQ ID # | Peptide |
|---|---|---|---|---|
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYIWAPLAGTCGVLLLSLVIT LYCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAGA TGGCGGAGGCCTACAGTGAGATTGGGATGAAAG GCGAGCGCCGGAGGGGCAAGGGGCACGATGGC CTTTACCAGGGTCTCAGTACAGCCACCAAGGACA CCTACGACGCCCTTCACATGCAAGCTCTTCCACC TCGT | 44 | RVKFSRSADAPAYQQGQNQ LYNELNLGRREEYDVLDKRR GRDPEMGGKPRRKNPQEGL YNELQKDMAEAYSEIGMKG ERRRGKGHDGLYQGLSTATK DTYDALHMQALPPR |
| STOP | | TGA | | STOP |

TABLE

Plasmid M: pBP2206-SFG-Myr-MyD88.CD40.Fv.Fv.T2A.aPSCAscFv.CD34e.CD8stm.zeta

| Fragment | SEQ ID # | Nucleotide | SEQ ID # | Peptide |
|---|---|---|---|---|
| Myristoylation peptide | 51 | ATGGGGAGTAGCAAGAGCAAGCCTAAGGACCCC AGCCAGCGC | 52 | MGSSKSKPKDPSQR |
| Linker | 53 | AGAGCATGC | 54 | RAC |
| MyD88 | 1 | ATGGCTGCAGGAGGTCCCGGCGCGGGGTCTGC GGCCCCGGTCTCCTCCACATCCTCCCTTCCCCT GGCTGCTCTCAACATGCGAGTGCGGCGCCGCCT GTCTCTGTTCTTGAACGTGCGGACACAGGTGGC GGCCGACTGGACCGCGCTGGCGGAGGAGATGG ACTTTGAGTACTTGGAGATCCGGCAACTGGAGAC ACAAGCGGACCCCACTGGCAGGCTGCTGGACGC CTGGCAGGGACGCCCTGGCGCCTCTGTAGGCC GACTGCTCGATCTGCTTACCAAGCTGGGCCGCG ACGACGTGCTGCTGGAGCTGGGACCCAGCATTG AGGAGGATTGCCAAAAGTATATCTTGAAGCAGCA GCAGGAGGAGGCTGAGAAGCCTTTACAGGTGGC CGCTGTAGACAGCAGTGTCCCACGGACAGCAGA GCTGGCGGGCATCACCACACTTGATGACCCCCT GGGGCATATGCCTGAGCGTTTCGATGCCTTCATC TGCTATTGCCCCAGCGACATC | 2 | MAAGGPGAGSAAPVSSTSSL PLAALNMRVRRRLSLFLNVR TQVAADWTALAEEMDFEYLE IRQLETQADPTGRLLDAWQG RPGASVGRLLDLLTKLGRDD VLLELGPSIEEDCQKYILKQ QQEEAEKPLQVAAVDSSVPR TAELAGITTLDDPLGHMPER FDAFICYCPSDI |
| Linker | 3 | CTCGAG | 4 | LE |
| CD40 signaling domain | 55 | AAAAAGGTGGCCAAGAAGCCAACCAATAAGGCC CCCCACCCCAAGCAGGAGCCCCAGGAGATCAAT TTTCCCGACGATCTTCCTGGCTCCAACACTGCTG CTCCAGTGCAGGAGACTTTACATGGATGCCAGC CGGTCACCCAGGAGGATGGCAAAGAGAGTCGCA TCTCAGTGCAGGAGAGACAG | 56 | KKVAKKPTNKAPHPKQEPQE INFPDDLPGSNTAAPVQETL HGCQPVTQEDGKESRISVQ Q |
| Linker | 9 | GGATCTGGCCAATTG | 10 | GSGQL |
| FKBPv. | 11 | GGCGTCCAAGTCGAAACCATTAGTCCCGGCGAT GGCAGAACATTTCCTAAAAGGGGACAAACATGTG TCGTCCATTATACAGGCATGTTGGAGGACGGCAA AAAGGTGGACAGTAGTAGAGATCGCAATAAACCT TTCAAATTCATGTTGGGAAAACAAGAAGTCATTAG GGGATGGGAGGAGGGCGTGGCTCAAATGTCCGT CGGCCAACGCGCTAAGCTCACCATCAGCCCCGA CTACGCATACGGCGCTACCGGACATCCCGGAAT TATTCCCCCTCACGCTACCTTGGTGTTTGACGTC GAACTGTTGAAGCTCGAA | 12 | GVQVETISPGDGRTFPKRGQ TCWHYTGMLEDGKKVDSSRD RNKPFKFMLGKQEVIRGWEE GVAQMSVGQRAKLTISPDY AYGATGHPGIIPPHATLVFDV ELLKLE |

TABLE-continued

Plasmid M: pBP2206-SFG-Myr-MyD88.CD40.Fv.Fv.T2A.aPSCAscFv.CD34e.CD8stm.zeta

| Fragment | SEQ ID # | Nucleotide | SEQ ID # | Peptide |
|---|---|---|---|---|
| Linker | 13 | GTCGAG | 14 | VE |
| FKBP$_v$ | 15 | GGAGTGCAGGTGGAGACTATCTCCCCAGGAGAC GGGCGCACCTTCCCCAAGCGCGGCCAGACCTGC GTGGTGCACTACACCGGGATGCTTGAAGATGGA AAGAAAGTTGATTCCTCCCGGGACAGAAACAAGC CCTTTAAGTTTATGCTAGGCAAGCAGGAGGTGAT CCGAGGCTGGGAAGAAGGGGTTGCCCAGATGAG TGTGGGTCAGAGAGCCAAACTGACTATATCTCCA GATTATGCCTATGGTGCCACTGGGCACCCAGGC ATCATCCCACCACATGCCACTCTCGTCTTCGATG TGGAGCTTCTAAAACTGGAA | 16 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 17 | CCGCGG | 18 | PR |
| T2A | 19 | GAGGGCAGAGGCAGCCTCCTGACATGTGGGGAC GTCGAGGAGAACCCTGGCCCA | 20 | EGRGSLLTCGDVEENPGP |
| Linker | 21 | CCTTGG | 22 | PW |
| Signal Peptide | 23 | ATGGAGTTCGGATTGAGCTGGCTGTTCCTGGTG GCAATACTCAAGGGCGTTCAATGTTCACGG | 24 | MEFGLSWLFLVAILKGVQCS R |
| PSCA(A11) V$_L$ | 25 | GACATCCAACTGACGCAAAGCCCATCTACACTCA GCGCTAGCATGGGGGACAGGGTCACAATCACGT GCTCTGCCTCAAGTTCCGTTAGGTTTATCCATTG GTATCAGCAGAAACCTGGAAAGGCCCCAAAAAG ACTGATCTATGATACCAGCAAGCTGGCTTCCGGA GTGCCCTCAAGGTTCTCAGGATCTGGCAGTGGG ACCGATTTCACCCTGACAATTAGCAGCCTTCAGC CAGAGGATTTCGCAACCTATTACTGTCAGCAATG GGGGTCCAGCCCATTCACTTTCGGCCAAGGAAC AAAGGTGGAGATAAAA | 26 | DIQLTQSPSTLSASMGDRVTI TCSASSSVRFIHWYQQKPGKA PKRLIYDTSKLASGVPSRFSG SGSGTDFTLTISSLQPEDFA TYYCQQWGSSPFTFGQGTK VEIK |
| Flex | 27 | GGCGGAGGAAGCGGAGGTGGGGGC | 28 | GGGSGGGG |
| Linker | 29 | CAGGTG | 30 | QV |
| PSCA(A11) V$_H$ | 31 | GAGGTGCAGCTCGTGGAGTATGGCGGGGGCCT GGTGCAGCCTGGGGGTAGTCTGAGGCTCTCCTG CGCTGCCTCTGGCTTTAACATTAAAGACTACTAC ATACATTGGGTGCGGCAGGCCCCAGGCAAGGG CTCGAATGGGTGGCCTGGATTGACCCTGAGAAT GGTGACACTGAGTTTGTCCCCAAGTTTCAGGGCA GAGCCACCATGAGCGCTGACACAAGCAAAACA CTGCTTATCTCCAAATGAATAGCCTGCGAGCTGA AGATACAGCAGTCTATTACTGCAAGACGGGAGGA TTCTGGGGCCAGGGAACTCTGGTGACAGTTAGTT CC | 32 | EVQLVEYGGGLVQPGGSLRL SCAASGFNIKDYYIHWVRQA PGKGLEWVAWIDPENGDTEF VPKFQGRATMSADTSKNTAY LQMNSLRAEDTAVYYCKTGG FWGQGTLVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 37 | GAACTTCCTACTCAGGGGACTTTCTCAAACGTTA GCACAAACGTAAGT | 38 | PAPRPPTPAPTIASQPLSLRP EACRPAAGGAVHTRGLDFACD |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYI-WAPLAGTCGVLLLSLVITL YCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAGA | 44 | RVKFSRSADAPAYQQGQNQ LYNELNLGRREEYDVLDKRR GRDPEMGGKPRRKNPQEGL YNELQKDKMAEAYSEIGMKG ERRRGKHDGLYQGLSTAT KDTYDALHMQALPPR |

TABLE-continued

| Plasmid M: pBP2206-SFG-Myr-MyD88.CD40.Fv.Fv.T2A.aPSCAscFv.CD34e.CD8stm.zeta | | | | |
|---|---|---|---|---|
| Fragment | SEQ ID # | Nucleotide | SEQ ID # | Peptide |
| | | TGGCGGAGGCCTACAGTGAGATTGGGATGAAAG GCGAGCGCCGGAGGGGCAAGGGGCACGATGGC CTTTACCAGGGTCTCAGTACAGCCACCAAGGACA CCTACGACGCCCTTCACATGCAAGCTCTTCCACC TCGT | | |
| STOP | | TGA | | STOP |

TABLE

| Plasmid N: pBP2208-SFG-CD40.Fv.Fv.T2A.aPSCAscFv.CD34e.CD8stm.zeta | | | | |
|---|---|---|---|---|
| Fragment | SEQ ID # | Nucleotide | SEQ ID # | Peptide |
| Leader | 47 | ATGCTCGAG | 48 | MLE |
| CD40 signaling domain | 55 | AAAAAGGTGGCCAAGAAGCCAACCAATAAGGCC CCCCACCCCAAGCAGGAGCCCCAGGAGATCAAT TTTCCCGACGATCTTCCTGGCTCCAACACTGCTG CTCCAGTGCAGGAGACTTTACATGGATGCCAGC CGGTCACCCAGGAGGATGGCAAAGAGAGTCGCA TCTCAGTGCAGGAGACAG | 56 | KKVAKKPTNKAPHPKQEPQE INFPDDLPGSNTAAPVQETLH GCQPVTQEDGKESRISVQER Q |
| Linker | 9 | GGATCTGGCCAATTG | 10 | GSGQL |
| FKBP$_{v'}$ | 11 | GGCGTCCAAGTCGAAACCATTAGTCCCGGCGAT GGCAGAACATTTCCTAAAAGGGGACAAACATGTG TCGTCCATTATACAGGCATGTTGGAGGACGGCAA AAAGGTGGACAGTAGTAGAGATCGCAATAAACCT TTCAAATTCATGTTGGGAAAACAAGAAGTCATTAG GGGATGGGAGGAGGGCGTGGCTCAAATGTCCGT CGGCCAACGCGCTAAGCTCACCATCAGCCCCGA CTACGCATACGGCGCTACCGGACATCCCGGAAT TATTCCCCCTCACGCTACCTTGGTGTTTGACGTC GAACTGTTGAAGCTCGAA | 12 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 13 | GTCGAG | 14 | VE |
| FKBP$_{v}$ | 15 | GGAGTGCAGGTGGAGACTATCTCCCCAGGAGAC GGGCGCACCTTCCCCAAGCGCGGCCAGACCTGC GTGGTGCACTACACCGGGATGCTTGAAGATGGA AAGAAAGTTGATTCCTCCCGGGACAGAAACAAGC CCTTTAAGTTTATGCTAGGCAAGCAGGAGGTGAT CCGAGGCTGGGAAGAAGGGGTTGCCCAGATGAG TGTGGGTCAGAGAGCCAAACTGACTATATCTCCA GATTATGCCTATGGTGCCACTGGGCACCCAGGC ATCATCCCACCACATGCCACTCTCGTCTTCGATG TGGAGCTTCTAAAACTGGAA | 16 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 17 | CCGCGG | 18 | PR |
| T2A | 19 | GAGGGCAGAGGCAGCCTCCTGACATGTGGGGAC GTCGAGGAGAACCCTGGCCCA | 20 | EGRGSLLTCGDVEENPGP |
| Linker | 21 | CCTTGG | 22 | PW |
| Signal Peptide | 23 | ATGGAGTTCGGATTGAGCTGGCTGTTCCTGGTG GCAATACTCAAGGGCGTTCAATGTTCACGG | 24 | MEFGLSWLFLVAILKGVQCS R |
| PSCA(A11) V$_L$ | 25 | GACATCCAACTGACGCAAAGCCCATCTACACTCA GCGCTAGCATGGGGGACAGGGTCACAATCACGT GCTCTGCCTCAAGTTCCGTTAGGTTTATCCATTG GTATCAGCAGAAACCTGGAAAGGCCCCAAAAAG ACTGATCTATGATACCAGCAAGCTGGCTTCCGGA GTGCCCTCAAGGTTCTCAGGATCTGGCAGTGGG ACCGATTTCACCCTGACAATTAGCAGCCTTCAGC CAGAGGATTTCGCAACCTATTACTGTCAGCAATG GGGGTCCAGCCCATTCACTTTCGGCCAAGGAAC AAAGGTGGAGATAAAA | 26 | DIQLTQSPSTLSASMGDRVTI TCSASSSVRFIHWYQQKPGKA PKRLIYDTSKLASGVPSRFSG SGSGTDFTLTISSLQPEDFA TYYCQQWGSSPFTFGQGTK VEIK |
| Flex | 27 | GGCGGAGGAAGCGGAGGTGGGGGC | 28 | GGGSGGGG |

TABLE-continued

Plasmid N: pBP2208-SFG-CD40.Fv.Fv.T2A.aPSCAscFv.CD34e.CD8stm.zeta

| Fragment | SEQ ID # Nucleotide | | SEQ ID # Peptide | |
|---|---|---|---|---|
| Linker | 29 | CAGGTG | 30 | QV |
| PSCA(A11) $V_H$ | 31 | GAGGTGCAGCTCGTGGAGTATGGCGGGGGCCT GGTGCAGCCTGGGGGTAGTCTGAGGCTCTCCTG CGCTGCCTCTGGCTTTAACATTAAAGACTACTAC ATACATTGGGTGCGGCAGGCCCCAGGCAAAGGG CTCGAATGGGTGGCCTGGATTGACCCTGAGAAT GGTGACACTGAGTTTGTCCCCAAGTTTCAGGGCA GAGCCACCATGAGCGCTGACACAAGCAAAAACA CTGCTTATCTCCAAATGAATAGCCTGCGAGCTGA AGATACAGCAGTCTATTACTGCAAGACGGGAGGA TTCTGGGGCCAGGGAACTCTGGTGACAGTTAGTT CC | 32 | EVQLVEYGGGLVQPGGSLRL SCAASGFNIKDYYIHWVRQA PGKGLEWVAWIDPENGDTEF VPKFQGRATMSADTSKNTAY LQMNSLRAEDTAVYYCKTGG FWGQGTLVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 37 | GAACTTCCTACTCAGGGGACTTTCTCAAACGTTA GCACAAACGTAAGT | 38 | PAPRPPTPAPTIASQPLSLRP EACRPAAGGAVHTRGLDFAC D |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYIWAPLAGTCGVLLLSLVIT LYCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAGA TGGCGGAGGCCTACAGTGAGATTGGGATGAAAG GCGAGCGCCGGAGGGGCAAGGGGCACGATGGC CTTTACCAGGGTCTCAGTACAGCCACCAAGGACA CCTACGACGCCCTTCACATGCAAGCTCTTCCACC TCGT | 44 | RVKFSRSADAPAYQQGQNQL YNELNLGRREEYDVLDKRR GRDPEMGGKPRRKNPQEGL YNELQKDKMAEAYSEIGMK GERRRGKGHDGLYQGLSTA TKDTYDALHMQALPPR |
| STOP | | TGA | | STOP |

TABLE

Plasmid O: pBP2209-SFG-Myr-CD40.Fv.Fv.T2A.aPSCAscFv.CD34e.CD8stm.zeta

| Fragment | SEQ ID # Nucleotide | | SEQ ID # Peptide | |
|---|---|---|---|---|
| Myristoylation peptide | 51 | ATGGGGAGTAGCAAGAGCAAGCCTAAGGACCCC AGCCAGCGC | 52 | MGSSKSKPKDPSQR |
| Linker | 53 | AGAGCATGC | 54 | RAC |
| CD40 signaling domain | 55 | AAAAAGGTGGCCAAGAAGCCAACCAATAAGGCC CCCCACCCCAAGCAGGAGCCCCAGGAGATCAAT TTTCCCGACGATCTTCCTGGCTCCAACACTGCTG CTCCAGTGCAGGAGACTTTACATGGATGCAGC CGGTCACCCAGGAGGATGGCAAGAGAGTCGCA TCTCAGTGCAGGAGAGACAG | 56 | KKVAKKPTNKAPHPKQEPQE INFPDDLPGSNTAAPVQETLH GCQPVTQEDGKESRISVQER Q |
| Linker | 9 | GGATCTGGCCAATTG | 10 | GSGQL |

TABLE-continued

Plasmid O: pBP2209-SFG-Myr-CD40.Fv.Fv.T2A.aPSCAscFv.CD34e.CD8stm.zeta

| Fragment | SEQ ID # | Nucleotide | SEQ ID # | Peptide |
|---|---|---|---|---|
| FKBP$_v$· | 11 | GGCGTCCAAGTCGAAACCATTAGTCCCGGCGAT GGCAGAACATTTCCTAAAAGGGGACAAACATGTG TCGTCCATTATACAGGCATGTTGGAGGACGGCAA AAAGGTGGACAGTAGTAGAGATCGCAATAAACCT TTCAAATTCATGTTGGGAAAACAAGAAGTCATTAG GGGATGGGAGGAGGGCGTGGCTCAAATGTCCGT CGGCCAACGCGCTAAGCTCACCATCAGCCCCGA CTACGCATACGGCGCTACCGGACATCCCGGAAT TATTCCCCCTCACGCTACCTTGGTGTTTGACGTC GAACTGTTGAAGCTCGAA | 12 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFDV ELLKLE |
| Linker | 13 | GTCGAG | 14 | VE |
| FKBP$_v$ | 15 | GGAGTGCAGGTGGAGACTATCTCCCCAGGAGAC GGGCGCACCTTCCCCAAGCGCGGCCAGACCTGC GTGGTGCACTACACCGGGATGCTTGAAGATGGA AAGAAAGTTGATTCCTCCCGGGACAGAAACAAGC CCTTTAAGTTTATGCTAGGCAAGCAGGAGGTGAT CCGAGGCTGGGAAGAAGGGGTTGCCCAGATGAG TGTGGGTCAGAGAGCCAAACTGACTATATCTCCA GATTATGCCTATGGTGCCACTGGGCACCCAGGC ATCATCCCACCACATGCCACTCTCGTCTTCGATG TGGAGCTTCTAAAACTGGAA | 16 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 17 | CCGCGG | 18 | PR |
| T2A | 19 | GAGGGCAGAGGCAGCCTCCTGACATGTGGGGAC GTCGAGGAGAACCCTGGCCCA | 20 | EGRGSLLTCGDVEENPGP |
| Linker | 21 | CCTTGG | 22 | PW |
| Signal Peptide | 23 | ATGGAGTTCGGATTGAGCTGGCTGTTCCTGGTG GCAATACTCAAGGGCGTTCAATGTTCACGG | 24 | MEFGLSWLFLVAILKGVQCS R |
| PSCA(A11) V$_L$ | 25 | GACATCCAACTGACGCAAAGCCCATCTACACTCA GCGCTAGCATGGGGGACAGGGTCACAATCACGT GCTCTGCCTCAAGTTCCGTTAGGTTTATCCATTG GTATCAGCAGAAACCTGGAAAGGCCCCAAAAAG ACTGATCTATGATACCAGCAAGCTGGCTTCCGGA GTGCCCTCAAGGTTCTCAGGATCTGGCAGTGGG ACCGATTTCACCCTGACAATTAGCAGCCTTCAGC CAGAGGATTTCGCAACCTATTACTGTCAGCAATG GGGGTCCAGCCCATTCACTTTCGGCCAAGGAAC AAAGGTGGAGATAAAA | 26 | DIQLTQSPSTLSASMGDRVTI TCSASSSVRFIHWYQQKPGKA PKRLIYDTSKLASGVPSRFSG SGSGTDFTLTISSLQPEDFA TYYCQQWGSSPFTFGQGTK VEIK |
| Flex | 27 | GGCGGAGGAAGCGGAGGTGGGGGC | 28 | GGGSGGGG |
| Linker | 29 | CAGGTG | 30 | QV |
| PSCA(A11) V$_H$ | 31 | GAGGTGCAGCTCGTGGAGTATGGCGGGGGCCT GGTGCAGCCTGGGGGTAGTCTGAGGCTCTCCTG CGCTGCCTCTGGCTTTAACATTAAAGACTACTAC ATACATTGGGTGCGGCAGGCCCCAGGCAAGGG CTCGAATGGGTGGCCTGGATTGACCCTGAGAAT GGTGACACTGAGTTTGTCCCCAAGTTTCAGGGCA GAGCCACCATGAGCGCTGACACAAGCAAAAACA CTGCTTATCTCCAAATGAATAGCCTGCGAGCTGA AGATACAGCAGTCTATTACTGCAAGACGGGAGGA TTCTGGGGCCAGGGAACTCTGGTGACAGTTAGTT CC | 32 | EVQLVEYGGGLVQPGGSLRL SCAASGFNIKDYYIHWVRQA PGKGLEWVAWIDPENGDTEF VPKFQGRATMSADTSKNTAY LQMNSLRAEDTAVYYCKTGG FWGQGTLVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVS TNVS |
| CD8 stalk | 37 | GAACTTCCTACTCAGGGGACTTTCTCAAACGTTA GCACAAACGTAAGT | 38 | PAPRPPTPAPTIASQPLSLRP EACRPAAGGAVHTRGLDFACD |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYIWAPLAGTCGVLLLSLVIT LYCNHRNRRRVCKCPR |
| Linker | 41 | GTCGAC | 42 | VD |

TABLE-continued

Plasmid O: pBP2209-SFG-Myr-CD40.Fv.Fv.T2A.aPSCAscFv.CD34e.CD8stm.zeta

| Fragment | SEQ ID # Nucleotide | | SEQ ID # Peptide | |
|---|---|---|---|---|
| CD3ζ | 43 | AGAGTGAAGTTCAGCAGGAGCGCAGACGCCCCC GCGTACCAGCAGGGCCAGAACCAGCTCTATAAC GAGCTCAATCTAGGACAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAGA TGGCGGAGGCCTACAGTGAGATTGGGATGAAAG GCGAGCGCCGGAGGGGCAAGGGGCACGATGGC CTTTACCAGGGTCTCAGTACAGCCACCAAGGACA CCTACGACGCCCTTCACATGCAAGCTCTTCCACC TCGT | 44 | RVKFSRSADAPAYQQGQNQ LYNELNLGRREEYDVLDKRR GRDPEMGGKPRRKNPQEGL YNELQKDKMAEAYSEIGMK GERRRGKGHDGLYQGLSTAT KDTYDALHMQALPPR |
| STOP | | TGA | | STOP |

TABLE

Plasmid P: pBP2212-SFG-MyD88.CD40.Fv.Fv.T2A.aPSCAscFv.CD34e.CD8stm.zeta

| Fragment | SEQ ID # Nucleotide | | SEQ ID # Peptide | |
|---|---|---|---|---|
| MyD88 | 1 | ATGGCTGCAGGAGGTCCCGGCGCGGGTCTGC GGCCCCGGTCTCCTCCACATCCTCCCTTCCCCT GGCTGCTCTCAACATGCGAGTGCGGCGCCGCCT GTCTCTGTTCTTGAACGTGCGGACACAGGTGGC GGCCGACTGGACCGCGCTGGCGGAGGAGATGG ACTTTGAGTACTTGGAGATCCGGCAACTGGAGAC ACAAGCGGACCCCACTGGCAGGCTGCTGGACGC CTGGCAGGGACGCCCTGGCGCCTCTGTAGGCC GACTGCTCGATCTGCTTACCAAGCTGGGCCGCG ACGACGTGCTGCTGGAGCTGGGACCCAGCATTG AGGAGGATTGCCAAAAGTATATCTTGAAGCAGCA GCAGGAGGAGGCTGAGAAGCCTTTACAGGTGGC CGCTGTAGACAGCAGTGTCCCACGGACAGCAGA CCTCGCGCCCATCACCACACTTCATGACCCCCT GGGGCATATGCCTGAGCGTTTCGATGCCTTCATC TGCTATTGCCCCAGCGACATC | 2 | MAAGGPGAGSAAPVSSTSSL PLAALNMRVRRRLSLFLNVR TQVAADWTALAEEMDFEYLE IRQLETQADPTGRLLDAWQG RPGASVGRLLDLLTKLGRDD VLLELGPSIEEDCQKYILKQQ QEEAEKPLQVAAVDSSVPRT AELAGITTLDDPLGHMPERFD AFICYCPSDI |
| Linker | 3 | CTCGAG | 4 | LE |
| CD40 signaling domain | 55 | AAAAAGGTGGCCAAGAAGCCAACCAATAAGGCC CCCCACCCCAAGCAGGAGCCCCAGGAGATCAAT TTTCCCGACGATCTTCCTGGCTCCAACACTGCTG CTCCAGTGCAGGAGACTTTACATGGATGCCAGC CGGTCACCCAGGAGGATGGCAAAGAGAGTCGCA TCTCAGTGCAGGAGAGACAG | 56 | KKVAKKPTNKAPHPKQEPQE INFPDDLPGSNTAAPVQETLH GCQPVTQEDGKESRISVQER Q |
| Linker | 9 | GGATCTGGCCAATTG | 10 | GSGQL |
| FKBP$_{v'}$ | 11 | GGCGTCCAAGTCGAAACCATTAGTCCCGGCGAT GGCAGAACATTTCCTAAAAGGGGACAAACATGTG TCGTCCATTATACAGGCATGTTGGAGGACGGCAA AAAGGTGGACAGTAGTAGAGATCGCAATAAACCT TTCAAATTCATGTTGGGAAAACAAGAAGTCATTAG GGGATGGGAGGGGCGTGGCTCAAATGTCCGT CGGCCAACGCGCTAAGCTCACCATCAGCCCCGA CTACGCATACGGCGCTACCGGACATCCCGGAAT TATTCCCCCTCACGCTACCTTGGTGTTTGACGTC GAACTGTTGAAGCTCGAA | 12 | GVQVETISPGDGRTFPKRGQ TCVVHYTGMLEDGKKVDSSR DRNKPFKFMLGKQEVIRGWE EGVAQMSVGQRAKLTISPDY AYGATGHPGIIPPHATLVFD VELLKLE |
| Linker | 13 | GTCGAG | 14 | VE |
| FKBP$_v$ | 15 | GGAGTGCAGGTGGAGACTATCTCCCAGGAGAC GGGCGCACCTTCCCCAAGCGCGGCCAGACCTGC GTGGTGCACTACACCGGGATGCTTGAAGATGGA AAGAAAGTTGATTCCTCCCGGGACAGAAACAAGC CCTTTAAGTTTATGCTAGGCAAGCAGGAGGTGAT CCGAGGCTGGGAAGAAGGGGTTGCCCAGATGAG | 16 | GVQVETISPGDGRTFPKRGQ TCWHYTGMLEDGKKVDSSR DRNKPFKFMLGKQEVIRGWE EGVAQMSVGQRAKLTISPDY AYGATGHPGIIPPHATLVFDV ELLKLE |

TABLE-continued

Plasmid P: pBP2212-SFG-MyD88.CD40.Fv.Fv.T2A.aPSCAscFv.CD34e.CD8stm.zeta

| Fragment | SEQ ID # | Nucleotide | SEQ ID # | Peptide |
|---|---|---|---|---|
| | | TGTGGGTCAGAGAGCCAAACTGACTATATCTCCA GATTATGCCTATGGTGCCACTGGGCACCCAGGC ATCATCCCACCACATGCCACTCTCGTCTTCGATG TGGAGCTTCTAAAACTGGAA | | |
| Linker | 17 | CCGCGG | 18 | PR |
| T2A | 19 | GAGGGCAGAGGCAGCCTCCTGACATGTGGGGAC GTCGAGGAGAACCCTGGCCCA | 20 | EGRGSLLTCGDVEENPGP |
| Linker | 21 | CCTTGG | 22 | PW |
| Signal Peptide | 23 | ATGGAGTTCGGATTGAGCTGGCTGTTCCTGGTG GCAATACTCAAGGGCGTTCAATGTTCACGG | 24 | MEFGLSWLFLVAILKGVQCS R |
| PSCA(A11) V$_L$ | 25 | GACATCCAACTGACGCAAAGCCCATCTACACTCA GCGCTAGCATGGGGACAGGGTCACAATCACGT GCTCTGCCTCAAGTTCCGTTAGGTTTATCCATTG GTATCAGCAGAAACCTGGAAAGGCCCCAAAAAG ACTGATCTATGATACCAGCAAGCTGGCTTCCGGA GTGCCCTCAAGGTTCTCAGGATCTGGCAGTGGG ACCGATTTCACCCTGACAATTAGCAGCCTTCAGC CAGAGGATTTCGCAACCTATTACTGTCAGCAATG GGGGTCCAGCCCATTCACTTTCGGCCAAGGAAC AAAGGTGGAGATAAAA | 26 | DIQLTQSPSTLSASMGDRVTI TCSASSSVRFIHWYQQKPGK APKRLIYDTSKLASGVPSRFS GSGSGTDFTLTISSLQPEDFA TYYCQQWGSSPFTFGQGTK VEIK |
| Flex | 27 | GGCGGAGGAAGCGGAGGTGGGGGC | 28 | GGGSGGGG |
| Linker | 29 | CAGGTG | 30 | QV |
| PSCA(A11) V$_H$ | 31 | GAGGTGCAGCTCGTGGAGTATGGCGGGGGCCT GGTGCAGCCTGGGGGTAGTCTGAGGCTCTCCTG CGCTGCCTCTGGCTTTAACATTAAAGACTACTAC ATACATTGGGTGCGGCAGGCCCCAGGCAAGGG CTCGAATGGGTGGCCTGGATTGACCCTGAGAAT GGTGACACTGAGTTTGTCCCCAAGTTTCAGGGCA GAGCCACCATGAGCGCTGACACAAGCAAAAACA CTGCTTATCTCCAAATGAATAGCCTGCGAGCTGA AGATACAGCAGTCTATTACTGCAAGACGGGAGGA TTCTGGGGCCAGGGAACTCTGGTGACAGTTAGTT CC | 32 | EVQLVEYGGGLVQPGGSLRL SCAASGFNIKDYYIHWVRQA PGKGLEWVAWIDPENGDTEF VPKFQGRATMSADTSKNTAY LQMNSLRAEDTAVYYCKTGG FWGQGTLVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 37 | GAACTTCCTACTCAGGGGACTTTCTCAAACGTTA GCACAAACGTAAGT | 38 | PAPRPPTPAPTIASQPLSLRP EACRPAAGGAVHTRGLDFAC D |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYIWAPLAGTCGVLLLSLVIT LYCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAGA TGGCGGAGGCCTACAGTGAGATTGGGATGAAAG GCGAGCGCCGGAGGGGCAAGGGGCACGATGGC CTTTACCAGGGTCTCAGTACAGCCACCAAGGACA CCTACGACGCCCTTCACATGCAAGCTCTTCCACC TCGT | 44 | RVKFSRSADAPAYQQGQNQ LYNELNLGRREEYDVLDKRR GRDPEMGGKPRRKNPQEGL YNELQKDKMAEAYSEIGMKG ERRRGKGHDGLYQGLSTATK DTYDALHMQALPPR |
| STOP | | TGA | | STOP |

TABLE

Plasmid Q: pBP414--pSFG-FKBP.ΔC9.T2A-αCD19.Q.CD8stm.ζ

| Fragment | SEQ ID # | Nucleotide | SEQ ID # | Peptide |
|---|---|---|---|---|
| Leader | 57 | ATGCTCGAGATGCTGGAG | 58 | MLEMLE |
| FKBP" | 59 | GGAGTGCAGGTGGAGACTATTAGCCCCGGAGAT GGCAGAACATTCCCCAAAAGAGGACAGACTTGC GTCGTGCATTATACTGGAATGCTGGAAGACGGCA AGAAGGTGGACAGCAGCCGGGACCGAAACAAGC CCTTCAAGTTCATGCTGGGGAAGCAGGAAGTGAT CCGGGGCTGGGAGGAAGGAGTCGCACAGATGT CAGTGGGACAGAGGGCCAAACTGACTATTAGCC CAGACTACGCTTATGGAGCAACCGGCCACCCCG GGATCATTCCCCCTCATGCTACACTGGTCTTCGA TGTGGAGCTGCTGAAGCTGGAA | 60 | GVQVETISPGDGRTFPKRGQ TCVVHYTGMLEDGKKFDSSR DRNKPFKFMLGKQEVIRGWE EGVAQMSVGQRAKLTISPDY AYGATGHPGIIPPHATLVFD VELLKLE |
| Linker | 61 | AGCGGAGGAGGATCCGGAGTGGAC | 62 | SGGGSGVD |
| Δcaspase9 | 63 | GGGTTTGGAGATGTGGGAGCCCTGGAATCCCTG CGGGGCAATGCCGATCTGGCTTACATCCTGTCTA TGGAGCCTTGCGGCCACTGTCTGATCATTAACAA TGTGAACTTCTGCAGAGAGCGGGCTGCGGAC CAGACAGGATCCAATATTGACTGTGAAAAGCTG CGGAGAAGGTTCTCTAGTCTGCACTTTATGGTCG AGGTGAAAGGCGATCTGACCGCTAAGAAAATGG TGCTGGCCCTGCTGGAACTGGCTCGGCAGGACC ATGGGGCACTGGATTGCTGCGTGGTCGTGATCC TGAGTCACGGCTGCCAGGCTTCACATCTGCAGTT CCCTGGGGCAGTCTATGGAACTGACGGCTGTCC AGTCAGCGTGGAGAAGATCGTGAACATCTTCAAC GGCACCTCTTGCCCAAGTCTGGGCGGGAAGCCC AAACTGTTCTTTATTCAGGCCTGTGGAGGCGAGC AGAAAGATCACGGCTTCGAAGTGGCTAGCACCT CCCCCGAGGACGAATCACCTGGAAGCAACCCTG AGCCAGATGCAACCCCCTTCCAGGAAGGCCTGA GGACATTTGACCAGCTGGATGCCATCTCAAGCCT GCCCACACCTTCTGACATTTTCGTCTCTTACAGTA CTTTCCCTGGATTTGTGAGCTGGCGCGATCCAAA GTCAGGCAGCTGGTACGTGGAGACACTGGACGA TATCTTTGAGCAGTGGGCCCATTCTGAAGACCTG CAGAGTCTGCTGCTGCGAGTGGCCAATGCTGTC TCTGTGAAGGGGATCTACAAACAGATGCCAGGAT GCTTCAACTTTCTGAGAAAGAAACTGTTCTTTAAG ACCTCCGCATCTAGGGCC | 64 | GFGDVGALESLRGNADLAYIL SMEPCGHCLIINNVNFCRES GLRTRTGSNIDCEKLRRRFS SLHFMVEVKGDLTAKKMVLA LLELARQDHGALDCCVVVIL SHGCQASHLQFPGAVYGTDG CPVSVEKIVNIFNGTSCPSL GGKPKLFFIQACGGEQKDHG FEVASTSPEDESPGSNPEPD ATPFQEGLRTFDQLDAISSL PTPSDIFVSYSTFPGFVSWR DPKSGSWYVETLDDIFEQWA HSEDLQSLLLRVANAVSVKG IYKQMPGCFNFLRKKLFFKT SASRA |
| Linker | 17 | CCGCGG | 18 | PR |
| T2A | 65 | GAAGGCCGAGGGAGCCTGCTGACATGTGGCGAT GTGGAGGAAAACCCAGGACCA | 20 | EGRGSLLTCGDVEENPGP |
| Linker | 66 | CCATGG | 22 | PW |
| Signal Peptide | 67 | ATGGAGTTTGGACTTTCTTGGTTGTTTTTGGTGG CAATTCTGAAGGGTGTCCAGTGTAGCAGG | 24 | MEFGLSWLFLVAILKGVQCS R |
| FMC63 VL | 68 | GACATCCAGATGACACAGACTACATCCTCCCTGT CTGCCTCTCTGGGAGACAGAGTCACCATCAGTTG CAGGGCAAGTCAGGACATTAGTAAATATTTAAATT GGTATCAGCAGAAACCAGATGGAACTGTTAAACT CCTGATCTACCATACATCAAGATTACACTCAGGA GTCCCATCAAGGTTCAGTGGCAGTGGGTCTGGA ACAGATTATTCTCTCACCATTAGCAACCTGGAGC AAGAAGATATTGCCACTTACTTTTGCCAACAGGG TAATACGCTTCCGTACACGTTCGGAGGGGGGAC TAAGTTGGAAATAACA | 69 | DIQMTQTTSSLSASLGDRVTI SCRASQDISKYLNWYQQKPD GTVKLLIYHTSRLHSGVPSR FSGSGSGTDYSLTISNLEQE DIATYFCQQGNTLPYTFGGG TKLEIT |
| Flex | 27 | GGCGGAGGAAGCGGAGGTGGGGGC | 28 | GGGSGGGG |
| FMC63 VH | 70 | GAGGTGAAACTGCAGGAGTCAGGACCTGGCCTG GTGGCGCCCTCACAGAGCCTGTCCGTCACATGC ACTGTCTCAGGGGTCTCATTACCCGACTATGGTG TAAGCTGGATTCGCCAGCCTCCACGAAAGGGTC TGGAGTGGCTGGGAGTAATATGGGGTAGTGAAA CCACATACTATAATTCAGCTCTCAAATCCAGACTG ACCATCATCAAGGACAACTCCAAGAGCCAAGTTT TCTTAAAAATGAACAGTCTGCAAACTGATGACAC | 71 | EVKLQESGPGLVAPSQSLSV TCTVSGVSLPDYGVSWIRQP PRKGLEWLGVIWGSETTYYN SALKSRLTIIKDNSKSQVFLK MNSLQTDDTAIYYCAKHYYY GGSYAMDYWGQGTSVTVSS |

TABLE-continued

Plasmid Q: pBP414--pSFG-FKBP.ΔC9.T2A-αCD19.Q.CD8stm.ζ

| Fragment | SEQ ID # Nucleotide | | SEQ ID # Peptide | |
|---|---|---|---|---|
| | AGCCATTTACTACTGTGCCAAACATTATTACTACG GTGGTAGCTATGCTATGGACTACTGGGGTCAAG GAACCTCAGTCACCGTCTCCTCA | | | |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 72 | CCCGCCCCAAGACCCCCCACACCTGCGCCGACC ATTGCTTCTCAACCCCTGAGTTTGAGACCCGAGG CCTGCCGGCCAGCTGCCGGCGGGGCCGTGCAT ACAAGAGGACTCGATTTCGCTTGCGAC | 38 | PAPRPPTPAPTIASQPLSLRP EACRPAAGGAVHTRGLDFAC D |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYI- WAPLAGTCGVLLLSLVITL YCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAGA TGGCGGAGGCCTACAGTGAGATTGGGATGAAAG GCGAGCGCGGAGGGGCAAGGGGCACGATGGC CTTTACCAGGGTCTCAGTACAGCCACCAAGGACA CCTACGACGCCCTTCACATGCAAGCTCTTCCACC TCGT | 44 | RVKFSRSADAPAYQQGQNQ LYNELNLGRREEYDVLDKRR GRDPEMGGKPRRKNPQEGL YNELQKDKMAEAYSEIGMKG ERRRGKGHDGLYQGLSTATK DTYDALHMQALPPR |

TABLE

Plasmid R: pBP0844--pSFG-FKBP.ΔC9.T2A-αCD19.Q.CD8stm.ζ.2A-MC

| Fragment | SEQ ID # Nucleotide | | SEQ ID # Peptide | |
|---|---|---|---|---|
| Leader | 57 | ATGCTCGAGATGCTGGAG | 58 | MLEMLE |
| FKBP" | 59 | GGAGTGCAGGTGGAGACTATTAGCCCCGGAGAT GGCAGAACATTCCCCAAAAGAGGACAGACTTGC GTCGTGCATTATACTGGAATGCTGGAAGACGGCA AGAAGGTGGACAGCAGCCGGGACCGAAACAAGC CCTTCAAGTTCATGCTGGGGAAGCAGGAAGTGAT CCGGGGCTGGGAGGAAGGAGTCGCACAGATGT CAGTGGGACAGAGGGCCAAACTGACTATTAGCC CAGACTACGCTTATGGAGCAACCGGCCACCCCG GGATCATTCCCCCTCATGCTACACTGGTCTTCGA TGTGGAGCTGCTGAAGCTGGAA | 60 | GVQVETISPGDGRTFPKRGQ TCVVHYTGMLEDGKKFDSSR DRNKPFKFMLGKQEVIRGWE EGVAQMSVGQRAKLTISPDY AYGATGHPGIIPPHATLVFD VELLKLE |
| Linker | 61 | AGCGGAGGAGGATCCGGAGTGGAC | 62 | SGGGSGVD |
| Δcaspase9 | 63 | GGGTTTGGAGATGTGGGAGCCCTGGAATCCCTG CGGGGCAATGCCGATCTGGCTTACATCCTGTCTA TGGAGCCTTGCGGCCACTGTCTGATCATTAACAA TGTGAACTTCTGCAGAGAGAGCGGGCTGCGGAC CAGAACAGGATCCAATATTGACTGTGAAAAGCTG CGGAGAAGGTTCTCTAGTCTGCACTTTATGGTCG AGGTGAAAGGCGATCTGACCGCTAAGAAAATGG TGCTGGCCCTGCTGGAACTGGCTCGGCAGGACC ATGGGGCACTGGATTGCTGCGTGGTCGTGATCC TGAGTCACGGCTGCCAGGCTTCACATCTGCAGTT CCCTGGGGCAGTCTATGGAACTGACGGCTGTCC AGTCAGCGTGGAGAAGATCGTGAACATCTTCAAC GGCACCTCTTGCCCAAGTCTGGGCGGGAAGCCC AAACTGTTCTTTATTCAGGCCTGTGGAGGCGAGC AGAAAGATCACGGCTTCGAAGTGGCTAGCACCT CCCCCGAGGACGAATCACCTGGAAGCAACCCTG AGCCAGATGCAACCCCCTTCCAGGAAGGCCTGA | 64 | GFGDVGALESLRGNADLAYIL SMEPCGHCLIINNVNFCRES GLRTRTGSNIDCEKLRRRFS SLHFMVEVKGDLTAKKMVLA LLELARQDHGALDCCVVVIL SHGCQASHLQFPGAVYGTDG CPVSVEKIVNIFNGTSCPSLG GKPKLFFIQACGGEQKDHGF EVASTSPEDESPGSNPEPDA TPFQEGLRTFDQLDAISSLPT PSDIFVSYSTFPGFVSWRDP KSGSWYVETLDDIFEQWAHS EDLQSLLLRVANAVSVKGIYK QMPGCFNFLRKKLFFKTSAS RA |

| | | TABLE-continued | | |
|---|---|---|---|---|
| Plasmid R: pBP0844--pSFG-FKBP.ΔC9.T2A-αCD19.Q.CD8stm.ζ.2A-MC | | | | |
| Fragment | SEQ ID # | Nucleotide | SEQ ID # | Peptide |
| | | GGACATTTGACCAGCTGGATGCCATCTCAAGCCT GCCCACACCTTCTGACATTTTCGTCTCTTACAGTA CTTTTCCCTGGATTTGTGAGCTGGCGCGATCCAAA GTCAGGCAGCTGGTACGTGGAGACACTGGACGA TATCTTTGAGCAGTGGGCCCATTCTGAAGACCTG CAGAGTCTGCTGCTGCGAGTGGCCAATGCTGTC TCTGTGAAGGGGATCTACAAACAGATGCCAGGAT GCTTCAACTTTCTGAGAAAGAAACTGTTCTTTAAG ACCTCCGCATCTAGGGCC | | |
| Linker | 17 | CCGCGG | 18 | PR |
| T2A | 65 | GAAGGCCGAGGGAGCCTGCTGACATGTGGCGAT GTGGAGGAAAACCCAGGACCA | 20 | EGRGSLLTCGDVEENPGP |
| Linker | 66 | CCATGG | 22 | PW |
| Signal Peptide | 67 | ATGGAGTTTGGACTTTCTTGGTTGTTTTTGGTGG CAATTCTGAAGGGTGTCCAGTGTAGCAGG | 24 | MEFGLSWLFLVAILKGVQCS R |
| FMC63 VL | 68 | GACATCCAGATGACACAGACTACATCCTCCCTGT CTGCCTCTCTGGGAGACAGAGTCACCATCAGTTG CAGGGCAAGTCAGGACATTAGTAAATATTTAAATT GGTATCAGCAGAAACCAGATGGAACTGTTAAACT CCTGATCTACCACACATCAAGATTACACTCAGGA GTCCCATCAAGGTTCAGTGGCAGTGGGTCTGGA ACAGATTATTCTCTCACCATTAGCAACCTGGAGC AAGAAGATATTGCCACTTACTTTTGCCAACAGGG TAATACGCTTCCGTACACGTTCGGAGGGGGGAC TAAGTTGGAAATAACA | 69 | DIQMTQTTSSLSASLGDRVTI SCRASQDISKYLNWYQQKPD GTVKLLIYHTSRLHSGVPSRF SGSGSGTDYSLTISNLEQEDI ATYFCQQGNTLPYTFGGGTK LEIT |
| Flex | 27 | GGCGGAGGAAGCGGAGGTGGGGGC | 28 | GGGSGGGG |
| FMC63 VH | 70 | GAGGTGAAACTGCAGGAGTCAGGACCTGGCCTG GTGGCGCCCTCACAGAGCCTGTCCGTCACATGC ACTGTCTCAGGGGTCTCATTACCCGACTATGGTG TAAGCTGGATTCGCCAGCCTCCACGAAAGGGTC TGGAGTGGCTGGGAGTAATATGGGGTAGTGAAA CCACATACTATAATTCAGCTCTCAAATCCAGACTG ACCATCATCAAGGACAACTCCAAGAGCCAAGTTT TCTTAAAAATGAACAGTCTGCAAACTGATGACAC AGCCATTTACTACTGTGCCAAACATTATTACTACG GTGGTAGCTATGCTATGGACTACTGGGGTCAAG GAACCTCAGTCACCGTCTCCTCA | 71 | EVKLQESGPGLVAPSQSLSV TCTVSGVSLPDYGVSWIRQP PRKGLEWLGVIWGSETTYYN SALKSRLTIIKDNSKSQVFLK MNSLQTDDTAIYYCAKHYYY GGSYAMDYWGQGTSVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 72 | CCCGCCCCAAGACCCCCCACACCTGCGCCGACC ATTGCTTCTCAACCCCTGAGTTTGAGACCCGAGG CCTGCCGGCCAGCTGCCGGCGGGGCCGTGCAT ACAAGAGGACTCGATTTCGCTTGCGAC | 38 | PAPRPPTPAPTIASQPLSRP EACRPAAGGAVHTRGLDFAC D |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYIWAPLAGTCGVLLLSLVIT LYCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAGA TGGCGGAGGCCTACAGTGAGATTGGGATGAAAG GCGAGCGCCGGAGGGGCAAGGGGCACGATGGC CTTTACCAGGGTCTCAGTACAGCCACCAAGGACA CCTACGACGCCCTTCACATGCAAGCTCTTCCACC TCGT | 44 | RVKFSRSADAPAYQQGQNQ LYNELNLGRREEYDVLDKRR GRDPEMGGKPRRKNPQEGL YNELQKDKMAEAYSEIGMKG ERRRGKGHDGLYQGLSTATK DTYDALHMQALPPR |
| Leader | 57 | ATGCTCGAGATGCTGGAG | 58 | MLEMLE |

TABLE-continued

Plasmid R: pBP0844--pSFG-FKBP.ΔC9.T2A-αCD19.Q.CD8stm.ζ.2A-MC

| Fragment | SEQ ID # | Nucleotide | SEQ ID # | Peptide |
|---|---|---|---|---|
| P2A | 73 | GCTACTAACTTCAGCCTGCTGAAGCAGGCTGGA GACGTGGAGGAGAACCCCGGGCCT | 74 | ATNFSLLKQAGDVEENPGP |
| MyD88 | 1 | ATGGCTGCAGGAGGTCCCGGCGCGGGGTCTGC GGCCCCGGTCTCCTCCACATCCTCCCTTCCCCT GGCTGCTCTCAACATGCGAGTGCGGCGCCGCCT GTCTCTGTTCTTGAACGTGCGGACACAGGTGGC GGCCGACTGGACCGCGCTGGCGGAGGAGATGG ACTTTGAGTACTTGGAGATCCGGCAACTGGAGAC ACAAGCGGACCCCACTGGCAGGCTGCTGGACGC CTGGCAGGGACGCCCTGGCGCCTCTGTAGGCC GACTGCTCGATCTGCTTACCAAGCTGGGCCGCG ACGACGTGCTGCTGGAGCTGGGACCCAGCATTG AGGAGGATTGCCAAAAGTATATCTTGAAGCAGCA GCAGGAGGAGGCTGAGAAGCCTTTACAGGTGGC CGCTGTAGACAGCAGTGTCCCACGGACAGCAGA GCTGGCGGGCATCACCACACTTGATGACCCCCT GGGGCATATGCCTGAGCGTTTCGATGCCTTCATC TGCTATTGCCCCAGCGACATC | 2 | MAAGGPGAGSAAPVSSTSSL PLAALNMRVRRRLSLFLNVR TQVAADWTALAEEMDFEYLE IRQLETQADPTGRLLDAWQG RPGASVGRLLDLLTKLGRDD VLLELGPSIEEDCQKYILKQQ QEEAEKPLQVAAVDSSVPRT AELAGITTLDDPLGHMPERFD AFICYCPSDI |
| Linker | 13 | GTCGAG | 14 | VE |
| CD40 | 75 | AAAAAGGTGGCCAAGAAGCCAACCAATAAGGCC CCCCACCCCAAGCAGGAGCCCCAGGAGATCAAT TTTCCCGACGATCTTCCTGGCTCCAACACTGCTG CTCCAGTGCAGGAGACTTTACATGGATGCCAACC GGTCACCCAGGAGGATGGCAAAGAGAGTCGCAT CTCAGTGCAGGAGAGACAG | 56 | KKVAKKPTNKAPHPKQEPQE INFPDDLPGSNTAAPVQETLH GCQPVTQEDGKESRISVQER Q |

TABLE

Plasmid S: pBP2103--pSFG-FKBP.ΔC9.T2A-αCD19.Q.CD8stm.ζ.2A-MC

| Fragment | SEQ ID # | Nucleotide | SEQ ID # | Peptide |
|---|---|---|---|---|
| Leader | 57 | ATGCTCGAGATGCTGGAG | 58 | MLEMLE |
| FKBP" | 59 | GGAGTGCAGGTGGAGACTATTAGCCCCGGAGAT GGCAGAACATTCCCCAAAAGAGGACAGACTTGC GTCGTGCATTATACTGGAATGCTGGAAGACGCA AGAAGGTGGACAGCAGCCGGGACCGAAACAAGC CCTTCAAGTTCATGCTGGGGAAGCAGGAAGTGAT CCGGGGCTGGGAGGAAGGAGTCGCACAGATGT CAGTGGGACAGAGGGCCAAACTGACTATTAGCC CAGACTACGCTTATGGCAACCGGCCACCCCG GGATCATTCCCCCTCATGCTACACTGGTCTTCGA TGTGGAGCTGCTGAAGCTGGAA | 60 | GVQVETISPGDGRTFPKRGQ TCVVHYTGMLEDGKKFDSSR DRNKPFKFMLGKQEVIRGWE EGVAQMSVGQRAKLTISPDY AYGATGHPGIIPPHATLVFDV ELLKLE |
| Linker | 61 | AGCGGAGGAGGATCCGGAGTGGAC | 62 | SGGGSGVD |
| Δcaspase9 | 63 | GGGTTTGGAGATGTGGGAGCCCTGGAATCCCTG CGGGGCAATGCCGATCTGGCTTACATCCTGTCTA TGGAGCCTTGCGGCCACTGTCTGATCATTAACAA TGTGAACTTCTGCAGAGAGAGCGGGCTGCGGAC CAGAACAGGATCCAATATTGACTGTGAAAAGCTG CGGAGAAGGTTCTCTAGTCTGCACTTTATGGTCG AGGTGAAAGGCGATCTGACCGCTAAGAAAATGG TGCTGGCCCTGCTGGAACTGGCTCGGCAGGACC ATGGGGCACTGGATTGCTGCGTGGTCGTGATCC TGAGTCACGGCTGCCAGGCTTCACATCTGCAGTT CCCTGGGGCAGTCTATGGAACTGACGGCTGTCC AGTCAGCGTGGAGAAGATCGTGAACATCTTCAAC GGCACCTCTTGCCCAAGTCTGGGCGGGAAGCCC AAACTGTTCTTTATTCAGGCCTGTGGAGGCGAGC AGAAAGATCACGGCTTCGAAGTGGCTAGCACCT CCCCCGAGGACGAATCACCTGGAAGCAACCCTG AGCCAGATGCAACCCCCTTCCAGGAAGGCCTGA GGACATTTGACCAGCTGGATGCCATCTCAAGCCT GCCCACACCTTCTGACATTTTCGTCTCTTACAGTA CTTTCCCTGGATTTGTGAGCTGGCGCGATCCAAA | 64 | GFGDVGALESLRGNADLAYIL SMEPCGHCLIINNVNFCRES GLRTRTGSNIDCEKLRRRFS SLHFMVEVKGDLTAKKMVLA LLELARQDHGALDCCVVIL SHGCQASHLQFPGAVYGTDG CPVSVEKIVNIFNGTSCPSL GGKPKLFFIQACGGEQKDHG FEVASTSPEDESPGSNPEPD ATPFQEGLRTFDQLDAISSL PTPSDIFVSYSTFPGFVSWR DPKSGSWYVETLDDIFEQWA HSEDLQSLLLRVANAVSVKG IYKQMPGCFNFLRKKLFFKT SASRA |

TABLE-continued

Plasmid S: pBP2103--pSFG-FKBP.ΔC9.T2A-αCD19.Q.CD8stm.ζ.2A-MC

| Fragment | SEQ ID # Nucleotide | | SEQ ID # Peptide | |
|---|---|---|---|---|
| | | GTCAGGCAGCTGGTACGTGGAGACACTGGACGA TATCTTTGAGCAGTGGGCCCATTCTGAAGACCTG CAGAGTCTGCTGCTGCGAGTGGCCAATGCTGTC TCTGTGAAGGGGATCTACAAACAGATGCCAGGAT GCTTCAACTTTCTGAGAAAGAAACTGTTCTTTAAG ACCTCCGCATCTAGGGCC | | |
| Linker | 17 | CCGCGG | 18 | PR |
| T2A | 65 | GAAGGCCGAGGGAGCCTGCTGACATGTGGCGAT GTGGAGGAAAACCCAGGACCA | 20 | EGRGSLLTCGDVEENPGP |
| Linker | 66 | CCATGG | 22 | PW |
| Signal Peptide | 67 | ATGGAGTTTGGACTTTCTTGGTTGTTTTTGGTGG CAATTCTGAAGGGTGTCCAGTGTAGCAGG | 24 | MEFGLSWLFLVAILKGVQCS R |
| FMC63 VL | 68 | GACATCCAGATGACACAGACTACATCCTCCCTGT CTGCCTCTCTGGGAGACAGAGTCACCATCAGTTG CAGGGCAAGTCAGGACATTAGTAAATATTTAAAT TGGTATCAGCAGAAACCAGATGGAACTGTTAAAC TCCTGATCTACCATACATCAAGATTACACTCAGG AGTCCCATCAAGGTTCAGTGGCAGTGGGTCTGGA ACAGATTATTCTCTCACCATTAGCAACCTGGAGC AAGAAGATATTGCCACTTACTTTTGCCAACAGGG TAATACGCTTCCGTACACGTTCGGAGGGGGGAC TAAGTTGGAAATAACA | 69 | DIQMTQTTSSLSASLGDRVTI SCRASQDISKYLNWYQQKPD GTVKLLIYHTSRLHSGVPSRF SGSGSGTDYSLTISNLEQEDI ATYFCQQGNTLPYTFGGGTK LEIT |
| Flex | 27 | GGCGGAGGAAGCGGAGGTGGGGGC | 28 | GGGSGGGG |
| FMC63 VH | 70 | GAGGTGAAACTGCAGGAGTCAGGACCTGGCCTG GTGGCGCCCTCACAGAGCCTGTCCGTCACATGC ACTGTCTCAGGGGTCTCATTACCCGACTATGGTG TAAGCTGGATTCGCCAGCCTCCACGAAAGGGTC TGGAGTGGCTGGGAGTAATATGGGGTAGTGAAA CCACATACTATAATTCAGCTCTCAAATCCAGACT GACCATCATCAAGGACAACTCCAAGAGCCAAGTT TTCTTAAAAATGAACAGTCTGCAAACTGATGACA CAGCCATTTACTACTGTGCCAAACATTATTACTA CGGTGGTAGCTATGCTATGGACTACTGGGGTCAA GGAACCTCAGTCACCGTCTCCTCA | 71 | EVKLQESGPGLVAPSQSLSV TCTVSGVSLPDYGVSWIRQP PRKGLEWLGVIWGSETTYYN SALKSRLTIIKDNSKSQVFLK MNSLQTDDTAIYYCAKHYYY GGSYAMDYWGQGTSVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 72 | CCCGCCCCAAGACCCCCCACACCTGCGCCGACC ATTGCTTCTCAACCCCTGAGTTTGAGACCCGAG GCCTGCCGGCCAGCTGCCGGCGGGGCCGTGCAT ACAAGAGGACTCGATTTCGCTTGCGAC | 38 | PAPRPPTPAPTIASQPLSLRP EACRPAAGGAVHTRGLDFAC D |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYIWAPLAGTCGVLLLSLVITL YCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAG ATGGCGGAGGCCTACAGTGAGATTGGGATGAAA GGCGAGCGCCGGAGGGGCAAGGGGCACGATGGC CTTTACCAGGGTCTCAGTACAGCCACCAAGGAC ACCTACGACGCCCTTCACATGCAAGCTCTTCCA CCTCGT | 44 | RVKFSRSADAPAYQQGQNQ LYNELNLRGRREEYDVLDKR RGRDPEMGGKPRRKNPQEGL YNELQKDKMAEAYSEIGMKG ERRRGKGHDGLYQGLSTATK DTYDALHMQALPPR |
| Leader | 57 | ATGCTCGAGATGCTGGAG | 58 | MLEMLE |
| P2A | 73 | GCTACTAACTTCAGCCTGCTGAAGCAGGCTGGA GACGTGGAGGAGAACCCCGGGCCT | 74 | ATNFSLLKQAGDVEENPGP |

TABLE-continued

Plasmid S: pBP2103--pSFG-FKBP.ΔC9.T2A-αCD19.Q.CD8stm.ζ.2A-MC

| Fragment | SEQ ID # | Nucleotide | SEQ ID # | Peptide |
|---|---|---|---|---|
| Myristoylation targeting peptide | 51 | ATGGGGAGTAGCAAGAGCAAGCCTAAGGACCCC AGCCAGCGC | 76 | MGSSKSKPKDPSQRLD |
| MyD88 | 1 | ATGGCTGCAGGAGGTCCCGGCGCGGGGTCTGC GGCCCCGGTCTCCTCCACATCCTCCCTTCCCCT GGCTGCTCTCAACATGCGAGTGCGGCGCCGCCT GTCTCTGTTCTTGAACGTGCGGACACAGGTGGC GGCCGACTGGACCGCGCTGGCGGAGGAGATGGA CTTTGAGTACTTGGAGATCCGGCAACTGGAGAC ACAAGCGGACCCCACTGGCAGGCTGCTGGACGT CTGGCAGGGACGCCCTGGCGCCTCTGTAGGCC GACTGCTCGATCTGCTTACCAAGCTGGGCCGCG ACGACGTGCTGCTGGAGCTGGGACCCAGCATTG AGGAGGATTGCCAAAAGTATATCTTGAAGCAGC AGCAGGAGGAGGCTGAGAAGCCTTTACAGGTGG CCGCTGTAGACAGCAGTGTCCCACGGACAGCAG AGCTGGCGGGCATCACCACACTTGATGACCCCC TGGGGCATATGCCTGAGCGTTTCGATGCCTTCA TCTGCTATTGCCCCAGCGACATC | 2 | MAAGGPGAGSAAPVSSTSSL PLAALNMRVRRRLSLFLNVR TQVAADWTALAEEMDFEYLE IRQLETQADPTGRLLDAWQG RPGASVGRLLDLLTKLGRDD VLLELGPSIEEDCQKYILKQ QQEEAEKPLQVAAVDSSVPR TAELAGITTLDDPLGHMPER FDAFICYCPSDI |
| Linker | 77 | GCGGCCGCT | 78 | AAA |
| 41BB | 79 | AAACGGGCAGAAAGAAACTCCTGTATATATTCA AACAACCATTTATGAGACCAGTACAAACTACTCA AGAGGAAGATGGCTGTAGCTGCCGATTTCCAGAA GAAGAAGAAGGAGGATGTGAACTG | 80 | KRGRKKLLYIFKQPFMRPVQ TTQEEDGCSCRFPEEEEGG CEL |

TABLE

Plasmid T: pBP2104--pSFG-FKBP.ΔC9.T2A-αCD19.Q.CD8stm.ζ.2A-MC

| Fragment | SEQ ID # | Nucleotide | SEQ ID # | Peptide |
|---|---|---|---|---|
| Leader | 57 | ATGCTCGAGATGCTGGAG | 58 | |
| FKBP" | 59 | GGAGTGCAGGTGGAGACTATTAGCCCCGGAGAT GGCAGAACATTCCCCAAAAGAGGACAGACTTGC GTCGTGCATTATACTGGAATGCTGGAAGACGGC AAGAAGGTGGACAGCAGCCGGGACCGAAACAAG CCCTTCAAGTTCATGCTGGGGAAGCAGGAAGTG ATCCGGGGCTGGGAGGAAGGAGTCGCACAGATG TCAGTGGGACAGAGGGCCAAACTGACTATTAGC CCAGACTACGCTTATGGAGCAACCGGCCACCCC GGGATCATTCCCCCTCATGCTACACTGGTCTTC GATGTGGAGCTGCTGAAGCTGGAA | 60 | |
| Linker | 61 | AGCGGAGGAGGATCCGGAGTGGAC | 62 | SGGGSGVD |
| Δcaspase9 | 63 | GGGTTTGGAGATGTGGGAGCCCTGGAATCCCTG CGGGGCAATGCCGATCTGGCTTACATCCTGTCTA TGGAGCCTTGCGGCCACTGTCTGATCATTAACAA TGTGAACTTCTGCAGAGAGAGCGGGCTGCGGACC AGAACAGGATCCAATATTGACTGTGAAAAGCTGC GGAGAAGGTTCTCTAGTCTGCACTTTATGGTCG AGGTGAAAGGCGATCTGACCGCTAAGAAAATGG TGCTGGCCCTGCTGGAACTGGCTCGACAGGACC ATGGGGCACTGGATTGCTGCGTGGTCGTGATCC TGAGTCACGGCTGCCAGGCTTCACATCTGCAGT TCCCTGGGGCAGTCTATGGAACTGACGGCTGTC CAGTCAGCGTGGAGAAGATCGTGAACATCTTCA ACGGCACCTCTTGCCCAAGTCTGGGCGGAAGC CCAAACTGTTCTTTATTCAGGCCTGTGGAGGCG AGCAGAAAGATCACGGCTTCGAAGTGGCTAGCA CCTCCCCCGAGGACGAATCACCTGGAAGCAACC CTGAGCCAGATGCAACCCCCTTCCAGGAAGGCC TGAGGACATTTGACCAGCTGGATGCCATCTCAA GCCTGCCCACACCTTCTGACATTTTCGTCTCTT ACAGTACTTTCCCTGGATTTGTGAGCTGGCGCG ATCCAAAGTCAGGCAGCTGGTACGTGGAGACAC | 64 | GFGDVGALESLRGNADLAYIL SMEPCGHCLIINNVNFCRES GLRTRTGSNIDCEKLRRRFS SLHFMVEVKGDLTAKKMVLA LLELARQDHGALDCCVVVILS HGCQASHLQFPGAVYGTDG CPVSVEKIVNIFNGTSCPSLG GKPKLFFIQACGGEQKDHGF EVASTSPEDESPGSNPEPDA TPFQEGLRTFDQLDAISSLPT PSDIFVSYSTFPGFVSWRDP KSGSWYVETLDDIFEQWAHS EDLQSLLLRVANAVSVKGIYK QMPGCFNFLRKKLFFKTSAS RA |

TABLE-continued

Plasmid T: pBP2104--pSFG-FKBP.ΔC9.T2A-αCD19.Q.CD8stm.ζ.2A-MC

| Fragment | SEQ ID # | Nucleotide | SEQ ID # | Peptide |
|---|---|---|---|---|
| | | TGGACGATATCTTTGAGCAGTGGGCCCATTCTG AAGACCTGCAGAGTCTGCTGCTGCGAGTGGCCA ATGCTGTCTCTGTGAAGGGGATCTACAAACAGA TGCCAGGATGCTTCAACTTTCTGAGAAAGAAAC TGTTCTTTAAGACCTCCGCATCTAGGGCC | | |
| Linker | 17 | CCGCGG | 18 | PR |
| T2A | 65 | GAAGGCCGAGGGAGCCTGCTGACATGTGGCGAT GTGGAGGAAAACCCAGGACCA | 20 | EGRGSLLTCGDVEENPGP |
| Linker | 66 | CCATGG | 22 | PW |
| Signal Peptide | 67 | ATGGAGTTTGGACTTTCTTGGTTGTTTTTGGTGG CAATTCTGAAGGGTGTCCAGTGTAGCAGG | 24 | MEFGLSWLFLVAILKGVQCS R |
| FMC63 VL | 68 | GACATCCAGATGACACAGACTACATCCTCCCTGT CTGCCTCTCTGGGAGACAGAGTCACCATCAGTTG CAGGGCAAGTCAGGACATTAGTAAATATTTAAATT GGTATCAGCAGAAACCAGATGGAACTGTTAAACT CCTGATCTACCATACATCAAGATTACACTCAGGA GTCCCATCAAGGTTCAGTGGCAGTGGGTCTGGA ACAGATTATTCTCTCACCATTAGCAACCTGGAGC AAGAAGATATTGCCACTTACTTTTGCCAACAGGG TAATACGCTTCCGTACACGTTCGGAGGGGGGAC TAAGTTGGAAATAACA | 69 | DIQMTQTTSSLSASLGDRVTI SCRASQDISKYLNWYQQKPD GTVKLLIYHTSRLHSGVPSRF SGSGSGTDYSLTISNLEQEDI ATYFCQQGNTLPYTFGGGTK LEIT |
| Flex | 27 | GGCGGAGGAAGCGGAGGTGGGGC | 28 | GGGSGGGG |
| FMC63 VH | 70 | GAGGTGAAACTGCAGGAGTCAGGACCTGGCCTG GTGGCGCCCTCACAGAGCCTGTCCGTCACATGC ACTGTCTCAGGGGTCTCATTACCCGACTATGGTG TAAGCTGGATTCGCCAGCCTCCACGAAAGGGTC TGGAGTGGCTGGGAGTAATATGGGGTAGTGAAA CCACATACTATAATTCAGCTCTCAAATCCAGACTG ACCATCATCAAGGACAACTCCAAGAGCCAAGTTT TCTTAAAAATGAACAGTCTGCAAACTGATGACAC AGCCATTTACTACTGTGCCAAACATTATTACTACG GTGGTAGCTATGCTATGGACTACTGGGGTCAAG GAACCTCAGTCACCGTCTCCTCA | 71 | EVKLQESGPGLVAPSQSLSV TCTVSGVSLPDYGVSWIRQP PRKGLEWLGVIWGSETTYYN SALKSRLTIIKDNSKSQVFLK MNSLQTDDTAIYYCAKHYYY GGSYAMDYWGQGTSVTVSS |
| Linker | 33 | GGATCC | 34 | GS |
| CD34 epitope | 35 | GAACTTCCTACTCAGGGGACTTTCTCAAACGTTA GCACAAACGTAAGT | 36 | ELPTQGTFSNVSTNVS |
| CD8 stalk | 72 | CCCGCCCCAAGACCCCCCACACCTGCGCCGACC ATTGCTTCTCAACCCCTGAGTTTGAGACCCCGAGG CCTGCCGGCCAGCTGCCGGCGGGGCCGTGCAT ACAAGAGGACTCGATTTCGCTTGCGAC | 38 | PAPRPPTPAPTIASQPLSLRP EACRPAAGGAVHTRGLDFAC D |
| CD8 transmembrane | 39 | ATCTATATCTGGGCACCTCTCGCTGGCACCTGTG GAGTCCTTCTGCTCAGCCTGGTTATTACTCTGTA CTGTAATCACCGGAATCGCCGCCGCGTTTGTAAG TGTCCCAGG | 40 | IYI- WAPLAGTCGVLLLSLVITL YCNHRNRRRVCKCPR |
| Linker | 41 | GTCGAC | 42 | VD |
| CD3ζ | 43 | AGAGTGAAGTTCAGCAGGAGCGCAGACGCCCCC GCGTACCAGCAGGGCCAGAACCAGCTCTATAAC GAGCTCAATCTAGGACGAAGAGAGGAGTACGAT GTTTTGGACAAGAGACGTGGCCGGGACCCTGAG ATGGGGGGAAAGCCGAGAAGGAAGAACCCTCAG GAAGGCCTGTACAATGAACTGCAGAAAGATAAGA TGGCGGAGGCCTACAGTGAGATTGGGATGAAAG GCGAGCGCCGGAGGGGCAAGGGGCACGATGGC CTTTACCAGGGTCTCAGTACAGCCACCAAGGACA CCTACGACGCCCTTCACATGCAAGCTCTTCCACC TCGT | 44 | RVKFSRSADAPAYQQGQNQ LYNELNLGRREEYDVLDKRR GRDPEMGGKPRRKNPQEGL YNELQKDKMAEAYSEIGMKG ERRRGKGHDGLYQGLSTATK DTYDALHMQALPPR |
| Leader | 57 | ATGCTCGAGATGCTGGAG | 58 | MLEMLE |
| P2A | 73 | GCTACTAACTTCAGCCTGCTGAAGCAGGCTGGA GACGTGGAGGAGAACCCCGGGCCT | 74 | ATNFSLLKQAGDVEENPGP |

TABLE-continued

Plasmid T: pBP2104--pSFG-FKBP.ΔC9.T2A-αCD19.Q.CD8stm.ζ.2A-MC

| Fragment | SEQ ID # | Nucleotide | SEQ ID # | Peptide |
|---|---|---|---|---|
| MyD88 | 1 | ATGGCTGCAGGAGGTCCCGGCGCGGGGTCTGC GGCCCCGGTCTCCTCCACATCCTCCCTTCCCCT GGCTGCTCTCAACATGCGAGTGCGGCGCCGCCT GTCTCTGTTCTTGAACGTGCGGACACAGGTGGC GGCCGACTGGACCGCGCTGGCGGAGGAGATGG ACTTTGAGTACTTGGAGATCCGGCAACTGGAGAC ACAAGCGGACCCCACTGGCAGGCTGCTGGACGC CTGGCAGGGACGCCCTGGCGCCTCTGTAGGCC GACTGCTCGATCTGCTTACCAAGCTGGGCCGCG ACGACGTGCTGCTGGAGCTGGGACCCAGCATTG AGGAGGATTGCCAAAAGTATATCTTGAAGCAGCA GCAGGAGGAGGCTGAGAAGCCTTTACAGGTGGC CGCTGTAGACAGCAGTGTCCCACGGACAGCAGA GCTGGCGGGCATCACCACACTTGATGACCCCT GGGGCATATGCCTGAGCGTTTCGATGCCTTCATC TGCTATTGCCCCAGCGACATC | 2 | MAAGGPGAGSAAPVSSTSSL PLAALNMRVRRRLSLFLNVR TQVAADWTALAEEMDFEYLE IRQLETQADPTGRLLDAWQG RPGASVGRLLDLLTKLGRDD VLLELGPSIEEDCQKYILKQQ QEEAEKPLQVAAVDSSVPRT AELAGITTLDDPLGHMPERFD AFICYCPSDI |
| Linker | 77 | GCGGCCGCT | 78 | AAA |
| 41BB | 79 | AAACGGGGCAGAAAGAAACTCCTGTATATATTCA AACAACCATTTATGAGACCAGTACAAACTACTCAA GAGGAAGATGGCTGTAGCTGCCGATTTCCAGAA GAAGAAGAAGGAGGATGTGAACTG | 80 | KRGRKKLLYIFKQPFMRPVQ TTQEEDGCSCRFPEEEEGG CEL |

Example 3: Inducible Activation of MyD88/CD40 Via a Small Molecule Rimiducid Enhances NKs Expansion and Antitumor Efficacy Against Hematological Malignancies NK cell-based therapy is a promising strategy for adoptive cancer immunotherapy but is limited by poor post-infusion persistence. Here, a novel inducible MyD88/CD40 platform was developed to activate NKs using the small molecule Rimiducid (Rim). Activated iMC modified NKs showed enhanced proliferation, prolonged persistence, and augmented antitumor efficacy in both MHC class I expression high and low tumor cells, which correlated with increased levels cytokine productions such as IFN-γ and TNF-α, and increased levels perforin and granzyme B as well as degranulation levels. Furthermore, IL-15, an inducible caspase-9 suicide gene (iRC9: a safety feature to preclude potential toxicity), and chimeric antigen receptors (CAR) targeting tumor specific antigens were also incorporated into the cells via γ-retroviral vectors. The results presented below demonstrated that NKs were able to be efficiently transduced, and that engineered NKs had dramatically enhanced antitumor activity and prolonged persistence in a xenograft THP-1 lymphoma murine model. Engineered NKs with a CAR significantly increased efficacy of NKs against leukemia/myeloma. The gene modified NKs were rapidly eliminated upon pharmacologic activation of the iRC9.

Materials and Methods

Cell Lines, Media, and Reagents

HEK293T, K562, HPAC, THP-1, NCIH929, U266, RPMI8226 were purchased from ATCC (Manassa, VA) and maintained in media per the suppliers' recommendation. CD56+NK cells were enriched with an NK isolation kit (Miltenyi Biotec, Inc., San Diego, CA), from peripheral blood mononuclear cells (PBMCs). PBMCs were isolated by a density-gradient technique (lymphoprep, Accurate Chemical & Scientific Corporation, Westbury, NY) from buffy coat blood obtained from the Gulf Coast Blood Bank. NKs were cultured in Stem cell growth medium (SCGM) (CellGenix GmbH, Freiburg, Germany) supplemented with 10% FBS, 1% pen/strep, 2 mM GlutaMax, and 200 U/ml recombinant human IL-2 (Miltenyi Biotec, Inc., San Diego, CA). Clinical-grade rimiducid was diluted in ethanol as a 100 µM solution for in vitro assays. For animal studies, rimiducid was further diluted into 0.9% saline. Research grade Temsirolimus (Sigma, St. Louis, MO) was dissolved in ethanol for in vitro assays and in Injection diluent (10% polyethylene glycol [PEG]-400+5% Tween-80, Sigma, St. Louis, MO) for animal studies.

Retroviral and Plasmid Constructs iMC contains a TIR domain-deleted version of the TLR adaptor protein MyD88, CD40 cytoplasmic region, and two tandem ligand-binding FKBP domains. iRC9 comprises tandem FRB and FKBPv domain fused with truncated caspase-9 (Duong, M. T., et al., Two-Dimensional Regulation of CAR-T Cell Therapy with Orthogonal Switches. Mol Ther Oncolytics, 2019. 12: p. 124-137). Synthetic DNA (Integrated DNA Technology, San Diego, CA) encoding human IL-15 was cloned into SFG iRC9.iMC using the enzyme site SacII/PflMI to generate pSFG-iRC9.IL15.iMC. These SFG retroviral vectors also consist a truncated human CD19 as a marker. G2A and T2A sequences were used to separate encoding genes. FIG. 1 shows a schematic representations of expression constructs that can be used to transduce NK cells.

A first generation CD123 CAR was generated with the 32716 scFV targeting CD123 (Foster, A. E., et al., Regulated Expansion and Survival of Chimeric Antigen Receptor-Modified T Cells Using Small Molecule-Dependent Inducible MyD88/CD40. Mol Ther, 2017. 25(9): p. 2176-2188; Mardiros, A., et al., T cells expressing CD123-specific chimeric antigen receptors exhibit specific cytolytic effector functions and antitumor effects against human acute myeloid leukemia. Blood, 2013. 122(18): p. 3138-48), CD8α stalk transmembrane domain, and the cytoplasmic CD3ζ domain.

iMC.BCMA. ζ.IL15 was generated by subcloning ScFV targeting BCMA (C12.A3.2L) and IL15 genes into pSFG iMC.CAR. ζ with XhoI/BamHI and SalI/MluI. All vectors contain CAR also had the QBEnd-10 minimal epitope (CD34 epitope) (Betts, M. R., et al., Sensitive and viable identification of antigen-specific CD8+ T cells by a flow cytometric assay for degranulation. J Immunol Methods, 2003. 281(1-2): p. 65-78) as the marker. Tumor cells or NKs were transduced with pSFG-eGFP-Firefly luciferase (eGFPFfluc) or pSFG-orange Nano-lantern *Renilla* luciferase (ONLRluc) for labelling.

Transduction of NK Cells or T Cells

Retroviral supernatants were produced by transient transfection of 293T cells as previously described (Foster, A. E., et al., Mol Ther, 2017. 25(9): p. 2176-2188). NKs were stimulated with recombinant human IL-15 (15 ng/ml) for 1 day. The next day, NKs were further activated with irradiated (100 Gy) K562 at the ratio of 2:1 feeder: NK, and 200 U/ml recombinant human IL-2 (all cytokines from Miltenyi Biotec, Inc., San Diego, CA). Four days later, NKs were subsequently transduced using retronectin (Takara Bio, Mountain View, CA) and spinfection technique and were stimulated again with irradiated K562 and IL-2. For double transduction, NKs were transduced at day 4 and day 5 after IL-2 and K562 stimulations. On day 14, transduced NKs were harvested for use. Transduction of T cells was performed as described before (Foster, A. E., et al., Mol Ther, 2017. 25(9): p. 2176-2188).

FIG. 3 shows methods to isolate, culture and transduce Natural Killer cells. Cell components from human blood sourced from healthy adult donors was separated by centrifugation in Ficoll with the 'buffy coat' further fractionated to provide peripheral blood mononuclear cells (T and B lymphocytes, NK cells and monocytes). NK cells were isolated by selection with a column of magnetic beads fused with antibody to CD56 expressed on NK cells.

Plasmids:

TABLE

| | | PBP2261-SFG-αCD123ScFV.CD34e.CD8stm.ZETA | | | |
|---|---|---|---|---|---|
| FRAGMENT | | NUCLEOTIDE | SEQ ID NO: | PEPTIDE | SEQ ID NO: |
| SIGNAL PEPTIDE | | ATGGAGTTCGGATTGAGCTGGCTGT TCCTGGTGGCAATACTCAAGGGCGT TCAATGTTCACGG | 23 | MEFGLSWLFLVAILKGVQCSR | 24 |
| CD123 VH | (32716) | CAGATCCAACTGGTGCAGTCAGGCC CGGAACTGAAGAAGCCAGGGGAGA CAGTCAAAATAAGTTGTAAAGCCAG CGGCTACATATTTACTAATTACGGG ATGAATTGGGTGAAGCAAGCGCCGG GCAAATCCTTTAAATGGATGGGGTG GATAAACACATACACAGGAGAGTCA ACGTACAGCGCGGACTTCAAAGGTC GATTCGCGTTCAGTCTCGAGACCAG CGCGAGTACAGCTTACCTCCACATC AACGATCTTAAAAACGAAGACACGG CAACCTATTTTTGCGCCCGGTCAGG CGGTTACGACCCTATGGACTATTGG GGCCAAGGGACCTCCGTTACGGTA | 81 | QIQLVQSGPELKKPGETVKISCKASG YIFTNYGMNWVKQAPGKSFKWMGWIN TYTGESTYSADFKGRFAFSLETSAST AYLHINDLKNEDTATYFCARSGGYDP MDYWGQGTSVTV | 82 |
| FLEX | | CTTCAGGCGGTGGCGGGAGTGGTG GAGGAGGCTCAGGCGGCGGGGGAT CA | 83 | SSGGGGSGGGGSGGGGS | 84 |
| CD123 VL | (32716) | GACATCGTACTGACCCAATCTCCCG CTAGCCTTGCAGTATCCTTGGGTCA ACGCGCTACAATAAGTTGCCGGGCT AGTGAGTCCGTAGACAACTATGGCA ACACCTTCATGCATTGGTACCAACAA AAACCAGGTCAGCCACCCAAACTTC TCATTTACAGAGCGTCTAATCTCGA AAGCGGCATCCCTGCTCGATTCTCT GGAAGCGGAAGTAGAACCGACTTTA CACTGACTATAAACCCCGTCGAAGC CGATGATGTTGCCACTTATTACTGT CAACAGAGCAATGAGGACCCACCGA CATTCGGTGCTGGTACCAAGCTGGA GTTGAAGGAGTCAAAATACGGGCCT CCCTGTCCC | 85 | DIVLTQSPASLAVSLGQRATISCRAS ESVDNYGNTFMHWYQQKPGQPPKLLI YRASNLESGIPARFSGSGSRTDFTLT INPVEADDVATYYCQQSNEDPPTFGA GTKLELKESKYGPPCP | 86 |
| LINKER | | GGATCC | 33 | GS | 34 |
| CD34 EPITOPE | | GAACTTCCTACTCAGGGGACTTTCT CAAACGTTAGCACAAACGTAAGT | 35 | ELPTQGTFSNVSTNVS | 36 |
| CD8 STALK | | GAACTTCCTACTCAGGGGACTTTCT CAAACGTTAGCACAAACGTAAGT | 37 | PAPRPPTPAPTIASQPLSLRPEACRP AAGGAVHTRGLDFACD | 38 |

TABLE-continued

PBP2261-SFG-αCD123ScFV.CD34e.CD8stm.ZETA

| FRAGMENT | NUCLEOTIDE | SEQ ID NO: | PEPTIDE | SEQ ID NO: |
|---|---|---|---|---|
| CD8 TRANSMEMBRANE | ATCTATATCTGGGCACCTCTCGCTG GCACCTGTGGAGTCCTTCTGCTCAG CCTGGTTATTACTCTGTACTGTAAT CACCGGAATCGCCGCCGCGTTTGTA AGTGTCCCAGG | 39 | IYIWAPLAGTCGVLLLSLVITLYCNH RNRRRVCKCPR | 40 |
| LINKER | GTCGAC | 41 | VD | 42 |
| CD3Z | AGAGTGAAGTTCAGCAGGAGCGCA GACGCCCCCGCGTACCAGCAGGGC CAGAACCAGCTCTATAACGAGCTC AATCTAGGACGAAGAGAGGAGTAC GATGTTTTGGACAAGAGACGTGGC CGGGACCCTGAGATGGGGGGAAAG CCGAGAAGGAAGAACCCTCAGGAA GGCCTGTACAATGAACTGCAGAAA GATAAGATGGCGGAGGCCTACAGT GAGATTGGGATGAAAGGCGAGCGC CGGAGGGGCAAGGGGCACGATGGC CTTTACCAGGGTCTCAGTACAGCC ACCAAGGACACCTACGACGCCCTT ACACATGCAGCTCTTCCACCTCGT | 43 | RVKFSRSADAPAYQQGQNQLYNELN LGRREEYDVLDKRRGRDPEMGGKPR RKNPQEGLYNELQKDKMAEAYSEIG MKGERRRGKGHDGLYQGLSTATKDT YDALHMQALPPR | 44 |
| STOP | TGA | | STOP | |

TABLE

PBP2818-pSFG-MYD88.CD40.Fv.Fv.T2A.αBCMAScFV.CD34e.CD8stm.ZETA

| FRAGMENT | NUCLEOTIDE | SEQ ID NO: | PEPTIDE | SEQ ID NO: |
|---|---|---|---|---|
| MYD88 | ATGGCTGCAGGAGGTCCCGGCGCG GGGTCTGCGGCCCCGGTCTCCTCC ACATCCTCCCTTCCCCTGGCTGCTC TCAACATGCGAGTGCGGCGCCGCC TGTCTCTGTTCTTGAACGTGCGGAC ACAGGTGGCGGCCGACTGGACCGC GCTGGCGGAGGAGATGGACTTTGA GTACTTGGAGATCCGGCAACTGGAG ACACAAGCGGACCCCACTGGCAGG CTGCTGGACGCCTGGCAGGGACGC CCTGGCGCCTCTGTAGGCCGACTG CTCGATCTGCTTACCAAGCTGGGCC GCGACGACGTGCTGCTGGAGCTGG GACCCAGCATTGAGGAGGATTGCCA AAAGTATATCTTGAAGCAGCAGCAG GAGGAGGCTGAGAAGCCTTTACAGG TGGCCGCTGTAGACAGCAGTGTCCC ACGGACAGCAGAGCTGGCGGGCAT CACCACACTTGATGACCCCCTGGGG CATATGCCTGAGCGTTTCGATGCCT TCATCTGCTATTGCCCCAGCGACAT C | 1 | MAAGGPGAGSAAPVSSTSSLPLAALN MRVRRRLSLFLNVRTQVAADWTALAE EMDFEYLEIRQLETQADPTGRLLDAW QGRPGASVGRLLDLLTKLGRDDVLLE LGPSIEEDCQKYILKQQQEEAEKPLQ VAAVDSSVPRTAELAGITTLDDPLGH MPERFDAFICYCPSDI | 2 |
| LINKER | GTCGAG | 13 | VE | 14 |
| CD40 | AAAAAGGTGGCCAAGAAGCCAACCA ATAAGGCCCCCCACCCCAAGCAGGA GCCCCAGGAGATCAATTTTCCCGAC GATCTTCCTGGCTCCAACACTGCTG CTCCAGTGCAGGAGACTTTACATGG ATGCCAACCGGTCACCCAGGAGGAT GGCAAAGAGAGTCGCATCTCAGTGC AGGAGAGACAG | 75 | KKVAKKPTNKAPHPKQEPQEINFPD DLPGSNTAAPVQETLHGCQPVTQED GKESRISVQERQ | 56 |
| LINKER | GTCGAG | 13 | VE | 14 |

TABLE-continued

PBP2818-pSFG-MYD88.CD40.Fv.Fv.T2A.αBCMAScFV.CD34e.CD8stm.ZETA

| FRAGMENT | NUCLEOTIDE | SEQ ID NO: | PEPTIDE | SEQ ID NO: |
|---|---|---|---|---|
| FKBPV' | GGCGTCCAAGTCGAAACCATTAGTC CCGGCGATGGCAGAACATTTCCTAA AAGGGGACAAACATGTGTCGTCCAT TATACAGGCATGTTGGAGGACGGCA AAAAGGTGGACAGTAGTAGAGATCG CAATAAACCTTTCAAATTCATGTTG GGAAAACAAGAAGTCATTAGGGGAT GGGAGGAGGGCGTGGCTCAAATGTC CGTCGGCCAACGCGCTAAGCTCACC ATCAGCCCCGACTACGCATACGGCG CTACCGGACATCCCGGAATTATTCC CCCTCACGCTACCTTGGTGTTTGAC GTCGAACTGTTGAAGCTCGAA | 11 | GVQVETISPGDGRTFPKRGQTCVVH YTGMLEDGKKVDSSRDRNKPFKFML GKQEVIRGWEEGVAQMSVGQRAKLT ISPDYAYGATGHPGIIPPHATLVFD VELLKLE | 12 |
| LINKER | GTCGAG | 13 | VE | 14 |
| FKBPV | GGAGTGCAGGTGGAGACTATCTCCC CAGGAGACGGGCGCACCTTCCCCA AGCGCGGCCAGACCTGCGTGGTGC ACTACACCGGGATGCTTGAAGATGG AAAGAAAGTTGATTCCTCCCGGGAC AGAAACAAGCCCTTTAAGTTTATGCT AGGCAAGCAGGAGGTGATCCGAGG CTGGGAAGAAGGGGTTGCCCAGAT GAGTGTGGGTCAGAGAGCCAAACTG ACTATATCTCCAGATTATGCCTATGG TGCCACTGGGCACCCAGGCATCATC CCACCACATGCCACTCTCGTCTTCG ATGTGGAGCTTCTAAAACTGGAA | 15 | GVQVETISPGDGRTFPKRGQTCVVH YTGMLEDGKKVDSSRDRNKPFKFML GKQEVIRGWEEGVAQMSVGQRAKLT ISPDYAYGATGHPGIIPPHATLVFD VELLKLE | 16 |
| LINKER | CCGCGG | 17 | PR | 18 |
| T2A | GAGGGCAGAGGCAGCCTCCTGACA TGTGGGGACGTCGAGGAGAACCCT GGCCCA | 19 | EGRGSLLTCGDVEENPGP | 20 |
| LINKER | CCTTGG | 21 | PW | 22 |
| SIGNAL PEPTIDE | ATGGAGTTCGGATTGAGCTGGCTGT TCCTGGTGGCAATACTCAAGGGCGT TCAATGTTCACGG | 23 | MEFGLSWLFLVAILKGVQCSR | 24 |
| BCMA (C123.A3.2) VL | GATATCGTGCTGACCCAGTCCCCCC CTAGCCTGGCCATGTCCCTGGGCAA ACGGGCCACCATCTCCTGCAGAGCC TCCGAGTCCGTGACCATCCTCGGCT CCCACCTGATCTACTGGTACCAGCA GAAGCCCGGCCAGCCTCCCACCCT CCTTATCCAGCTGGCCAGCAACGTG CAGACCGGCGTGCCCGCTAGATTCT CCGGCAGCGGCTCTAGAACCGACTT CACCCTGACCATCGACCCCGTGGAA GAGGACGATGTCGCCGTGTACTATT GCCTGCAGTCCAGAACCATCCCTAG GACATTCGGCGGAGGAACCAAGCT GGAGATCAAA | 87 | DIVLTQSPPSLAMSLGKRATISCRASE SVTILGSHLIYWYQQKPGQPPTLLIQL ASNVQTGVPARFSGSGSRTDFTLTID PVEEDDVAVYYCLQSRTIPRTFGGGT KLEIK | 88 |
| FLEX | GGGGGCGGTGGCAGCGGTGGCGG TGGGTCTGGGGGCGGAGGCTCT | 89 | GGGGSGGGGSGGGGS | 90 |
| BCMA (C123.A3.2) VH | CAGATCCAGCTGGTGCAGTCCGGC CCCGAGCTGAAGAAACCCGGCGAG ACCGTGAAGATCTCCTGCAAGGCCA GCGGCTACACCTTCAGACACTACAG CATGAACTGGGTGAAGCAGGCCCCT | 91 | QIQLVQSGPELKKPGETVKISCKASGY TFRHYSMNWVKQAPGKGLKWMGRIN TESGVPIYADDFKGRFAFSVETSASTA YLVINNLKDEDTASYFCSNDYLYSLDF WGQGT ALTVSS | 92 |

TABLE-continued

PBP2818-pSFG-MYD88.CD40.Fv.Fv.T2A.αBCMAScFV.CD34e.CD8stm.ZETA

| FRAGMENT | NUCLEOTIDE | SEQ ID NO: | PEPTIDE | SEQ ID NO: |
|---|---|---|---|---|
| | GGCAAGGGCCTGAAGTGGATGGGC CGGATCAACACCGAGTCCGGCGTG CCCATCTACGCCGACGATTTCAAGG GCAGATTCGCCTTCAGCGTGGAGAC CTCCGCCTCTACCGCCTACCTGGTG ATCAACAATCTGAAGGACGAGGACA CCGCCTCCTACTTCTGCAGCAACGA CTACCTGTACAGCCTGGACTTCTGG GGCCAGGGCACCGCCCTGACCGTG AGCTCCG | | | |
| LINKER | GGATCC | 33 | GS | 34 |
| CD34 EPITOPE | GAACTTCCTACTCAGGGGACTTTCT CAAACGTTAGCACAAACGTAAGT | 35 | ELPTQGTFSNVSTNVS | 36 |
| CD8 STALK | GAACTTCCTACTCAGGGGACTTTCT CAAACGTTAGCACAAACGTAAGT | 37 | PAPRPPTPAPTIASQPLSLRPEACRPA AGGAVHTRGLDFACD | 38 |
| CD8 TRANSMEMBRANE | ATCTATATCTGGGCACCTCTCGCTG GCACCTGTGGAGTCCTTCTGCTCAG CCTGGTTATTACTCTGTACTGTAATC ACCGGAATCGCCGCCGCGTTTGTAA GTGTCCCAGG | 39 | IYIWAPLAGTCGVLLLSLVITLYCNHRN RRRVCKCPR | 40 |
| LINKER | GTCGAC | 41 | VD | 42 |
| CD3Z | AGAGTGAAGTTCAGCAGGAGCGCA GACGCCCCCGCGTACCAGCAGGGC CAGAACCAGCTCTATAACGAGCTCA ATCTAGGACGAAGAGAGGAGTACGA TGTTTTGGACAAGAGACGTGGCCGG GACCCTGAGATGGGGGGAAAGCCG AGAAGGAAGAACCCTCAGGAAGGC CTGTACAATGAACTGCAGAAAGATA AGATGGCGGAGGCCTACAGTGAGAT TGGGATGAAAGGCGAGCGCCGGAG GGGCAAGGGGCACGATGGCCTTTA CCAGGGTCTCAGTACAGCCACCAAG GACACCTACGACGCCCTTCACATGC AAGCTCTTCCACCTCGT | 43 | RVKFSRSADAPAYQQGQNQLYNELN LGRREEYDVLDKRRGRDPEMGGKPR RKNPQEGLYNELQKDKMAEAYSEIGM KGERRRGKGHDGLYQGLSTATKDTY DALHMQALPPR | 44 |
| LINKER | GGATCTGGCGGCCGC | 93 | GSGGR | 94 |
| T2A | GAGGGAAGGGGAAGTCTTCTAACAT GCGGGGACGTGGAGGAAAATCCCG GGCCC | 95 | EGRGSLLTCGDVEENPGP | 20 |
| IL-15 | GAGGGAAGGGGAAGTCTTCTAACAT GCGGGGACGTGGAGGAAAATCCCG GGCCCATGAGAATTTCGAAACCACA TTTGAGAAGTATTTCCATCCAGTGCT ACTTGTGTTTACTTCTAAACAGTCAT TTTCTAACTGAAGCTGGCATTCATGT CTTCATTTTGGGCTGTTTCAGTGCAG GGCTTCCTAAAACAGAAGCCAACTG GGTGAATGTAATAAGTGATTTGAAAA AAATTGAAGACCTTATTCAATCTATG CACATTGATGCTACTTTATATACGGA AAGTGATGTTCACCCCAGTTGCAAA GTAACAGCAATGAAGTGCTTTCTCTT GGAGTTACAAGTTATTTCACTTGAGT CCGGAGATGCAAGTATTCATGATAC AGTAGAAAATCTGATCATCCTAGCAA ACAACAGTTTGTCTTCTAATGGGAAT GTAACAGAATCTGGATGCAAAGAAT GTGAGGAACTGGAGGAGAAGAACAT CAAGGAATTTTTGCAGAGTTTTGTAC ATATTGTCCAAATGTTCATCAACACT | 96 | MRISKPHLRSISIQCYLCLLLNSHFLTE AGIHVFILGCFSAGLPKTEANWVNVIS DLKKIEDLIQSMHIDATLYTESDVHPSC KVTAMKCFLLELQVISLESGDASIHDT VENLIILANNSLSSNGNVTESGCKECE ELEEKNIKEFLQSFVHIVQMFINT | 97 |
| STOP | TGA | | STOP | |

TABLE

| | | PBP1385-PSFG-FRB.FKBP.ΔC9.T2A-ΔCD19 | | |
|---|---|---|---|---|
| FRAGMENT | NUCLEOTIDE | SEQ ID NO: | PEPTIDE | SEQ ID NO: |
| LEADER PEPTIDE | ATGCTCGAGCAATTG | 98 | MLEQL | 99 |
| FRB | GAAATGTGGCATGAAGGGTTGGAAG AAGCTTCAAGGCTGTACTTCGGAGA GAGGAACGTGAAGGGCATGTTTGAG GTTCTTGAACCTCTGCACGCCATGA TGGAACGGGGACCGCAGACACTGA AAGAAACCTCTTTTAATCAGGCCTA CGGCAGAGACCTGATGGAGGCCCAA GAATGGTGTAGAAAGTATATGAAAT CCGGTAACGTGAAAGACCTGACTCA GGCCTGGGACCTTTATTACCATGTG TTCAGGCGGATCAGTAAG | 100 | EMWHEGLEEASRLYFGERNVKGMFE VLEPLHAMMERGPQTLKETSFNQAY GRDLMEAQEWCRKYMKSGNVKDLTQ AWDLYYHVFRRISK | 101 |
| LINKER | GGCGGGCAATTG | 102 | GGQL | 103 |
| FKBP WT | GGCGTCCAAGTCGAAACCATTAGTC CCGGCGATGGCAGAACATTTCCTAA AAGGGGACAAACATGTGTCGTCCAT TATACAGGCATGTTGGAGGACGGCA AAAAGTTCGACAGTAGTAGAGATCG CAATAAACCTTTCAAATTCATGTTG GGAAAACAAGAAGTCATTAGGGGAT GGGAGGAGGGCGTGGCTCAAATGTC CGTCGGCCAACGCGCTAAGCTCACC ATCAGCCCCGACTACGCATACGGCG CTACCGGACATCCCGGAATTATTCC CCCTCACGCTACCTTGGTGTTTGAC GTCGAACTGTTGAAGCTC | 104 | GVQVETISPGDGRTFPKRGQTCVVHY TGMLEDGKKFDSSRDRNKPFKFMLG KQEVIRGWEEGVAQMSVGQRAKLTIS PDYAYGATGHPGIIPPHATLVFDVEL LKL | 105 |
| LINKER | TCAGGCGGTGGCTCAGGTCCATGG | 106 | SGGGSGPW | 107 |
| ΔCASPASE9 | GGATTTGGTGATGTCGGTGCTCTTG AGAGTTTGAGGGGAAATGCAGATTT GGCTTACATCCTGAGCATGGAGCCC TGTGGCCACTGCCTCATTATCAACA ATGTGAACTTCTGCCGTGAGTCCGG GCTCCGCACCCGCACTGGCTCCAAC ATCGACTGTGAGAAGTTGCGGCGTC GCTTCTCCTCGCTGCATTTCATGGT GGAGGTGAAGGGCGACCTGACTGC CAAGAAAATGGTGCTGGCTTTGCTG GAGCTGGCGCGGCAGGACCACGGT GCTCTGGACTGCTGCGTGGTGGTCA TTCTCTCTCACGGCTGTCAGGCCAG CCACCTGCAGTTCCCAGGGGCTGTC TACGGCACAGATGGATGCCCTGTGT CGGTCGAGAAGATTGTGAACATCTT CAATGGGACCAGCTGCCCCAGCCT GGGAGGGAAGCCCAAGCTCTTTTTC ATCCAGGCCTGTGGTGGGGAGCAG AAAGACCATGGGTTTGAGGTGGCCT CCACTTCCCCTGAAGACGAGTCCCC TGGCAGTAACCCCGAGCCAGATGCC ACCCCGTTCCAGGAAGGTTTGAGGA CCTTCGACCAGCTGGACGCCATATC TAGTTTGCCCACACCCAGTGACATC TTTGTGTCCTACTCTACTTTCCCAGG TTTTGTTTCCTGGAGGGACCCCAAG AGTGGCTCCTGGTACGTTGAGACCC TGGACGACATCTTTGAGCAGTGGGC TCACTCTGAAGACCTGCAGTCCCTC CTGCTTAGGGTCGCTAATGCTGTTT CGGTGAAAGGGATTTATAAACAGAT GCCTGGTTGCTTTAATTTCCTCCGG AAAAAACTTTTCTTTAAAACATCAGC TAGCAGAGCC | 108 | GFGDVGALESLRGNADLAYILSMEPC GHCLIINNVNFCRESGLRTRTGSNID CEKLRRRFSSLHFMVEVKGDLTAKKM VLALLELARQDHGALDCCVVVILSHG CQASHLQFPGAVYGTDGCPVSVEKIV NIFNGTSCPSLGGKPKLFFIQACGGE QKDHGFEVASTSPEDESPGSNPEPDA TPFQEGLRTFDQLDAISSLPTPSDIF VSYSTFPGFVSWRDPKSGSWYVETLD DIFEQWAHSEDLQSLLLRVANAVSVK KQMPGCFNFLRKKLFFKTSASRA GIY | 64 |
| LINKER | GGATCTGGACCGCGG | 109 | GSGPR | 110 |
| T2A | GAAGGCCGAGGGAGCCTGCTGACA TGTGGCGATGTGGAGGAAAACCCAG GACCA | 65 | EGRGSLLTCGDVEENPGP | 20 |

TABLE-continued

PBP1385-PSFG-FRB.FKBP.ΔC9.T2A-ΔCD19

| FRAGMENT | NUCLEOTIDE | SEQ ID NO: | PEPTIDE | SEQ ID NO: |
|---|---|---|---|---|
| ΔCD19 | ATGCCACCACCTCGCCTGCTGTTCT TTCTGCTGTTCCTGACACCTATGGA GGTGCGACCTGAGGAACCACTGGT CGTGAAGGTCGAGGAAGGCGACAA TGCCGTGCTGCAGTGCCTGAAAGGC ACTTCTGATGGGCCAACTCAGCAGC TGACCTGGTCCAGGGAGTCTCCCCT GAAGCCTTTTCTGAAACTGAGCCTG GGACTGCCAGGACTGGGAATCCACA TGCGCCCTCTGGCTATCTGGCTGTT CATCTTCAACGTGAGCCAGCAGATG GGAGGATTCTACCTGTGCCAGCCAG GACCACCATCCGAGAAGGCCTGGC AGCCTGGATGGACCGTCAACGTGGA GGGGTCTGGAGAACTGTTTAGGTGG AATGTGAGTGACCTGGGAGGACTGG GATGTGGGCTGAAGAACCGCTCCTC TGAAGGCCCAAGTTCACCCTCAGGG AAGCTGATGAGCCCAAAACTGTACG TGTGGGCCAAAGATCGGCCCGAGAT CTGGGAGGGAGAACCTCCATGCCT GCCACCTAGAGACAGCCTGAATCAG AGTCTGTCACAGGATCTGACAATGG CCCCCGGGTCCACTCTGTGGCTGTC TTGTGGAGTCCCACCCGACAGCGTG TCCAGAGGCCCTCTGTCCTGGACCC ACGTGCATCCTAAGGGGCCAAAAAG TCTGCTGTCACTGGAACTGAAGGAC GATCGGCCTGCCAGAGACATGTGG GTCATGGAGACTGGACTGCTGCTGC CACGAGCAACCGCACAGGATGCTG GAAAATACTATTGCCACCGGGGCAA TCTGACAATGTCCTTCCATCTGGAG ATCACTGCAAGGCCCGTCGTGTGGC ACTGGCTGCTGCGAACCGGAGGAT GGAAGGTCAGTGCTGTGACACTGGC ATATCTGATCTTTTGCCTGTGCTCCC TGGTGGGCATTCTGCATCTGCAGAG AGCCCTGGTGCTGCGGAGAAAGAG AAAGAGAATGACTGACCCAACAAGA AGGTTT | 111 | MPPPRLLFFLLFLTPMEVRPEEPLV VKVEEGDNAVLQCLKGTSDGPTQQL TWSRESPLKPFLKLSLGLPGLGIHM RPLAIWLFIFNVSQQMGGFYLCQPG PPSEKAWQPGWTVNVEGSGELFRWN VSDLGGLGCGLKNRSSEGPSSPSGK LMSPKLYVWAKDRPEIWEGEPPCLP PRDSLNQSLSQDLTMAPGSTLWLSC GVPPDSVSRGPLSWTHVHPKGPKSL LSLELKDDRPARDMWVMETGLLLPR ATAQDAGKYYCHRGNLTMSFHLEIT ARPVLWHWLLRTGGWKVSAVTLAYL IFCLCSLVGILHLQRALVLRRKRKR MTDPTRRF | 112 |
| STOP | TGA | | STOP | |

NK Cell Proliferation Assay

NKs from healthy donors were activated by IL-15, followed by k562 and IL-2. On the day of transduction, activated NKs were labeled with CellTrace Violet Cell proliferation dye (ThermoFisher Scientific, Grand Island, NY) per the manufacturer's protocol. NKs were subsequently transduced with iRC9 or iRC9.iMC and stimulated with K562 and IL-2 in the absence or presence of 1 nM Rimiducid. After culturing 9 days, viable NKs (CD56+ CD3−) were then analyzed for dilution of dye.

CD107a and Intracellular Staining

CD107a degranulation and intracellular cytokine IFN-γ, TNF-α, perforin, granzyme B productions were measured as reported (Betts, M. R., et al., J Immunol Methods, 2003. 281(1-2): p. 65-78]. Briefly, NKs modified with iRC9 or iRC9.iMC vectors were co-cultured with or without THP-1 tumor targets at 1:1 DT ratio in the presence or absence of 1 nM Rimiducid for 4-hour incubation. Anti CD107a-PE antibody (eBiosciense, San Diego, CA) was added during the first hour, followed by the secretion inhibitor monensin (2 uM, Biolegend, San Diego, CA) and Brefeldin A (5 μg/ml, Biolegend, San Diego, CA) treatment for the next 3 hrs. Cells were then washed, stained with surface antibodies anti-CD19-BV421, anti-CD56-APCcy7, anti-CD3-FITC (Biolegend, San Diego, CA). For intracellular staining, gene modified NKs were co-cultured with or without THP-1 and rimiducid for overnight. Secretion inhibitors were added. Cells were harvested, washed, stained with surface antibodies anti-CD56-APCcy7 and anti-CD19-PE or anti-CD56 PE and anti-CD19 BV421 (Biolegend, San Diego, CA), fixed, permeabilized and stained intracellularly with anti-IFN-γ-APC, anti-TNF-α-APC (BD Bioscience, San Jose, CA), anti-Perforin-APC/cy7 (Biolegend, San Diego, CA), or anti-Granzyme B-AF647 (BD Bioscience, San Jose, CA).

Immunophenotype of Transduced Cells

Transduced NKs or T cells were stained with anti-CD56-APCcy7 (NK) or anti-CD3-Percep.Cy5 (T) and anti-CD19-BV421 for iMC or iRC9 transgene expression. For CAR-transduced cells, anti-CD34 QBEnd-10-PE (Abnova) was used to determine transduction efficiency. Phenotypic analysis of NKs none-transduced (NT), iRC9, iRC9.iMC, or iRC9.IL15.iMC transduced cells were assessed by multicolor flow cytometry using the following three sets antibody panels: anti-NKP30-AF647, anti-CD16-AF488, anti-CD19-PE, anti-CD56-APC cy7, and anti-CD178 (Fas-L)-BV421; anti-DNAM-1-FITC, anti-NKG2D-APC, anti-CD56-APCcy7, anti-CD19-PE, and anti-NKP46 BV421; anti-CD95 (Fas)-PEcy7, anti-CD56-APCcy7, anti-CD19-

BV421, and anti-NKP44 Percep/cy5.5. All antibodies were purchased from Biolegend except otherwise stated. Flow cytometry was performed using NovoCyte flow cytometer and the data were analyzed using ACEA NovoExpress software (ACEA Biosciences Inc, San Diego, CA).

Cytokine Production

Production of IFN-γ by NKs transduced with iRC9, iRC9.iMC, or iRC9.IL15.iMC in the presence of various concentration rimiducid was analyzed by ELISA (eBioscience, San Diego, CA). In some experiments, cytokines production was analyzed using a 29-cytokine/chemokine multiplex array (Milliplex MAP; Millipore) system with a multiplex reader (Bio-Plex MAGPIX, Bio-rad)

Immunoblotting

Details of immunoblotting were described before (Foster, A. E., et al., Mol Ther, 2017. 25(9): p. 2176-2188; Duong, M. T., et al., Mol Ther Oncolytics, 2019. 12: p. 124-137; Collinson-Pautz, M. R., et al., Leukemia, 2019). Antibodies specific for phospho-NF-κB p65, phospho-IκBα, phospho-p38, phospho-ERK1/2, phospho-SAPK/JNK, TRAF3, and TRAF6 were purchased from Cell signaling Technology Inc (Danvers, MA). Antibodies specific for MyD88 and β-actin were purchased from Santa Cruz Biotechnology (Dallas, Texas).

Cytotoxicity and Co-Culture Assays

To access cytotoxicity, gene-modified NK cells were co-cultured with THP-1 or other targets labeled with eGFPFfluc as noted in figure legend at multiple E:T ratios in the presence or absence of 1 nM Rimiducid (for short term assay, NKs were pretreated with rimiducid for 6 days). Cytotoxicity was measured by luciferase activity assay 24 hrs later following the manufacturer's protocols. The findings are reported as specific lysis relative to THP-1 or other tumor cell targets. Additional co-culture assays were analyzed by flow cytometry for the frequency of tumor cells GFP+ populations. In some long term assays, gene modified NKs were co-cultured with tumor cell targets either labeled with eGFP or RFP for 7 days in the presence of 200 U/ml IL-2. Tumor cells growths were monitored by real-time fluorescent microscopy (IncuCyte; Essen Biosciences).

In Vivo Studies

NOD/SCID/γc−/− (NSG) mice (Jackson laboratory, Bar Harbor, ME) were maintained at the Bellicum Pharmaceuticals AAALAC approved vivarium. These studies were approved by the Bellicum Pharmaceuticals Institutional Animal Care and Use Committee (IACUC). For NK persistence study, $10^7$ double transduced NKs (indicated transgenes and eGFPFfluc) in 100 μLPBS were tail vein injected into NSG mice (8 weeks old female). Rimiducid or vehicle were administered via i.p. injection at the dose of 1 mg/kg weekly. In the NK persistence study with THP-1 tumor targets, two times $5\times10^6$ double transduced NKs (indicated transgenes and ONLRluc) were tail vein injected 5 days before and 12 days after $10^6$ THP-1-eGFPFfluc engraftment. For CAR-NK experiments, $10^7$ gene modified NKs were tail vein injected 3 days after $10^6$ THP-1-eGFPFfluc engraftment. In vivo NK presence or tumor growth was measured by weekly bioluminescence imaging (BLI) by i.p. injection of 150 mg/kg D-luciferin (firefly luciferase) or 150 ng Coelenterazine-h (renilla luciferase; Perkin Elmer, Waltham, MA) and imaged using the IVIS imaging system (Perkin Elmer). Photon whole body emission in a region of interest was assessed. Signal quantitation was measured as average radiance (photons/second/cm$^2$/steradian). Weight measurement was performed at least once a week. Endpoint analysis involved FACS analysis of splenocyte, bone marrow, or peripheral blood.

Statistics

All statistical tests (noted in figure legends) were carried out and analyzed using GraphPad Prism software (version 8.0, GraphPad, software). Data are presented as means±SEM. All t tests were 2-tailed. All ANOVA were two-way. P values of less than 0.05 were considered significant.

Figure 15A:
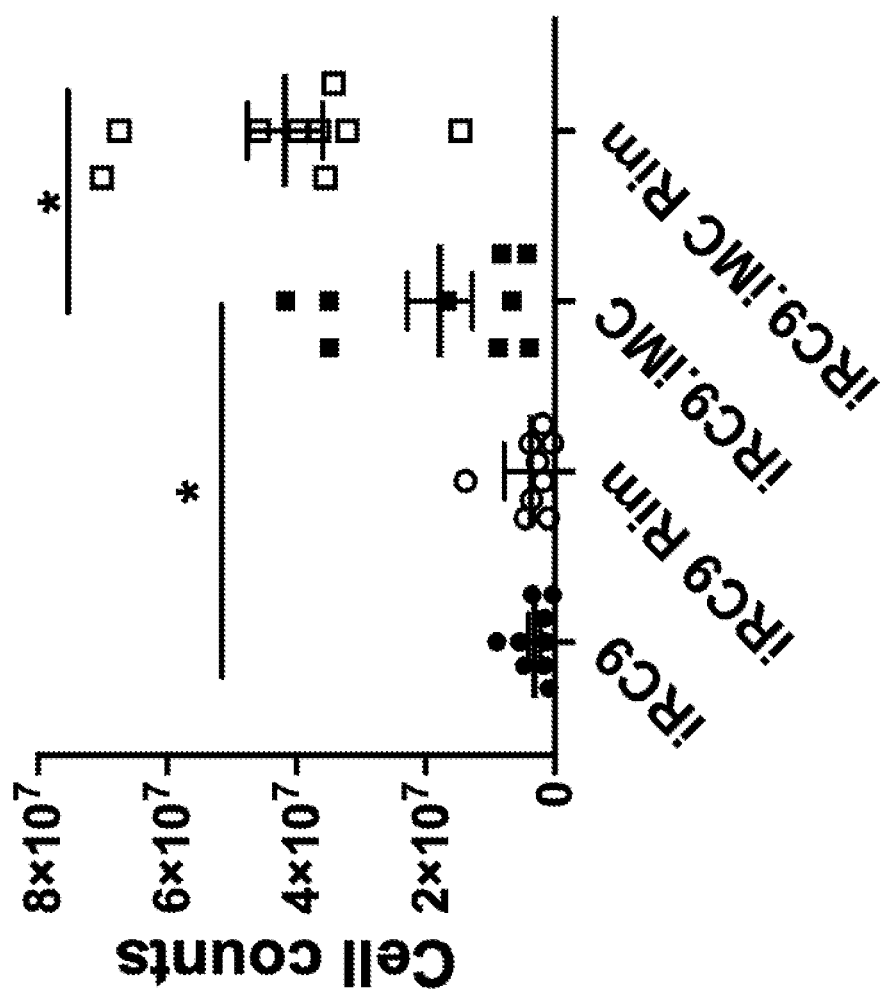
FIGS. 15A-15F: Rim-mediated iMC activation increases NK cells proliferation. NK cells were transduced with iMC.iRC9 or iRC9 at day 4 post activation. The cells were further stimulated by irradiated K562 feeder cells 5 days after transduction with/without 1 nM rimiducid. At day 14, cells were counted using Acridine orange (AO) and propidium iodide ("AOPI" staining) (FIG. 15A).
Figure 15B:
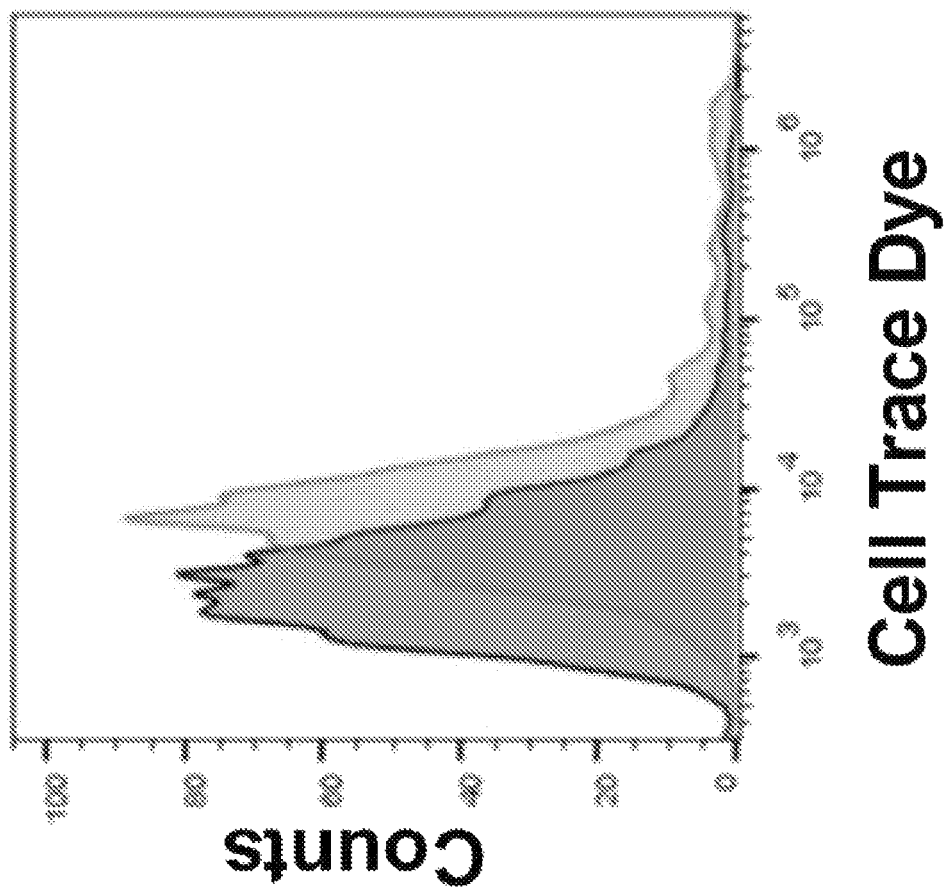
Figure 15C:
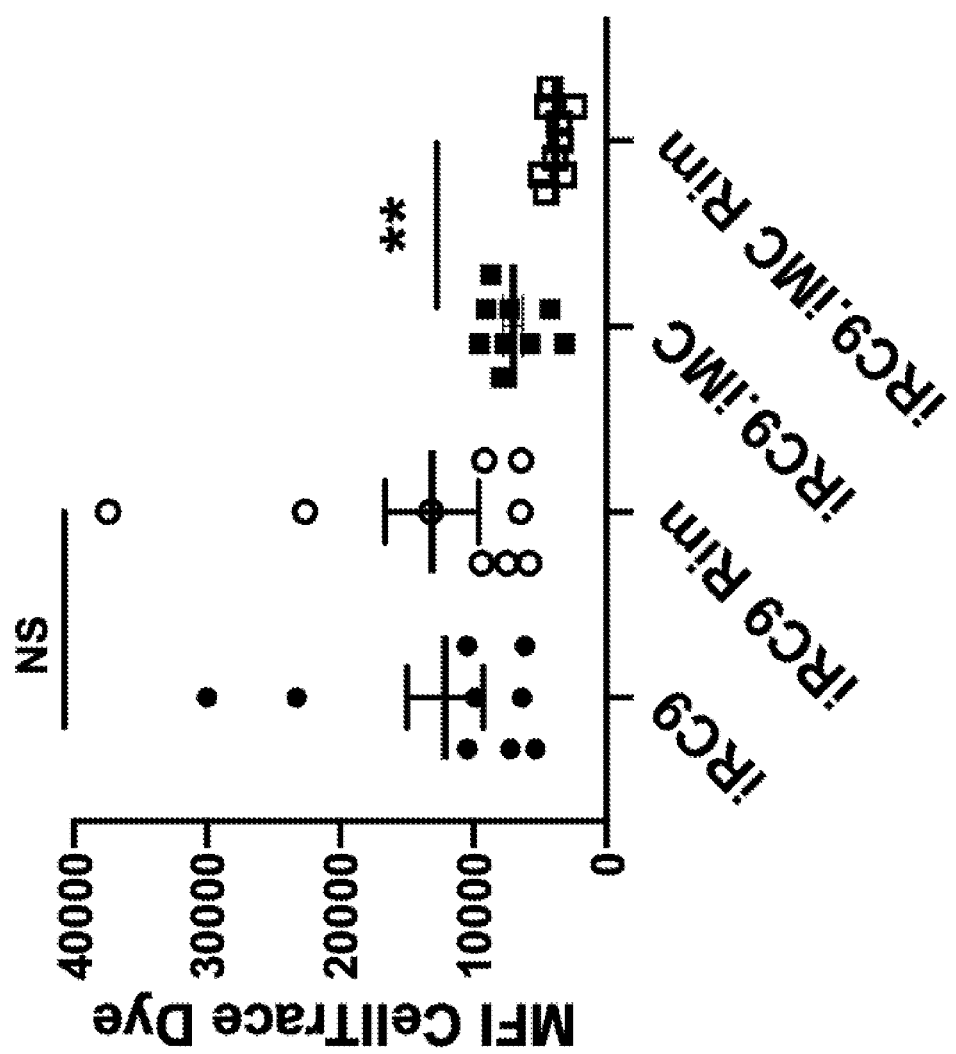

Results iMC Modified NKs Show Enhanced Proliferation Upon Rimiducid Activation iMC effects on NKs proliferation were tested. A bicistronic retroviral vector encoding iRC9 followed by iMC were used to transduce activated NKs on day 4. iRC9 encoding vector served as the control. At day 9, those gene modified NKs were re-stimulated with irradiated k562 in the presence of 0 or 1 nM Rim. At day 14 of culture, iRC9.iMC modified group contained increased numbers of viable NK cells compared with the iRC9 group. Furthermore, rimiducid treatment resulted in significantly enhancement of NK expansion (FIG. 15A). These findings were confirmed by Cell Trace dye dilution data—showing markedly increased proliferation in the rimiducid-treated compared with non-rimiducid administrated iRC9.iMC NKs (FIGS. 15B and 15C). In contrast, there is no significant Rimiducid effect observed in iRC9 gene modified NK group (FIG. 15C). These observations indicated that basal iMC signal by itself increases NK proliferation, further enhancement would be achieved by dimerization of iMC molecule controlled by Rimiducid (Rim). Additionally, the expression level of iRC9 or iRC9.iMC were similar. The mean iRC9 NK transduction efficiency was 67.8% (range, 37.2-93.2%; n=9), statistically not different from the iRC9.iMC NKs (mean, 73.7%; range, 50.3-93.6%; n=9), at day 14 of culture as determined by hCD19+ percentage.

Figure 15D:
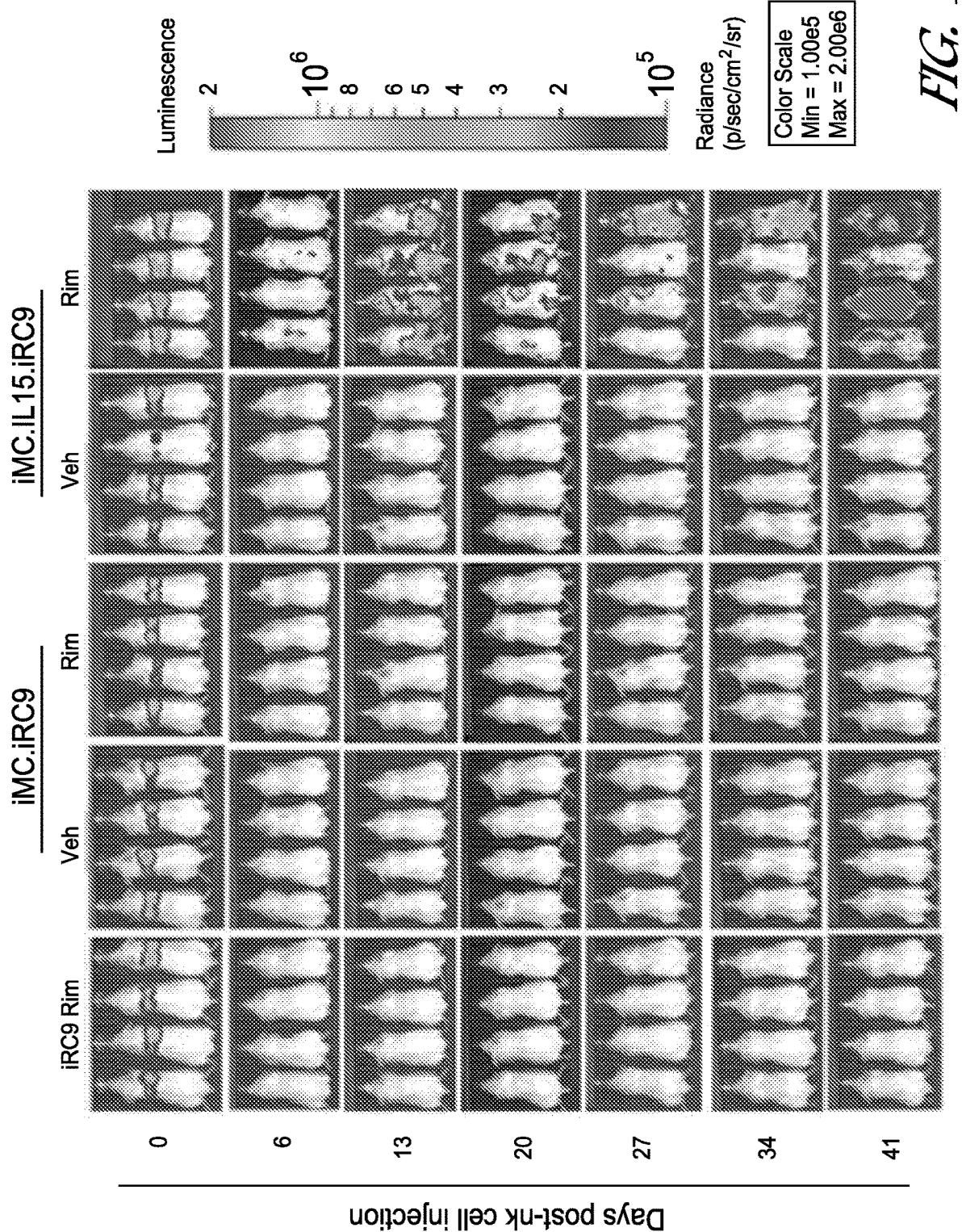
Figure 15E:
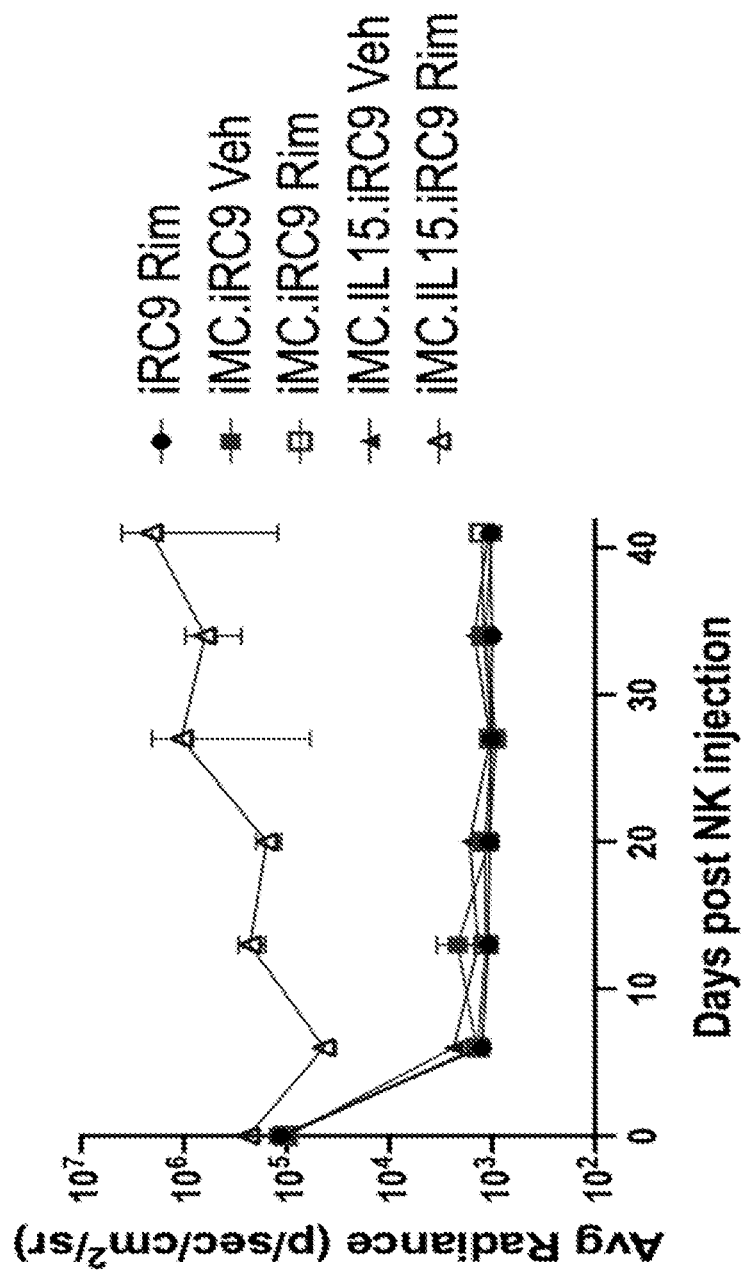
Figure 23A:
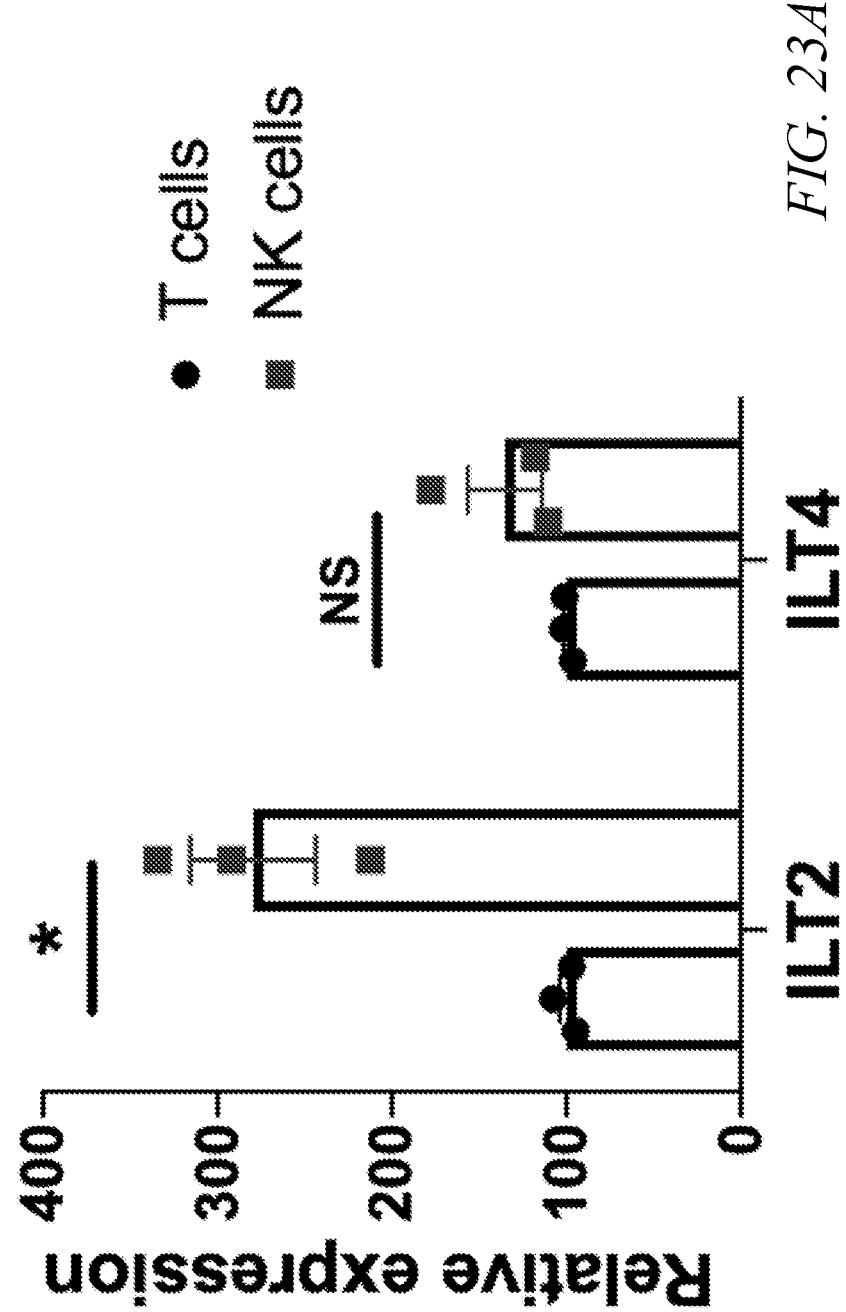
FIGS. 23A-23C.
Figure 23B:
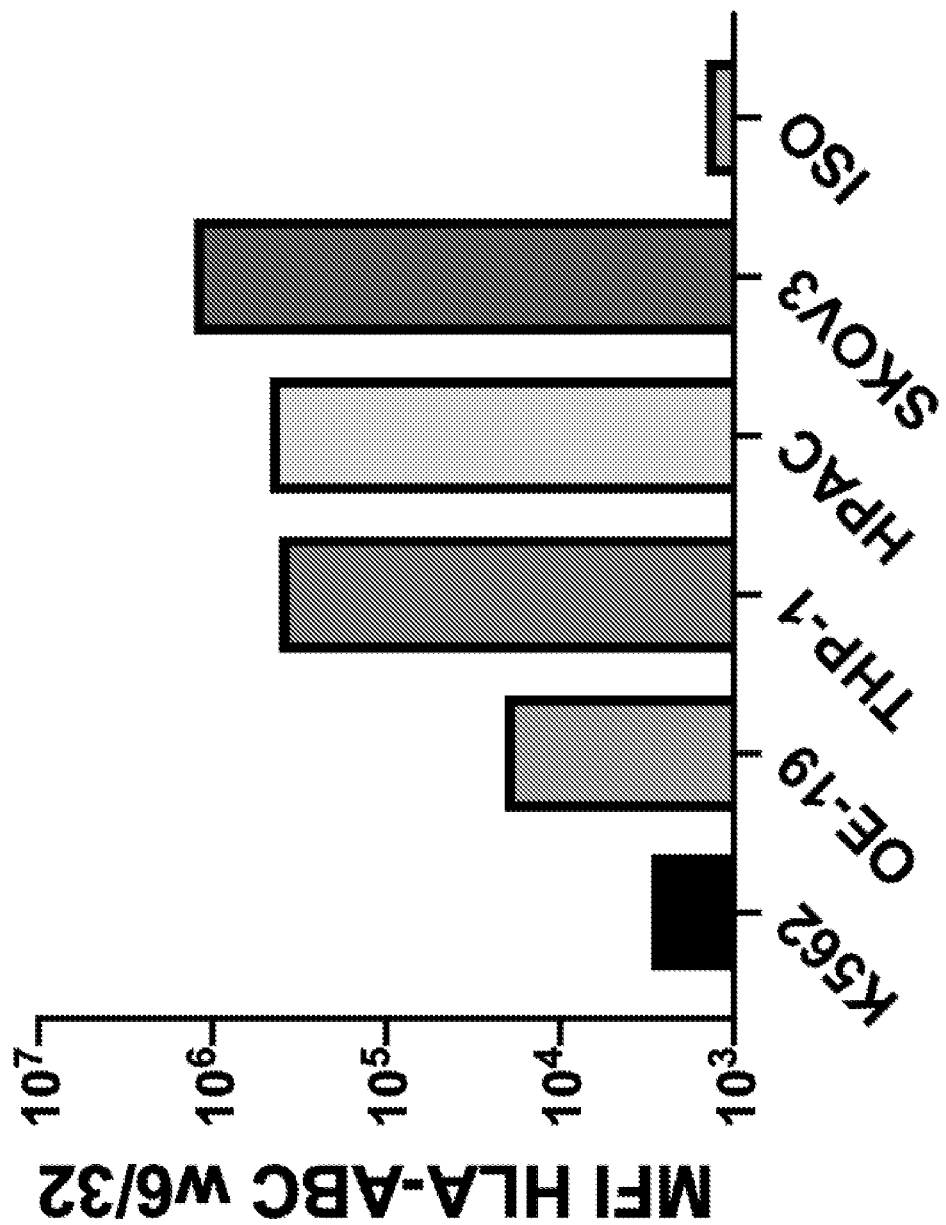
Figure 23C:
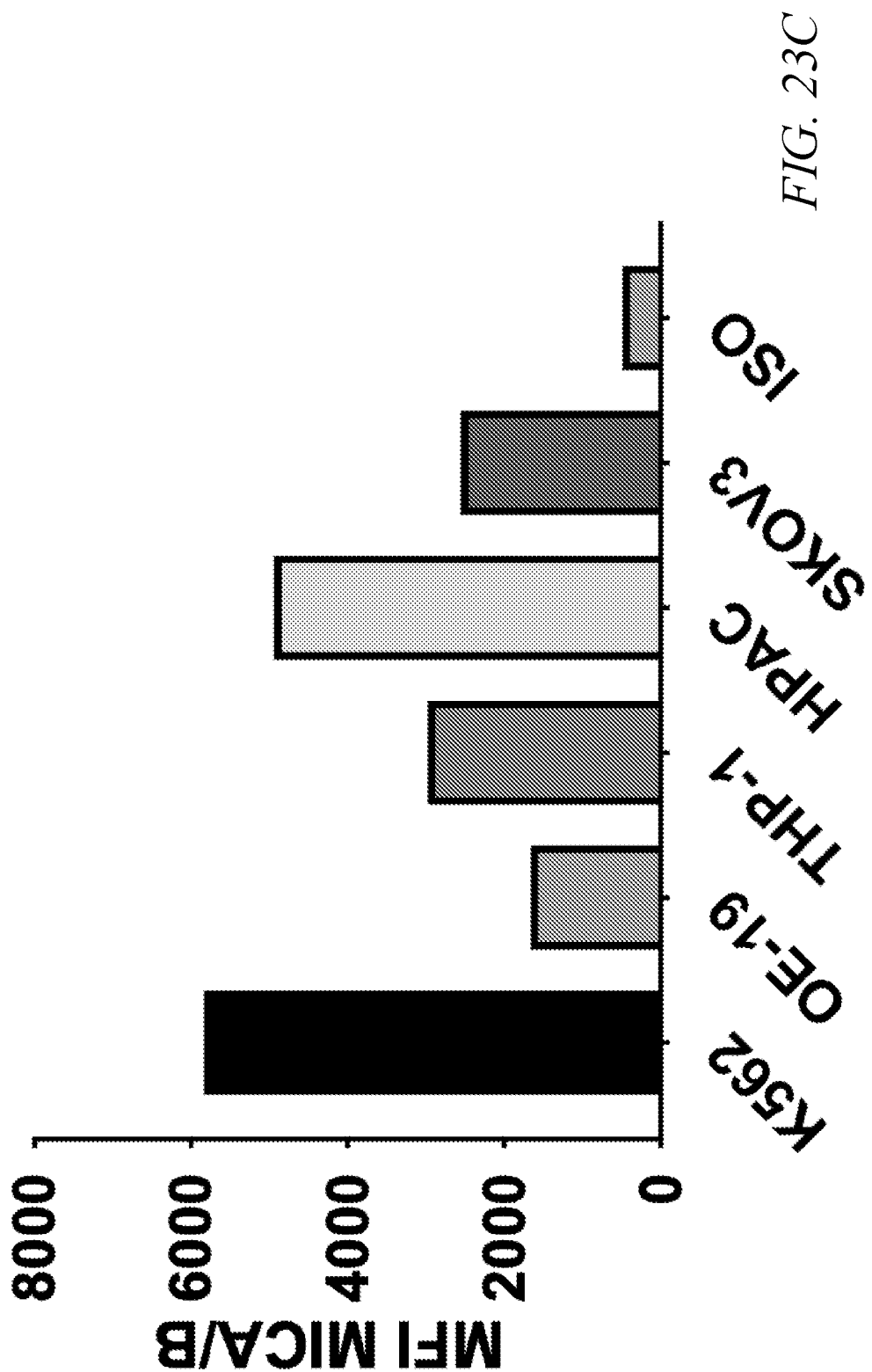
Figure 24A:
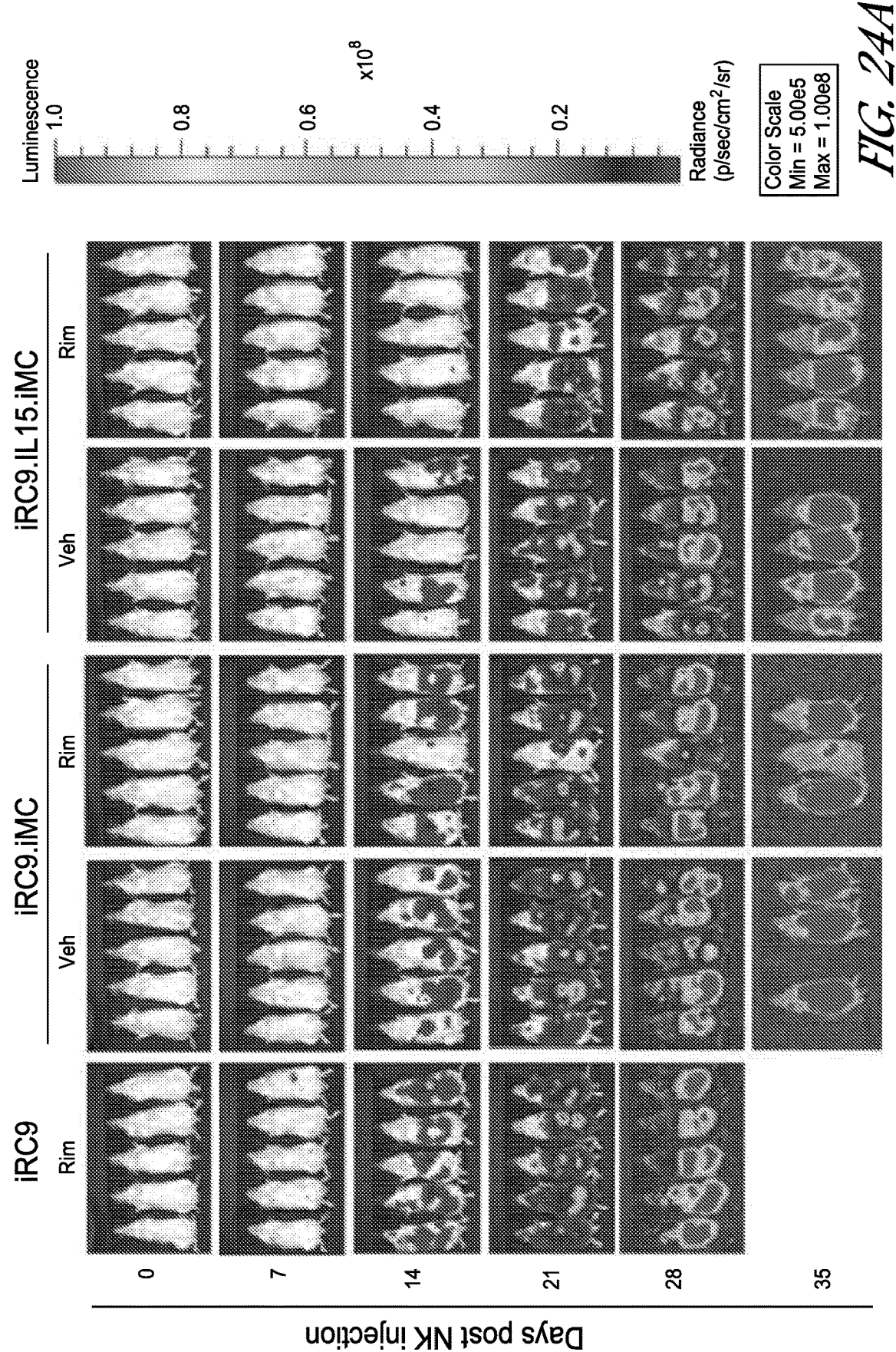
FIGS. 24A-24C: DS NKs anti-tumor efficacy in vivo.
Figure 24B:
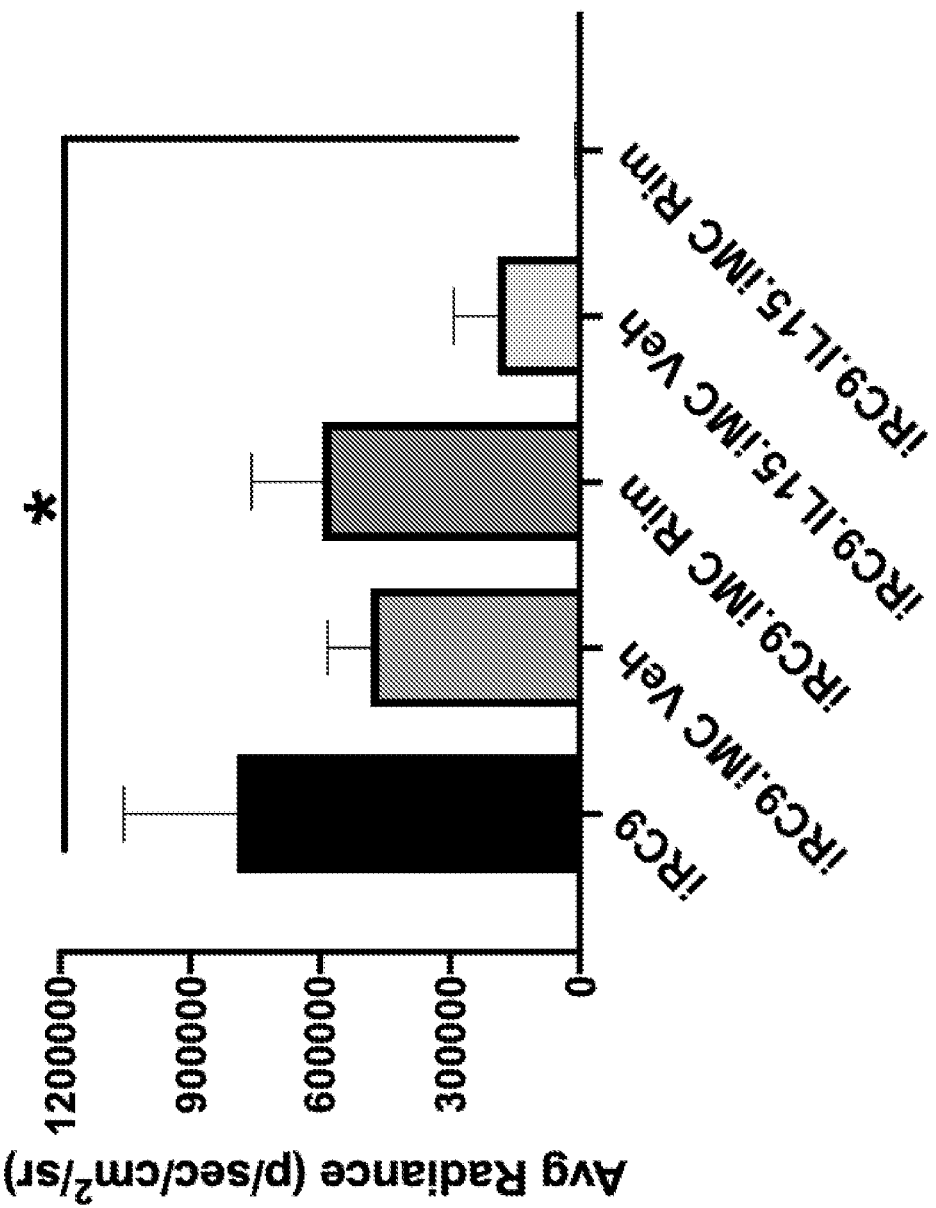
Figure 24C:
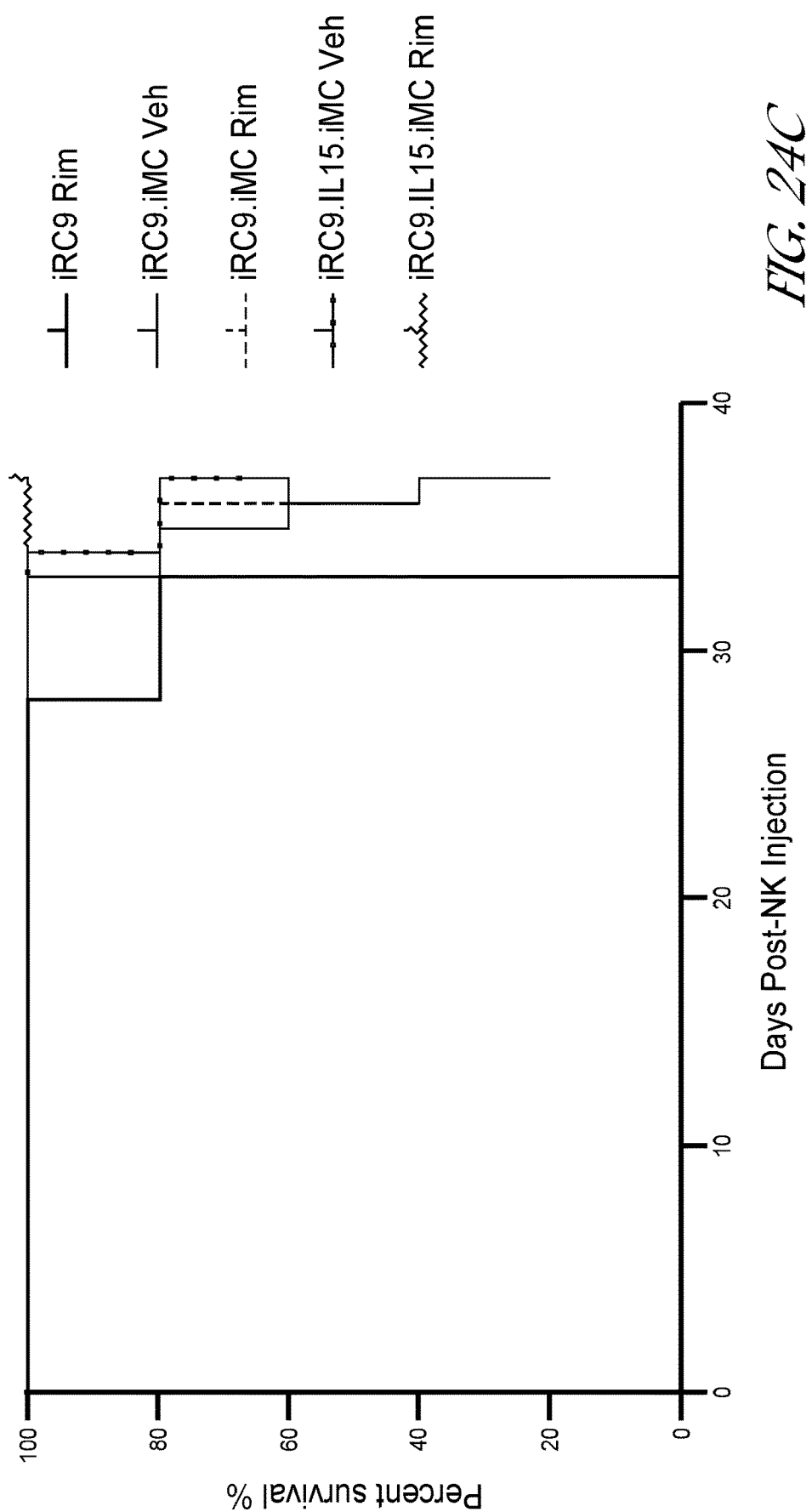

Next it was investigated whether iMC modified NKs would have improved persistence in vivo. Here, human IL-15 gene was incorporated by a T2A sequence to generate a tricistronic vector iRC9.IL15.iMC—ectopically producing IL-15 to support NK survival and proliferation. All gene modified NKs were label with an eGFP-firefly luciferase fusion protein (eGFPFfluc) by a retroviral vector for tracking in vivo (FIG. 15D). The bioluminescent imaging (BLI) signal rapidly decreased in NOD.Cg-Prkdc$^{scid}$Il2rg$^{tm1Wjl}$/SzJ (NSG) mice injected with iRC9 modified NKs, as well as iRC9.iMC modified NKs, supporting the hypothesis that IL-15 is indispensable for survival of NKs. Although mouse and human IL-15 share 65% amino acid sequence identity, there is poor interspecies cross-reactivity. Strikingly, rimiducid activation of iRC9.iMC modified NKs by rimiducid in association with IL-15 expression dramatically increased NK persistence and proliferation (FIGS. 15 D and 15E) for at least one month without any tumor targets stimulation. Especially, mouse 2 had 31.9-fold BLI signal enhancement on day 41 post-injection, and mouse 4 had 18.9-fold BLI increase on day 27 post-injection. Moreover, iMC modified NKs proliferated further in response to THP-1 tumor cell targets (FIG. 15F), similar to a feeder cell effect. Rimiducid further boosted iRC9.IL15.iMC modified NK proliferation. Surprisingly, rimiducid activation markedly increased iRC9.iMC modified NKs proliferation in the absence of IL-15 beginning since day 33 post-injection (p<0.01 iRC9.iMC rimiducid group vs vehicle group). These provide strong evidence to support that iMC itself would significantly improve NK cell proliferation and persistence in vivo.

iMC Enhances NK Cell Cytotoxicity Against Tumor Targets Upon Rimiducid Activation The effects of iMC on NKs function were tested. iRC9 or iRC9.iMC gene modified NK cells were exposed to eGFPF-fluc modified HPAC or THP-1 tumor targets. Specific firefly luciferase activity was measured after 24 hrs. At all effector to target (E:T) ratios tested, iRC9.iMC modified NK cells had greater killing of HAPC (a NK resistant pancreatic adenocarcinoma cell line; high MHC Class I level, FIGS. 23A-23C), compared with control iRC9 modified NKs. Rimiducid treatment further augmented tumor cell killing (FIG. 24A). For a NK sensitive AML cell line THP-1 (low MICA/B expression, FIGS. 23A-23C) basal iMC was sufficient to augment cytotoxicty against tumor cells markedly. While only further dilution of iRC9.iMC modified NKs (1:4, p=0.002; 1:8, p=0.026; iRC9.iMC vs iRC9.iMC Rim) showed rimiducid-depended killing (FIG. 24B). This observation was confirmed by flow cytometry analysis of 48 hr co-culture (FIG. 24C, 24D). The percentage of THP-1 tumor cells, identified as GFP+ population, greatly decreased when comparing iRC9.iMC or iRC9.IL15.iMC with non-transduced (NT) or iRC9 modified NKs. It was noted that iRC9.IL15.iMC exhibits similar rimiducid-dependent target killing effects as iRC9.iMC except the killing capacity is slight reduced. Without being bound by any theory, one possible explanation for this result is that there is a lower level of iMC expression in iRC9.IL15.iMC modified NK cells (Data not shown). Comparable rimiducid-dependent killing of target cells by iMC modified NK cells was also observed in OE19 and K562 (data not shown). These data strongly suggested that the inducible iMC signal could be used to augment NK cytotoxicity against a variety of tumor cell targets—both NK sensitive and resistant.

Figure 16A:
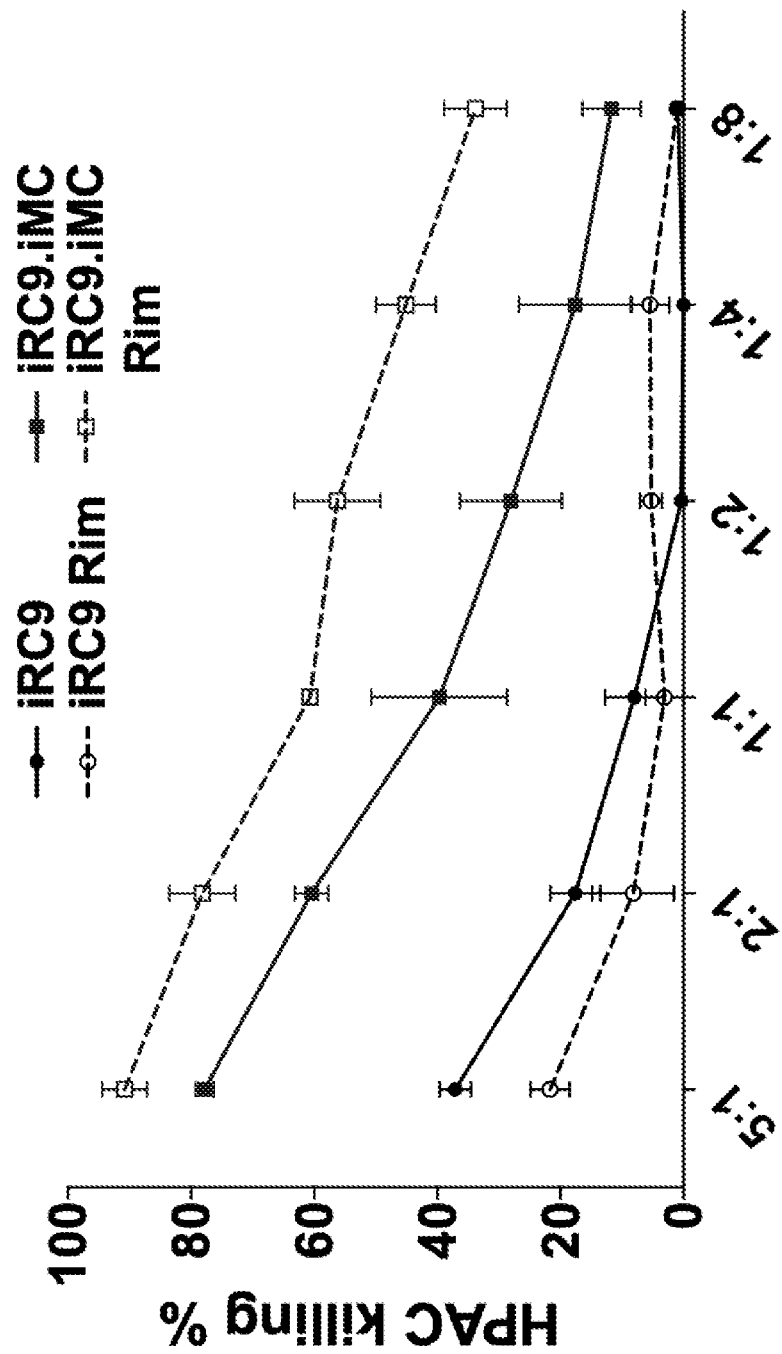
FIGS. 16A-16A-I. Rimiducid-mediated iMC activation enhances NK cells anti-tumor functions. NK cells transduced with iRC9.iMC or iRC9 were tested for their lytic capacity of tumor cell targets. NK cells were co-cultured with HPAC-GFPFfluc (FIG. 16A) or THP-1-GFPFfluc (FIG. 16B) at different effector-to-target (E:T) ratio for 24 hrs. Tumor cells killing percentages were calculated by relative luciferase activity. N=4.
Figure 16B:
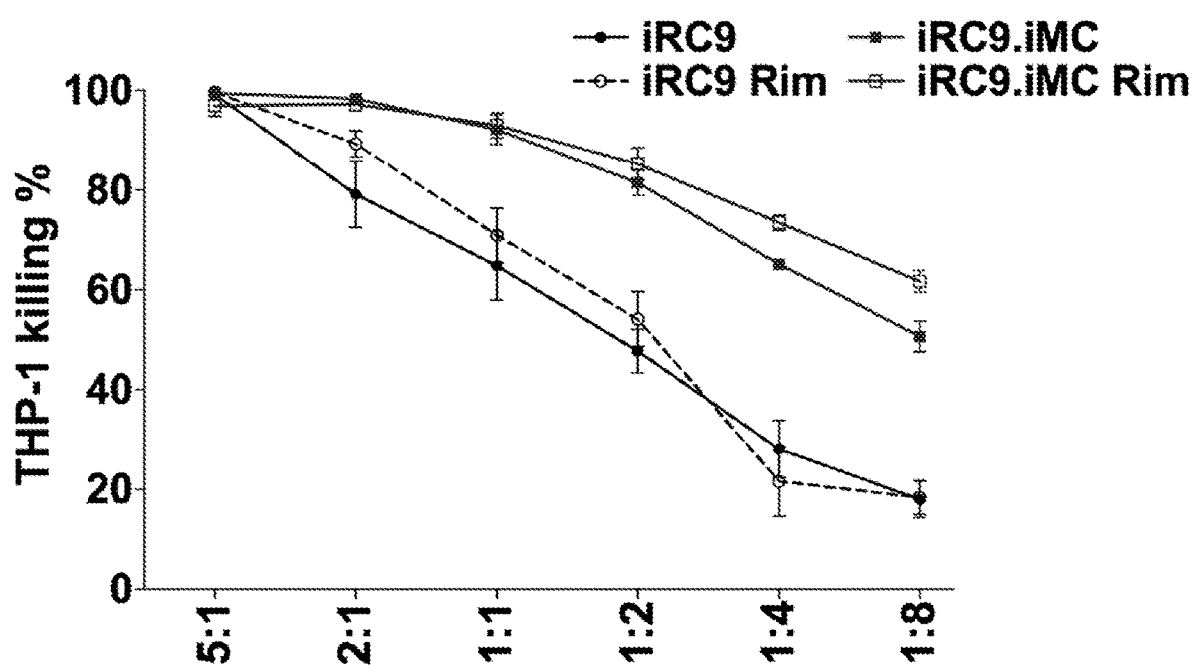
(FIGS. 16C and 16D) Flow cytometry analysis of THP-1-GFPFfluc cells co-cultured with iRC9, iRC9.iMC, or iRC9.IL15.iMC transduced or non-transduced (NT) NKs for 2 days with/without rimiducid 1 nM. Representative flow plots were shown at the E:T ratio of 1:1. Live cells were gated by forward, side scatter and fixable viability dye before. THP-1 population was gated as GFP+ population. 3 donors with E:T ratio 3:1, 1:1, 1:3. Data expressed as means with standard errors. 2-way ANOVA was used do comparisons for A, B, D; P<0.0001.
(FIGS. 16E-16I) iRC9 or iRC9.iMC transduced NKs were incubated with/without THP-1 targets for 4 hrs (FIG. 16E), or overnight (FIGS. 16F-16I) with or without 1 nM Rim. Percentage of surface CD107a (FIG. 16E), intracellular IFN-γ (FIG. 16F), and TNF-α (FIG. 16G), were measured by flow cytometry. MFI of perforin (FIG. 16H) and granzymeB (FIG. 16I) were measured in NKs co-culture with THP-1 overnight. Transduced NK cells were first gated as CD56+CD19+ population. Paired t test was used to compare groups. *p<0.05; **p<0.01.
Figure 16C:
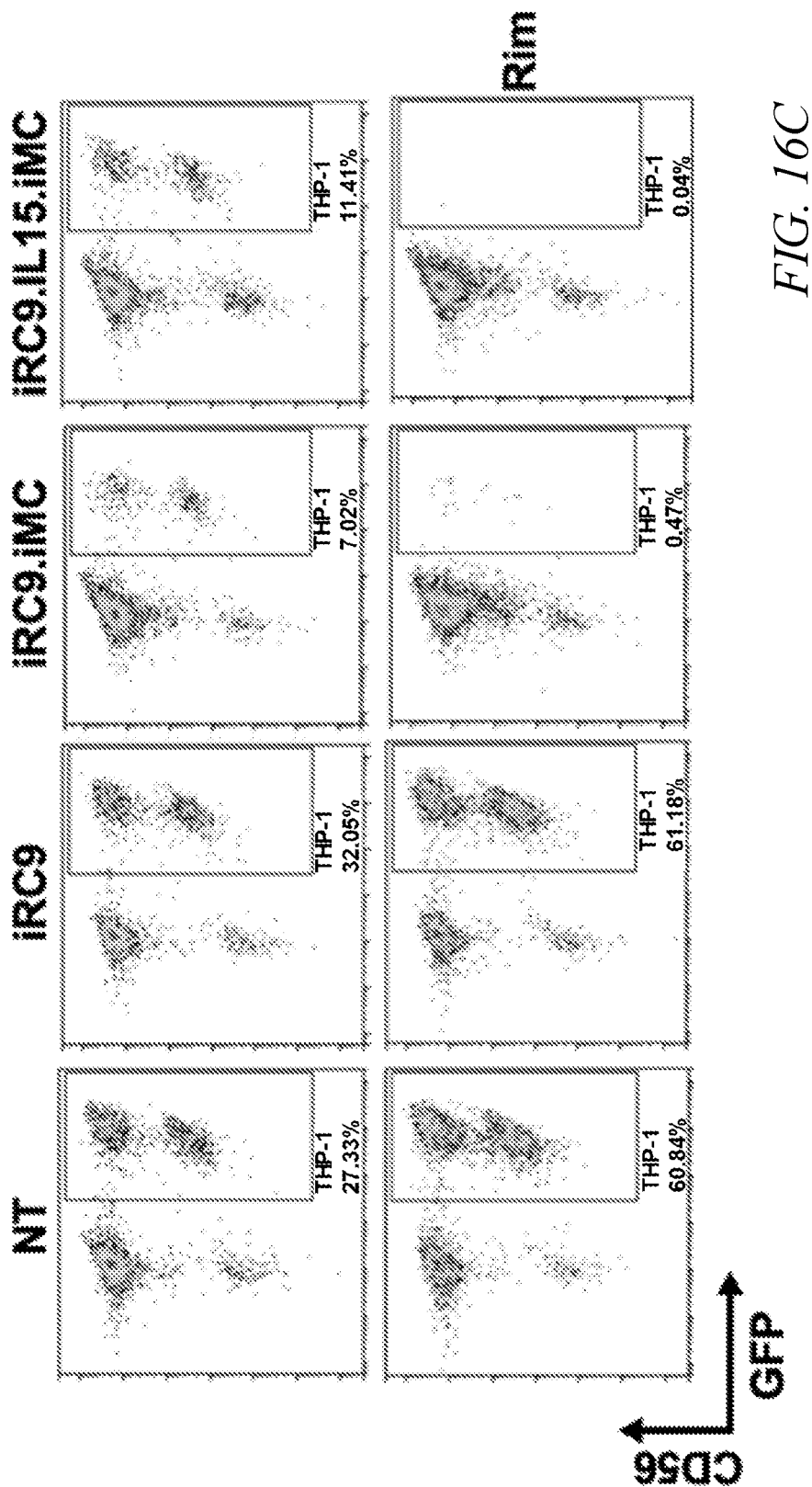
Figure 16D:
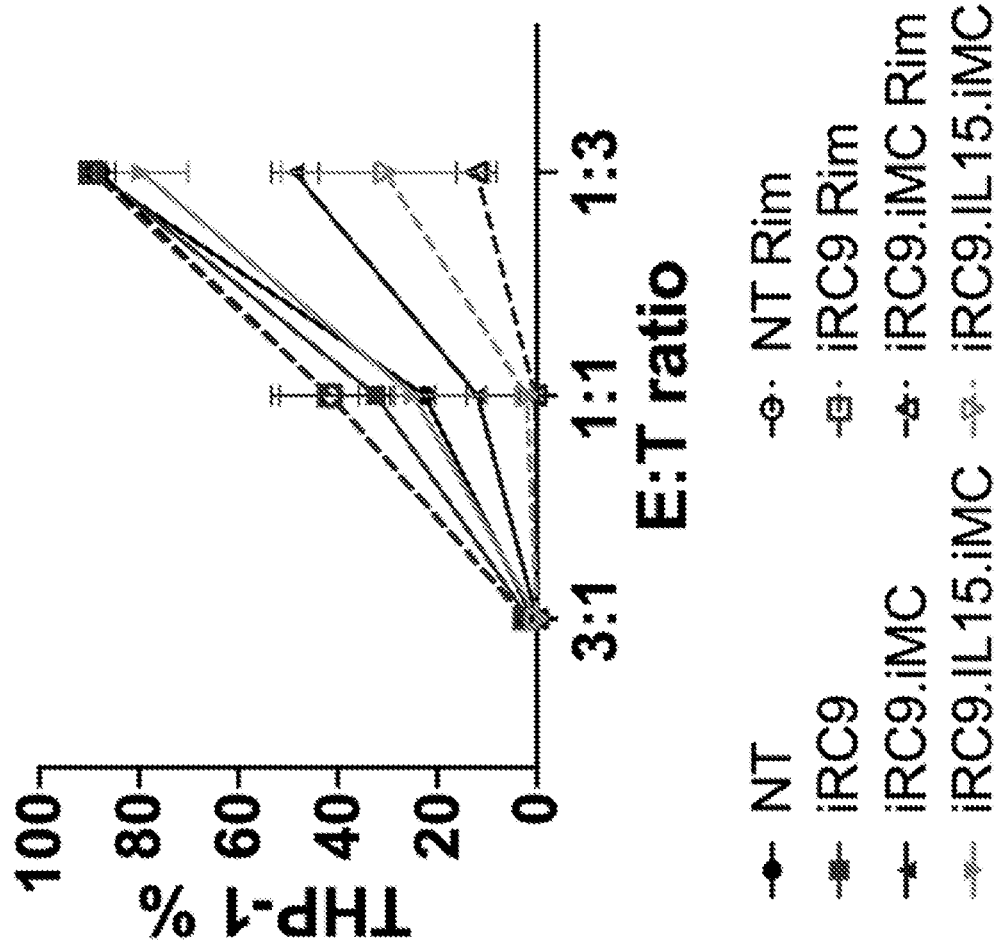
Figure 16E:
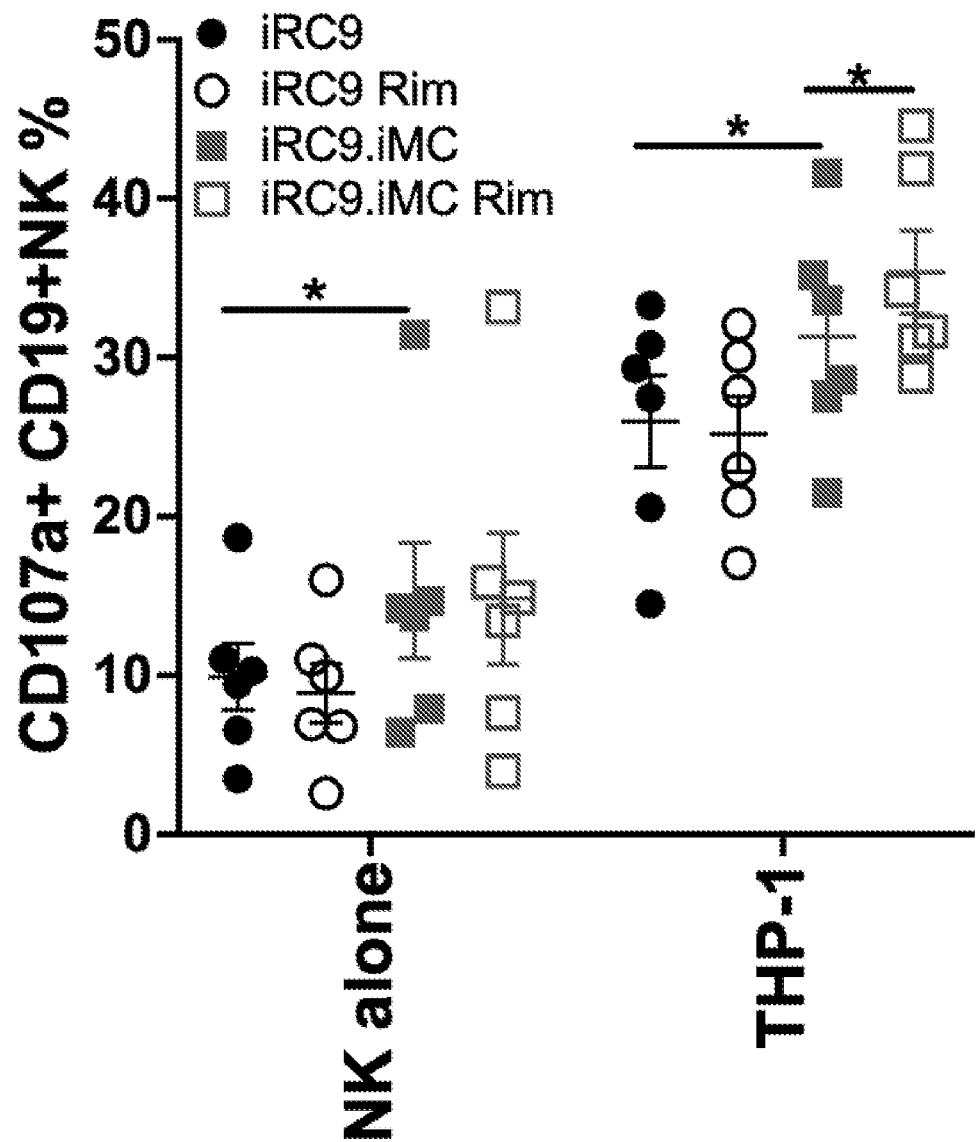
Figure 17:
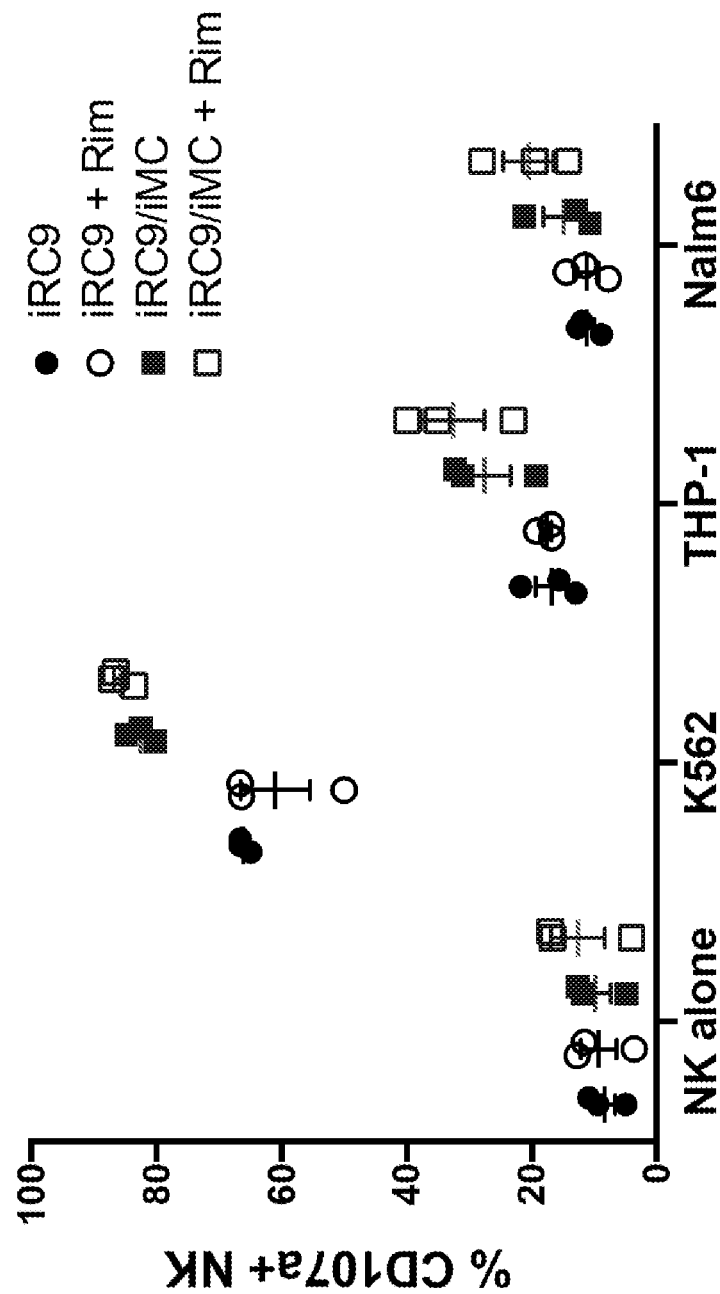
FIG. 17 shows levels of surface CD107a expressed by NK cells transduced with retrovirus encoding iRC9 or iRC9 and iMC when co-cultured with tumor targets K562, THP-1 or Nalm6 or alone in the absence or presence of rimiducid (Rim).

The most prominent feature of NK cells is their cytolytic activity. NK cells inject cytotoxic granules to their target. This process is termed degranulation and is marked by the expression of CD107a on the cell surface of NK cells. Therefore, the CD107a surface expression, a marker of degranulation, was examined. When cultured alone, a low proportion of transduced NK cells have surface expression of CD107a. Co-culture of transduced cells with the tumor targets K562, THP1 or Nalm6 increases the proportion of NK cells that degranulate. This proportion is elevated in iMC-expressing cells, indicating that even tonic iMC signaling is sufficient to sensitize the NK cells to respond to tumors. iRC9.iMC modified NK cells showed an increased percentage of surface CD107a+ population compared with iRC9 modified NK cells in response to THP-1 tumor targets; and these effects were further enhanced by rimiducid treatment (FIG. 16E). Basal CD107a surface expression was upregulated in iRC9.iMC group in the absence of tumor targets (FIG. 16E). The observations were likewise perceived in responses to other tumor targets k562 and Nalm6 (data not shown; FIG. 17), suggesting that iMC increases NK cells' secretion of cytolytic granules.

Figure 16F:
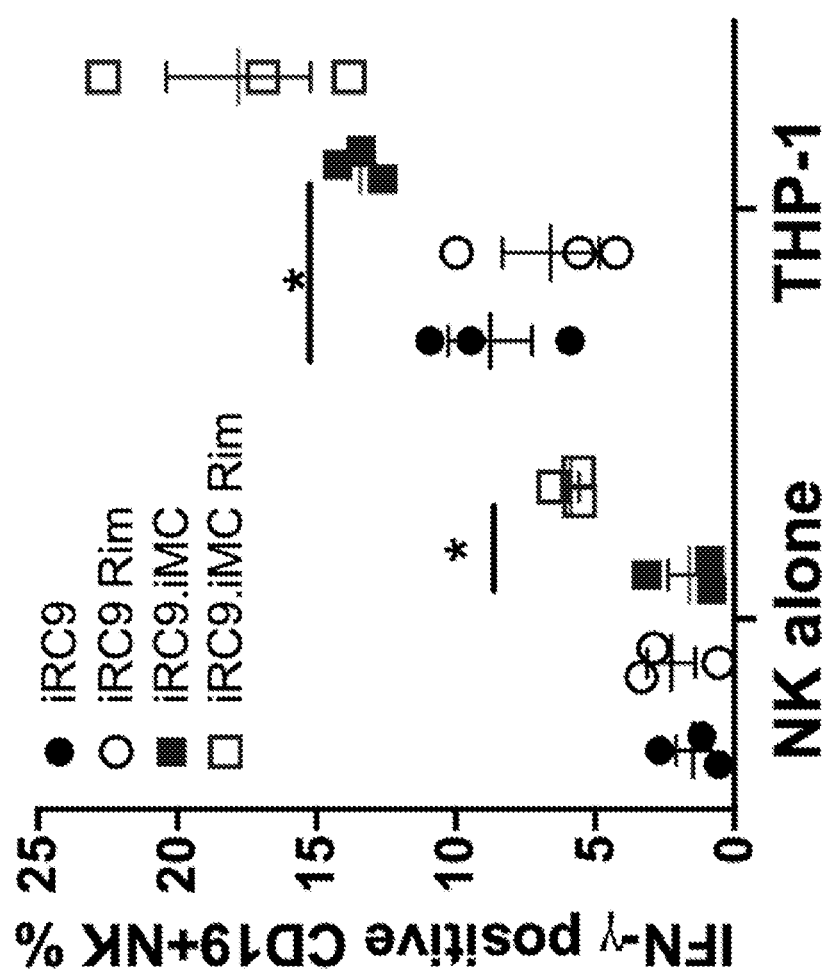
Figure 16G:
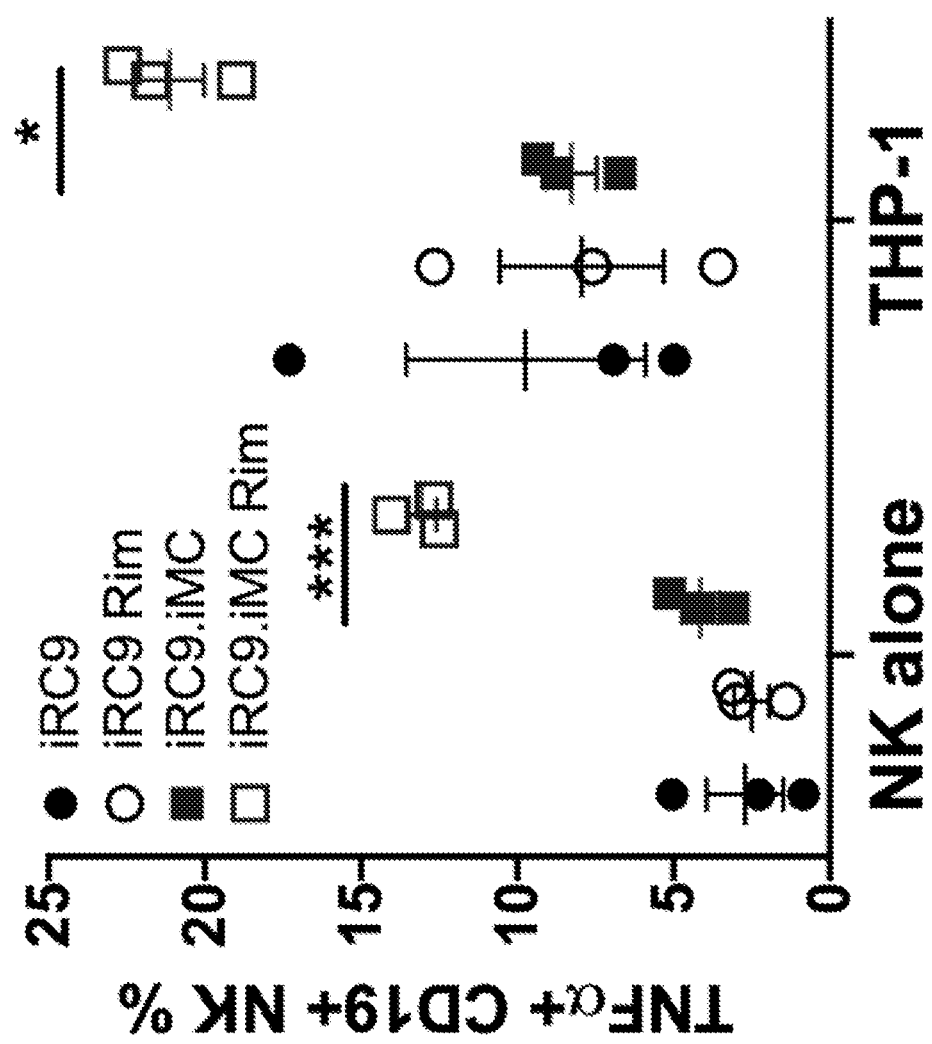

IFN-γ (FIG. 16F) and TNF-α (FIG. 16G) production were next evaluated. iMC with rimiducid activation markedly enhanced NK cells' producing ability of these effector cytokines.

Figure 16H:
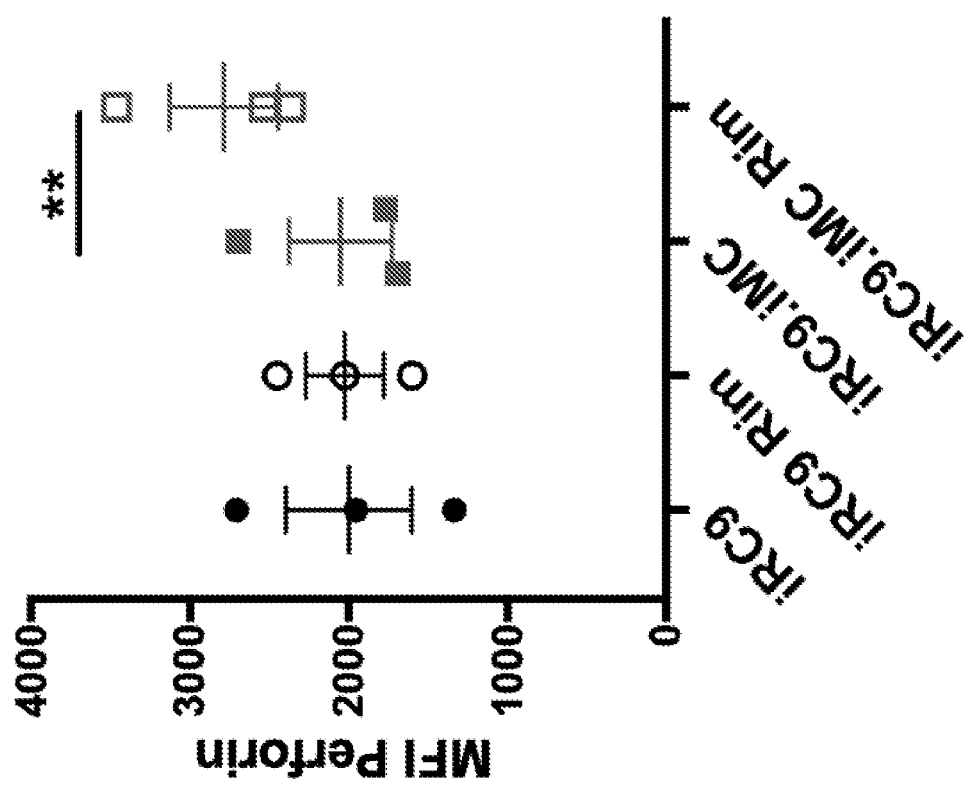
Figure 16I:
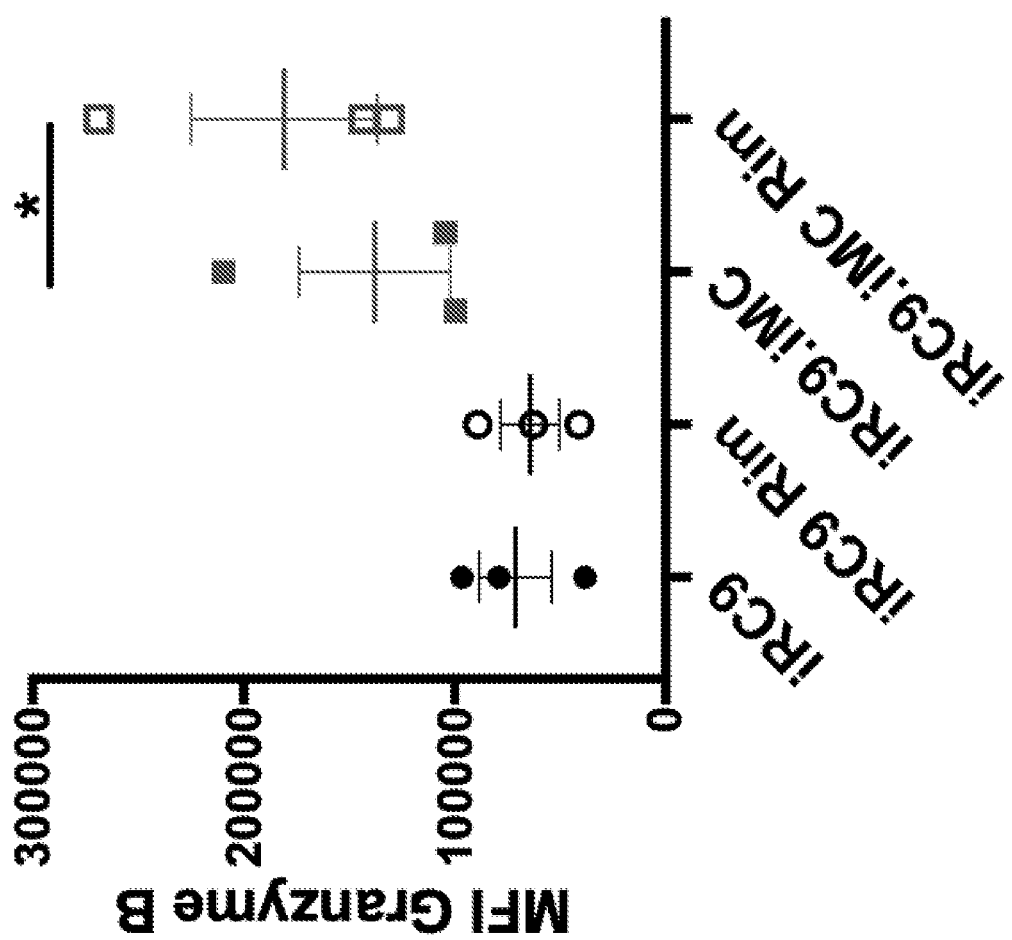

One mechanism used by NK cells to kill target cells is the direct secretion of cytotoxic granules that include the protease granzyme B through pores formed by the protein perforin. Perforin (FIG. 16H) and granzyme B (FIG. 16I) production in responses to THP-1 targets were assesse by intracellular staining. As expected, rimiducid activated iRC9.iMC modified NK cells showed significant increased levels of granzyme B and perforin within the NK cells, which correlates with the enhancement of NK cell cytotoxicity with iMC activity. Interestingly, granzyme B but not perforin had a slightly upregulated basal production in iRC9.iMC modified NKs, compared with iRC9 modified NK cells, although it was not statistically significant (FIG. 16H, 16I). Taken together, these data suggest that iMC with rimiducid stimulation resulted in actively enhanced production of effector granules (perforin and granzyme B) and cytokines (IFN-γ and TNF-α) in response to tumor cell targets, which correlates with increased NK cell cytotoxicity with iMC rimiducid activation.

Phenotypic and Functional Profiling of iMC Modified NKs Cells

Figure 15F:
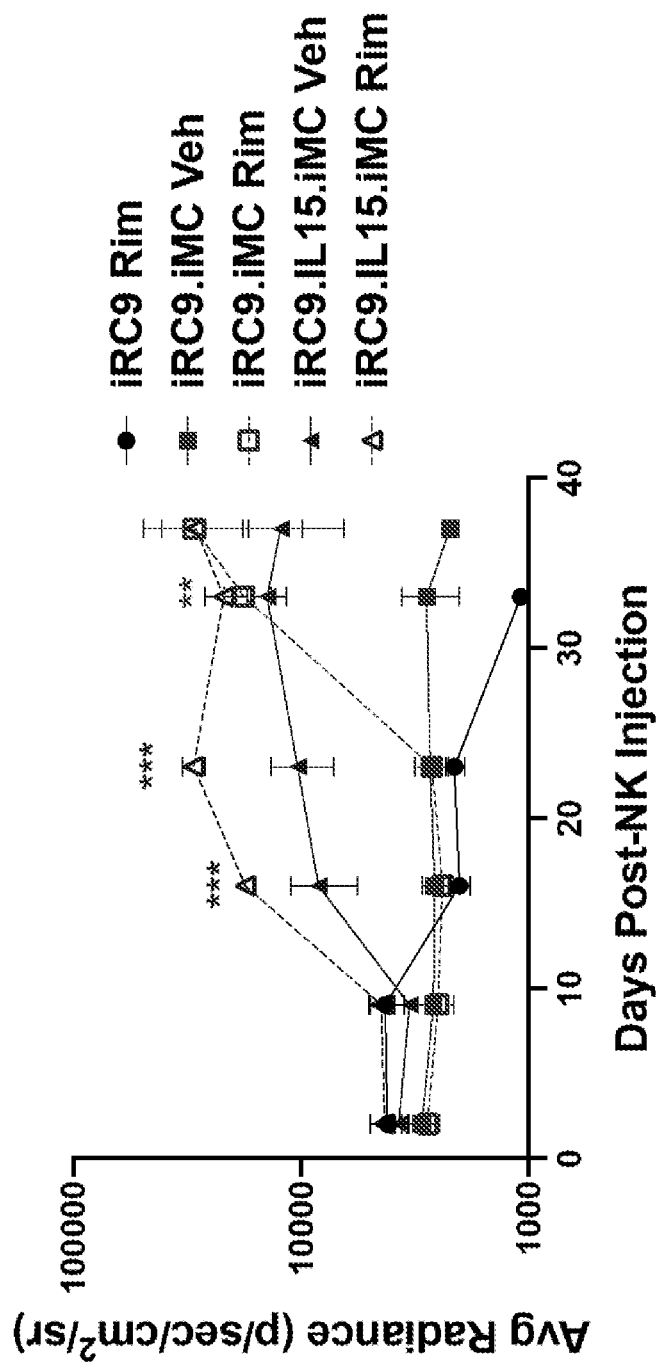
Figure 18A:
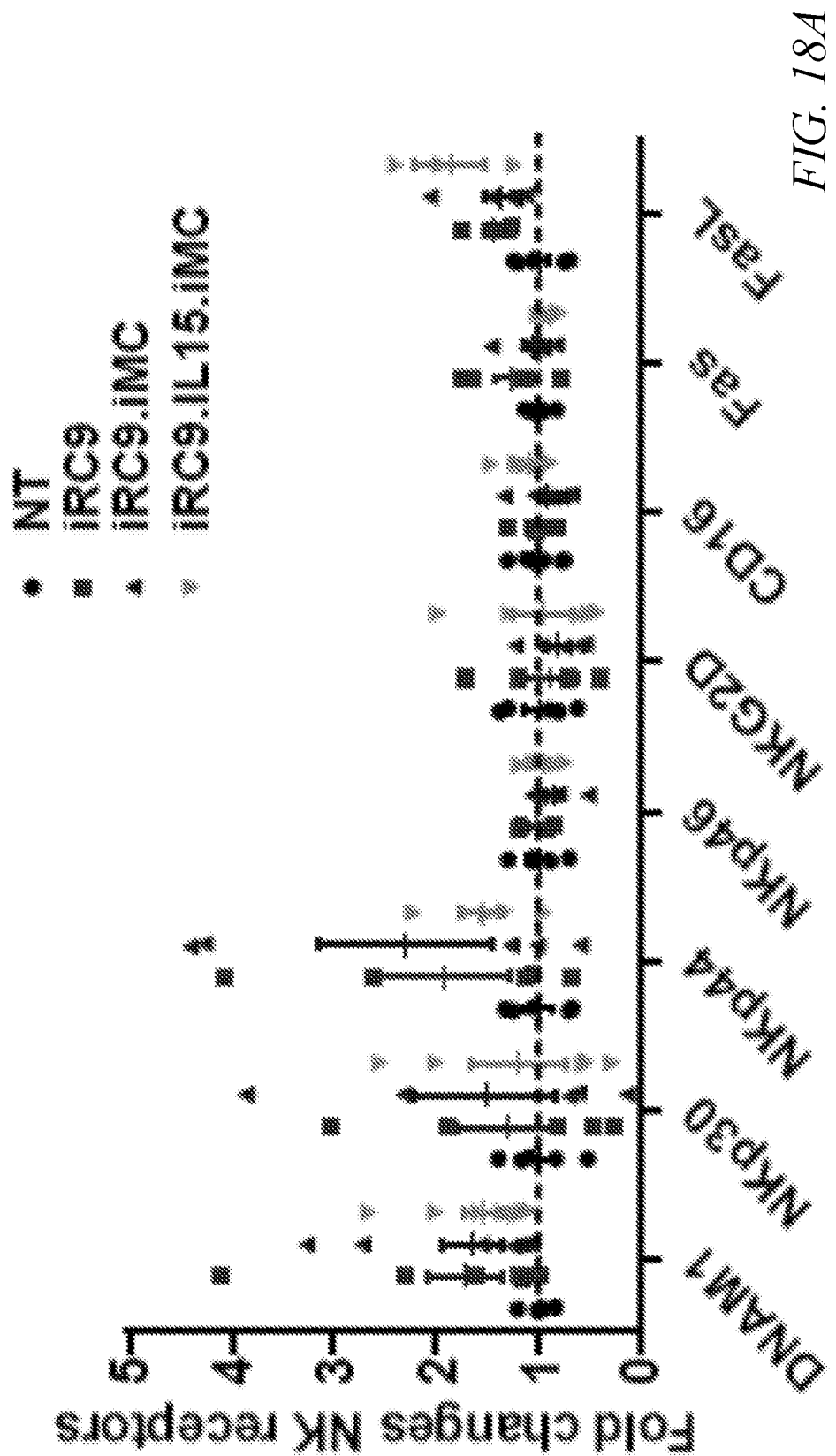
FIGS. 18A-18E Phenotype of iMC transduced NK cells.
Figure 18B:
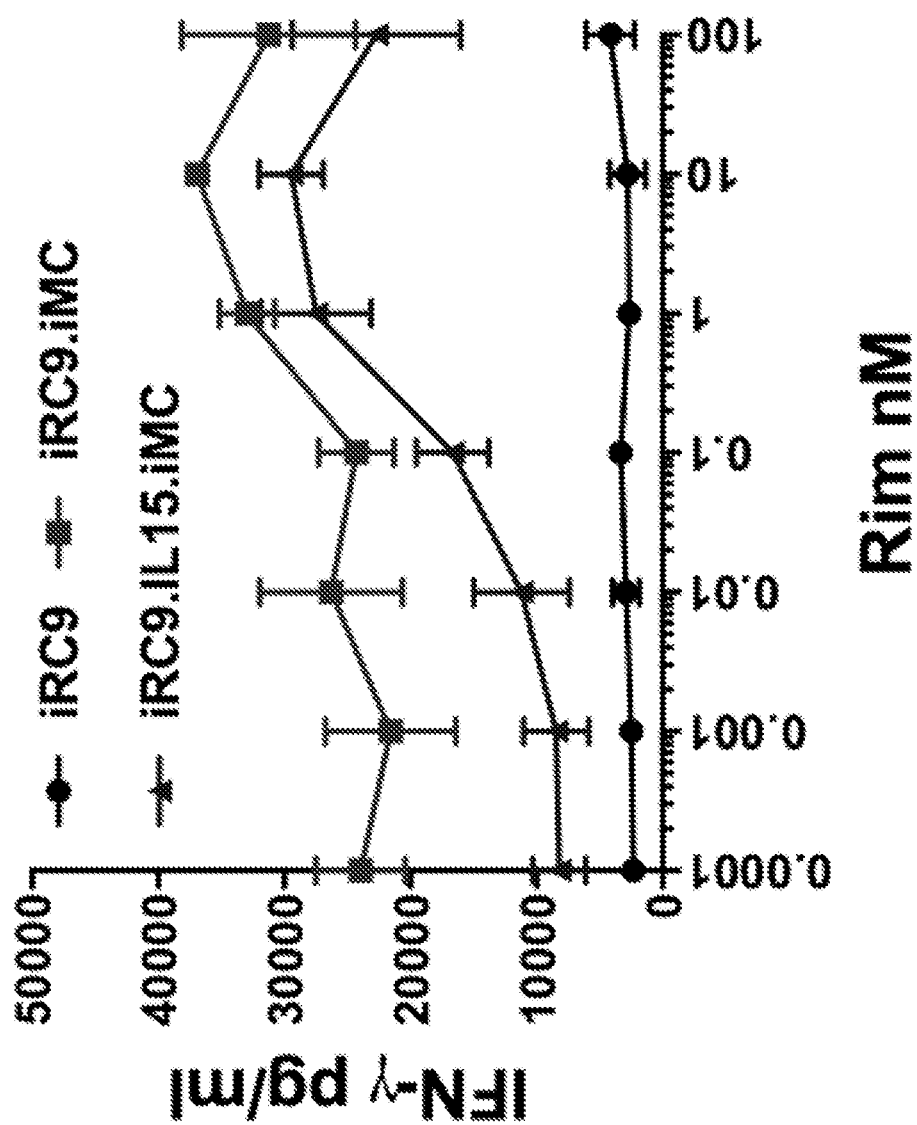
Figure 18C:
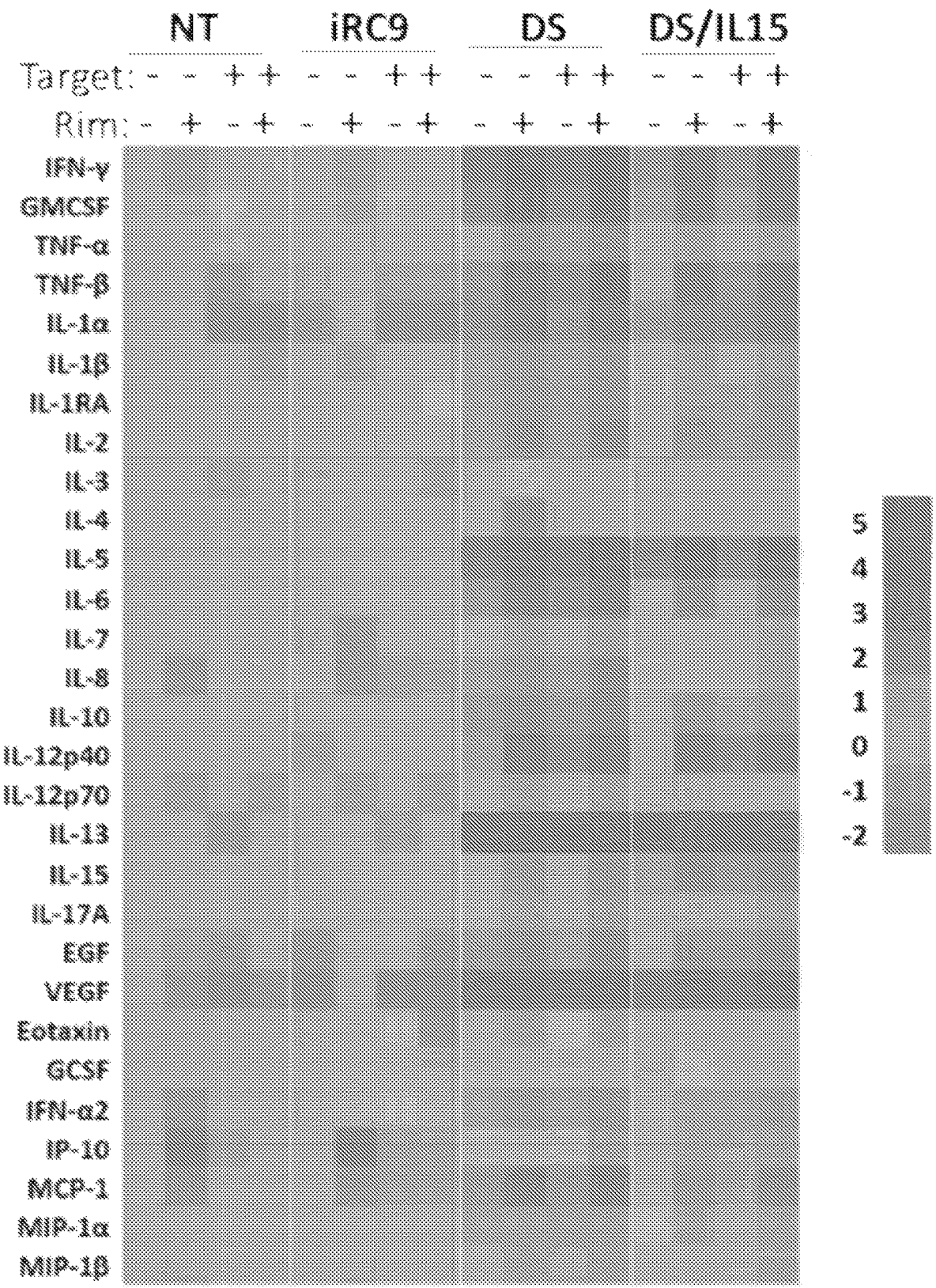
Figure 18D:
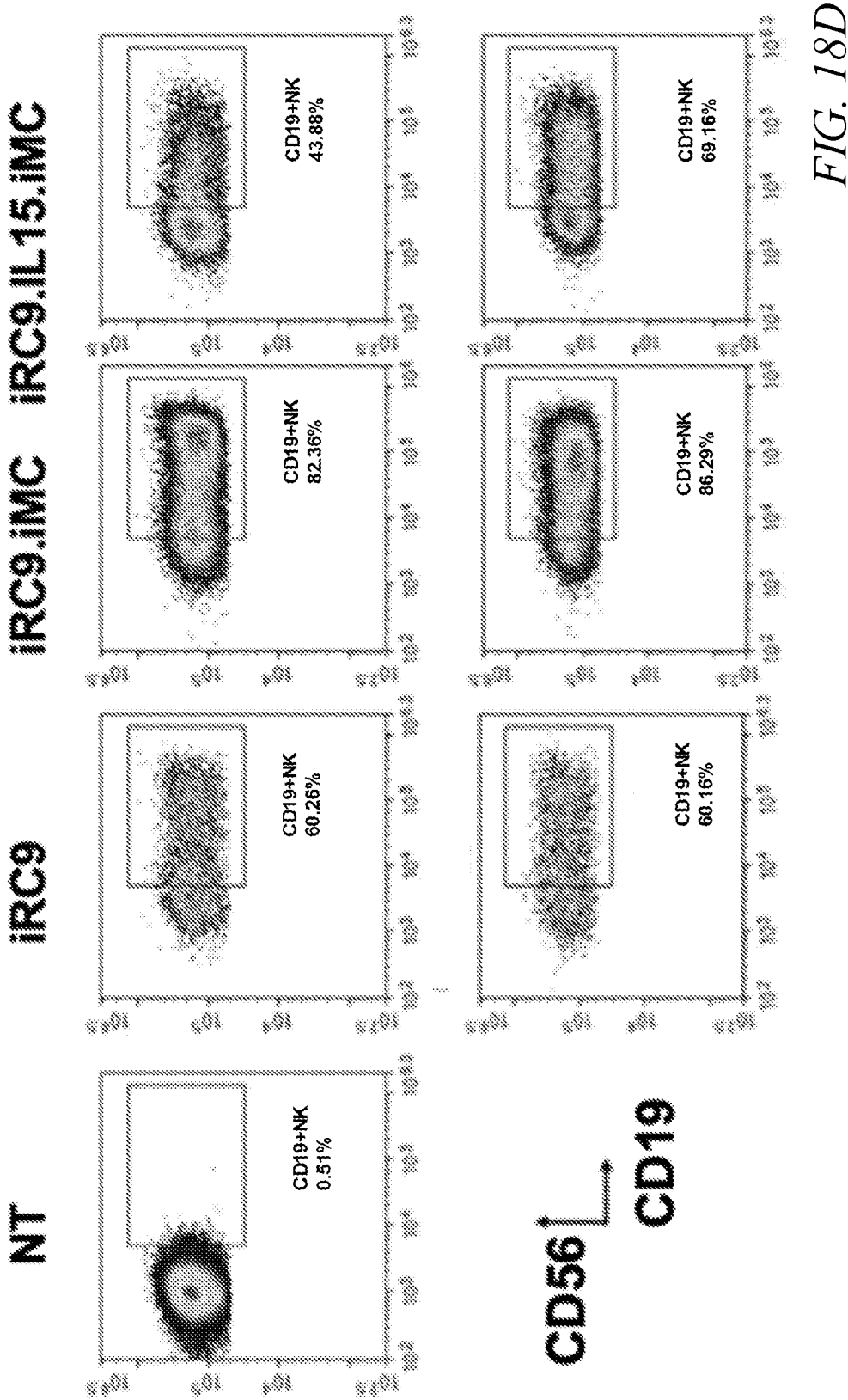
Figure 18E:
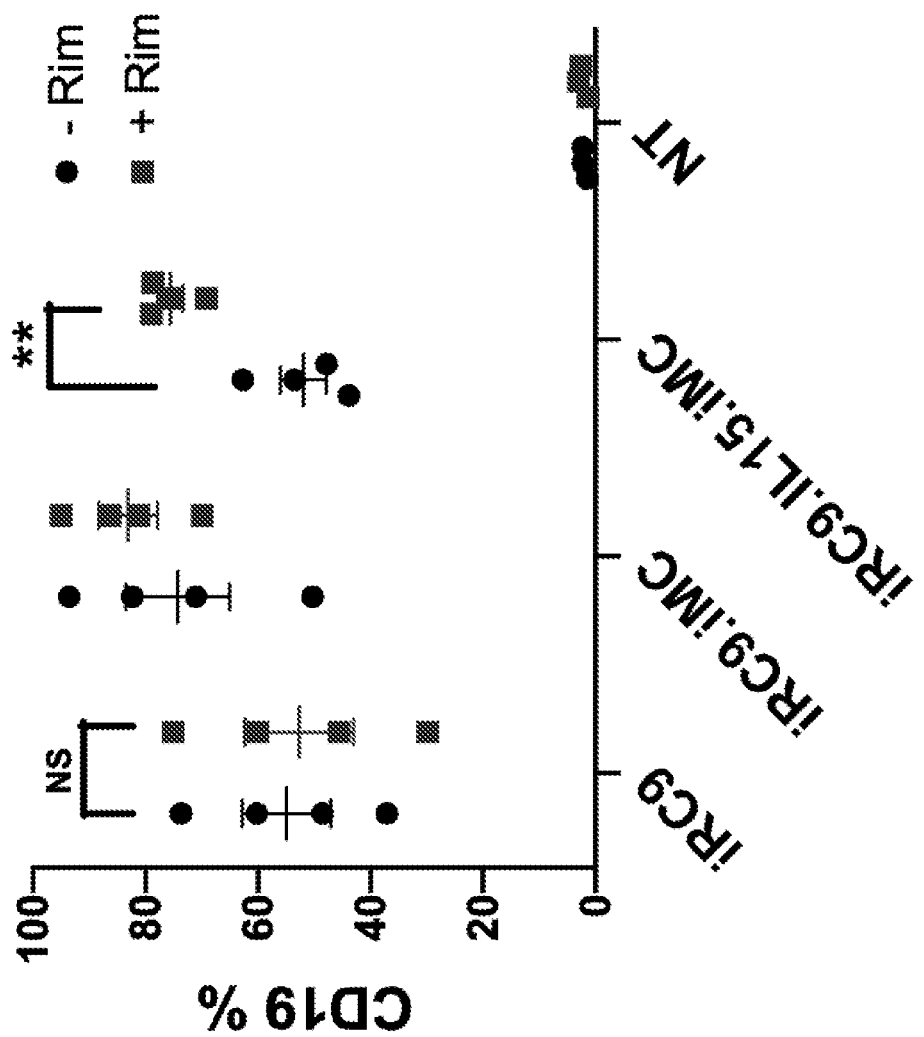

NK cell activating receptors are essential for NK cell activation and recognition of targets. Upon infection or malignant transformation, these ligands typically upregulate and activate NK cells for specific attack and elimination of target cells. To explore the iMC effects on various NK receptors, mutiparameter flow cytometry was performed. iRC9.iMC or iRC9.IL15.iMC modified NKs actually exhibited a phenotype very similar to that of iRC9 modified NKs (FIG. 18A). Rimiducid administration also did not increase surface NK cell receptor expression (data not shown), indicating that iMC enhancement of NK cell cytotoxicity is unlikely due to better identification of tumor targets via up-regulation of NK cell activating receptors. Interestingly, compared with NT group, gene modified NK cells had increased DNAM1, natural cytotoxicity receptors (NCR) NKP30, NKP44, and FasL surface levels (FIG. 18A), possibly due to retroviral infection, adding a rationale for retroviral vector approach in NK cell-based therapy. Previous reports regarding the effects of IL-15 on NK receptors are controversial (Liu, E., et al., Cord blood NK cells engineered to express IL-15 and a CD19-targeted CAR show long-term persistence and potent antitumor activity. Leukemia, 2018. 32(2): p. 520-531; Elpek, K. G., et al., Mature natural killer cells with phenotypic and functional alterations accumulate upon sustained stimulation with IL-15/IL-15Ralpha complexes. Proc Natl Acad Sci USA, 2010. 107(50): p. 21647-52). The present study suggests that NK cells, at least when transduced with iMC display no signs of dysfunction or anergy with transgene level IL-15 presence.

iMC modified NK cells were further characterized in terms of cytokine production. IFN-γ is the major effector cytokine produced by NK cells and plays important roles in modulating the immune responses (Hammer, Q., T. Ruckert, and C. Romagnani, Natural killer cell specificity for viral infections. Nat Immunol, 2018. 19(8): p. 800-808). Rimiducid administration dramatically increased IFN-γ production at the co-culture supernatant in a dose-dependent manner (FIG. 18B). With 1 nM rimiducid treatment, IFN-γ production of iRC9.iMC modified NK cells was 12.3±1.42 fold that of iRC9; iRC9.IL15.iMC modified NK cells had 10.3±2.83 fold IFN-γ productions compared with iRC9 modified NK cells. An extensive cytokine profiling analysis was performed using a multiplex assay. Among the 29 cytokines/chemokines tested, iRC9.iMC modified NK cells generally demonstrated more cytokine production compared with iRC9 modified or non-transduced NK cells in a rimiducid-dependent fashion, especially certain cytokines/chemokines had greater fold change including IFN-γ, GM-CSF, TNF-α, TNF-β, IL-5, IL-12p40, IL-13, EGF, vEGF, and MCP-1 (FIG. 18C). iRC9.IL15.iMC modified NK cells demonstrated a similar cytokine production pattern, but produced slightly lower amounts as compared to iRC9.iMC modified NK cells except for IL-15. IL-15 was undetectable in supernatants collected from non-transduced or iRC9 modified NK cells. iRC9.IL15.iMC modified NK cells produced moderate amounts of IL-15 (12.52±2.38 pg/ml·$10^6$ cells); the transgene expression significantly increased with rimiducid activation (27.88±21.66 pg/ml·$10^6$ cells), in keeping with the enhanced proliferation of NK cells in culture. Surprisingly, iRC9.iMC modified NK cells produced small amounts of IL-15 (9.97±1.23 pg/ml·$10^6$ cells) with rimiducid activation, providing one explanation for the in vivo finding that iRC9.iMC with rimiducid activation and tumor target stimulation showed an NK cell expansion at 30 days post injection in the absence of external IL-15 support (FIG. 15F).

Rimiducid Facilitates Selective Enrichment of iMC Gene Modified NK Cells

Interestingly, the transduction efficiency increased in iMC gene modified NK cells with rimiducidactivation (FIGS. 18 D and E). Briefly, transduced or non-transduced NK cells were treated with or without 1 nM rimiducid together with irradiated k562 and IL-2 at day 9 after activation. At day 14 of culture, the transduction efficiency was determined by hCD19 surface staining, since a truncated version of hCD19 was incorporated as a marker in the constructs. CD19+ percentage did not change much in iRC9 modified NK cells; whereas the CD19+ rate of iRC9.IL15.iMC modified NK cells increased dramatically from 52%±8.2%, to 75.7%±4.6% (p=0.002) upon 1 nM rimiducid administration, indicating that iMC gene modified NK cells outgrow the non-modified NK cells. Upregulation of transgene expression as the main reason can be excluded since short time treatment (1 or 2 days rimiducid treatment) did not result in significant CD19+ cell population changes (data not shown). This observation further supports that iMC activation by rimiducid leads to enhanced NK cell proliferation. CD19+ percentage also increased in iRC9.iMC modified NK cells (74.3%+18.5% to 83.1%+10.5%), but not reached statistical significance (FIG. 18E).

Improving iMC Gene Modified NK Cell Cytotoxicity Via ADCC Effects

Next, the in vivo efficacy of iMC modified NK cells was evaluated in an established leukemia xenograft model in NSG mice. Animals were intravenously injected with two doses of $5\times10^6$ NKs modified with iRC9, iRC9.iMC, or iRC9.IL15.iMC, at day 5 and day 17 post luciferase-expressing THP-1 cells (THP-1eGFPFfluc) infusion. Animals also received intraperitoneal either 1 mg/kg rimiducid or vehicle weekly. Leukemia development was monitored by in vivo BLI. Only iRC9.IL15.iMC modified NK cell group with rimiducid treatment showed significant tumor control compared with iRC9 modified NK cells (p=0.017) at day 14 post NK cell infusion (FIGS. 24A and 24B). However, the effects were not durable. Despite no significant difference of BLI signals at late time points, significant prolonged survival was observed (p<0.0001) in iRC9.IL15.iMC modified NK cells with rimiducid therapy FIG. 24C.

Figure 19A:
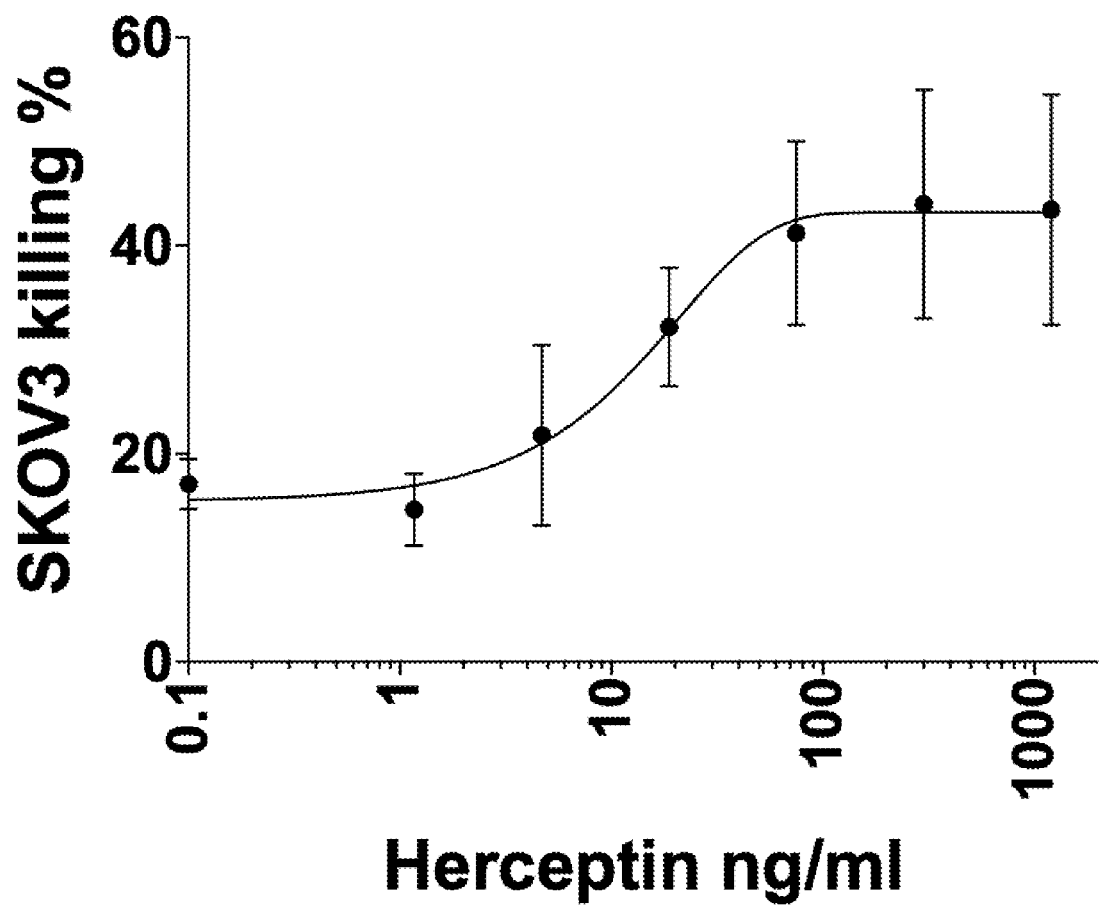
FIGS. 19A-19D Enhancing NK cell anti-tumor efficacy by antibody-dependent cellular cytotoxicity.
Figure 19B:
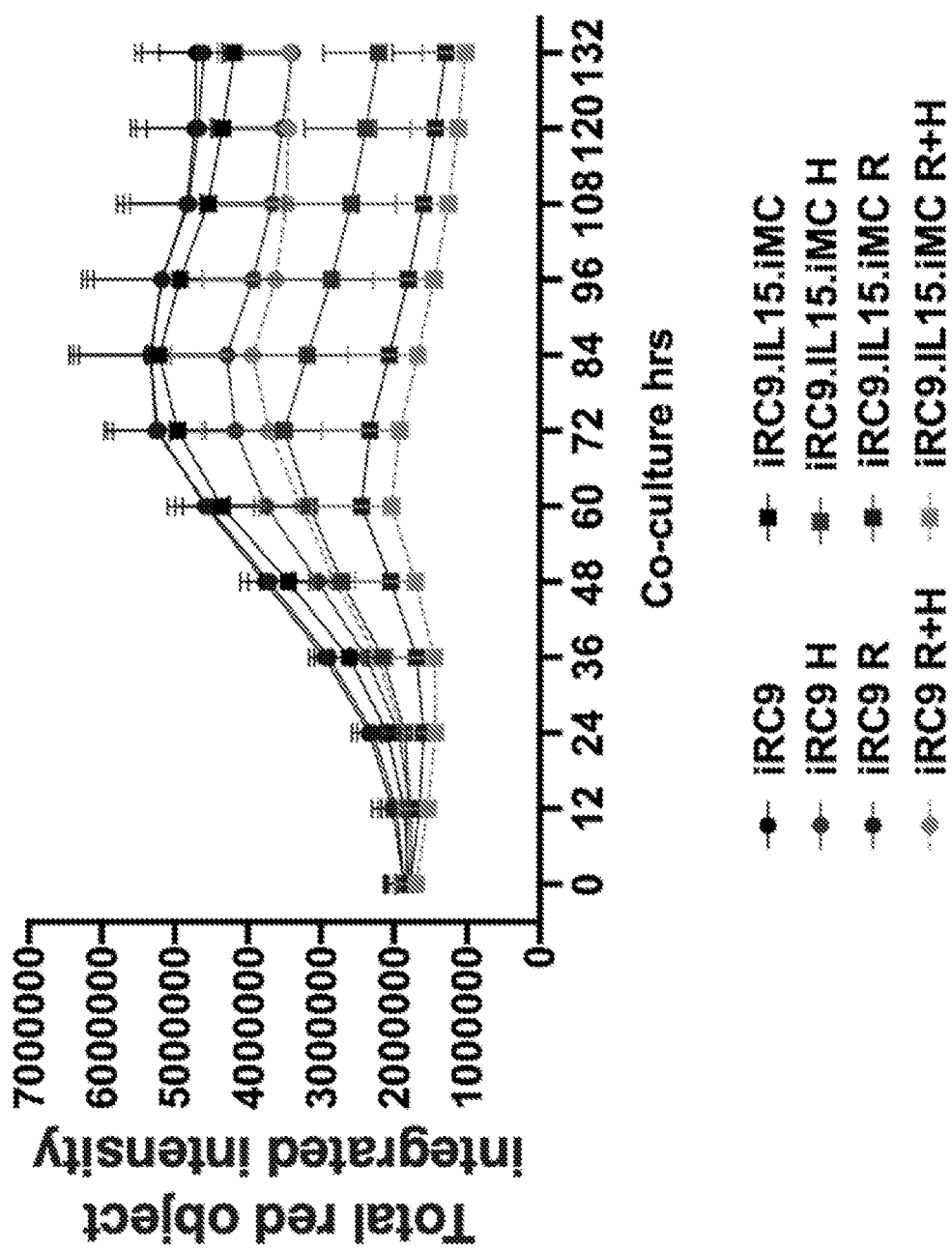
Figure 19C:
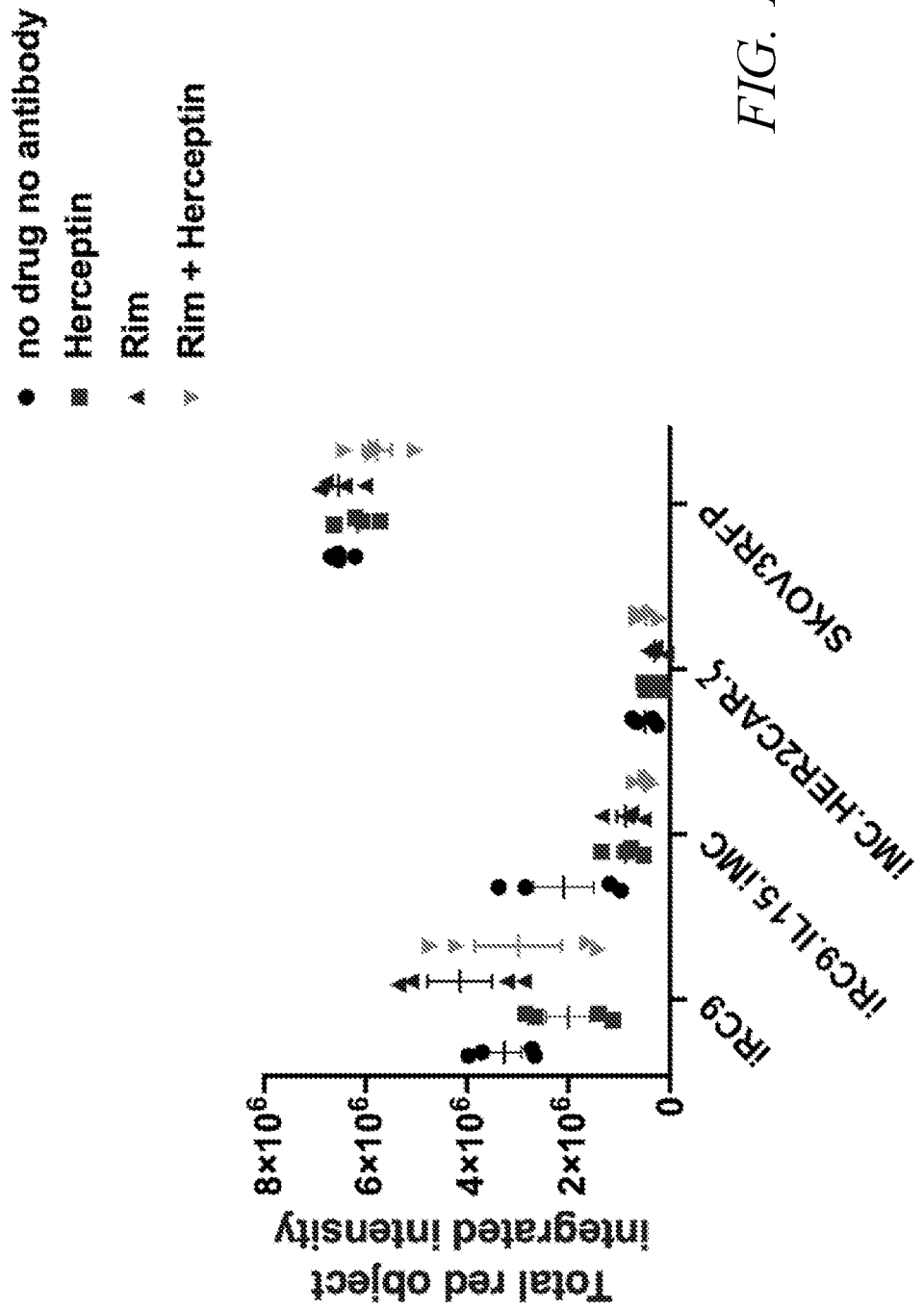
Figure 19D:
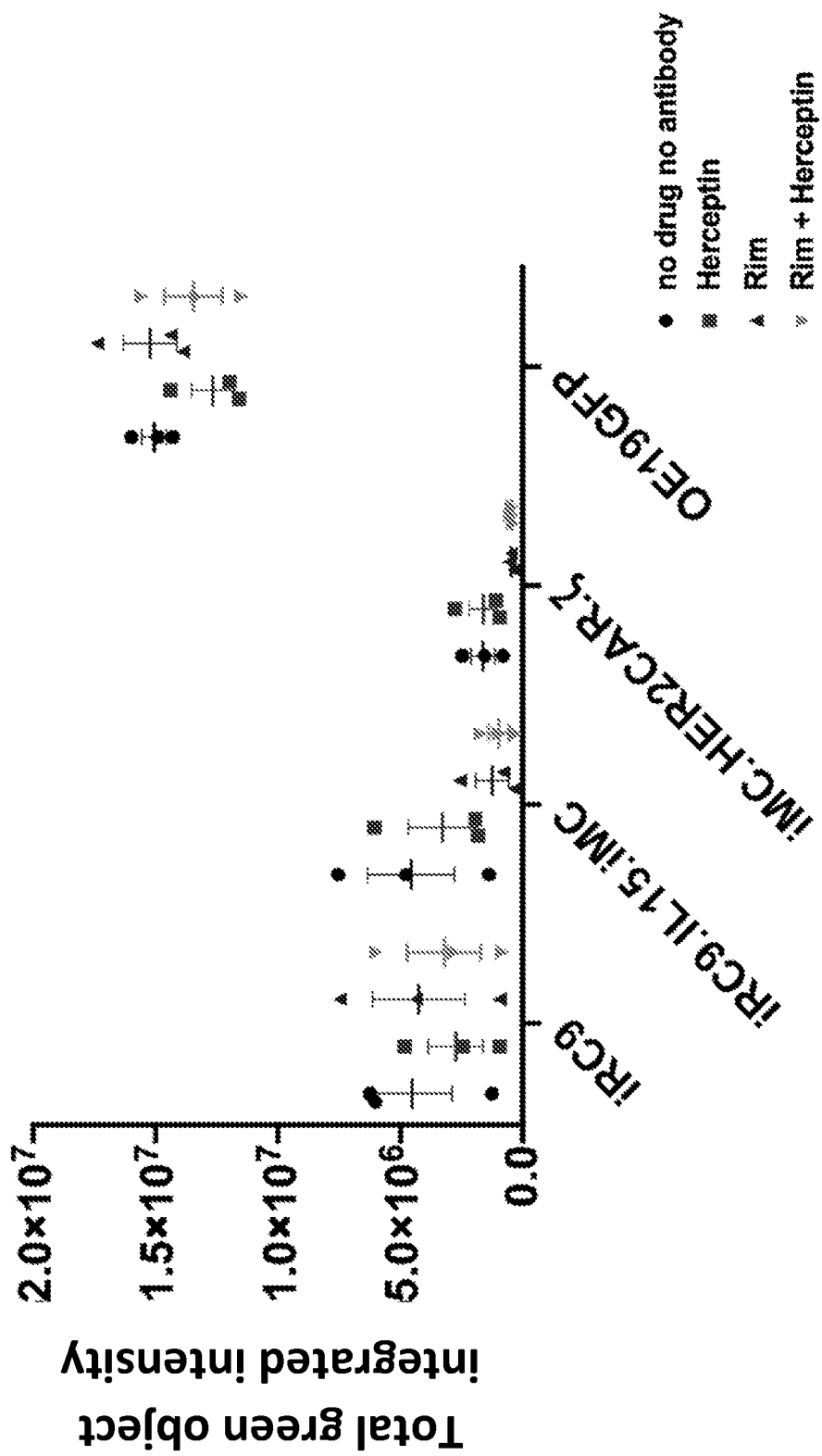

Antibody-dependent cell-mediated cytotoxicity (ADCC) is one of the mechanisms by which NK cells are involved in tumor cells killing. Therefore, the ability of Herceptin, a monoclonal antibody, to improve iMC modified NK cell cytotoxicity against human epidermal growth factor receptor 2-positive (HER2+) tumor cells was investigated. As shown in FIG. 19A, Herceptin indeed improved iRC9.IL15.iMC modified NK cell killing of SKOV3, a HER2+ ovarian adenocarcinoma cell line (High MHC class I expression, FIGS. 23B-23C), in a dose dependent manner (FIG. 19A). Even in iRC9 modified NK cells, Herceptin improved NK cell-mediated tumor target killing. However, Herceptin enhancement was moderate compared with rimiducid activation (FIGS. 19B, 19C, and 19D). There were little synergistic effects of Herceptin Rimiducid combination treatments. Interestingly, here a bicistronic vector iMC.HER2CAR.ζ was tested. Expressing a single chain variable fragment (scFv) targeting HER2 on the NK cell surface dramatically improved SKOV3 killing compared with iRC9.IL15.iMC modified NK cells, in the presence or absence of rimiducid (FIG. 19C). A similar trend was also observed in an NK sensitive gastric adenocarcinoma cell line (MHC class I expression low, MICA/B expression low, FIGS. 23A-23B) 0E19 (FIG. 19D). Adding Herceptin did not affect iMC.HER2CAR.ζ cytotoxicity against SKOV3 or 0E19 (FIGS. 19C and 19D). Taken together, these data indicate that expressing tumor-specific chimeric antigen receptors (CAR) in NK cells might be a good strategy for efficient and selective killing of cancer cells expressing the respective target antigen on cell surface.

Figures 1, 20A:
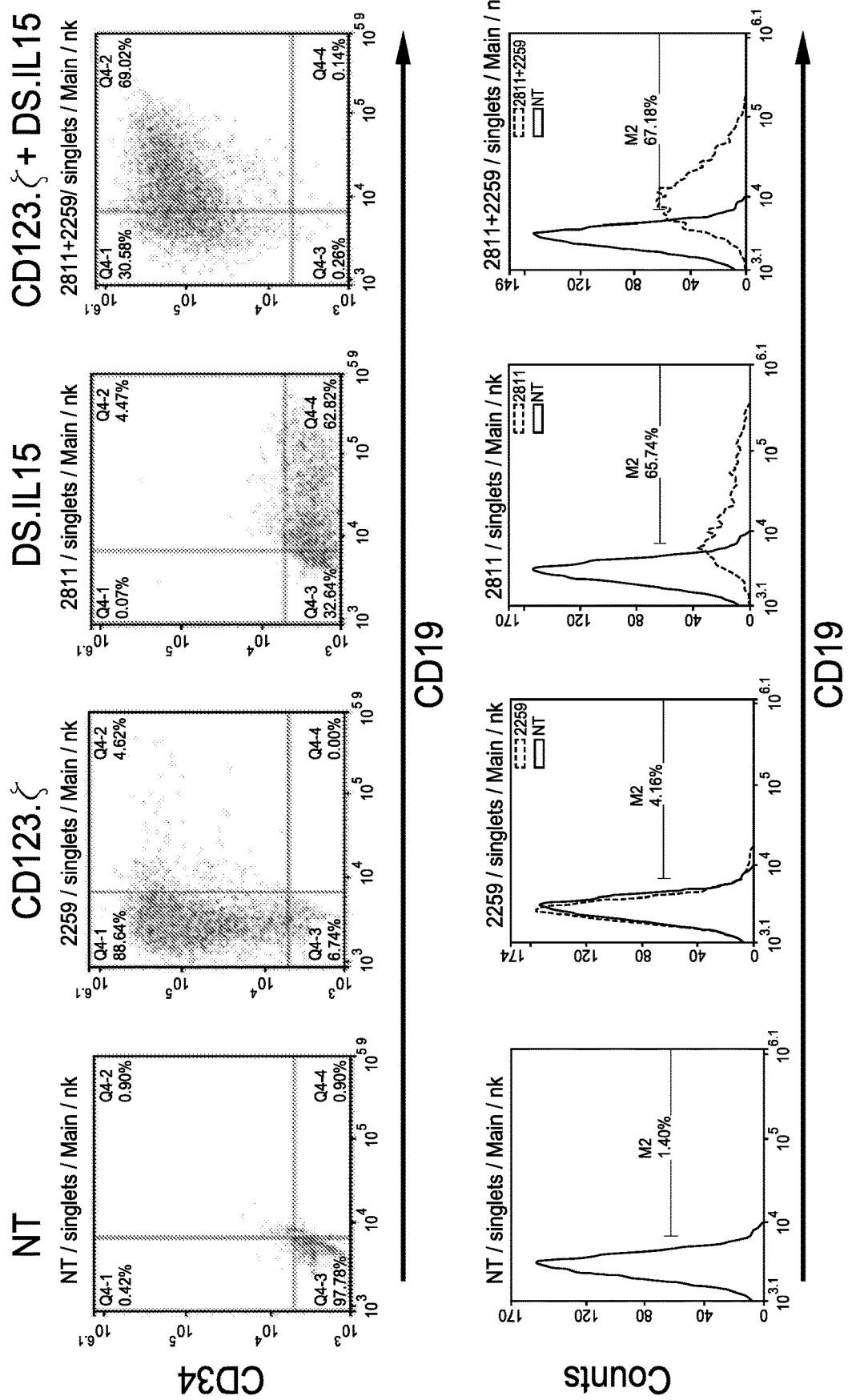
FIGS. 20A-20G iMC activation by rimiducid enhances anti-tumor efficacy of CD123-CAR NK cells against leukemia.
Figures 2, 20A:
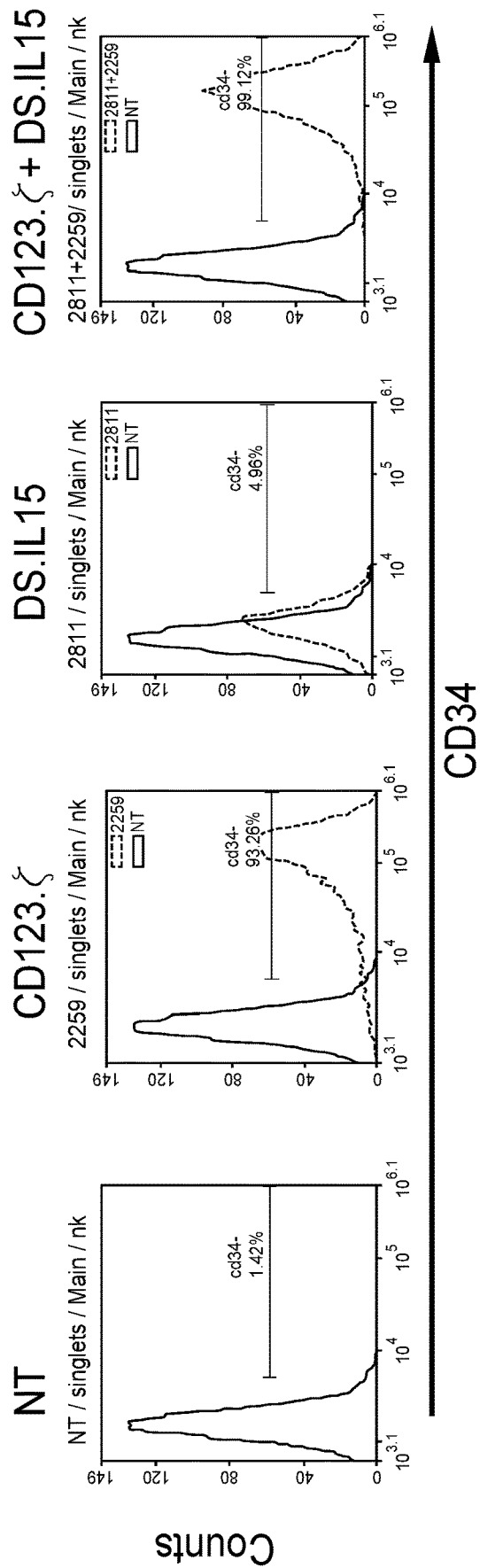

Augmentation of iMC Modified NK Tumor Controlling Efficacy with Antigen Specific CAR Next it was evaluated whether adding a CAR would improve the tumor controlling efficacy of iMC modified NK cells. CARs comprise a fusion of an extracellular targeting domain and an intracellular signaling domain to direct an effector cell specifically to a target cell expressing a cell surface marker expressed on the cell surface. The targeting domain is most commonly a single chain variable fragment (scFV) derived from an antibody specific for the expressed target antigen. The signaling domain is commonly derived from the T cell receptor (TCR) zeta (ζ) chain in a 'first generation' CAR. Second generation CARs contain an additional signaling moiety designed to enhance the proliferation and survival of cells expressing the CAR. NK cells were transduced with retroviral vectors encoding a first-generation CAR targeting CD123 (BP2259) alone, or cotransduced with BP2811 encoding iRC9 (FRB-FKBP12-Caspase-9), IL-15, the ΔCD19 marker, and iMC (FKBP12v36-FKBP12v36-MyD88-CD40), referred below as Dual switch.IL15 or dual-switch (DS) NK cells. NK cells were also transduced with BP2811 alone. Transgene expression of CD123 CAR was accesses by hCD34, whereas expression of iRC9.IL15.iMC (DS.IL15) was determined by hCD19 staining (FIG. 20A). Transduction with CD123.ζ retrovirus was highly efficient (>90%), comparable to that of double transduction. Dual switch.IL15 transgene expression (~65%) was also similar between single and double transductions (FIG. 20A).

Figure 20B:
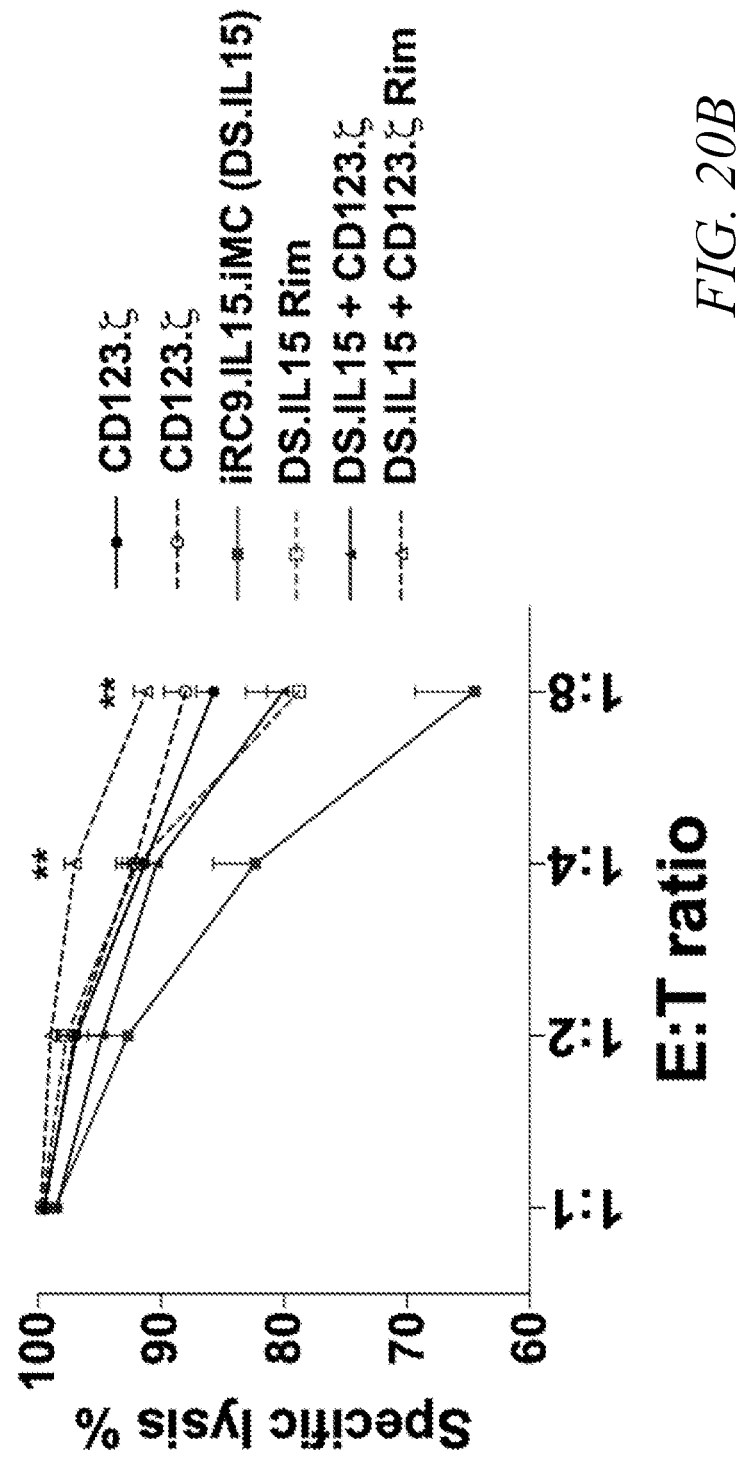
Figure 21:
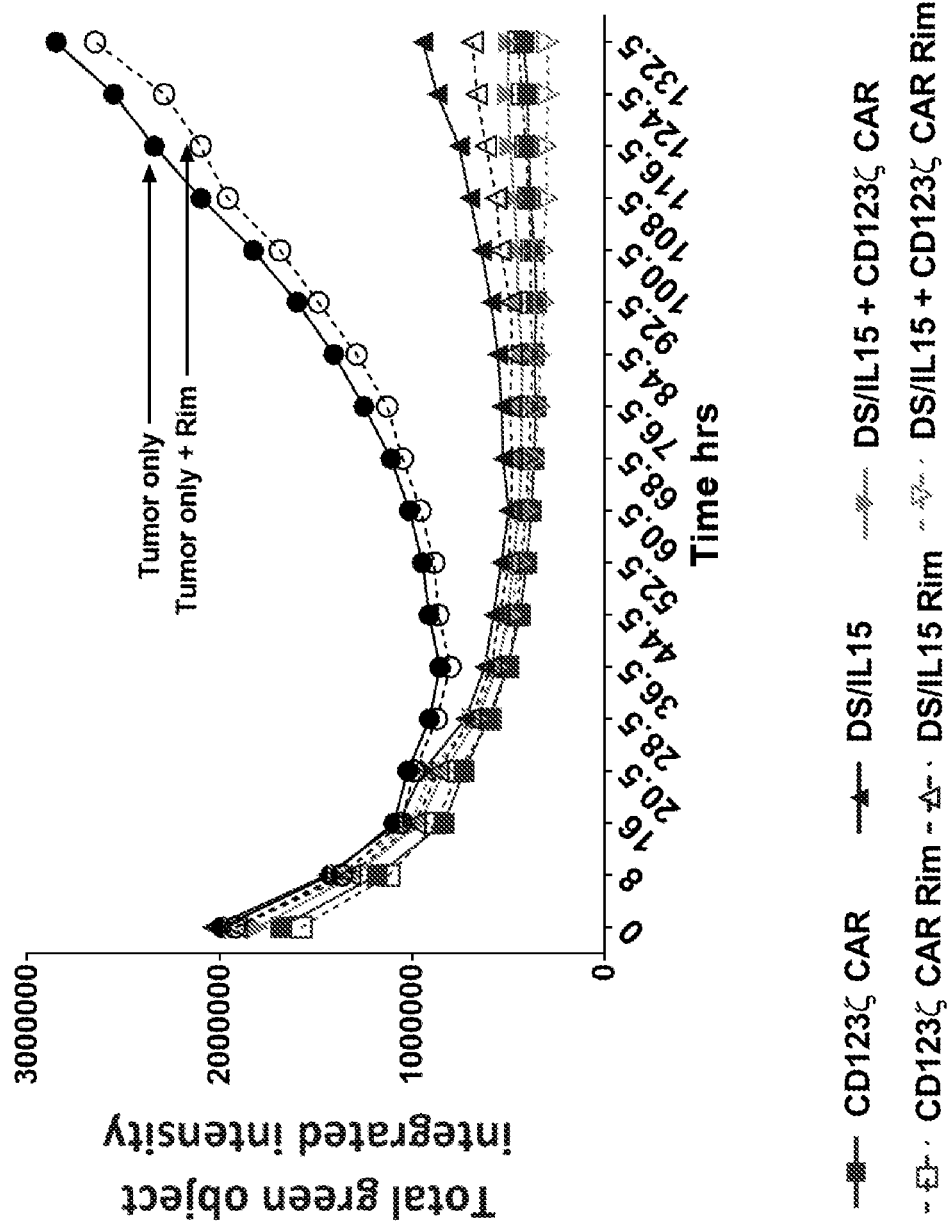
FIG. 21 provides a line graph of expansion of THP-1 target cells incubated with modified NK cells transduced with the nucleic acid vectors as discussed in Example 3 below, with lines representing results obtained at 132.5 hours, from top to bottom: tumor only, tumor only+ Rim; DS/IL15; DS/IL15+ Rim; DS/IL15+CD123ζ CAR; CD123ζ CAR; CD123ζ CAR+ Rim; DS/IL15+CD123ζ CAR+ Rim.

Transduced healthy donor NK cells were expanded in IL-2 and were co-cultured with CD123-expressing THP1 target cells engineered to express the marker protein GFP-ffluc with which cell growth can be measured by green fluorescence or luciferase activity. The co-cultures were performed at decreasing effector (the NK cells) to target (THP1-GFPffluc) ratios (E:T ratios). After 24 hours of drug treatment the amount of luciferase activity remaining in the GFP-ffluc target cells relative to untreated controls was an indirect assay for NK cell-directed cell killing. The results are displayed in FIG. 20B. At low E:T ratios in the absence of iMC activation by rimiducid, dual-switch (DS) NK cells displayed modest cytotoxicity that increased with rimiducid treatment. Coexpression of the CD123 CAR increased cytotoxicity of cells containing the dual-switch construct and this cytotoxicity was also elevated by incubation of rimiducid to activate iMC. Expression of the CD123CAR alone also exhibited substantial cytotoxicity, but this was not stimulated by rimiducid treatment because of the absence of iMC. Similar results were observed when target cell growth over six days of co-culture was examined in an Incucyte incubator/microscope (FIG. 21). The expansion of THP-1 target cells was controlled substantially by incubation with dual-switch NK cells without the CD123 CAR and this tumor cell control was enhanced by treatment with rimiducid or by co-expression of the CD123CAR.

Figure 20C:
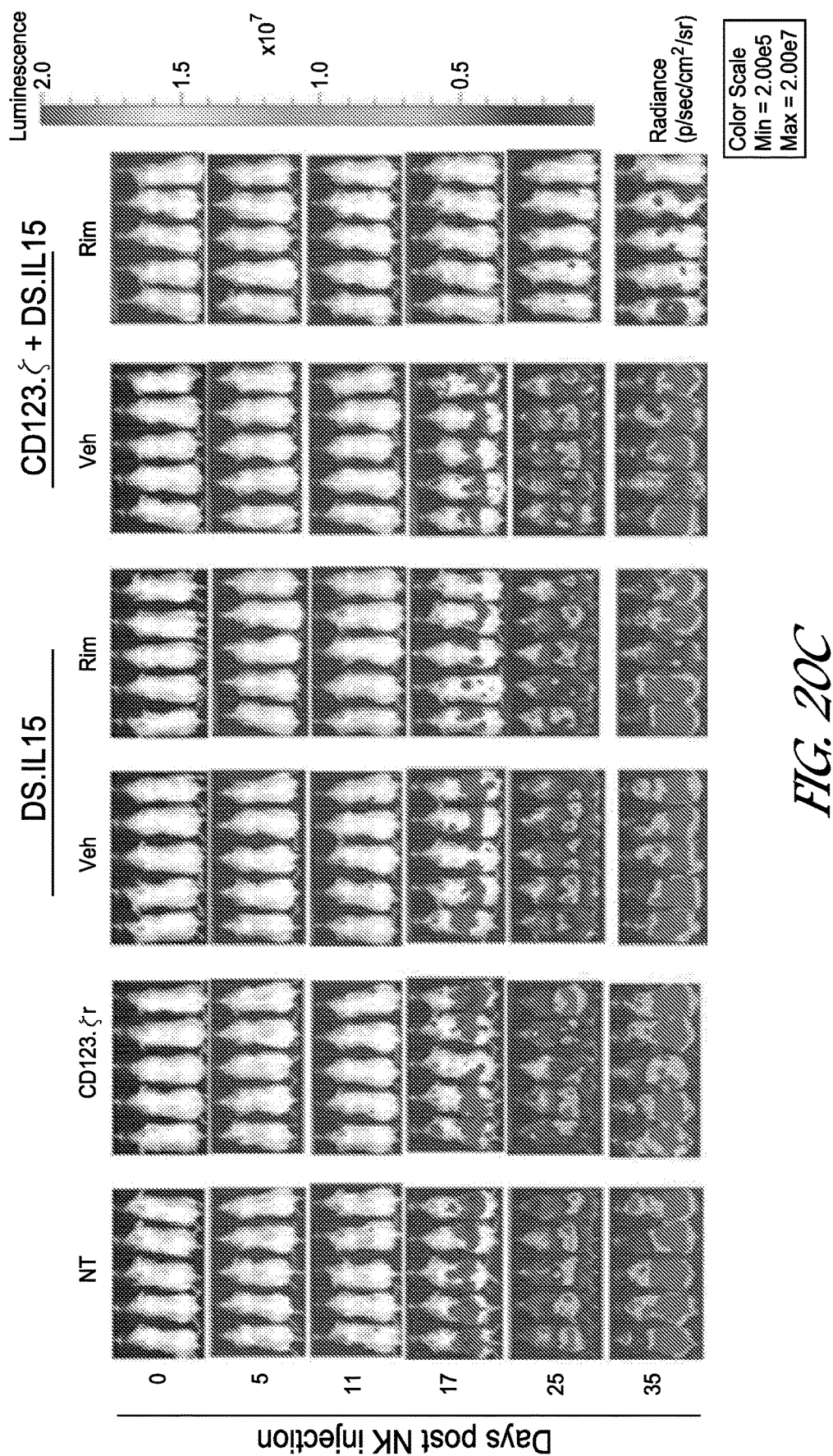
Figure 20D:
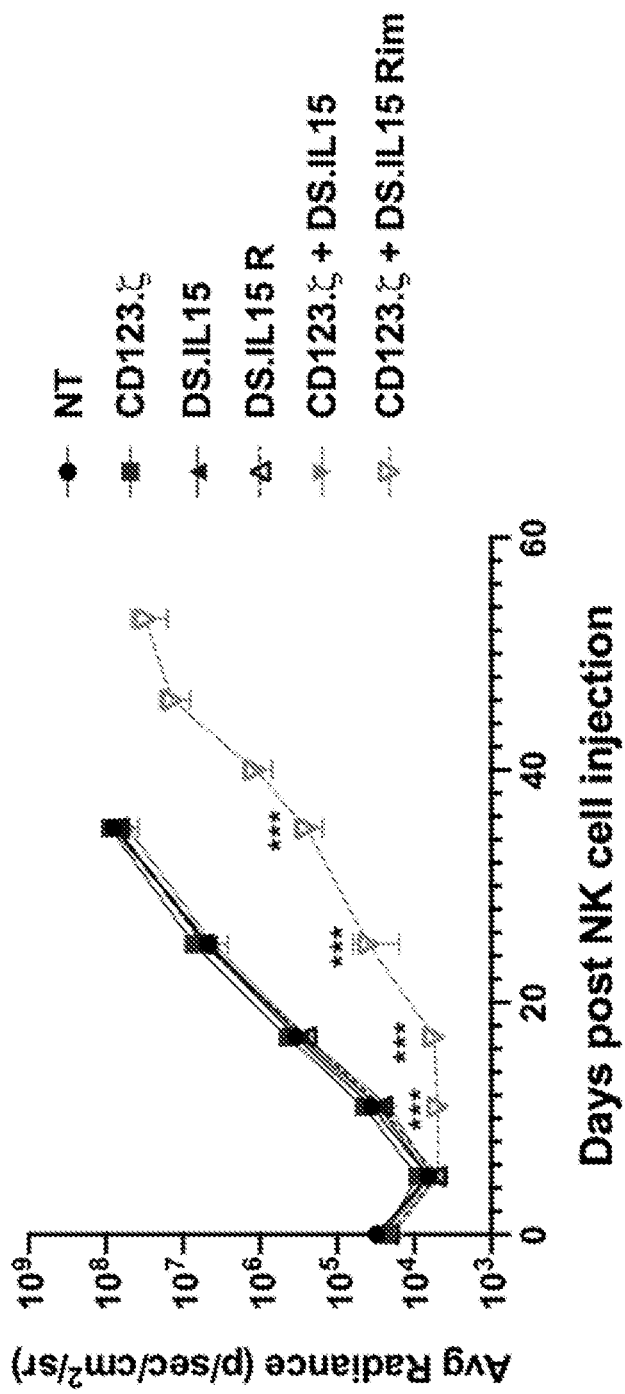
Figure 20E:
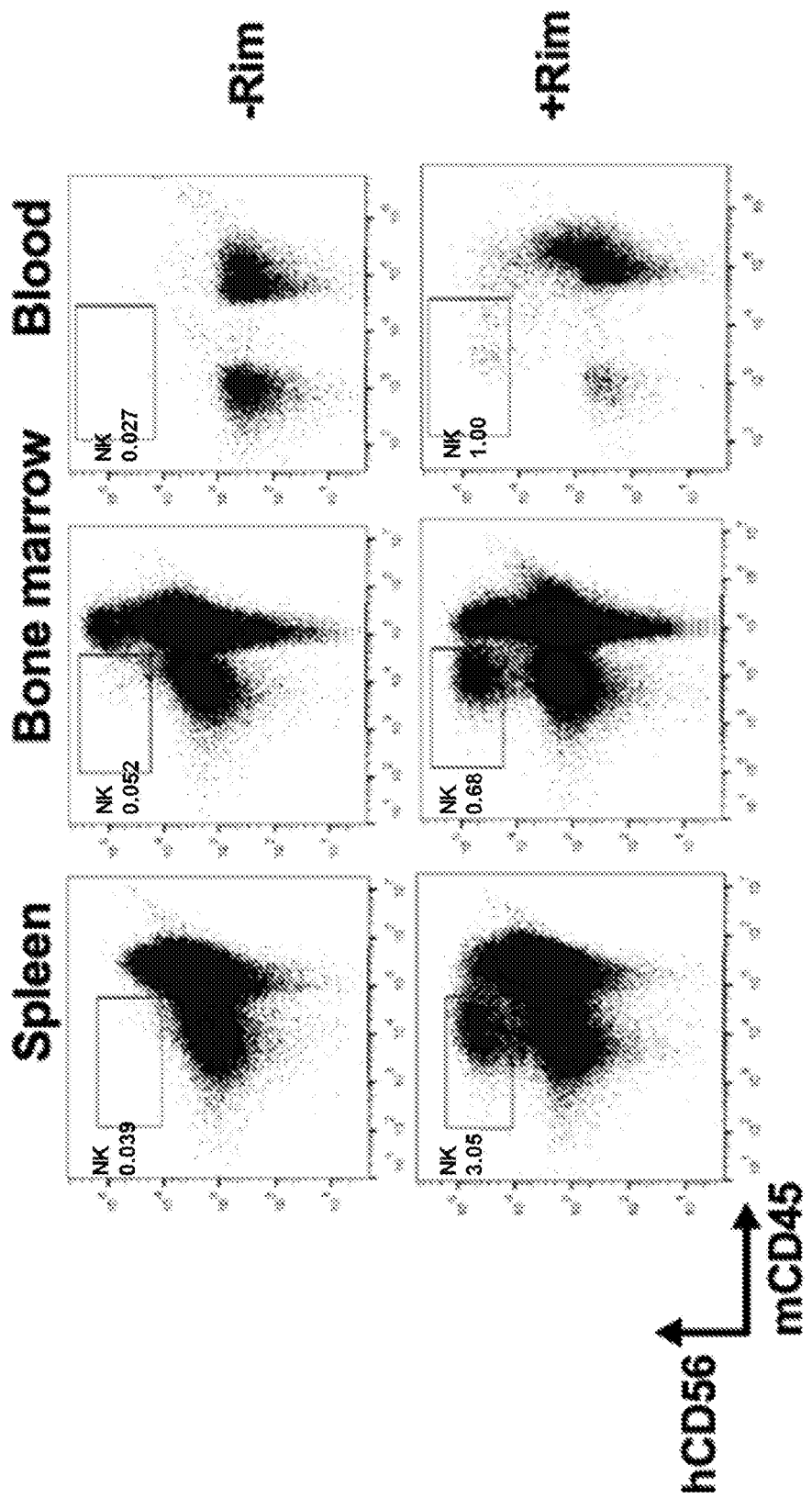
Figure 20F:
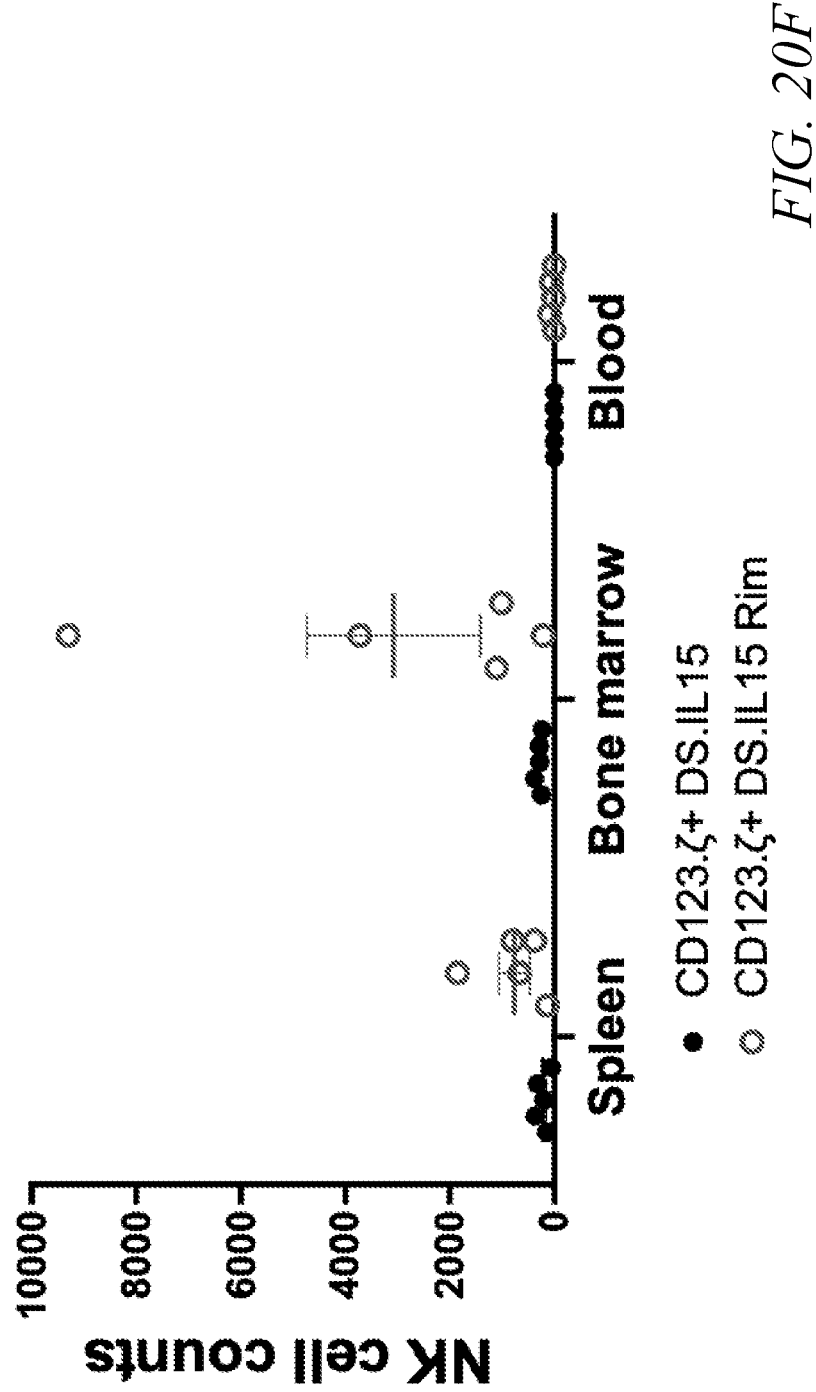
Figure 20G:
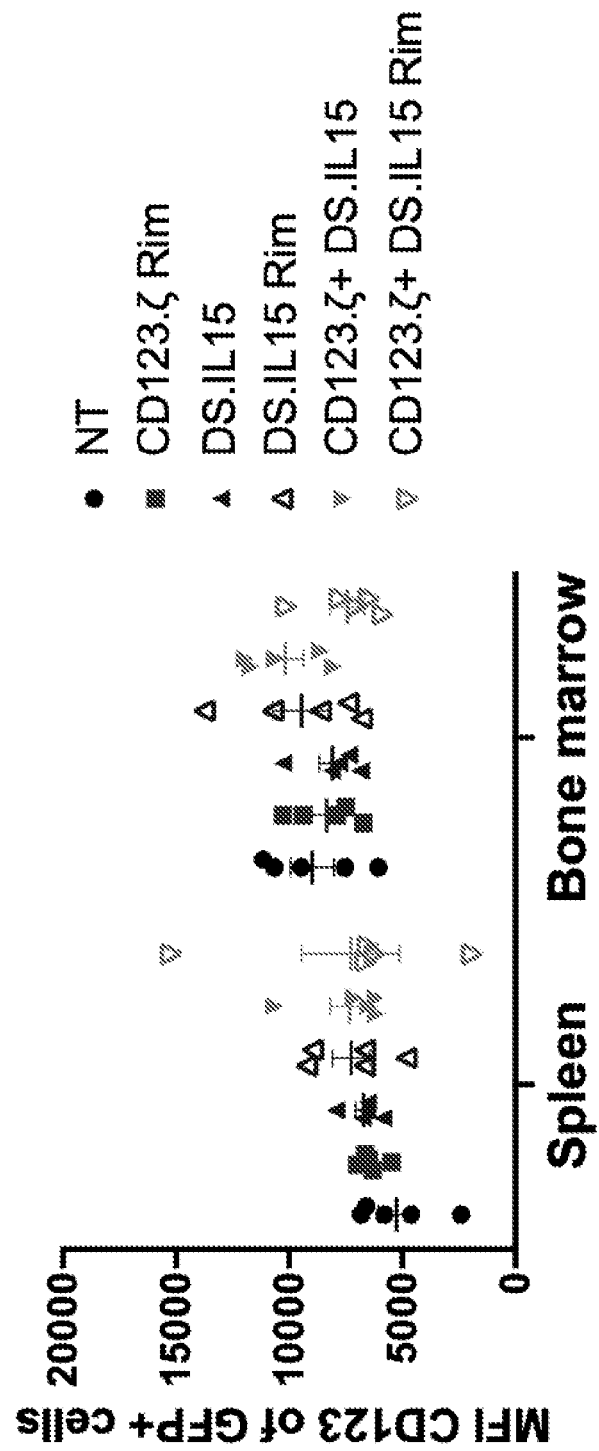

Control of THP1 tumor expansion was also examined in a mouse xenograft model. Immunosuppressed (NSG) mice were engrafted intravenously (i.v.) with $10^7$ human NKs that were non-transduced (NT) or transduced with retrovirus encoding CD123ζ CAR, DS (iMC+iRC9)/IL15, or DS (iMC+iRC9)/IL15+CD123ζ CAR; 3 days following i.v. implantation of $10^6$THP-1.GFPffluc tumor cells. Rimiducid (1 mg/kg/week) or vehicle was administered i.p. weekly. Tumor expansion was measured weekly by bioluminescent intensity (BLI) of a D-luciferin substrate reactive with the GFPfflucifense expressed in the THP1 cells in an IVIS imager (Perkin-Elmer). The results are displayed in FIGS. 20C and 20D. Controlled, or reduced expansion of the tumor cells was observed only in the mice that had been engrafted with NK cells expressing the dual-switch, IL-15, and CD123ζ CAR construct, where the mice were also treated with rimiducid. As observed with CD123.ζ+DS.IL15, NKs frequency and numbers were increased by rimiducid treatment, especially in spleen and bone marrow (FIGS. 20E and 20F). Given the tumor was not completely eliminated, CD123 expression on GFP+ cells were determined (FIG. 20G). No significant changes of CD123 expression ruled out selection of tumor cells antigen-loss, indicative of feasible multiple dose therapy for better efficacy.

Figure 22A:
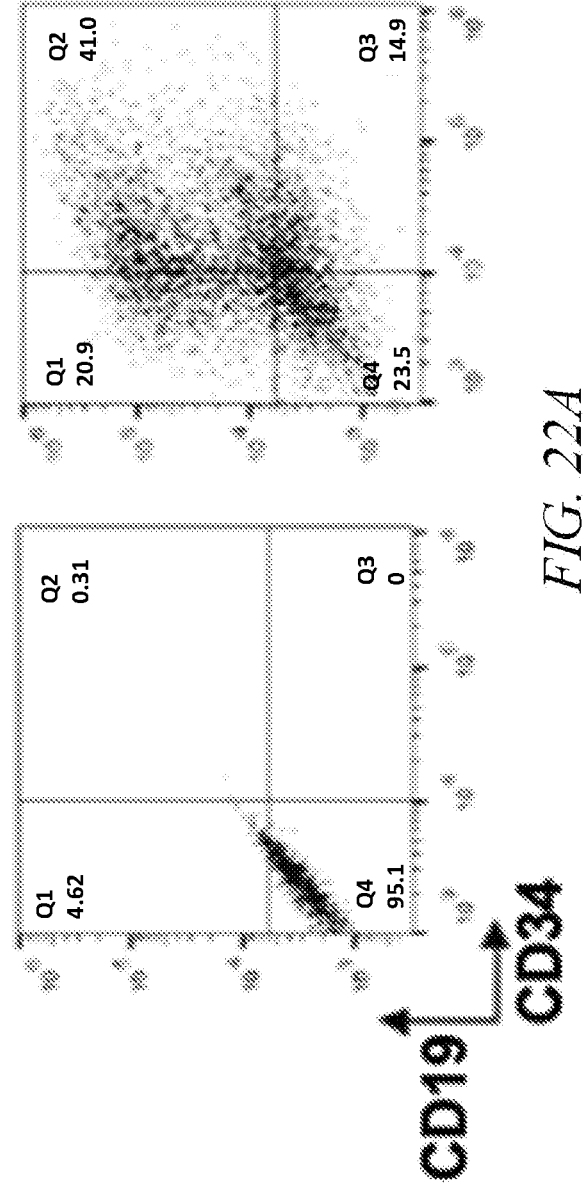
FIGS. 22A-22G iMC enhanced anti-tumor efficacy of BCMA-CAR NK against THP-1 tumor in NSG mice.
Figure 22B:
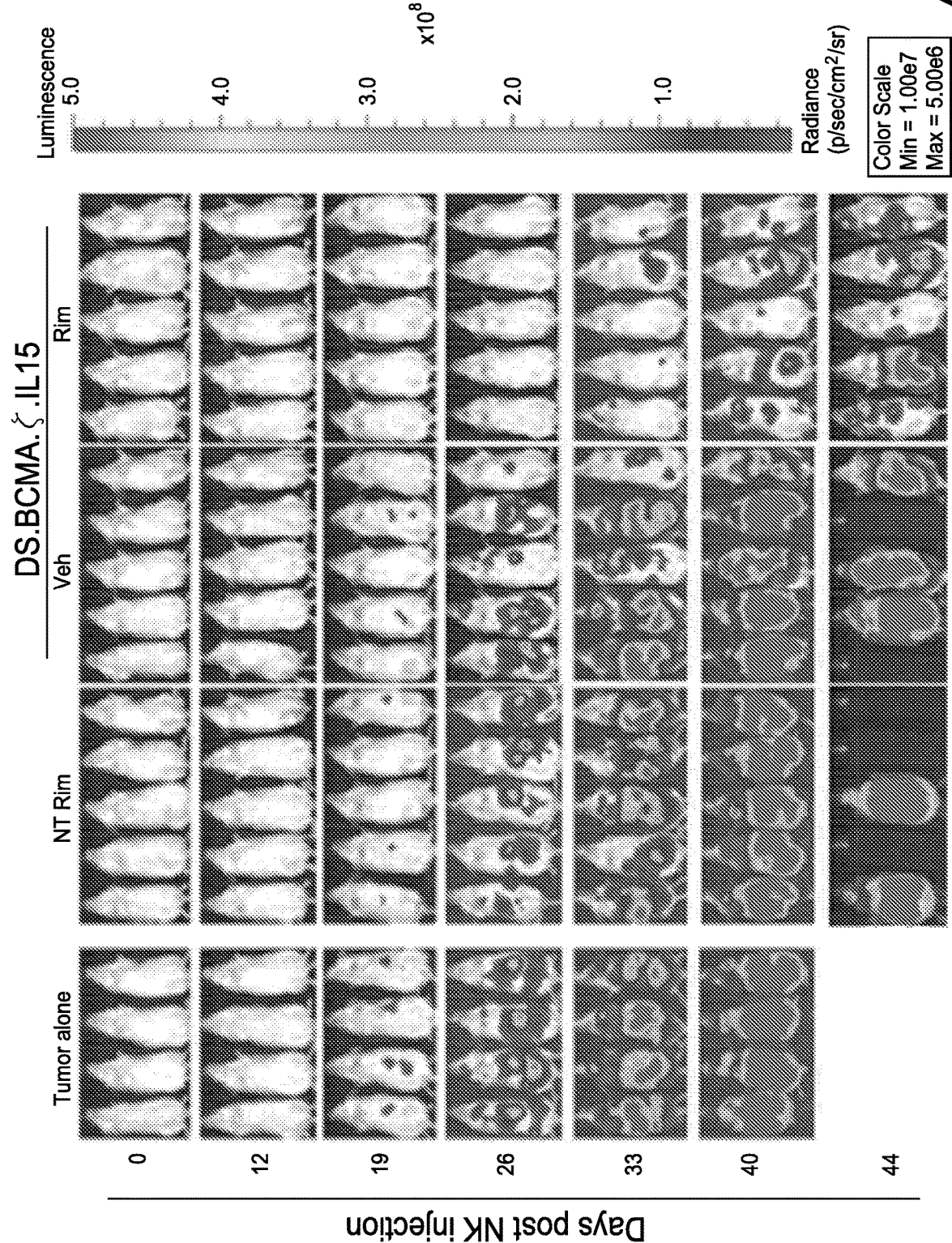
Figure 22C:
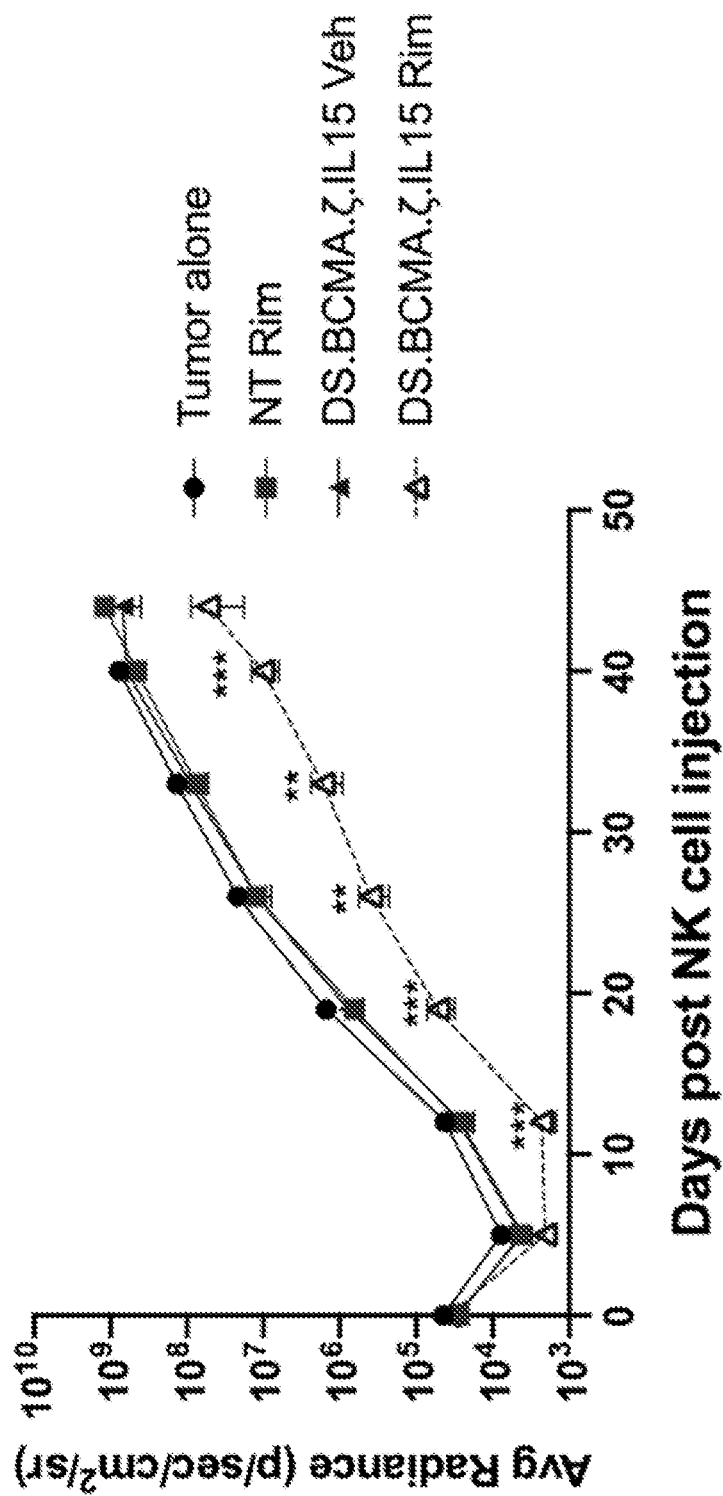
Figure 22D:
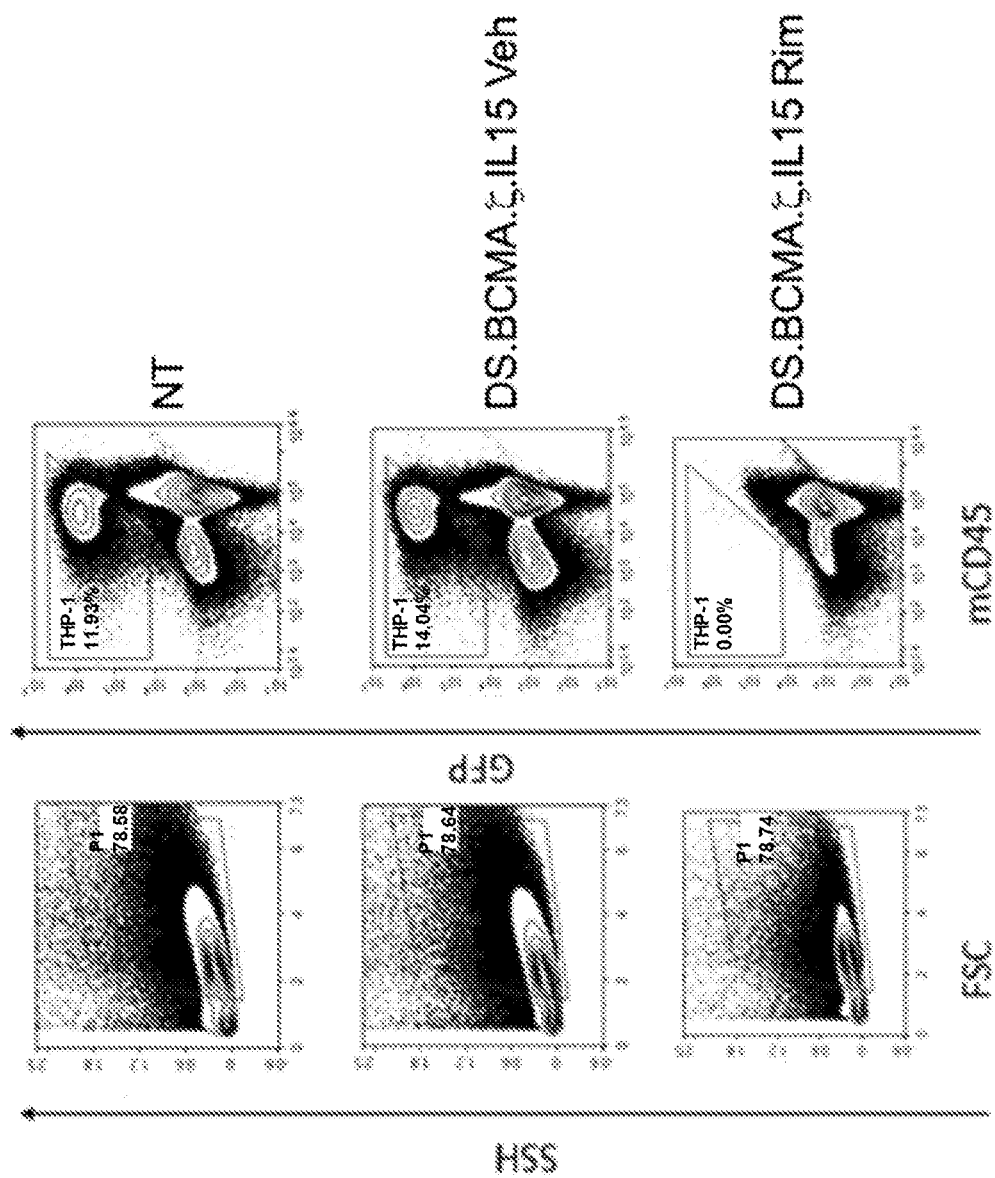
Figure 22E:
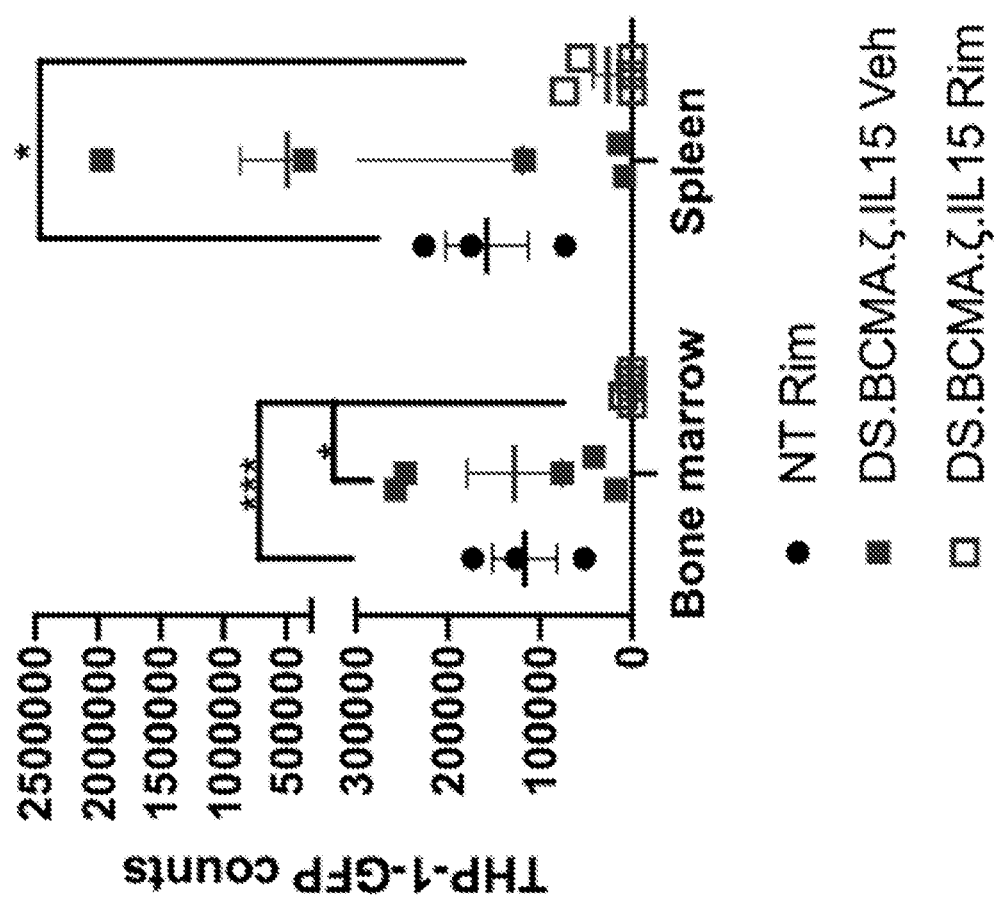
Figure 22F:
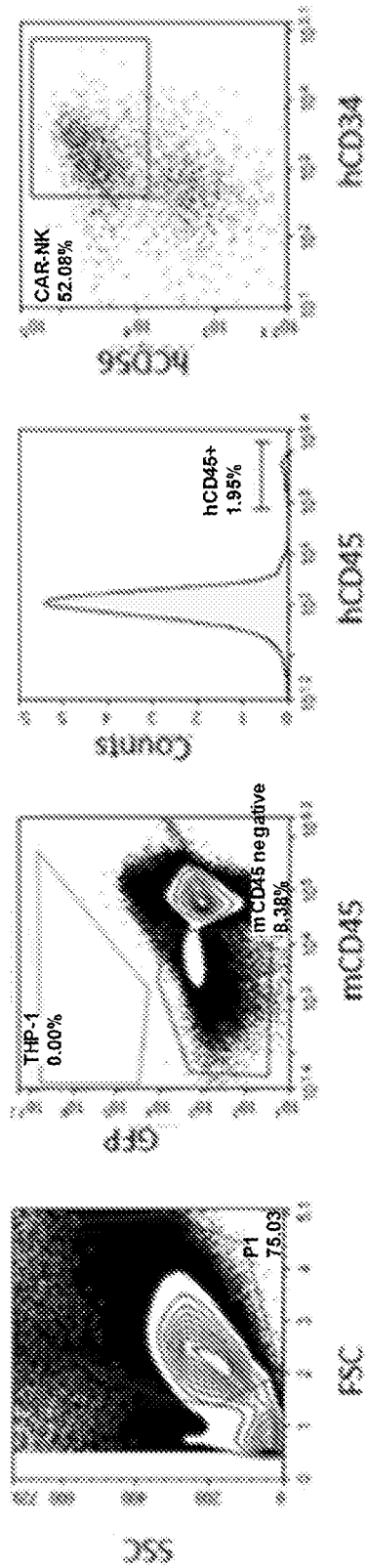
Figure 22G:
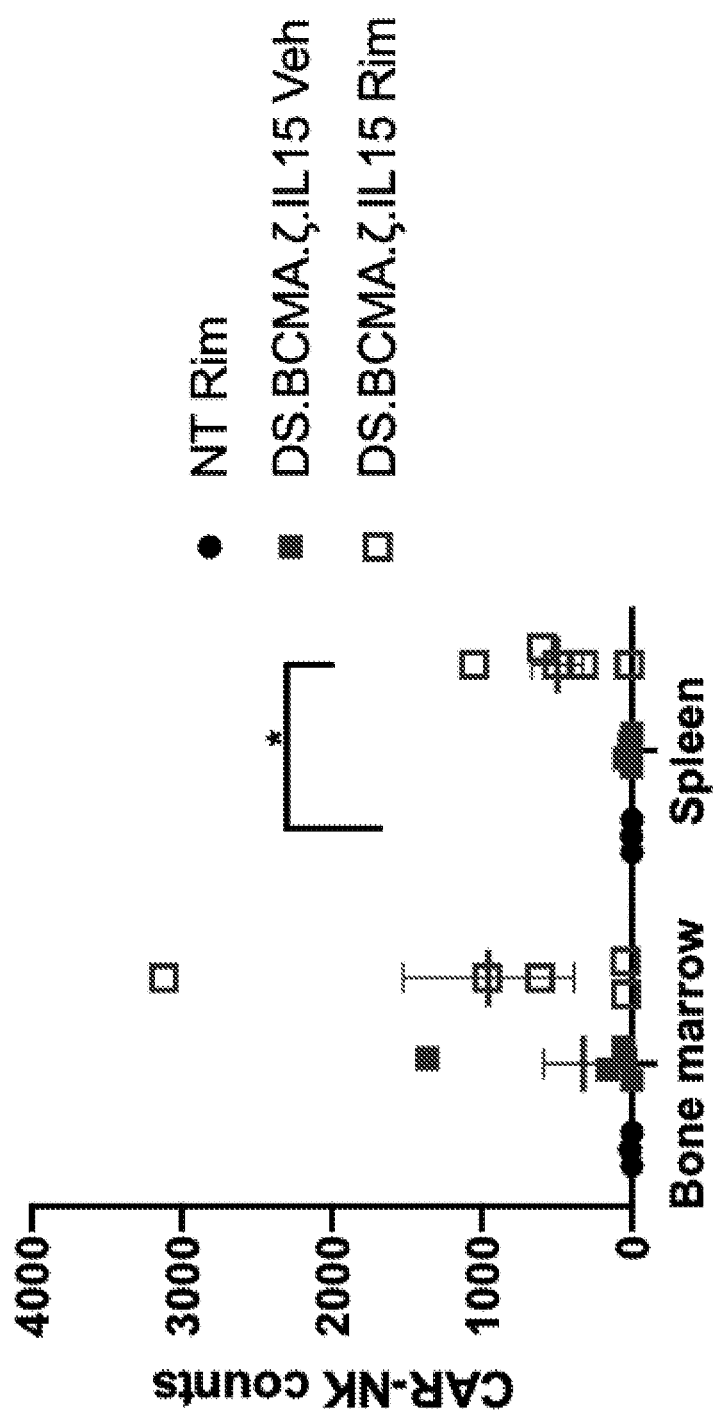

The efficacy of CAR-NK cells with iMC was also investigated in a different platform. THP-1 cells expressed high level of B cell maturation antigen (BCMA) on their surface (FIG. 26C). A tricistronic vector encoding iMC followed by a scFv targeting BCMA and IL15 (iMC.BCMA.ζ.IL15) was generated. Activated NK cells were first transduced with a retroviral vector encoding iMC.BCMA.ζ.IL15, followed by second transduction with iRC9 encoding retrovirus (Duong, M. T., et al., Two-Dimensional Regulation of CAR-T Cell Therapy with Orthogonal Switches. Mol Ther Oncolytics, 2019. 12: p. 124-137), to generate DS.BCMA.ζ.IL15 modified NK cells with a transduction efficiency >40% for double positive cells (FIG. 22A). To determine the in vivo efficacy, THP-1eGFPFfluc bearing mice were intravenously injected with 107 NT or DS.BCMA.ζ.IL15 modified NKs. Certain groups also received i.p. rimiducid (1 mg/kg). As shown in FIGS. 22B and 22C, rimiducid-dependent iMC activation was required for effective tumor controlling for 44 days post NKs injections. From day 40 to day 48, mice were euthanized, no or little frequency/numbers of GFP+ tumor cells was detected in bone marrow and spleen of DS.BCMA.ζ.IL15 modified NK cell group with rimiducid, compared with the non-rimiducid-group or NT group (FIGS. 22D and 22E), consistent with efficient rimiducid-dependent control of tumor by DS.BCMA.ζ.IL15 modified NK cells. Around day 48, higher frequencies/numbers of CAR-expressing NKs were identified in the bone marrow and spleens of mice treated with DS.BCMA.ζ.IL15 modified NKs with rimiducid (FIGS. 22F and 22G), suggesting proliferation and successful homing of gene modified NK cells to sites of disease in a rimiducid-dependent fashion.

Control of iMC Enhanced NK Activity by an Inducible Safety Switch

Figure 25A:
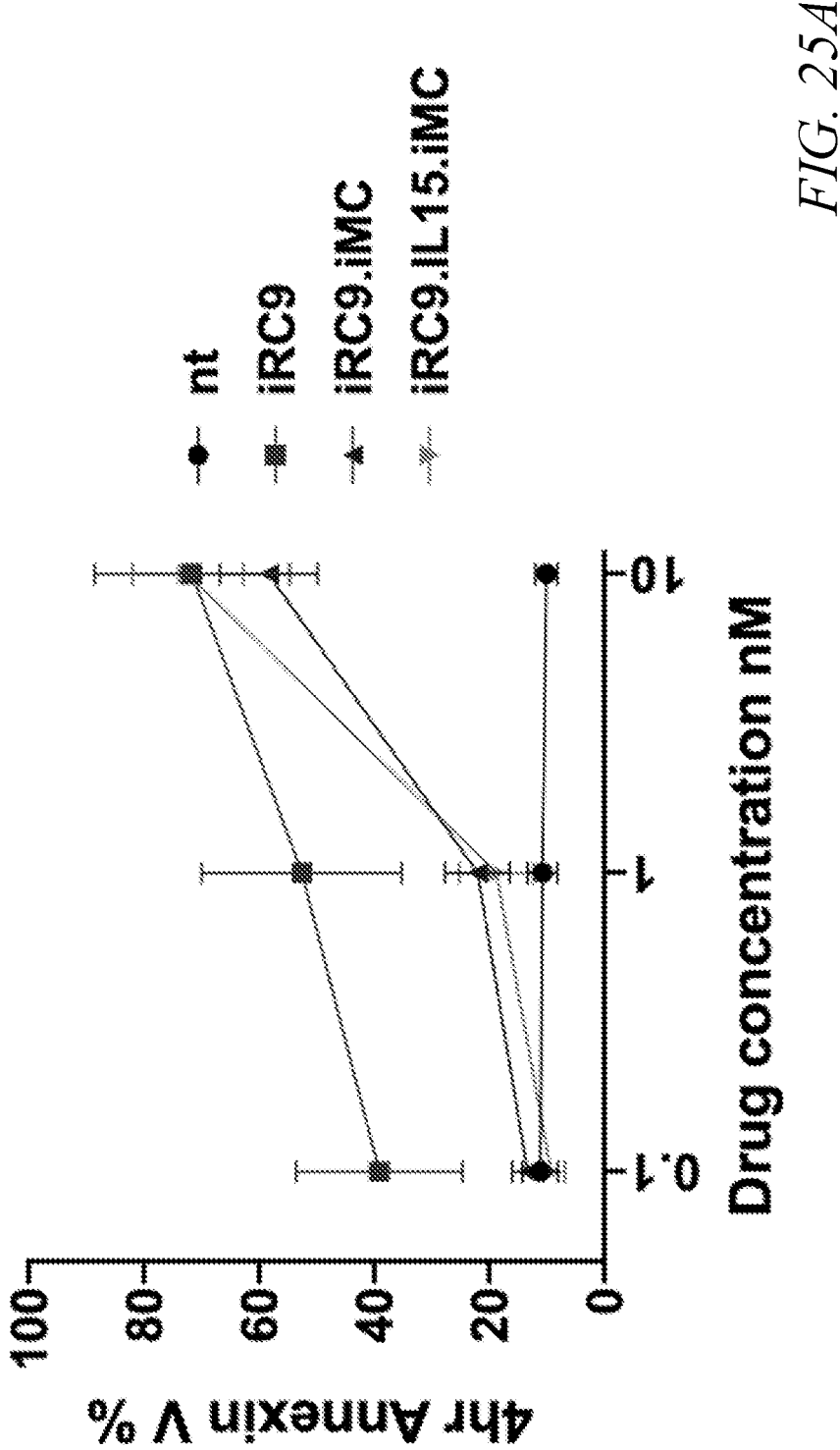
FIGS. 25A-25D: Safety switch in NKs. NT NK or NK transduced with iRC9, iRC9.iMC, or iRC9.IL15.iMC were administrated with temsirolimus at the concentration 0, 0.1, 1, and 10 nM for 4 hrs.
Figure 25B:
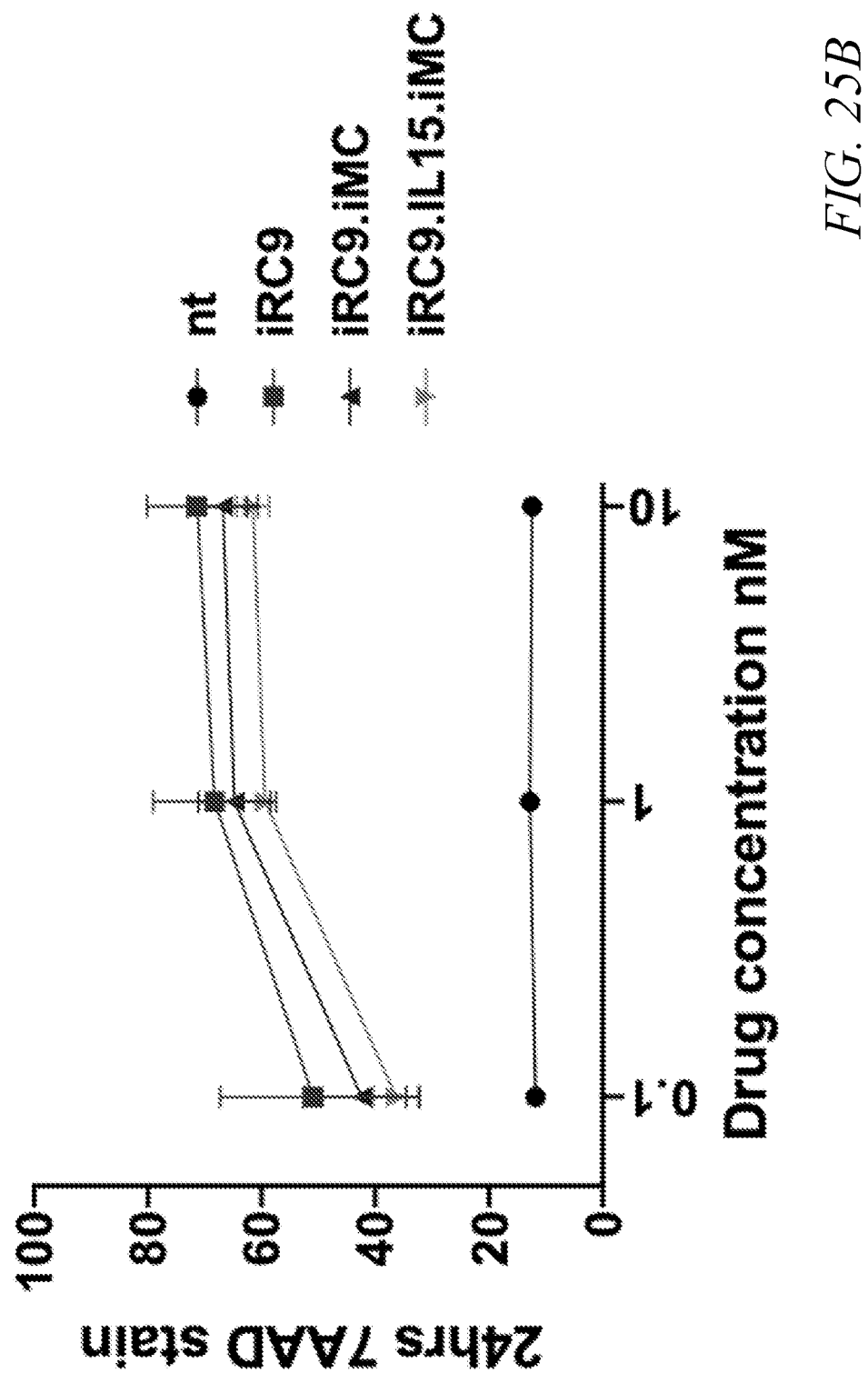
Figure 25C:
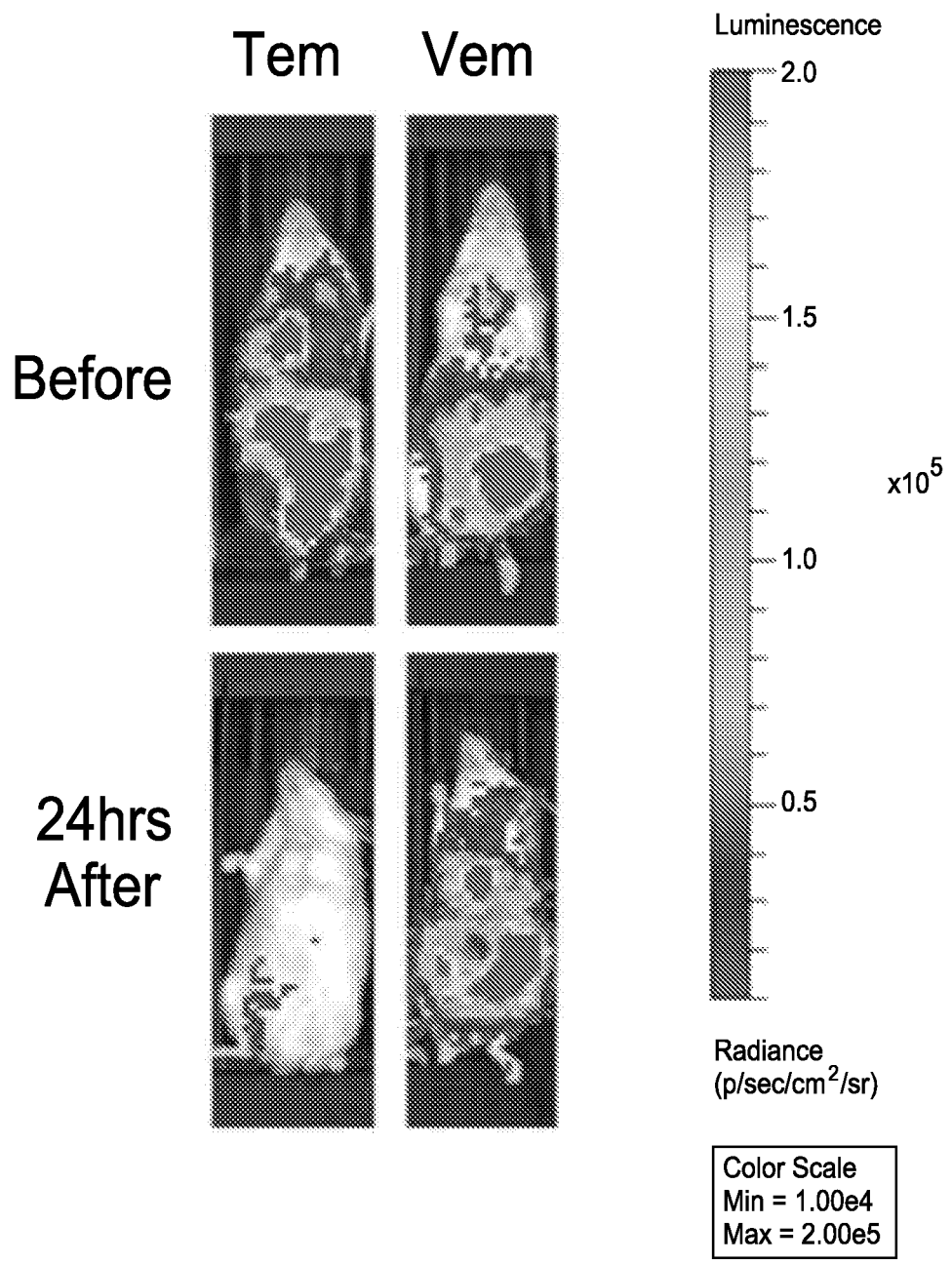
Figure 25D:
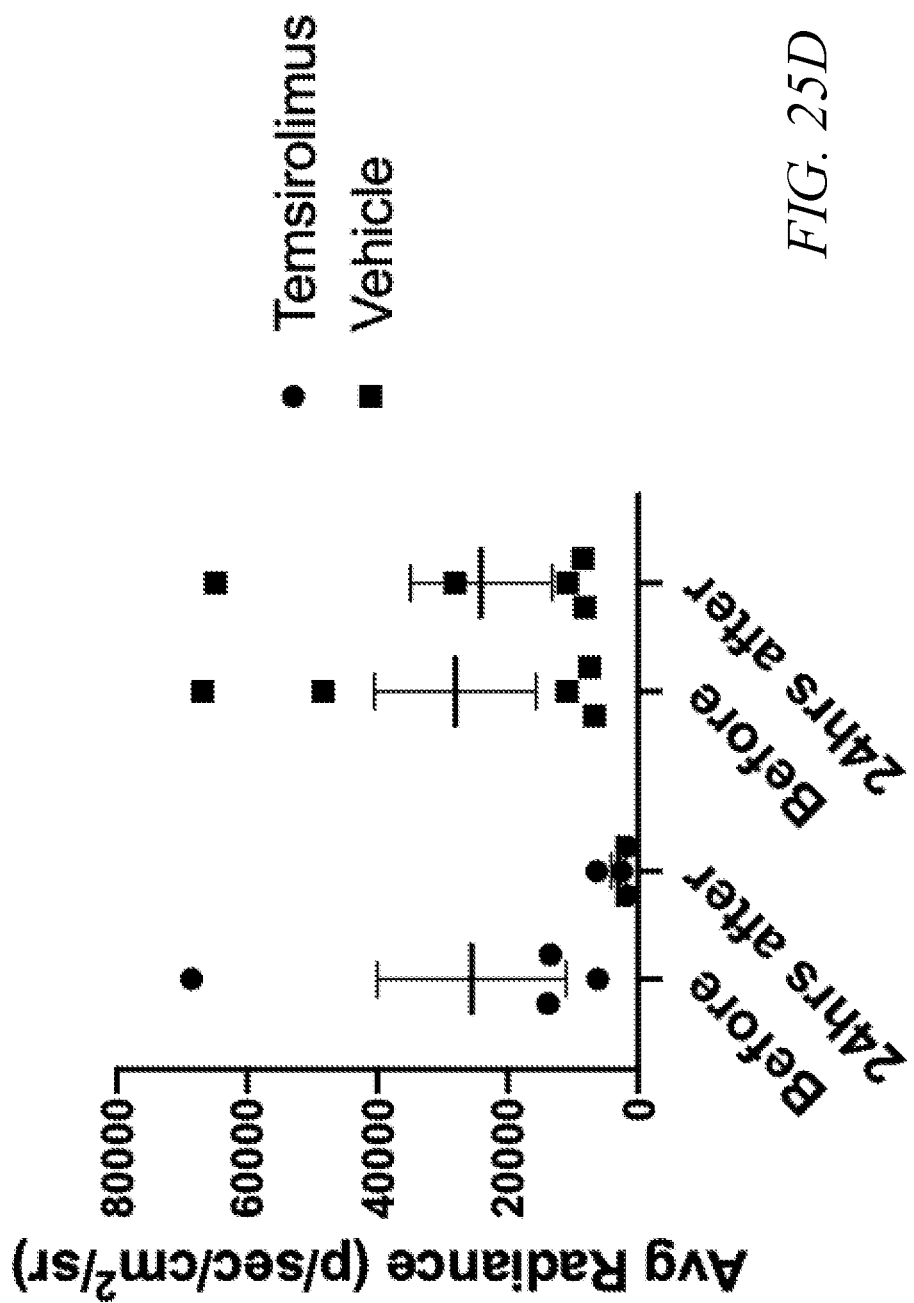
Figure 25E:
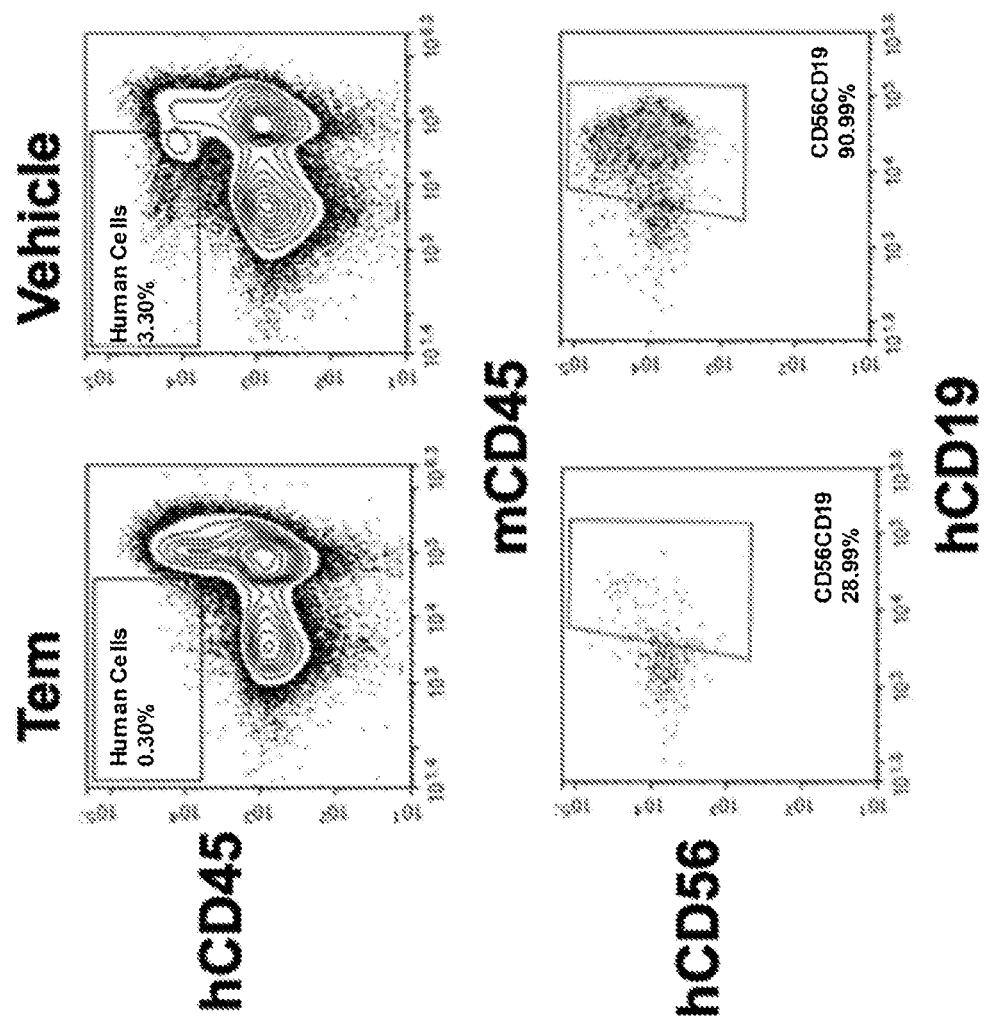
FIGS. 25E-25G: 9 NSG mice engrafted with iRC9.IL15.iMC were randomly divided into two groups. 4 Four mice were applied administered 1 mg/kg temsirolimus i.p., whereas 5 mice were administrated with same volume vehicle. Before injection and 24 hrs. later, firefly luciferase BLI was determined for to measure NK presence in vivo (FIG. 25E). Mice were then euthanized. Spleens were analyzed for the presence of NK cells by flow cytometry. NK cells were identified as hCD45+mCD45− populations (FIG. 25F). Transduced NKcells were identified as hCD45+mCD45-hCD56+hCD19+ populations (FIG. 25G). Student t test was used to do comparisonscompare groups. ***P<0.001.
Figure 25G:
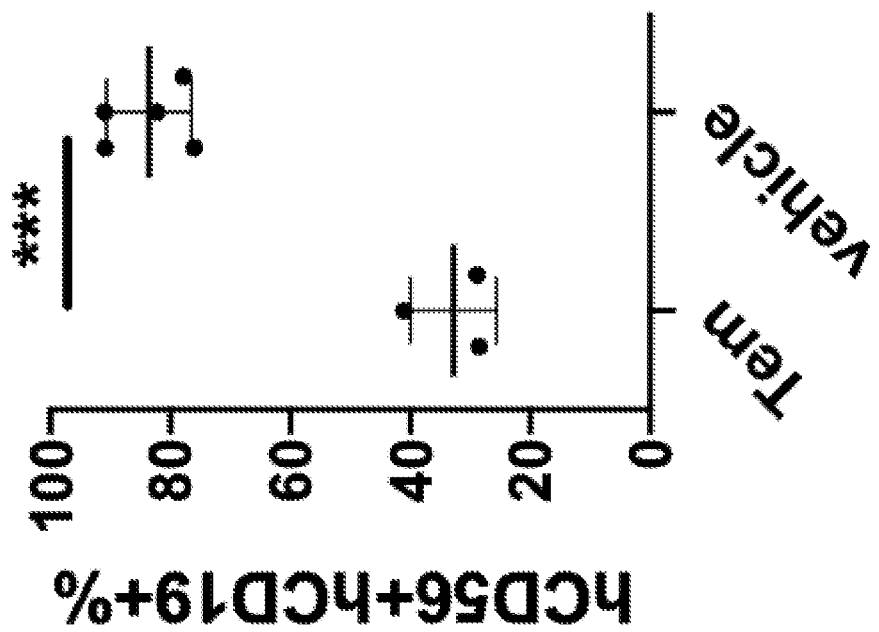
Figure 25F:
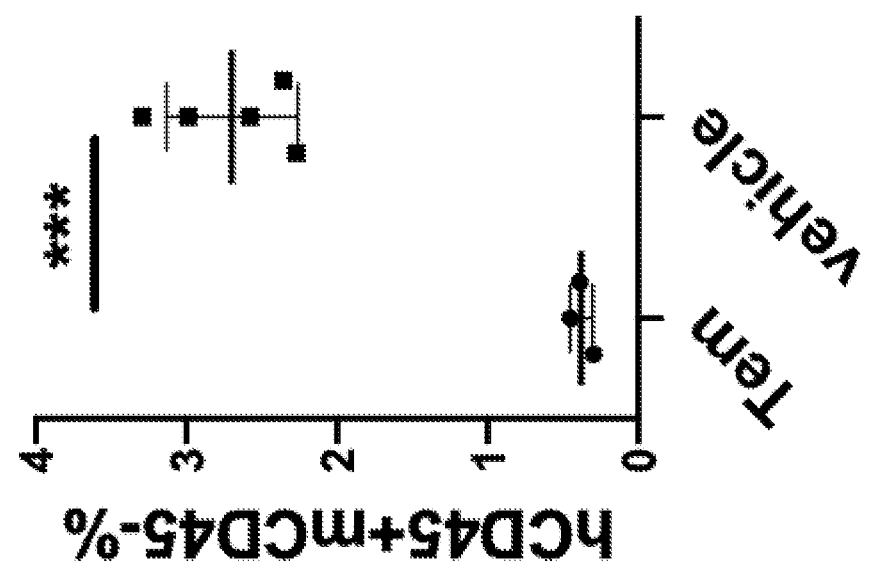

To prevent potential uncontrolled expansion of the gene modified NK cells, as well as associated cytokine release syndrome (CRS) and GvHD, a suicide gene iRC9 was incorporated into the constructs. The addition of 10 nM temsirolimus to cultures induced apoptosis as early as 4 hrs but had no effect on the viability of non-transduced NK cells (FIGS. 25A and 25B). The suicide gene was also effective in vivo. Mice engrafted with THP-1 tumor received iRC9.IL15.iMC-transduced NKs labeled with oNL *renilla* luciferase. Mice were then either treated with the dimerizer temsirolimus or vehicle control. Within 24 hrs, BLI signal dramatically reduced by temsirolimus but not vehicle control (FIGS. 25C and 25D). Frequency of gene modified NK cells was significantly reduced in the spleens of temsirolimus treated mice (FIGS. 25E, 25F, and 25G).

Comparisons of DS. CAR-NK Vs DS. CAR-T Therapy in BCMA Expression Tumor Cells

Figure 26A:
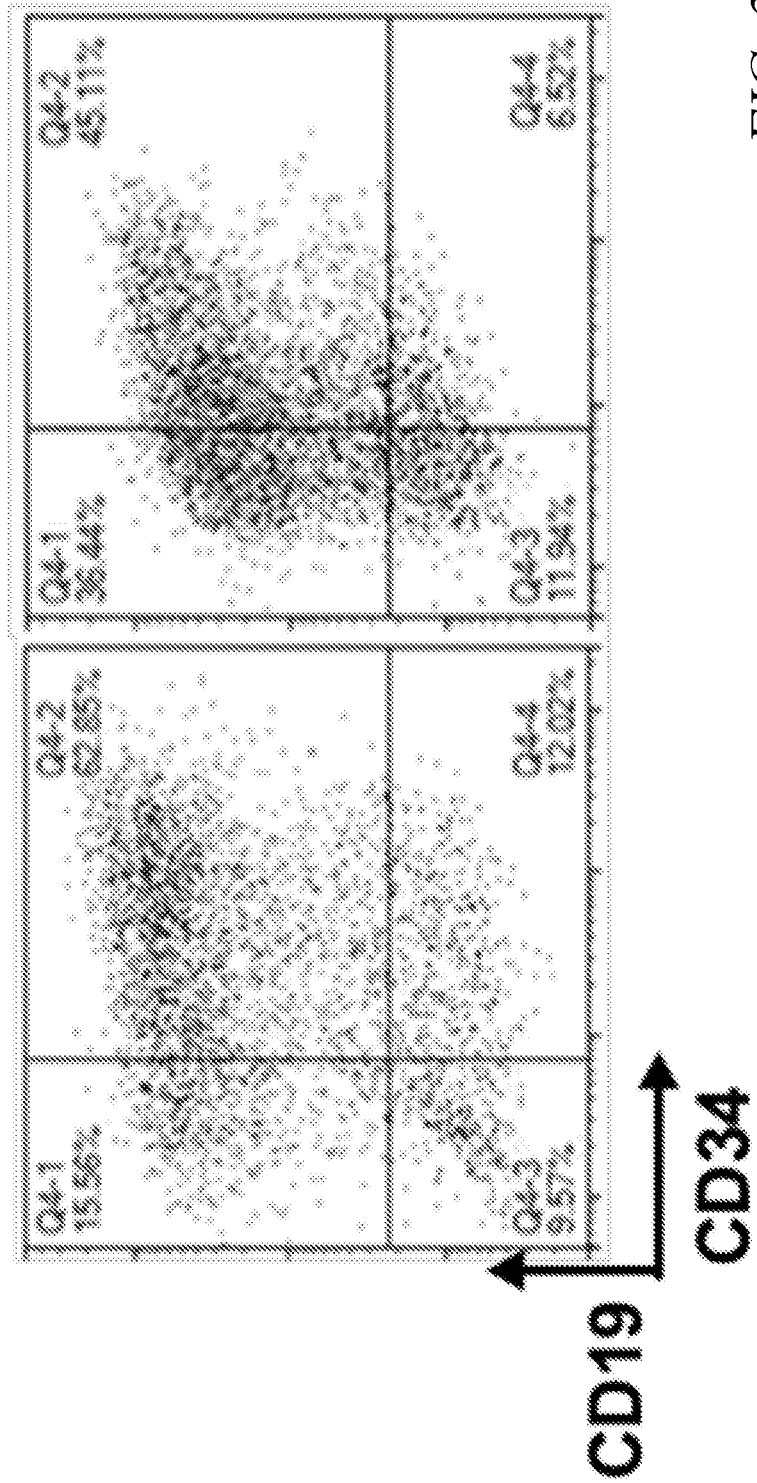
Figure 26B:
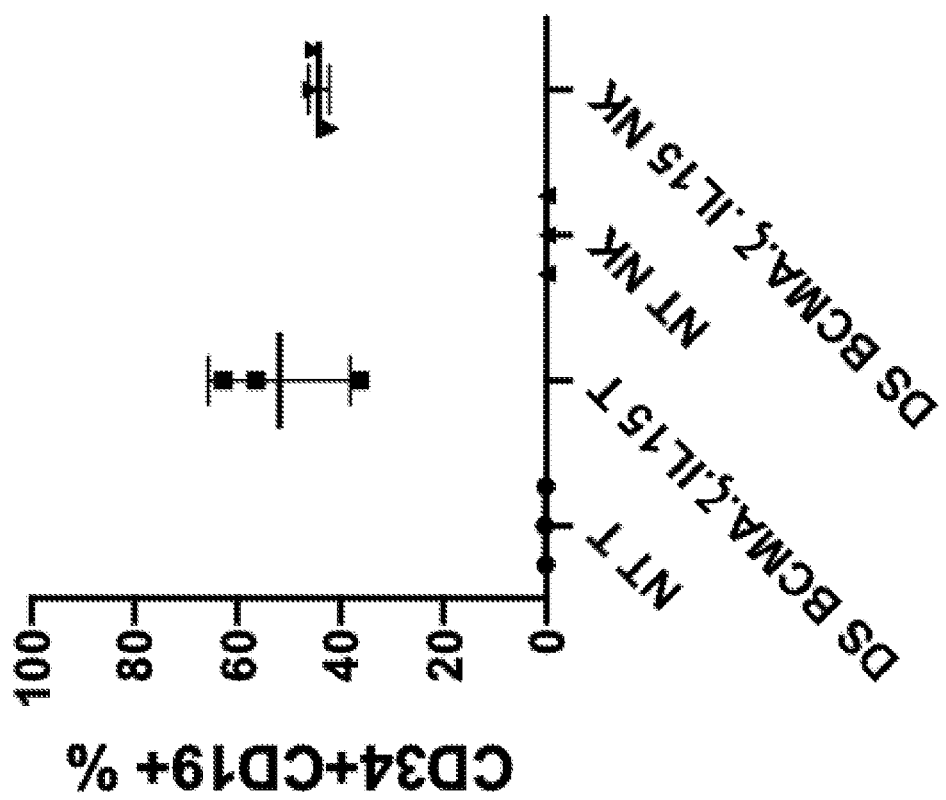
Figure 26E:
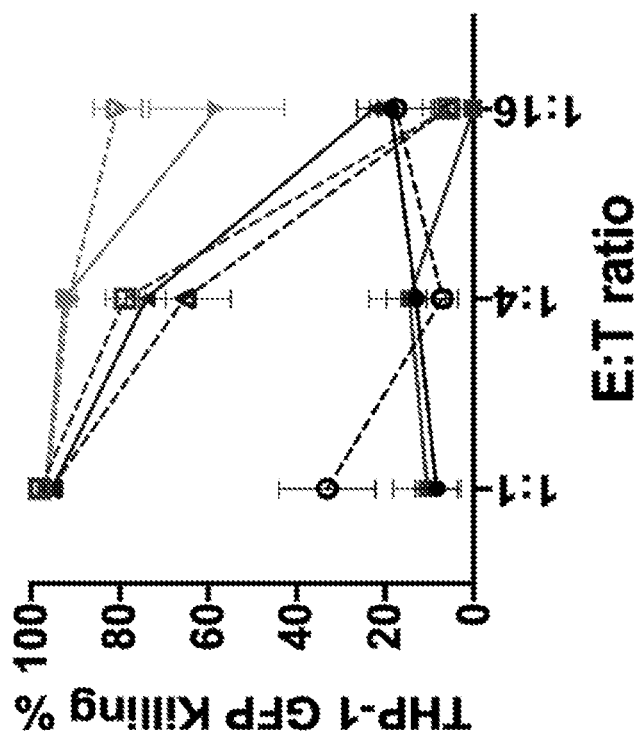
Figure 26D:
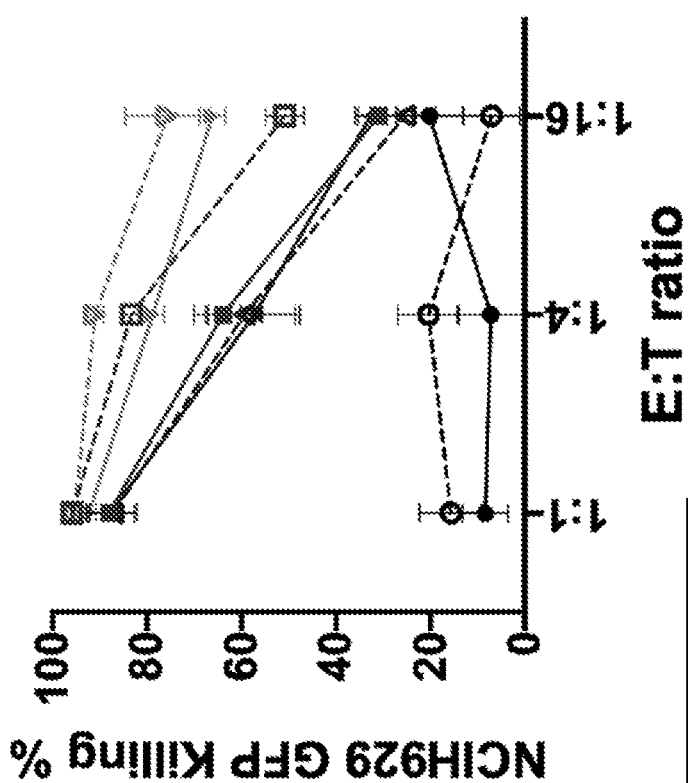
Figure 26G:
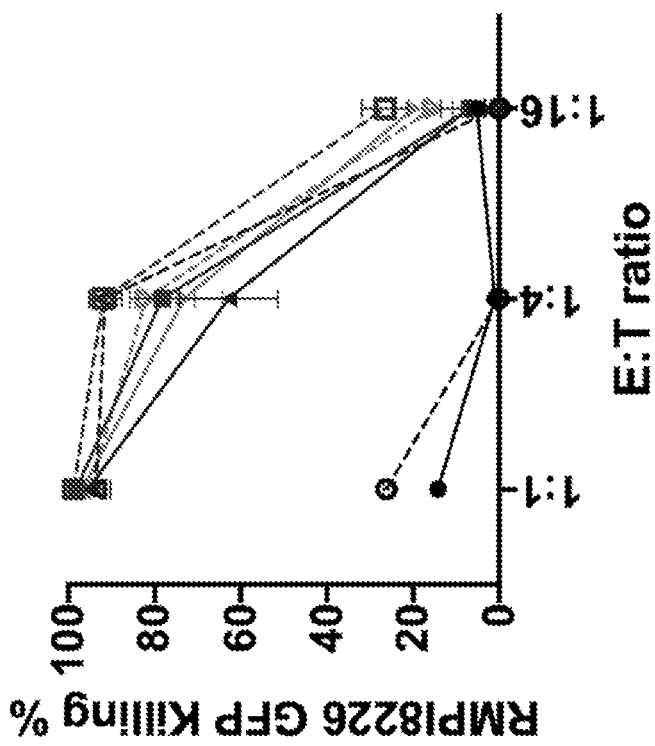
Figure 26F:
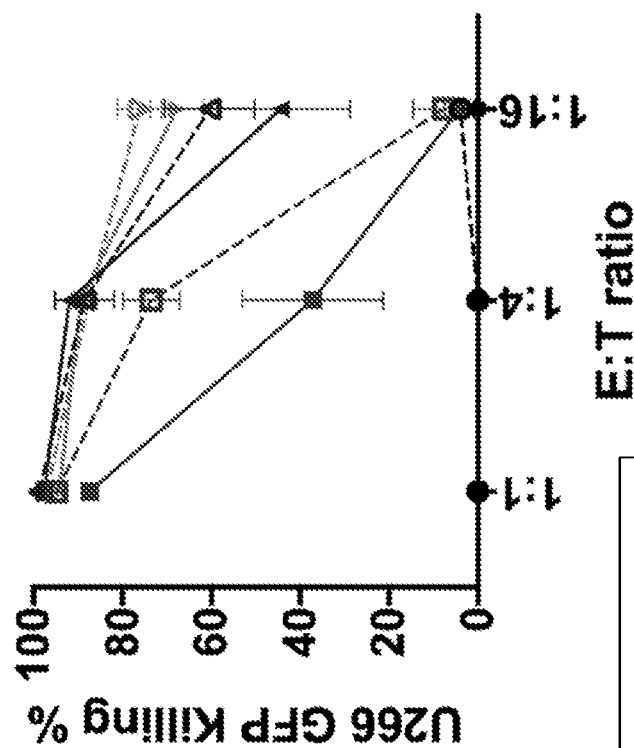
Figure 26H:
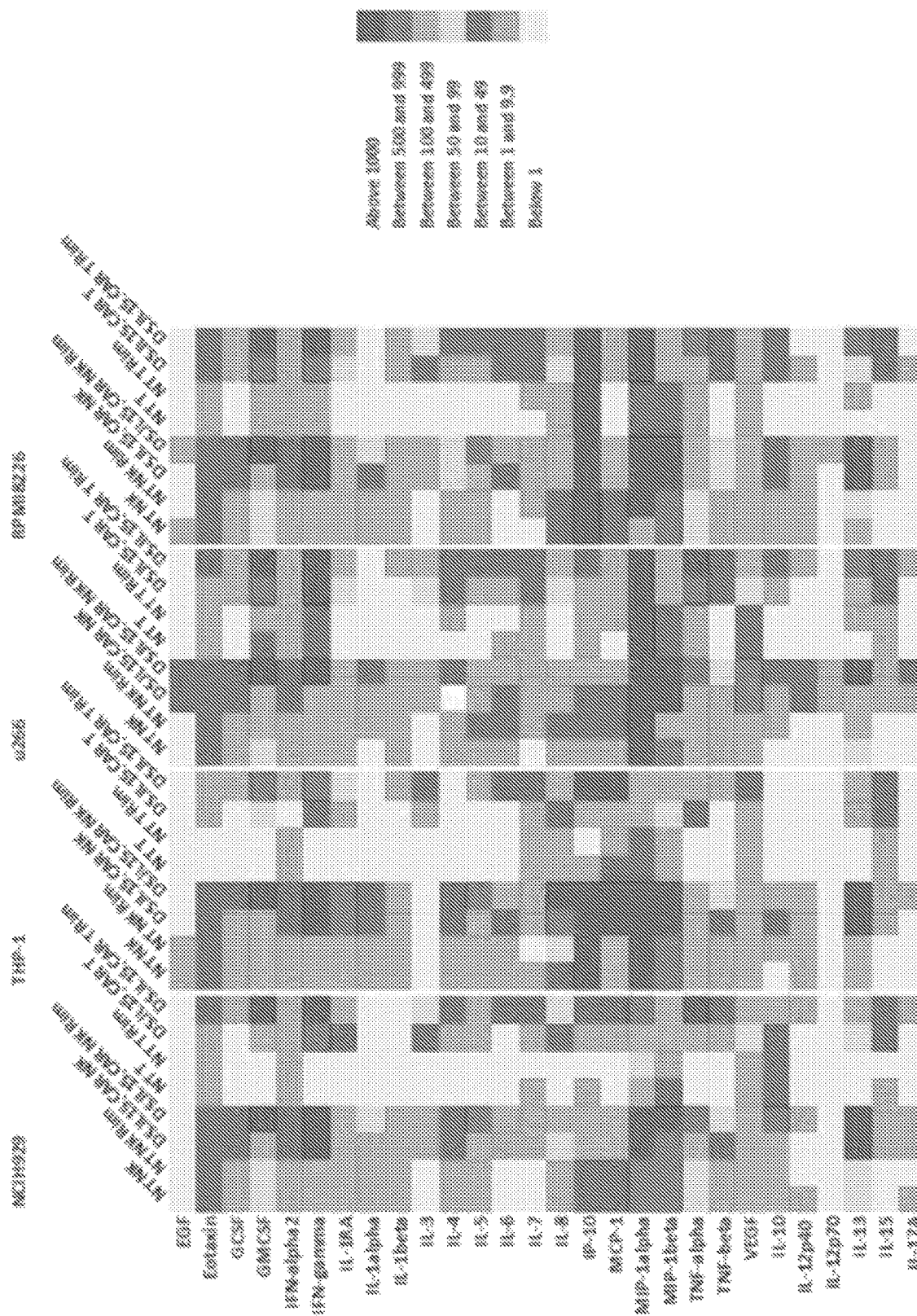

CAR-T therapy against lymphoid malignancies has produced striking clinical results. Therefore, DS.BCMA.ζ.IL15 modified NK cell cytotoxicity, in comparisons with same donors DS.BCMA.ζ.IL15 modified T cells was evaluated. T cells and NK cells showed equivalent transduction efficiencies (FIGS. 26A and 26B). Four plasmacytoma/leukemia cell lines were tested with BCMA antigen expression level ranging from high to moderate: NCIH929, THP-1, U266, and RPM18226 (FIG. 26C). Untransduced or transduced NK or T cells were co-cultured with BCMA expressing tumor targets each at decreasing E:T ratios and tumor cell growth was monitored for 140 hours in an Incucyte microscope incubator. The fluorescence of the tumor cell co-cultures at 140 hours relative to that of the tumor cells incubated alone at 140 hours was measured and the degree of tumor control calculated as percentage of killing by T or NK cells. Non-transduced T cells (NT) displayed poor cytotoxicity in this assay, which was not improved with rimiducid treatment. Dual switch CAR-T cells had increased cytotoxicity relative to non-transduced T cells and this toxicity was enhanced by activation of iMC with rimiducid. Non-transduced NK cells exhibited innate anti-tumor cytotoxicity that was similar to that observed with dual switch-CAR-T cells. Interestingly, DS.BCMA.ζ.IL15 modified NKs showed superior rimiducid-dependent killing compared with DS.BCMA.ζ.IL15 modified T cells in BCMA high antigen expression cell lines; whereas comparable or a little less effective in BCMA moderate antigen expression tumor cell lines U266 and RPMI8226 (FIGS. 26D, 26E, 26F, and 26G). Cytokine profiling data further demonstrated that DS.BCMA.ζ.IL15 modified NK cells generally produced more cytokines compared with T cells (FIG. 26H). These data indicate that NK cell-based therapy poses the potential for better efficacy than CAR-T therapy in vitro. Moreover, ILT2, the inhibitory receptors, expression was higher in NKs compared with T cells (but not ILT4, FIG. 23A), suggesting a safe feature of NK cells for less GVHD.

iMC Blocks NK Cell Inefficacy Following Cryostorage

FIG. 13A shows that iMC blocks NK cell inefficacy following cryostorage. Transduced NK cells were maintained in standard culture conditions. Cells were slowly frozen in 90% foetal calf serum/10% dimethylsulfoxide and stored below −150° C. for up to four weeks. Overall NK cell viability after freeze-thaw was similar for each group. The graphs provided in FIGS. 13B and 13C relate to efficacy. Cell viability was poor in for each transductant immediately following thawing and replating but recovered over three days of standard culture. NK cells prior to and after the indicated period of recovery from freeze/thaw were cultured with THP1-luciferase targets for 24 hours at an E:T of 3:1 (FIG. 13B) or 1:1 (FIG. 13C) to assess killing efficacy. Dual switch NK cells with iMC were capable of regaining their potency over 48 to 72 hours after cryostorage while cells lacking iMC lacked efficacy.

Example 4.—Expression of a Constitutively Active MyD88/CD40 with an Inducible Proapoptotic Safety Switch Confers Rimiducid Inducible Ablation of CAR-NK Expansion and Anti-Tumor Efficacy Against Hematological Malignancies In certain applications, it is desirable to maintain the activity of MyD88-CD40 in a constitutive fashion to promote stable NK cell expansion and anti-tumor activity. A possible limitation of such a strategy is toxicity resulting from MC overactivity through excessive cytokine release or off tumor targeting. Retroviral constructs driving the expression of a first-generation chimeric antigen receptor (scFv-transmembrane liner-CD3ζ) and MyD88/CD40 separated by a P2A sequence engineered to have inefficient cotranslational cleavage provides expression of the first-generation CAR and a fusion protein between the CAR and MC that provides constitutive activation of MC at the cell membrane (Collinson-Pautz et al., *Leukemia* Feb. 28 2019 (doi: 10.1038/s41375-019-0417-9)). Inclusion of inducible caspase-9 in (FKBPv-ΔC9) the retroviral vector permits apoptotic cell ablation upon the addition of rimiducid. The present example demonstrates that constitutive activation through MC drives NK cell expansion, antitumor efficacy and cytokine production to a degree similar to that of inducible MC when activated by rimiducid but that activation of the iCaspase-9 safety switch blocks the activity of the NK cells.

Materials and Methods

Methods for determination of NK cell proliferation, cytokine release into cell supernatant and control of tumor cell growth in coculture assays were as described in the previous examples. Additional plasmid material is described below. Plasmids:

TABLE

PBP2819-SFG-FKBPv.ΔCaspase9-T2A-αBCMA(C12.A3.2).CD8STM.zeta-P2A-MyD88.CD40-T2A-IL15

| Fragment | Nucleotide | SEQ ID NO: | Peptide | SEQ ID NO: |
|---|---|---|---|---|
| Leader peptide | ATGCTCGAGATGCTGGAG | 57 | MLEMLE | 58 |
| FKBPv | GGAGTGCAGGTGGAGACTATTAGCC CCGGAGATGGCAGAACATTCCCCAA AAGAGGACAGACTTGCGTCGTGCAT TATACTGGAATGCTGGAAGACGGCA AGAAGGTGGACAGCAGCCGGGACC GAAACAAGCCCTTCAAGTTCATGCT GGGGAAGCAGGAAGTGATCCGGGG CTGGGAGGAAGGAGTCGCACAGAT GTCAGTGGGACAGAGGGCCAAACT GACTATTAGCCCAGACTACGCTTAT GGAGCAACCGGCCACCCCGGGATC ATTCCCCCTCATGCTACACTGGTCTT CGATGTGGAGCTGCTGAAGCTGGAA | 113 | GVQVETISPGDGRTFPKRGQTCVVHY TGMLEDGKKVDSSRDRNKPFKFMLG KQEVIRGWEEGVAQMSVGQRAKLTIS PDYAYGATGHPGIIPPHATLVFDVELL KLE | 16 |
| Linker | AGCGGAGGAGGATCCGGAGTGGAC | 61 | SGGGSGVD | 62 |
| Δcaspase9 | GGGTTTGGAGATGTGGGAGCCCTG GAATCCCTGCGGGGCAATGCCGATC TGGCTTACATCCTGTCTATGGAGCC TTGCGGCCACTGTCTGATCATTAAC AATGTGAACTTCTGCAGAGAGAGCG GGCTGCGGACCAGAACAGGATCCA ATATTGACTGTGAAAAGCTGCGGAG AAGGTTCTCTAGTCTGCACTTTATGG TCGAGGTGAAAGGCGATCTGACCGC TAAGAAAATGGTGCTGGCCCTGCTG GAACTGGCTCGGCAGGACCATGGG GCACTGGATTGCTGCGTGGTCGTGA TCCTGAGTCACGGCTGCCAGGCTTC ACATCTGCAGTTCCCTGGGGCAGTC TATGGAACTGACGGCTGTCCAGTCA GCGTGGAGAAGATCGTGAACATCTT CAACGGCACCTCTTGCCCAAGTCTG GGCGGGAAGCCCAAACTGTTCTTTA TTCAGGCCTGTGGAGGCGAGCAGA AAGATCACGGCTTCGAAGTGGCTAG CACCTCCCCCGAGGACGAATCACCT GGAAGCAACCCTGAGCCAGATGCAA CCCCCTTCCAGGAAGGCCTGAGGA CATTTGACCAGCTGGATGCCATCTC AAGCCTGCCCACACCTTCTGACATT TTCGTCTCTTACAGTACTTTCCCTGG ATTTGTGAGCTGGCGCGATCCAAAG TCAGGCAGCTGGTACGTGGAGACAC TGGACGATATCTTTGAGCAGTGGGC CCATTCTGAAGACCTGCAGAGTCTG | 63 | GFGDVGALESLRGNADLAYILSMEPC GHCLIINNVNFCRESGLRTRTGSNIDC EKLRRRFSSLHFMVEVKGDLTAKKMV LALLELARQDHGALDCCVVVILSHGC QASHLQFPGAVYGTDGCPVSVEKIVNI FNGTSCPSLGGKPKLFFIQACGGEQK DHGFEVASTSPEDESPGSNPEPDATP FQEGLRTFDQLDAISSLPTPSDIFVSY STFPGFVSWRDPKSGSWYVETLDDIF EQWAHSEDLQSLLLRVANAVSVKGIY KQMPGCFNFLRKKLFFKTSASRA | 64 |

TABLE-continued

PBP2819-SFG-FKBPv.ΔCaspase9-T2A-αBCMA(C12.A3.2).CD8STM.zeta-P2A-MyD88.CD40-T2A-IL15

| Fragment | Nucleotide | SEQ ID NO: | Peptide | SEQ ID NO: |
|---|---|---|---|---|
| | CTGCTGCGAGTGGCCAATGCTGTCT CTGTGAAGGGGATCTACAAACAGAT GCCAGGATGCTTCAACTTTCTGAGA AAGAAACTGTTCTTTAAGACCTCCG CATCTAGGGCC | | | |
| Linker | CCGCGG | 17 | PR | 18 |
| T2A | GAGGGCAGAGGCAGCCTCCTGACA TGTGGGGACGTCGAGGAGAACCCT GGCCCA | 19 | EGRGSLLTCGDVEENPGP | 20 |
| Linker | CCTTGG | 21 | PW | 22 |
| Signal Peptide | ATGGAGTTCGGATTGAGCTGGCTGT TCCTGGTGGCAATACTCAAGGGCGT TCAATGTTCACGG | 23 | MEFGLSWLFLVAILKGVQCSR | 24 |
| BCMA (C123.A3.2) V$_L$ | GATATCGTGCTGACCCAGTCCCCCC CTAGCCTGGCCATGTCCCTGGGCAA ACGGGCCACCATCTCCTGCAGAGCC TCCGAGTCCGTGACCATCCTCGGCT CCCACCTGATCTACTGGTACCAGCA GAAGCCCGGCCAGCCTCCCACCCT CCTTATCCAGCTGGCCAGCAACGTG CAGACCGGCGTGCCCGCTAGATTCT CCGGCAGCGGCTCTAGAACCGACTT CACCCTGACCATCGACCCCGTGGAA GAGGACGATGTCGCCGTGTACTATT GCCTGCAGTCCAGAACCATCCCTAG GACATTCGGCGGAGGAACCAAGCT GGAGATCAAA | 87 | DIVLTQSPPSLAMSLGKRATISCRASE SVTILGSHLIYWYQQKPGQPPTLLIQL ASNVQTGVPARFSGSGSRTDFTLTID PVEEDDVAVYYCLQSRTIPRTFGGGT KLEIK | 88 |
| Flex | GGGGGCGGTGGCAGCGGTGGCGG TGGGTCTGGGGGCGGAGGCTCT | 89 | GGGGSGGGGSGGGGS | 90 |
| BCMA (C123.A3.2) V$_H$ | CAGATCCAGCTGGTGCAGTCCGGC CCCGAGCTGAAGAAACCCGGCGAG ACCGTGAAGATCTCCTGCAAGGCCA GCGGCTACACCTTCAGACACTACAG CATGAACTGGGTGAAGCAGGCCCCT GGCAAGGGCCTGAAGTGGATGGGC CGGATCAACACCGAGTCCGGCGTG CCCATCTACGCCGACGATTTCAAGG GCAGATTCGCCTTCAGCGTGGAGAC CTCCGCCTCTACCGCCTACCTGGTG ATCAACAATCTGAAGGACGAGGACA CCGCCTCCTACTTCTGCAGCAACGA CTACCTGTACAGCCTGGACTTCTGG GGCCAGGGCACCGCCCTGACCGTG AGCTCCG | 91 | QIQLVQSGPELKKPGETVKISCKASG YTFRHYSMNWVKQAPGKGLKWMGRIN TESGVPIYADDFKGRFAFSVETSAST AYLVINNLKDEDTASYFCSNDYLYSL DFWGQGTALTVSS | 92 |
| Linker | GGATCC | 33 | GS | 34 |
| CD34 epitope | GAACTTCCTACTCAGGGGACTTTCT CAAACGTTAGCACAAACGTAAGT | 35 | ELPTQGTFSNVSTNVS | 36 |
| CD8 stalk | GAACTTCCTACTCAGGGGACTTTCT CAAACGTTAGCACAAACGTAAGT | 37 | PAPRPPTPAPTIASQPLSLRPEACRPA AGGAVHTRGLDFACD | 38 |
| CD8 transmembrane | ATCTATATCTGGGCACCTCTCGCTG GCACCTGTGAGTCCTTCTGCTCAG CCTGGTTATTACTCTGTACTGTAAT CACCGGAATCGCCGCCGCGTTTGTA AGTGTCCCAGG | 39 | IYIWAPLAGTCGVLLLSLVITLYCNHRN RRRVCKCPR | 40 |
| Linker | GTCGAC | 41 | VD | 42 |
| CD3ζ | AGAGTGAAGTTCAGCAGGAGCGCA GACGCCCCCGCGTACCAGCAGGGC CAGAACCAGCTCTATAACGAGCTCA ATCTAGGACGAAGAGAGGAGTACGA TGTTTTGGACAAGAGACGTGGCCGG | 43 | RVKFSRSADAPAYQQGQNQLYNELN LGRREEYDVLDKRRGRDPEMGGKPR RKNPQEGLYNELQKDKMAEAYSEIG MKGERRRGKGHDGLYQGLSTATKDT YDALHMQALPPR | 44 |

TABLE-continued

PBP2819-SFG-FKBPv.ΔCaspase9-T2A-αBCMA(C12.A3.2).CD8STM.zeta-P2A-MyD88.CD40-T2A-IL15

| Fragment | Nucleotide | SEQ ID NO: | Peptide | SEQ ID NO: |
|---|---|---|---|---|
| | GACCCTGAGATGGGGGAAAGCCG AGAAGGAAGAACCCTCAGGAAGGC CTGTACAATGAACTGCAGAAAGATA AGATGGCGGAGGCCTACAGTGAGAT TGGGATGAAAGGCGAGCGCCGGAG GGGCAAGGGGCACGATGGCCTTTA CCAGGGTCTCAGTACAGCCACCAAG GACACCTACGACGCCCTTCACATGC AAGCTCTTCCACCTCGT | | | |
| P2A | GCAACGAATTTTTCCCTGCTGAAACA GGCAGGGGACGTAGAGGAAAATCC TGGTCCT | 114 | ATNFSLLKQAGDVEENPGP | 74 |
| MYD88 | ATGGCTGCAGGAGGTCCCGGCGCG GGGTCTGCGGCCCCGGTCTCCTCC ACATCCTCCCTTCCCCTGGCTGCTC TCAACATGCGAGTGCGGCGCCGCC TGTCTCTGTTCTTGAACGTGCGGAC ACAGGTGGCGGCCGACTGGACCGC GCTGGCGGAGGAGATGGACTTTGA GTACTTGGAGATCCGGCAACTGGAG ACACAAGCGGACCCCACTGGCAGG CTGCTGGACGCCTGGCAGGGACGC CCTGGCGCCTCTGTAGGCCGACTG CTCGATCTGCTTACCAAGCTGGGCC GCGACGACGTGCTGCTGGAGCTGG GACCCAGCATTGAGGAGGATTGCCA AAAGTATATCTTGAAGCAGCAGCAG GAGGAGGCTGAGAAGCCTTTACAGG TGGCCGCTGTAGACAGCAGTGTCCC ACGGACAGCAGAGCTGGCGGGCAT CACCACACTTGATGACCCCCTGGGG CATATGCCTGAGCGTTTCGATGCCT TCATCTGCTATTGCCCCAGCGACAT C | 1 | MAAGGPGAGSAAPVSSTSSLPLAALN MRVRRRLSLFLNVRTQVAADWTALAE EMDFEYLEIRQLETQADPTGRLLDAW QGRPGASVGRLLDLLTKLGRDDVLLE LGPSIEEDCQKYILKQQQEEAEKPLQ VAAVDSSVPRTAELAGITTLDDPLGH MPERFDAFICYCPSDI | 2 |
| Linker | GTCGAG | 13 | VE | 14 |
| CD40 | AAAAAGGTGGCCAAGAAGCCAACCA ATAAGGCCCCCCACCCCAAGCAGGA GCCCCAGGAGATCAATTTTCCCGAC GATCTTCCTGGCTCCAACACTGCTG CTCCAGTGCAGGAGACTTTACATGG ATGCCAACCGGTCACCCAGGAGGAT GGCAAAGAGTCGCATCTCAGTGC AGGAGAGACA | 115 | KKVAKKPTNKAPHPKQEPQEINFPDD LPGSNTAAPVQETLHGCQPVTQEDG KESRISVQERQ | 56 |
| Linker | GGATCTGCGGCCGC | 93 | GSGGR | 94 |
| T2A | GAGGGAAGGGGAAGTCTTCTAACAT GCGGGGACGTGGAGGAAAATCCCG GGCCC | 95 | EGRGSLLTCGDVEENPGP | 20 |
| STOP | TGA | | STOP | |
| IL-15 | ATGAGAATTTCGAAACCACATTTGAG AAGTATTTCCATCCAGTGCTACTTGT GTTTACTTCTAAACAGTCATTTTCTA ACTGAAGCTGGCATTCATGTCTTCAT TTTGGGCTGTTTCAGTGCAGGGCTT CCTAAAACAGAAGCCAACTGGGTGA ATGTAATAAGTGATTTGAAAAAAATT GAAGACCTTATTCAATCTATGCACAT TGATGCTACTTTATATACGGAAAGTG ATGTTCACCCCAGTTGCAAAGTAAC AGCAATGAAGTGCTTTCTCTTGGAG TTACAAGTTATTTCACTTGAGTCCGG AGATGCAAGTATTCATGATACAGTAG AAAATCTGATCATCCTAGCAAACAAC AGTTTGTCTTCTAATGGGAATGTAAC AGAATCTGGATGCAAAGAATGTGAG | 116 | MRISKPHLRSISIQCYLCLLLNSHFLT EAGIHVFILGCFSAGLPKTEANWVNVI SDLKKIEDLIQSMHIDATLYTESDVHP SCKVTAMKCFLLELQVISLESGDASIH DTVENLIILANNSLSSNGNVTESGCKE CEELEEKNIKEFLQSFVHIVQMFINT | 97 |

TABLE-continued

PBP2819-SFG-FKBPv.ΔCaspase9-T2A-αBCMA(C12.A3.2).CD8STM.zeta-P2A-MyD88.CD40-T2A-IL15

| Fragment | Nucleotide | SEQ ID NO: Peptide | SEQ ID NO: |
|---|---|---|---|
| | GAACTGGAGGAGAAGAACATCAAGG AATTTTTGCAGAGTTTTGTACATATT GTCCAAATGTTCATCAACACT | | |
| STOP | TGA | STOP | STOP |

Results

Constitutive Activation of MC Supports Enhanced Proliferation of NK Cells

Figure 27:
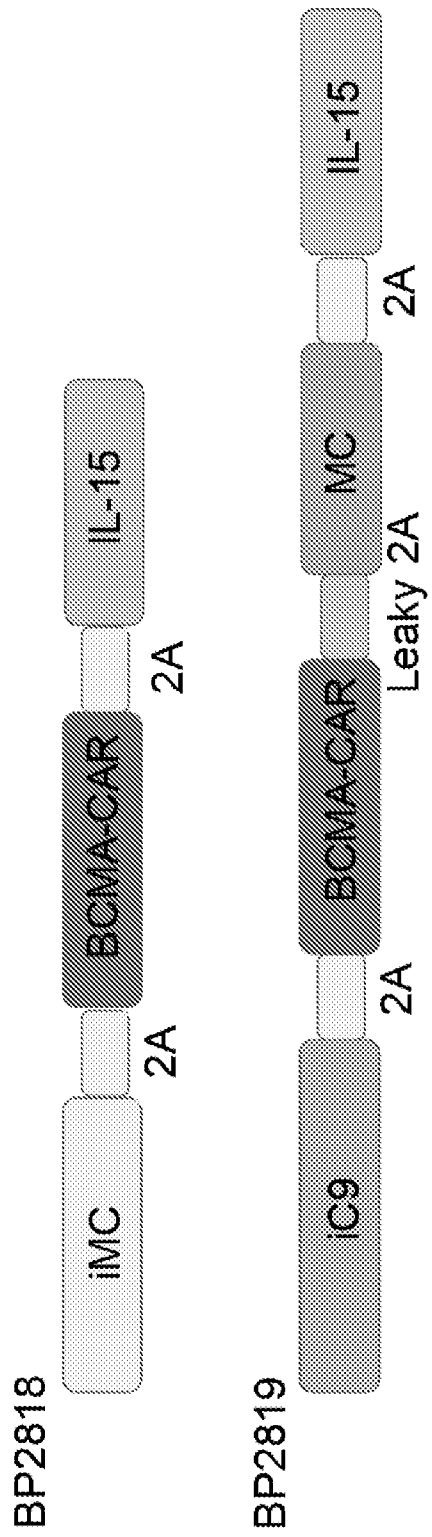
FIG. 27: Plasmid DNA constructs were created to generate γ-retroviruses encoding iMC with a CAR and IL-15 each separated by 2A cotranslational cleavage sites (2818) or a constitutively active clone (2819) in which inefficient cleavage at the 2A site between the CAR and MC (lacking Fv) creates a CAR-MC fusion product that is constitutively active.
Figure 28:
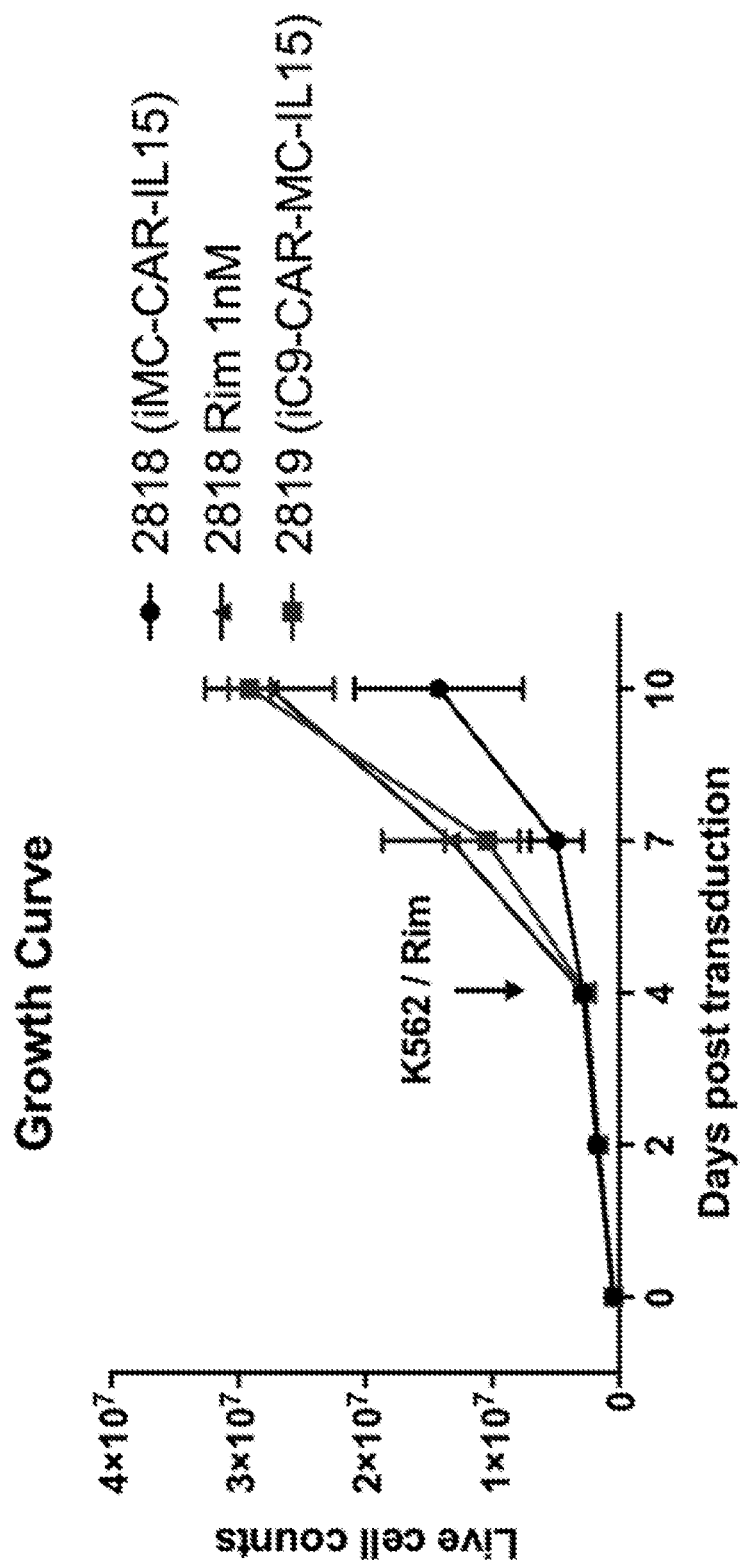
FIG. 28: $5 \times 10^5$ NK cells derived from three donors were transduced with retrovirus encoding inducible MC (2818) or constitutively active MC (2819) and were cultured with IL-2 in the presence or absence of rimiducid as indicated. At Day 4, NK cell cultures were further stimulated with irradiated K562 cells. Cell counts were determined at the indicated days.

Activated NK cells were prepared and transduced with retroviral constructs encoding iMC, IL-15 and a first-generation BCMA-directed CAR or with a four cistron construct encoding iC9 (rimiducid inducible Caspase-9), IL-15, the same CAR and MC lacking FKBP sequences (FIG. 27). The 2A cotranslational cleavage site separating the CAR and MC was engineered to support cotranslational cleavage inefficiently by removing the GSG containing linker 5' to the 2A sequence. This 'leaky' cotranslational cleavage produces a fusion CAR with MC expressed at the cell membrane. This MC at the membrane is constitutively active. In the absence of rimiducid, this constitutively-active MC supported NK cell growth to a degree similar to CAR-NK cells expressing iMC when stimulated with rimiducid, and greater than iMC CAR-NK cells not treated with rimiducid (FIG. 28). During the growth assay, cells were co-cultured with K562 cells to further activate the transduced NK cells.

Figure 29A:
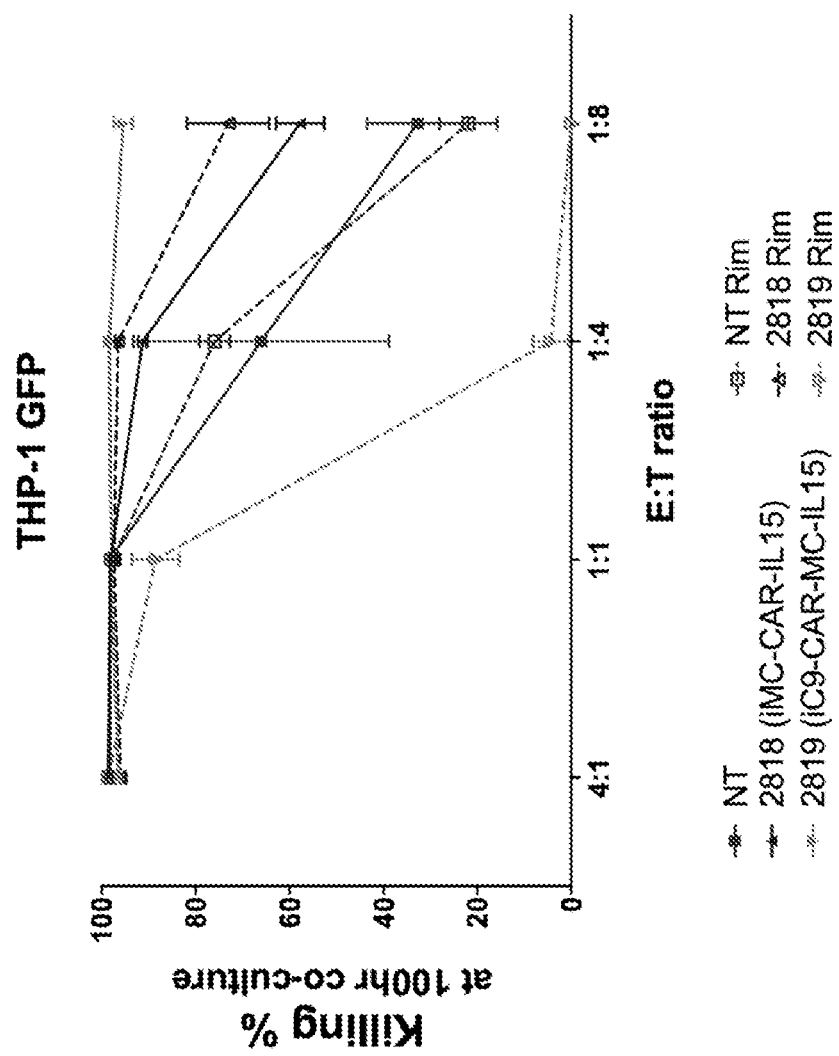
FIGS. 29A-29C: NK cells derived from three donors were transduced with retrovirus encoding inducible MC (2818) or constitutively active MC (2819) and were co-cultured (with IL-2) with BCMA-expressing THP-1 cells (FIG. 29A), RPMI8226 (FIG. 29B) or BCMA-negative Nalm6 cells (FIG. 29C) in the presence or absence of Rimiducid as indicated. In each case the relative amount of NK effectors to tumor targets (E:T) was varied as indicated. Co-cultures containing GFP-labeled tumor targets were incubated in an incucyte microscope and fluorescence monitored over time. Mean fluorescence relative to cultures without NK cells at 100 or 140 hours incubation are indicated.
Figure 29B:
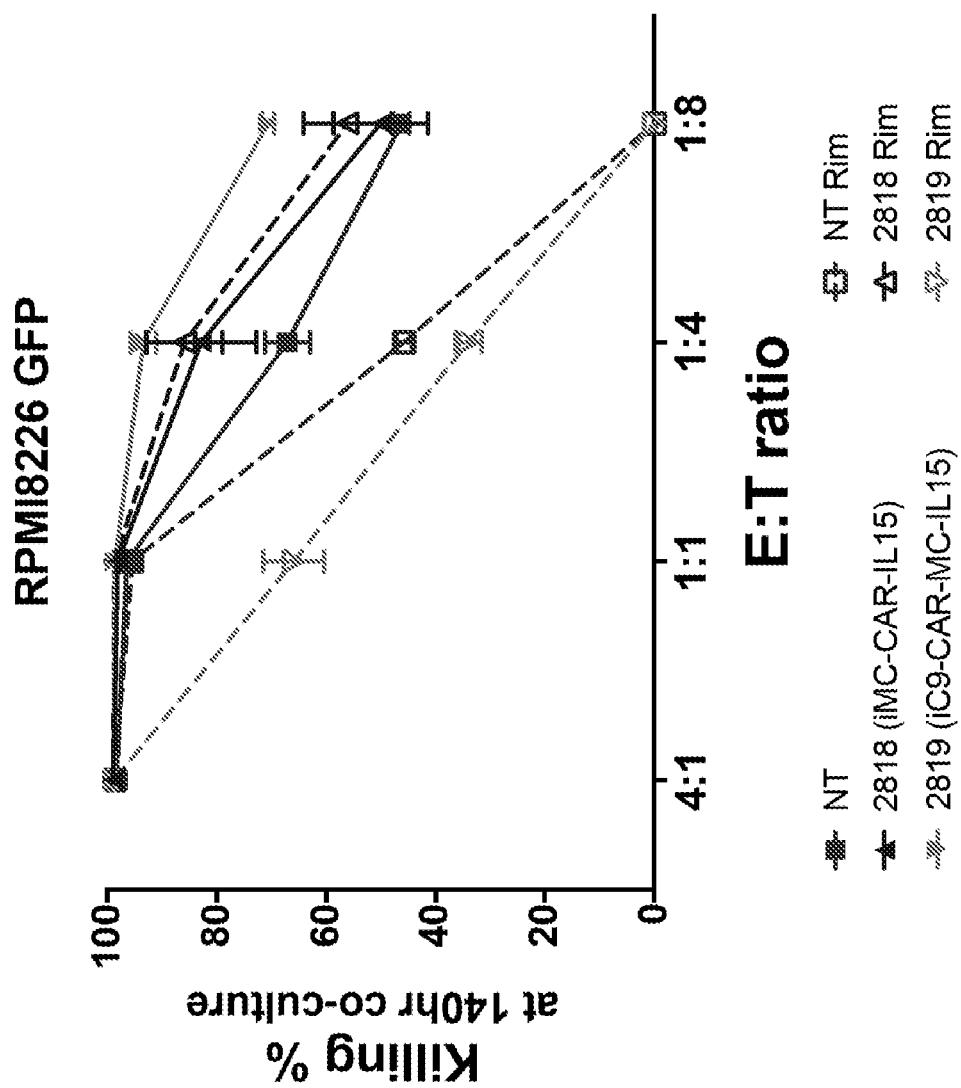
Figure 29C:
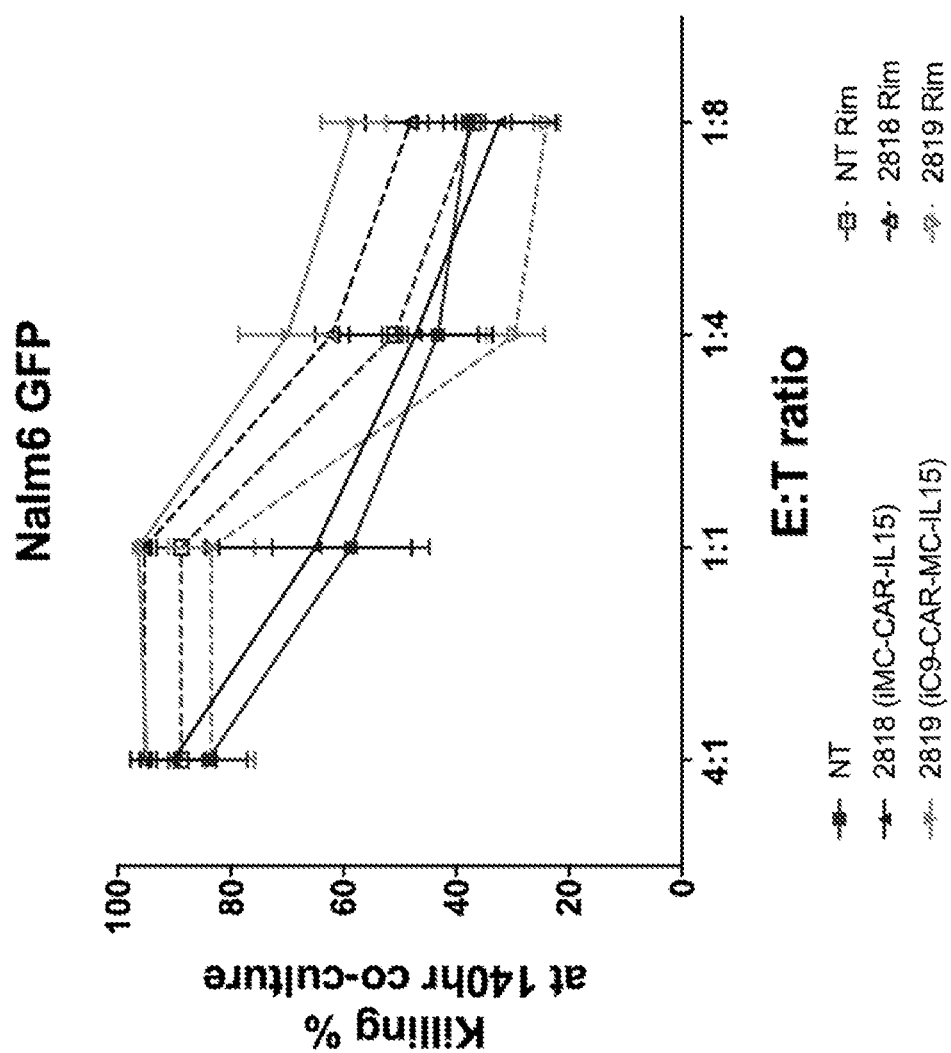
Figure 30A:
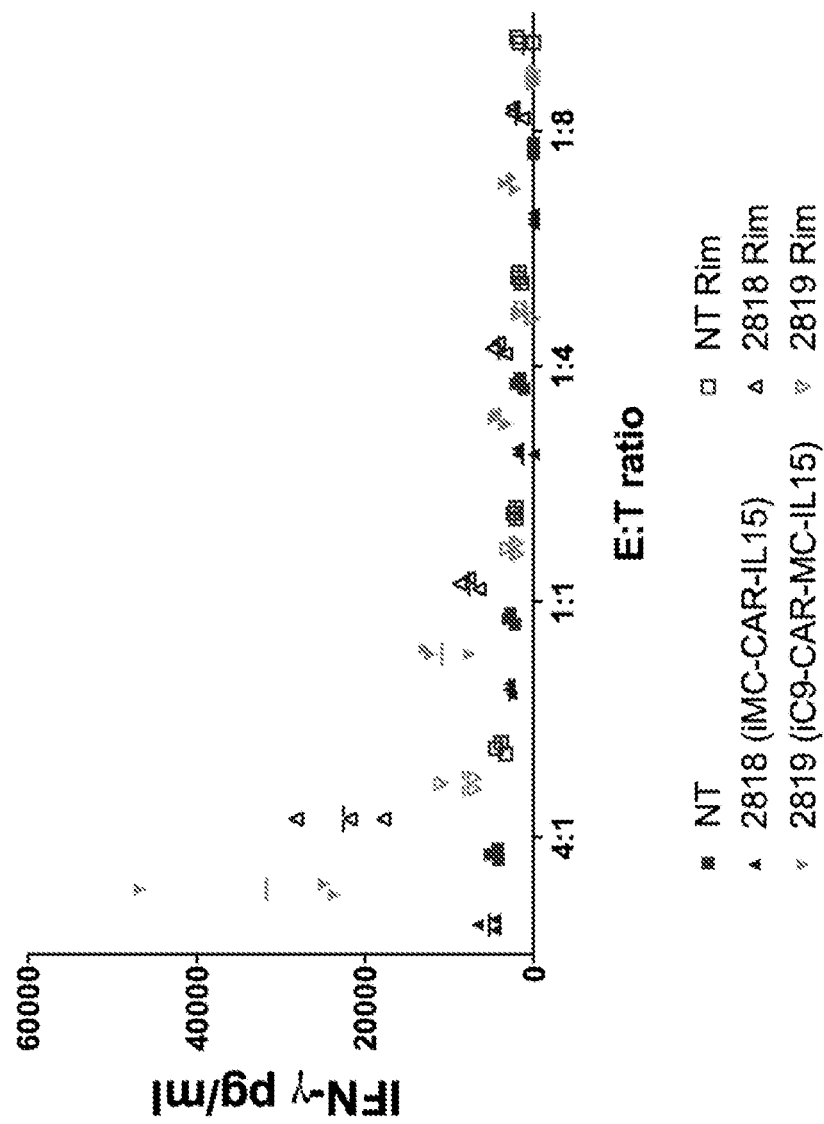
FIGS. 30A-30C: NK cells derived from three donors were transduced with retrovirus encoding inducible MC (2818) or constitutively active MC (2819) and were co-cultured (with IL-2) with BCMA-expressing THP-1 cells (FIG. 30A), RPM18226 (FIG. 30B) or BCMA-negative Nalm6 cells (FIG. 30C) in the presence or absence of Rimiducid as indicated. In each case the relative amount of NK effectors to tumor targets (E:T) was varied as indicated. Supernatant was taken after 24 hours of coculture and Interferon-γ levels determined by ELISA.
Figure 30B:
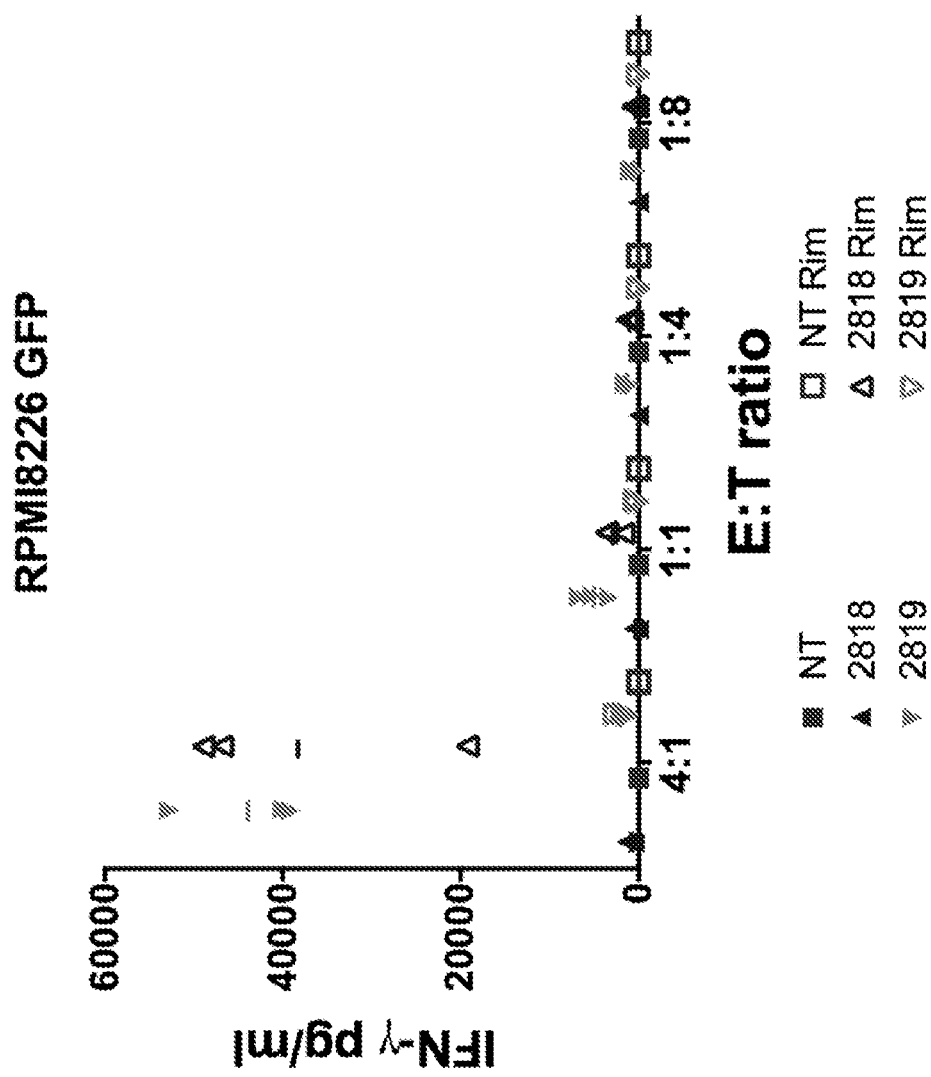
Figure 30C:
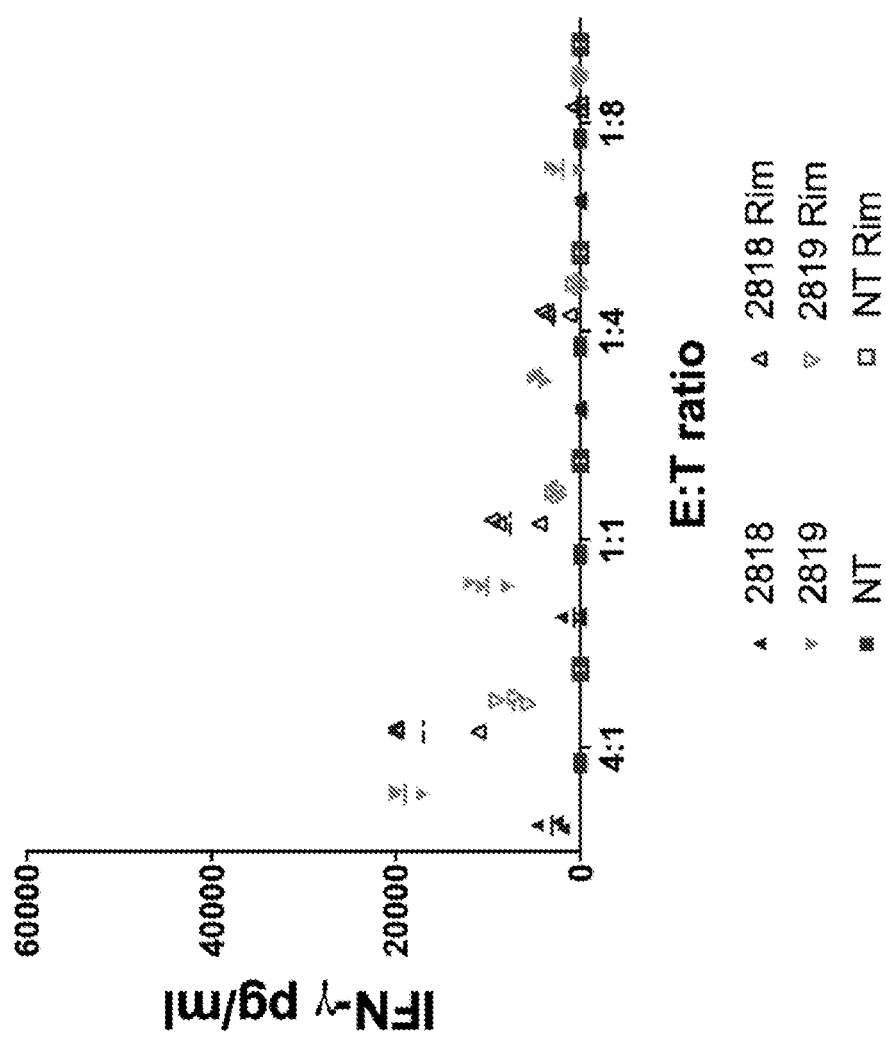

Constitutively Activated MC Supports Enhanced Anti-Tumor Cell Killing that is Blocked by Activation of the iC9 Safety Switch Activated NK cells were prepared from three donors and transduced with the CAR constructs encoding inducible MC (BP2818) or the constitutively active MC species that also encodes the rimiducid-inducible Caspase-9 (BP2819). Co-culture assays were prepared with three different tumor lines, THP-1 which expresses BCMA, the target protein to which the CAR is directed, RPM18226 another BCMA expressing cell line or Nalm6 which does not express BCMA. Use of a cell line that is not specifically targeted by the CAR permitted an assessment of the intrinsic capacity of the NK cells to target tumors and whether inducible or constitutive MC activity augments this anti-tumor activity. Co-culture assays were performed at decreasing effector (NK cells) to target (the tumor cells) ratios (E:T) ratios such that increased anti-tumor efficacy will be evident as greater tumor cell killing when the numbers of NK cells presented are low. In co-culture assays with THP-1 targets in an Incucyte microscope/incubator, non-transduced (NT) NK cells showed robust killing activity up to an E:T ratio of 1:1 with activity reduced at lower E:T ratios (FIG. 29) This intrinsic NK cell killing against the target served as a standard for the capacity of the CAR-containing NK cells. At low E:T ratios CAR-NK cells with inducible MC demonstrated enhanced killing activity relative to non-transduced NK cells and this activity was further enhanced by rimiducid activation of iMC. Constitutively active MC (2819) supported the greatest antitumor efficacy with essentially complete eradication of the target at a low E:T ratio of 1:8. Activation of the iC9 safety switch with rimiducid in NK cells transduced with 2819 caused greatly reduced anti-THP1 efficacy as only the untransduced NK cells remained in the coculture. Similar results were observed when RPMI8226 were targeted. When Nalm6 cells that were not targeted by the CAR were co-cultured, a similar pattern was observed, but the degree of enhanced activity from constitutive MC relative to iMC/rimiducid was less evident. This may indicate that the constitutive activity of MC when fused to the CAR is enhanced by the ligation of the CAR with its protein target. The activation of CAR-NK cells containing constitutive and inducible MC was also assessed by the release of interferon-γ over 48 hours in response to engagement with tumor targets (FIG. 30). When challenged with either THP-1 or RPM18266 cells that are targeted by the CAR, high levels of this cytokine were produced and released into the media. Cells with constitutive MC produced slightly more IFN-γ than cells with rim-activated iMC while low levels were produced by cells containing iMC but uninduced with rimiducid. MC activity still generated elevated cytokine release in the absence of CAR engagement by coculturing with Nalm6 cells, but levels were lower than observed with BCMA expressing cells as expected.

Example 5: Representative Embodiments

Provided hereafter are examples of certain embodiments of the technology.

A1. A modified natural killer (NK) cell, comprising a polynucleotide encoding a chimeric polypeptide, wherein the chimeric polypeptide comprises a) a ligand binding region; and
  b) a signaling region, comprising
   i) a MyD88 polypeptide;
   ii) a truncated MyD88 polypeptide lacking the TIR domain;
   iii) a MyD88 polypeptide and a CD40 cytoplasmic polypeptide region lacking the CD40 extracellular domain;
   iv) a truncated MyD88 polypeptide lacking the TIR domain and a CD40 cytoplasmic polypeptide region lacking the CD40 extracellular domain;
   v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
   vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
   vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

A2. The method of A1 wherein the NK cells are cryostored.

A3. The method of A1 or A2 wherein the modified NK cell has been stored at a temperature of −150° C. or below.

A4-A120. Reserved.

B1. A method for cryopreserving NK cells, comprising storing modified NK cells at a temperature below 0° C., wherein the NK cells comprise a polynucleotide encoding a chimeric polypeptide, wherein the chimeric polypeptide comprises
 a) a ligand binding region; and
 b) a signaling region, comprising
  i) a MyD88 polypeptide;
  ii) a truncated MyD88 polypeptide lacking the TIR domain;
  iii) a MyD88 polypeptide and a CD40 cytoplasmic polypeptide region lacking the CD40 extracellular domain;
  iv) a truncated MyD88 polypeptide lacking the TIR domain and a CD40 cytoplasmic polypeptide region lacking the CD40 extracellular domain;
  v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
  vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
  vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

B2-B120. Reserved.

C1. A method for growing NK cells ex vivo, comprising incubating modified NK cells in cell culture medium, wherein the NK cells comprise a polynucleotide encoding a chimeric polypeptide, wherein the chimeric polypeptide comprises
 a) a ligand binding region; and
 b) a signaling region, comprising
  i) a MyD88 polypeptide;
  ii) a truncated MyD88 polypeptide lacking the TIR domain;
  iii) a MyD88 polypeptide and a CD40 cytoplasmic polypeptide region lacking the CD40 extracellular domain;
  iv) a truncated MyD88 polypeptide lacking the TIR domain and a CD40 cytoplasmic polypeptide region lacking the CD40 extracellular domain;
  v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
  vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
  vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

C2-C120. Reserved.

D1. A method for thawing NK cells comprising thawing frozen modified NK cells, wherein the NK cells comprise a polynucleotide encoding a chimeric polypeptide, wherein the chimeric polypeptide comprises
 a) a ligand binding region; and
 b) a signaling region, comprising
  i) a MyD88 polypeptide;
  ii) a truncated MyD88 polypeptide lacking the TIR domain;
  iii) a MyD88 polypeptide and a CD40 cytoplasmic polypeptide region lacking the CD40 extracellular domain;
  iv) a truncated MyD88 polypeptide lacking the TIR domain and a CD40 cytoplasmic polypeptide region lacking the CD40 extracellular domain;
  v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
  vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
  vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40
 wherein the modified NK cells have been stored at a temperature of 0° C. or below.

D2-D120. Reserved

E1. A method for stimulating an immune response comprising transfecting or transducing a NK cell ex vivo with a nucleic acid comprising a polynucleotide encoding a chimeric polypeptide, wherein the chimeric polypeptide comprises
 a) a ligand binding region; and
 b) a signaling region, comprising
  i) a MyD88 polypeptide;
  ii) a truncated MyD88 polypeptide lacking the TIR domain;
  iii) a MyD88 polypeptide and a CD40 cytoplasmic polypeptide region lacking the CD40 extracellular domain;

iv) a truncated MyD88 polypeptide lacking the TIR domain and a CD40 cytoplasmic polypeptide region lacking the CD40 extracellular domain;
v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

E2. The method of embodiment E1, comprising the step of transfecting or transducing NK cells with a second nucleic acid comprising a polynucleotide encoding a second chimeric polypeptide.

E3. The method of embodiment E1 or E2, comprising contacting the modified NK cells with an antibody.

E4. The method of any one of embodiments E1-E3, wherein the immune response is a cytotoxic response.

E5. The method of any one of embodiments E1-E4, wherein the immune response is a cytolytic response.

E6. The method of any one of embodiments E1-E5, wherein the immune response is an anti-tumor response.

E7. The method of any one of embodiments E1-E6, comprising contacting the modified NK cells with an antibody that binds to an antigen on a tumor.

E8-E120. Reserved.

F1. A method comprising administering modified NK cells to a subject, wherein the modified NK cells comprise a polynucleotide encoding a chimeric polypeptide, wherein the chimeric polypeptide comprises
a) a ligand binding region; and
b) a signaling region, comprising
i) a MyD88 polypeptide;
ii) a truncated MyD88 polypeptide lacking the TIR domain;
iii) a MyD88 polypeptide and a CD40 cytoplasmic polypeptide region lacking the CD40 extracellular domain;
iv) a truncated MyD88 polypeptide lacking the TIR domain and a CD40 cytoplasmic polypeptide region lacking the CD40 extracellular domain;
v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

F2. The method of embodiment F1, wherein the subject has a disease or condition associated with an elevated expression of a target antigen expressed by a target cell.

F3. The method of embodiment F1, wherein a tumor has been detected in the subject.

F4. The method of any one of embodiments F1 to F3, comprising administering a ligand to the subject, wherein the ligand binds to the ligand binding region of a first chimeric polypeptide and the ligand binding region of a second chimeric polypeptide, resulting in the multimerization of the first chimeric polypeptide and the second chimeric polypeptide.

F5. The method of embodiment F2 or F4, comprising administering an effective amount of a ligand that binds to the ligand binding region of the chimeric polypeptide to reduce the number or concentration of target antigen or target cells in the subject.

F6. The method of embodiment F3 or F4, comprising administering an effective amount of a ligand that binds to the first ligand binding region and the second ligand binding region of the chimeric polypeptide to reduce the size of the tumor in the subject.

F7. The method of any one of embodiments F4-F6, wherein the ligand is administered after the modified NK cells are administered to the subject.

F8. The method of embodiment F2, F4, F5, or F7, wherein the modified NK cells have been primed with an antibody that binds to the target antigen before administration of the modified NK cells to the subject.

F9. The method of embodiment F3, F4, F6, or F7, wherein the modified NK cells have been primed with an antibody that binds to a tumor antigen before administration of the modified NK cells to the subject.

F10. The method of embodiment F2, F4, F5, F7, or F8, comprising measuring the number or concentration of target cells in a first sample obtained from the subject before administering the modified NK cells, measuring the number or concentration of target cells in a second sample obtained from the subject after administering the modified NK cells, and determining an increase or decrease of the number or concentration of target cells in the second sample compared to the number or concentration of target cells in the first sample.

F11. The method of embodiment F4, F5, F7, or F8, comprising measuring the number or concentration of target cells in a first sample obtained from the subject before administering the ligand, measuring the number or concentration of target cells in a second sample obtained from the subject after administering the ligand, and determining an increase or decrease of the number or concentration of target cells in the second sample compared to the number or concentration of target cells in the first sample.

F12. The method of embodiment F3, F4, F6, F7, or F9, comprising measuring the size of a tumor in the subject before administering the modified NK cells, measuring the size of a tumor in the subject after administering the modified NK cells, and determining an increase or decrease of the size of the tumor following administration of the modified NK cells.

F13. The method of embodiment F4, F6, F7, or F9, comprising measuring the size of a tumor in the subject before administering the ligand, measuring the size of a tumor in the subject after administering the ligand, and determining an increase or decrease of the size of the tumor following administration of the ligand.

F14. The method of any one of embodiments F1-F13, wherein the subject has received a stem cell transplant before or at the same time as administration of the modified NK cells.

F15. The method of any one of embodiments F1-F14, wherein the modified NK cells wherein the ligand binding region comprises a first polynucleotide encoding a first FKBP12v36 ligand binding region and a second FKBP12v36 ligand binding region, and wherein said signaling region comprises a truncated MyD88 polypeptide lacking the TIR domain and a CD40 cytoplasmic polypeptide region lacking the CD40 extracellular domain, F16. The method of embodiment F15, wherein the NK cell further comprises a second polynucleotide encoding an IL-15 polypeptide, and a third polynucleotide encoding a chimeric antigen receptor.

F17. The method of any one of embodiments F1-F15, wherein the modified NK cells further comprise a nucleic acid comprising a polynucleotide encoding a chimeric apoptotic polypeptide comprising an FKBP12 binding region, an FRB binding region or an FRB variant binding region, and a Caspase-9 polypeptide lacking the CARD domain.

F18. The method of any one of embodiments F1-F14, wherein the modified NK cells comprise a nucleic acid comprising a first polynucleotide encoding a first FKBP12v36 ligand binding region and a second FKBP12v36 ligand binding region, a truncated MyD88 polypeptide lacking the TIR domain and a CD40 cytoplasmic polypeptide region lacking the CD40 extracellular domain, a second polynucleotide encoding an IL-15 polypeptide, and a third polynucleotide encoding a chimeric apoptotic polypeptide comprising an FKBP12 binding region, an FRB binding region or an FRB variant binding region, and a Caspase-9 polypeptide lacking the CARD domain.

F19. The method of embodiment F18, wherein the modified NK cells comprise a nucleic acid comprising a polynucleotide encoding a chimeric antigen receptor.

F20. The method of embodiment F16 or F19, wherein the CAR targets HER2, PSCA, CD123 or BCMA.

F21. The method of any one of embodiments F1-F20, wherein the subject has an immune response.

F22. The method of any one of embodiments F1-F21, comprising contacting the modified NK cells with an antibody.

F23. The method of embodiment F21 or F22, wherein the immune response is a cytotoxic response.

F24. The method of any one of embodiments F21-F23, wherein the immune response is a cytolytic response.

F25. The method of any one of embodiments F21-F24, wherein the immune response is an anti-tumor response.

F26. The method of any one of embodiments F21-F25, comprising contacting the modified NK cells with an antibody that binds to an antigen on a tumor.

F27. The method of any one of embodiments F21-F26, wherein IL-15 is not administered to the subject within one week of administration of the modified NK cells.

F28. The method of any one of embodiments F21-F26, wherein IL-15 is not administered to the subject within two weeks of administration of the modified NK cells.

F29. The method of any one of embodiments F21-F28, wherein one dose of the modified NK cells is administered.

F30. The method of embodiment F29, wherein an immune response is detected in the subject following administration of the modified NK cells.

F31. The method of embodiment F30, comprising administering to the subject a ligand that binds to the ligand binding region in said chimeric polypeptide, and an immune response is detected in the subject following administration of the ligand.

F32. The method of embodiment F30- or F31, wherein the immune response is directed against a tumor in the subject.

F33. The method of any one of embodiments F1-F31, wherein the subject has cancer.

F34. The method of any one of embodiments F1-F33, wherein the subject has been diagnosed as having one or more tumors, and number of tumor cells is reduced following administration of the modified NK cell.

F35. The method of any one of embodiments F1-F34, wherein the subject has been diagnosed as having one or more tumors, and the size of one or more tumors is reduced following administration of the modified NK cell.

F36. The method of any one of embodiments F1-F35, wherein the subject has been diagnosed as having a hyperproliferative disease.

F37. The method of embodiment F34 or F35, comprising administering to the subject a ligand that binds to the ligand biding region, and a reduction in the number of tumor cells or the size of one or more tumors is detected in the subject following administration of the ligand.

F38. The method of embodiment F34, F35, or F37, wherein the modified NK cells are contacted with an antibody that binds to an antigen on the tumor before administration of the modified NK cells to the subject.

G1. A kit comprising modified natural killer (NK) cells, wherein the modified NK cells comprise a polynucleotide encoding a chimeric polypeptide, comprising
  a) a ligand binding region; and
  b) a signaling region, comprising
    i) a MyD88 polypeptide;
    ii) a truncated MyD88 polypeptide lacking the TIR domain;
    iii) a MyD88 polypeptide and a CD40 cytoplasmic polypeptide region lacking the CD40 extracellular domain;
    iv) a truncated MyD88 polypeptide lacking the TIR domain and a CD40 cytoplasmic polypeptide region lacking the CD40 extracellular domain;
    v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
    vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
    vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40
  wherein the modified NK cells have been stored at a temperature of $-0°$ C. or below.

G2. The kit of embodiment of G1, wherein the modified NK cells have been stored at a temperature of $-150°$ C. or below.

G3. The kit of any embodiment G1 or G2, comprising a ligand that binds to the ligand binding region.

G4. The kit of any one of embodiments G1-G3, comprising an antibody.

G5. The kit of embodiment G4, wherein the antibody binds to an antigen on a target cell.

I6. The kit of embodiment G5, wherein the antibody is formulated for priming the NK cells stimulate an immune response against the target cell.

G7. The kit of embodiment G5 or G6 wherein the target cell is a tumor cell.

G10. The kit of any one of embodiments G1-G9, wherein the ligand binding region comprising a first ligand binding region and a second ligand binding region wherein the first ligand binding region has a different amino acid sequence than the second ligand binding region, and the first and second ligand binding regions bind to a heterodimeric ligand.

G11. The kit of embodiment G10, wherein the first ligand binding region binds to a first portion of the heterodimeric ligand, and the second ligand binding region binds to a second portion of the heterodimeric ligand.

H1. A modified natural killer (NK) cell, comprising a first and a second polynucleotide, wherein the first polynucleotide encodes a chimeric polypeptide comprising
 a) a ligand binding region; and
 b) a signaling region, comprising
  i) a MyD88 polypeptide;
  ii) a truncated MyD88 polypeptide lacking the TIR domain;
  iii) a MyD88 polypeptide and a CD40 cytoplasmic polypeptide region lacking the CD40 extracellular domain;
  iv) a truncated MyD88 polypeptide lacking the TIR domain and a CD40 cytoplasmic polypeptide region lacking the CD40 extracellular domain;
  v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
  vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
  vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40; and
the second polynucleotide encodes a IL-15 polypeptide.

H2. The modified NK cell of embodiment HI, wherein the ligand binding region comprises a first polynucleotide encoding a first FKBP12v36 ligand binding region and a second FKBP12v36 ligand binding region, and wherein said signaling region comprises a truncated MyD88 polypeptide lacking the TIR domain and a CD40 cytoplasmic polypeptide region lacking the CD40 extracellular domain.

H3. The modified NK cell of embodiment H1 or H2 comprising a third polynucleotide encoding a chimeric apoptotic polypeptide comprising a ligand binding region, and a Caspase-9 polypeptide lacking the CARD domain.

H4. The modified NK cell of embodiment H3, wherein said ligand binding region in chimeric apoptotic polypeptide is an FKBP12 binding region, an FRB binding region or an FRB variant binding region.

H5. The modified NK cell of any one of embodiments H1-H4, wherein the modified cell comprises a first polynucleotide encoding a first FKBP12v36 ligand binding region and a second FKBP12v36 ligand binding region, a truncated MyD88 polypeptide lacking the TIR domain and a CD40 cytoplasmic polypeptide region lacking the CD40 extracellular domain, a second polynucleotide encoding an IL-15 polypeptide, and a third polynucleotide encoding a chimeric apoptotic polypeptide comprising an FKBP12 binding region, an FRB binding region or an FRB variant binding region, and a Caspase-9 polypeptide lacking the CARD domain.

H6. The modified NK cell of any one of embodiments H1-5, comprising a nucleic acid comprising a polynucleotide encoding a chimeric antigen receptor.

H7. The modified NK cell of embodiment H6, wherein the CAR targets PSMA, PSCA, Muc1 CD19, ROR1, Mesothelin, GD2, CD123, Muc16, CD33, CD38, CD44v6, Her2/Neu, CD20, CD30, BCMA, PRAME, NY-ESO-1, or EGFRvIII.

I1. A nucleic acid, comprising a first and a second polynucleotide, wherein the first polynucleotide encodes a chimeric polypeptide comprising
 a) a ligand binding region; and
 b) a signaling region, comprising
  i) a MyD88 polypeptide;
  ii) a truncated MyD88 polypeptide lacking the TIR domain;
  iii) a MyD88 polypeptide and a CD40 cytoplasmic polypeptide region lacking the CD40 extracellular domain;
  iv) a truncated MyD88 polypeptide lacking the TIR domain and a CD40 cytoplasmic polypeptide region lacking the CD40 extracellular domain;
  v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
  vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
  vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40
and the second polynucleotide encodes a IL-15 polypeptide.

I2. The nucleic acid of embodiment I1, wherein the nucleic acid comprises a polynucleotide that encodes a chimeric antigen receptor (CAR) or a T-cell receptor.

I3. The nucleic acid of embodiment I1 or I2, wherein the nucleic acid comprises a first polynucleotide encoding a first FKBP12v36 ligand binding region and a second FKBP12v36 ligand binding region, a truncated MyD88 polypeptide lacking the TIR domain and a CD40 cytoplasmic polypeptide region lacking the CD40 extracellular domain, a second polynucleotide encoding an IL-15 polypeptide, and a third polynucleotide encoding a chimeric antigen receptor.

I4. The nucleic acid of embodiment I2 or I3, wherein the CAR targets HER2, PSCA, CD123 or BCMA.

I5. The nucleic acid of embodiment I1, wherein the nucleic acid comprises a first polynucleotide encoding a first FKBP12v36 ligand binding region and a second FKBP12v36 ligand binding region, a truncated MyD88 polypeptide lacking the TIR domain and a CD40 cytoplasmic polypeptide region lacking the CD40 extracellular domain, a second polynucleotide encoding an IL-15 polypeptide, and a third polynucleotide encoding a chimeric apoptotic polypeptide comprising an FKBP12 binding region, an FRB binding region or an FRB variant binding region, and a Caspase-9 polypeptide lacking the CARD domain.

I6. The nucleic acid of any one of embodiments I1-I5, wherein the nucleic acid comprises a polynucleotide encoding a marker polypeptide.

I7. The nucleic acid of embodiment I6, wherein the marker polypeptide is a ΔCD19 polypeptide.

I8. A modified NK cell comprising a nucleic acid of any one of embodiments I1-I7.

I9. A pharmaceutical composition comprising a modified NK cell or a nucleic acid of any one of embodiments A1-A3, H1-H7 or I1-I8.

I10. The modified NK cell, method, kit, nucleic acid, or pharmaceutical composition of any one of preceding embodiments, wherein the ligand is rimiducid, AP20187, or AP1510.

J1. A modified natural killer (NK) cell, comprising a first and a second polynucleotide, wherein the first polynucleotide encodes a chimeric polypeptide comprising
a signaling region, comprising
viii) a MyD88 polypeptide;
ix) a truncated MyD88 polypeptide lacking the TIR domain;
x) a MyD88 polypeptide and a CD40 cytoplasmic polypeptide region lacking the CD40 extracellular domain;
xi) a truncated MyD88 polypeptide lacking the TIR domain and a CD40 cytoplasmic polypeptide region lacking the CD40 extracellular domain;
xii) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
xiii) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
xiv) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40; and
the second polynucleotide encodes a IL-15 polypeptide.

J2. The modified NK cell of embodiment J1, wherein the chimeric polypeptide does not comprise a membrane-targeting region.

J3. The modified NK cell of embodiment J1, wherein the chimeric polypeptide does not comprise a ligand binding region.

J2. The modified NK cell of embodiment J1, wherein the chimeric polypeptide comprises a membrane-targeting region.

K1. The modified NK cell, method, kit, nucleic acid, or pharmaceutical composition of any one of embodiments A1-J2, wherein the cells are not grown on feeder cells.

K2. The modified NK cell, method, kit, nucleic acid, or pharmaceutical composition of any one of embodiments A1-K1, wherein the cell has been stored at a temperature of −150° C. or below for more than 24 hours.

K3. The modified NK cell, method, kit, nucleic acid, or pharmaceutical composition of any one of embodiments A1-K2, wherein the cell has been stored at a temperature of −150° C. or below for more than one week.

K4. The modified NK cell, method, kit, nucleic acid, or pharmaceutical composition of any one of embodiments A1-K3, wherein the cell has been stored at a temperature of −150° C. or below for more than three weeks.

K5. The modified NK cell, method, kit, nucleic acid, or pharmaceutical composition of any one of embodiments A1-K4, wherein the cells have not been contacted with exogenous IL-15.

K6. The modified NK cell, method, kit, nucleic acid, or pharmaceutical composition of any one of embodiments A1-K5, wherein the cell has been thawed following cryostorage.

K7. The modified NK cell, method, kit, nucleic acid, or pharmaceutical composition of any one of embodiments A1-K6, wherein the cell has been primed with an antibody following cryostorage.

K8. The modified NK cell, method, kit, nucleic acid, or pharmaceutical composition of any one of embodiments A1-K7, wherein the signaling region comprises a truncated MyD88 polypeptide lacking the TIR domain.

K9. The modified NK cell, method, kit, nucleic acid, or pharmaceutical composition of any one of embodiments A1-K7, wherein the signaling region comprises a truncated MyD88 polypeptide lacking the TIR domain and a CD40 cytoplasmic polypeptide region lacking the CD40 extracellular domain.

K10. The modified NK cell, method, kit, nucleic acid, or pharmaceutical composition of any one of embodiments A1-K7, wherein the signaling region comprises a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions.

K11. The modified NK cell, method, kit, nucleic acid, or pharmaceutical composition of embodiment K10, wherein the co-stimulatory polypeptide cytoplasmic signaling region is selected from the group consisting of CD27, CD28, ICOS, 4-1BB, RANK/TRANCE-R, and OX40.

K12. The modified NK cell, method, kit, nucleic acid, or pharmaceutical composition of embodiment K10, wherein the co-stimulatory polypeptide cytoplasmic signaling region is selected from the group consisting of CD28, 4-1BB, OX40, and ICOS.

K13. The modified NK cell, method, kit, nucleic acid, or pharmaceutical composition of embodiment K10, wherein the co-stimulatory polypeptide cytoplasmic signaling region is selected from the group consisting of CD27, CD28, ICOS, 4-1BB, and OX40.

K14. The modified NK cell, method, kit, nucleic acid, or pharmaceutical composition of any one of embodiments K8-K13, wherein the co-stimulatory polypeptide lacks an extracellular domain or lacks a functional extracellular domain.

K15. The modified NK cell, method, kit, nucleic acid, or pharmaceutical composition of any one of embodiments A1-K10, wherein the truncated MyD88 polypeptide comprises the amino acid sequence of the full length MyD88 sequence of SEQ ID NO: 118, wherein the truncated MyD88 polypeptide lacks the TIR domain, or a functional fragment thereof.

K16. The modified NK cell, method, kit, nucleic acid, or pharmaceutical composition of any one of embodiments A1-K10, wherein the truncated MyD88 polypeptide does not comprise contiguous amino acid residues 156 to the C-terminus of the full length MyD88 polypeptide.

K17. The modified NK cell, method, kit, nucleic acid, or pharmaceutical composition of any one of embodiments A1-K10, wherein the truncated MyD88 polypeptide does not comprise contiguous amino acid residues 152 to the C-terminus of the full length MyD88 polypeptide.

K18. The modified NK cell, method, kit, nucleic acid, or pharmaceutical composition of any one of embodiments A1-K10, wherein the truncated MyD88 polypeptide does not comprise contiguous amino acid residues 173 to the C-terminus of the full length MyD88 polypeptide.

K19. The modified NK cell, method, kit, nucleic acid, or pharmaceutical composition of any one of embodiments A1-K10, or K15-K18, wherein the full length MyD88 polypeptide comprises the amino acid sequence of SEQ ID NO: 118.

K20. The modified NK cell, method, kit, nucleic acid, or pharmaceutical composition of any one of embodiments A1-N3 or K15-K19, wherein the truncated MyD88 polypeptide consists of the amino acid sequence of SEQ ID NO: 119 or SEQ ID NO: 2, or a functional fragment thereof.

K21. The modified NK cell, method, kit, nucleic acid, or pharmaceutical composition of any one of embodiments A1-K10 or K15-K19, wherein the truncated MyD88 polypeptide has the amino acid sequence of SEQ ID NO: 119 or SEQ ID NO: 2, or an amino acid sequence 90% or more identical to SEQ ID NO: 119 or SEQ ID NO: 2.

K22. The modified NK cell, method, kit, nucleic acid, or pharmaceutical composition of any one of embodiments A1-K10 or K15-K19, wherein the truncated MyD88 polypeptide has the amino acid sequence of SEQ ID NO: 119 or SEQ ID NO: 2, or an amino acid sequence 95% or more identical to SEQ ID NO: 119 or SEQ ID NO: 2.

K23. The modified NK cell, method, kit, nucleic acid, or pharmaceutical composition of any one of embodiments A1-K10 or K15-K19, wherein the truncated MyD88 polypeptide has the amino acid sequence of SEQ ID NO: 119 or SEQ ID NO: 2.

K24. The modified NK cell, method, kit, nucleic acid, or pharmaceutical composition of any one of embodiments A1-K23, wherein the signaling region comprises a CD40 cytoplasmic polypeptide and lacks the CD40 extracellular domain.

K25. The modified NK cell, method, kit, nucleic acid, or pharmaceutical composition of any one of embodiments A1-K24, wherein the CD40 cytoplasmic polypeptide has the amino acid sequence of SEQ ID NO: 56, or an amino acid sequence 90% or more identical to SEQ ID NO: 56.

K26. The modified NK cell, method, kit, nucleic acid, or pharmaceutical composition of any one of embodiments A1-K24, wherein the CD40 cytoplasmic polypeptide has the amino acid sequence of SEQ ID NO: 56 or an amino acid sequence 95% or more identical to SEQ ID NO: 56.

K27. The modified NK cell, method, kit, nucleic acid, or pharmaceutical composition of any one of embodiments A1-K24, wherein the CD40 cytoplasmic polypeptide has the amino acid sequence of SEQ ID NO: 56.

K28. The modified NK cells, methods, pharmaceutical compositions, or kits of any one of embodiments A1-K27, wherein the modified NK cells comprise a polynucleotide that encodes a chimeric antigen receptor (CAR).

K29. The modified NK cells, methods, pharmaceutical compositions, or kits of embodiment K28, wherein the CAR comprises a transmembrane region, a cell activation region, and an antigen recognition region.

K30. The modified NK cells, methods, pharmaceutical compositions, or kits of embodiment K29, wherein the cell activation region is a T-cell activation region.

K31. The modified NK cells, methods, pharmaceutical compositions, or kits of embodiment K29, wherein the T-cell activation region is a CD3 zeta-chain region.

K32. The modified NK cells, methods, pharmaceutical compositions, or kits of any one of embodiments K29-K31, wherein the antigen recognition region specifically binds to a molecule chosen from PSMA, PSCA, Muc1, CD19, ROR1, Mesothelin, GD2, CD123, Muc16, CD33, CD38, CD44v6, and Her2/Neu.

K33. The modified NK cells, methods, pharmaceutical compositions, or kits of any one of embodiments K29-K32, wherein the antigen recognition moiety binds to an antigen on a cell involved in a hyperproliferative disease or to a viral or bacterial antigen.

K34. The modified NK cells, methods, pharmaceutical compositions, or kits of any one of embodiments K29-K33, wherein the antigen recognition moiety binds to an antigen selected from the group consisting of PSMA, PSCA, MUC1, CD19, ROR1, Mesothelin, GD2, CD123, MUC16, Her2/NE, CD20, CD30, BCMA, PRAME, NY-ESO-1, and EGFRvIII.

Non-limiting examples are provided herein of methods, sequences, and ligands, for expressing chimeric proteins in immune system cells, measuring levels of cytokines, assaying immune activity, activating chimeric proteins by contacting modified immune cells with multimeric ligands, assaying anti-tumor activity, and treatment of subjects using modified immune cells. In some examples, these methods are exemplified using immune cells other than natural killer cells, such as, for example, T cells. These methods may be applied essentially as described, to obtain, assay, and use, the modified cells, for example modified NK cells, of the present application.

Example 6: Representative Embodiments

Provided hereafter are examples of certain embodiments of the technology.

A1. A cryostored and modified natural killer (NK) cell, comprising a polynucleotide encoding a chimeric polypeptide, wherein the chimeric polypeptide comprises
  c) a first ligand binding region;
  d) a second ligand binding region; and
  e) a signaling region, comprising
    viii) a MyD88 polypeptide;
    ix) a truncated MyD88 polypeptide lacking the TIR domain;
    x) a MyD88 polypeptide and a CD40 cytoplasmic polypeptide region lacking the CD40 extracellular domain;

xi) a truncated MyD88 polypeptide lacking the TIR domain and a CD40 cytoplasmic polypeptide region lacking the CD40 extracellular domain;
xii) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
xiii) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
xiv) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40 wherein the modified NK cell has been stored at a temperature of −150° C. or below.

A2-A120. Reserved.

B1. A method for cryopreserving NK cells, comprising storing modified NK cells at a temperature below 0° C., wherein the NK cells comprise a polynucleotide encoding a chimeric polypeptide, wherein the chimeric polypeptide comprises
c) a first ligand binding region;
d) a second ligand binding region; and
e) a signaling region, comprising
viii) a MyD88 polypeptide;
ix) a truncated MyD88 polypeptide lacking the TIR domain;
x) a MyD88 polypeptide and a CD40 cytoplasmic polypeptide region lacking the CD40 extracellular domain;
xi) a truncated MyD88 polypeptide lacking the TIR domain and a CD40 cytoplasmic polypeptide region lacking the CD40 extracellular domain;
xii) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
xiii) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
xiv) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

B2-B120. Reserved.

C1. A method for growing NK cells ex vivo, comprising incubating modified NK cells in cell culture medium, wherein the NK cells comprise a polynucleotide encoding a chimeric polypeptide, wherein the chimeric polypeptide comprises
c) a first ligand binding region;
d) a second ligand binding region; and
e) a signaling region, comprising
viii) a MyD88 polypeptide;
ix) a truncated MyD88 polypeptide lacking the TIR domain;
x) a MyD88 polypeptide and a CD40 cytoplasmic polypeptide region lacking the CD40 extracellular domain;
xi) a truncated MyD88 polypeptide lacking the TIR domain and a CD40 cytoplasmic polypeptide region lacking the CD40 extracellular domain;
xii) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
xiii) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
xiv) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

C2-C120. Reserved.

D1. A method for thawing NK cells comprising thawing frozen modified NK cells, wherein the NK cells comprise a polynucleotide encoding a chimeric polypeptide, wherein the chimeric polypeptide comprises
c) a first ligand binding region;
d) a second ligand binding region; and
e) a signaling region, comprising
viii) a MyD88 polypeptide;
ix) a truncated MyD88 polypeptide lacking the TIR domain;
x) a MyD88 polypeptide and a CD40 cytoplasmic polypeptide region lacking the CD40 extracellular domain;
xi) a truncated MyD88 polypeptide lacking the TIR domain and a CD40 cytoplasmic polypeptide region lacking the CD40 extracellular domain;
xii) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
xiii) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
xiv) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40 wherein the modified NK cells have been stored at a temperature of 0° C. or below.

D2. The method of embodiment D1, comprising the step of transfecting or transducing NK cells with a nucleic acid comprising a polynucleotide encoding the chimeric polypeptide.

D3. The method of any one of embodiments D1-D2, comprising cooling the modified NK cells to a temperature of 0° C. or below.

D4. The method of any one of embodiments D1-D3, comprising cooling the modified NK cells to a temperature of −150° C. or below.

D5. The method of any one of embodiments D1-D4, comprising thawing the modified NK cells.

D6-D120. Reserved.

E1. A method for stimulating an immune response comprising transfecting or transducing a NK cell ex vivo with a nucleic acid comprising a polynucleotide encoding a chimeric polypeptide, wherein the chimeric polypeptide comprises
- c) a first ligand binding region;
- d) a second ligand binding region; and
- e) a signaling region, comprising
  - viii) a MyD88 polypeptide;
  - ix) a truncated MyD88 polypeptide lacking the TIR domain;
  - x) a MyD88 polypeptide and a CD40 cytoplasmic polypeptide region lacking the CD40 extracellular domain;
  - xi) a truncated MyD88 polypeptide lacking the TIR domain and a CD40 cytoplasmic polypeptide region lacking the CD40 extracellular domain;
  - xii) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
  - xiii) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
  - xiv) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

E2. The method of embodiment E1, comprising the step of transfecting or transducing NK cells with a nucleic acid comprising a polynucleotide encoding the chimeric polypeptide.

E3. The method of any one of embodiments E1-E2, comprising contacting the modified NK cells with an antibody.

E4. The method of any one of embodiments E1-E3, wherein the immune response is a cytotoxic response.

E5. The method of any one of embodiments E1-E4, wherein the immune response is a cytolytic response.

E6. The method of any one of embodiments E1-E5, wherein the immune response is an anti-tumor response.

E7. The method of any one of embodiments E1-E6, comprising contacting the modified NK cells with an antibody that binds to an antigen on a tumor.

E8-E120. Reserved.

F1. A method for stimulating an immune response comprising administering modified NK cells to a subject, wherein the modified NK cells comprise a polynucleotide encoding a chimeric polypeptide, wherein the chimeric polypeptide comprises
- c) a first ligand binding region;
- d) a second ligand binding region; and
- e) a signaling region, comprising
  - viii) a MyD88 polypeptide;
  - ix) a truncated MyD88 polypeptide lacking the TIR domain;
  - x) a MyD88 polypeptide and a CD40 cytoplasmic polypeptide region lacking the CD40 extracellular domain;
  - xi) a truncated MyD88 polypeptide lacking the TIR domain and a CD40 cytoplasmic polypeptide region lacking the CD40 extracellular domain;
  - xii) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
  - xiii) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
  - xiv) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

F2. The method of embodiment F1, wherein the subject has a disease or condition associated with an elevated expression of a target antigen expressed by a target cell.

F3. The method of embodiment F1, wherein a tumor has been detected in the subject.

F4. The method of any one of embodiments F1 to F3, comprising administering a ligand to the subject, wherein the ligand binds to the first ligand binding region of a first chimeric polypeptide and a second ligand binding region of a second chimeric polypeptide, resulting in the multimerization of the first chimeric polypeptide and the second chimeric polypeptide.

F4.1. The method of any one of embodiments F2 or F4, comprising administering an effective amount of a ligand that binds to the first ligand binding region and the second ligand binding region of the chimeric polypeptide to reduce the number or concentration of target antigen or target cells in the subject.

F4.2 The method of any one of embodiments F3 or F4, comprising administering an effective amount of a ligand that binds to the first ligand binding region and the second ligand binding region of the chimeric polypeptide to reduce the size of the tumor in the subject.

F5. The method of any one of embodiments F4-F4.2, wherein the ligand is administered after the modified NK cells are administered to the subject.

F6. The method of any one of embodiments F2, F4, F4.1, or F5, wherein the modified NK cells have been primed with an antibody that binds to the target antigen before administration of the modified NK cells to the subject.

F7. The method of any one of embodiments F3, F4, F4.2, or F5, wherein the modified NK cells have been primed with an antibody that binds to a tumor antigen before administration of the modified NK cells to the subject.

F8. The method of any one of embodiments F2, F4, F4.1, F5, or F6, comprising measuring the number or concentration of target cells in a first sample obtained from the subject before administering the modified NK cells, measuring the number or concentration of target cells in a second sample obtained from the subject after administering the modified NK cells, and determining an increase or decrease of the number or concentration of target cells in the second sample compared to the number or concentration of target cells in the first sample.

F8.1. The method of any one of embodiments F4, F4.1, F5, or F6, comprising measuring the number or concentration of target cells in a first sample obtained from the subject before administering the ligand, measuring the number or concentration of target cells in a second sample obtained from the subject after administering the ligand, and determining an increase or decrease of the number or concentration of target cells in the second sample compared to the number or concentration of target cells in the first sample.

F8.2. The method of any one of embodiments F8 or F8.1, wherein the concentration of target cells in the second sample is decreased compared to the concentration of target cells in the first sample.

F8.3. The method of any one of embodiments F8 or F8.1, wherein the concentration of target cells in the second sample is increased compared to the concentration of target cells in the first sample.

F8.4. The method of any one of embodiments F3, F4, F4.2, F5, or F7, comprising measuring the size of a tumor in the subject before administering the modified NK cells, measuring the size of a tumor in the subject after administering the modified NK cells, and determining an increase or decrease of the size of the tumor following administration of the modified NK cells.

F8.5. The method of any one of embodiments F4, F4.2, F5, or F7, comprising measuring the size of a tumor in the subject before administering the ligand, measuring the size of a tumor in the subject after administering the ligand, and determining an increase or decrease of the size of the tumor following administration of the ligand.

F8.6. The method of any one of embodiments F8.4 or F8.5, wherein the size of the tumor is decreased following administration of the modified NK cells.

F8.7. The method of any one of embodiments F8.4 or F8.5, wherein the size of the tumor is increased following administration of the modified NK cells.

F8.8. The method of any one of embodiments F8.4 or F8.5, wherein the size of the tumor is decreased following administration of the ligand.

F8.9. The method of any one of embodiments F8.4 or F8.5, wherein the size of the tumor is increased following administration of the ligand.

F8.10. The method of any one of embodiments F1-F8.9, wherein the subject has received a stem cell transplant before or at the same time as administration of the modified NK cells.

F11. The method of any one of embodiments F1-F10, wherein the modified NK cells comprise a nucleic acid comprising a first polynucleotide encoding a first FKBP12v36 ligand binding region and a second FKBP12v36 ligand binding region, a truncated MyD88 polypeptide lacking the TIR domain and a CD40 cytoplasmic polypeptide region lacking the CD40 extracellular domain, a second polynucleotide encoding an IL-15 polypeptide, and a third polynucleotide encoding a chimeric antigen receptor.

F12. The method of embodiment F11, wherein the CAR targets CD123 or BCMA.

F13. The method of any one of embodiments F11-F11, wherein the modified NK cells comprise a nucleic acid comprising a polynucleotide encoding a chimeric apoptotic polypeptide comprising an FKBP12 binding region, an FRB binding region or an FRB variant binding region, and a Caspase-9 polypeptide lacking the CARD domain.

F14. The method of any one of embodiments F1-F10, wherein the modified NK cells comprise a nucleic acid comprising a first polynucleotide encoding a first FKBP12v36 ligand binding region and a second FKBP12v36 ligand binding region, a truncated MyD88 polypeptide lacking the TIR domain and a CD40 cytoplasmic polypeptide region lacking the CD40 extracellular domain, a second polynucleotide encoding an IL-15 polypeptide, and a third polynucleotide encoding a chimeric apoptotic polypeptide comprising an FKBP12 binding region, an FRB binding region or an FRB variant binding region, and a Caspase-9 polypeptide lacking the CARD domain.

F15. The method of embodiment F14, wherein the modified NK cells comprise a nucleic acid comprising a polynucleotide encoding a chimeric antigen receptor.

F16. The method of embodiment F15, wherein the CAR targets CD123 or BCMA.

F17-F99. Reserved.

F100. The method of any one of embodiments F1-F99, wherein the subject has an immune response.

F101. The method of any one of embodiments F1-F100, comprising contacting the modified NK cells with an antibody.

F102. The method of any one of embodiments F100-F101, wherein the immune response is a cytotoxic response.

F103. The method of any one of embodiments F100-F102, wherein the immune response is a cytolytic response.

F104. The method of any one of embodiments F100-F103, wherein the immune response is an anti-tumor response.

F105. The method of any one of embodiments F100-F104, comprising contacting the modified NK cells with an antibody that binds to an antigen on a tumor.

F106. The method of any one of embodiments F100-F105, wherein IL-15 is not administered to the subject within one week of administration of the modified NK cells.

F107. The method of any one of embodiments F100-F105, wherein IL-15 is not administered to the subject within two weeks of administration of the modified NK cells.

F108. The method of any one of embodiments F100-F107, wherein one dose of the modified NK cells is administered.

F109. The method of embodiment F108, wherein an immune response is detected in the subject following administration of the modified NK cells.

F110. The method of embodiment F109, comprising administering a ligand that binds to the first ligand domain and the second ligand domain to the subject, and an immune response is detected in the subject following administration of the ligand.

F111. The method of any one of embodiments F109-F111, wherein the immune response is directed against a tumor in the subject.

F112. The method of any one of embodiments F1-F111, wherein the subject has cancer.

F113. The method of any one of embodiments F1-F112, wherein the subject has been diagnosed as having one or more tumors, and number of tumor cells is reduced following administration of the modified NK cell.

F114. The method of any one of embodiments F1-F113, wherein the subject has been diagnosed as having one or more tumors, and the size of one or more tumors is reduced following administration of the modified NK cell.

F115. The method of any one of embodiments F1-F114, wherein the subject has been diagnosed as having a hyperproliferative disease.

F116. The method of any one of embodiments F113 or F114, comprising administering a ligand that binds to the first ligand domain and the second ligand domain to the subject, and a reduction in the number of tumor cells or the size of one or more tumors is detected in the subject following administration of the ligand.

F117. The method of any one of embodiments F113, F114, or F116, wherein the modified NK cells are contacted with an antibody that binds to an antigen on the tumor before administration of the modified NK cells to the subject.

F118-F120. Reserved.

G1. A method for treating a subject having a disease or condition associated with an elevated expression of a target antigen expressed by a target cell, comprising transplanting an effective amount of modified NK cells into the subject; wherein the modified NK cells comprise a polynucleotide encoding a chimeric polypeptide, wherein the chimeric polypeptide comprises
  a) a first ligand binding region;
  b) a second ligand binding region; and
  c) a signaling region, comprising
    i) a MyD88 polypeptide;
    ii) a truncated MyD88 polypeptide lacking the TIR domain;
    iii) a MyD88 polypeptide and a CD40 cytoplasmic polypeptide region lacking the CD40 extracellular domain;
    iv) a truncated MyD88 polypeptide lacking the TIR domain and a CD40 cytoplasmic polypeptide region lacking the CD40 extracellular domain;
    v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
    vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
    vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

G2. The method of embodiment G1, wherein the target antigen is a tumor antigen.

G3. A method for reducing the size of a tumor in a subject, comprising transplanting an effective amount of modified NK cells into the subject; wherein the modified NK cells comprise a polynucleotide encoding a chimeric polypeptide, wherein the chimeric polypeptide comprises
  a) a first ligand binding region;
  b) a second ligand binding region; and
  c) a signaling region, comprising
    i) a MyD88 polypeptide;
    ii) a truncated MyD88 polypeptide lacking the TIR domain;
    iii) a MyD88 polypeptide and a CD40 cytoplasmic polypeptide region lacking the CD40 extracellular domain;
    iv) a truncated MyD88 polypeptide lacking the TIR domain and a CD40 cytoplasmic polypeptide region lacking the CD40 extracellular domain;
    v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
    vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
    vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.
    viii) G2. The method of embodiment G1, comprising administering an effective amount of a ligand that binds to the FKBP12 variant region of the chimeric costimulating polypeptide to reduce the number or concentration of target antigen or target cells in the subject.

G3.1. The method of any one of embodiments F1 to F3, comprising administering a ligand to the subject, wherein the ligand binds to the first ligand binding region of a first chimeric polypeptide and a second ligand binding region of a second chimeric polypeptide, resulting in the multimerization of the first chimeric polypeptide and the second chimeric polypeptide.

G4. The method of any one of embodiments G1-G3.1, comprising administering an effective amount of a ligand that binds to the first ligand binding region and the second ligand binding region of the chimeric costimulating polypeptide to reduce the number or concentration of target antigen or target cells in the subject.

G5. The method of embodiment G4, wherein the ligand is administered after the modified NK cells are administered to the subject.

G6. The method of any one of embodiments G1-G2 or G4-G5, wherein the modified NK cells have been primed with an antibody that binds to the target antigen before administration of the modified NK cells to the subject.

G7. The method of any one of embodiments G2-G6, wherein the modified NK cells have been primed with an antibody that binds to a tumor antigen before administration of the modified NK cells to the subject.

G8. The method of any one of embodiments G1-G2, or G4-G7, comprising measuring the number or concentration of target cells in a first sample obtained from the subject before administering the modified NK cells, measuring the number or concentration of target cells in a second sample obtained from the subject after administering the modified NK cells, and determining an increase or decrease of the number or concentration of target cells in the second sample compared to the number or concentration of target cells in the first sample.

G8.1. The method of any one of embodiments G4-G8, comprising measuring the number or concentration of target cells in a first sample obtained from the subject before administering the ligand, measuring the number or concentration of target cells in a second sample obtained from the subject after administering the ligand, and determining an increase or decrease of the number or concentration of target cells in the second sample compared to the number or concentration of target cells in the first sample.

G8.2. The method of any one of embodiments G8 or G8.1, wherein the concentration of target cells in the second sample is decreased compared to the concentration of target cells in the first sample.

G8.3. The method of any one of embodiments G8 or G8.1, wherein the concentration of target cells in the second sample is increased compared to the concentration of target cells in the first sample.

G8.4. The method of any one of embodiments G3-G5, or G7, comprising measuring the size of a tumor in the subject before administering the modified NK cells, measuring the size of a tumor in the subject after administering the modified NK cells, and determining an increase or decrease of the size of the tumor following administration of the modified NK cells.

G8.5. The method of any one of embodiments G4-G5, G7, or G8.4, comprising measuring the size of a tumor in the subject before administering the ligand, measuring the size of a tumor in the subject after administering the ligand, and determining an increase or decrease of the size of the tumor following administration of the ligand.

G8.6. The method of any one of embodiments G8.4 or G8.5, wherein the size of the tumor is decreased following administration of the modified NK cells.

G8.7. The method of any one of embodiments G8.4 or G8.5, wherein the size of the tumor is increased following administration of the modified NK cells.

G8.8. The method of any one of embodiments G8.4 or G8.5, wherein the size of the tumor is decreased following administration of the ligand.

G8.9. The method of any one of embodiments G8.4 or G8.5, wherein the size of the tumor is increased following administration of the ligand.

G8.10. The method of any one of embodiments G1-G8.9, wherein the subject has received a stem cell transplant before or at the same time as administration of the modified NK cells.

G8.11. The method of any one of embodiments G1-G8.10, wherein IL-15 is not administered to the subject within forty eight hours before or one week after administration of the modified NK cells.

G8.12. The method of any one of embodiments G1-G8.11, wherein IL-2 is not administered to the subject within forty eight hours before or one week after administration of the modified NK cells.

G9-G99. Reserved.

G100. The method of any one of embodiments G1-G99, wherein the subject has an immune response.

G102. The method of any one of embodiments G100-G101, wherein the immune response is a cytotoxic response.

G103. The method of any one of embodiments G100-G102, wherein the immune response is a cytolytic response.

G104. The method of any one of embodiments G100-G103, wherein the immune response is an anti-tumor response.

G105. The method of any one of embodiments G100-G104, comprising contacting the modified NK cells with an antibody that binds to an antigen on a tumor.

G106. The method of any one of embodiments G100-G105, wherein IL-15 is not administered to the subject within one week of administration of the modified NK cells.

G107. The method of any one of embodiments G100-G105, wherein IL-15 is not administered to the subject within two weeks of administration of the modified NK cells.

G108. The method of any one of embodiments G100-G107, wherein one dose of the modified NK cells is administered.

G109. The method of embodiment G108, wherein an immune response is detected in the subject following administration of the modified NK cells.

G110. The method of embodiment G109, comprising administering a ligand that binds to the first ligand domain and the second ligand domain to the subject, and an immune response is detected in the subject following administration of the ligand.

G111. The method of any one of embodiments G109-G111, wherein the immune response is directed against a tumor in the subject.

G112. The method of any one of embodiments G1-G111, wherein the subject has cancer.

G113. The method of any one of embodiments G1-G112, wherein the subject has been diagnosed as having one or more tumors, and number of tumor cells is reduced following administration of the modified NK cell.

G114. The method of any one of embodiments G1-G113, wherein the subject has been diagnosed as having one or more tumors, and the size of one or more tumors is reduced following administration of the modified NK cell.

G115. The method of any one of embodiments G1-G114, wherein the subject has been diagnosed as having a hyperproliferative disease.

G116. The method of any one of embodiments G113 or G114, comprising administering a ligand that binds to the first ligand domain and the second ligand domain to the subject, and a reduction in the number of tumor cells or the size of one or more tumors is detected in the subject following administration of the ligand.

G117. The method of any one of embodiments G113, G114, or G116, wherein the modified NK cells are contacted with an antibody that binds to an antigen on the tumor before administration of the modified NK cells to the subject.

G118-G120. Reserved.

H1. A method of administering a ligand to a human subject who has undergone cell therapy using modified NK cells, wherein the modified NK cells comprise a polynucleotide encoding a chimeric polypeptide, wherein the chimeric polypeptide comprises
   a) a first ligand binding region;
   b) a second ligand binding region; and
   c) a signaling region, comprising
      i) a MyD88 polypeptide;
      ii) a truncated MyD88 polypeptide lacking the TIR domain;
      iii) a MyD88 polypeptide and a CD40 cytoplasmic polypeptide region lacking the CD40 extracellular domain;

iv) a truncated MyD88 polypeptide lacking the TIR domain and a CD40 cytoplasmic polypeptide region lacking the CD40 extracellular domain;
v) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
vi) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
vii) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40, wherein the method comprises administering a ligand to the subject, wherein the ligand binds to the first ligand binding region of a first chimeric polypeptide and the second ligand binding region of a second chimeric polypeptide, resulting in multimerization of the first and the second chimeric polypeptides.

H2. The method of embodiment H1, wherein the subject has a disease or condition associated with an elevated expression of a target antigen expressed by a target cell.

H3. The method of embodiment H1, wherein a tumor has been detected in the subject.

H4-H5. Reserved.

H6. The method of embodiment H2, wherein the modified NK cells have been primed with an antibody that binds to the target antigen before administration of the modified NK cells to the subject.

H7. The method of embodiments H3, wherein the modified NK cells have been primed with an antibody that binds to a tumor antigen before administration of the modified NK cells to the subject.

H8. The method of any one of embodiments H2 or H6, comprising measuring the number or concentration of target cells in a first sample obtained from the subject before administering the ligand, measuring the number or concentration of target cells in a second sample obtained from the subject after administering the ligand, and determining an increase or decrease of the number or concentration of target cells in the second sample compared to the number or concentration of target cells in the first sample.

H8.1. The method of embodiment H8, wherein the concentration of target cells in the second sample is decreased compared to the concentration of target cells in the first sample.

H8.2. The method of embodiment H8, wherein the concentration of target cells in the second sample is increased compared to the concentration of target cells in the first sample.

H8.3. The method of any one of embodiments H3 or H7, comprising measuring the size of a tumor in the subject before administering the ligand, measuring the size of a tumor in the subject after administering the ligand, and determining an increase or decrease of the size of the tumor following administration of the ligand.

H8.4. The method of embodiment H8.3, wherein the size of the tumor is decreased following administration of the ligand.

H8.5. The method of embodiment H8.3, wherein the size of the tumor is increased following administration of the ligand.

H8.6. The method of any one of embodiments H1-H8.5, wherein the subject has received a stem cell transplant before or at the same time as administration of the modified NK cells.

H8.7. The method of any one of embodiments H1-H8.6, wherein IL-15 is not administered to the subject within forty eight hours before or one week after administration of the modified NK cells.

H9-H99. Reserved.

H100. The method of any one of embodiments H1-H99, wherein the subject has an immune response.

H101. The method of any one of embodiments H1-H100, comprising contacting the modified NK cells with an antibody.

H102. The method of any one of embodiments H100-H101, wherein the immune response is a cytotoxic response.

H103. The method of any one of embodiments H100-H102, wherein the immune response is a cytolytic response.

H104. The method of any one of embodiments H100-H103, wherein the immune response is an anti-tumor response.

H105. The method of any one of embodiments H100-H104, comprising contacting the modified NK cells with an antibody that binds to an antigen on a tumor.

H106. The method of any one of embodiments H100-H105, wherein IL-15 is not administered to the subject within one week of administration of the modified NK cells.

H107. The method of any one of embodiments H100-H105, wherein IL-15 is not administered to the subject within two weeks of administration of the modified NK cells.

H108. The method of any one of embodiments H100-H107, wherein one dose of the modified NK cells is administered.

H109. The method of embodiment H108, wherein an immune response is detected in the subject following administration of the modified NK cells.

H110. The method of embodiment H109, comprising administering a ligand that binds to the first ligand domain and the second ligand domain to the subject, and an immune response is detected in the subject following administration of the ligand.

H111. The method of any one of embodiments H109-H111, wherein the immune response is directed against a tumor in the subject.

H112. The method of any one of embodiments H1-H111, wherein the subject has cancer.

H113. The method of any one of embodiments H1-H112, wherein the subject has been diagnosed as having one or more tumors, and number of tumor cells is reduced following administration of the modified NK cell.

H114. The method of any one of embodiments H1-H113, wherein the subject has been diagnosed as having one or more tumors, and the size of one or more tumors is reduced following administration of the modified NK cell.

H115. The method of any one of embodiments H1-H114, wherein the subject has been diagnosed as having a hyperproliferative disease.

H116. The method of any one of embodiments H113 or H114, comprising administering a ligand that binds to the first ligand domain and the second ligand domain to the subject, and a reduction in the number of tumor cells or the size of one or more tumors is detected in the subject following administration of the ligand.

H117. The method of any one of embodiments H113, H114, or H116, wherein the modified NK cells are contacted with an antibody that binds to an antigen on the tumor before administration of the modified NK cells to the subject.

H118-H120. Reserved.

I1. A kit comprising modified natural killer (NK) cells, wherein the modified NK cells comprise a polynucleotide encoding a chimeric polypeptide, comprising
    c) a first ligand binding region;
    d) a second ligand binding region; and
    e) a signaling region, comprising
        viii) a MyD88 polypeptide;
        ix) a truncated MyD88 polypeptide lacking the TIR domain;
        x) a MyD88 polypeptide and a CD40 cytoplasmic polypeptide region lacking the CD40 extracellular domain;
        xi) a truncated MyD88 polypeptide lacking the TIR domain and a CD40 cytoplasmic polypeptide region lacking the CD40 extracellular domain;
        xii) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
        xiii) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
        xiv) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40
wherein the modified NK cells have been stored at a temperature of −150° C. or below.

I3. The kit of any one of embodiments I1-I2, comprising a ligand that binds to the first ligand binding region and binds to the second ligand binding region.

I4. The kit of any one of embodiments I1-I3, comprising an antibody.

I5. The kit of embodiment I4, wherein the antibody binds to an antigen on a target cell.

I6. The kit of embodiment I5, wherein the antibody is formulated for priming the NK cells stimulate an immune response against the target cell.

I7. The kit of any one of embodiments I5 or I6 wherein the target cell is a tumor cell.

I8-19. Reserved.

I10. The kit of any one of embodiments I1-I9, wherein the first ligand binding region has a different amino acid sequence than the second ligand binding region, and the first and second ligand binding regions bind to a heterodimeric ligand.

I11. The kit of embodiment I10, wherein the first ligand binding region binds to a first portion of the heterodimeric ligand, and the second ligand binding region binds to a second portion of the heterodimeric ligand.

I12. The kit of embodiment I11, wherein the chimeric polypeptide of any one of embodiments I1-I11 is a first chimeric polypeptide, the cell comprises a second chimeric polypeptide, the first ligand binding region of the first chimeric polypeptide and the second ligand binding region of the second chimeric polypeptide binds to the second portion of the heterodimeric ligand.

I12-I120. Reserved.

I200. A modified natural killer (NK) cell, comprising a first and a second polynucleotide, wherein the first polynucleotide encodes a chimeric polypeptide comprising
    c) a first ligand binding region;
    d) a second ligand binding region; and
    e) a signaling region, comprising
        xv) a MyD88 polypeptide;
        xvi) a truncated MyD88 polypeptide lacking the TIR domain;
        xvii) a MyD88 polypeptide and a CD40 cytoplasmic polypeptide region lacking the CD40 extracellular domain;
        xviii) a truncated MyD88 polypeptide lacking the TIR domain and a CD40 cytoplasmic polypeptide region lacking the CD40 extracellular domain;
        xix) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
        xx) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or
        xxi) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40; and
    the second polynucleotide encodes a IL-15 polypeptide.

I201-I220. Reserved.

I400. A nucleic acid, comprising a first and a second polynucleotide, wherein the first polynucleotide encodes a chimeric polypeptide comprising
    c) a first ligand binding region;
    d) a second ligand binding region; and
    e) a signaling region, comprising
        viii) a MyD88 polypeptide;
        ix) a truncated MyD88 polypeptide lacking the TIR domain;
        x) a MyD88 polypeptide and a CD40 cytoplasmic polypeptide region lacking the CD40 extracellular domain;
        xi) a truncated MyD88 polypeptide lacking the TIR domain and a CD40 cytoplasmic polypeptide region lacking the CD40 extracellular domain;
        xii) a MyD88 polypeptide and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions;
        xiii) a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions; or xiv) a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40 and the second polynucleotide encodes a IL-15 polypeptide.

I401. The nucleic acid of any one of embodiments I401-I494, wherein the nucleic acid comprises a polynucleotide that encodes a chimeric antigen receptor (CAR) or a T-cell receptor.

I402. The nucleic acid of embodiment I401, wherein the nucleic acid comprises a first polynucleotide encoding a first FKBP12v36 ligand binding region and a second FKBP12v36 ligand binding region, a truncated MyD88 polypeptide lacking the TIR domain and a CD40 cytoplasmic polypeptide region lacking the CD40 extracellular domain, a second polynucleotide encoding an IL-15 polypeptide, and a third polynucleotide encoding a chimeric antigen receptor.

I403. The nucleic acid of any one of embodiments I401 or I402, wherein the CAR targets CD123 or BCMA.

I404. A modified NK cell comprising a nucleic acid of any one of embodiments I400-I403.

I405. The modified NK cell of embodiment I404 comprising a nucleic acid comprising a polynucleotide encoding a chimeric apoptotic polypeptide comprising an FKBP12 binding region, an FRB binding region or an FRB variant binding region, and a Caspase-9 polypeptide lacking the CARD domain.

I406. The nucleic acid of embodiment I400, wherein the nucleic acid comprises a first polynucleotide encoding a first FKBP12v36 ligand binding region and a second FKBP12v36 ligand binding region, a truncated MyD88 polypeptide lacking the TIR domain and a CD40 cytoplasmic polypeptide region lacking the CD40 extracellular domain, a second polynucleotide encoding an IL-15 polypeptide, and a third polynucleotide encoding a chimeric apoptotic polypeptide comprising an FKBP12 binding region, an FRB binding region or an FRB variant binding region, and a Caspase-9 polypeptide lacking the CARD domain.

I407. A modified NK cell comprising a nucleic acid of embodiment I406.

I408. The modified NK cell of embodiment I407, comprising a nucleic acid comprising a polynucleotide encoding a chimeric antigen receptor.

I409. The modified NK cell of embodiment 408, wherein the CAR targets CD123 or BCMA.I410. The nucleic acid of any of embodiments I400-I403, or I406, wherein the nucleic acid comprises a polynucleotide encoding a marker polypeptide.

I411. The nucleic acid of embodiment I410, wherein the marker polypeptide is a ΔCD19 polypeptide.

I412. The modified NK cell of any one of embodiments I404-I405, or I407-I409, wherein the nucleic acid encoding the chimeric antigen receptor the nucleic acid encoding the chimeric apoptotic polypeptide comprises a polynucleotide encoding a marker polypeptide.

I413. The modified NK cell of embodiment I412, wherein the marker polypeptide is a ΔCD19 polypeptide.

I414-420. Reserved.

J1. A pharmaceutical composition prepared by a method of any one of embodiments B1-B120, C1-C120, or D1-D120.

J2. A pharmaceutical composition comprising a modified NK cell or a nucleic acid of any one of embodiments A1-A120, I200-I220 or I401-420.

J3-J20. Reserved.

L1. The modified NK cell, method, kit, nucleic acid, or pharmaceutical composition of any one of embodiments A1-J20, comprising a polynucleotide encoding a IL-15 polypeptide.

L2-L9. Reserved.

L10. The modified NK cell, method, kit, nucleic acid, or pharmaceutical composition of any one of embodiments A1-L9, wherein the first ligand binding region has a different amino acid sequence than the second ligand binding region, and the first and second ligand binding regions bind to a heterodimeric ligand.

L11. The modified NK cell, method, kit, nucleic acid, or pharmaceutical composition of embodiment L10, wherein the first ligand binding region binds to a first portion of the heterodimeric ligand, and the second ligand binding region binds to a second portion of the heterodimeric ligand.

L12. The modified NK cell, method, kit, nucleic acid, or pharmaceutical composition of embodiment L11, wherein the chimeric polypeptide of any one of embodiments L1-L11 is a first chimeric polypeptide, the cell comprises a second chimeric polypeptide, the first ligand binding region of the first chimeric polypeptide binds to the first portion of the heterodimeric ligand and the second ligand binding region of the second chimeric polypeptide binds to the second portion of the heterodimeric ligand.

L13. The modified NK cell, method, kit, nucleic acid, or pharmaceutical composition of embodiment L12, wherein the first and second chimeric polypeptides dimerize upon binding of the heterodimeric ligand to the first ligand binding region of the first chimeric polypeptide and the second ligand binding region of the second chimeric polypeptide.

L14. The modified NK cell, method, kit, nucleic acid, or pharmaceutical composition of any one of embodiments L10-L13, wherein the heterodimeric ligand is rapamycin or a rapamycin analog.

L15. The modified NK cell, method, kit, nucleic acid, or pharmaceutical composition of any one of embodiments L10-L14, wherein the first ligand binding region is an FK506 binding protein 12 (FKBP12) region and the second ligand binding region is an FKBP12-Rapamycin-binding domain of mTOR (FRB) region, or an FRB variant polypeptide region.

L16. The modified NK cell, method, kit, nucleic acid, or pharmaceutical composition of any one of embodiments L10-L15, wherein the first portion of the heterodimeric ligand binds to the first ligand binding region with 100 times or more affinity than it binds to the second ligand binding region.

L17. The modified NK cell, method, kit, nucleic acid, or pharmaceutical composition of any one of embodiments L10-L16, wherein the second portion of the heterodimeric ligand binds to the second ligand binding region with 100 times or more affinity than it binds to the first ligand binding region.

L18. Reserved.

L19. The modified NK cell, method, kit, nucleic acid, or pharmaceutical composition of any one of embodiments A1-L9, wherein the first ligand binding region and the second ligand binding region are the same.

L20. The modified NK cell, method, kit, nucleic acid, or pharmaceutical composition of embodiment L19, wherein the first ligand binding region and the second ligand binding region bind to a homodimeric ligand.

L21. The modified NK cell, method, kit, nucleic acid, or pharmaceutical composition of embodiment L20, wherein the first ligand binding region of a first chimeric polypeptide binds to a first portion of the homodimeric ligand and the second ligand binding region of a second chimeric polypeptide binds to the second portion of the homodimeric ligand.

L22. The modified NK cell, method, kit, nucleic acid, or pharmaceutical composition of embodiment L21, wherein the first and second chimeric polypeptides dimerize upon binding of the homodimeric ligand to the first ligand binding region of the first chimeric polypeptide and the second ligand binding region of the second chimeric polypeptide.

L23. The modified NK cell, method, kit, nucleic acid, or pharmaceutical composition of any one of embodiments L20-L22, wherein the first portion of the homodimeric ligand binds to the first ligand binding region with an affinity from 1-10 times the affinity that it binds to the second ligand binding region.

L24. The modified NK cell, method, kit, nucleic acid, or pharmaceutical composition of any one of embodiments L20-L22, wherein the second portion of the homodimeric ligand binds to the second ligand binding region with an affinity from 1-10 times the affinity than it binds to the first ligand binding region.

L25. The modified NK cell, method, kit, nucleic acid, or pharmaceutical composition of any one of embodiments L20-L24, wherein the ligand is rimiducid, AP20187, or AP1510.

L26. The modified NK cell, method, kit, nucleic acid, or pharmaceutical composition of any one of embodiments L20-L25, wherein the first ligand binding region and the second ligand binding region are FKBP12 variant regions.

L27. The modified NK cell, method, kit, nucleic acid, or pharmaceutical composition of any one of embodiments A1-L26, wherein the chimeric polypeptide does not comprise a membrane-targeting region.

L28. The modified NK cell, method, kit, nucleic acid, or pharmaceutical composition of any one of embodiments A1-L27, wherein the chimeric polypeptide does not comprise a first ligand binding region.

L29. The modified NK cell, method, kit, nucleic acid, or pharmaceutical composition of any one of embodiments A1-L28, wherein the chimeric polypeptide does not comprise a first ligand binding region.

L30. The modified NK cell, method, kit, nucleic acid, or pharmaceutical composition of any one of embodiments A1-L19, wherein the chimeric polypeptide comprises a FKBP12 binding region, a FRB binding region, and a truncated MyD88 polypeptide lacking the TIR domain.

L31. The modified NK cell, method, kit, nucleic acid, or pharmaceutical composition of any one of embodiments A1-L19, wherein the chimeric polypeptide comprises a FKBP12 binding region, a FRB variant binding region, and a truncated MyD88 polypeptide lacking the TIR domain.

L32. The modified NK cell, method, kit, nucleic acid, or pharmaceutical composition of any one of embodiments A1-L19, wherein the chimeric polypeptide comprises a FKBP12 binding region, a $FRB_L$ binding region, and a truncated MyD88 polypeptide lacking the TIR domain.

L33. The modified NK cell, method, kit, nucleic acid, or pharmaceutical composition of any one of embodiments A1-L19, wherein the chimeric polypeptide comprises a FKBP12 binding region, a FRB binding region, a truncated MyD88 polypeptide lacking the TIR domain, and a CD40 cytoplasmic polypeptide region lacking the CD40 extracellular domain.

L34. The modified NK cell, method, kit, nucleic acid, or pharmaceutical composition of any one of embodiments A1-L19, wherein the chimeric polypeptide comprises a FKBP12 binding region, a FRB variant binding region, a truncated MyD88 polypeptide lacking the TIR domain, and a CD40 cytoplasmic polypeptide region lacking the CD40 extracellular domain.

L34. The modified NK cell, method, kit, nucleic acid, or pharmaceutical composition of any one of embodiments A1-L19, wherein the chimeric polypeptide comprises a FKBP12 binding region, a $FRB_L$ binding region, a truncated MyD88 polypeptide lacking the TIR domain, and a CD40 cytoplasmic polypeptide region lacking the CD40 extracellular domain.

L35-L39. Reserved.

L40. The modified NK cell, method, kit, nucleic acid, or pharmaceutical composition of any one of embodiments A1-L9 or L20-L29, wherein the chimeric polypeptide comprises a first FKBP12v36 region, a second FKBP12v36 region, and a truncated MyD88 polypeptide lacking the TIR domain.

L41. The modified NK cell, method, kit, nucleic acid, or pharmaceutical composition of any one of embodiments A1-L9 or L20-L29, wherein the chimeric polypeptide comprises a first FKBP12v36 region, a second FKBP12v36 region, a truncated MyD88 polypeptide lacking the TIR domain, and a CD40 cytoplasmic polypeptide region lacking the CD40 extracellular domain.

L41.1. The modified NK cell, method, kit, nucleic acid, or pharmaceutical composition of any one of embodiments A1-L41, wherein the modified NK cell is contacted with antibody to direct antibody-directed cellular cytotoxicity.

L41.2. The modified NK cell, method, kit, nucleic acid, or pharmaceutical composition of embodiment L41.1, wherein the antibody is Herceptin (4D5) or Rituxan.

L42. The modified NK cell, method, kit, nucleic acid, or pharmaceutical composition of any one of embodiments A1-A41.2, wherein the cell comprises a polynucleotide that encodes a chimeric antigen receptor (CAR).

M1. The modified NK cell, method, kit, nucleic acid, or pharmaceutical composition of any one of embodiments A1-L42, wherein the cells are not grown on feeder cells.

M2. The modified NK cell, method, kit, nucleic acid, or pharmaceutical composition of any one of embodiments A1-M1, wherein the cell has been stored at a temperature of −150° C. or below for more than 24 hours.

M3. The modified NK cell, method, kit, nucleic acid, or pharmaceutical composition of any one of embodiments A1-M2, wherein the cell has been stored at a temperature of −150° C. or below for more than one week.

M4. The modified NK cell, method, kit, nucleic acid, or pharmaceutical composition of any one of embodiments A1-M3, wherein the cell has been stored at a temperature of −150° C. or below for more than three weeks.

M5. The modified NK cell, method, kit, nucleic acid, or pharmaceutical composition of any one of embodiments A1-M4, wherein the cells have been contacted with a ligand that binds to the first and second ligand binding regions.

M6. The modified NK cell, method, kit, nucleic acid, or pharmaceutical composition of any one of embodiments A1-M5, wherein the cells have not been contacted with a ligand that binds to the first and second ligand binding regions.

M7. The modified NK cell, method, kit, nucleic acid, or pharmaceutical composition of any one of embodiments A1-M6, wherein the cells have not been contacted with exogenous IL-15.

M8. The modified NK cell, method, kit, nucleic acid, or pharmaceutical composition of any one of embodiments A1-M7, comprising the step of transfecting or transducing NK cells with a nucleic acid comprising a polynucleotide encoding the chimeric polypeptide.

M8-M49. Reserved.

M50. The modified NK cell, method, kit, nucleic acid, or pharmaceutical composition of any one of embodiments A1-M4, wherein the cell has been contacted with a ligand that binds to the first and second ligand binding regions before cryostorage.

M51. The modified NK cell, method, kit, nucleic acid, or pharmaceutical composition of any one of embodiments A1-M4, wherein the cell has not been contacted with a ligand that binds to the first and second ligand binding regions before cryostorage.

M52. The modified NK cell, method, kit, nucleic acid, or pharmaceutical composition of any one of embodiments A1-A51, wherein the cell has not been contacted with exogenous IL-15 before cryostorage.

M53-M59. Reserved.

M60. The modified NK cell, method, kit, nucleic acid, or pharmaceutical composition of any one of embodiments A1-M59, wherein the cell has been thawed following cryostorage.

M61. The modified NK cell, method, kit, nucleic acid, or pharmaceutical composition of any one of embodiments A1-M59, wherein the cell has been primed with an antibody following cryostorage.

M62. The modified NK cell, method, kit, nucleic acid, or pharmaceutical composition of embodiment M61, wherein the antibody binds to a tumor antigen.

M63. The modified NK cell, method, kit, nucleic acid, or pharmaceutical composition of any one of embodiments A1-M62, wherein the antibody is Herceptin or Rituxan.

M64-M69. Reserved.

M70. The modified NK cell, method, kit, nucleic acid, or pharmaceutical composition of any one of embodiments M60-M69, wherein the thawed NK cells have a 20 percent or greater efficacy than thawed NK cells that do not express the chimeric protein of any one of embodiments A1-M69.

M71. The modified NK cell, method, kit, nucleic acid, or pharmaceutical composition of any one of embodiments M60-M69, wherein the thawed NK cells have a 50 percent or greater efficacy than thawed NK cells that do not express a chimeric protein of any one of embodiments A1-M69.

M72. The modified NK cell, method, kit, nucleic acid, or pharmaceutical composition of any one of embodiments M70-M71, wherein efficacy is determined by assaying NK cell-mediated tumor cell death, NK cell proliferation, or NK cell survival.

M73. The modified NK cell, method, kit, nucleic acid, or pharmaceutical composition of embodiment M72, wherein the tumor cell is a THP1 tumor cell.

M74. The modified NK cell, method, kit, nucleic acid, or pharmaceutical composition of any one of embodiments M60-M73, wherein the thawed NK cells have the same level of viability as thawed NK cells that do not express the chimeric protein of any one of embodiments A1-M69.

M75. The modified NK cell, method, kit, nucleic acid, or pharmaceutical composition of any one of embodiments M60-M73, wherein the thawed NK cells have within 10 percent of the viability of thawed NK cells that do not express the chimeric protein of any one of embodiments A1-M69.

M76. The modified NK cell, method, kit, nucleic acid, or pharmaceutical composition of any one of embodiments M71-M75, wherein the efficacy is measured two days or more after the thawed NK cells are placed in growth medium under growing conditions.

M77. The modified NK cell, method, kit, nucleic acid, or pharmaceutical composition of any one of embodiments M71-M75, wherein the efficacy is measured three days or more after the thawed NK cells are placed in growth medium under growing conditions.

M78. The modified NK cell, method, kit, nucleic acid, or pharmaceutical composition of any one of embodiments of any one of embodiments A1-M77, comprising contacting the modified NK cells with an antibody.

M79. The method of any one of embodiments B1-M78, further comprising contacting the modified NK cell with a ligand that binds to the first ligand binding region of a first chimeric polypeptide and to the second ligand binding region of a second chimeric polypeptide, resulting in multimerization of the chimeric polypeptides.

M80. The modified NK cell, method, kit, nucleic acid, or pharmaceutical composition of any one of embodiments A1-M77, wherein the modified NK cell secretes IL-15.

M81. The modified NK cell, method, kit, nucleic acid, or pharmaceutical composition of embodiment M80, wherein the modified NK cell secretes two fold or more IL-15 than an NK cell that does not express the chimeric protein of any one of embodiments A1-M69.

M82. The modified NK cell, method, kit, nucleic acid, or pharmaceutical composition of embodiment M80, wherein the modified NK cell secretes 100 times or more IL-15 than an NK cell that does not express the chimeric protein of any one of embodiments A1-M69.

M83. The modified NK cell, method, kit, nucleic acid, or pharmaceutical composition of any one of embodiments A1-M82, wherein the modified NK cell secretes ten times or more IFN-γ than an NK cell that does not express the chimeric protein of any one of embodiments A1-M69.

M84. The modified NK cell, method, kit, nucleic acid, or pharmaceutical composition of any one of embodiments A1-M82, wherein the modified NK cell secretes 100 times or more IFN-γ than an NK cell that does not express the chimeric protein of any one of embodiments A1-M69.

M85. The modified NK cell, method, kit, nucleic acid, or pharmaceutical composition of any one of embodiments A1-M84, wherein the modified NK cell secretes ten times or more GM-CSF than an NK cell that does not express the chimeric protein of any one of embodiments A1-M69.

M86. The modified NK cell, method, kit, nucleic acid, or pharmaceutical composition of any one of embodiments A1-M84, wherein the modified NK cell secretes 100 times or more GM-CSF than an NK cell that does not express the chimeric protein of any one of embodiments A1-M69.

M87. The modified NK cell, method, kit, nucleic acid, or pharmaceutical composition of any one of embodiments A1-M86, wherein the modified NK cell secretes ten times or more TNF-α than an NK cell that does not express the chimeric protein of any one of embodiments A1-M69.

M88. The modified NK cell, method, kit, nucleic acid, or pharmaceutical composition of any one of embodiments A1-M86, wherein the modified NK cell secretes 100 times or more TNF-α than an NK cell that does not express the chimeric protein of any one of embodiments A1-M69.

M89. The modified NK cell, method, kit, nucleic acid, or pharmaceutical composition of any one of embodiments A1-M88, wherein the modified NK cell secretes ten times or more MIP-1α than an NK cell that does not express the chimeric protein of any one of embodiments A1-M69.

M90. The modified NK cell, method, kit, nucleic acid, or pharmaceutical composition of any one of embodiments A1-M88, wherein the modified NK cell secretes 100 times or more MIP-1α than an NK cell that does not express the chimeric protein of any one of embodiments A1-M69.

M91. The modified NK cell, method, kit, nucleic acid, or pharmaceutical composition of any one of embodiments A1-M90, wherein the modified NK cell secretes ten times or more MIP-1β than an NK cell that does not express the chimeric protein of any one of embodiments A1-M69.

M92. The modified NK cell, method, kit, nucleic acid, or pharmaceutical composition of any one of embodiments A1-M90, wherein the modified NK cell secretes 100 times or more MIP-1β than an NK cell that does not express the chimeric protein of any one of embodiments A1-M69.

M93. The modified NK cell, method, kit, nucleic acid, or pharmaceutical composition of any one of embodiments M80-M92, wherein the modified NK cell is contacted with a tumor cell or tumor cell line before determining the amount of a secreted cytokine, wherein the cytokine is selected from the group consisting of IL-15, IFN-γ, GM-CSF, TNF-α, MIP-1α, and MIP-1β.

M94. The modified NK cell, method, kit, nucleic acid, or pharmaceutical composition of any one of embodiments M80-M93, wherein the modified NK cell is contacted with a ligand that binds to the first and second ligand binding regions before determining the amount of a secreted cytokine, wherein the cytokine is selected from the group consisting of IL-15, IFN-γ, GM-CSF, TNF-α, MIP-1α, and MIP-1β.

M95. The modified NK cell, method, kit, nucleic acid, or pharmaceutical composition of any one of embodiments A1-M94, wherein the modified NK cells proliferate at a quicker rate than NK cells that do not express the chimeric protein of any one of embodiments E1-E69.

M96. The modified NK cell, method, kit, nucleic acid, or pharmaceutical composition of any one of embodiments A1-M95, wherein the modified NK cells have a greater survival rate than NK cells that do not express the chimeric protein of any one of embodiments E1-E69.

M97. The modified NK cell, method, kit, nucleic acid, or pharmaceutical composition method of any one of embodiments M95 or M96, wherein the NK cells are grown in the presence of exogenous IL-2.

N1. The modified NK cell, method, kit, nucleic acid, or pharmaceutical composition of any one of embodiments A1-M97, wherein the signaling region comprises a truncated MyD88 polypeptide lacking the TIR domain.

N2. The modified NK cell, method, kit, nucleic acid, or pharmaceutical composition of any one of embodiments A1-M97, wherein the signaling region comprises a truncated MyD88 polypeptide lacking the TIR domain and a CD40 cytoplasmic polypeptide region lacking the CD40 extracellular domain.

N3. The modified NK cell, method, kit, nucleic acid, or pharmaceutical composition of any one of embodiments A1-M97, wherein the signaling region comprises a truncated MyD88 polypeptide lacking the TIR domain and a co-stimulatory polypeptide cytoplasmic signaling region selected from the group consisting of CD27, CD28, ICOS, 4-1BB, RANK/TRANCE-R, OX40, CD30, TweakR, TAC1, BCMA and HVEM cytoplasmic signaling regions.

N3.1. The modified NK cell, method, kit, nucleic acid, or pharmaceutical composition of embodiment N4, wherein the co-stimulatory polypeptide cytoplasmic signaling region is selected from the group consisting of CD27, CD28, ICOS, 4-1BB, RANK/TRANCE-R, and OX40.

N3.2. The modified NK cell, method, kit, nucleic acid, or pharmaceutical composition of embodiment N4, wherein the co-stimulatory polypeptide cytoplasmic signaling region is selected from the group consisting of CD28, 4-1BB, OX40, and ICOS.

N3.3. The modified NK cell, method, kit, nucleic acid, or pharmaceutical composition of embodiment N4, wherein the co-stimulatory polypeptide cytoplasmic signaling region is selected from the group consisting of CD27, CD28, CD40, ICOS, 4-1BB, CD40, RANK/TRANCE-R, and OX40.

N3.4. The modified NK cell, method, kit, nucleic acid, or pharmaceutical composition of embodiment N4, wherein the co-stimulatory polypeptide cytoplasmic signaling region is selected from the group consisting of CD27, CD28, ICOS, 4-1BB, and OX40.

N3.5. The modified NK cell, method, kit, nucleic acid, or pharmaceutical composition of any one of embodiments N3-N3.4, wherein the co-stimulatory polypeptide lacks an extracellular domain or lacks a functional extracellular domain.

N4. The modified NK cell, method, kit, nucleic acid, or pharmaceutical composition of any one of embodiments A1-M97, wherein the signaling region comprises a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

N4.1. The modified NK cell, method, kit, nucleic acid, or pharmaceutical composition of embodiment N4, wherein the signaling region comprises a first co-stimulatory polypeptide cytoplasmic signaling region selected from the group consisting of CD27, CD28, ICOS, 4-1BB, RANK/TRANCE-R, and OX40, and a second co-stimulatory polypeptide cytoplasmic signaling region selected from the group consisting of CD27, CD28, ICOS, 4-1BB, RANK/TRANCE-R, and OX40.

N4.2. The modified NK cell, method, kit, nucleic acid, or pharmaceutical composition of embodiment N4, wherein the signaling region comprises a first co-stimulatory polypeptide cytoplasmic signaling region selected from the group consisting of CD28, 4-1BB, OX40, and ICOS, and a second co-stimulatory polypeptide cytoplasmic signaling region selected from the group consisting of CD28, 4-1BB, OX40, and ICOS.

N4.3. The modified NK cell, method, kit, nucleic acid, or pharmaceutical composition of embodiment N4, wherein the signaling region comprises a first co-stimulatory polypeptide cytoplasmic signaling region selected from the group consisting of CD27, CD28, CD40, ICOS, 4-1BB, CD40, RANK/TRANCE-R, and OX40, and a second co-stimulatory polypeptide cytoplasmic signaling region selected from the group consisting of CD27, CD28, CD40, ICOS, 4-1BB, CD40, RANK/TRANCE-R, and OX40.

N4.4. The modified NK cell, method, kit, nucleic acid, or pharmaceutical composition of embodiment N4, wherein the signaling region comprises a first co-stimulatory polypeptide cytoplasmic signaling region selected from the group consisting of CD27, CD28, ICOS, 4-1BB, and OX40, and a second co-stimulatory polypeptide cytoplasmic signaling region selected from the group consisting of CD27, CD28, ICOS, 4-1BB, and OX40.

N4.5. The modified NK cell, method, kit, nucleic acid, or pharmaceutical composition of any one of embodiments N4-N4.4, wherein the first and second co-stimulatory polypeptides lack an extracellular domain or lacks a functional extracellular domain.

N5. The modified NK cell, method, kit, nucleic acid, or pharmaceutical composition of any one of embodiments A1-N3, wherein the truncated MyD88 polypeptide comprises the amino acid sequence of the full length MyD88 sequence of SEQ ID NO: 118, wherein the truncated MyD88 polypeptide lacks the TIR domain, or a functional fragment thereof.

N6. The modified NK cell, method, kit, nucleic acid, or pharmaceutical composition of any one of embodiments A1-N3, wherein the truncated MyD88 polypeptide does not comprise contiguous amino acid residues 156 to the C-terminus of the full length MyD88 polypeptide.

N7. The modified NK cell, method, kit, nucleic acid, or pharmaceutical composition of any one of embodiments A1-N3, wherein the truncated MyD88 polypeptide does not comprise contiguous amino acid residues 152 to the C-terminus of the full length MyD88 polypeptide.

N8. The modified NK cell, method, kit, nucleic acid, or pharmaceutical composition of any one of embodiments A1-N3, wherein the truncated MyD88 polypeptide does not comprise contiguous amino acid residues 173 to the C-terminus of the full length MyD88 polypeptide.

N9. The modified NK cell, method, kit, nucleic acid, or pharmaceutical composition of any one of embodiments A1-N3, or N5-N8, wherein the full length MyD88 polypeptide comprises the amino acid sequence of SEQ ID NO: 118.

N10. The modified NK cell, method, kit, nucleic acid, or pharmaceutical composition of any one of embodiments A1-N3, or N5-N9, wherein the truncated MyD88 polypeptide consists of the amino acid sequence of SEQ ID NO: 119, or a functional fragment thereof.

N11. The modified NK cell, method, kit, nucleic acid, or pharmaceutical composition of any one of embodiments A1-N3, or N5-N9, wherein the truncated MyD88 polypeptide has the amino acid sequence of SEQ ID NO: 119 or an amino acid sequence 90% or more identical to SEQ ID NO: 119.

N12. The modified NK cell, method, kit, nucleic acid, or pharmaceutical composition of any one of embodiments A1-N3, or N5-N9, wherein the truncated MyD88 polypeptide has the amino acid sequence of SEQ ID NO: 119 or an amino acid sequence 95% or more identical to SEQ ID NO: 119.

N13. The modified NK cell, method, kit, nucleic acid, or pharmaceutical composition of any one of embodiments A1-N3, or N5-N9, wherein the truncated MyD88 polypeptide has the amino acid sequence of SEQ ID NO: 119.

N14. The modified NK cell, method, kit, nucleic acid, or pharmaceutical composition of any one of embodiments A1-N13, wherein the signaling region comprises a CD40 cytoplasmic polypeptide and lacks the CD40 extracellular domain.

N15. The modified NK cell, method, kit, nucleic acid, or pharmaceutical composition of any one of embodiments A1-N14, wherein the CD40 cytoplasmic polypeptide has the amino acid sequence of SEQ ID NO: 56 or an amino acid sequence 90% or more identical to SEQ ID NO: 56.

N16. The modified NK cell, method, kit, nucleic acid, or pharmaceutical composition of any one of embodiments A1-N14, wherein the CD40 cytoplasmic polypeptide has the amino acid sequence of SEQ ID NO: 56.

N18-N39: Reserved.

N40. The modified NK cell, method, kit, nucleic acid, or pharmaceutical composition of any one of embodiments A1-N39, wherein the first binding region comprises a FKBP12 region.

N41. The modified NK cell, method, kit, nucleic acid, or pharmaceutical composition of any one of embodiments A1-N39, wherein the first binding region consists of a FKBP12 region.

N42. The modified NK cell, method, kit, nucleic acid, or pharmaceutical composition of any one of embodiments A1-N39, wherein the second binding region comprises a FKBP12-Rapamycin Binding (FRB) region or a FRB variant polypeptide region.

N43. The modified NK cell, method, kit, nucleic acid, or pharmaceutical composition of any one of embodiments A1-N39, wherein the second binding region consists of a FKBP12-Rapamycin Binding (FRB) region or a FRB variant polypeptide region.

N44. The modified NK cell, method, kit, nucleic acid, or pharmaceutical composition of any one of embodiments A1-N39, wherein the first binding region comprises a FKBP12 region and the second binding region comprises a FRB region.

N45. The modified NK cell, method, kit, nucleic acid, or pharmaceutical composition of any one of embodiments A1-N39, wherein the first binding region comprises a FKBP12 region and the second binding region comprises a FRB variant polypeptide region.

N46. The modified NK cell, method, kit, nucleic acid, or pharmaceutical composition of any one of embodiments A1-N39, wherein the first binding region consists of a FKBP12 region and the second binding region consists of a FRB region.

N47. The modified NK cell, method, kit, nucleic acid, or pharmaceutical composition of any one of embodiments A1-N39, wherein the first binding region consists of a FKBP12 region and the second binding region consists of a FRB variant polypeptide region.

N48. The modified NK cell, method, kit, nucleic acid, or pharmaceutical composition of any one of embodiments A1-N39, wherein the first multimerizing region comprises a FKBP12 region and the second multimerizing region comprises a FRB region.

N49. The modified NK cell, method, kit, nucleic acid, or pharmaceutical composition of any one of embodiments A1-N39, wherein the first multimerizing region comprises a FKBP12 region and the second multimerizing region comprises a FRB variant polypeptide region.

N50. The modified NK cell, method, kit, nucleic acid, or pharmaceutical composition of any one of embodiments N50.1 The modified NK cell, method, kit, nucleic acid, or pharmaceutical composition of any one of embodiments A1-N48, wherein the FKBP12 region has the amino acid sequence of SEQ ID NO: 16 or an amino acid sequence 90% or more identical to SEQ ID NO: 16.

N51. The modified NK cell, method, kit, nucleic acid, or pharmaceutical composition of any one of embodiments A1-N48, wherein the FKBP12 region has the amino acid sequence of SEQ ID NO: 60 or an amino acid sequence 95% or more identical to SEQ ID NO: 60.

N52. The modified NK cell, method, kit, nucleic acid, or pharmaceutical composition of any one of embodiments A1-N48, wherein the FKBP12 region has the amino acid sequence of SEQ ID NO: 60.

N53. The modified NK cell, method, kit, nucleic acid, or pharmaceutical composition of any one of embodiments A1-N52, wherein the FRB region has the amino acid sequence of SEQ ID NO: 101 or an amino acid sequence 90% or more identical to SEQ ID NO: 101.

N54. The modified NK cell, method, kit, nucleic acid, or pharmaceutical composition of any one of embodiments A1-N52, wherein the FRB region has the amino acid sequence of SEQ ID NO: 101 or an amino acid sequence 95% or more identical to SEQ ID NO: 101.

N55. The modified NK cell, method, kit, nucleic acid, or pharmaceutical composition of any one of embodiments A1-N52, wherein the FRB region has the amino acid sequence of SEQ ID NO: 101.

N56. The modified NK cell, method, kit, nucleic acid, or pharmaceutical composition of any one of embodiments A1-N55, wherein the FRB variant polypeptide region has an amino acid substitution at position 2098 chosen from valine, leucine and isoleuceine.

N56.1. The modified NK cell, method, kit, nucleic acid, or pharmaceutical composition of any one of embodiments A1-N55, wherein the FRB variant polypeptide region binds to a C7 rapalog.

N56.2. The modified NK cell, method, kit, nucleic acid, or pharmaceutical composition of any one of embodiments A1-N55, wherein the FRB variant polypeptide region comprises an amino acid substitution at position T2098 or W2101.

N56.3. The modified NK cell, method, kit, nucleic acid, or pharmaceutical composition of any one of embodiments A1-N55, wherein the FRB variant polypeptide region is selected from the group consisting of KLW (T2098L) (FRBL), KTF (W2101F), and KLF (T2098L, W2101F).

N57. The modified NK cell, method, kit, nucleic acid, or pharmaceutical composition of any one of embodiments A1-N52, wherein the FRB variant polypeptide region has the amino acid sequence of SEQ ID NO: 121.

N58-N59. Reserved.

N60. The modified NK cell, method, kit, nucleic acid, or pharmaceutical composition of any one of embodiments A1-N39, or N53-N57, wherein the first ligand binding region comprises a FKBP12 variant polypeptide region.

N61. The modified NK cell, method, kit, nucleic acid, or pharmaceutical composition of any one of embodiments A1-N39, or N53-N57, wherein the first ligand binding region consists of a FKBP12 variant polypeptide region.

N62. The modified NK cell, method, kit, nucleic acid, or pharmaceutical composition of any one of embodiments A1-N39, wherein the second ligand binding region comprises a FKBP12 variant polypeptide region.

N63. The modified NK cell, method, kit, nucleic acid, or pharmaceutical composition of any one of embodiments A1-N39, wherein the second ligand binding region consists of a FKBP12 variant polypeptide region.

N64. The modified NK cell, method, kit, nucleic acid, or pharmaceutical composition of any one of embodiments A1-N39, wherein the first ligand binding region comprises a FKBP12 variant polypeptide region, and the second ligand binding region comprises a FKBP12 variant polypeptide region.

N65. The modified NK cell, method, kit, nucleic acid, or pharmaceutical composition of any one of embodiments A1-N39, wherein the first ligand binding region consists of a FKBP12 variant polypeptide region and the second ligand binding region consists of a FKBP12 variant polypeptide region.

N66. The modified NK cell, method, kit, nucleic acid, or pharmaceutical composition of any one of embodiments A1-N39, or N60-N65, wherein the FKBP12 variant region has an amino acid sequence of SEQ ID NO: 60, or an amino acid sequence 90% or more identical to SEQ ID NO: 60. comprising an amino acid substitution at position 36 chosen from valine, leucine, isoleuceine and alanine.

N67. The modified NK cell, method, kit, nucleic acid, or pharmaceutical composition of any one of embodiments A1-N39, or N60-N65, wherein the FKBP12 variant region has an amino acid sequence of SEQ ID NO: 60, or an amino acid sequence 95% or more identical to SEQ ID NO: 60 comprising an amino acid substitution at position 36 chosen from valine, leucine, isoleuceine and alanine.

N68. The modified NK cell, method, kit, nucleic acid, or pharmaceutical composition of any one of embodiments A1-N39, or N60-N65, wherein the FKBP12 variant region has an amino acid sequence of SEQ ID NO: 60, comprising an amino acid substitution at position 36 chosen from valine, leucine, isoleuceine and alanine.

N69. The modified NK cell, method, kit, nucleic acid, or pharmaceutical composition of any one of embodiments A1-N39, or N60-N65, wherein the FKBP12 variant region comprises an amino acid substitution at position 36 chosen from valine, leucine, isoleuceine and alanine.

N70. The modified NK cell, method, kit, nucleic acid, or pharmaceutical composition of any one of embodiments A1-N39, or N60-N69, wherein the FKBP12 variant region comprises an amino acid substitution at position 36, wherein the amino acid substitution at position 36 is valine.

N71. The modified NK cell, method, kit, nucleic acid, or pharmaceutical composition of any one of embodiments A1-N39, or N60-N69, wherein the FKBP12 variant region has an amino acid sequence of SEQ ID NO: 16, or an amino acid sequence 90% or more identical to SEQ ID NO: 16.

N72. The modified NK cell, method, kit, nucleic acid, or pharmaceutical composition of any one of embodiments A1-N39, or N60-N69, wherein the FKBP12 variant region has an amino acid sequence of SEQ ID NO: 16, or an amino acid sequence 95% or more identical to SEQ ID NO: 16.

N73. The modified NK cell, method, kit, nucleic acid, or pharmaceutical composition of any one of embodiments A1-N39, or N60-N69, wherein the FKBP12 variant region has an amino acid sequence of SEQ ID NO: 16.

N73.1. The modified NK cell, method, kit, nucleic acid, or pharmaceutical composition of any one of embodiments A1-N39, or N60-N69, wherein the first and second ligand binding regions together are Fv'Fvls.

N73.2. The modified NK cell, method, kit, nucleic acid, or pharmaceutical composition of embodiment N73.1, wherein Fv'Fvls comprises two linked polypeptides comprising the amino acid sequence of SEQ ID NO: 12 and the amino acid sequence of SEQ ID NO: 16.

N73.3. The modified NK cell, method, kit, nucleic acid, or pharmaceutical composition of embodiment N73.1, wherein Fv'Fvls comprises two linked polypeptide encoded by the nucleic acid sequences of SEQ ID NO: 11 and SEQ ID NO: 15.

N74. The modified NK cell, method, kit, nucleic acid, or pharmaceutical composition of any one of embodiments A1-N73, wherein the ligand is a heterodimeric ligand comprising a first portion and a second portion, the first portion of the ligand is capable of binding to the first ligand binding region, and the second portion is capable of binding to the second ligand binding region.

N75. The modified NK cell, method, kit, nucleic acid, or pharmaceutical composition of embodiment N74, wherein the first portion of the heterodimeric ligand binds to the first ligand binding region with 100 times or more greater affinity than the first portion binds to the second ligand binding region.

N76. The modified NK cell, method, kit, nucleic acid, or pharmaceutical composition of any one of embodiments N74 or N75, wherein the second portion of the heterodimeric ligand binds to the second ligand binding region with 100 times or more greater affinity than the second portion binds to the first ligand binding region.

N77. The modified NK cell, method, kit, nucleic acid, or pharmaceutical composition of any one of embodiments A1-N76, wherein the heterodimeric ligand is rapamycin.

N77. The modified NK cell, method, kit, nucleic acid, or pharmaceutical composition of any one of embodiments A1-N76, wherein the heterodimeric ligand is a rapalog.

N78. The modified NK cell, method, kit, nucleic acid, or pharmaceutical composition of embodiment N77, wherein the rapalog is selected from the group consisting of S-o,p-dimethoxyphenyl (DMOP)-rapamycin, R-Isopropoxyrapamycin, S-Butanesulfonamidorap, R and S C7-ethyloxyrapamycin, R and S C7-isopropyloxyrapamycin, R and S C7-isobutylrapamycin, R and S ethylcarbamaterapamycin, R and S C7-phenylcarbamaterapamycin, R and S C7-(3-methyl)indole rapamycin, temsirolimus, everolimus, zotarolimus, and R and S C7-(7-methyl)indole rapamycin.

N79. The modified NK cell, method, kit, nucleic acid, or pharmaceutical composition of any one of embodiments A1-N73, wherein the ligand is a homodimeric ligand comprising a first portion and a second portion, the first portion of the ligand is capable of binding to the first ligand binding region and is capable of binding to the second ligand binding region, and the second portion of the ligand is capable of binding to the first ligand binding region and is capable of binding to the second ligand binding region.

N80. The modified NK cell, method, kit, nucleic acid, or pharmaceutical composition of any one of embodiments A1-N73 or N79, wherein the ligand is rimiducid.

N81. The modified NK cell, method, kit, nucleic acid, or pharmaceutical composition of any one of embodiments A1-N73, or N79, wherein the ligand is AP20187 or AP1510.

N82-N89. Reserved.

N90. The method of any one of embodiments F1-N89, wherein the cells are autologous cells.

N91. The method of any one of embodiments F1-N89, wherein the cells are allogeneic cells.

N92. The method of any one of embodiments F1-N91, wherein the cells are obtained from bone marrow, cord blood, or peripheral blood.

N93. The method of any one of embodiments F1-N92, further comprising
identifying the presence, absence or stage of a condition or disease in a subject; and
transmitting an indication to administer the ligand, maintain a subsequent dosage of the ligand, or adjust a subsequent dosage of the ligand administered to the subject based on the presence, absence or stage of the condition or disease identified in the subject.

N94. The method of any one of embodiments F1-N93, wherein the subject has been diagnosed as having a tumor.

N95. The method of any one of embodiments F1-N94, wherein the subject has cancer.

N96. The method of any one of embodiments F1-N94, wherein the subject has a solid tumor.

N97. The method of any one of embodiments N95 or N96, wherein the cancer is present in the blood or bone marrow of the subject.

N98. The method of any one of embodiments N1-N94, wherein the subject has a blood or bone marrow disease.

N99. The method of any one of embodiments F1-N98, wherein the subject has been diagnosed with any condition or condition that can be alleviated by stem cell transplantation.

N100. The method of any one of embodiments F1-N99, wherein the subject has been diagnosed with sickle cell anemia or metachromatic leukodystrophy.

N101. The method of any one of embodiments F1-N100, wherein the subject has been diagnosed with a condition selected from the group consisting of a primary immune deficiency condition, hemophagocytosis lymphohistiocytosis (HAH) or other hemophagocytic condition, an inherited marrow failure condition, a hemoglobinopathy, a metabolic condition, and an osteoclast condition.

N102. The method of any one of embodiments F1-N100, wherein the subject has been diagnosed with a disease or condition selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-10 Receptor Deficiency, GATA 2 deficiency, X-linked lymphoproliferative disease (XAP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis.

N103. The method of any one of embodiments F1-N100, wherein the subject has been diagnosed with leukemia.

N104. The method of any one of embodiments F1-N100, wherein the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

N105. The modified NK cells, methods, pharmaceutical compositions, or kits of any one of embodiments A1-N104, wherein the modified NK cells comprise a polynucleotide that encodes a chimeric antigen receptor (CAR).

N106. The modified NK cells, methods, pharmaceutical compositions, or kits of embodiment N105, wherein the CAR comprises a transmembrane region, a cell activation region, and an antigen recognition region.

N107. The modified NK cells, methods, pharmaceutical compositions, or kits of embodiment N106, wherein the cell activation region is a T-cell activation region.

N108. The modified NK cells, methods, pharmaceutical compositions, or kits of embodiment N107, wherein the T-cell activation region is a CD3 zeta-chain region.

N109. The modified NK cells, methods, pharmaceutical compositions, or kits of any one of embodiments N106-N108, wherein the antigen recognition region specifically binds to a molecule chosen from PSMA, PSCA, Muc1 CD19, ROR1, Mesothelin, GD2, CD123, Muc16, CD33, CD38, CD44v6, and Her2/Neu.

N110. The modified NK cells, methods, pharmaceutical compositions, or kits of any one of embodiments N106-N109, wherein the antigen recognition moiety binds to an antigen on a cell involved in a hyperproliferative disease or to a viral or bacterial antigen.

N111. The modified NK cells, methods, pharmaceutical compositions, or kits of any one of embodiments N106-N110, wherein the antigen recognition moiety binds to an antigen selected from the group consisting of PSMA, PSCA, MUC1, CD19, ROR1, Mesothelin, GD2, CD123, MUC16, Her2/NE, CD20, CD30, BCMA, PRAME, NY-ESO-1, and EGFRvIII.

N112. The modified NK cell, method, kit, nucleic acid, or pharmaceutical composition of any one of embodiments A1-N113, wherein the modified NK cells have been primed with an antibody.

N113. The modified NK cell, method, kit, nucleic acid, or pharmaceutical composition of embodiment N112, wherein the antibody is capable of binding to an antigen on a tumor cell.

N114. The modified NK cell, method, kit, nucleic acid, or pharmaceutical composition of embodiment N112, wherein the antibody is selected from the group of antibodies that are capable of binding to an antigen on an infected cell.

T1. The modified NK cell, method, kit, nucleic acid, or pharmaceutical composition of any one of embodiments A1-N114, wherein the modified NK cell comprises a polynucleotide encoding a chimeric pro-apoptotic polypeptide, wherein the chimeric pro-apoptotic polypeptide comprises a third ligand binding region and a pro-apoptotic polypeptide region.

T2. The modified NK cell, method, kit, nucleic acid, or pharmaceutical composition of embodiment T1, wherein the first and second ligand binding regions of the chimeric polypeptide bind to a homodimeric ligand with 100 times greater affinity or more than the homodimeric ligand binds to the third ligand binding region of the chimeric pro-apoptotic polypeptide.

T3. The modified NK cell, method, kit, nucleic acid, or pharmaceutical composition of embodiment T1, wherein the first and second ligand binding regions of the chimeric polypeptide bind to a heterodimeric ligand with 100 times greater affinity or more than the heterodimeric ligand binds to the third ligand binding region of the chimeric pro-apoptotic polypeptide.

T3. The modified NK cell, method, kit, nucleic acid, or pharmaceutical composition of any one of embodiments T1 or T2, wherein the third ligand binding region binds to a ligand with 100 times greater affinity or more than the ligand binds to the first ligand binding region.

T4. The modified NK cell, method, kit, nucleic acid, or pharmaceutical composition of any one of embodiments T1-T3, wherein the third ligand binding region binds to a ligand with 100 times greater affinity or more than the ligand binds to the second ligand binding region.

T5. The modified NK cell, method, kit, nucleic acid, or pharmaceutical composition of any one of embodiments T1-T4, wherein the pro-apoptotic polypeptide is selected from the group consisting of Caspase 1, 2, 3, 4, 5, 6, 7, 8, 9, 10, 11, 12, 13, or 14, FADD (DED), APAF1 (CARD), CRADD/RAIDD CARD), ASC (CARD), Bax, Bak, Bcl-xL, Bcl-2, RIPK3, and RIPK1-RHIM.

T6. The modified NK cell, method, kit, nucleic acid, or pharmaceutical composition of any one of embodiments T1-T5, wherein the pro-apoptotic polypeptide is a caspase polypeptide.

T6.1. The modified NK cell, method, kit, nucleic acid, or pharmaceutical composition of embodiment T6, wherein the caspase polypeptide lacks the CARD domain.

T7. The modified NK cell, method, kit, nucleic acid, or pharmaceutical composition of any one of embodiments T1-T4, wherein the pro-apoptotic polypeptide is a Caspase-9 polypeptide.

T8. The modified NK cell, method, kit, nucleic acid, or pharmaceutical composition of embodiment T7, wherein the Caspase-9 polypeptide lacks the CARD domain.

T9. The modified NK cell, method, kit, nucleic acid, or pharmaceutical composition of any one of embodiments T7-T8, wherein the Caspase-9 polypeptide has the amino acid sequence of SEQ ID NO: 64 or an amino acid sequence 90% or more identical to SEQ ID NO: 64.

T10. The modified NK cell, method, kit, nucleic acid, or pharmaceutical composition of any one of embodiments T7-T8, wherein the Caspase-9 polypeptide has the amino acid sequence of SEQ ID NO: 27 or an amino acid sequence 95% or more identical to SEQ ID NO: 64.

T11. The modified NK cell, method, kit, nucleic acid, or pharmaceutical composition of any one of embodiments T7-T8, wherein the Caspase-9 polypeptide has the amino acid sequence of SEQ ID NO: 64.

T12. The modified NK cell, method, kit, nucleic acid, or pharmaceutical composition of any one of embodiments T7-T8 the caspase polypeptide is a modified Caspase-9 polypeptide comprising an amino acid substitution selected from a catalytically active caspase variant disclosed in Table 1 of U.S. Patent Application Nos. 62/816,799, 62/668,223, and 62/756,442, or as described in U.S. Pat. Nos. 9,434,935, 9,932,572 and 9,913,882, or U.S. Patent Application Publication Nos. 2018-0251746 A1 and 2018-0243384 A1.

T13. The modified NK cell, method, kit, nucleic acid, or pharmaceutical composition of any one of embodiments T7-T10 or T12, wherein the caspase polypeptide is a modified Caspase-9 polypeptide and has an amino acid substitution selected from the group consisting of D330A, D330E, and N405Q.

T14. The modified NK cell, method, kit, nucleic acid, or pharmaceutical composition of any one of embodiments T1-T13, wherein the third ligand binding region comprises a first multimerizing region and a second multimerizing region.

T15. The modified NK cell, method, kit, nucleic acid, or pharmaceutical composition of embodiment
T14, wherein the first multimerizing region has a different amino acid sequence than the second multimerizing region, and the first and second multimerizing regions bind to a heterodimeric ligand.

T16. The modified NK cell, method, kit, nucleic acid, or pharmaceutical composition of embodiment T15, wherein the first multimerizing region binds to binds to a first portion of the heterodimeric ligand, and the second multimerizing region binds to a second portion of the heterodimeric ligand.

T17. The modified NK cell, method, kit, nucleic acid, or pharmaceutical composition of embodiment T16, wherein the chimeric pro-apoptotic polypeptide of any one of embodiments T1-T16 is a first chimeric pro-apoptotic polypeptide, the cell comprises a second chimeric pro-apoptotic polypeptide, the first ligand binding region of the first chimeric pro-apoptotic polypeptide binds to a first portion of the heterodimeric ligand and the second ligand multimerizing region of the second chimeric pro-apoptotic polypeptide binds to a second portion of the heterodimeric ligand.

T18. The modified NK cell, method, kit, nucleic acid, or pharmaceutical composition of embodiment T17, wherein the first and second chimeric polypeptides dimerize upon binding of the heterodimeric ligand to the first multimerizing region of the first chimeric pro-apoptotic polypeptide and the second multimerizing region of the second chimeric pro-apoptotic polypeptide.

T19. The modified NK cell, method, kit, nucleic acid, or pharmaceutical composition of any one of embodiments T15-T18, wherein the heterodimeric ligand is rapamycin or a rapamycin analog.

T20. The modified NK cell, method, kit, nucleic acid, or pharmaceutical composition of any one of embodiments T14-T19, wherein the first multimerizing region is an FK506 binding protein 12 (FKBP12) region and the second multimerizing region is an FKBP12-Rapamycin-binding domain of mTOR (FRB) region, or an FRB variant polypeptide region.

T21. The modified NK cell, method, kit, nucleic acid, or pharmaceutical composition of any one of embodiments T14-T20, wherein the first portion of the heterodimeric ligand binds to the first multimerizing region with 100 times or more affinity than it binds to the second multimerizing region.

T22. The modified NK cell, method, kit, nucleic acid, or pharmaceutical composition of any one of embodiments T14-T21, wherein the second portion of the heterodimeric ligand binds to the multimerizing region with 100 times or more affinity than it binds to the first multimerizing region.

T23. The modified NK cell, method, kit, nucleic acid, or pharmaceutical composition of any one of embodiments T19-T22, wherein the first and second ligand binding regions of the chimeric polypeptide comprise FKBP12 variant polypeptide regions.

T24. The modified NK cell, method, kit, nucleic acid, or pharmaceutical composition of any one of embodiments T14-T23, wherein the first and second ligand binding regions of the chimeric polypeptide comprise FKBP12v36 regions.

T25-T30 Reserved.

T31. The modified NK cell, method, kit, nucleic acid, or pharmaceutical composition of any one of embodiments T1-T13, wherein the third ligand binding region binds to a homodimeric ligand.

T32. The modified NK cell, method, kit, nucleic acid, or pharmaceutical composition of any one of embodiments T1-T13, or T31, wherein the third ligand binding region of a first chimeric pro-apoptotic polypeptide binds to a first portion of the homodimeric ligand and the third ligand binding region of a second chimeric pro-apoptotic polypeptide binds to the second portion of the homodimeric ligand.

T33. The modified NK cell, method, kit, nucleic acid, or pharmaceutical composition of embodiment T31, wherein the first and second chimeric pro-apoptotic polypeptides dimerize upon binding of the homodimeric ligand to the third ligand binding region of the first chimeric pro-apoptotic polypeptide and the third ligand binding region of the second chimeric pro-apoptotic polypeptide.

T34. The modified NK cell, method, kit, nucleic acid, or pharmaceutical composition of any one of embodiments T31-T33, wherein the ligand is rimiducid, AP20187, or AP1510.

T35. The modified NK cell, method, kit, nucleic acid, or pharmaceutical composition of any one of embodiments T31-T34, wherein the third ligand binding region comprises a FKBP12 variant region.

T36. The modified NK cell, method, kit, nucleic acid, or pharmaceutical composition of any one of embodiments T31-T35, wherein the third ligand binding region comprises a FKBP12v36 region.

T37. The modified NK cell, method, kit, nucleic acid, or pharmaceutical composition of any one of embodiments T31-T36, wherein the chimeric polypeptide comprises a FKBP12 binding region, a FRB binding region T38. The modified NK cell, method, kit, nucleic acid, or pharmaceutical composition of any one of embodiments T31-T37, wherein the chimeric polypeptide comprises a FKBP12 binding region and a FRB binding region or FRB variant binding region.

T39. Reserved.

T40. The modified NK cell, method, kit, nucleic acid, or pharmaceutical composition of any one of embodiments T1-T40, wherein
the chimeric polypeptide comprises a FKBP12 binding region, an FRB binding region or an FRB variant binding region, and a truncated MyD88 polypeptide lacking the TIR domain; and
the chimeric pro-apoptotic polypeptide comprises a FKBP12v36 region and a Caspase-9 polypeptide lacking the CARD domain.

T41. The modified NK cell, method, kit, nucleic acid, or pharmaceutical composition of any one of embodiments T1-T40, wherein
the chimeric polypeptide comprises a FKBP12 binding region, an FRB binding region or an FRB variant binding region, a truncated MyD88 polypeptide lacking the TIR domain, and a CD40 cytoplasmic polypeptide region lacking the CD40 extracellular domain; and
the chimeric pro-apoptotic polypeptide comprises a FKBP12v36 region and a Caspase-9 polypeptide lacking the CARD domain.

T42. The modified NK cell, method, kit, nucleic acid, or pharmaceutical composition of any one of embodiments T1-T40, wherein
the chimeric polypeptide comprises two FKBP12v36 regions, and a truncated MyD88 polypeptide lacking the TIR domain; and
the chimeric pro-apoptotic polypeptide comprises a FKBP12 binding region, an FRB binding region or an FRB variant binding region, and a Caspase-9 polypeptide lacking the CARD domain.

T42.1. The modified NK cell, method, kit, nucleic acid, or pharmaceutical composition of any one of embodiments T1-T40, wherein
the chimeric polypeptide comprises two FKBP12v36 regions, a truncated MyD88 polypeptide lacking the TIR domain, and a CD40 cytoplasmic polypeptide region lacking the CD40 extracellular domain; and
the chimeric pro-apoptotic polypeptide comprises a FKBP12 binding region, an FRB binding region or an FRB variant binding region, and a Caspase-9 polypeptide lacking the CARD domain.

T43. The method of any one of embodiments T1-T42.1, comprising administering to the subject a ligand that binds to the third ligand binding region in an amount effective to kill at least 30% of the cells that express the chimeric pro-apoptotic polypeptide.

T44. The method of any one of embodiments T1-T42.1, comprising administering to the subject a ligand that binds to the third ligand binding region in an amount effective to kill at least 60% of the cells that express the chimeric pro-apoptotic polypeptide.

T45. The method of any one of embodiments T1-T42.1, comprising administering to the subject a ligand that binds to the third ligand binding region in an amount effective to kill at least 90% of the cells that express the chimeric pro-apoptotic polypeptide.

T46. The method of any one of embodiments T43-T45, wherein the third ligand binding region is capable of binding to rapamycin or to a rapalog.

T47. The method of any one of embodiments T43-T46, wherein the ligand is rapamycin or a rapalog.

T48. The method of embodiment T47, wherein the rapalog is selected from the group consisting of S-o,p-dimethoxyphenyl (DMOP)-rapamycin, R-Isopropoxyrapamycin, S-Butanesulfonamidorap, R and S C7-ethyloxyrapamycin, R and S C7-isopropyloxyrapamycin, R and S C7-isobutyl-rapamycin, R and S ethylcarbamaterapamycin, R and S C7-phenylcarbamaterapamycin, R and S C7-(3-methyl)indole rapamycin, temsirolimus, everolimus, zotarolimus, and R and S C7-(7-methyl)indole rapamycin.

T49. The method of anyone of embodiments T43-T45, wherein the third ligand binding region is capable of binding to rimiducid.

T50. The method of any one of embodiments T43-T45, wherein the ligand is rimiducid.

T51. The method of any one of embodiments T43-T50, wherein more than one dose of the ligand is administered to the subject.

T52. The method of any one of embodiments T43-T51, comprising
identifying a presence or absence of a condition in the subject that requires the removal of the modified NK cells from the subject; and
administering a ligand that binds to the third binding region, maintaining a subsequent dosage of the ligand, or adjusting a subsequent dosage of the ligand to the subject based on the presence or absence of the condition identified in the subject.

T53. The method of any one of embodiments T43-T51 comprising
receiving information comprising presence or absence of a condition in the subject that requires the removal of the modified NK cells from the subject; and
administering a ligand that binds to the third binding region, maintaining a subsequent dosage of the ligand, or adjusting a subsequent dosage of the ligand to the subject based on the presence or absence of the condition identified in the subject.

T54. The method of any one of embodiments T43-T51, comprising
identifying a presence or absence of a condition in the subject that requires the removal of the modified NK cells from the subject; and
transmitting the presence, absence or stage of the condition identified in the subject to a decision maker who administers a ligand that binds to the third binding region, maintains a subsequent dosage of the ligand, or adjusts a subsequent dosage of the ligand administered to the subject based on the presence, absence or stage of the condition identified in the subject.

T55. The method of any one of embodiments T43-T51, further comprising
identifying a presence or absence of a condition in the subject that requires the removal of the modified NK cells from the subject; and
transmitting an indication to administer a ligand that binds to the third binding region, maintain a subsequent dosage of the ligand, or adjust a subsequent dosage of the ligand administered to the subject based on the presence, absence or stage of the condition identified in the subject.

T56-T59. Reserved.

T60. The modified NK cell, method, kit, nucleic acid, or pharmaceutical composition of any one of embodiments T1-T59, wherein the third ligand binding region comprises a FKBP12 region having the amino acid sequence of SEQ ID NO: 60 or an amino acid sequence 90% or more identical to SEQ ID NO: 60.

T61. The modified NK cell, method, kit, nucleic acid, or pharmaceutical composition of any one of embodiments T1-T59, wherein the third ligand binding region comprises a FKBP12 region having the amino acid sequence of SEQ ID NO: 60 or an amino acid sequence 95% or more identical to SEQ ID NO: 60.

T62. The modified NK cell, method, kit, nucleic acid, or pharmaceutical composition of any one of embodiments T1-T59, wherein the third ligand binding region comprises a FKBP12 region having the amino acid sequence of SEQ ID NO: 60.

T63. The modified NK cell, method, kit, nucleic acid, or pharmaceutical composition of any one of embodiments T1-T62, wherein the third ligand binding region comprises a FRB region having the amino acid sequence of SEQ ID NO: 60 or an amino acid sequence 90% or more identical to SEQ ID NO: 60.

T64. The modified NK cell, method, kit, nucleic acid, or pharmaceutical composition of any one of embodiments T1-T62, wherein the third ligand binding region comprises a FRB region having the amino acid sequence of SEQ ID NO: 101 or an amino acid sequence 95% or more identical to SEQ ID NO: 101.

T65. The modified NK cell, method, kit, nucleic acid, or pharmaceutical composition of any one of embodiments T1-T62, wherein the third ligand binding region comprises a FRB region having the amino acid sequence of SEQ ID NO: 101.

T66. The modified NK cell, method, kit, nucleic acid, or pharmaceutical composition of any one of embodiments T1-T62, wherein the FRB variant polypeptide region has an amino acid substitution at position 2098 chosen from valine, leucine and isoleuceine.

T67. The modified NK cell, method, kit, nucleic acid, or pharmaceutical composition of any one of embodiments T1-T62, wherein the third ligand binding region comprises a FRB variant polypeptide region having the amino acid sequence of SEQ ID NO: 121.

T68. The modified NK cell, method, kit, nucleic acid, or pharmaceutical composition of any one of embodiments T1-T59 wherein the third ligand binding region comprises a FKBP12 variant region having an amino acid sequence of SEQ ID NO:60, or an amino acid sequence 90% or more identical to SEQ ID NO: 60 comprising an amino acid substitution at position 36 chosen from valine, leucine, isoleuceine and alanine.

T69. The modified NK cell, method, kit, nucleic acid, or pharmaceutical composition of any one of embodiments T1-T59, wherein the third ligand binding region comprises a FKBP12 variant region having an amino acid sequence of SEQ ID NO: 60, or an amino acid sequence 95% or more identical to SEQ ID NO: 60 comprising an amino acid substitution at position 36 chosen from valine, leucine, isoleuceine and alanine.

T70. The modified NK cell, method, kit, nucleic acid, or pharmaceutical composition of any one of embodiments T1-T59, wherein the third ligand binding region comprises a FKBP12 variant region having an amino acid sequence of SEQ ID NO: 60, comprising an amino acid substitution at position 36 chosen from valine, leucine, isoleuceine and alanine.

T71. The modified NK cell, method, kit, nucleic acid, or pharmaceutical composition of any one of embodiments T1-T59, wherein the third ligand binding region comprises a FKBP12 variant region comprising an amino acid substitution at position 36 chosen from valine, leucine, isoleuceine and alanine.

T72. The modified NK cell, method, kit, nucleic acid, or pharmaceutical composition of any one of embodiments T1-T59, wherein the third ligand binding region comprises a FKBP12 variant region comprising an amino acid substitution at position 36, wherein the amino acid substitution at position 36 is valine.

T73. The modified NK cell, method, kit, nucleic acid, or pharmaceutical composition of any one of embodiments T1-T59, wherein the third ligand binding region comprises a FKBP12 variant region having an amino acid sequence of SEQ ID NO: 16, or an amino acid sequence 90% or more identical to SEQ ID NO: 16.

T74. The modified NK cell, method, kit, nucleic acid, or pharmaceutical composition of any one of embodiments T1-T59, wherein the third ligand binding region comprises a FKBP12 variant region having an amino acid sequence of SEQ ID NO: 16, or an amino acid sequence 95% or more identical to SEQ ID NO: 16.

T75. The modified NK cell, method, kit, nucleic acid, or pharmaceutical composition of any one of embodiments T1-T59, wherein the third ligand binding region comprises a FKBP12 variant region having an amino acid sequence of SEQ ID NO: 16.

U1. The modified NK cell, method, kit, nucleic acid, or pharmaceutical composition of any one of embodiments A1-T75, wherein the first and second polynucleotides are present on the same nucleic acid.

U2. The modified NK cell, method, kit, nucleic acid, or pharmaceutical composition of any one of embodiments T1-T75, wherein the first and second polynucleotides, and the polynucleotide that encodes the chimeric pro-apoptotic polypeptide are present on the same nucleic acid.

Example 7: Additional Nucleotide and Amino Acid Sequences (MyD88 nucleotide sequence)
SEQ ID NO: 117
```
atggctgcaggaggtcccggcgcggggtctgcggccccggtct
cctccacatcctcccttccctggctgctctcaacatgcgagt
gcggcgccgcctgtctctgttcttgaacgtgcggacacaggtg
gcggccgactggaccgcgctggcggaggagatggactttgagt
acttggagatccggcaactggagacacaagcggaccccactgg
caggctgctggacgcctggcagggacgccctggcgcctctgta
ggccgactgctcgagctgcttaccaagctgggccgcgacgacg
tgctgctggagctgggacccagcattgaggaggattgccaaaa
gtatatcttgaagcagcagcaggaggaggctgagaagcctta
caggtggccgctgtagacagcagtgtcccacggacagcagagc
tggcgggcatcaccacacttgatgaccccctggggcatatgcc
tgagcgtttcgatgccttcatctgctattgccccagcgacatc
cagtttgtgcaggagatgatccggcaactggaacagacaaact
atcgactgaagttgtgtgtgtctgaccgcgatgtcctgcctgg
cacctgtgtctggtctattgctagtgagctcatcgaaaagagg
tgccgccggatggtggtggttgtctctgatgattacctgcaga
gcaaggaatgtgacttccagaccaaatttgcactcagcctctc
tccaggtgcccatcagaagcgactgatccccatcaagtacaag
gcaatgaagaaagagttccccagcatcctgaggttcatcactg
tctgcgactacaccaaccc ctgcaccaaatcttggttctggac
tcgccttgccaaggccttgtccctgccc
```

(MyD88 amino acid sequence)
SEQ ID NO: 118
```
M A A G G P G A G S A A P V S S T S S L P L A
A L N M R V R R R L S L F L N V R T Q V A A D
W T A L A E E M D F E Y L E I R Q L E T Q A D
P T G R L L D A W Q G R P G A S V G R L L E L
L T K L G R D D V L L E L G P S I E E D C Q K
Y I L K Q Q Q E E A E K P L Q V A A V D S S V
P R T A E L A G I T T L D D P L G H M P E R F
D A F I C Y C P S D I Q F V Q E M I R Q L E Q
T N Y R L K L C V S D R D V L P G T C V W S I
A S E L I E K R C R R M V V V S D D Y L Q S
K E C D F Q T K F A L S L S P G A H Q K R L I
P I K Y K A M K K E F P S I L R F I T V C D Y
T N P C T K S W F W T R L A K A L S L P
```

(MyD88L (TIR-deleted))
SEQ ID NO: 119
MAAGGPGAGSAAPVSSTSSLPLAALNMRVRRRLSLFLNVRTQVAAD
VVTALAEEMDFEYLEIRQLETQADPTGRLLDAWQGRPGASVGRLLD
LLTKLGRDDVLLELGPSIEEDCQKYILKQQQEEAEKPLQVAAVDSS
VPRTAELAGITTLDDPLGHMPERFDAFICYCPSDIQ (FRBL)
SEQ ID NO: 121
QLEMWHEGLEEASRLYFGERNVKGMFEVLEPLHAMMERGPQTLKET
SFNQAYGRDLMEAQEWCRKYMKSGNVKDLLQAWDLYYHVFRRISK

*        *        *

The entirety of each patent, patent application, publication and document referenced herein hereby is incorporated by reference. Citation of the above patents, patent applications, publications and documents are not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A nucleic acid, comprising a first polynucleotide and a second polynucleotide, wherein the first polynucleotide encodes a chimeric polypeptide comprising:
   a) a ligand binding region; and
   b) a signaling region, comprising
      a MyD88 polypeptide and a CD40 cytoplasmic polypeptide region lacking the CD40 extracellular domain, or
      a truncated MyD88 polypeptide lacking the TIR domain and a CD40 cytoplasmic polypeptide region lacking the CD40 extracellular domain; and
   wherein the second polynucleotide encodes an IL-15 polypeptide.

2. A modified natural killer (NK) cell, comprising a first polynucleotide and a second polynucleotide, wherein the first polynucleotide encodes a chimeric polypeptide comprising:
   a) a ligand binding region; and
   b) a signaling region, comprising
      a MyD88 polypeptide and a CD40 cytoplasmic polypeptide region lacking the CD40 extracellular domain, or
      a truncated MyD88 polypeptide lacking the TIR domain and a CD40 cytoplasmic polypeptide region lacking the CD40 extracellular domain;
   wherein the second polynucleotide encodes an IL-15 polypeptide.

3. The modified NK cell of claim 2, wherein the ligand binding region comprises
   a) two copies of FKBP12v36; or
   b) an FKBP12 polypeptide and an FKBP-rapamycin-binding (FRB) polypeptide or FRB variant polypeptide.

4. The modified NK cell of claim 2, which further comprises a third polynucleotide, wherein the third polynucleotide encodes
   a) a chimeric antigen receptor (CAR) or a T cell receptor (TCR); further wherein the CAR or TCR targets
      i. PSMA, PSCA, Muc1, CD19, RORI, Mesothelin, GD2, CD123, Muc16, CD33, CD38, CD44v6, Her2/Neu, CD20, CD30, BCMA, PRAME, NY-ESO-1, or EGFRvIII; or
      ii. HER-2, PSCA, CD123, or BCMA.

5. The modified NK cell of claim 2, which further comprises a third polynucleotide, wherein the third polynucleotide encodes a chimeric pro-apoptotic polypeptide comprising a second ligand binding region and a caspase-9 polypeptide lacking the caspase activation domain (CARD domain), and wherein the ligand binding region of the chimeric polypeptide is different than the second ligand binding domain of the chimeric pro-apoptotic polypeptide.

6. The modified NK cell of claim 2, which further comprises a third polynucleotide, wherein the third polynucleotide encodes a chimeric pro-apoptotic polypeptide comprising a second ligand binding region and a caspase-9 polypeptide lacking the caspase activation domain (CARD domain), wherein the ligand binding region of the chimeric polypeptide comprises two copies of FKBP12v36, and wherein the second ligand binding domain of the chimeric pro-apoptotic polypeptide comprises an FRB binding polypeptide or FRB variant polypeptide, and an FKBP polypeptide.

7. The modified NK cell of claim 4, which further comprises a fourth polynucleotide, wherein the fourth polynucleotide encodes a chimeric pro-apoptotic polypeptide comprising a second ligand binding region and a caspase-9 polypeptide lacking the caspase activation domain (CARD domain), and wherein the ligand binding region of the chimeric polypeptide
   a) is different than the second ligand binding domain of the chimeric pro-apoptotic polypeptide; or
   b) comprises two copies of FKBP12v36, and wherein the second ligand binding domain of the chimeric pro-apoptotic polypeptide comprises an FRB binding polypeptide or FRB variant polypeptide, and an FKBP polypeptide.

8. The modified NK cell of claim 2, which further comprises a third polynucleotide, wherein the third polynucleotide encodes a chimeric pro-apoptotic polypeptide comprising a second ligand binding region and a caspase-9 polypeptide lacking the caspase activation domain (CARD domain), wherein the ligand binding region of the chimeric polypeptide comprises an FRB binding polypeptide or FRB variant polypeptide, and an FKBP polypeptide, and the second ligand binding domain of the chimeric pro-apoptotic polypeptide comprises two copies of FKBP12v36.

9. A modified natural killer (NK) cell, comprising a first polynucleotide and a second polynucleotide, wherein the first polynucleotide encodes a chimeric polypeptide comprising a signaling region, wherein the signaling region comprises:
   a MyD88 polypeptide and a CD40 cytoplasmic polypeptide region lacking the CD40 extracellular domain, or
   a truncated MyD88 polypeptide lacking the TIR domain and a CD40 cytoplasmic polypeptide region lacking the CD40 extracellular domain;
wherein the second polynucleotide encodes an IL-15 polypeptide.

10. The modified NK cell of claim 2, wherein the signaling region comprises a truncated MyD88 polypeptide lacking the TIR domain and a CD40 cytoplasmic polypeptide region lacking the CD40 extracellular domain.

11. The modified NK cell of claim 2, wherein the truncated MyD88 polypeptide lacking the TIR domain comprises the amino acid sequence of
   a) SEQ ID NO: 119 or an amino acid sequence that is 90% identical to SEQ ID NO: 119; or
   b) SEQ ID NO: 2 or an amino acid sequence that is 90% identical to SEQ ID NO: 2.

12. The modified NK cell of claim 9, wherein the truncated MyD88 polypeptide lacking the TIR domain comprises the amino acid sequence of
   a) SEQ ID NO: 119 or an amino acid sequence that is 90% identical to SEQ ID NO: 119; or
   b) SEQ ID NO: 2 or an amino acid sequence that is 90% identical to SEQ ID NO: 2.

13. The modified NK cell of claim 2, wherein
   a) the modified NK cells
      i. are or have been cryostored; or
      ii. have been stored at a temperature of −150° C. or below; or
      iv have not been contacted with exogenous IL-15; or
   b) the ligand which binds to the ligand binding domain of the chimeric polypeptide is
      i. rimiducid, AP20187 or AP1510; or
      ii. rapamycin or a rapalog.

14. A method for stimulating an immune response comprising administering modified NK cells of claim 2 to a subject;
   wherein
      (a) the subject has a disease or condition associated with an elevated level of expression of a target antigen expressed by a target cell; or
      (b) a tumor has been detected in the subject.

15. A method for stimulating an immune response comprising administering (i) modified NK cells claim 2 to a subject and (ii) a ligand that binds to the ligand binding region of the chimeric polypeptide; wherein the ligand is administered after the modified NK cells are administered to the subject.

16. The method of claim 15, wherein the subject has a disease or condition associated with an elevated level of expression of a target antigen expressed by a target cell;
   further wherein the ligand is administered to the subject in amount effective to reduce the number or concentration of the target antigen or target cells in the subject.

17. The method of claim 14, wherein
   (a) the subject has cancer;
   (b) the subject has been diagnosed as having a hyperproliferative disease;
   (c) the subject has been diagnosed with sickle cell anemia or metachromatic eukodystrophy;
   (d) the subject has been diagnosed with a condition selected from the group consisting of a primary immune deficiency condition, hemophagocytosis lymphohistiocytosis (HAH) or another hemophagocytic condition, an inherited marrow failure condition, a hemoglobinopathy, a metabolic condition, and an osteoclast condition;

(e) the subject has been diagnosed with a disease or condition selected from the group consisting of Severe Combined Immune Deficiency (SCID), Combined Immune Deficiency (CID), Congenital T-cell Defect/Deficiency, Common Variable Immune Deficiency (CVID), Chronic Granulomatous Disease, IPEX (Immune deficiency, polyendocrinopathy, enteropathy, X-linked) or IPEX-like, Wiskott-Aldrich Syndrome, CD40 Ligand Deficiency, Leukocyte Adhesion Deficiency, DOCA 8 Deficiency, IL-10 Deficiency/IL-IO Receptor Deficiency, GATA 2 deficiency, X-linked lymphoproliferative disease (XAP), Cartilage Hair Hypoplasia, Shwachman Diamond Syndrome, Diamond Blackfan Anemia, Dyskeratosis Congenita, Fanconi Anemia, Congenital Neutropenia, Sickle Cell Disease, Thalassemia, Mucopolysaccharidosis, Sphingolipidoses, and Osteopetrosis;

(f) the subject has been diagnosed with leukemia; or (g) the subject has been diagnosed with an infection of viral etiology selected from the group consisting HIV, influenza, Herpes, viral hepatitis, Epstein Bar, polio, viral encephalitis, measles, chicken pox, Cytomegalovirus (CMV), adenovirus (ADV), HHV-6 (human herpesvirus 6, I), and Papilloma virus, or has been diagnosed with an infection of bacterial etiology selected from the group consisting of pneumonia, tuberculosis, and syphilis, or has been diagnosed with an infection of parasitic etiology selected from the group consisting of malaria, trypanosomiasis, leishmaniasis, trichomoniasis, and amoebiasis.

18. A method for reducing the number of modified NK cells in the event of a negative symptom or condition, comprising administering to a subject who has been previously been administered modified NK cells of claim 5 a ligand that binds to the second ligand binding region of the chimeric pro-apoptotic polypeptide in an amount effective to reduce the number or concentration of the modified NK cells in the subject;

wherein the amount is effective to kill
(a) at least 30% of the cells that express the chimeric pro-apoptotic polypeptide;
(b) at least 60% of the cells that express the chimeric pro-apoptotic polypeptide; or
(c) at least 90% of the cells that express the chimeric pro-apoptotic polypeptide further wherein the negative symptom or condition is graft-versus-host disease.

* * * * *

UNITED STATES PATENT AND TRADEMARK OFFICE
CERTIFICATE OF CORRECTION

| | | |
|---|---|---|
| PATENT NO. | : 12,410,231 B2 | Page 1 of 1 |
| APPLICATION NO. | : 17/053275 | |
| DATED | : September 9, 2025 | |
| INVENTOR(S) | : Joseph Henri Bayle et al. | |

It is certified that error appears in the above-identified patent and that said Letters Patent is hereby corrected as shown below:

In the Specification

In Column 1, Line 7, delete "May 7, 20198" and insert --May 7, 2018-- therefor.

Signed and Sealed this
Twenty-first Day of October, 2025

John A. Squires
*Director of the United States Patent and Trademark Office*